US012122761B2

(12) United States Patent
Calhoun et al.

(10) Patent No.: US 12,122,761 B2
(45) Date of Patent: *Oct. 22, 2024

(54) 2-AZASPIRO[3.4]OCTANE DERIVATIVES AS M4 AGONISTS

(71) Applicant: NOVARTIS AG, Basel (CH)

(72) Inventors: Amy Calhoun, Cambridge, MA (US); Xin Chen, Lexington, MA (US); Kevin Matthew Gardinier, Arlington, MA (US); Edward Charles Hall, Boston, MA (US); Keith Jendza, Boston, MA (US); Nancy Labbe-Giguere, Arlington, MA (US); James Neef, Stow, MA (US); Daniel Steven Palacios, Cambridge, MA (US); Ming Qian, Watertown, MA (US); Michael David Shultz, Lexington, MA (US); Christopher G. Thomson, Herts (GB); Kate Yaping Wang, Boxborough, MA (US); Fan Yang, West Roxbury, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/062,356

(22) Filed: Dec. 6, 2022

(65) Prior Publication Data

US 2023/0212139 A1 Jul. 6, 2023

Related U.S. Application Data

(63) Continuation of application No. 17/065,360, filed on Oct. 7, 2020, now Pat. No. 11,548,865.

(60) Provisional application No. 62/912,980, filed on Oct. 9, 2019.

(51) Int. Cl.
*C07D 401/04* (2006.01)
*A61K 45/06* (2006.01)

(52) U.S. Cl.
CPC ............ *C07D 401/04* (2013.01); *A61K 45/06* (2013.01)

(58) Field of Classification Search
CPC .............................. A61K 45/06; C07D 401/04
See application file for complete search history.

(56) References Cited

U.S. PATENT DOCUMENTS 11,485,742 B2 * 11/2022 Calhoun ................. A61P 25/00
11,548,865 B2 * 1/2023 Calhoun .............. C07D 401/14
2015/0232443 A1 8/2015 Brown et al.
2017/0037025 A1 2/2017 Brown et al.
2018/0072727 A1 3/2018 Congreve et al.
2018/0228791 A1 8/2018 Brown et al.
2018/0362507 A1 12/2018 Brown et al.
2019/0389849 A1 12/2019 Brown et al.
2021/0130365 A1 5/2021 Calhoun et al.
2024/0140959 A1 * 5/2024 Calhoun ................ A61P 25/18

FOREIGN PATENT DOCUMENTS

RU 2010135253 A 4/2012
WO WO 2004/043955 A1 5/2004
WO WO 2005/080376 A1 9/2005
WO WO 2006/006490 A2 1/2006
WO WO 2006/058294 A2 6/2006
WO WO 2008/024497 A1 2/2008
WO WO 2010/049146 A1 5/2010
WO WO 2010/084499 A2 7/2010
WO WO 2012/112743 A1 8/2012
WO WO 2013/013308 A1 1/2013
WO WO 2014/039489 A1 3/2014
WO WO 2014/045031 A1 3/2014
WO 2015/118342 A1 8/2015
WO WO 2016/067043 A1 5/2016
WO WO 2016/147011 A1 9/2016
WO WO 2017/021728 A1 2/2017
WO WO 2017/021729 A1 2/2017
WO WO 2017/021730 A1 2/2017

(Continued)

OTHER PUBLICATIONS

Murray; Biological Psychiatry 2014, 75, 542-552. https://doi.org/10.1016/j.biopsych.2013.08.020 (Year: 2014).*

Notification of Transmittal of the International Search Report and the Written Opinion of the International Searching Authority, or the Declaration, dated Nov. 23, 2020, issued in International Patent Appl. No. PCT/IB2020/059430, filed Oct. 7, 2020.

Notification of Transmittal of the International Search Report and the Written Opinion of the International Searching Authority, or the Declaration, dated Nov. 23, 2020, issued in International Patent Appl. No. PCT/IB2020/059431, filed Oct. 7, 2020.

(Continued)

*Primary Examiner* — Daniel R Carcanague

(74) *Attorney, Agent, or Firm* — McCarter & English, LLP; Michael J. DeGrazia

(57) ABSTRACT

Provided herein are compounds according to Formula (I)

(I)

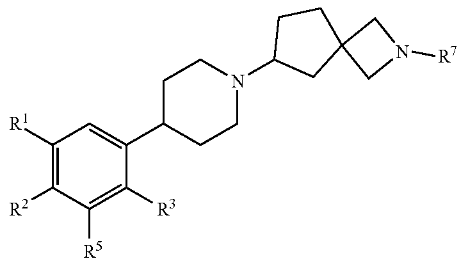

or a pharmaceutically acceptable salt thereof, wherein $R^1$, $R^2$, $R^3$, $R^5$, and $R^7$ are defined herein. Also provided herein are pharmaceutical compositions comprising a compound of Formula (I) as well as the use of such compounds as M4 receptor agonists.

25 Claims, 2 Drawing Sheets

(56) References Cited

FOREIGN PATENT DOCUMENTS

| | | | |
|---|---|---|---|
| WO | WO 2017/077292 | A1 | 5/2017 |
| WO | WO 2017/214367 | A1 | 12/2017 |
| WO | 2018069732 | A1 | 4/2018 |
| WO | WO 2018153312 | A1 | 8/2018 |
| WO | WO 2018/175746 | A1 | 9/2018 |
| WO | 2018229511 | A1 | 12/2018 |
| WO | WO 2019/183636 | A1 | 9/2019 |
| WO | WO 2019/243850 | A1 | 12/2019 |

OTHER PUBLICATIONS

Yang et al., Discovery of Selective M4 Muscarinic Acelylcholine Receptor Agonists with Novel Carbamate Isosteres, ACS Medicinal Chemistry Letters 2019 10 (6), 941-948.
Felder et al., Current status of muscarinic M1 and M4 receptors as drug targets for neurodegenerative diseases. Neuropharmacology. Jul. 1, 2018;136(Pt C):449-458.
Foster et al., Activation of M1 and M4 muscarinic receptors as potential treatments for Alzheimer's disease and schizophrenia. Neuropsychiatr Dis Treat. Jan. 28, 2014;10:183-91.
Takai et al., Discovery and Development of Muscarinic Acetylcholine M4 Activators as Promising Therapeutic Agents for CNS Diseases. Chem Pharm Bull (Tokyo). 2018;66(1):37-44.

* cited by examiner

2-AZASPIRO[3.4]OCTANE DERIVATIVES AS M4 AGONISTS

1. CROSS REFERENCE TO RELATED APPLICATIONS

This application is a continuation of application Ser. No. 17/065,360, filed Oct. 7, 2020, and claims the benefit of U.S. Provisional Application No. 62/912,980, filed on Oct. 9, 2019, all of which are incorporated herein by reference in their entirety.

2. FIELD

Provided herein are novel 2-azaspiro[3.4]octane compounds that act as M4 receptor agonists, as well as pharmaceutical compositions thereof, uses for the treatment of conditions, diseases and disorders related to the M4 receptor, which include, but are not limited to, psychosis, hyperkinetic movement disorders, cognitive dysfunction, and substance use disorders.

3. BACKGROUND

Acetylcholine, a major neurotransmitter in the central and peripheral nervous system, signals by activating its ionotropic (nicotinic) and G-protein coupled (muscarinic) receptors. Five muscarinic receptors (M1-M5) have been identified with differential expression and signaling. The M1, M3 and M5 receptors are coupled to Gq proteins that activate phospholipase C. Phospholipase C hydrolyses membrane phosphoinositides into inositol triphosphate ($IP_3$) and diacylglycerol (DAG), which elevate intracellular calcium and activate a number of signaling pathways. The M2 and M4 receptors are coupled to $G_{i/o}$ proteins which inhibit adenylyl cyclase production and decrease cyclic adenosine monophosphate (cAMP) levels, having an inhibitory effect on cell function. The M1 receptors are predominantly expressed in the forebrain (cortex, hippocampus, striatum and thalamus) and on salivary glands (*Brain Res Mol Brain Res* 2005, 133(1):6-11; *Br. J. Pharmacol* 2006, 148, 565-578; *Pharmacol Ther* 2008, 117: 232-243). The M2 receptors are expressed in the brain, and also highly expressed in the heart where they mediate vagal nerve innervation and can affect the heart rate (*Br. J. Pharmacol* 2006, 148, 565-578; *Pharmacol Ther* 2008, 117: 232-243). The M3 receptors are mostly expressed in the smooth muscles of peripheral tissues, including the gastrointestinal track, bladder, eye, and sweat and salivary glands (Br. J. Pharmacol 2006, 148, 565-578). The M4 receptors are enriched in the brain and are mainly expressed in the striatum, a brain area involved in dopamine release and signaling (*J Neurosci* 1994 14(5): 3351-3363; *Proc Natl Acad Sci USA* 1999, 96(18): 10483-10488; *Pharmacol Ther* 2008, 117: 232-243). The M5 receptors are expressed on vasculature, including the cerebral blood vessels (*Proc Natl Acad Sci USA* 2001, 98(24): 14096-14101).

In the central nervous system, muscarinic receptors have been shown to play a central role in cognition and regulation of dopaminergic signaling (Neuron 2017, 94(3): 431-446). Of particular interest are M4 receptors that are highly expressed in the striatum. Genetic deletion of M4 receptors causes a hyper-dopaminergic phenotype in rodents. M4 knock-out mice have been shown to have elevated striatal dopamine levels and increased locomotor activity (*Proc Natl Acad Sci USA* 1999, 96(18): 10483-10488.; *FASEB J* 2004, 18(12):1410-1412). Consistent with these observations, pharmacological activation of M4 receptors decreases amphetamine-induced dopamine release and reverses amphetamine hyperlocomotion in mice (*Neuropsychopharm* 2004, 39: 1578-1593). Thus, these results indicate that M4 receptors can act as a negative regulator of dopamine release and signaling in the striatum.

Increased dopamine tone in the striatum is strongly associated with psychotic symptoms in schizophrenia and other disorders, including psychotic depression, bipolar disorder, Huntington's disease and Alzheimer's disease (*Lancet* 1988, 2:119-125; *Schizophr Bull* 2009, 35:549-562). Current antipsychotic drugs act primarily by blocking the action of dopamine at D2 receptors. However, they have limited efficacy and serious side effects, including drug-induced Parkinsonism, tardive dyskinesia, Q-Tc prolongation, weight gain and metabolic syndrome which lead to poor patient compliance (*N Engl J Med* 2005, 353:1209-23).

Activation of muscarinic M4 receptors has been shown to downregulate striatal dopamine signaling and thereby may provide an alternative way to treat psychosis. In support of this notion, the muscarinic agonist xanomeline showed robust antipsychotic efficacy when tested in two clinical trials in Alzheimer disease (*Arch Neurol* 1997, 54(4):465-473) and schizophrenia patients (*Am J Psychiatry* 2008, 165(8):1033-1039). However, its treatment was associated with a number of side effects, including nausea, vomiting, excessive salivation, dyspepsia and chills, which stopped its clinical development. Xanomeline is a pan muscarinic agonist that activates all muscarinic receptor subtypes. Studies suggest that the antipsychotic efficacy of xanomeline is primarily mediated by the activation of M4 receptors. The M4 receptors are highly expressed in the human striatum (*Schizophr Res* 2015, 169: 83-88.) and the antipsychotic-like effects of xanomeline on dopamine-mediated behaviors are eliminated in M4 knock-out mice (*Eur J Pharmacol* 2009, 603: 147-149; *J Neurosci* 2011, 31(16):5905-5908.). In contrast, xanomeline's side effects are most likely due to the activation of M2 and M3 receptors which are expressed in the heart, digestive tract and salivary glands (*CNS Drug Rev* 2003, 9:159-186; *Br. J. Pharmacol* 2006, 148, 565-578). Thus, M4 selective agonists are likely to retain xanomeline's antipsychotic efficacy without causing cholinergic side effects.

Consequently, compounds that act as M4 receptor agonists may be useful for treatment of M4 related conditions.

4. SUMMARY

In one embodiment, provided herein is a compound according to Formula (I)

(I)

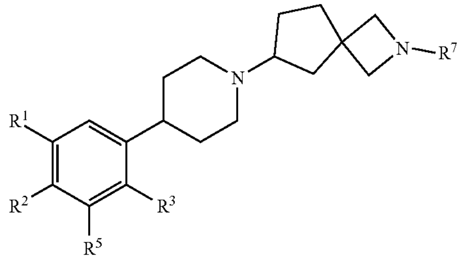

or a pharmaceutically acceptable salt thereof, wherein $R^1$ is halogen or hydrogen;

$R^2$ is halogen or hydrogen;

$R^3$ is $C_{1-6}$ alkyl, said alkyl is optionally substituted with one or two substituents independently selected from the group consisting of 4 to 6-membered heterocycloalkyl and —OH, 5 to 6-membered heteroaryl, 3 to 6-membered cycloalkyl, said cycloalkyl is optionally substituted with one —OH, 5 to 6-membered heterocycloalkyl, said heterocycloalkyl is optionally substituted with one —OH, or

—$OR^4$;

$R^4$ is

—$CF_3$,

—$CF_2H$, $C_{1-6}$ alkyl, said alkyl is optionally substituted with one or two $R^6$, 3 to 6-membered cycloalkyl, 4 to 7-membered heterocycloalkyl, said heterocycloalkyl is optionally substituted with one $R^6$, 5 to 6-membered heteroaryl, or $R^4$ is one of the following groups:

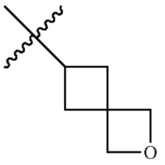

or

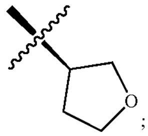

;

$R^5$ is halogen or hydrogen;

each $R^6$ is independently halogen,

—OH,

—$CF_3$,

—$CF_2H$, cyano,

—$OCF_3$,

—$OCH_3$,

—O-heterocycloalkyl, $C_1$-$C_4$ alkyl, 4 to 7-membered heterocycloalkyl, said heterocycloalkyl is optionally substituted with one or two substituents independently selected from the group consisting of halogen, —OH, and $C_{1-3}$ alkyl, 5 to 6-membered heteroaryl, said heteroaryl is optionally substituted with one or two $C_{1-3}$ alkyl, 3 to 6-membered cycloalkyl, said cycloalkyl is optionally substituted with one —$CF_3$, or each of $R^6$ is independently one of the following groups:

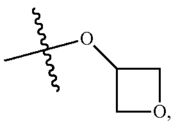

,

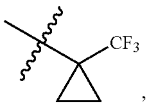

,

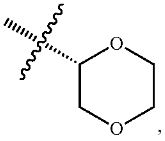

,

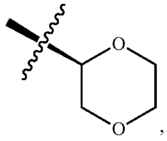

,

-continued

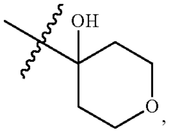

,

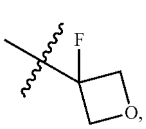

,

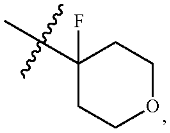

,

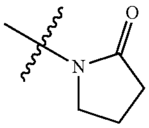

, or

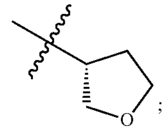

;

$R^7$ is a 5 to 6-membered heteroaryl, said heteroaryl is optionally substituted with one substituent selected from the group consisting of $C_1$-$C_6$ alkyl, —$CF_3$, and halogen, or $C(O)R^8$; and $R^8$ is 3 to 6-membered cycloalkyl, said cycloalkyl is optionally substituted with one halogen, or 4 to 6-membered heterocycloalkyl.

In one embodiment, provided herein is a compound according to Formula (Ia)

(Ia)

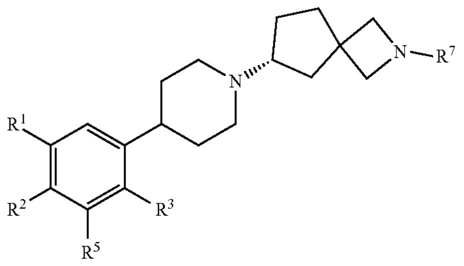

or a pharmaceutically acceptable salt or stereoisomer thereof.

In one embodiment, provided herein is a compound according to Formula (Ib)

(Ib)

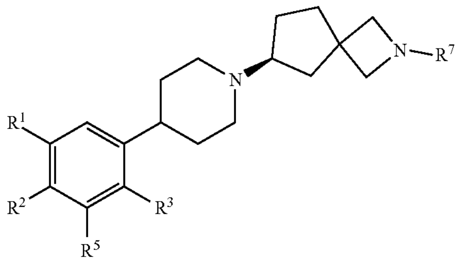

or a pharmaceutically acceptable salt or stereoisomer thereof.

In one embodiment, $R^1$ is selected from the group consisting of H, chloro, and fluoro.

In one embodiment, $R^2$ is H or fluoro.

In one embodiment, $R^5$ is H or fluoro.

In one embodiment, $R^1$, $R^2$, and $R^5$ are H.

In one embodiment, $R^3$ is selected from the group consisting of:

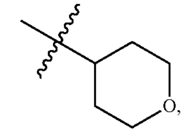
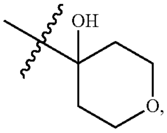
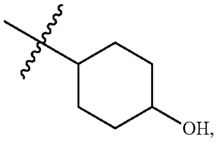
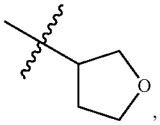
,
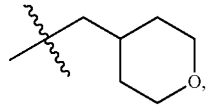
and
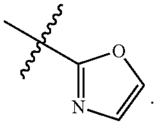
.

In another embodiment, $R^3$ is $—OR^4$.

In one embodiment, $R^4$ is selected from the group consisting of $—CH_3$, $—CF_3$, $—CF_2H$, $—CH_2CH_3$, $—CH(CH_3)_2$, $—CH_2CF_2H$, $—CH_2CH_2F$, $—(CH_2)_2CF_3$, $—CH_2C(CH_3)_2F$, $—(CH_2)_2OCF_3$, $—(CH_2)_2OH$, $—(CH_2)_2OCH_3$, $—CH_2C(CH_3)_2OH$, $—(CH_2)_2C(CH_3)_2OH$, $—(CH_2)_2C(CH_3)_2OCH_3$, $—CH_2C(CH_3)_2OCH_3$, $—(CH_2)_2CN$, and $—CH_2CH(CH_3)_2$. In another embodiment, $R^4$ is selected from the group consisting of:

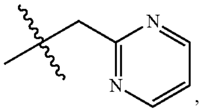
,
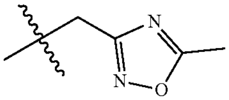
,
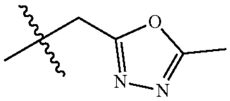
,
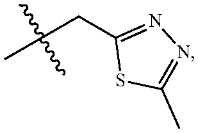
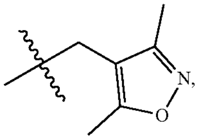
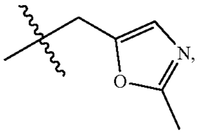
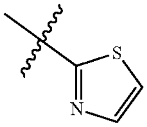
,
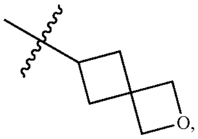
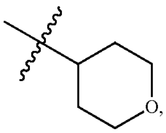
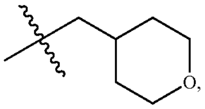
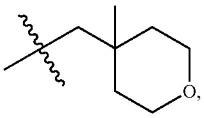
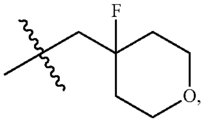
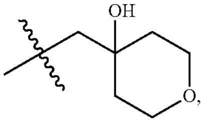
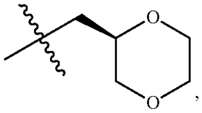
,
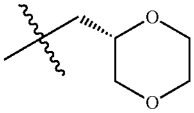
, -continued

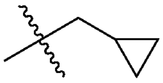
,
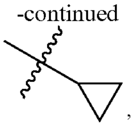
,
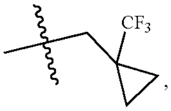
,
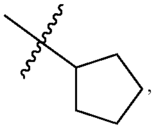
,
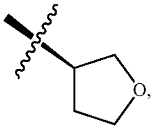
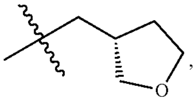
,
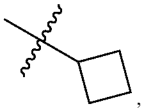
,
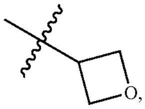
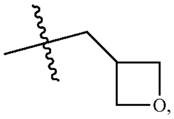
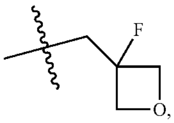
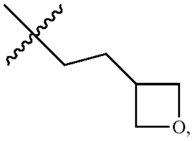
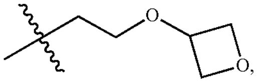
and
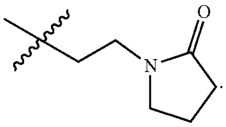
.

In one embodiment, $R^7$ is 5 to 6-membered heteroaryl or $—C(O)R^8$. In another embodiment. $R^7$ is

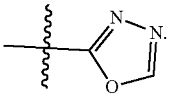 [SMILES: *c1nnco1]

In other embodiments, $R^7$ is $—C(O)R^8$.

In one embodiment, $R^8$ is 4 to 6-membered heterocycloalkyl or 3 to 6-membered cycloalkyl. In another embodiment, $R^8$ is 4 to 6-membered heterocycloalkyl. In other preferred embodiments, $R^8$ is

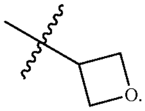 [SMILES: *C1COC1]

In certain embodiments, $R^8$ is 3 to 6-membered cycloalkyl, said 3 to 6-membered cycloalkyl is substituted with one halogen.

In one embodiment, provided herein is a compound selected from the group consisting of:

(R)-2-(6-(4-(2-((2-oxaspiro[3.3]heptan-6-yl)oxy)phenyl)piperidin-1-yl)-2-azaspiro[3.4]octan-2-yl)-1,3,4-oxadiazole;

(R)-2-(6-(4-(2-((2-oxaspiro[3.3]heptan-6-yl)oxy)-5-fluorophenyl)piperidin-1-yl)-2-azaspiro[3.4]octan-2-yl)-1,3,4-oxadiazole;

2-((R)-6-(4-(2-(((R)-1,4-dioxan-2-yl)methoxy)phenyl)piperidin-1-yl)-2-azaspiro[3.4]octan-2-yl)-1,3,4-oxadiazole;

(R)-2-(6-(4-(2-(oxetan-3-yloxy)phenyl)piperidin-1-yl)-2-azaspiro[3.4]octan-2-yl)-1,3,4-oxadiazole;

2-((R)-6-(4-(2-(((S)-1,4-dioxan-2-yl)methoxy)phenyl)piperidin-1-yl)-2-azaspiro[3.4]octan-2-yl)-1,3,4-oxadiazole;

(R)-ethyl 5-(6-(4-(2-hydroxyphenyl)piperidin-1-yl)-2-azaspiro[3.4]octan-2-yl)-1,3,4-oxadiazole-2-carboxylate;

(R)-2-(6-(4-(2-(oxetan-3-ylmethoxy)phenyl)piperidin-1-yl)-2-azaspiro[3.4]octan-2-yl)-1,3,4-thiadiazole;
(R)-2-(6-(4-(2-((3-fluorooxetan-3-yl)methoxy)phenyl)piperidin-1-yl)-2-azaspiro[3.4]octan-2-yl)-1,3,4-thiadiazole;
(R)-2-(6-(4-(2-((tetrahydro-2H-pyran-4-yl)methoxy)phenyl)piperidin-1-yl)-2-azaspiro[3.4]octan-2-yl)-1,3,4-thiadiazole;
(R)-2-(6-(4-(2-((4-fluorotetrahydro-2H-pyran-4-yl)methoxy)phenyl)piperidin-1-yl)-2-azaspiro[3.4]octan-2-yl)-1,3,4-thiadiazole;
(R)-6-(4-(2-(oxetan-3-yloxy)phenyl)piperidin-1-yl)-2-(pyrimidin-5-yl)-2-azaspiro[3.4]octane;
(R)-2-(pyrimidin-5-yl)-6-(4-(2-((tetrahydro-2H-pyran-4-yl)oxy)phenyl)piperidin-1-yl)-2-azaspiro[3.4]octane;
(R)-2-(pyrimidin-5-yl)-6-(4-(2-((tetrahydro-2H-pyran-4-yl)methoxy)phenyl)piperidin-1-yl)-2-azaspiro[3.4]octane;
(R)-6-(4-(2-(oxetan-3-ylmethoxy)phenyl)piperidin-1-yl)-2-(pyrimidin-5-yl)-2-azaspiro[3.4]octane;
(R)-6-(4-(2-((2-oxaspiro[3.3]heptan-6-yl)oxy)phenyl)piperidin-1-yl)-2-(pyrimidin-5-yl)-2-azaspiro[3.4]octane;
(R)-2-(pyrimidin-5-yl)-6-(4-(2-(((R)-tetrahydrofuran-3-yl)oxy)phenyl)piperidin-1-yl)-2-azaspiro[3.4]octane;
(R)-1-(2-(1-(2-(1,3,4-oxadiazol-2-yl)-2-azaspiro[3.4]octan-6-yl)piperidin-4-yl)phenoxy)-2-methylpropan-2-ol;
2-((R)-6-(4-(2-(((R)-tetrahydrofuran-3-yl)oxy)phenyl)piperidin-1-yl)-2-azaspiro[3.4]octan-2-yl)-1,3,4-oxadiazole;
(R)-ethyl 5-(6-(4-(2-(2-methoxyethoxy)phenyl)piperidin-1-yl)-2-azaspiro[3.4]octan-2-yl)-1,3,4-oxadiazole-2-carboxylate;
(R)-2-(6-(4-(2-((4-fluorotetrahydro-2H-pyran-4-yl)methoxy)phenyl)piperidin-1-yl)-2-azaspiro[3.4]octan-2-yl)-1,3,4-oxadiazole;
(R)-2-(6-(4-(2-((4-methyltetrahydro-2H-pyran-4-yl)methoxy)phenyl)piperidin-1-yl)-2-azaspiro[3.4]octan-2-yl)-1,3,4-oxadiazole;
(R)-2-(6-(4-(2-((tetrahydro-2H-pyran-4-yl)oxy)phenyl)piperidin-1-yl)-2-azaspiro[3.4]octan-2-yl)-1,3,4-oxadiazole;
(R)-2-(6-(4-(2-((tetrahydro-2H-pyran-4-yl)methoxy)phenyl)piperidin-1-yl)-2-azaspiro[3.4]octan-2-yl)-1,3,4-oxadiazole;
(R)-2-(6-(4-(2-(tetrahydro-2H-pyran-4-yl)phenyl)piperidin-1-yl)-2-azaspiro[3.4]octan-2-yl)-1,3,4-oxadiazole;
(R)-2-(6-(4-(5-fluoro-2-(tetrahydro-2H-pyran-4-yl)phenyl)piperidin-1-yl)-2-azaspiro[3.4]octan-2-yl)-1,3,4-oxadiazole;
2-((6R)-6-(4-(5-fluoro-2-(tetrahydrofuran-3-yl)phenyl)piperidin-1-yl)-2-azaspiro[3.4]octan-2-yl)-1,3,4-oxadiazole;
2-((6R)-6-(4-(2-(tetrahydrofuran-3-yl)phenyl)piperidin-1-yl)-2-azaspiro[3.4]octan-2-yl)-1,3,4-oxadiazole;
(R)-2-(6-(4-(2-((tetrahydro-2H-pyran-4-yl)methyl)phenyl)piperidin-1-yl)-2-azaspiro[3.4]octan-2-yl)-1,3,4-oxadiazole;
(R)-2-(6-(4-(2-(oxazol-2-yl)phenyl)piperidin-1-yl)-2-azaspiro[3.4]octan-2-yl)-1,3,4-oxadiazole;
(1S,4s)-4-(2-(1-((R)-2-(1,3,4-oxadiazol-2-yl)-2-azaspiro[3.4]octan-6-yl)piperidin-4-yl)phenyl)cyclohexan-1-ol;
(1R,4r)-4-(2-(1-((R)-2-(1,3,4-oxadiazol-2-yl)-2-azaspiro[3.4]octan-6-yl)piperidin-4-yl)phenyl)cyclohexan-1-ol;
(1s,4r)-4-(2-(1-((R)-2-(1,3,4-oxadiazol-2-yl)-2-azaspiro[3.4]octan-6-yl)piperidin-4-yl)phenyl)cyclohexan-1-ol;
(1r,4r)-4-(2-(1-((R)-2-(1,3,4-oxadiazol-2-yl)-2-azaspiro[3.4]octan-6-yl)piperidin-4-yl)phenyl)cyclohexan-1-ol;
(R)-2-(6-(4-(2-(oxetan-3-yloxy)phenyl)piperidin-1-yl)-2-azaspiro[3.4]octan-2-yl)-1,3,4-thiadiazole;
2-((R)-6-(4-(2-(((R)-1,4-dioxan-2-yl)methoxy)phenyl)piperidin-1-yl)-2-azaspiro[3.4]octan-2-yl)-1,3,4-thiadiazole;
2-((R)-6-(4-(2-(((S)-1,4-dioxan-2-yl)methoxy)phenyl)piperidin-1-yl)-2-azaspiro[3.4]octan-2-yl)-1,3,4-thiadiazole;
(R)-2-(6-(4-(2-methoxyphenyl)piperidin-1-yl)-2-azaspiro[3.4]octan-2-yl)-1,3,4-thiadiazole;
(R)-2-(6-(4-(3-fluoro-2-(oxetan-3-yloxy)phenyl)piperidin-1-yl)-2-azaspiro[3.4]octan-2-yl)-1,3,4-thiadiazole;
(R)-2-(6-(4-(2-(2-methoxyethoxy)phenyl)piperidin-1-yl)-2-azaspiro[3.4]octan-2-yl)-1,3,4-thiadiazole;
(R)-1-(2-(1-(2-(1,3,4-thiadiazol-2-yl)-2-azaspiro[3.4]octan-6-yl)piperidin-4-yl)phenoxy)-2-methylpropan-2-ol;
(R)-4-(2-(1-(2-(1,3,4-thiadiazol-2-yl)-2-azaspiro[3.4]octan-6-yl)piperidin-4-yl)phenoxy)-2-methylbutan-2-ol;
(R)-5-(6-(4-(2-methoxyphenyl)piperidin-1-yl)-2-azaspiro[3.4]octan-2-yl)isothiazole;
(R)-5-(6-(4-(2-(2-methoxyethoxy)phenyl)piperidin-1-yl)-2-azaspiro[3.4]octan-2-yl)-1,2,4-thiadiazole;
(R)-1-(2-(1-(2-(1,2,4-thiadiazol-5-yl)-2-azaspiro[3.4]octan-6-yl)piperidin-4-yl)phenoxy)-2-methylpropan-2-ol;
(R)-4-(2-(1-(2-(1,2,4-thiadiazol-5-yl)-2-azaspiro[3.4]octan-6-yl)piperidin-4-yl)phenoxy)-2-methylbutan-2-ol;
(R)-5-(6-(4-(2-methoxyphenyl)piperidin-1-yl)-2-azaspiro[3.4]octan-2-yl)-3-methyl-1,2,4-thiadiazole;
(R)-1-(5-fluoro-2-(1-(2-(4-methyloxazol-2-yl)-2-azaspiro[3.4]octan-6-yl)piperidin-4-yl)phenoxy)-2-methylpropan-2-ol;
(R)-2-methyl-1-(2-(1-(2-(4-methyloxazol-2-yl)-2-azaspiro[3.4]octan-6-yl)piperidin-4-yl)phenoxy)propan-2-ol;
(R)-3-(6-(4-(2-methoxyphenyl)piperidin-1-yl)-2-azaspiro[3.4]octan-2-yl)-1,2,4-oxadiazole;
(R)-6-(4-(2-methoxyphenyl)piperidin-1-yl)-2-(pyrimidin-5-yl)-2-azaspiro[3.4]octane formate salt;
(R)-2-methyl-1-(2-(1-(2-(pyrimidin-5-yl)-2-azaspiro[3.4]octan-6-yl)piperidin-4-yl)phenoxy)propan-2-ol formate salt;
(R)-2-methyl-1-(2-(1-(2-(4-methylpyrimidin-5-yl)-2-azaspiro[3.4]octan-6-yl)piperidin-4-yl)phenoxy)propan-2-ol formate salt;
(R)-6-(4-(2-methoxyphenyl)piperidin-1-yl)-2-(6-methylpyridin-3-yl)-2-azaspiro[3.4]octane formate salt;
(R)-6-(4-(2-methoxyphenyl)piperidin-1-yl)-2-(2-methylpyrimidin-5-yl)-2-azaspiro[3.4]octane;
(R)-2-(5-fluoropyridin-3-yl)-6-(4-(2-methoxyphenyl)piperidin-1-yl)-2-azaspiro[3.4]octane;
(R)-6-(4-(2-methoxyphenyl)piperidin-1-yl)-2-(6-methylpyrazin-2-yl)-2-azaspiro[3.4]octane;
(R)-6-(4-(2-methoxyphenyl)piperidin-1-yl)-2-(pyrazin-2-yl)-2-azaspiro[3.4]octane;
(R)-6-(4-(2-methoxyphenyl)piperidin-1-yl)-2-(3-(trifluoromethyl)pyrazin-2-yl)-2-azaspiro[3.4]octane;
(R)-6-(4-(2-methoxyphenyl)piperidin-1-yl)-2-(3-methylpyrazin-2-yl)-2-azaspiro[3.4]octane;
(R)-6-(4-(2-methoxyphenyl)piperidin-1-yl)-2-(pyridin-3-yl)-2-azaspiro[3.4]octane;
(R)-2-(6-methylpyridin-3-yl)-6-(4-(2-(((R)-tetrahydrofuran-3-yl)oxy)phenyl)piperidin-1-yl)-2-azaspiro[3.4]octane;
(R)-6-(4-(2-methoxyphenyl)piperidin-1-yl)-2-(4-methyl-1,3,5-triazin-2-yl)-2-azaspiro[3.4]octane;
(R)-2-(6-chloropyridazin-3-yl)-6-(4-(2-methoxyphenyl)piperidin-1-yl)-2-azaspiro[3.4]octane;
(R)-6-(4-(2-methoxyphenyl)piperidin-1-yl)-2-(pyridazin-3-yl)-2-azaspiro[3.4]octane;
(R)-6-(4-(5-chloro-2-methoxyphenyl)piperidin-1-yl)-2-(pyridazin-4-yl)-2-azaspiro[3.4]octane;
(R)-6-(4-(2-((tetrahydro-2H-pyran-4-yl)methoxy)phenyl)piperidin-1-yl)-2-(1,3,5-triazin-2-yl)-2-azaspiro[3.4]octane;

(R)-2-(3,6-dichloropyridazin-4-yl)-6-(4-(2-methoxyphenyl)piperidin-1-yl)-2-azaspiro[3.4]octane;

(R)-6-(4-(2-methoxyphenyl)piperidin-1-yl)-2-(pyridazin-4-yl)-2-azaspiro[3.4]octane;

(R)-2-methyl-1-(2-(1-(2-(3-methylpyrazin-2-yl)-2-azaspiro[3.4]octan-6-yl)piperidin-4-yl)phenoxy)propan-2-ol;

(R)-1-(2-(1-(2-(1,3,5-triazin-2-yl)-2-azaspiro[3.4]octan-6-yl)piperidin-4-yl)phenoxy)-2-methylpropan-2-ol;

(R)-6-(4-(5-fluoro-2-methoxyphenyl)piperidin-1-yl)-2-(pyridazin-4-yl)-2-azaspiro[3.4]octane;

(R)-6-(4-(3-fluoro-2-(oxetan-3-yloxy)phenyl)piperidin-1-yl)-2-(pyrimidin-5-yl)-2-azaspiro[3.4]octane;

(R)-6-(4-(2-(2-methoxyethoxy)phenyl)piperidin-1-yl)-2-(pyridazin-3-yl)-2-azaspiro[3.4]octane;

(R)-6-(4-(2-(2-methoxyethoxy)phenyl)piperidin-1-yl)-2-(5-methylpyrazin-2-yl)-2-azaspiro[3.4]octane;

(R)-6-(4-(2-(2-methoxyethoxy)phenyl)piperidin-1-yl)-2-(pyridazin-4-yl)-2-azaspiro[3.4]octane;

(R)-2-(5-fluoropyridin-3-yl)-6-(4-(2-(tetrahydro-2H-pyran-4-yl)phenyl)piperidin-1-yl)-2-azaspiro[3.4]octane;

(R)-2-(pyrimidin-5-yl)-6-(4-(2-(tetrahydro-2H-pyran-4-yl)phenyl)piperidin-1-yl)-2-azaspiro[3.4]octane;

(R)-2-(6-fluoropyridin-3-yl)-6-(4-(2-(tetrahydro-2H-pyran-4-yl)phenyl)piperidin-1-yl)-2-azaspiro[3.4]octane;

(R)-6-(4-(2-methoxyphenyl)piperidin-1-yl)-2-(5-methylpyrazin-2-yl)-2-azaspiro[3.4]octane;

(R)-(6-(4-(5-fluoro-2-methoxyphenyl)piperidin-1-yl)-2-azaspiro[3.4]octan-2-yl)(oxetan-3-yl)methanone;

(R)-(6-(4-(2-(difluoromethoxy)-4-fluorophenyl)piperidin-1-yl)-2-azaspiro[3.4]octan-2-yl)(oxetan-3-yl)methanone;

(R)-(6-(4-(4-fluoro-2-methoxyphenyl)piperidin-1-yl)-2-azaspiro[3.4]octan-2-yl)(oxetan-3-yl)methanone;

(R)-(6-(4-(4-fluoro-2-isopropoxyphenyl)piperidin-1-yl)-2-azaspiro[3.4]octan-2-yl)(oxetan-3-yl)methanone;

(R)-(6-(4-(2-cyclopropoxyphenyl)piperidin-1-yl)-2-azaspiro[3.4]octan-2-yl)(oxetan-3-yl)methanone;

(R)-(6-(4-(2-(2-fluoro-2-methylpropoxy)phenyl)piperidin-1-yl)-2-azaspiro[3.4]octan-2-yl)(oxetan-3-yl)methanone;

(R)-oxetan-3-yl(6-(4-(2-(thiazol-2-yloxy)phenyl)piperidin-1-yl)-2-azaspiro[3.4]octan-2-yl)methanone;

(R)-3-(2-(1-(2-(oxetane-3-carbonyl)-2-azaspiro[3.4]octan-6-yl)piperidin-4-yl)phenoxy)propanenitrile;

oxetan-3-yl((R)-6-(4-(2-(((R)-tetrahydrofuran-3-yl)methoxy)phenyl)piperidin-1-yl)-2-azaspiro[3.4]octan-2-yl)methanone;

(R)-(6-(4-(2-isobutoxyphenyl)piperidin-1-yl)-2-azaspiro[3.4]octan-2-yl)(oxetan-3-yl)methanone;

(R)-(6-(4-(2-(cyclopentyloxy)phenyl)piperidin-1-yl)-2-azaspiro[3.4]octan-2-yl)(oxetan-3-yl)methanone;

(R)-(6-(4-(2-cyclobutoxyphenyl)piperidin-1-yl)-2-azaspiro[3.4]octan-2-yl)(oxetan-3-yl)methanone;

(R)-(6-(4-(2-(cyclopropylmethoxy)phenyl)piperidin-1-yl)-2-azaspiro[3.4]octan-2-yl)(oxetan-3-yl)methanone;

(R)-(6-(4-(2-ethoxyphenyl)piperidin-1-yl)-2-azaspiro[3.4]octan-2-yl)(oxetan-3-yl)methanone;

(R)-(6-(4-(2-isopropoxyphenyl)piperidin-1-yl)-2-azaspiro[3.4]octan-2-yl)(oxetan-3-yl)methanone;

(R)-(6-(4-(2-(2-hydroxy-2-methylpropoxy)phenyl)piperidin-1-yl)-2-azaspiro[3.4]octan-2-yl)(oxetan-3-yl)methanone;

(R)-(1-fluorocyclopropyl)(6-(4-(2-(pyrimidin-2-ylmethoxy)phenyl)piperidin-1-yl)-2-azaspiro[3.4]octan-2-yl)methanone;

(S)-(1-fluorocyclopropyl)(6-(4-(2-(pyrimidin-2-ylmethoxy)phenyl)piperidin-1-yl)-2-azaspiro[3.4]octan-2-yl)methanone;

(R)-(1-fluorocyclopropyl)(6-(4-(2-(2-hydroxyethoxy)phenyl)piperidin-1-yl)-2-azaspiro[3.4]octan-2-yl)methanone;

(S)-(1-fluorocyclopropyl)(6-(4-(2-(2-hydroxyethoxy)phenyl)piperidin-1-yl)-2-azaspiro[3.4]octan-2-yl)methanone;

(R)-(6-(4-(2-(cyclopropylmethoxy)phenyl)piperidin-1-yl)-2-azaspiro[3.4]octan-2-yl)(1-fluorocyclopropyl)methanone;

(R)-(6-(4-(2-(cyclopropylmethoxy)phenyl)piperidin-1-yl)-2-azaspiro[3.4]octan-2-yl)(1-fluorocyclopropyl)methanone;

(R)-1-(2-(2-(1-(2-(1-fluorocyclopropane-1-carbonyl)-2-azaspiro[3.4]octan-6-yl)piperidin-4-yl)phenoxy)ethyl)pyrrolidin-2-one formate salt;

(S)-1-(2-(2-(1-(2-(1-fluorocyclopropane-1-carbonyl)-2-azaspiro[3.4]octan-6-yl)piperidin-4-yl)phenoxy)ethyl)pyrrolidin-2-one formate salt;

(R)-(1-fluorocyclopropyl)(6-(4-(2-((tetrahydro-2H-pyran-4-yl)methoxy)phenyl)piperidin-1-yl)-2-azaspiro[3.4]octan-2-yl)methanone;

(S)-(1-fluorocyclopropyl)(6-(4-(2-((tetrahydro-2H-pyran-4-yl)methoxy)phenyl)piperidin-1-yl)-2-azaspiro[3.4]octan-2-yl)methanone;

(R)-(1-fluorocyclopropyl)(6-(4-(2-((5-methyl-1,3,4-thiadiazol-2-yl)methoxy)phenyl)piperidin-1-yl)-2-azaspiro[3.4]octan-2-yl)methanone;

(S)-(1-fluorocyclopropyl)(6-(4-(2-((5-methyl-1,3,4-thiadiazol-2-yl)methoxy)phenyl)piperidin-1-yl)-2-azaspiro[3.4]octan-2-yl)methanone;

(R)-(6-(4-(2-ethoxyphenyl)piperidin-1-yl)-2-azaspiro[3.4]octan-2-yl)(1-fluorocyclopropyl)methanone;

(S)-(6-(4-(2-ethoxyphenyl)piperidin-1-yl)-2-azaspiro[3.4]octan-2-yl)(1-fluorocyclopropyl)methanone;

(R)-(6-(4-(2-(cyclopropylmethoxy)phenyl)piperidin-1-yl)-2-azaspiro[3.4]octan-2-yl)(1-fluorocyclopropyl)methanone;

(R)-(6-(4-(2-(cyclopropylmethoxy)phenyl)piperidin-1-yl)-2-azaspiro[3.4]octan-2-yl)(1-fluorocyclopropyl)methanone;

(R)-(6-(4-(2-((3,5-dimethylisoxazol-4-yl)methoxy)phenyl)piperidin-1-yl)-2-azaspiro[3.4]octan-2-yl)(1-fluorocyclopropyl)methanone;

(S)-(6-(4-(2-((3,5-dimethylisoxazol-4-yl)methoxy)phenyl)piperidin-1-yl)-2-azaspiro[3.4]octan-2-yl)(1-fluorocyclopropyl)methanone;

(R)-(1-fluorocyclopropyl)(6-(4-(2-((2-methyloxazol-5-yl)methoxy)phenyl)piperidin-1-yl)-2-azaspiro[3.4]octan-2-yl)methanone;

(S)-(1-fluorocyclopropyl)(6-(4-(2-((2-methyloxazol-5-yl)methoxy)phenyl)piperidin-1-yl)-2-azaspiro[3.4]octan-2-yl)methanone;

(R)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;

(S)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;

(R)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;

(S)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;

(R)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;

(S)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;
(R)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;
(S)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;
(R)-(1-fluorocyclopropyl)(6-(4-(2-(3,3,3-trifluoropropoxy)phenyl)piperidin-1-yl)-2-azaspiro[3.4]octan-2-yl)methanone;
(S)-(1-fluorocyclopropyl)(6-(4-(2-(3,3,3-trifluoropropoxy)phenyl)piperidin-1-yl)-2-azaspiro[3.4]octan-2-yl)methanone;
(R)-(1-fluorocyclopropyl)(6-(4-(2-(3-hydroxy-3-methylbutoxy)phenyl)piperidin-1-yl)-2-azaspiro[3.4]octan-2-yl)methanone;
(S)-(1-fluorocyclopropyl)(6-(4-(2-(3-hydroxy-3-methylbutoxy)phenyl)piperidin-1-yl)-2-azaspiro[3.4]octan-2-yl)methanone;
(R)-(6-(4-(2-(3-hydroxy-3-methylbutoxy)phenyl)piperidin-1-yl)-2-azaspiro[3.4]octan-2-yl)(oxetan-3-yl)methanone;
(R)-oxetan-3-yl(6-(4-(2-(2-(trifluoromethoxy)ethoxy)phenyl)piperidin-1-yl)-2-azaspiro[3.4]octan-2-yl)methanone;
(R)-oxetan-3-yl(6-(4-(2-(2-(oxetan-3-yloxy)ethoxy)phenyl)piperidin-1-yl)-2-azaspiro[3.4]octan-2-yl)methanone;
(R)-(1-fluorocyclopropyl)(6-(4-(2-(3-methoxy-3-methylbutoxy)phenyl)piperidin-1-yl)-2-azaspiro[3.4]octan-2-yl)methanone;
(S)-(1-fluorocyclopropyl)(6-(4-(2-(3-methoxy-3-methylbutoxy)phenyl)piperidin-1-yl)-2-azaspiro[3.4]octan-2-yl)methanone;
(R)-oxetan-3-yl(6-(4-(2-(3,3,3-trifluoropropoxy)phenyl)piperidin-1-yl)-2-azaspiro[3.4]octan-2-yl)methanone;
(R)-(6-(4-(2-(2-methoxy-2-methylpropoxy)phenyl)piperidin-1-yl)-2-azaspiro[3.4]octan-2-yl)(oxetan-3-yl)methanone;
(R)-oxetan-3-yl(6-(4-(2-((1-(trifluoromethyl)cyclopropyl)methoxy)phenyl)piperidin-1-yl)-2-azaspiro[3.4]octan-2-yl)methanone;
(R)-(6-(4-(2-(2,2-difluoroethoxy)phenyl)piperidin-1-yl)-2-azaspiro[3.4]octan-2-yl)(oxetan-3-yl)methanone;
(R)-oxetan-3-yl(6-(4-(2-(2-(oxetan-3-yl)ethoxy)phenyl)piperidin-1-yl)-2-azaspiro[3.4]octan-2-yl)methanone;
(S)-(6-(4-(5-chloro-2-methoxyphenyl)piperidin-1-yl)-2-azaspiro[3.4]octan-2-yl)(1-fluorocyclopropyl)methanone;
(R)-(6-(4-(5-chloro-2-methoxyphenyl)piperidin-1-yl)-2-azaspiro[3.4]octan-2-yl)(1-fluorocyclopropyl)methanone;
(S)-(6-(4-(5-chloro-2-methoxyphenyl)piperidin-1-yl)-2-azaspiro[3.4]octan-2-yl)(1-fluorocyclopropyl)methanone;
(R)-(6-(4-(5-chloro-2-methoxyphenyl)piperidin-1-yl)-2-azaspiro[3.4]octan-2-yl)(1-fluorocyclopropyl)methanone;
(S)-(6-(4-(2-methoxyphenyl)piperidin-1-yl)-2-azaspiro[3.4]octan-2-yl)(oxetan-3-yl)methanone;
(R)-(6-(4-(2-methoxyphenyl)piperidin-1-yl)-2-azaspiro[3.4]octan-2-yl)(oxetan-3-yl)methanone;
(S)-(6-(4-(2-methoxyphenyl)piperidin-1-yl)-2-azaspiro[3.4]octan-2-yl)(oxetan-3-yl)methanone;
(R)-(6-(4-(2-methoxyphenyl)piperidin-1-yl)-2-azaspiro[3.4]octan-2-yl)(oxetan-3-yl)methanone;
(S)-(6-(4-(2-(difluoromethoxy)phenyl)piperidin-1-yl)-2-azaspiro[3.4]octan-2-yl)(oxetan-3-yl)methanone;
(R)-(6-(4-(2-(difluoromethoxy)phenyl)piperidin-1-yl)-2-azaspiro[3.4]octan-2-yl)(oxetan-3-yl)methanone citrate salt;
(S)-(6-(4-(2-(difluoromethoxy)phenyl)piperidin-1-yl)-2-azaspiro[3.4]octan-2-yl)(oxetan-3-yl)methanone;
(R)-(6-(4-(2-(difluoromethoxy)phenyl)piperidin-1-yl)-2-azaspiro[3.4]octan-2-yl)(oxetan-3-yl)methanone citrate salt;
(S)-oxetan-3-yl(6-(4-(2-(trifluoromethoxy)phenyl)piperidin-1-yl)-2-azaspiro[3.4]octan-2-yl)methanone;
(R)-oxetan-3-yl(6-(4-(2-(trifluoromethoxy)phenyl)piperidin-1-yl)-2-azaspiro[3.4]octan-2-yl)methanone;
(R)-(1-fluorocyclopropyl)(6-(4-(2-(trifluoromethoxy)phenyl)piperidin-1-yl)-2-azaspiro[3.4]octan-2-yl)methanone;
(S)-(1-fluorocyclopropyl)(6-(4-(2-(trifluoromethoxy)phenyl)piperidin-1-yl)-2-azaspiro[3.4]octan-2-yl)methanone;
(R)-(1-fluorocyclopropyl)(6-(4-(2-(trifluoromethoxy)phenyl)piperidin-1-yl)-2-azaspiro[3.4]octan-2-yl)methanone;
(S)-(1-fluorocyclopropyl)(6-(4-(2-(trifluoromethoxy)phenyl)piperidin-1-yl)-2-azaspiro[3.4]octan-2-yl)methanone;
(R)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;
(S)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;
(R)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;
(S)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;
(R)-(1-fluorocyclopropyl)(6-(4-(2-((tetrahydro-2H-pyran-4-yl)oxy)phenyl)piperidin-1-yl)-2-azaspiro[3.4]octan-2-yl)methanone;
(S)-(1-fluorocyclopropyl)(6-(4-(2-((tetrahydro-2H-pyran-4-yl)oxy)phenyl)piperidin-1-yl)-2-azaspiro[3.4]octan-2-yl)methanone;
(R)-(1-fluorocyclopropyl)(6-(4-(2-((tetrahydro-2H-pyran-4-yl)oxy)phenyl)piperidin-1-yl)-2-azaspiro[3.4]octan-2-yl)methanone;
(S)-(1-fluorocyclopropyl)(6-(4-(2-((tetrahydro-2H-pyran-4-yl)oxy)phenyl)piperidin-1-yl)-2-azaspiro[3.4]octan-2-yl)methanone;
(R)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;
(S)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;
(R)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;
(S)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;
(R)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(R)-(1-fluorocyclopropyl)(6-(4-(2-(tetrahydro-2H-pyran-4-yl)phenyl)piperidin-1-yl)-2-azaspiro[3.4]octan-2-yl)methanone;

(S)-(1-fluorocyclopropyl)(6-(4-(2-(tetrahydro-2H-pyran-4-yl)phenyl)piperidin-1-yl)-2-azaspiro[3.4]octan-2-yl)methanone;

(R)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(S)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(R)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(S)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(R)-6-(4-(5-fluoro-2-(tetrahydro-2H-pyran-4-yl)phenyl)piperidin-1-yl)-2-(pyrimidin-5-yl)-2-azaspiro[3.4]octane;

(S)-6-(4-(5-fluoro-2-(tetrahydro-2H-pyran-4-yl)phenyl)piperidin-1-yl)-2-(pyrimidin-5-yl)-2-azaspiro[3.4]octane;

(R)-6-(4-(5-fluoro-2-(tetrahydro-2H-pyran-4-yl)phenyl)piperidin-1-yl)-2-(pyrimidin-5-yl)-2-azaspiro[3.4]octane;

(S)-6-(4-(5-fluoro-2-(tetrahydro-2H-pyran-4-yl)phenyl)piperidin-1-yl)-2-(pyrimidin-5-yl)-2-azaspiro[3.4]octane;

(R)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(S)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(R)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(S)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(R)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(R)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-2-(6-(4-(2-methoxyphenyl)piperidin-1-yl)-2-azaspiro[3.4]octan-2-yl)oxazole;

(R)-2-(6-(4-(2-methoxyphenyl)piperidin-1-yl)-2-azaspiro[3.4]octan-2-yl)oxazole;

(S)-2-(6-(4-(2-methoxyphenyl)piperidin-1-yl)-2-azaspiro[3.4]octan-2-yl)oxazole;

(R)-2-(6-(4-(2-methoxyphenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)oxazole;

(S)-2-(6-(4-(2-(trifluoromethoxy)phenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)oxazole;

(S)-2-(6-(4-(2-(trifluoromethoxy)phenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)-1,3,4-thiadiazole;

(S)-2-(6-(4-(2-(trifluoromethoxy)phenyl)piperidin-1-yl)-2-azaspiro[3.4]octan-2-yl)-1,3,4-thiadiazole;

(R)-2-(6-(4-(2-(trifluoromethoxy)phenyl)piperidin-1-yl)-2-azaspiro[3.4]octan-2-yl)-1,3,4-thiadiazole;

(S)-2-(6-(4-(2-(trifluoromethoxy)phenyl)piperidin-1-yl)-2-azaspiro[3.4]octan-2-yl)-1,3,4-thiadiazole;

(R)-2-(6-(4-(2-(difluoromethoxy)phenyl)piperidin-1-yl)-2-azaspiro[3.4]octan-2-yl)-1,3,4-thiadiazole;

(S)-2-(6-(4-(2-(difluoromethoxy)phenyl)piperidin-1-yl)-2-azaspiro[3.4]octan-2-yl)-1,3,4-thiadiazole;

(R)-2-(6-(4-(2-(difluoromethoxy)phenyl)piperidin-1-yl)-2-azaspiro[3.4]octan-2-yl)-1,3,4-thiadiazole;

(S)-2-(6-(4-(2-(difluoromethoxy)phenyl)piperidin-1-yl)-2-azaspiro[3.4]octan-2-yl)-1,3,4-thiadiazole;

(R)-5-(6-(4-(2-methoxyphenyl)piperidin-1-yl)-2-azaspiro[3.4]octan-2-yl)-1,2,4-thiadiazole;

(S)-5-(6-(4-(2-methoxyphenyl)piperidin-1-yl)-2-azaspiro[3.4]octan-2-yl)-1,2,4-thiadiazole;

(R)-5-(6-(4-(2-methoxyphenyl)piperidin-1-yl)-2-azaspiro[3.4]octan-2-yl)-1,2,4-thiadiazole;

(S)-5-(6-(4-(2-methoxyphenyl)piperidin-1-yl)-2-azaspiro[3.4]octan-2-yl)-1,2,4-thiadiazole;

(R)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone; and (S)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone, or a pharmaceutically acceptable salt thereof.

In one embodiment, provided herein is a compound selected from the group consisting of:

(R)-2-(6-(4-(2-(tetrahydro-2H-pyran-4-yl)phenyl)piperidin-1-yl)-2-azaspiro[3.4]octan-2-yl)-1,3,4-oxadiazole;

(S)-2-(6-(4-(2-(tetrahydro-2H-pyran-4-yl)phenyl)piperidin-1-yl)-2-azaspiro[3.4]octan-2-yl)-1,3,4-oxadiazole;

(R)-(1-fluorocyclopropyl)(6-(4-(2-(tetrahydro-2H-pyran-4-yl)phenyl)piperidin-1-yl)-2-azaspiro[3.4]octan-2-yl)methanone;

(S)-(1-fluorocyclopropyl)(6-(4-(2-(tetrahydro-2H-pyran-4-yl)phenyl)piperidin-1-yl)-2-azaspiro[3.4]octan-2-yl)methanone;

(R)-2-(pyrimidin-5-yl)-6-(4-(2-(tetrahydro-2H-pyran-4-yl)phenyl)piperidin-1-yl)-2-azaspiro[3.4]octane;

(S)-oxetan-3-yl(6-(4-(2-(trifluoromethoxy)phenyl)piperidin-1-yl)-2-azaspiro[3.4]octan-2-yl)methanone; and (R)-oxetan-3-yl(6-(4-(2-(trifluoromethoxy)phenyl)piperidin-1-yl)-2-azaspiro[3.4]octan-2-yl)methanone, or a pharmaceutically acceptable salt thereof.

In one embodiment, provided herein is a compound selected from the group consisting of:

(R)-2-(6-(4-(2-(tetrahydro-2H-pyran-4-yl)phenyl)piperidin-1-yl)-2-azaspiro[3.4]octan-2-yl)-1,3,4-oxadiazole, having the following structure:

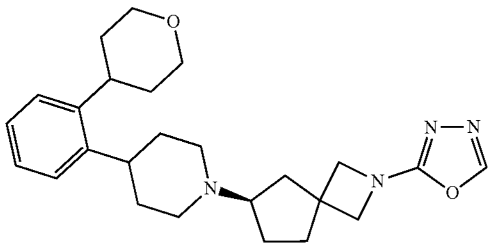
;

(R)-(1-fluorocyclopropyl)(6-(4-(2-(tetrahydro-2H-pyran-4-yl)phenyl)piperidin-1-yl)-2-azaspiro[3.4]octan-2-yl)methanone, having the following structure:

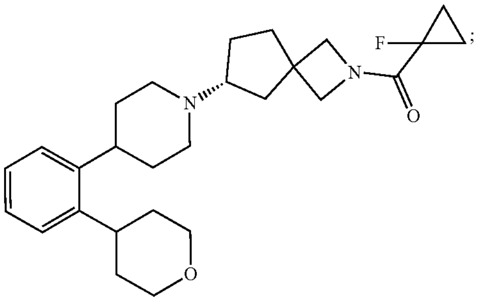 [SMILES: O=C(N1CC2(CC[C@@H](N3CCC(c4ccccc4C4CCOCC4)CC3)C2)C1)C1(F)CC1]
;

(R)-2-(pyrimidin-5-yl)-6-(4-(2-(tetrahydro-2H-pyran-4-yl)phenyl)piperidin-1-yl)-2-azaspiro[3.4]octane, having the following structure:

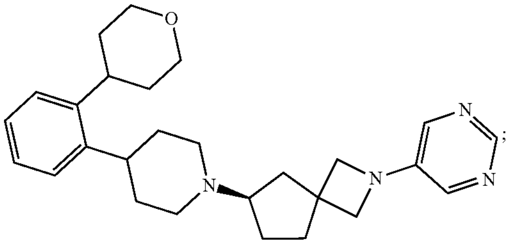 [SMILES: c1ccc(C2CCN([C@@H]3CCC4(C3)CN(c3cncnc3)C4)CC2)c(C2CCOCC2)c1]
;

and (R)-oxetan-3-yl(6-(4-(2-(trifluoromethoxy)phenyl)piperidin-1-yl)-2-azaspiro[3.4]octan-2-yl)methanone, having the following structure:

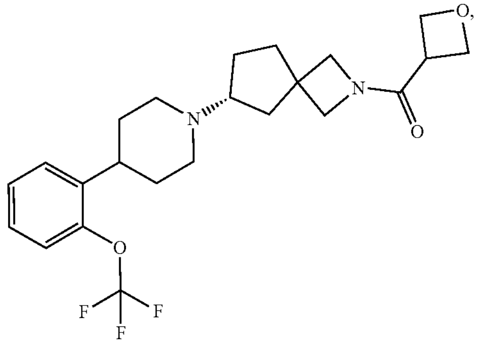 [SMILES: O=C(C1COC1)N1CC2(CC[C@@H](N3CCC(c4ccccc4OC(F)(F)F)CC3)C2)C1]
, or a pharmaceutically acceptable salt thereof.

In one embodiment, provided herein is a pharmaceutical composition comprising a compound provided herein or a pharmaceutically acceptable salt thereof.

In one embodiment, provided herein is a method for the treatment of a M4 related a condition, disease or disorder comprising administration of a therapeutically effective amount of a compound provided herein or a pharmaceutically acceptable salt thereof to a patient in need of treatment thereof.

In one embodiment, provided herein is a method for the treatment of psychosis comprising administration of a therapeutically effective amount of a compound provided herein or a pharmaceutically acceptable salt thereof to a patient in need of treatment thereof. In some embodiments, the psychosis is associated with schizophrenia, schizoaffective disorder, psychotic depression, bipolar disorder with psychotic features, Alzheimer's disease, Parkinson's Disease, post-traumatic stress disorder or frontotemporal dementia. In preferred embodiments, the psychosis is associated with Alzheimer's disease.

In one embodiment, provided herein is a method for the treatment of cognitive dysfunction comprising administration of a therapeutically effective amount of a compound provided herein or a pharmaceutically acceptable salt thereof to a subject in need of treatment thereof.

In one embodiment, provided herein is a method for the treatment of a hyperkinetic movement disorder comprising administration of a therapeutically effective amount of a compound provided herein or a pharmaceutically acceptable salt thereof to a subject in need of treatment thereof.

In one embodiment, provided herein is a method for treatment of substance use disorders comprising administration of a therapeutically effective amount of a compound provided herein or a pharmaceutically acceptable salt thereof to a subject in need of treatment thereof.

In one embodiment, provided herein is a method of treating a condition, disease or disorder which is treated with a M4 receptor agonist comprising administration of a therapeutically effective amount of a compound provided herein or a pharmaceutically acceptable salt thereof and an antidepressant to a subject in need of treatment thereof.

In one embodiment, provided herein is a method for the treatment of a condition, disease or disorder which is treated with a M4 receptor agonist comprising administration of a therapeutically effective amount of a compound provided herein or a pharmaceutically acceptable salt thereof in conjunction with computer-assisted psychosocial or behavioral therapy.

5. BRIEF DESCRIPTION OF THE DRAWINGS

6. DETAILED DESCRIPTION

6.1. Definitions

Figure 1:
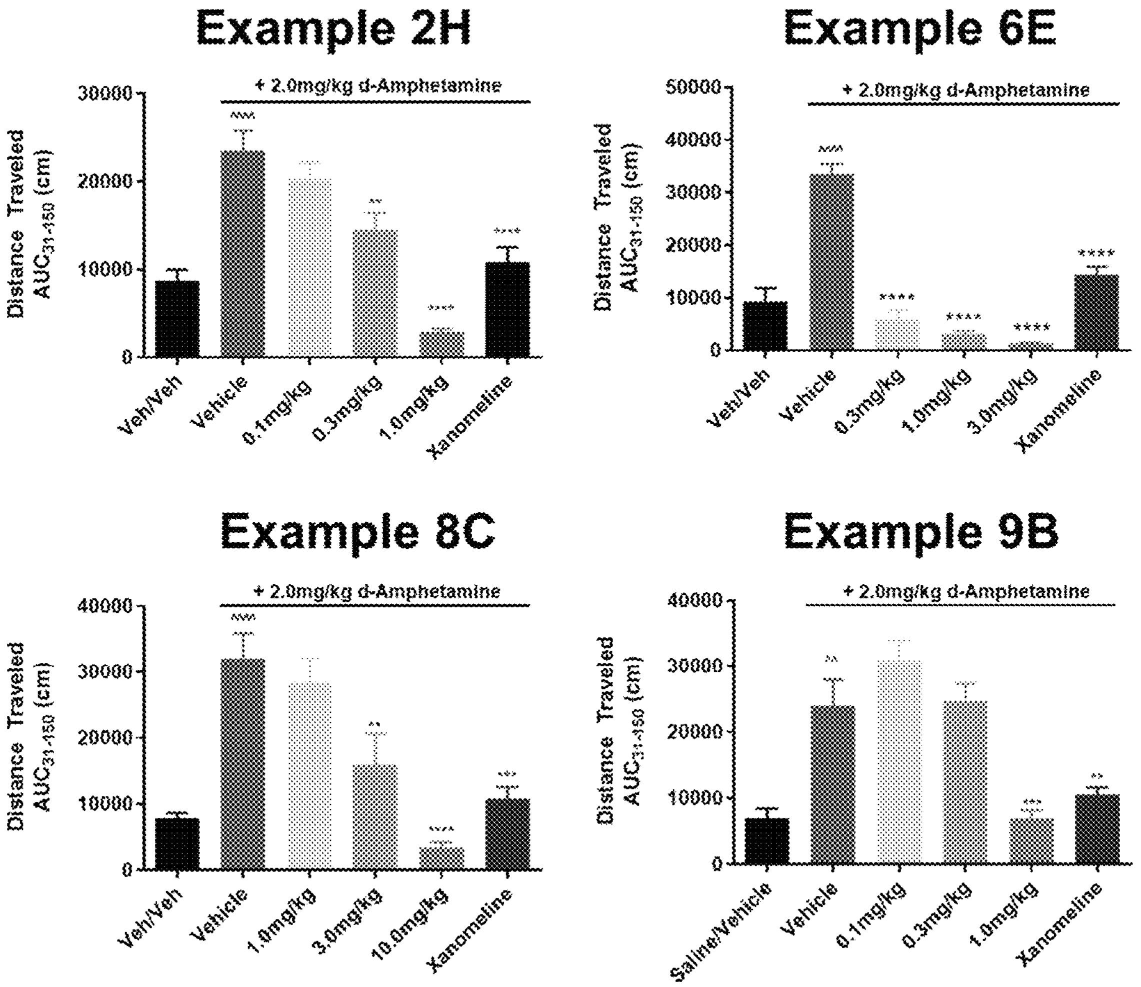
FIG. 1 illustrates the effect of Example 2H, Example 6E, Example 8C, and Example 9B on the hyperactivity in mice induced by the stimulant d-amphetamine using a mouse amphetamine induced hyperlocomotion assay.

"Alkyl" as used herein refers to a monovalent saturated hydrocarbon chain having the specified number of carbon atoms. For example, $C_{1-3}$ alkyl refers to an alkyl group having from 1 to 3 carbon atoms. Alkyl groups may be optionally substituted with one or more substituents as defined in Formula (I). Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

"Cycloalkyl" as used herein refers to a saturated hydrocarbon ring system having the specified number of carbon atoms. Cycloalkyl groups are monocyclic or bicyclic ring systems. For example, $C_{3-7}$ cycloalkyl refers to a cycloalkyl group having from 3 to 7 carbon atoms. Cycloalkyl groups may be optionally substituted with one or more substituents as defined in Formula (I). Examples of cycloalkyl groups include, but are not limited to, cyclopropyl, cyclobutyl, cyclopentyl and cyclohexyl.

"Halo" or "halogen" as used herein refers to a fluoro, chloro, or bromo group.

"Haloalkyl" as used herein refers to an alkyl group, having the specified number of carbon atoms, wherein at least one hydrogen atom attached to a carbon atom within the alkyl group is replaced with halo. The number of halo substituents includes, but is not limited to, 1, 2, 3, 4, 5, or 6 substituents. Haloalkyl includes, but is not limited to, monofluoromethyl, difluoroethyl, and trifluoromethyl.

"Heteroaryl" as used herein refers to an aromatic ring system containing one or more heteroatoms. Heteroaryl groups containing more than one heteroatom may contain different heteroatoms. Heteroaryl groups may be optionally substituted with one or more substituents as defined in Formula (I). Heteroaryl groups may be monocyclic ring systems or fused bicyclic ring systems. Monocyclic heteroaryl rings have from 5 to 6 ring atoms. Bicyclic heteroaryl rings have from 8 to 10 member atoms. Bicyclic heteroaryl rings include those ring systems wherein a heteroaryl ring is fused to a phenyl ring. Heteroaryl includes, but is not limited to, pyrrolyl, pyrazolyl, imidazolyl, oxazolyl, isoxazolyl, oxadiazolyl (including 1,3,4-oxadiazolyl and 1,2,4-oxadiazolyl), thiazolyl, isothiazolyl, thiadiazolyl (including 1,3,4-thiadiazolyl), furanyl, furanzanyl, thienyl, triazolyl, pyridinyl (including 2-, 3-, and 4-pyridinyl), pyrimidinyl, pyridazinyl, pyrazinyl, trazinyl, tetrazinyl, tetrazolyl, indonyl, isoindolyl, indolizinyl, indazolyl, purinyl, quinolinyl, isoquinolinyl, quinoxalinyl, quinazolinyl, benzimidazolyl, benzopyranyl, benzopyranyl, benzoxazolyl, benzoisoxazolyl, benzofuranyl, benzothiazolyl, benzothienyl, naphthyridinyl, 1H-pyrrolo[2,3-b]pyridinyl, tetrazolo[1,5-a]pyridinyl, imidazo[2,1-b][1,3,4]thiadiazolyl and the like.

"5-6 membered heteroaryl" as used herein refers to a heteroaryl group defined above, having 5 or 6 ring atoms and containing 1 to 4 heteroatoms. Examples of a 5-6 membered heteroaryl include, but are not limited to, thiazole, oxazole, isoxazole, 1,3,4-thiadiazole, 1,2,4-oxadiazole, 1,2,4-oxadiazole, 1,3,4-oxadiazole, 1,2,5-thiadiazole, 1H-imidazole, 1H-pyrazole, pyridine, pyrimidine, 1,3,5-triazine and the like.

"Heteroatom" as used herein refers to a nitrogen, oxygen, or sulfur atom.

"Heterocyclic" or "heterocycloalkyl" as used herein refers to a saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic includes ring systems wherein a sulfur atom is oxidized to form SO or $SO_2$. Heterocyclic groups may be optionally substituted with one or more substituents as defined in Formula (I). Heterocyclic groups are monocyclic, bicyclic, spiro, or fused or bridged bicyclic ring systems. Monocyclic heterocyclic rings have 3 to 7 ring atoms. Examples of monocyclic heterocyclic groups include pyranyl, tetrahydropyranyl, oxetanyl, tetrahydrofuranyl, dihydrofuranyl, 1,4-dioxanyl, morpholinyl, 1,4-dithianyl, piperazinyl, piperidinyl, 1,3-dioxolanyl, imidazolidinyl, imidazolinyl, pyrrolinyl, pyrrolidinyl, tetrahydropyranyl, dihydropyranyl, oxathiolanyl, dithiolanyl, 1,3-dioxanyl, 1,4-dioxanyl, 1,3-dithianyl, oxathianyl, thiomorpholinyl, tetrahydro-thiopyran 1,1-dioxide, 1,4-diazepanyl, and the like. Examples of bicyclic heterocyclic groups include 3-oxabicyclo[3.1.0]hexane and the like. Examples of bridged heterocyclic groups include 2-azabicyclo[2.2.1]heptanyl and the like. Examples of spiro heterocyclic groups include 2-oxaspiro[3.3]heptanyl and the like.

"4 to 6 membered heterocyclic" or "4 to 6 membered heterocycloaryl" as used herein refers to a heterocyclic group as defined above, having from 4 to 6 ring atoms and containing from 1 to 3 heteroatoms. Examples of 4 to 6 membered heterocyclic include but are not limited to, oxetanyl, pyrrolidinyl, morpholinyl, piperazinyl, piperidinyl, 1,4-diazepanyl, 3-oxabicyclo[3.1.0]hexanyl and the like.

"5 to 6 membered heterocyclic" or "5 to 6 membered heterocycloaryl" as used herein refers to a heterocyclic group as defined above, having from 5 to 6 ring atoms and containing from 1 to 3 heteroatoms. Examples of 5 to 6 membered heterocyclic include but are not limited to, pyrrolidinyl, morpholinyl, piperazinyl, piperidinyl, 1,4-diazepanyl, 3-oxabicyclo[3.1.0]hexanyl and the like.

"3 to 9 membered heterocyclic" or "3 to 9 membered heterocycloaryl" as used herein refers to a heterocyclic group as defined above, having from 3 to 9 ring atoms and containing from 1 to 3 heteroatoms. Examples of 3-9 membered heterocyclic include but are not limited to, pyrrolidinyl, morpholinyl, piperazinyl, piperidinyl, 1,4-diazepanyl, 2-oxaspiro[3.3]heptanyl, 3-oxabicyclo[3.1.0]hexanyl and the like.

"Optionally substituted" as used herein indicates that a group, such as an alkyl, heteroaryl and heterocyclic, may be unsubstituted or the group may be substituted with one or more substituents as defined in Formula (I).

"Salt" or "salts" as used herein refers to an acid addition or base addition salt of a compound provided herein. "Salts" include in particular "pharmaceutically acceptable salts". "Pharmaceutically acceptable salts" as used herein refers to salts that retain the biological effectiveness and properties of the compounds according to Formula (I) and, which typically are not biologically or otherwise undesirable. In many cases, the compounds according to Formula (I) are capable of forming acid and/or base salts by virtue of the presence of amino and/or carboxyl groups or groups similar thereto. The skilled artisan will appreciate that salts, including pharmaceutically acceptable salts, of the compounds according to Formula (I) may be prepared. These salts may be prepared in situ during the final isolation and purification of the compound, or by separately reacting the purified compound in its free acid or free base form with a suitable base or acid, respectively.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases, such as carboxylate, sulfonate and phosphate salts.

In certain embodiments, provided herein are compounds according to Formula (I) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, formate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate or xinafoate salt form. In certain embodiments, provided herein are compounds according to Formula (I) in formate or citrate salt form.

"Isomers" refers to different compounds according to Formula (I) that have the same molecular formula but differ in arrangement and configuration of the atoms.

"Optical isomer" or "stereoisomer" refers to any of the various stereo isomeric configurations which may exist for a given compound provided herein and includes geometric isomers. It is understood that a substituent may be attached at a chiral center of a carbon atom. Therefore, compounds provided herein include enantiomers, diastereomers or racemates of the compound.

Depending on the choice of the starting materials and procedures, the compounds according to Formula (I) can be present in the form of one of the possible stereoisomers or as mixtures thereof, for example as pure optical isomers, or as stereoisomer mixtures, such as racemates and diastereoisomer mixtures, depending on the number of asymmetric carbon atoms. The compounds according to Formula (I) provided herein are meant to include all such possible stereoisomers, including racemic mixtures, diastereomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compounds according to Formula (I) can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, a compound provided herein can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of the compounds according to Formula (I) or of intermediates thereof can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds according to Formula (I) into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds according to Formula (I) or racemic intermediates can also be resolved by chiral chromatography, e.g., high pressure liquid chromatography (HPLC) using a chiral adsorbent.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds according to Formula (I) include, for example, isotopes of hydrogen.

Further, incorporation of certain isotopes, particularly deuterium (i.e., $^{2}H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound provided herein. The concentration of deuterium, may be defined by the isotopic enrichment factor. "Isotopic enrichment factor" as used herein means the ratio between the isotopic abundance and the natural abundance of a specified isotope. If a substituent in a compound provided herein is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

For example, Formula (I) may be deuterated as shown in Formula (Ic):

(Ic)

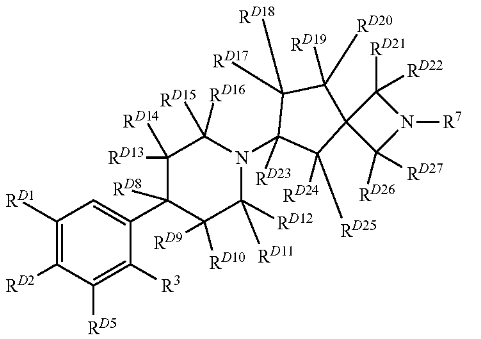

or a pharmaceutically acceptable salt thereof, wherein $R^3$ and $R^7$ are as defined in Formula (I); and $R^{D1}$, $R^{D2}$, $R^{D5}$, and $R^{D8}$-$R^{D27}$ are each independently D or halogen.

Other examples of isotopes that can be incorporated into compounds according to Formula (I) include isotopes of hydrogen, carbon, nitrogen, oxygen, phosphorous, fluorine, and chlorine, such as $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. Accordingly it should be understood that compounds according to Formula (I) includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds according to Formula (I) can generally be prepared by conventional techniques known to those skilled in the art or by processes analogous to those described in the accompanying Examples and preparations using an appropriate isotopically-labeled reagents in place of the non-labeled reagent previously employed.

"Administration" and "administering" and "administer" as used herein refer to the manner in which a compound provided herein (e.g., a compound according to Formula (I)) is presented to a subject.

"Subject" or "patient" as used herein refers to a living organism suffering from one or more of the diseases or disorders described here that can be treated by administration of a pharmaceutical composition described herein. Examples of subjects include mammals (e.g., humans and animals such as dogs, cows, horses, monkeys, pigs, guinea pigs, sheep, goats, cats, mice, rabbits, rats, and transgenic non-human animals). In certain embodiments, the subject is a primate. In certain embodiments, the subject is a human, e.g., a human suffering from, at risk of suffering from, or potentially capable of suffering from a disease described herein. In particular embodiments, the subject is an adult human at least about 18 years of age. In particular embodiments, the subject is an adult human from about 18 to about 75 years of age. In some embodiments, the subject is a human child up to about 18 years of age.

"Treat", "treating" or "treatment" of any disease or disorder as used herein refers to relieve, alleviate, delay, reduce, reverse, or improve at least one symptom of a condition in a subject. The term "treating" may also mean to arrest, delay the onset (i.e., the period prior to clinical manifestation of a disease) and/or reduce the risk of developing or worsening a condition. In certain embodiments, the term "treating" refers to relieving, alleviating, delaying of progression, reducing, reversing, or improving at least one symptom of a condition selected from psychosis, including psychosis associated with schizophrenia, schizoaffective disorder, psychotic depression, bipolar disorder with psychotic features, Alzheimer's Disease, Parkinson's Disease, post-traumatic stress disorder, and frontotemporal dementia, hyperkinetic movement disorders, including but not limited to Tourette's Syndrome, chorea and tardive dyskinesia, cognitive dysfunction, including but not limited to cognitive dysfunction associated with schizophrenia, Alzheimer's Disease, frontotemporal dementia, schizoaffective disorder, and depression; and/or substance use disorders.

"Prevent", "preventing" or "prevention" of any disease or disorder as used herein refers to the prophylactic treatment of the disease or disorder; or delaying the onset or progression of the disease or disorder.

"Pharmaceutical composition" as used herein refers to a compound provided herein, or a pharmaceutically acceptable salt thereof, together with at least one pharmaceutically acceptable carrier, in a form suitable for oral or parenteral administration.

"Pharmaceutically acceptable carrier" as used herein refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

A "therapeutically effective amount" of a compound provided herein as used herein refers to an amount of the compound that will elicit the biological or medical response of a subject, for example, increase enzyme or a protein activity, or ameliorate symptoms, alleviate conditions, slow or delay disease progression, or prevent a disease, etc. In one embodiment, the term "a therapeutically effective amount" refers to the amount of the compound provided herein that, when administered to a subject, is effective to (1) at least partially alleviate, prevent and/or ameliorate a condition, or a disorder or a disease (i) mediated by M4, or (ii) associated with M4 activity, or (iii) characterized by activity (normal or abnormal) of M4; or (2) increase the activity of M4. In another embodiment, the term "a therapeutically effective amount" refers to the amount of the compound provided herein that, when administered to a cell, or a tissue, or a non-cellular biological material, or a medium, is effective to increase the activity of M4.

"Inhibit", "inhibition" or "inhibiting" as used herein refers to the reduction or suppression of a given condition, symptom, or disorder, or disease, or a significant decrease in the baseline activity of a biological activity or process.

A subject is "in need of" a treatment if such subject would benefit biologically, medically or in quality of life from such treatment.

"Substance use disorder" or "SUD" as used herein is defined with reference to DSM-5 criteria (i.e., according to the Diagnostic and Statistical Manual of Mental Disorders. $5^{th}$ Edition, Washington, DC: American Psychiatric Association, 2013; hereinafter "DSM-5"), the entire contents of which are incorporated herein by reference. The term "substance use disorder" as used herein is defined as when the recurrent use of alcohol and/or drugs causes clinically and functionally significant impairment, such as health problems, disability, and failure to meet major responsibilities at work, school, or home. According to the DSM-5, a diagnosis of substance use disorder is based on evidence of impaired control, social impairment, risky use, and pharmacological criteria. Substance use disorder includes, for example, alcohol use disorder, tobacco use disorder, *cannabis* use disorder, stimulant use disorder, hallucinogen use disorder and opioid use disorder.

"Psychosocial or behavioral therapy" as used herein refers to, but not limited to, cognitive behavioral therapy (e.g., as described in *Arch. Gen. Psychiatry* 1999; 56:493-502), interpersonal therapy (e.g., as described in *Psychol Addict Behav* 2009; 23(1): 168-174), contingency management based therapy e.g., as described in *Psychol Addict Behav* 2009; 23(1): 168-174; in *J. Consul. Clin. Psychol.* 2005; 73(2): 354-59; or in *Case Reports in Psychiatry*, Vol. 2012, Article ID 731638), community reinforcement approach based therapy (e.g., as described in *Drug Alcohol Depend* 2004; 74:1-13), motivational interviewing based therapy (e.g., as described in *J. Consul. Clin. Psychol.* 2001; 69(5): 858-62), motivational enhancement based therapy (e.g., as described in *Drug Alcohol Depend* 2007, 91:97-101) or meditation based therapy, such as transcendental meditation based therapy (e.g., as described in Addiction 2004; 99(7): 862-874 or *J. Consul. Clin. Psychol.* 2000; 68(3): 515-52); in particular contingency management based therapy.

"Standardized psychological treatment" or "standardized psychological support" as used herein refers to standard counselling sessions, for example once a week, in particular counselling focused on cocaine consumption.

"Computer-assisted" or "computer-assistance" as used herein refers to psychosocial or behavioral therapy comprising the use of electronic or digital tools such as online tools, smartphones, laptops, tablets, wireless devices or health Apps.

Unless specified otherwise, "a compound provided herein" or "compounds provided herein" refers to compounds of Formula (I) and subformulae thereof, including Formula (Ia), (Ib), and (Ic), and any exemplified compounds and salts thereof, as well as all stereoisomers (including diastereoisomers and enantiomers), rotamers, tautomers and isotopically labeled compounds (including deuterium substitutions), as well as inherently formed moieties.

"A," "an," "the" and similar terms as used herein (especially in the context of the claims) are to be construed to cover both the singular and plural unless otherwise indicated herein or clearly contradicted by the context.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

If there is a discrepancy between a depicted structure and a chemical name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure of portion of the structure.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed.

6.2. Compounds

In one embodiment, provided herein is a compound according to Formula (I)

(I)

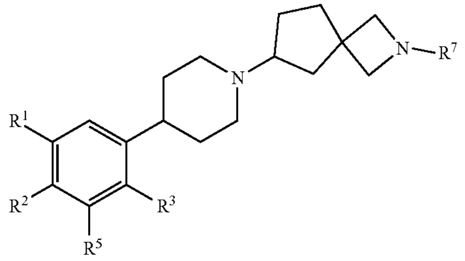

or a pharmaceutically acceptable salt thereof, wherein $R^1$ is halogen or hydrogen;

$R^2$ is halogen or hydrogen;

$R^3$ is

- $C_{1-6}$ alkyl, said alkyl is optionally substituted with one or two substituents independently selected from the group consisting of 4 to 6-membered heterocycloalkyl and —OH,
- 5 to 6-membered heteroaryl,
- 3 to 6-membered cycloalkyl, said cycloalkyl is optionally substituted with one —OH,
- 5 to 6-membered heterocycloalkyl, said heterocycloalkyl is optionally substituted with one —OH, or
- —$OR^4$;

$R^4$ is
- —$CF_3$,
- —$CF_2H$,
- $C_{1-6}$ alkyl, said alkyl is optionally substituted with one or two $R^6$,
- 3 to 6-membered cycloalkyl,
- 4 to 7-membered heterocycloalkyl, said heterocycloalkyl is optionally substituted with one $R^6$,
- 5 to 6-membered heteroaryl, or
- $R^4$ is one of the following groups:

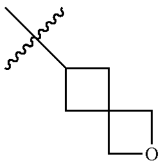

or

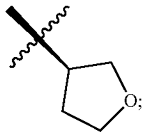

$R^5$ is halogen or hydrogen;

each $R^6$ is independently
- halogen,
- —OH,
- —$CF_3$,
- —$CF_2H$,
- cyano,
- —$OCF_3$,
- —$OCH_3$,
- —O-heterocycloalkyl,
- $C_1$-$C_4$ alkyl,
- 4 to 7-membered heterocycloalkyl, said heterocycloalkyl is optionally substituted with one or two substituents independently selected from the group consisting of halogen, —OH, and $C_{1-3}$ alkyl,
- 5 to 6-membered heteroaryl, said heteroaryl is optionally substituted with one or two $C_{1-3}$ alkyl,
- 3 to 6-membered cycloalkyl, said cycloalkyl is optionally substituted with one —$CF_3$, or
- each of $R^6$ is independently one of the following groups:

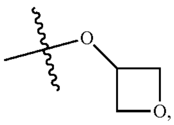

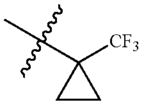

,

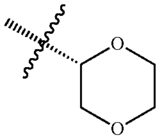

,

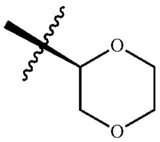

,

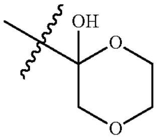

,

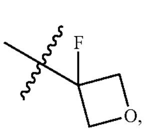

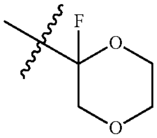

,

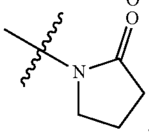

, or

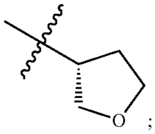

;

$R^7$ is
- a 5 to 6-membered heteroaryl, said heteroaryl is optionally substituted with one substituent selected from the group consisting of $C_1$-$C_6$ alkyl, —$CF_3$, and halogen, or
- $C(O)R^8$; and $R^8$ is
- 3 to 6-membered cycloalkyl, said cycloalkyl is optionally substituted with one halogen, or
- 4 to 6-membered heterocycloalkyl.

In one embodiment, provided herein is a compound according to Formula (Ia)

(Ia)

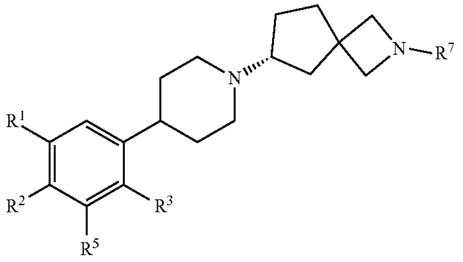

or a pharmaceutically acceptable salt or stereoisomer thereof.

In one embodiment, provided herein is a compound according to Formula (Ib)

(Ib)

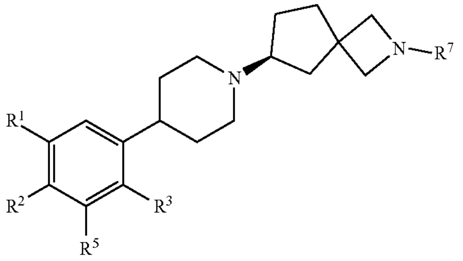

or a pharmaceutically acceptable salt or stereoisomer thereof.

In one embodiment, $R^1$ is selected from the group consisting of H, chloro, and fluoro.

In one embodiment, $R^2$ is H or fluoro.

In one embodiment, $R^5$ is H or fluoro.

In one embodiment, $R^1$, $R^2$, and $R^5$ are H.

In one embodiment, $R^3$ is selected from the group consisting of:

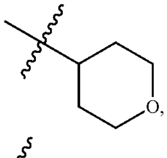

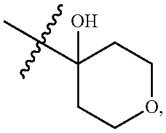

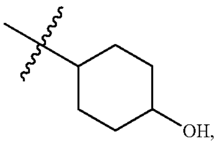

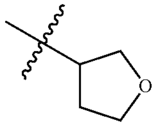

,

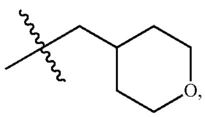

and

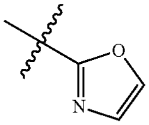

.

In another embodiment, $R^3$ is —$OR^4$.

In one embodiment, $R^4$ is selected from the group consisting of $-CH_3$, $-CF_3$, $-CF_2H$, $-CH_2CH_3$, $-CH(CH_3)_2$, $-CH_2CF_2H$, $-CH_2CH_2F$, $-(CH_2)_2CF_3$, $-CH_2C(CH_3)_2F$, $-(CH_2)_2OCF_3$, $-(CH_2)_2OH$, $-(CH_2)_2OCH_3$, $-CH_2C(CH_3)_2OH$, $-(CH_2)_2C(CH_3)_2OH$, $-(CH_2)_2C(CH_3)_2OCH_3$, $-CH_2C(CH_3)_2OCH_3$, $-(CH_2)_2CN$, and $-CH_2CH(CH_3)_2$. In another embodiment, $R^4$ is selected from the group consisting of:

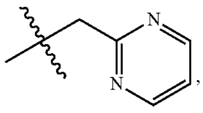, 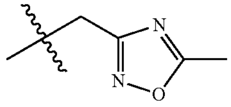,

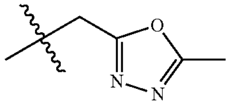, 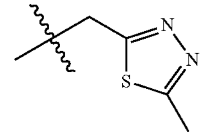,

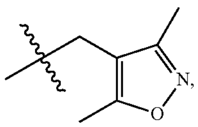 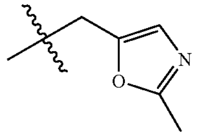,

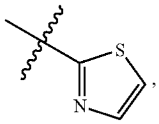, 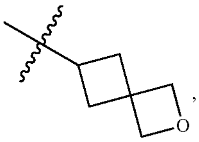,

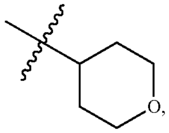 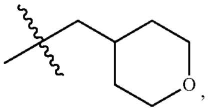

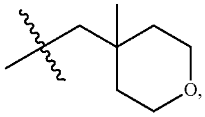 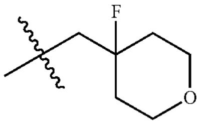

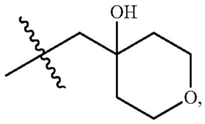 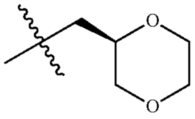,

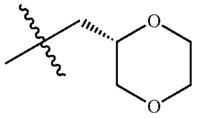, 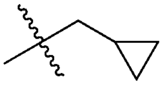,

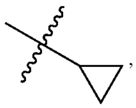, 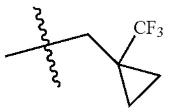, 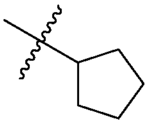,

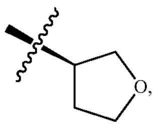 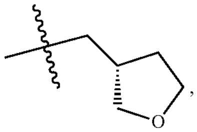,

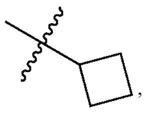, 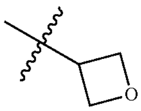 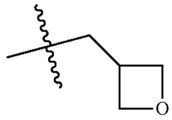

-continued

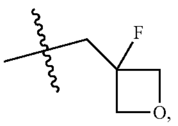 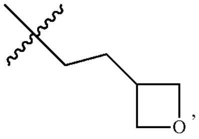

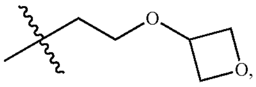 and 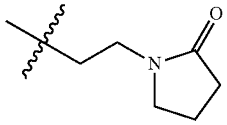.

In one embodiment, $R^7$ is 5 to 6-membered heteroaryl or —C(O)R. In another embodiment. $R^7$ is

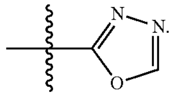

In other embodiments, $R^7$ is —C(O)$R^8$.

In one embodiment, $R^8$ is 4 to 6-membered heterocycloalkyl or 3 to 6-membered cycloalkyl. In another embodiment, $R^8$ is 4 to 6-membered heterocycloalkyl. In other preferred embodiments, $R^8$ is

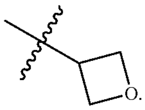 [SMILES: *C1COC1]

In certain embodiments, $R^8$ is 3 to 6-membered cycloalkyl, said 3 to 6-membered cycloalkyl is substituted with one halogen.

In one embodiment, provided herein is a compound selected from the group consisting of:

(R)-2-(6-(4-(2-((2-oxaspiro[3.3]heptan-6-yl)oxy)phenyl)piperidin-1-yl)-2-azaspiro[3.4]octan-2-yl)-1,3,4-oxadiazole;

(R)-2-(6-(4-(2-((2-oxaspiro[3.3]heptan-6-yl)oxy)-5-fluorophenyl)piperidin-1-yl)-2-azaspiro[3.4]octan-2-yl)-1,3,4-oxadiazole;

2-((R)-6-(4-(2-(((R)-1,4-dioxan-2-yl)methoxy)phenyl)piperidin-1-yl)-2-azaspiro[3.4]octan-2-yl)-1,3,4-oxadiazole;

(R)-2-(6-(4-(2-(oxetan-3-yloxy)phenyl)piperidin-1-yl)-2-azaspiro[3.4]octan-2-yl)-1,3,4-oxadiazole;

2-((R)-6-(4-(2-(((S)-1,4-dioxan-2-yl)methoxy)phenyl)piperidin-1-yl)-2-azaspiro[3.4]octan-2-yl)-1,3,4-oxadiazole;

(R)-ethyl 5-(6-(4-(2-hydroxyphenyl)piperidin-1-yl)-2-azaspiro[3.4]octan-2-yl)-1,3,4-oxadiazole-2-carboxylate;

(R)-2-(6-(4-(2-(oxetan-3-ylmethoxy)phenyl)piperidin-1-yl)-2-azaspiro[3.4]octan-2-yl)-1,3,4-thiadiazole;

(R)-2-(6-(4-(2-((3-fluorooxetan-3-yl)methoxy)phenyl)piperidin-1-yl)-2-azaspiro[3.4]octan-2-yl)-1,3,4-thiadiazole;

(R)-2-(6-(4-(2-((tetrahydro-2H-pyran-4-yl)methoxy)phenyl)piperidin-1-yl)-2-azaspiro[3.4]octan-2-yl)-1,3,4-thiadiazole;

(R)-2-(6-(4-(2-((4-fluorotetrahydro-2H-pyran-4-yl)methoxy)phenyl)piperidin-1-yl)-2-azaspiro[3.4]octan-2-yl)-1,3,4-thiadiazole;

(R)-6-(4-(2-(oxetan-3-yloxy)phenyl)piperidin-1-yl)-2-(pyrimidin-5-yl)-2-azaspiro[3.4]octane;

(R)-2-(pyrimidin-5-yl)-6-(4-(2-((tetrahydro-2H-pyran-4-yl)oxy)phenyl)piperidin-1-yl)-2-azaspiro[3.4]octane;

(R)-2-(pyrimidin-5-yl)-6-(4-(2-((tetrahydro-2H-pyran-4-yl)methoxy)phenyl)piperidin-1-yl)-2-azaspiro[3.4]octane;
(R)-6-(4-(2-(oxetan-3-ylmethoxy)phenyl)piperidin-1-yl)-2-(pyrimidin-5-yl)-2-azaspiro[3.4]octane;
(R)-6-(4-(2-((2-oxaspiro[3.3]heptan-6-yl)oxy)phenyl)piperidin-1-yl)-2-(pyrimidin-5-yl)-2-azaspiro[3.4]octane;
(R)-2-(pyrimidin-5-yl)-6-(4-(2-(((R)-tetrahydrofuran-3-yl)oxy)phenyl)piperidin-1-yl)-2-azaspiro[3.4]octane;
(R)-1-(2-(1-(2-(1,3,4-oxadiazol-2-yl)-2-azaspiro[3.4]octan-6-yl)piperidin-4-yl)phenoxy)-2-methylpropan-2-ol;
2-((R)-6-(4-(2-(((R)-tetrahydrofuran-3-yl)oxy)phenyl)piperidin-1-yl)-2-azaspiro[3.4]octan-2-yl)-1,3,4-oxadiazole;
(R)-ethyl 5-(6-(4-(2-(2-methoxyethoxy)phenyl)piperidin-1-yl)-2-azaspiro[3.4]octan-2-yl)-1,3,4-oxadiazole-2-carboxylate;
(R)-2-(6-(4-(2-((4-fluorotetrahydro-2H-pyran-4-yl)methoxy)phenyl)piperidin-1-yl)-2-azaspiro[3.4]octan-2-yl)-1,3,4-oxadiazole;
(R)-2-(6-(4-(2-((4-methyltetrahydro-2H-pyran-4-yl)methoxy)phenyl)piperidin-1-yl)-2-azaspiro[3.4]octan-2-yl)-1,3,4-oxadiazole;
(R)-2-(6-(4-(2-((tetrahydro-2H-pyran-4-yl)oxy)phenyl)piperidin-1-yl)-2-azaspiro[3.4]octan-2-yl)-1,3,4-oxadiazole;
(R)-2-(6-(4-(2-((tetrahydro-2H-pyran-4-yl)methoxy)phenyl)piperidin-1-yl)-2-azaspiro[3.4]octan-2-yl)-1,3,4-oxadiazole;
(R)-2-(6-(4-(2-(tetrahydro-2H-pyran-4-yl)phenyl)piperidin-1-yl)-2-azaspiro[3.4]octan-2-yl)-1,3,4-oxadiazole;
(R)-2-(6-(4-(5-fluoro-2-(tetrahydro-2H-pyran-4-yl)phenyl)piperidin-1-yl)-2-azaspiro[3.4]octan-2-yl)-1,3,4-oxadiazole;
2-((6R)-6-(4-(5-fluoro-2-(tetrahydrofuran-3-yl)phenyl)piperidin-1-yl)-2-azaspiro[3.4]octan-2-yl)-1,3,4-oxadiazole;
2-((6R)-6-(4-(2-(tetrahydrofuran-3-yl)phenyl)piperidin-1-yl)-2-azaspiro[3.4]octan-2-yl)-1,3,4-oxadiazole;
(R)-2-(6-(4-(2-((tetrahydro-2H-pyran-4-yl)methyl)phenyl)piperidin-1-yl)-2-azaspiro[3.4]octan-2-yl)-1,3,4-oxadiazole;
(R)-2-(6-(4-(2-(oxazol-2-yl)phenyl)piperidin-1-yl)-2-azaspiro[3.4]octan-2-yl)-1,3,4-oxadiazole;
(1S,4s)-4-(2-(1-((R)-2-(1,3,4-oxadiazol-2-yl)-2-azaspiro[3.4]octan-6-yl)piperidin-4-yl)phenyl)cyclohexan-1-ol;
(1R,4r)-4-(2-(1-((R)-2-(1,3,4-oxadiazol-2-yl)-2-azaspiro[3.4]octan-6-yl)piperidin-4-yl)phenyl)cyclohexan-1-ol;
(1s,4r)-4-(2-(1-((R)-2-(1,3,4-oxadiazol-2-yl)-2-azaspiro[3.4]octan-6-yl)piperidin-4-yl)phenyl)cyclohexan-1-ol;
(1r,4r)-4-(2-(1-((R)-2-(1,3,4-oxadiazol-2-yl)-2-azaspiro[3.4]octan-6-yl)piperidin-4-yl)phenyl)cyclohexan-1-ol;
(R)-2-(6-(4-(2-(oxetan-3-yloxy)phenyl)piperidin-1-yl)-2-azaspiro[3.4]octan-2-yl)-1,3,4-thiadiazole;
2-((R)-6-(4-(2-(((R)-1,4-dioxan-2-yl)methoxy)phenyl)piperidin-1-yl)-2-azaspiro[3.4]octan-2-yl)-1,3,4-thiadiazole;
2-((R)-6-(4-(2-(((S)-1,4-dioxan-2-yl)methoxy)phenyl)piperidin-1-yl)-2-azaspiro[3.4]octan-2-yl)-1,3,4-thiadiazole;
(R)-2-(6-(4-(2-methoxyphenyl)piperidin-1-yl)-2-azaspiro[3.4]octan-2-yl)-1,3,4-thiadiazole;
(R)-2-(6-(4-(3-fluoro-2-(oxetan-3-yloxy)phenyl)piperidin-1-yl)-2-azaspiro[3.4]octan-2-yl)-1,3,4-thiadiazole;
(R)-2-(6-(4-(2-(2-methoxyethoxy)phenyl)piperidin-1-yl)-2-azaspiro[3.4]octan-2-yl)-1,3,4-thiadiazole;
(R)-1-(2-(1-(2-(1,3,4-thiadiazol-2-yl)-2-azaspiro[3.4]octan-6-yl)piperidin-4-yl)phenoxy)-2-methylpropan-2-ol;
(R)-4-(2-(1-(2-(1,3,4-thiadiazol-2-yl)-2-azaspiro[3.4]octan-6-yl)piperidin-4-yl)phenoxy)-2-methylbutan-2-ol;
(R)-5-(6-(4-(2-methoxyphenyl)piperidin-1-yl)-2-azaspiro[3.4]octan-2-yl)isothiazole;
(R)-5-(6-(4-(2-(2-methoxyethoxy)phenyl)piperidin-1-yl)-2-azaspiro[3.4]octan-2-yl)-1,2,4-thiadiazole;
(R)-1-(2-(1-(2-(1,2,4-thiadiazol-5-yl)-2-azaspiro[3.4]octan-6-yl)piperidin-4-yl)phenoxy)-2-methylpropan-2-ol;
(R)-4-(2-(1-(2-(1,2,4-thiadiazol-5-yl)-2-azaspiro[3.4]octan-6-yl)piperidin-4-yl)phenoxy)-2-methylbutan-2-ol;
(R)-5-(6-(4-(2-methoxyphenyl)piperidin-1-yl)-2-azaspiro[3.4]octan-2-yl)-3-methyl-1,2,4-thiadiazole;
(R)-1-(5-fluoro-2-(1-(2-(4-methyloxazol-2-yl)-2-azaspiro[3.4]octan-6-yl)piperidin-4-yl)phenoxy)-2-methylpropan-2-ol;
(R)-2-methyl-1-(2-(1-(2-(4-methyloxazol-2-yl)-2-azaspiro[3.4]octan-6-yl)piperidin-4-yl)phenoxy)propan-2-ol;
(R)-3-(6-(4-(2-methoxyphenyl)piperidin-1-yl)-2-azaspiro[3.4]octan-2-yl)-1,2,4-oxadiazole;
(R)-6-(4-(2-methoxyphenyl)piperidin-1-yl)-2-(pyrimidin-5-yl)-2-azaspiro[3.4]octane formate salt;
(R)-2-methyl-1-(2-(1-(2-(pyrimidin-5-yl)-2-azaspiro[3.4]octan-6-yl)piperidin-4-yl)phenoxy)propan-2-ol formate salt;
(R)-2-methyl-1-(2-(1-(2-(4-methylpyrimidin-5-yl)-2-azaspiro[3.4]octan-6-yl)piperidin-4-yl)phenoxy)propan-2-ol formate salt;
(R)-6-(4-(2-methoxyphenyl)piperidin-1-yl)-2-(6-methylpyridin-3-yl)-2-azaspiro[3.4]octane formate salt;
(R)-6-(4-(2-methoxyphenyl)piperidin-1-yl)-2-(2-methylpyrimidin-5-yl)-2-azaspiro[3.4]octane;
(R)-2-(5-fluoropyridin-3-yl)-6-(4-(2-methoxyphenyl)piperidin-1-yl)-2-azaspiro[3.4]octane;
(R)-6-(4-(2-methoxyphenyl)piperidin-1-yl)-2-(6-methylpyrazin-2-yl)-2-azaspiro[3.4]octane;
(R)-6-(4-(2-methoxyphenyl)piperidin-1-yl)-2-(pyrazin-2-yl)-2-azaspiro[3.4]octane;
(R)-6-(4-(2-methoxyphenyl)piperidin-1-yl)-2-(3-(trifluoromethyl)pyrazin-2-yl)-2-azaspiro[3.4]octane;
(R)-6-(4-(2-methoxyphenyl)piperidin-1-yl)-2-(3-methylpyrazin-2-yl)-2-azaspiro[3.4]octane;
(R)-6-(4-(2-methoxyphenyl)piperidin-1-yl)-2-(pyridin-3-yl)-2-azaspiro[3.4]octane;
(R)-2-(6-methylpyridin-3-yl)-6-(4-(2-(((R)-tetrahydrofuran-3-yl)oxy)phenyl)piperidin-1-yl)-2-azaspiro[3.4]octane;
(R)-6-(4-(2-methoxyphenyl)piperidin-1-yl)-2-(4-methyl-1,3,5-triazin-2-yl)-2-azaspiro[3.4]octane;
(R)-2-(6-chloropyridazin-3-yl)-6-(4-(2-methoxyphenyl)piperidin-1-yl)-2-azaspiro[3.4]octane;
(R)-6-(4-(2-methoxyphenyl)piperidin-1-yl)-2-(pyridazin-3-yl)-2-azaspiro[3.4]octane;
(R)-6-(4-(5-chloro-2-methoxyphenyl)piperidin-1-yl)-2-(pyridazin-4-yl)-2-azaspiro[3.4]octane;
(R)-6-(4-(2-((tetrahydro-2H-pyran-4-yl)methoxy)phenyl)piperidin-1-yl)-2-(1,3,5-triazin-2-yl)-2-azaspiro[3.4]octane;
(R)-2-(3,6-dichloropyridazin-4-yl)-6-(4-(2-methoxyphenyl)piperidin-1-yl)-2-azaspiro[3.4]octane;
(R)-6-(4-(2-methoxyphenyl)piperidin-1-yl)-2-(pyridazin-4-yl)-2-azaspiro[3.4]octane;
(R)-2-methyl-1-(2-(1-(2-(3-methylpyrazin-2-yl)-2-azaspiro[3.4]octan-6-yl)piperidin-4-yl)phenoxy)propan-2-ol;
(R)-1-(2-(1-(2-(1,3,5-triazin-2-yl)-2-azaspiro[3.4]octan-6-yl)piperidin-4-yl)phenoxy)-2-methylpropan-2-ol;
(R)-6-(4-(5-fluoro-2-methoxyphenyl)piperidin-1-yl)-2-(pyridazin-4-yl)-2-azaspiro[3.4]octane;
(R)-6-(4-(3-fluoro-2-(oxetan-3-yloxy)phenyl)piperidin-1-yl)-2-(pyrimidin-5-yl)-2-azaspiro[3.4]octane;
(R)-6-(4-(2-(2-methoxyethoxy)phenyl)piperidin-1-yl)-2-(pyridazin-3-yl)-2-azaspiro[3.4]octane;

(R)-6-(4-(2-(2-methoxyethoxy)phenyl)piperidin-1-yl)-2-(5-methylpyrazin-2-yl)-2-azaspiro[3.4]octane;
(R)-6-(4-(2-(2-methoxyethoxy)phenyl)piperidin-1-yl)-2-(pyridazin-4-yl)-2-azaspiro[3.4]octane;
(R)-2-(5-fluoropyridin-3-yl)-6-(4-(2-(tetrahydro-2H-pyran-4-yl)phenyl)piperidin-1-yl)-2-azaspiro[3.4]octane;
(R)-2-(pyrimidin-5-yl)-6-(4-(2-(tetrahydro-2H-pyran-4-yl)phenyl)piperidin-1-yl)-2-azaspiro[3.4]octane;
(R)-2-(6-fluoropyridin-3-yl)-6-(4-(2-(tetrahydro-2H-pyran-4-yl)phenyl)piperidin-1-yl)-2-azaspiro[3.4]octane;
(R)-6-(4-(2-methoxyphenyl)piperidin-1-yl)-2-(5-methylpyrazin-2-yl)-2-azaspiro[3.4]octane;
(R)-(6-(4-(5-fluoro-2-methoxyphenyl)piperidin-1-yl)-2-azaspiro[3.4]octan-2-yl)(oxetan-3-yl)methanone;
(R)-(6-(4-(2-(difluoromethoxy)-4-fluorophenyl)piperidin-1-yl)-2-azaspiro[3.4]octan-2-yl)(oxetan-3-yl)methanone;
(R)-(6-(4-(4-fluoro-2-methoxyphenyl)piperidin-1-yl)-2-azaspiro[3.4]octan-2-yl)(oxetan-3-yl)methanone;
(R)-(6-(4-(4-fluoro-2-isopropoxyphenyl)piperidin-1-yl)-2-azaspiro[3.4]octan-2-yl)(oxetan-3-yl)methanone;
(R)-(6-(4-(2-cyclopropoxyphenyl)piperidin-1-yl)-2-azaspiro[3.4]octan-2-yl)(oxetan-3-yl)methanone;
(R)-(6-(4-(2-(2-fluoro-2-methylpropoxy)phenyl)piperidin-1-yl)-2-azaspiro[3.4]octan-2-yl)(oxetan-3-yl)methanone;
(R)-oxetan-3-yl(6-(4-(2-(thiazol-2-yloxy)phenyl)piperidin-1-yl)-2-azaspiro[3.4]octan-2-yl)methanone;
(R)-3-(2-(1-(2-(oxetane-3-carbonyl)-2-azaspiro[3.4]octan-6-yl)piperidin-4-yl)phenoxy)propanenitrile;
oxetan-3-yl((R)-6-(4-(2-(((R)-tetrahydrofuran-3-yl)methoxy)phenyl)piperidin-1-yl)-2-azaspiro[3.4]octan-2-yl)methanone;
(R)-(6-(4-(2-isobutoxyphenyl)piperidin-1-yl)-2-azaspiro[3.4]octan-2-yl)(oxetan-3-yl)methanone;
(R)-(6-(4-(2-(cyclopentyloxy)phenyl)piperidin-1-yl)-2-azaspiro[3.4]octan-2-yl)(oxetan-3-yl)methanone;
(R)-(6-(4-(2-cyclobutoxyphenyl)piperidin-1-yl)-2-azaspiro[3.4]octan-2-yl)(oxetan-3-yl)methanone;
(R)-(6-(4-(2-(cyclopropylmethoxy)phenyl)piperidin-1-yl)-2-azaspiro[3.4]octan-2-yl)(oxetan-3-yl)methanone;
(R)-(6-(4-(2-ethoxyphenyl)piperidin-1-yl)-2-azaspiro[3.4]octan-2-yl)(oxetan-3-yl)methanone;
(R)-(6-(4-(2-isopropoxyphenyl)piperidin-1-yl)-2-azaspiro[3.4]octan-2-yl)(oxetan-3-yl)methanone;
(R)-(6-(4-(2-(2-hydroxy-2-methylpropoxy)phenyl)piperidin-1-yl)-2-azaspiro[3.4]octan-2-yl)(oxetan-3-yl)methanone;
(R)-(1-fluorocyclopropyl)(6-(4-(2-(pyrimidin-2-ylmethoxy)phenyl)piperidin-1-yl)-2-azaspiro[3.4]octan-2-yl)methanone;
(S)-(1-fluorocyclopropyl)(6-(4-(2-(pyrimidin-2-ylmethoxy)phenyl)piperidin-1-yl)-2-azaspiro[3.4]octan-2-yl)methanone;
(R)-(1-fluorocyclopropyl)(6-(4-(2-(2-hydroxyethoxy)phenyl)piperidin-1-yl)-2-azaspiro[3.4]octan-2-yl)methanone;
(S)-(1-fluorocyclopropyl)(6-(4-(2-(2-hydroxyethoxy)phenyl)piperidin-1-yl)-2-azaspiro[3.4]octan-2-yl)methanone;
(R)-(6-(4-(2-(cyclopropylmethoxy)phenyl)piperidin-1-yl)-2-azaspiro[3.4]octan-2-yl)(1-fluorocyclopropyl)methanone;
(R)-(6-(4-(2-(cyclopropylmethoxy)phenyl)piperidin-1-yl)-2-azaspiro[3.4]octan-2-yl)(1-fluorocyclopropyl)methanone;
(R)-1-(2-(2-(1-(2-(1-fluorocyclopropane-1-carbonyl)-2-azaspiro[3.4]octan-6-yl)piperidin-4-yl)phenoxy)ethyl)pyrrolidin-2-one formate salt;
(S)-1-(2-(2-(1-(2-(1-fluorocyclopropane-1-carbonyl)-2-azaspiro[3.4]octan-6-yl)piperidin-4-yl)phenoxy)ethyl)pyrrolidin-2-one formate salt;
(R)-(1-fluorocyclopropyl)(6-(4-(2-((tetrahydro-2H-pyran-4-yl)methoxy)phenyl)piperidin-1-yl)-2-azaspiro[3.4]octan-2-yl)methanone;
(S)-(1-fluorocyclopropyl)(6-(4-(2-((tetrahydro-2H-pyran-4-yl)methoxy)phenyl)piperidin-1-yl)-2-azaspiro[3.4]octan-2-yl)methanone;
(R)-(1-fluorocyclopropyl)(6-(4-(2-((5-methyl-1,3,4-thiadiazol-2-yl)methoxy)phenyl)piperidin-1-yl)-2-azaspiro[3.4]octan-2-yl)methanone;
(S)-(1-fluorocyclopropyl)(6-(4-(2-((5-methyl-1,3,4-thiadiazol-2-yl)methoxy)phenyl)piperidin-1-yl)-2-azaspiro[3.4]octan-2-yl)methanone;
(R)-(6-(4-(2-ethoxyphenyl)piperidin-1-yl)-2-azaspiro[3.4]octan-2-yl)(1-fluorocyclopropyl)methanone;
(S)-(6-(4-(2-ethoxyphenyl)piperidin-1-yl)-2-azaspiro[3.4]octan-2-yl)(1-fluorocyclopropyl)methanone;
(R)-(6-(4-(2-(cyclopropylmethoxy)phenyl)piperidin-1-yl)-2-azaspiro[3.4]octan-2-yl)(1-fluorocyclopropyl)methanone;
(R)-(6-(4-(2-(cyclopropylmethoxy)phenyl)piperidin-1-yl)-2-azaspiro[3.4]octan-2-yl)(1-fluorocyclopropyl)methanone;
(R)-(6-(4-(2-((3,5-dimethylisoxazol-4-yl)methoxy)phenyl)piperidin-1-yl)-2-azaspiro[3.4]octan-2-yl)(1-fluorocyclopropyl)methanone;
(S)-(6-(4-(2-((3,5-dimethylisoxazol-4-yl)methoxy)phenyl)piperidin-1-yl)-2-azaspiro[3.4]octan-2-yl)(1-fluorocyclopropyl)methanone;
(R)-(1-fluorocyclopropyl)(6-(4-(2-((2-methyloxazol-5-yl)methoxy)phenyl)piperidin-1-yl)-2-azaspiro[3.4]octan-2-yl)methanone;
(S)-(1-fluorocyclopropyl)(6-(4-(2-((2-methyloxazol-5-yl)methoxy)phenyl)piperidin-1-yl)-2-azaspiro[3.4]octan-2-yl)methanone;
(R)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;
(S)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;
(R)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;
(S)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;
(R)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;
(S)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;
(R)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;
(S)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;
(R)-(1-fluorocyclopropyl)(6-(4-(2-(3,3,3-trifluoropropoxy)phenyl)piperidin-1-yl)-2-azaspiro[3.4]octan-2-yl)methanone;
(S)-(1-fluorocyclopropyl)(6-(4-(2-(3,3,3-trifluoropropoxy)phenyl)piperidin-1-yl)-2-azaspiro[3.4]octan-2-yl)methanone;

(R)-(1-fluorocyclopropyl)(6-(4-(2-(3-hydroxy-3-methylbutoxy)phenyl)piperidin-1-yl)-2-azaspiro[3.4]octan-2-yl)methanone;

(S)-(1-fluorocyclopropyl)(6-(4-(2-(3-hydroxy-3-methylbutoxy)phenyl)piperidin-1-yl)-2-azaspiro[3.4]octan-2-yl)methanone;

(R)-(6-(4-(2-(3-hydroxy-3-methylbutoxy)phenyl)piperidin-1-yl)-2-azaspiro[3.4]octan-2-yl)(oxetan-3-yl)methanone;

(R)-oxetan-3-yl(6-(4-(2-(2-(trifluoromethoxy)ethoxy)phenyl)piperidin-1-yl)-2-azaspiro[3.4]octan-2-yl)methanone;

(R)-oxetan-3-yl(6-(4-(2-(2-(oxetan-3-yloxy)ethoxy)phenyl)piperidin-1-yl)-2-azaspiro[3.4]octan-2-yl)methanone;

(R)-(1-fluorocyclopropyl)(6-(4-(2-(3-methoxy-3-methylbutoxy)phenyl)piperidin-1-yl)-2-azaspiro[3.4]octan-2-yl)methanone;

(S)-(1-fluorocyclopropyl)(6-(4-(2-(3-methoxy-3-methylbutoxy)phenyl)piperidin-1-yl)-2-azaspiro[3.4]octan-2-yl)methanone;

(R)-oxetan-3-yl(6-(4-(2-(3,3,3-trifluoropropoxy)phenyl)piperidin-1-yl)-2-azaspiro[3.4]octan-2-yl)methanone;

(R)-(6-(4-(2-(2-methoxy-2-methylpropoxy)phenyl)piperidin-1-yl)-2-azaspiro[3.4]octan-2-yl)(oxetan-3-yl)methanone;

(R)-oxetan-3-yl(6-(4-(2-((1-(trifluoromethyl)cyclopropyl)methoxy)phenyl)piperidin-1-yl)-2-azaspiro[3.4]octan-2-yl)methanone;

(R)-(6-(4-(2-(2,2-difluoroethoxy)phenyl)piperidin-1-yl)-2-azaspiro[3.4]octan-2-yl)(oxetan-3-yl)methanone;

(R)-oxetan-3-yl(6-(4-(2-(2-(oxetan-3-yl)ethoxy)phenyl)piperidin-1-yl)-2-azaspiro[3.4]octan-2-yl)methanone;

(S)-(6-(4-(5-chloro-2-methoxyphenyl)piperidin-1-yl)-2-azaspiro[3.4]octan-2-yl)(1-fluorocyclopropyl)methanone;

(R)-(6-(4-(5-chloro-2-methoxyphenyl)piperidin-1-yl)-2-azaspiro[3.4]octan-2-yl)(1-fluorocyclopropyl)methanone;

(S)-(6-(4-(5-chloro-2-methoxyphenyl)piperidin-1-yl)-2-azaspiro[3.4]octan-2-yl)(1-fluorocyclopropyl)methanone;

(R)-(6-(4-(5-chloro-2-methoxyphenyl)piperidin-1-yl)-2-azaspiro[3.4]octan-2-yl)(1-fluorocyclopropyl)methanone;

(S)-(6-(4-(2-methoxyphenyl)piperidin-1-yl)-2-azaspiro[3.4]octan-2-yl)(oxetan-3-yl)methanone;

(R)-(6-(4-(2-methoxyphenyl)piperidin-1-yl)-2-azaspiro[3.4]octan-2-yl)(oxetan-3-yl)methanone;

(S)-(6-(4-(2-methoxyphenyl)piperidin-1-yl)-2-azaspiro[3.4]octan-2-yl)(oxetan-3-yl)methanone;

(R)-(6-(4-(2-methoxyphenyl)piperidin-1-yl)-2-azaspiro[3.4]octan-2-yl)(oxetan-3-yl)methanone;

(S)-(6-(4-(2-(difluoromethoxy)phenyl)piperidin-1-yl)-2-azaspiro[3.4]octan-2-yl)(oxetan-3-yl)methanone;

(R)-(6-(4-(2-(difluoromethoxy)phenyl)piperidin-1-yl)-2-azaspiro[3.4]octan-2-yl)(oxetan-3-yl)methanone citrate salt;

(S)-(6-(4-(2-(difluoromethoxy)phenyl)piperidin-1-yl)-2-azaspiro[3.4]octan-2-yl)(oxetan-3-yl)methanone;

(R)-(6-(4-(2-(difluoromethoxy)phenyl)piperidin-1-yl)-2-azaspiro[3.4]octan-2-yl)(oxetan-3-yl)methanone citrate salt;

(S)-oxetan-3-yl(6-(4-(2-(trifluoromethoxy)phenyl)piperidin-1-yl)-2-azaspiro[3.4]octan-2-yl)methanone;

(R)-oxetan-3-yl(6-(4-(2-(trifluoromethoxy)phenyl)piperidin-1-yl)-2-azaspiro[3.4]octan-2-yl)methanone;

(R)-(1-fluorocyclopropyl)(6-(4-(2-(trifluoromethoxy)phenyl)piperidin-1-yl)-2-azaspiro[3.4]octan-2-yl)methanone;

(S)-(1-fluorocyclopropyl)(6-(4-(2-(trifluoromethoxy)phenyl)piperidin-1-yl)-2-azaspiro[3.4]octan-2-yl)methanone;

(R)-(1-fluorocyclopropyl)(6-(4-(2-(trifluoromethoxy)phenyl)piperidin-1-yl)-2-azaspiro[3.4]octan-2-yl)methanone;

(S)-(1-fluorocyclopropyl)(6-(4-(2-(trifluoromethoxy)phenyl)piperidin-1-yl)-2-azaspiro[3.4]octan-2-yl)methanone;

(R)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;

(S)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;

(R)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;

(S)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;

(R)-(1-fluorocyclopropyl)(6-(4-(2-((tetrahydro-2H-pyran-4-yl)oxy)phenyl)piperidin-1-yl)-2-azaspiro[3.4]octan-2-yl)methanone;

(S)-(1-fluorocyclopropyl)(6-(4-(2-((tetrahydro-2H-pyran-4-yl)oxy)phenyl)piperidin-1-yl)-2-azaspiro[3.4]octan-2-yl)methanone;

(R)-(1-fluorocyclopropyl)(6-(4-(2-((tetrahydro-2H-pyran-4-yl)oxy)phenyl)piperidin-1-yl)-2-azaspiro[3.4]octan-2-yl)methanone;

(S)-(1-fluorocyclopropyl)(6-(4-(2-((tetrahydro-2H-pyran-4-yl)oxy)phenyl)piperidin-1-yl)-2-azaspiro[3.4]octan-2-yl)methanone;

(R)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;

(S)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;

(R)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;

(S)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;

(R)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(R)-(1-fluorocyclopropyl)(6-(4-(2-(tetrahydro-2H-pyran-4-yl)phenyl)piperidin-1-yl)-2-azaspiro[3.4]octan-2-yl)methanone;

(S)-(1-fluorocyclopropyl)(6-(4-(2-(tetrahydro-2H-pyran-4-yl)phenyl)piperidin-1-yl)-2-azaspiro[3.4]octan-2-yl)methanone;

(R)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(S)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(R)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(S)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(R)-6-(4-(5-fluoro-2-(tetrahydro-2H-pyran-4-yl)phenyl)piperidin-1-yl)-2-(pyrimidin-5-yl)-2-azaspiro[3.4]octane;

(S)-6-(4-(5-fluoro-2-(tetrahydro-2H-pyran-4-yl)phenyl)piperidin-1-yl)-2-(pyrimidin-5-yl)-2-azaspiro[3.4]octane;

(R)-6-(4-(5-fluoro-2-(tetrahydro-2H-pyran-4-yl)phenyl)piperidin-1-yl)-2-(pyrimidin-5-yl)-2-azaspiro[3.4]octane;

(S)-6-(4-(5-fluoro-2-(tetrahydro-2H-pyran-4-yl)phenyl)piperidin-1-yl)-2-(pyrimidin-5-yl)-2-azaspiro[3.4]octane;

(R)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(S)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(R)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(S)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(R)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(R)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-2-(6-(4-(2-methoxyphenyl)piperidin-1-yl)-2-azaspiro[3.4]octan-2-yl)oxazole;

(R)-2-(6-(4-(2-methoxyphenyl)piperidin-1-yl)-2-azaspiro[3.4]octan-2-yl)oxazole;

(S)-2-(6-(4-(2-methoxyphenyl)piperidin-1-yl)-2-azaspiro[3.4]octan-2-yl)oxazole;

(R)-2-(6-(4-(2-methoxyphenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)oxazole;

(S)-2-(6-(4-(2-(trifluoromethoxy)phenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)oxazole;

(S)-2-(6-(4-(2-(trifluoromethoxy)phenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)-1,3,4-thiadiazole;

(S)-2-(6-(4-(2-(trifluoromethoxy)phenyl)piperidin-1-yl)-2-azaspiro[3.4]octan-2-yl)-1,3,4-thiadiazole;

(R)-2-(6-(4-(2-(trifluoromethoxy)phenyl)piperidin-1-yl)-2-azaspiro[3.4]octan-2-yl)-1,3,4-thiadiazole;

(S)-2-(6-(4-(2-(trifluoromethoxy)phenyl)piperidin-1-yl)-2-azaspiro[3.4]octan-2-yl)-1,3,4-thiadiazole;

(R)-2-(6-(4-(2-(difluoromethoxy)phenyl)piperidin-1-yl)-2-azaspiro[3.4]octan-2-yl)-1,3,4-thiadiazole;

(S)-2-(6-(4-(2-(difluoromethoxy)phenyl)piperidin-1-yl)-2-azaspiro[3.4]octan-2-yl)-1,3,4-thiadiazole;

(R)-2-(6-(4-(2-(difluoromethoxy)phenyl)piperidin-1-yl)-2-azaspiro[3.4]octan-2-yl)-1,3,4-thiadiazole;

(S)-2-(6-(4-(2-(difluoromethoxy)phenyl)piperidin-1-yl)-2-azaspiro[3.4]octan-2-yl)-1,3,4-thiadiazole;

(R)-5-(6-(4-(2-methoxyphenyl)piperidin-1-yl)-2-azaspiro[3.4]octan-2-yl)-1,2,4-thiadiazole;

(S)-5-(6-(4-(2-methoxyphenyl)piperidin-1-yl)-2-azaspiro[3.4]octan-2-yl)-1,2,4-thiadiazole;

(R)-5-(6-(4-(2-methoxyphenyl)piperidin-1-yl)-2-azaspiro[3.4]octan-2-yl)-1,2,4-thiadiazole;

(S)-5-(6-(4-(2-methoxyphenyl)piperidin-1-yl)-2-azaspiro[3.4]octan-2-yl)-1,2,4-thiadiazole;

(R)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone; and (S)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone, or a pharmaceutically acceptable salt thereof.

In one embodiment, provided herein is a compound selected from the group consisting of:

(R)-2-(6-(4-(2-(tetrahydro-2H-pyran-4-yl)phenyl)piperidin-1-yl)-2-azaspiro[3.4]octan-2-yl)-1,3,4-oxadiazole;

(S)-2-(6-(4-(2-(tetrahydro-2H-pyran-4-yl)phenyl)piperidin-1-yl)-2-azaspiro[3.4]octan-2-yl)-1,3,4-oxadiazole;

(R)-(1-fluorocyclopropyl)(6-(4-(2-(tetrahydro-2H-pyran-4-yl)phenyl)piperidin-1-yl)-2-azaspiro[3.4]octan-2-yl)methanone;

(S)-(1-fluorocyclopropyl)(6-(4-(2-(tetrahydro-2H-pyran-4-yl)phenyl)piperidin-1-yl)-2-azaspiro[3.4]octan-2-yl)methanone;

(R)-2-(pyrimidin-5-yl)-6-(4-(2-(tetrahydro-2H-pyran-4-yl)phenyl)piperidin-1-yl)-2-azaspiro[3.4]octane;

(S)-oxetan-3-yl(6-(4-(2-(trifluoromethoxy)phenyl)piperidin-1-yl)-2-azaspiro[3.4]octan-2-yl)methanone; and (R)-oxetan-3-yl(6-(4-(2-(trifluoromethoxy)phenyl)piperidin-1-yl)-2-azaspiro[3.4]octan-2-yl)methanone, or a pharmaceutically acceptable salt thereof.

In one embodiment, provided herein is a compound selected from the group consisting of:

(R)-2-(6-(4-(2-(tetrahydro-2H-pyran-4-yl)phenyl)piperidin-1-yl)-2-azaspiro[3.4]octan-2-yl)-1,3,4-oxadiazole, having the following structure:

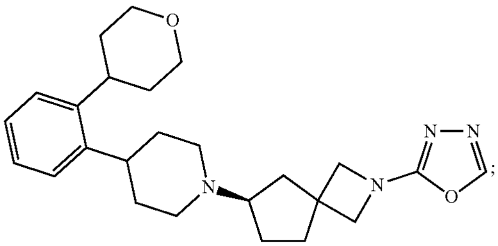 [SMILES: c1ccc(C2CCN([C@@H]3CCC4(C3)CN(c3nnco3)C4)CC2)c(C2CCOCC2)c1]

;

(R)-(1-fluorocyclopropyl)(6-(4-(2-(tetrahydro-2H-pyran-4-yl)phenyl)piperidin-1-yl)-2-azaspiro[3.4]octan-2-yl)methanone, having the following structure:

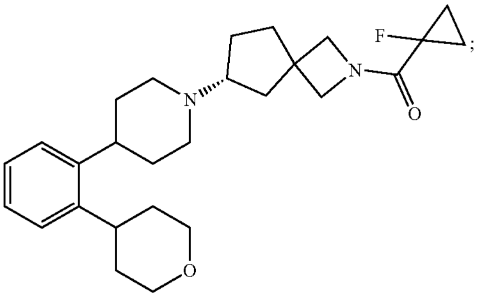 [SMILES: O=C(N1CC2(CC[C@@H](N3CCC(c4ccccc4C4CCOCC4)CC3)C2)C1)C1(F)CC1]

;

(R)-2-(pyrimidin-5-yl)-6-(4-(2-(tetrahydro-2H-pyran-4-yl)phenyl)piperidin-1-yl)-2-azaspiro[3.4]octane, having the following structure:

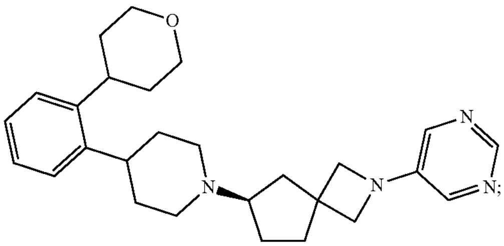 [SMILES: c1ccc(C2CCN([C@@H]3CCC4(C3)CN(c3cncnc3)C4)CC2)c(C2CCOCC2)c1]

;

and (R)-oxetan-3-yl(6-(4-(2-(trifluoromethoxy)phenyl)piperidin-1-yl)-2-azaspiro[3.4]octan-2-yl)methanone, having the following structure:

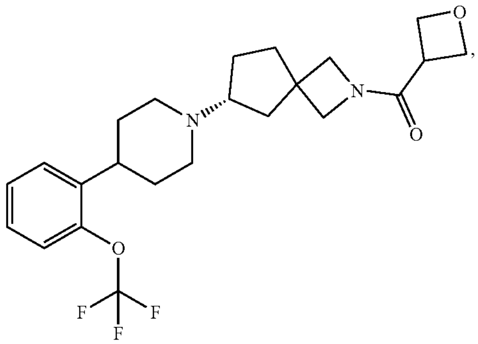 [SMILES: O=C(C1COC1)N1CC2(CC[C@@H](N3CCC(c4ccccc4OC(F)(F)F)CC3)C2)C1]

, or a pharmaceutically acceptable salt thereof.

In one embodiment, provided herein is a pharmaceutical composition comprising a compound provided herein or a pharmaceutically acceptable salt thereof.

6.3. Pharmaceutical Compositions

In one embodiment, provided herein is a pharmaceutical composition comprising a compound provided herein, or a pharmaceutically acceptable salt thereof, and a pharmaceutically acceptable carrier. In another embodiment, provided herein is a pharmaceutical composition comprising a therapeutically effective amount of a compound of Formula (I), or a pharmaceutically acceptable salt thereof, and a pharmaceutically acceptable carrier. In another embodiment, provided herein is a pharmaceutical composition comprising a compound of Formula (I), or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g., by injection, infusion, transdermal or topical administration), and rectal administration. Topical administration may also pertain to inhalation or intranasal application. The pharmaceutical compositions provided herein can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of the following:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethylene glycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

The pharmaceutical compositions provided herein can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound or the pharmaceutical composition thereof is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds provided herein can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

6.4. Methods of Use

In one embodiment, the compounds provided herein are in free form or in pharmaceutically acceptable salt form and have activity as muscarinic M4 receptor agonists. In a specific embodiment, provided herein are compounds according to Formula (I) in free form or in pharmaceutically acceptable salt form having activity as muscarinic M4 receptor agonists. A significant advantage of the compounds provided herein is that they are highly selective for the M4 receptor, relative to the M1, M2, and M3 receptor subtypes and thus are thought to retain their desired activity in the brain but not produce unwanted cholinergic side effects. The muscarinic activity of the compounds provided herein can be determined using the CHRM4 $Ca^{++}$ Flux Assay described in Section 8.2 below.

By virtue of their M4 receptor agonist activity, the compounds provided herein may be useful in the treatment of:

- Psychosis, including psychosis associated with schizophrenia, schizoaffective disorder, psychotic depression, bipolar disorder with psychotic features, Alzheimer's Disease, Parkinson's Disease, post-traumatic stress disorder, and frontotemporal dementia;
- Hyperkinetic Movement Disorders, including but not limited to Tourette's Syndrome, chorea and tardive dyskinesia;
- Cognitive dysfunction, including but not limited to cognitive dysfunction associated with schizophrenia, Alzheimer's Disease, frontotemporal dementia, schizoaffective disorder, and depression; and/or
- Substance Use Disorders.

In one embodiment, provided herein is a method of treating a condition, disease or disorder which is treated by a M4 receptor agonist comprising administration of a therapeutically effective amount of a compound according to Formula (I) or a pharmaceutically acceptable salt thereof to a subject in need of treatment thereof. In a further embodiment, the condition, disease or disorder is psychosis, including but not limited to, psychosis associated with schizophrenia, schizoaffective disorder, psychotic depression, bipolar disorder with psychotic features, Alzheimer's disease, Parkinson's Disease, post-traumatic stress disorder, and frontotemporal dementia. In a specific embodiment, the psychosis is associated with Alzheimer's disease.

In another embodiment, provided herein is a method of treating a hyperkinetic movement disorder, such as Tourette's syndrome, chorea or tardive dyskinesia, comprising administration of a therapeutically effective amount of a compound according to Formula (I) or a pharmaceutically acceptable salt thereof to a subject in need of treatment thereof. In some embodiments, the hyperkinetic movement disorder is associated with schizophrenia, schizoaffective disorder, psychotic depression, bipolar disorder with psychotic features, Alzheimer's disease, or frontotemporal dementia. In specific embodiment, the hyperkinetic movement disorder is associated with Alzheimer's disease.

In another embodiment, provided herein is a method of treating cognitive dysfunction, such as cognitive dysfunction associated with schizophrenia, Alzheimer's disease, frontotemporal dementia, schizoaffective disorder, or depression, comprising administration of a therapeutically effective amount of a compound according to Formula (I) or a pharmaceutically acceptable salt thereof to a subject in need of treatment thereof. In a specific embodiment, the cognitive dysfunction is associated with Alzheimer's disease.

In another embodiment, provided herein is a method of treating substance use disorders comprising administration of a therapeutically effective amount of a compound according to Formula (I) or a pharmaceutically acceptable salt thereof to a subject in need of treatment thereof.

In one embodiment, provided herein is the use of a compound according to Formula (I) or a pharmaceutically acceptable salt thereof in therapy. In a further embodiment, the therapy is selected from a condition, disease or disorder which is treated by a M4 receptor agonist. In another embodiment, the condition, disease or disorder is selected from the afore-mentioned list, suitably psychosis, including but not limited to, psychosis associated with schizophrenia, schizoaffective disorder, psychotic depression, bipolar disorder with psychotic features, Alzheimer's disease, Parkinson's Disease, post-traumatic stress disorder, and frontotemporal dementia. In a specific embodiment, the psychosis is associated with Alzheimer's disease In another embodiment, provided herein is the use of a compound according to Formula (I) or a pharmaceutically acceptable salt thereof in a hyperkinetic movement disorder, such as Tourette's syndrome, chorea or tardive dyskinesia. In some embodiments, the hyperkinetic movement disorder is associated with schizophrenia, schizoaffective disorder, psychotic depression, bipolar disorder with psychotic features, Alzheimer's disease, or frontotemporal dementia. In specific embodiment, the hyperkinetic movement disorder is associated with Alzheimer's disease.

In another embodiment, provided herein is the use of a compound according to Formula (I) or a pharmaceutically acceptable salt thereof in cognitive dysfunction, for example cognitive dysfunction associated with schizophrenia, Alzheimer's disease, frontotemporal dementia, schizoaffective disorder, or depression. In a specific embodiment, the cognitive dysfunction is associated with Alzheimer's disease.

In another embodiment, provided herein is the use of a compound according to Formula (I) or a pharmaceutically acceptable salt thereof in substance use disorders.

In another embodiment, provided herein is the use of a compound according to Formula (I) or a pharmaceutically acceptable salt thereof for the manufacture of a medicament. In a further embodiment, the medicament is for treatment of a condition, disease or disorder which is treated by a M4 receptor agonist. In another embodiment, the condition, disease or disorder is psychosis, including but not limited to, psychosis associated with schizophrenia, schizoaffective disorder, psychotic depression, bipolar disorder with psychotic features, Alzheimer's disease, Parkinson's Disease, post-traumatic stress disorder, and frontotemporal dementia.

In another embodiment, provided herein is the use of a compound according to Formula (I) or a pharmaceutically acceptable salt thereof for the manufacture of a medicament for the treatment of a hyperkinetic movement disorder, such as Tourette's syndrome, chorea or tardive dyskinesia. In some embodiments, the hyperkinetic movement disorder is associated with schizophrenia, schizoaffective disorder, psychotic depression, bipolar disorder with psychotic features, Alzheimer's disease, or frontotemporal dementia. In specific embodiment, the hyperkinetic movement disorder is associated with Alzheimer's disease.

In another embodiment, provided herein is the use of a compound according to Formula (I) or a pharmaceutically acceptable salt thereof for the manufacture of a medicament for the treatment of cognitive dysfunction, for example cognitive dysfunction associated with schizophrenia, Alzheimer's disease, frontotemporal dementia, schizoaffective disorder, or depression. In a specific embodiment, the cognitive dysfunction is associated with Alzheimer's disease.

In another embodiment, provided herein is the use of a compound according to Formula (I) or a pharmaceutically acceptable salt thereof for the manufacture of a medicament for the treatment of substance use disorders.

In another embodiment, provided herein is a compound according to Formula (I) or a pharmaceutically acceptable salt thereof for use in the treatment of a condition, disease or disorder which is treated by a M4 receptor agonist. In a further embodiment, the condition, disease or disorder is selected from the afore-mentioned list, suitably psychosis, including but not limited to, psychosis associated with schizophrenia, schizoaffective disorder, psychotic depression, bipolar disorder with psychotic features, Alzheimer's disease, Parkinson's Disease, post-traumatic stress disorder, and frontotemporal dementia. In a specific embodiment, the psychosis is associated with Alzheimer's disease.

In another embodiment, provided herein is a compound according to Formula (I) or a pharmaceutically acceptable salt thereof for use in the treatment of a hyperkinetic movement disorder, such as Tourette's syndrome, chorea or tardive dyskinesia. In some embodiments, the hyperkinetic movement disorder is associated with schizophrenia, schizoaffective disorder, psychotic depression, bipolar disorder with psychotic features, Alzheimer's disease, or frontotemporal dementia. In specific embodiment, the hyperkinetic movement disorder is associated with Alzheimer's disease.

In another embodiment, provided herein is a compound of Formula (I) or a pharmaceutically acceptable salt thereof for use in the treatment of cognitive dysfunction, for example cognitive dysfunction associated with schizophrenia, Alzheimer's disease, frontotemporal dementia, schizoaffective disorder, or depression. In a specific embodiment, the cognitive dysfunction is associated with Alzheimer's disease.

In another embodiment, provided herein is a compound of Formula (I) or a pharmaceutically acceptable salt thereof for use in the treatment of substance use disorders.

A compound according to Formula (I) or a pharmaceutically acceptable salt thereof may be administered either simultaneously with, or before or after, one or more other therapeutic agents. The compounds according to Formula (I) may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a subject in combination with a compound provided herein.

In the combination therapies provided herein, a compound according to Formula (I) and the other therapeutic agent may be manufactured and/or formulated by the same or different manufacturers. Moreover, the compounds provided herein and the other therapeutic may be brought together into a combination therapy: (i) prior to release of the combination product to physicians (e.g., in the case of a kit comprising a compound provided herein and the other therapeutic agent); (ii) by the physician themselves (or under the guidance of the physician) shortly before administration; (iii) in the patient themselves, e.g., during sequential administration of a compound provided herein and the other therapeutic agent.

A compound according to Formula (I) or a pharmaceutically acceptable salt thereof may be administered with an antipsychotic, suitably a first-generation antipsychotic such as chlorpromazine (thorazine), haloperidol, mesoridazine, thioridazine, thiothixene, pimozide, fluphenazine or perphenazine, a second-generation antipsychotic such as clozapine, olanzapine, risperidone, quetiapine, aripiprazole, asenapine, brexpiprazole, cariprazine, iloperidone, ziprasidone, lurasidone, pimavanserin or paliperidone. In certain embodiments, a compound according to Formula (I) or a pharmaceutically acceptable salt thereof may be administered with an antipsychotic and a cholinesterase inhibitor, such as donepizil, rivastigmine tartrate, galantamine, tacrine or memantine. In certain embodiments, a compound according to Formula (I) or a pharmaceutically acceptable salt thereof may be administered with an antipsychotic and a mood stabilizer, such as lithium, divalproex sodium, carbamazepine or lamotrigine.

A compound according to Formula (I) or a pharmaceutically acceptable salt thereof may be administered with an antidepressant, suitably a selective serotonin reuptake inhibitor such as sertraline, fluoxetine, fluvoxamine, escitalopram, paroxetine or citalopram, a serotonin-norepinephrine reuptake inhibitor such as vortioxetine, venlafaxine, desvenlafaxine, milnacipran, duloxetine or levomilnacipran, a phenylpiperazine antidepressant such as nefazodone, vilazodone or trazodone, reversible monoamine oxidase inhibitors such as moclobemide, melatonin agonists such as agomelatine, serotonin agonists such as mirtazapine, N-methyl-D-aspartate receptor antagonists such as esketamine and ketamine, and monoamine oxidase inhibitors such as tranylcypromine, phenelzine, transdermal selegiline or isocarboxazid.

A compound according to Formula (I) or a pharmaceutically acceptable salt thereof may be administered in conjunction with standardize psychological treatment, for example at individual or group therapy. In another embodiment, a compound according to Formula (I) or a pharmaceutically acceptable salt thereof may be administered in conjunction with psychosocial or behavioral therapy either through standardized psychological treatment or through computer-assistance. In certain embodiment, the computer-assistance is by means of a digital or electronic device such as online tools, smartphones, laptops, tablets, wireless devices or health Apps.

In a further embodiment, provided herein is a method of treatment of a condition, disease or disorder which is treated with a M4 receptor agonist comprising administration of a therapeutically effective amount of a compound according to Formula (I) or a pharmaceutically acceptable salt thereof and an antipsychotic to a subject in need of treatment thereof. In certain embodiments, provided herein is a method of treatment of a condition, disease or disorder which is treated with a M4 receptor agonist comprising administration of a therapeutically effective amount of a compound according to Formula (I) or a pharmaceutically acceptable salt thereof, an antipsychotic, and a cholinesterase inhibitor to a subject in need of treatment thereof. In certain embodiments, provided herein is a method of treatment of a condition, disease or disorder which is treated with a M4 receptor agonist comprising administration of a therapeutically effective amount of a compound according to Formula (I) or a pharmaceutically acceptable salt thereof, an antipsychotic, and a mood stabilizer to a subject in need of treatment thereof.

In a further embodiment, provided herein is a method of treatment of a condition, disease or disorder which is treated with a M4 receptor agonist comprising administration of a therapeutically effective amount of a compound according to Formula (I) or a pharmaceutically acceptable salt thereof and an antidepressant to a subject in need of treatment thereof.

In a further embodiment, provided herein is the use of a compound according to Formula (I) or a pharmaceutically acceptable salt thereof in a condition, disease or disorder which is treated with a M4 receptor agonist, wherein the use is combined with an antipsychotic. In certain embodiments, provided herein is the use of a compound according to Formula (I) or a pharmaceutically acceptable salt thereof in a condition, disease or disorder which is treated with a M4 receptor agonist, wherein the use is combined with an antipsychotic and a cholinesterase inhibitor. In certain embodiments, provided herein is the use of a compound according to Formula (I) or a pharmaceutically acceptable salt thereof in a condition, disease or disorder which is treated with a M4 receptor agonist, wherein the use is combined with an antipsychotic and a mood stabilizer.

In a further embodiment, provided herein is the use of a compound according to Formula (I) or a pharmaceutically acceptable salt thereof in a condition, disease or disorder which is treated with a M4 receptor agonist, wherein the use is combined with an antidepressant.

In a further embodiment, provided herein is the use of a compound according to Formula (I) or a pharmaceutically acceptable salt thereof for the manufacture of a medicament for treatment of a condition, disease or disorder which is treated with a M4 receptor agonist wherein the use is combined with an antipsychotic. In certain embodiments, provided herein is the use of a compound according to Formula (I) or a pharmaceutically acceptable salt thereof for the manufacture of a medicament for treatment of a condition, disease or disorder which is treated with a M4 receptor agonist wherein the use is combined with an antipsychotic and a cholinesterase inhibitor. In certain embodiments, provided herein is the use of a compound according to Formula (I) or a pharmaceutically acceptable salt thereof for the manufacture of a medicament for treatment of a condition, disease or disorder which is treated with a M4 receptor agonist wherein the use is combined with an antipsychotic and a mood stabilizer.

In a further embodiment, provided herein is the use of a compound according to Formula (I) or a pharmaceutically acceptable salt thereof for the manufacture of a medicament for treatment of a condition, disease or disorder which is treated with a M4 receptor agonist wherein the use is combined with an antidepressant.

In a further embodiment, provided herein is the use of a compound according to Formula (I) or a pharmaceutically acceptable salt thereof in a condition, disease or disorder which is treated with a M4 receptor agonist, wherein the use is combined with computer-assisted psychosocial or behavioral therapy.

In a further embodiment, provided herein is a method for the treatment of a condition, disease or disorder which is treated with a M4 receptor agonist comprising administration of a therapeutically effective amount of a compound according to Formula (I) or a pharmaceutically acceptable salt thereof in conjunction with computer-assisted psychosocial or behavioral therapy.

In a further embodiment, provided herein is the use of a compound according to Formula (I) or a pharmaceutically acceptable salt thereof for the manufacture of a medicament for treatment of a condition, disease or disorder which is treated by a M4 receptor agonist wherein the use is combined computer-assisted psychosocial or behavioral therapy.

6.5. Methods of Making

The compounds provided herein may be made by a variety of methods, including standard chemistry. Suitable synthetic routes are depicted in the schemes below.

The compounds provided herein may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (see T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds provided herein.

Those skilled in the art will recognize if a stereocenter exists in the compounds provided herein. Accordingly, the compounds provided herein include both possible stereoisomers and includes not only racemic compounds but the individual enantiomers and/or diastereomers as well. When a compound provided herein is desired as a single enantiomer or diastereomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-Interscience, 1994).

The compounds provided herein can be prepared according to the sequence shown in Scheme 1 below.

Scheme 1

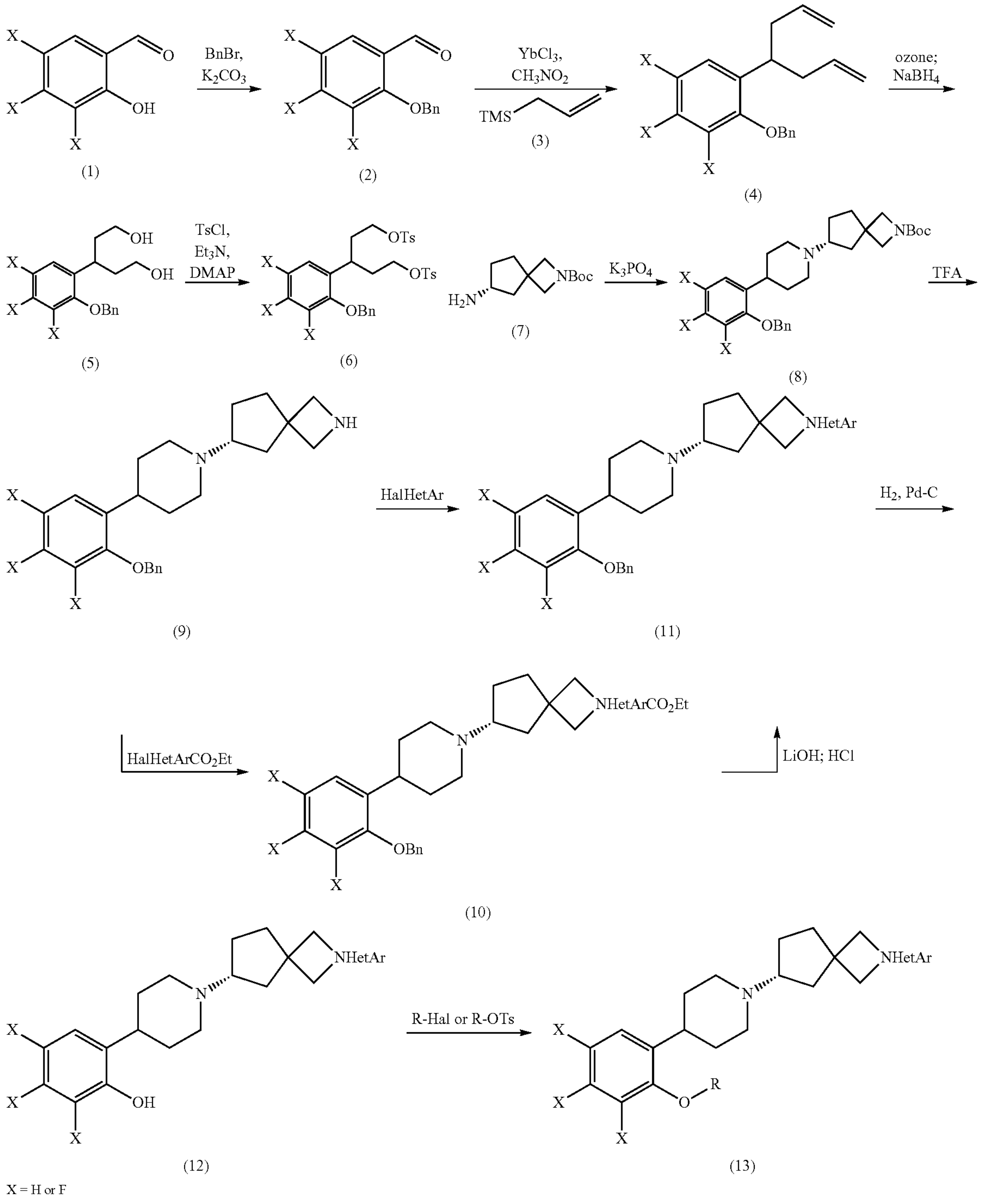

In Scheme 1, aldehyde 1 can be alkylated with benzyl bromide to generate protected aldehyde 2, which can then be allylated with allyltrimethylsilane with a Lewis acid such as ytterbium chloride to give the bis-allylated compound 4. The two vinyl groups can be oxidized with an oxidant such as ozone and in the subsequent presence of a hydride source such as sodium borohydride a diol such as compound 5 can be generated. The diol can then be activated with tosyl chloride to generate the active diol 6, which can react with an amine, such as amine 7, in the presence of a base such as potassium phosphate to give tertiary amine 8. This compound can be deprotected in the presence of an acid such as trifluoroacetic acid to generate a free amine, such as amine 9. The free amine can react with a heteroaryl halide under Buchwald-Hartwig or nucleophilic aromatic substitution conditions to yield a heteroaryl compound such as 11.

Alternatively, the heteroaryl group can contain an ethyl ester such as in 10, which can then be hydrolyzed with an aqueous base such as lithium hydroxide and then decarboxylated with an acid such as hydrochloric acid to give the decarboxylated heteroaryl 10. The phenol can then be deprotected such as by hydrogen and palladium catalysis to yield a free phenol such as 12, which can then be alkylated with a halide or tosylate to give compounds such as 13.

Alternatively, compounds provided herein can be prepared as depicted in Scheme 2 below.

Scheme 2

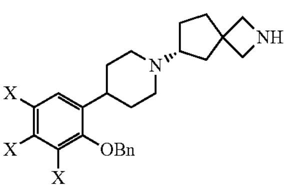

(9)

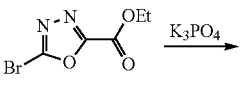

(14)

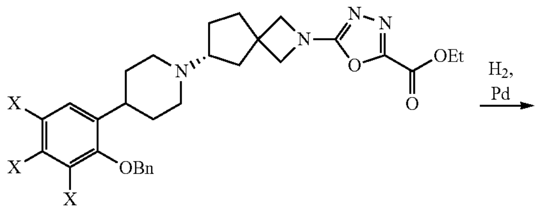

(15)

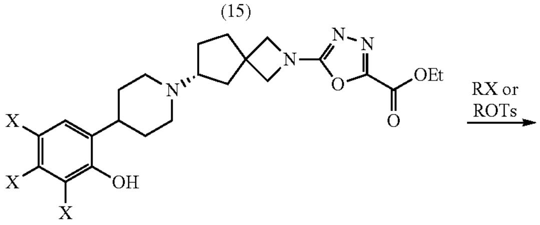

(16)

-continued

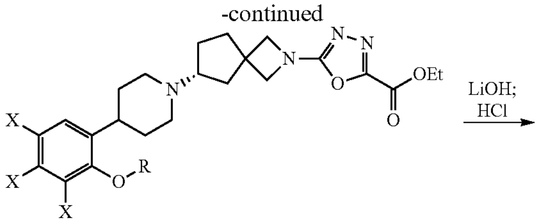

(17)

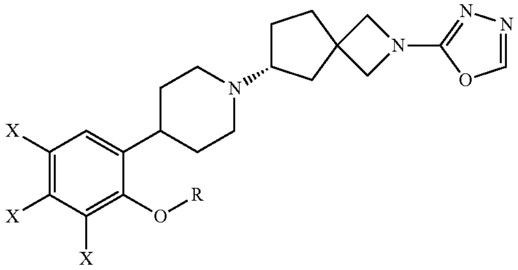

(18)

X = H or F

In Scheme 2, the free amine 9 can react with the bromo-oxadiazole 14 in the presence of a base such as potassium phosphate to generate oxadiazole 15. The benzyl group can subsequently be deprotected with hydrogen and palladium catalysis to yield a phenol such as 16 which can further react with an alkyl halide or tosylate to give substituted phenols such as 17. The ethyl group can then be hydrolyzed with an aqueous base such as lithium hydroxide and the resulting acid can be decarboxylated with an acid such as hydrochloric acid to generate mono-substituted oxadiazoles such as 18.

Alternatively, compounds provided herein can be prepared as shown in Scheme 3 below.

Scheme 3

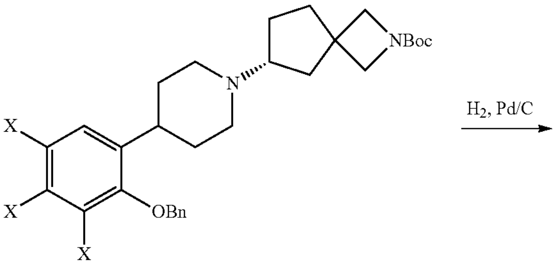

(8)

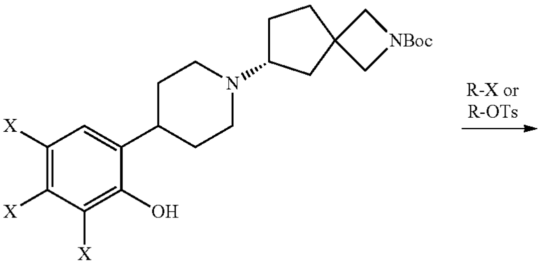

(19)

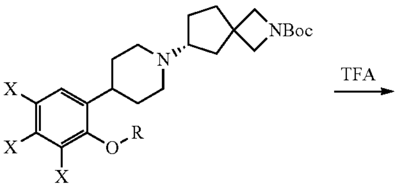

(20)

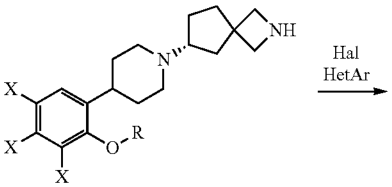

(21)

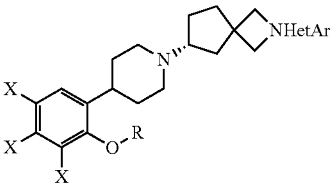

(23)

-continued

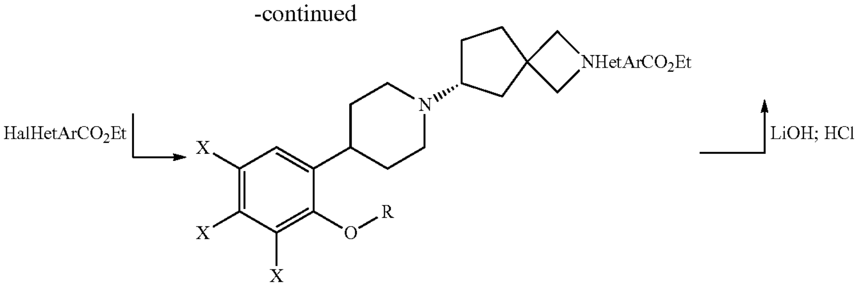

(22)

X = H or F

In Scheme 3, compounds such as 8 from Scheme 1 can be deprotected with hydrogen and palladium catalysis to generate free phenols such 19 that can be further elaborated with an alkyl halide or tosylate to yield a substituted phenol such as 20. The amine can then be deprotected with an acid such as trifluoroacetic acid to yield a free amine such as 21 that can react with a heteroaryl halide under Buchwald-Hartwig or nucleophilic aromatic substitution conditions to give a heteroaryl such as 23. Alternatively, free amine 21 can react with a heteroaryl halide also substituted with an ethyl ester to produce a compound such as 22. The ethyl ester can then be hydrolyzed with an aqueous base such as lithium hydroxide and the resulting acid can be decarboxylated with an acid such as hydrochloric acid to generate examples such as 23.

Alternatively, compounds provided herein can be prepared as shown in Scheme 4 below.

Scheme 4

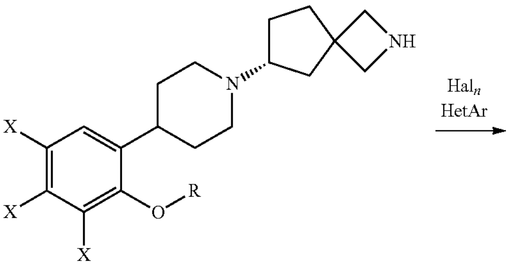

(21)

-continued

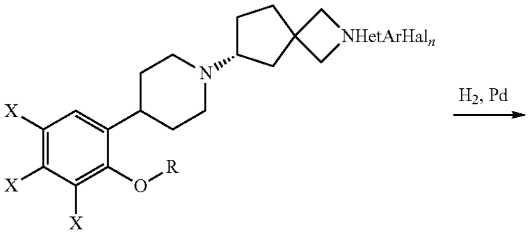

(24)

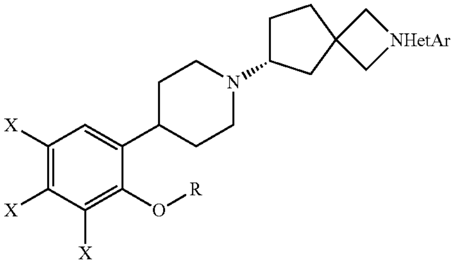

(25)

X = H or F

In Scheme 4, compounds such as 21 from Scheme 3 can react with heteroaryls containing multiple halogens to give substituted heteroaryls such as 24. These halogens can also be reduced with hydrogen under palladium catalysis to yield de-halogenated heteroaryls such as 25.

Scheme 5

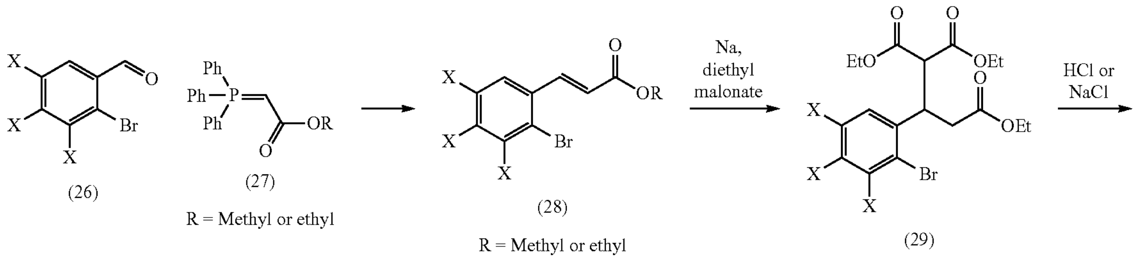

(26)

(27)

R = Methyl or ethyl (28)

R = Methyl or ethyl (29)

-continued

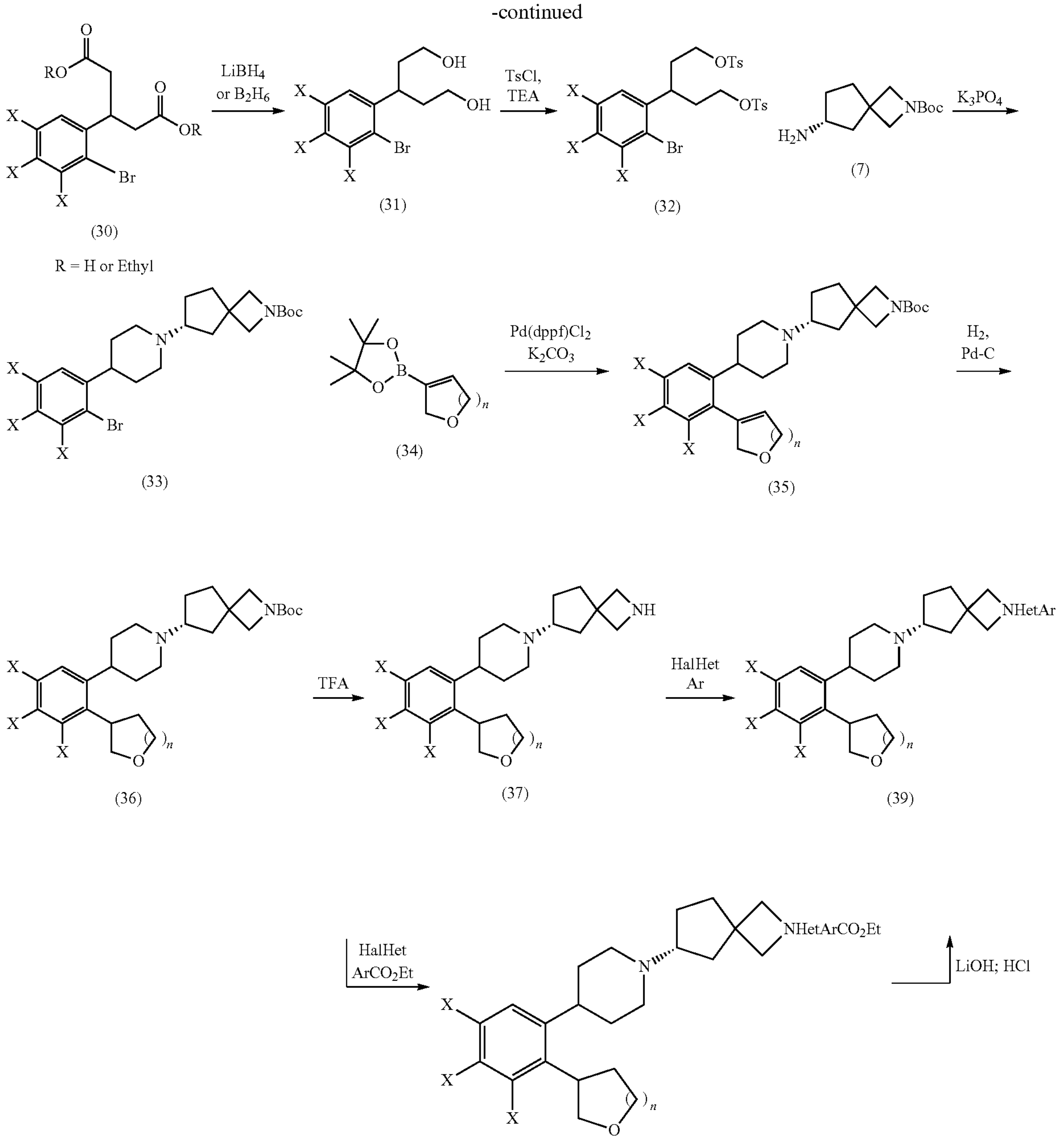

(30) R = H or Ethyl (31) (32) (7) (33) (34) (35) (36) (37) (39) (38)

In Scheme 5, an aldehyde such as 26 can react with a phosphorus reagent such as 27 to generate an unsaturated ester such as 28. The ester can then react with diethyl malonate to generate a triester such as 23 which can be decarboxylated with an acid such as hydrochloric acid or sodium chloride to generate a di-acid or di-ester such as 30. A diol such as 31 can then be generated with a reducing agent such as lithium borohydride or borane and the diol can be activated with tosyl chloride. Exposing di-tosylate 32 to an amine such as 7 in the presence of a base such as potassium phosphate can then yield a tertiary amine such as 33. The aryl bromide 33 can then be used as a substrate in a Suzuki-Miyaura cross coupling with a boronic ester such as 34 in the presence of palladium catalyst and base. An unsaturated ring such as 35 can then be reduced such as with hydrogen and palladium catalyst to yield a saturated ring such as 36. The amine can then be deprotected with an acid such as trifluoroacetic acid and the resulting free amine 37 can react with a heteroaryl halide under Buchwald-Hartwig or nucleophilic aromatic substitution conditions to yield examples such as 39. Alternatively, free amines such as 31 can react with a heteroaryl halide containing an ethyl ester to give an ester substituted heteroaryl such as 38. The ester can then be hydrolyzed with an aqueous base such as lithium hydroxide and the resulting acid can be decarboxylated to yield examples such as 39.

Alternatively, compounds provided herein can be prepared as shown in Scheme 6 below.

Scheme 6

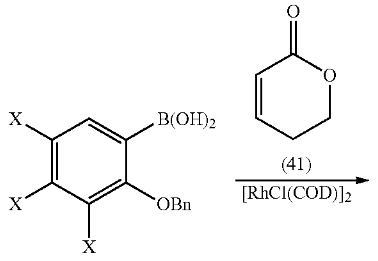

(40)

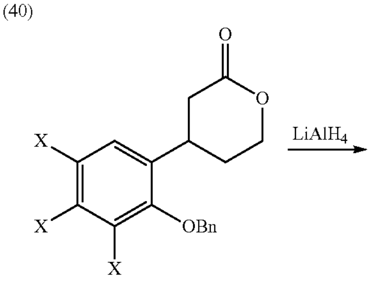

(42)

-continued

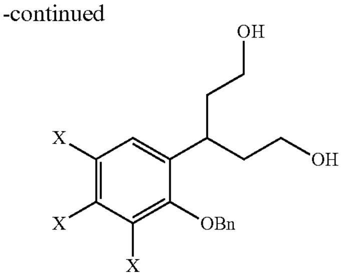

(43)

In Scheme 6, a boronic acid such as 40 can react with an unsaturated lactone such as 41 under rhodium catalysis to give a saturated lactone such as 42. The lactone can then be reduced with a reducing agent such as lithium borohydride to yield a diol such as 43. Diols such as 43 can then intersect with the synthetic route shown in Scheme 1.

Alternatively, compounds provided herein can be prepared as shown in Scheme 7 below.

Scheme 7

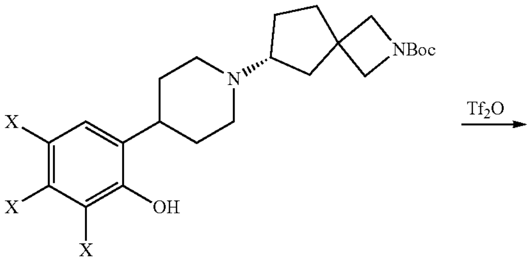

(19)

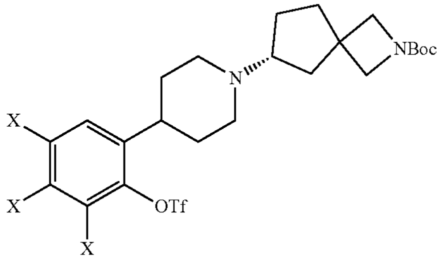

(44)

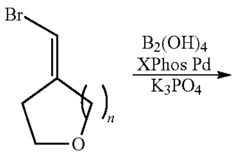

(45)

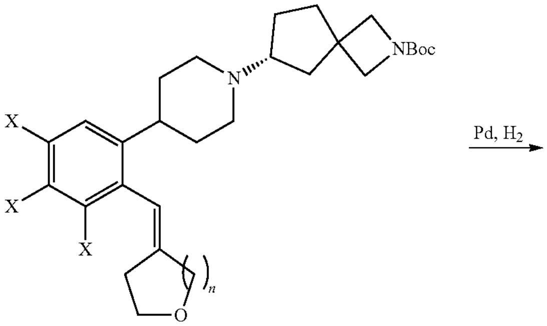

(46)

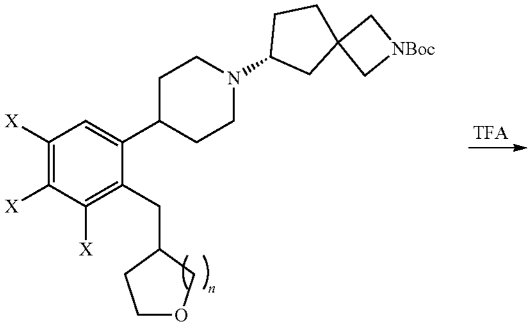

(47)

-continued

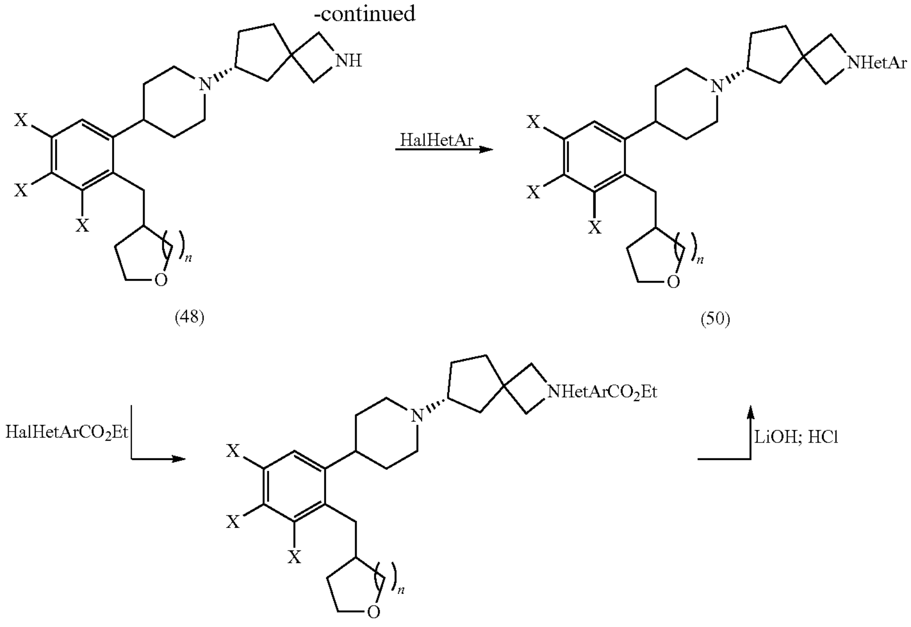

(48) (50) (49)

In Scheme 7, free phenols such as 19 can be activated as triflates such as 44. Triflates such as 44 can be transformed into boronic acid such as with tetrahydroxydiboron with palladium catalysis and the resulting boronic acid can react with vinyl bromides such as 45 to form unsaturated compounds such as 46. Compounds such as 46 can be reduced with hydrogen in the presence of palladium to generate saturated compounds such as 47 which can be deprotected with an acid such as TFA. The free amine generated can then react with a heteroaryl halide under Buchwald-Hartwig or nucleophilic aromatic substitution conditions to generate examples such as 50. Alternatively, the amine can react with a heteroaryl halide that contains an ethyl ester to generate an ester such as 49. The ester can then be hydrolyzed with an aqueous base such as lithium hydroxide and the resulting acid can then be decarboxylated with an aqueous acid such as HCl to give examples such as 50.

Scheme 8

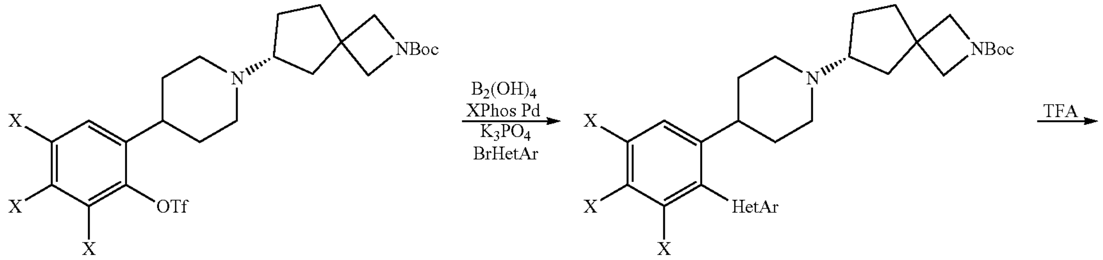

(44) (51)

-continued

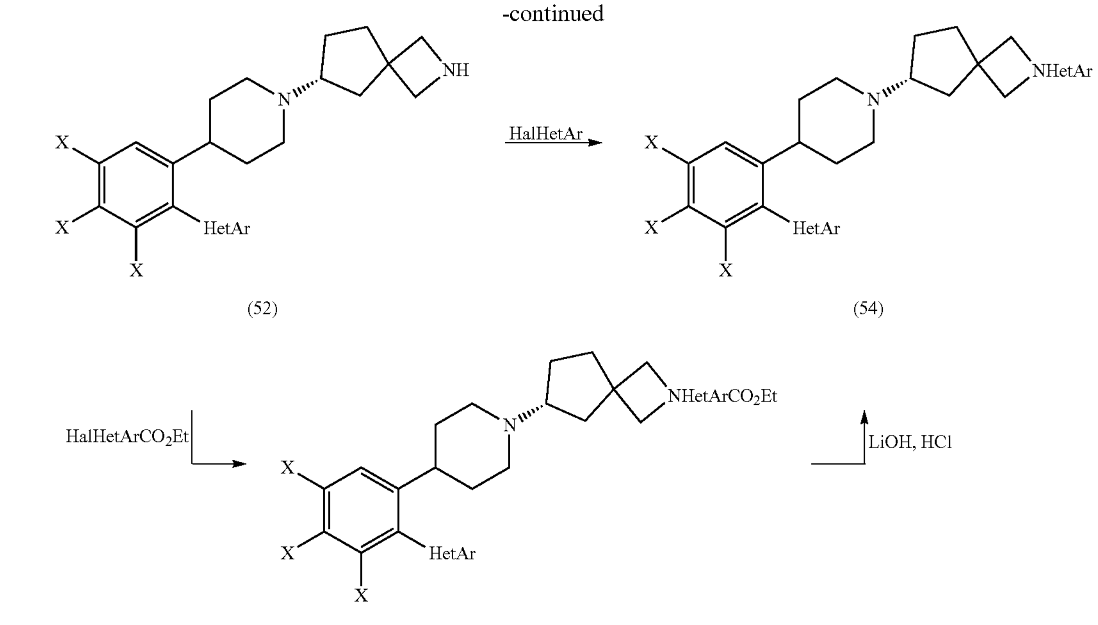

(52)

(54)

(53)

X = H or halide

In Scheme 8, aryl triflates such as 44 can be activated with tetrahydroxydiboron with palladium catalysis and then react with heteroaryl bromides in the presence of palladium to generate heteroaryl compounds such as 51. The amine can then be deprotected with an acid such as TFA to generate free amines such as 52 that can react with a heteroaromatic halide under Buchwald-Hartwig or nucleophilic aromatic substitution conditions to generate examples such as 54. Alternatively, the amine can react with a heteroaromatic halide that contains an ethyl ester to yield esters such as 53. The ester can then be hydrolyzed with an aqueous base such as lithium hydroxide and the resulting acid can be decarboxylated with an acid such as HCl to give examples such as 54.

Alternatively, compounds provided herein can be prepared as shown in Scheme 9 below.

Scheme 9

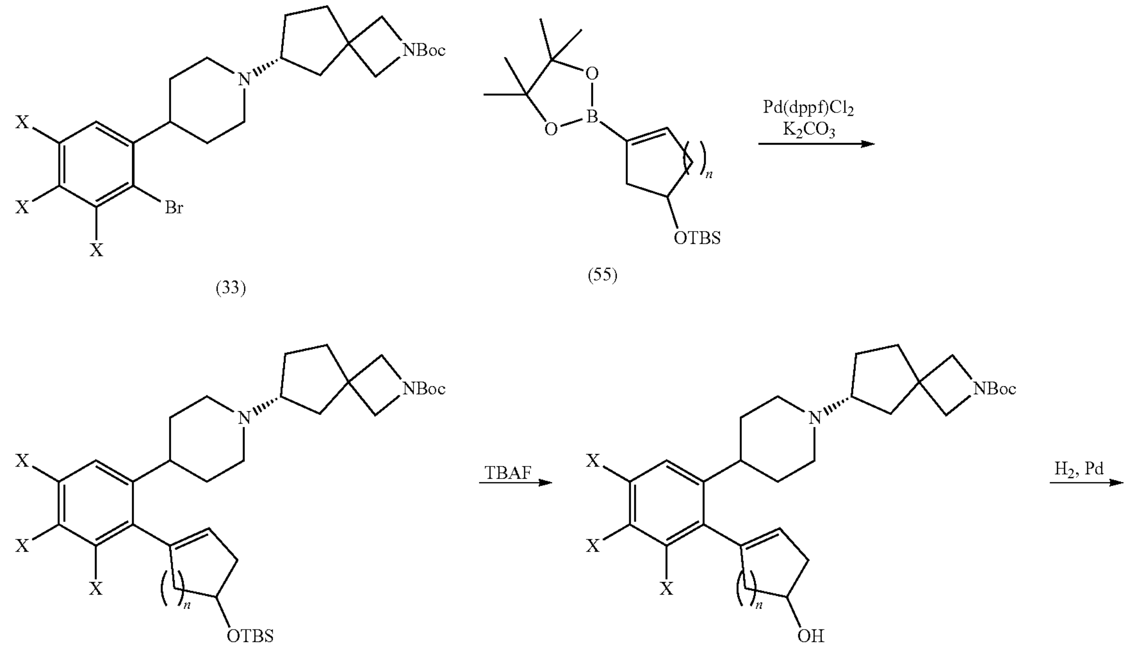

(33)

(55)

(56)

(57)

-continued

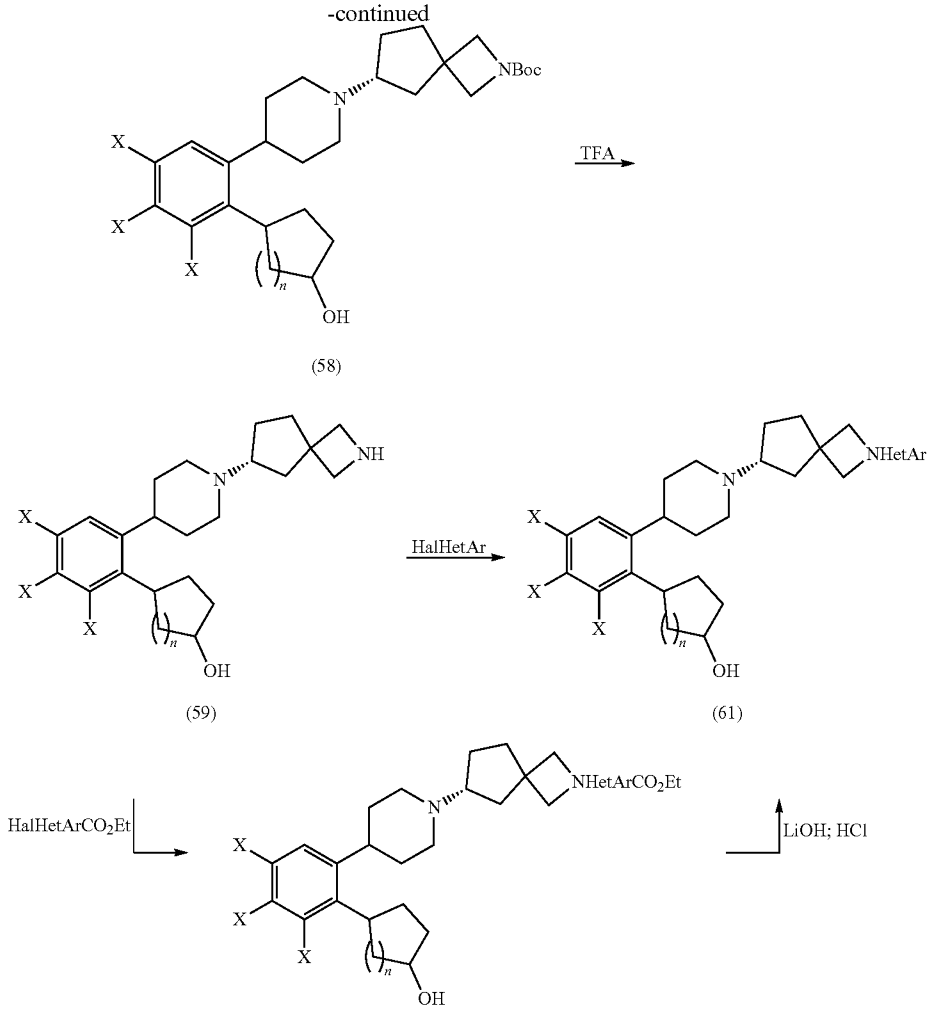

(58) (59) (61) (60)

X = H or halide

In Scheme 9, an aryl bromide such as 33 can be reacted with a cycloalkyl boronic acid such as 55 to give unsaturated rings such as 56. The alcohol can then be deprotected with a fluoride source such as tetrabutylammonium fluoride to give free alcohols such as 57 and the olefin can then be reduced with hydrogen and palladium catalysis to give saturated rings such as 58. The amine can then be deprotected with an acid such as trifluoroacetic acid and the resulting free amine 59 can react with a heteroaromatic halide to give examples such as 61. Alternatively, the amine can react with a heteroaromatic halide that contains an ester to give esters such as 60. The ester can then be hydrolyzed with an aqueous base such as lithium hydroxide and the resulting acid can then be decarboxylated with an acid such as HCl to give examples such as 61.

Alternatively, compounds provided herein can be prepared as shown in Scheme 10.

Scheme 10

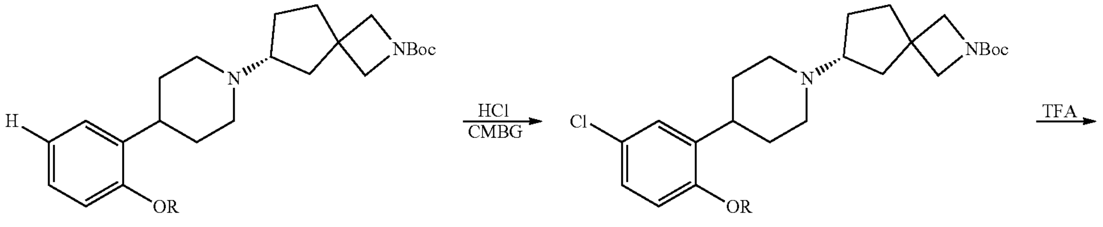

(62) (63)

-continued

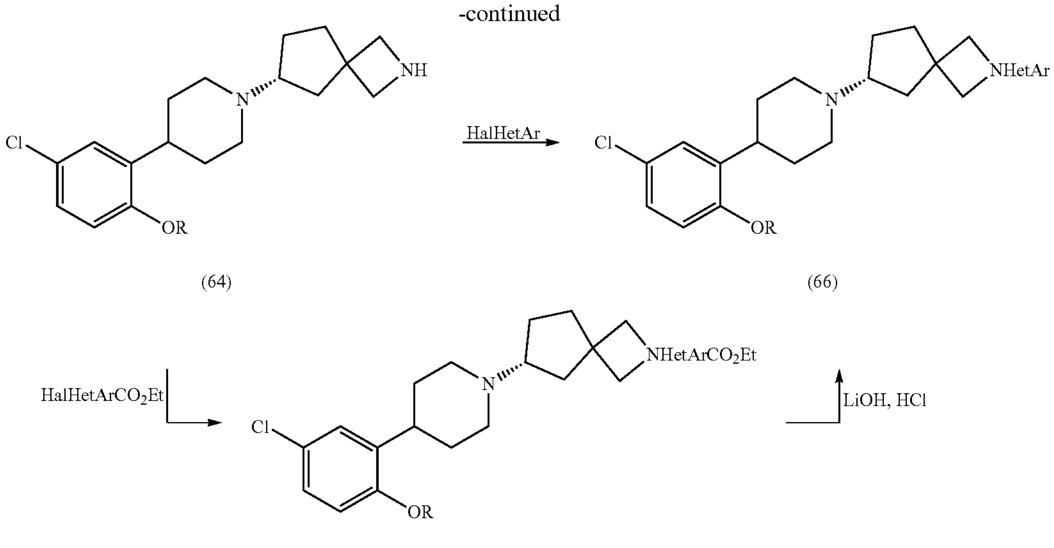

(64) (66) (65)

In Scheme 10, an intermediate with a hydrogen at the five position such as 62 can be chlorinated with a reagent such as CMBG in the presence of HCl to give chlorinated aryl rings such as 63. The Boc group can then be removed to give free amines such as 64 and the free amine can then react with a halogen containing heteroaromatic under Buchwald-Hartwig or nucleophilic aromatic substitution conditions to give examples such as 66. Alternatively, the amine can react with a heteroaromatic containing an ethyl ester to generate esters such as 65. The ester can then be hydrolyzed by an aqueous base such as lithium hydroxide and the resulting acid can be decarboxylated with an acid such as HCl to give examples such as 66.

Alternatively, compounds provided herein can be prepared as shown in Scheme 11.

Scheme 11

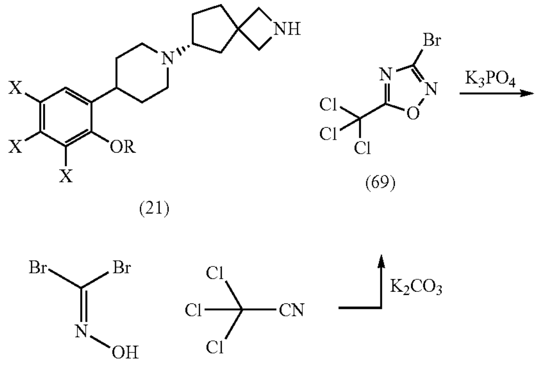

(21) (69) (67) (68)

-continued

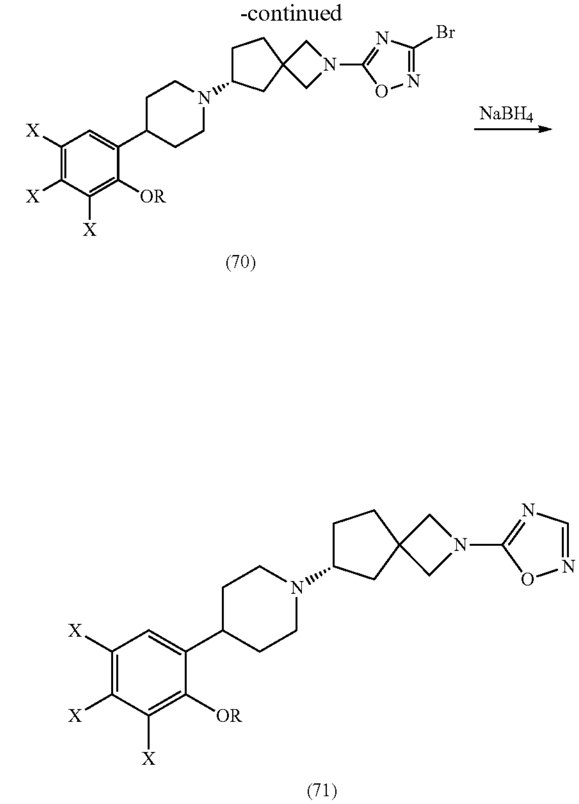

(70) (71)

X = H or halide

In Scheme 11, dibromo compounds such as 67 can be combined with nitriles such as 68 to generate oxadiazoles such as 69. These can be combined with free amines such as 21 to yield bromo oxadiazoles such 70. The bromine can then be removed with a reducing agent such as sodium borohydride to yield examples such as 71.

Alternatively, compounds provided herein can be prepared as shown in Scheme 12 below.

Scheme 12

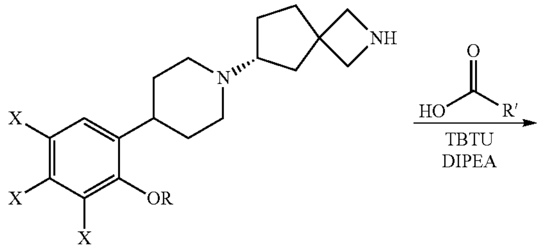

(21)

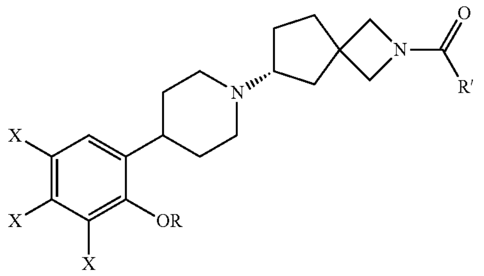

(72)

X = H or halide

In Scheme 12, free amines such as 21 can be reacted with an acid in the presence of an amide bond forming reagent such as TBTU and a base such as DIPEA to generate amides such as 72. Alternatively, compounds provided herein can be prepared as shown in Scheme 13 below.

Scheme 13

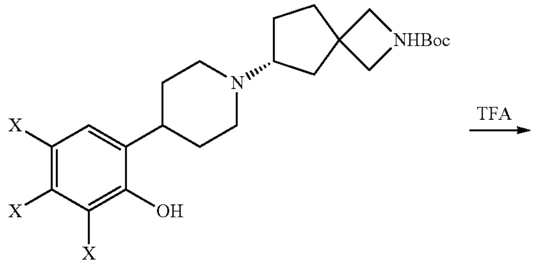

(19)

-continued

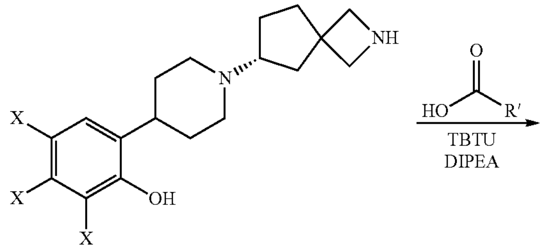

(73)

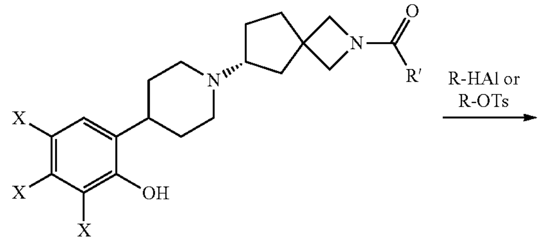

(74)

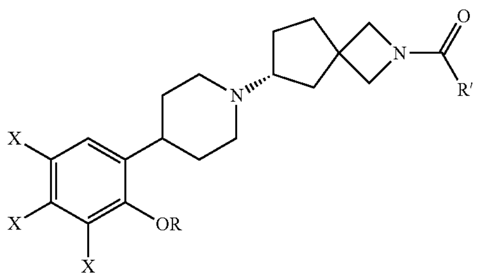

(75)

X = H or halide

In Scheme 13, protected amines such as 19 can be deprotected by an acid such as TFA and the resulting amines such as 73 can react with an acid in the presence of an amide bond forming reagent such as TBTU and a base such as DIPEA to generate amides such as 74. The free phenol can then be alkylated with an alkyl halide or tosylate to generate examples such as 75.

Alternatively, compounds provided herein can be prepared as shown in Scheme 14 below.

Scheme 14

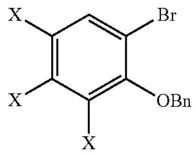

(76)

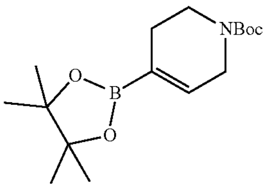

(77)

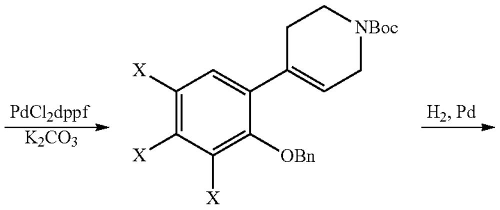

(78)

-continued

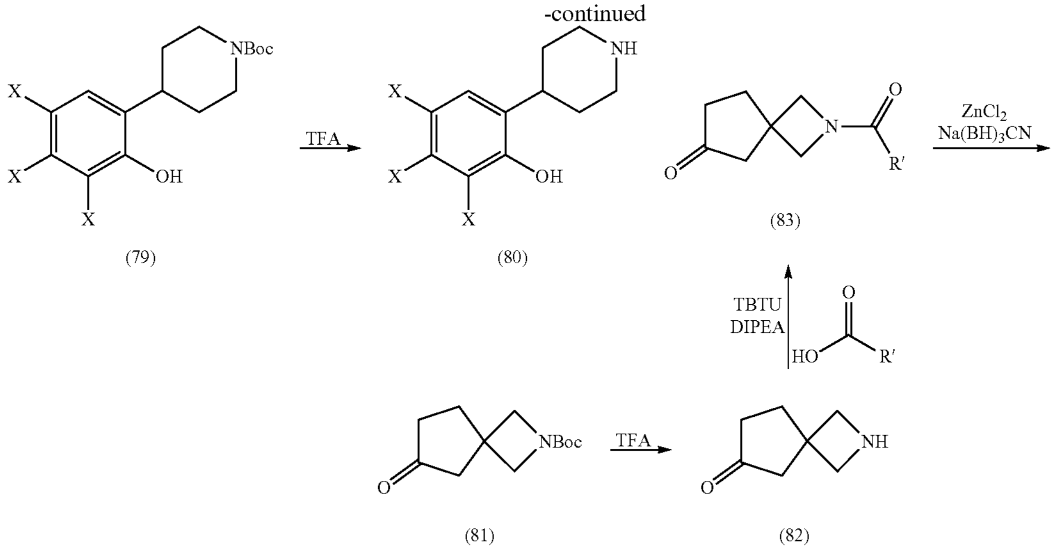

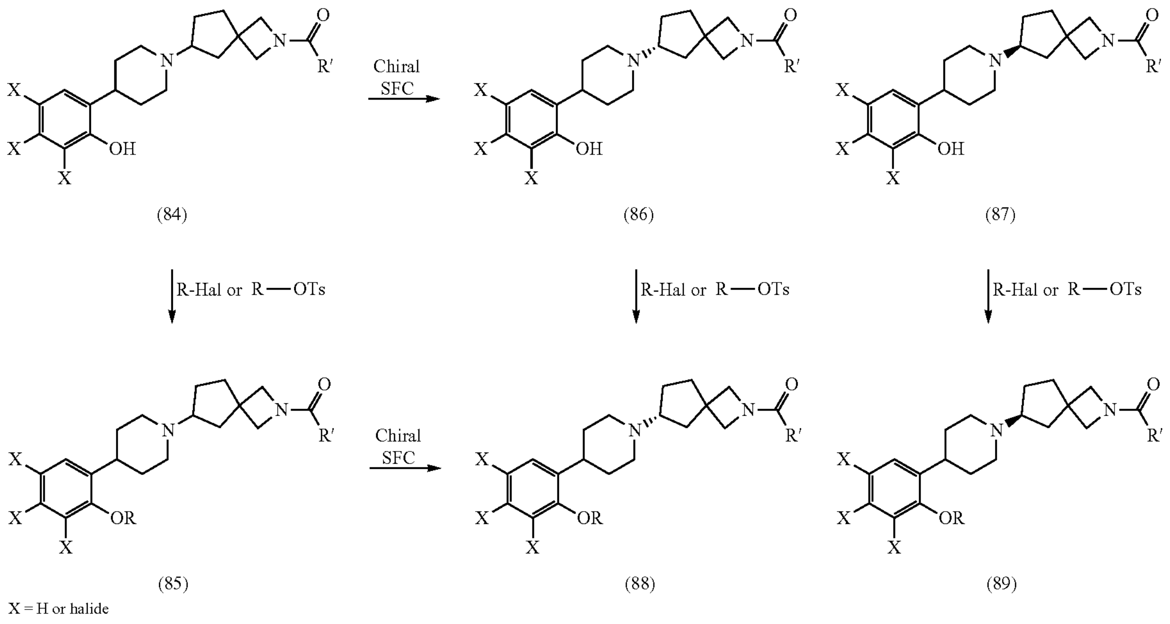

In Scheme 14, aryl bromides such as 76 can react with vinyl pinacol esters such as 77 under Suzuki-Miyaura conditions to generate unsaturated piperidines such as 78. The olefin can be reduced and the benzyl group can then be removed with hydrogen and palladium catalyst to generate phenols such as 79. The amine can then be deprotected with an acid such as TFA to generate free amines such as 80. Concurrently, amines such as 81 can be deprotected with an acid such as TFA and the resulting free amine 82 can react with an acid in the presence of an amide bond forming reagent such as TBTU and a base such as DIPEA to generate amides such as 83. Free amines such as 80 can then react with ketones such as 83 in the presence of a Lewis acid such as zinc chloride and a reducing agent such as sodium cyanoborohydride to generate tertiary amines such as 84. The phenol can then be alkylated to generated substituted phenols such as 85 and the individual enantiomers such as 88 and 89 can then be resolved through chiral SFC. Alternatively, the individual enantiomers of phenols such as 84 can be separated using chiral SFC to generate the individual enantiomers such as 86 and 87 and the free phenol in compounds such as this can react with an alkyl halide or alkyl tosylate to generate single enantiomers such as 88 and 89.

Alternatively, compounds provided herein can be prepared as show in Scheme 15 below.

Scheme 15

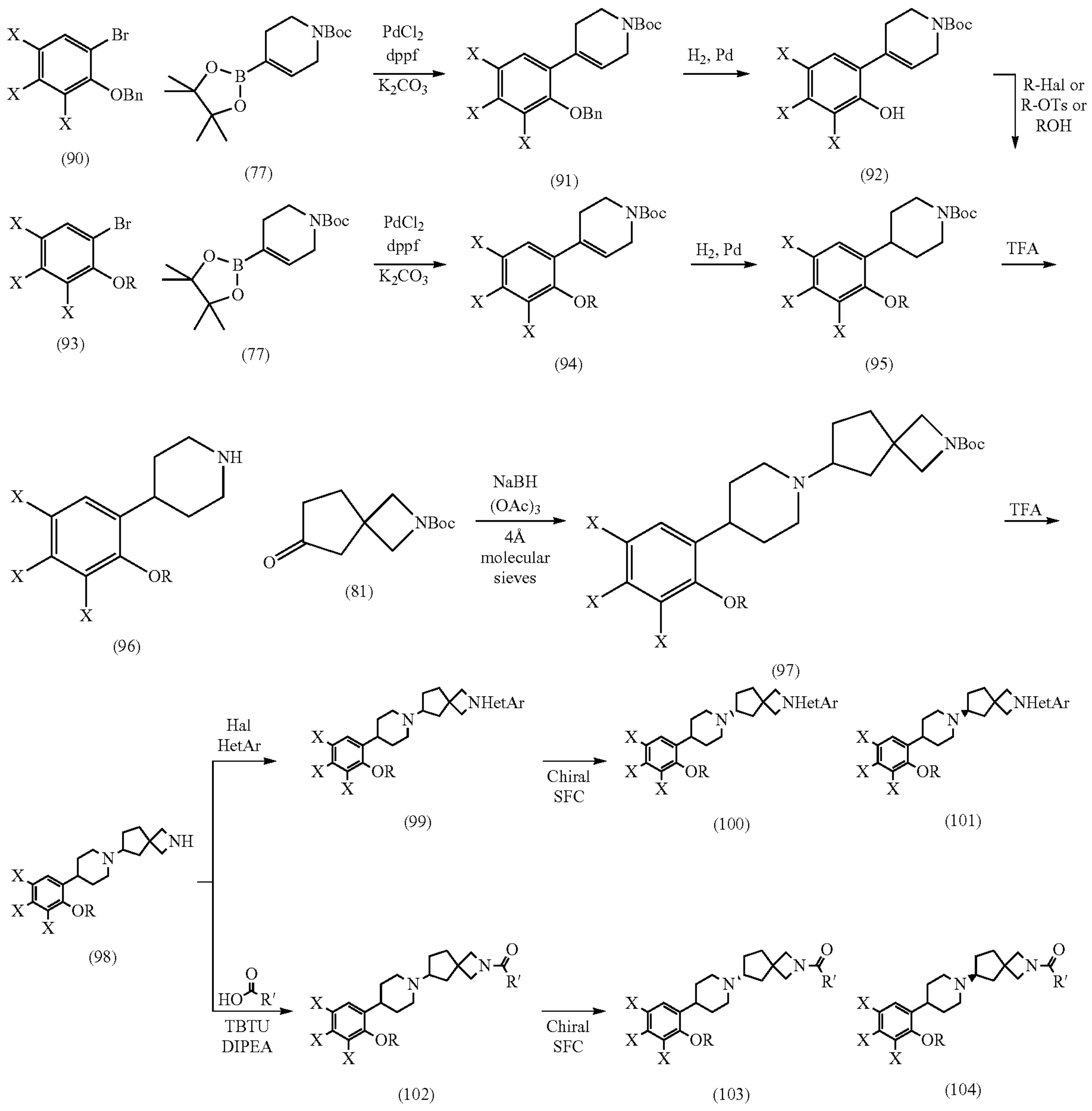

X = H or halide

In Scheme 15 aryl bromides such as 90 can react with pinacol boronic esters such as 77 under Suzuki-Miyaura conditions to generate unsaturated piperidines such as 91. The benzyl group can be reduced with hydrogen and palladium catalysis to generate free phenols such as 92 and the phenol can react with an alkyl halide or alkyl tosylate or alcohol under Mitsunobu conditions to generate substituted phenols such as 95. Alternatively, aryl bromides such as 93 can be reacted with a pinacol boronic ester such as 77 under Suzuki-Miyaura conditions to generate unsaturated piperidines such as 94. The olefin can be reduced with hydrogen and palladium catalysis to give compounds such as 95 which can be deprotected with an acid such as TFA to generate free amines such as 96. The amine can react with ketones such as 81 with a reducing agent such as sodium triacetoxyborohydride and a de-hydrating agent such as 4A molecular sieves to generate tertiary amines such as 97. The amine can then be deprotected with an acid such as TFA to generate free amines such as 98. The free amine can react with a heteroaromatic halide under Buchwald-Hartwig or nucleophilic aromatic substitution conditions to generate heteroaryls such as 99. These compounds can then be resolved into individual enantiomers such as 100 and 101 using chiral SFC. Alternatively, free amines such as 98 can react with an acid in the presence of an amide bond forming reagent such as TBTU and a base such as DIPEA to generate amides such as 102. The individual enantiomers such as 103 and 104 can then be resolved with chiral SFC.

Alternatively, compounds provided herein can be prepared as described in Scheme 16 below.

Scheme 16

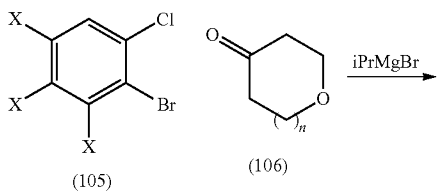

(105) (106)

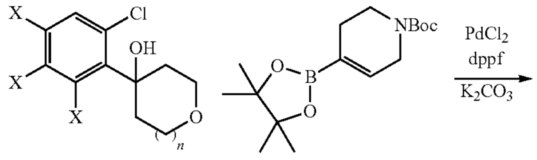

(107) (77)

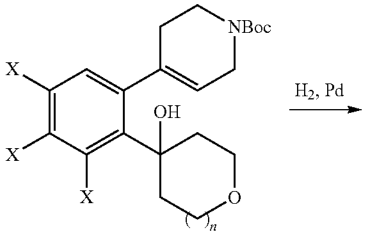

(108)

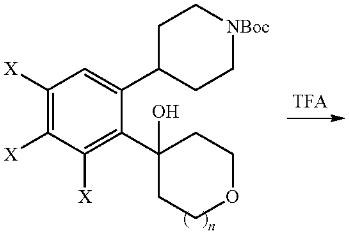

(109)

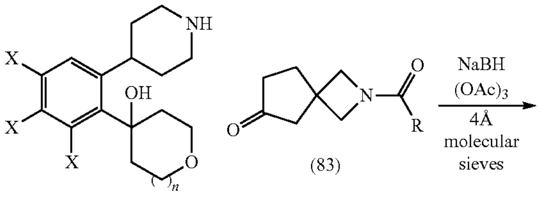

(110) (83)

-continued

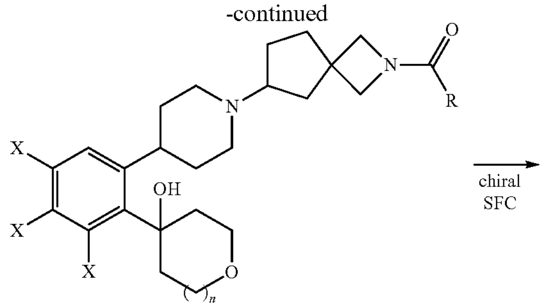

(111)

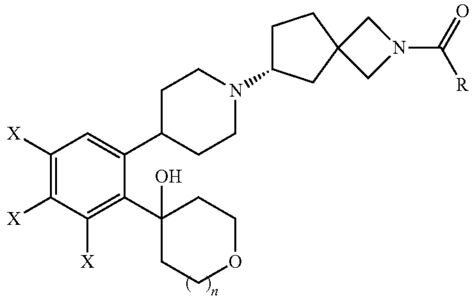

(112)

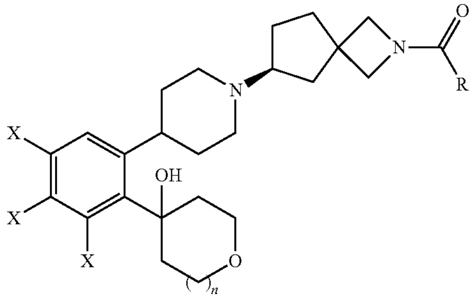

(113)

X = H or halide

In Scheme 16, aryl bromides such as 105 can react with ketones such as 106 in the presence of an organometallic such as iso-propyl magnesium bromide to yield tertiary alcohols such as 107. The aryl chloride can then react with pinacol boronic esters such as 77 under Suzuki-Miyaura conditions to yield unsaturated piperidines such as 108. The olefin can then be reduced with hydrogen and palladium catalysis to yield piperidines such as 109 and the amine can be deprotected with an acid such as TFA to generate free amines such as 110. The amine can then react with ketones such as 83 in the presence of a dehydrating agent such as 4A molecular sieves and a reducing agent such as sodium triacetoxy borohydride to yield racemic tertiary amines such as 111. The individual enantiomers 112 and 113 can then be resolved with chiral SFC.

Alternatively, compounds provided herein can be prepared as shown in Scheme 17 below.

Scheme 17

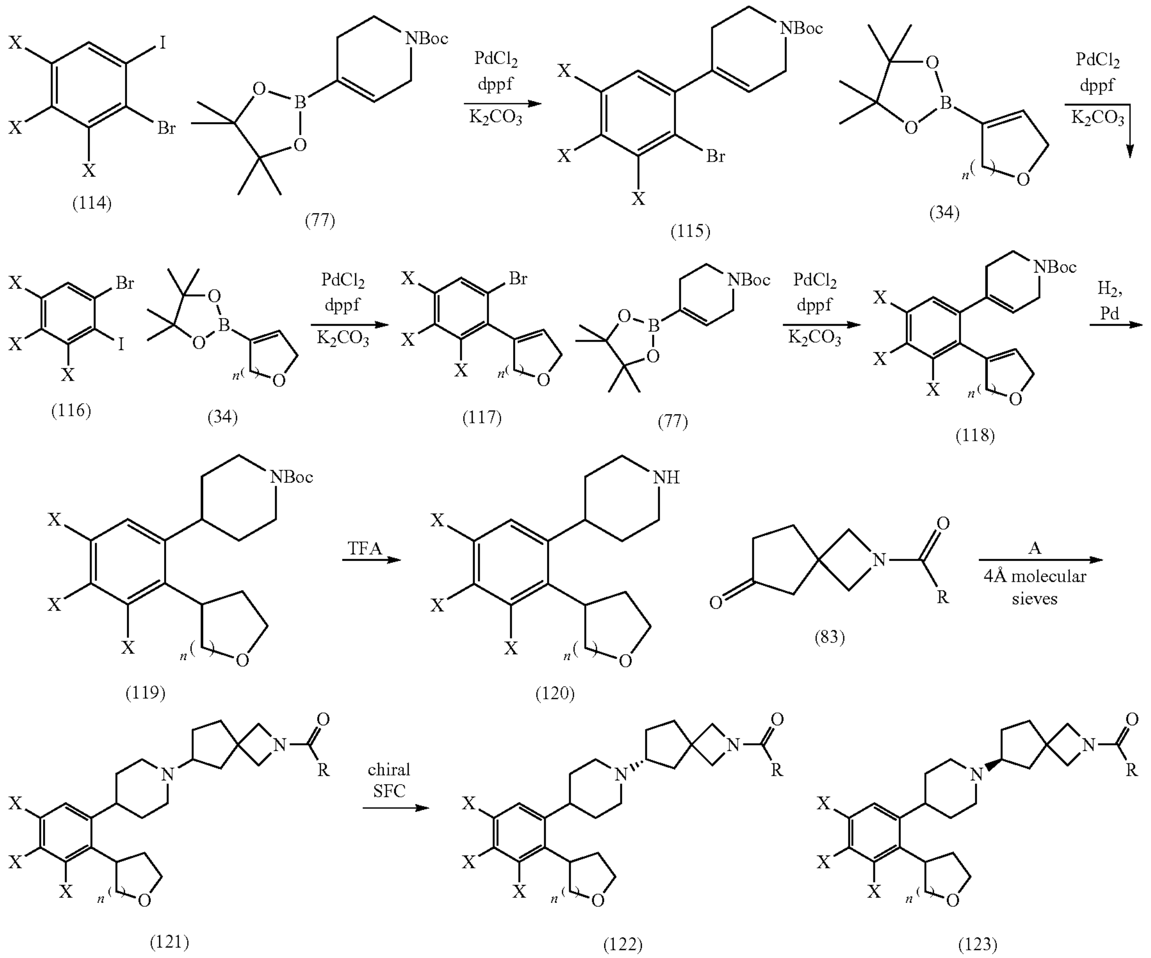

(114) (77) (115) (34) (116) (34) (117) (77) (118) (119) (120) (83) (121) (122) (123)

X = H or halide

In Scheme 17, aryl iodides such as 114 can react with pinacol boronic esters such as 77 under Suzuki-Miyaura conditions to generate unsaturated piperidines such as 115. The aryl bromide can then react with pinacol boronic esters such as 34 under Suzuki-Miyaura conditions to generate unsaturated rings such as 118. Alternatively, aryl iodides such as 116 can react with pinacol esters such as 34 under Suzuki-Miyaura conditions to yield unsaturated rings such as 117. The aryl bromide can then react with pinacol boronic esters such as 77 under Suzuki-Miyaura conditions to generate unsaturated piperidines such as 118. The olefin can then be reduced with hydrogen and palladium catalysis to generate saturated piperidines such as 119 which can be deprotected with an acid such as TFA to generate free amines such as 120. The amine can then react with ketones such as 83 in the presence of a dehydrating agent such as 4A molecular sieves and a reducing agent such as sodium triacetoxy borohydride to yield tertiary amines such as 121. The individual enantiomers 122 and 123 can then be resolved with chiral SFC. Alternatively, compounds provided herein can be described as described in Scheme 18 below.

Scheme 18

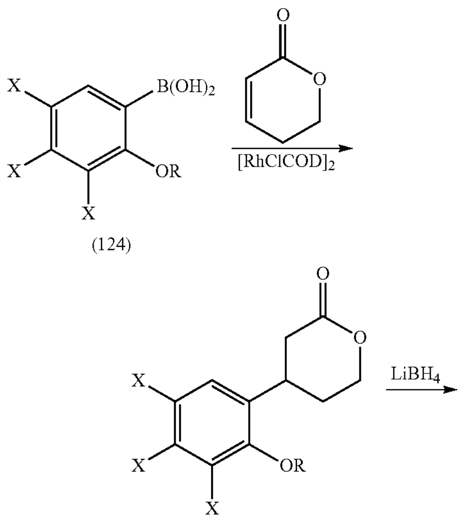

(124) (125)

-continued

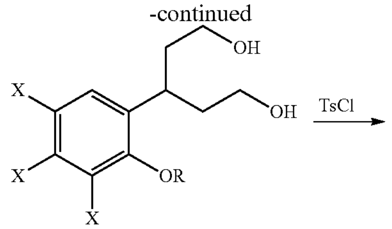

(126)

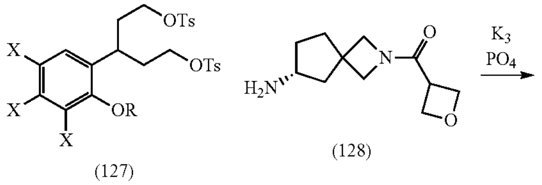

(127)

(128)

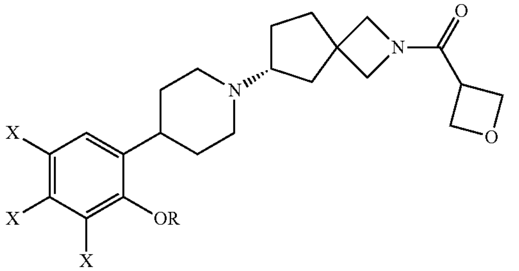

(129)

X = H or F

In Scheme 18, boronic acid 124 can be combined with an unsaturated lactone under rhodium catalysis to generate saturated lactones such as 125. The lactone can then be reduced to a diol such as 126 using a reducing agent such as lithium borohydride and the resulting diol can be activated as a bis-tosylate as 127. The activated diol can then react with a primary amine such as 128 in the presence of a based such as potassium phosphate to give compounds such as 129.

7. INCORPORATION BY REFERENCE

The entire disclosure of each of the patent documents and scientific articles cited herein are incorporated by reference for all purposes.

8. EXAMPLES

The present disclosure is further illustrated by the following examples, which are intended to be illustrative only and not limiting in any way. It is to be understood that resort may be had to various other embodiments, modifications, and equivalents thereof which may suggest themselves to those skilled in the art without departing from the spirit of the present disclosure and/or scope of the appended claims.

8.1. Synthesis of Intermediates and Examples

Abbreviations used are those conventional in the art or the following:

Å angstrom(s)
AcOH acetic acid
ATP adenosine triphosphate
AUC area under curve
BINAP (2,2'-bis(diphenylphosphino)-1,1'-binaphthyl)
BOC tert-Butyloxycarbonyl
BrettPhos Pd G3 [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate
tBu tert-butyl
C Celsius
cAMP cyclic adenosine mono-phosphate
CBMG 2-Chloro-1,3-bis(methoxycarbonyl)guanidine
CDI carbonyldiimidazole
DAST Diethylaminosulfur trifluoride
DCE 1,2 dichloroethane
DCM dichloromethane
DEA Diethylamine
DEAD Diethyl azodicarboxylate
DIEA/DIPEA N, N-Diisopropylethylamine
DIAD Diisopropyl azodicarboxylate
DME 1,2-dimethoxyethane
DMEM Dulbecco's Modified Eagle Medium
DMF N,N-dimethylformamide
DMSO dimethylsulfoxide
DPBS Dulbecco's Phosphate Buffered Saline
EtOAc Ethyl acetate
EtOH Ethyl alcohol
FBS Fetal Bovine Serum
FCC flash column chromatography
g gram(s)
h/hr hour(s)
HATU 1-[Bis(dimethylamino)methylene]-1H-1,2,3-triazolo[4,5-b]pyridinium 3-oxide Hexafluorophosphate
HBSS Hanks' balanced salt solution
HBTU 1-[bis(dimethylamino)methylene]-1H benzotriazoliumhexafluorophosphate(1-) 3-oxide
HEPES 4-(2-hydroxyethyl)-1-piperazineethanesulfonic acid)
HOBt 1-hydroxy-7-azabenzotriazole
HPLC high pressure liquid chromatography
Hz Hertz
IPA isopropyl alcohol
J coupling constant
kg kilogram(s)
L liter(s)
LCMS liquid chromatography and mass spectrometry
Me Methyl
MHz Megahertz
mm millimeter(s)
mM millimolar
MTBE methyl tert-butyl ether
MS mass spectrometry
min minute(s)
mg milligram(s)
mL milliliter(s)
mmol millimole(s)
m/z mass to charge ratio
nm nanometer(s)
nM nanomolar
NMR nuclear magnetic resonance
Pd palladium
Pd/C, Pd—C palladium on carbon
$Pd(dba)_2$ bis(dibenzylideneacetone)palladium(0)
$Pd_2(dba)_3$ tris(dibenzylideneacetone)dipalladium(0)
$Pd(dppf)Cl_2$ dichloro[1,1'-bis(diphenylphosphino)ferrocene]palladium(II)
PE petroleum ether
ppm parts per million
psi pounds per square inch
rac racemic RB round bottom
rpm revolutions per minute
RT room temperature
Rt retention time
RuPhos Pd G2 Chloro(2-dicyclohexylphosphino-2',6'-diisopropoxy-1,1'-biphenyl)[2-(2'-amino-1,1'-biphenyl)] palladium(II)
SCX strong cation exchange
SFC Supercritical fluid chromatography
TBTU 2-(1H-Benzotriazole-1-yl)-1,1,3,3-tetramethylaminium tetrafluoroborate
TC tissue culture
TEA triethylamine
TFA trifluoroacetic acid
THE tetrahydrofuran
TPGS-750-M DL-α-Tocopherol methoxypolyethylene glycol succinate solution
μL microliter(s)
μM micromolar
UPLC ultra performance liquid chromatography
UV ultraviolet
Xantphos 4,5-Bis(diphenylphosphino)-9,9-dimethylxanthene
Xphos Pd G2 Chloro(2-dicyclohexylphosphino-2',4',6'-triisopropyl-1,1'-biphenyl)[2-(2'-amino-1,1'-biphenyl)] palladium(II)

General Procedures:

Where no preparative route is described, the material is commercially available. Commercial reagents were used without additional purification unless otherwise stated. Room temperature (RT) is approximately 20-25° C. $^1$H NMR were recorded at 400 MHz on a Bruker instrument and processed with mNOVA. Chemical shifts are reported as parts per million (ppm) relative to tetramethylsilane and coupling constants (J) are reported in Hertz. Abbreviations for multiplicity are: s=singlet, d=doublet, t=triplet, q=quartet, dd=doublet of doublet, dt=doublet of triplets, br=broad.

LCMS Method 1:

Instrument: Waters Acquity UPLC, photodiode array detector; Column: AcQuity UPLC BEH $C_{18}$ 1.7 μm, 21×30 mm; 2 min run time, 2% solvent B from 0 to 0.1 min, 2→98% solvent B:solvent A from 0.1 to 1.8 min, 98% solvent B for 0.2 min. Solvents: Solvent A=0.1% formic acid in water (v/v), solvent B=0.1% formic acid in acetonitrile (v/v). Injection volume 2-5 uL; UV detection array 210-400, Mass detection 120-1250 (electrospray ionization); column at 50° C.; flow rate 1.0 mL/min.

LCMS Method 2:

Instrument: Waters Acquity UPLC, photodiode array detector; Column: AcQuity UPLC BEH $C_{18}$ 1.7 μm 21×50 mm; 2 min run time, 2% solvent B from 0 to 0.1 min, 2→98% solvent B:solvent A from 0.1 to 1.8 min, 98% solvent B for 0.2 min. Solvents: Solvent A=5 mM ammonium hydroxide in water, solvent B=5 mM ammonium hydroxide in acetonitrile. Injection volume 2-5 uL; UV detection array 210-400, Mass detection 120-1250 (electrospray ionization); column at 50° C.; flow rate 1.0 mL/min.

LCMS Method 3:

Instrument: Waters Acquity UPLC, photodiode array detector; Column AcQuity UPLC BEH $C_{18}$ 1.7 μm 21×30 mm; 5.2 min run time, 2→98% solvent B:solvent A from 0 to 5.15 min, 98% solvent B from 5.15 to 5.20 min. Solvents: Solvent A=0.1% formic acid in water (v/v), solvent B=0.1% formic acid in acetonitrile (v/v). Injection volume 2-5 uL; UV detection array 210-400, Mass detection 120-1600; column at 50° C., flow rate 1.0 mL/min.

LCMS Method 4:

Instrument: Waters Acquity UPLC, photodiode array detector; Column AcQuity UPLC BEH $C_{18}$ 1.7 μm 21×30 mm; 5.2 min run time, 2→98% solvent B:solvent A from 0 to 5.15 min, 98% solvent B from 5.15 to 5.20 min. Solvents: Solvent A=5 mM ammonium hydroxide in water, solvent B=5 mM ammonium hydroxide in acetonitrile). Injection volume 2-5 uL; UV detection array 210-400, Mass detection 120-1600; column at 50° C., flow rate 1.0 mL/min.

LCMS Method 5:

Instrument: Agilent 1200 LC/G1956A, diode array detector; Column: Chromolith Flash Cis, 1.6 micron 2×25 mm; 1.5 minute run time, 5-95% solvent B: solvent A from 0→1.2 minutes and then 95% solvent B from 1.21→1.5 minutes. Solvents: Solvent A=0.0375% TFA in Water (v/v), Solvent B=0.01875% TFA in Acetonitrile (v/v). Injection volume 2-5 uL; UV detection 220 and 254 nM, Mass detection 100-1000 (electrospray ionization); column at 50° C.; Flow rate 1.5 mL/min.

LCMS Method 6:

Instrument: SHIMADZU LCMS-2020, photo diode array detector; Column: Kinetex EVO Cis, 5 uM, 1×30 mm; 1.55 minute run time, 5→95% solvent B:solvent A from 0→1.20 minutes and then 95% solvent B from 1.21 minutes to 1.55 minutes. Solvents: Solvent A=0.025% $NH_4OH$ in water/v), Solvent B=acetonitrile. Injection volume 2-5 uL; UV detection 220 and 254 nM, Mass detection 100-100 (electrospray ionization); column at 40° C.; Flow rate 1.5 mL/min.

Intermediate 1A: 3-(2-(benzyloxy)phenyl)pentane-1,5-diyl bis(4-methylbenzenesulfonate)

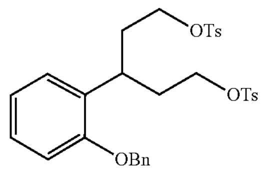

Step 1: 4-(2-(benzyloxy)phenyl)tetrahydro-2H-pyran-2-one

Potassium hydroxide (3.95 g, 70.3 mmol) in water (17.50 mL) was added dropwise to a solution of $[RhCl(COD)]_2$ (0.347 g, 0.703 mmol), (2-(benzyloxy)phenyl)boronic acid (commercially available, 22.46 g, 98 mmol) and 5,6-dihydro-2H-pyran-2-one (commercially available, 6.06 mL, 70.3 mmol) in 1,4-dioxane (175 mL) at 0° C. over a period of 2 mins. The temperature of reaction was then raised to 35° C. and stirred for 16 h. The reaction was diluted with EtOAc (200 mL) and 2M HC (50 mL). The aqueous solution was separated and back extracted with EtOAc (50 mL). The combined organic layers were dried over $MgSO_4$ and the solvent was removed under reduced pressure. The crude mixture was then purified by FCC (0→60% EtOAc/heptanes) to yield the title compound (19.49 g, 68.3 mmol).

LCMS: Rt=1.03 min (LCMS Method 1); MS m/z 283.5 $[M+H]^+$.

$^1$H NMR (400 MHz, $CD_3OD$) δ 7.49-7.27 (m, 5H), 7.20 (ddd, J=14.8, 7.5, 1.8 Hz, 2H), 7.05 (dd, J=8.1, 1.2 Hz, 1H), 6.99-6.89 (m, 1H), 5.13 (s, 2H), 4.49-4.27 (m, 2H), 3.71-

3.50 (m, 1H), 2.85 (dd, J=17.2, 6.4 Hz, 1H), 2.68 (dd, J=17.2, 9.8 Hz, 1H), 2.10 (m, 2H).

Step 2: 3-(2-(benzyloxy)phenyl)pentane-1,5-diol

Lithium aluminum hydride (76 mL, 76 mmol, 1M in THF) was added to a stirred solution of 4-(2-(benzyloxy) phenyl)tetrahydro-2H-pyran-2-one (19.49 g, 69.0 mmol) in anhydrous THE (400 mL) at 0° C. and then the reaction mixture was stirred for 2 h at 0° C. The reaction was quenched by water (10 mL) at −5° C. until gas production ceased and then a solution of NaOH (25 g) in water (25 mL) was portion-wise added to the mixture at 0° C. $Na_2SO_4$ (300 g) was next added to the reaction mixture and was stirred for 60 min. The mixture was filtered and the solvent was removed under reduced pressure. The crude product was purified by FCC (0-10% MeOH/DCM) to yield the title compound (19.3 g, 64.1 mmol).

LCMS: Rt=0.85 min (LCMS Method 1); MS m/z 287.3 $[M+H]^+$.

$^1H$ NMR (400 MHz, $CDCl_3$) δ 7.51-7.31 (m, 5H), 7.26-7.16 (m, 2H), 7.07-6.95 (m, 2H), 5.11 (s, 2H), 3.61-3.35 (m, 5H), 1.92 (m, 4H), 1.66 (s, 2H).

Step 3: 3-(2-(benzyloxy)phenyl)pentane-1,5-diyl bis(4-methylbenzenesulfonate)

To the solution of 3-(2-(benzyloxy)phenyl)pentane-1,5-diol (19.31 g, 67.4 mmol) and triethylamine (41.4 mL, 297 mmol) in MeCN (40 mL) at −5° C. was added TsCl (28.3 g, 148 mmol) and DMAP (0.824 g, 6.74 mmol). After addition, the reaction was stirred at RT for 16 h. The solvent was removed under reduced pressure. The crude product was dissolved in DCM (200 mL) and washed with water (25 mL) and brine (25 mL) then dried over $Na_2SO_4$ and filtered. The DCM was removed under reduced pressure and the crude was purified by FCC (0→50% EtOAc/heptanes) to yield the title compound.

LCMS: Rt=1.37 min (LCMS Method 2).

$^1H$ NMR (400 MHz, $CDCl_3$) δ 7.74-7.63 (m, 4H), 7.46-7.33 (m, 5H), 7.30 (s, 4H), 7.20-7.13 (m, 1H), 6.99-6.72 (m, 3H), 5.00 (s, 2H), 4.01-3.61 (m, 4H), 3.15 (m, 1H), 2.45 (s, 6H), 2.03 (m, 2H), 1.89 (m, 2H).

Intermediate 1B: 3-(2-(benzyloxy)-5-fluorophenyl) pentane-1,5-diyl bis(4-methylbenzenesulfonate)

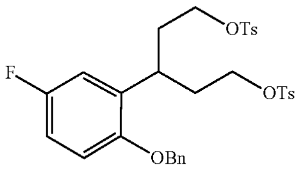 [SMILES: Cc1ccc(S(=O)(=O)OCCC(CCOS(=O)(=O)c2ccc(C)cc2)c2cc(F)ccc2OCc2ccccc2)cc1]

Step 1: 4-(2-(benzyloxy)-5-fluorophenyl)tetrahydro-2H-pyran-2-one (5-(benzyloxy)-2-fluorophenyl)boronic acid (commercially available, 24 g, 98 mmol), 5,6-dihydro-2H-pyran-2-one (commercially available, 6.06 mL, 70.3 mmol) and [RhCl(COD)]2 (0.5 g, 1.014 mmol), were dissolved in dioxane (180 mL) and cooled to −10° C. Then, potassium hydroxide (4.38 g, 78 mmol) was dissolved in water (17.8 mL) and added to the dioxane solution dropwise over 10 min. The reaction was then warmed to 35° C. and stirred for 2 hours. The reaction was neutralized with 1M HCl (to pH 3), then concentrated under vacuum to remove the dioxane. The residue was then diluted with water (50 mL) and extracted with EtOAc (3×300 mL) the organics were combined and concentrated under vacuum. The crude was purified by FCC (0→100% EtOAc/heptanes) to yield the title compound (19.65 g, 78 mmol).

LCMS: RT=1.07 min (LCMS Method 2); MS m/z 301.4 $[M+H]^+$.

Step 2: 3-(2-(benzyloxy)-5-fluorophenyl)pentane-1,5-diol

Lithium aluminum hydride (31.2 mL, 71.8 mmol, 2M THF) was added to a stirred solution of 4-(2-(benzyloxy)-5-fluorophenyl)tetrahydro-2H-pyran-2-one (19.6 g, 65.3 mmol) in dry THE (384 mL) at 0° C. The reaction mixture was stirred for 2 h at −5° C. under $N_2$. The reaction was quenched by $H_2O$ (10 mL) at −5° C. until gas production ceased and then a solution of NaOH (25 g) in water (25 mL) was portion-wise added to the mixture at 0° C. $Na_2SO_4$ (300 g) was added to the reaction mixture and was stirred for 60 min. The mixture was filtered and the solvent was removed under reduced pressure. The crude product was purified by FCC (0-10% MeOH/DCM) to yield the title compound (17.8 g, 55.6 mmol).

LCMS: Rt=0.90 min (LCMS Method 2); MS m/z 304.4 $[M+H]^+$.

$^1H$ NMR (400 MHz, $CDCl_3$) δ 7.51-7.31 (m, 5H), 7.01-6.81 (m, 3H), 5.06 (s, 2H), 3.59-3.47 (m, 3H), 3.46-3.31 (m, 2H), 2.06-1.89 (m, 4H), 1.81-1.73 (m, 2H).

Step 3: 3-(2-(benzyloxy)-5-fluorophenyl)pentane-1,5-diyl bis(4-methylbenzenesulfonate)

3-(2-(benzyloxy)-5-fluorophenyl)pentane-1,5-diol (17.8 g, 58.5 mmol) and TEA (35.9 mL, 257 mmol) were dissolved in MeCN (200 mL) and cooled to −5° C. TsCl (24.53 g, 129 mmol) and DMAP (0.714 g, 5.85 mmol) were added and the reaction was warmed to RT and stirred for 16 h. The solvent was removed under reduced pressure. The crude product was dissolved in DCM (300 mL) and washed with water (1×25 mL) and brine (1×25 mL), dried over $Na_2SO_4$, filtered and concentrated. The crude product was purified by FCC (0→50% EtOAc/heptanes) to yield the title compound (22.8 g, 37.2 mmol).

LCMS Rt=1.37 min (LCMS Method 2); MS m/z 630.4 $[M+NH_4]^+$.

Intermediate 1D: 3-(2-bromophenyl)pentane-1,5-diyl bis(4-methylbenzenesulfonate) Wuxi

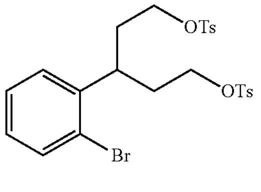 [SMILES: Cc1ccc(S(=O)(=O)OCCC(CCOS(=O)(=O)c2ccc(C)cc2)c2ccccc2Br)cc1]

Step 1: triethyl 2-(2-bromophenyl)propane-1,1,3-tricarboxylate

Na (27.04 g, 1180 mmol) was added to EtOH (1.5 L) in several batches under nitrogen and then the reaction was stirred at 25° C. until the solid was completely dissolved. Then diethyl malonate (188 g, 1180 mmol) was added to the EtOH solution and the resulting mixture was stirred at 25° C. for 0.5 hr. Next, ethyl (E)-3-(2-bromophenyl)acrylate 3 (J. Med. Chem. 1990, 33, 909-918) 150 g, 0.588 mol) was added to the mixture which was then stirred for 16 hours at 80° C. The solution was then concentrated and the residue was purified by FCC (2-20% EtOAc/PE) to yield the title intermediate (133 g, 0.320 mol) as a colorless oil.

$^1H$ NMR (400 MHz, $CDCl_3$) δ 7.57-7.48 (m, 1H), 7.30-7.18 (m, 2H), 7.11-7.00 (m, 1H), 4.48-4.36 (m, 1H), 4.24-4.13 (m, 2H), 4.07-3.90 (m, 5H), 3.00-2.84 (m, 2H), 1.26-1.20 (m, 3H), 1.13-0.99 (m, 6H).

Step 2: diethyl 3-(2-bromophenyl)pentanedioate

To a solution of triethyl 2-(2-bromophenyl)propane-1,1,3-tricarboxylate (133 g, 320 mmol) in DMSO (500 mL) was added NaCl (56 g, 960 mmol) and water (17 g, 960 mmol). The mixture was stirred at 160° C. for 6 hours. The reaction mixture was then quenched with water (500 mL) and extracted with MTBE (3×500 mL). The combined organic phases were washed with brine (500 mL) dried over sodium sulfate, filtered and concentrated to give the title intermediate (105 g, 306 mmol) as a yellow oil which was used in the next step without further purification.

$^1H$ NMR (400 MHz, $CDCl_3$) δ 7.58-7.55 (m, 1H), 7.28-7.25 (m, 2H), 7.10-7.08 (m, 1H), 4.20-4.15 (m, 1H), 4.09-4.04 (m, 4H), 2.79-2.70 (m, 4H), 1.19-1.15 (m, 6H).

Step 3: 3-(2-bromophenyl)pentane-1,5-diol

To a suspension of $LiAlH_4$ (29 g, 765 mmol) in THE (800 mL) cooled to 0° C. was added dropwise a solution of diethyl 3-(2-bromophenyl)pentanedioate (105 g, 306 mmol) in THE (200 mL). Following the addition, the reaction was warmed to 25° C. and stirred for 2 hours. The reaction mixture was then added dropwise to a solution of 2 N HCl (2L) and then extracted with EtOAc (3×500 mL). The combined organic extracts were washed with brine (500 mL), dried over sodium sulfate, filtered, and concentrated. The residue was purified by FCC (10-100% EtOAc/DCM (3:1)/PE) to yield a white solid. The solid was triturated with EtOAc (100 mL) and filtered and washed with cold EtOAc (2×50 mL) to afford the title intermediate (47.2 g, 182 mmol) as a white solid.

$^1H$ NMR (400 MHz, $CD_3OD$) δ 7.55-7.53 (m, 1H), 7.33-7.32 (m, 2H), 7.10-7.06 (m, 1H), 3.47-3.39 (m, 5H), 1.96-1.86 (m, 4H).

Step 5: 3-(2-bromophenyl)pentane-1,5-diyl bis(4-methylbenzenesulfonate)

3-(2-bromophenyl)pentane-1,5-diol (10.1 g, 39.0 mmol) was dissolved in MeCN (200 mL) and 4-methylbenzene-1-sulfonyl chloride (17.09 g, 90 mmol) and N,N-dimethylpyridin-4-amine (0.476 g, 3.90 mmol) were added. The resulting solution was cooled to 0° C. and triethylamine (32.4 ml, 234 mmol) was added dropwise. The reaction mixture was warmed to RT and the colorless solution color became brown and then it became turbid. The reaction mixture was stirred at RT for 5 hours. The reaction mixture was concentrated, diluted with DCM (300 mL) and washed with 1N HCl solution (2×50 mL), dried over sodium sulfate, filtered and concentrated under reduced pressure. The crude was purified by FCC (0-50% EtOAc/Heptanes) to obtain a colorless solid as the title compound (21.2 g, 35.9 mmol).

LCMS Rt=1.37 min (LCMS Method 2); MS m/z 586.1 $[M+NH_4]+$.

$^1H$ NMR (400 MHz, $CD_2Cl_2$) δ 7.76-7.68 (m, 4H), 7.50 (dd, J=8.0, 1.2 Hz, 1H), 7.36 (d, J=8.2 Hz, 4H), 7.28-7.20 (m, 1H), 7.12-7.01 (m, 2H), 3.92-3.86 (m, J=10.0, 6.2 Hz, 2H), 3.84-3.78 (m, J=9.9, 7.0 Hz, 2H), 3.47-3.31 (m, 1H), 2.47 (s, 6H), 2.04-1.90 (dt, J=13.2, 7.0 Hz, 4H).

Intermediate 1E: 3-(2-(benzyloxy)-4-fluorophenyl) pentane-1,5-diyl bis(4-methylbenzenesulfonate)

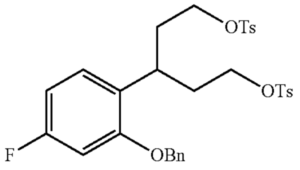 [SMILES: Cc1ccc(S(=O)(=O)OCCC(CCOS(=O)(=O)c2ccc(C)cc2)c2ccc(F)cc2OCc2ccccc2)cc1]

Step 1: 2-(benzyloxy)-4-fluoro-1-(hepta-1,6-dien-4-yl)benzene

A 250 mL round bottom flask was charged with 2-(benzyloxy)-4-fluorobenzaldehyde (commercially available, 23.90 g, 104 mmol) followed by nitromethane (250 mL). Then ytterbium(III) chloride (7.25 g, 26.0 mmol) was added to the reaction and the mixture was stirred for 15 min at RT. After 15 min of stirring, allyltrimethylsilane (41.2 mL, 260 mmol) was slowly added over 5 min. The mixture was stirred overnight at RT. The reaction was concentrated and the crude product was purified by FCC (0→30% EtOAc/heptanes) to yield the title compound as a clear, colorless oil (22.64 g, 72.6 mmol).

LCMS: Rt=1.43 min (LCMS Method 1).

$^1H$ NMR (400 MHz, $CDCl_3$) δ 7.38-7.19 (m, 5H), 6.97 (dd, 1H), 6.61-6.47 (m, 2H), 5.57 (m, 2H), 4.95 (s, 2H), 4.90-4.78 (m, 4H), 3.19 (t, 1H), 2.29 (m, 4H).

Step 2: 3-(2-(benzyloxy)-4-fluorophenyl)pentane-1,5-diol 2-(benzyloxy)-4-fluoro-1-(hepta-1,6-dien-4-yl)benzene (22.64 g, 76 mmol) was dissolved in MeOH (450 mL) and cooled to −78° C. Next, ozone was bubbled through the reaction mixture for 120 min over which time the reaction turned a pale purple color. Nitrogen was then bubbled through the reaction for 20 min and it was then warmed to 0° C. and $NaBH_4$ (28.9 g, 764 mmol) was added to the reaction portion wise over 4 h and the reaction was then stirred for 16 hours at RT. The reaction was then poured into DCM and sat $NH_4Cl$ was added and the mixture was stirred at RT for 1 h. The organic layer was separated and washed with water and brine then dried over $Na_2SO_4$ and filtered. The solvent was removed under reduced pressure. The resulting product (15.22 g, 50.0 mmol) was taken forward without further purification.

LCMS: Rt=0.90 min (LCMS Method 1); MS m/z 305.2 $[M+H]^+$.

$^1$H NMR (400 MHz, $CDCl_3$) δ 7.36-7.22 (m, 6H), 7.03 (m, 1H), 6.64-6.57 (m, 2H), 4.95 (s, 2H), 3.42 (m, 2H), 3.31 (m, 2H), 1.92-1.81 (m, 2H), 1.79-1.64 (m, 2H).

Step 3: 3-(2-(benzyloxy)-4-fluorophenyl)pentane-1,5-diyl bis(4-methylbenzenesulfonate)

3-(2-(benzyloxy)-4-fluorophenyl)pentane-1,5-diol (6.96 g, 22.87 mmol) was dissolved in MeCN (150 mL) and TEA (13.63 mL, 98 mmol) was added and the reaction was cooled to 0° C. The reaction was incubated for 10 min and then TsCl (9.59 g, 50.3 mmol) and DMAP (0.559 g, 4.57 mmol) were added. The reaction was slowly warmed to RT and stirred overnight. The reaction was then diluted with water and extracted with DCM. The combined organic layers were dried over magnesium sulfate, filtered and concentrated. The residue was then purified by FCC (0→60% EtOAc/heptanes) to yield the title compound (8.91 g, 14.54 mmol).

LCMS: Rt=1.35 min (LCMS Method 1); MS m/z 630.3 $[M+NH_4]^+$.

$^1$H NMR (400 MHz, $CDCl_3$) δ 7.68-7.61 (m, 4H), 7.42-7.32 (m, 5H), 7.27 (m, 4H), 6.57 (dd, J=10.9, 2.4 Hz, 1H), 6.46 (td, J=8.3, 2.4 Hz, 1H), 4.93 (s, 2H), 3.90-3.80 (m, 2H), 3.74 (ddd, J=9.8, 8.1, 6.1 Hz, 2H), 3.08 (dt, J=9.7, 4.9 Hz, 1H), 2.43 (s, 6H), 1.98 (m, 3H), 1.92-1.80 (m, 2H).

Intermediate 1F: 3-(2-bromo-5-fluorophenyl)pentane-1,5-diyl bis(4-methylbenzenesulfonate)

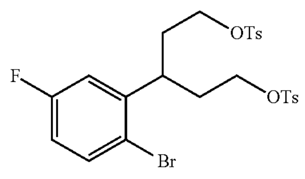 [SMILES: Cc1ccc(S(=O)(=O)OCCC(CCOS(=O)(=O)c2ccc(C)cc2)c2cc(F)ccc2Br)cc1]

Step 1: triethyl 2-(2-bromo-5-fluorophenyl)propane-1,1,3-tricarboxylate

Sodium metal (25.25 g, 1.10 mol) was added to EtOH (1.5 L) in several batches under $N_2$ gas flow and the reaction mixture was stirred at 25° C. until the solid dissolved. Next, diethyl malonate (176 g, 1.10 mol) was added to the mixture and stirred at 25° C. for 30 minutes, ethyl (E)-3-(2-bromo-5-fluorophenyl)acrylate (150 g, 0.55 mol; Preparation in Org. Biomol. Chem. 2012, 10, 3655-3661) was added to the reaction mixture and the reaction was stirred for 16 hours at 80° C. The reaction mixture was then concentrated and the residue was purified by FCC (2-10% EtOAc/petroleum ether) to the title intermediate (140 g, 323 mmol) as a colorless oil.

$^1$H NMR (400 MHz, $CDCl_3$) δ 7.51 (dd, J=5.5, 8.8 Hz, 1H), 7.02 (dd, J=3.1, 9.8 Hz, 1H), 6.83 (m, 1H), 4.38 (q, J=7.4 Hz, 1H), 4.24-4.18 (m, 2H), 4.10-3.97 (m, 4H), 3.92 (m, 1H), 2.91 (d, J=7.1 Hz, 2H), 1.23 (t, J=7.2 Hz, 3H), 1.13 (t, J=7.2 Hz, 6H).

Step 2: 3-(2-bromo-5-fluorophenyl)pentanedioic acid

Triethyl 2-(2-bromo-5-fluorophenyl)propane-1,1,3-tricarboxylate (140 g, 323 mmol) was dissolved in HCl (36.5%, 1L) and was stirred at 100° C. for 48 hr. The solution was the concentrated to give the title intermediate (109 g, 358 mmol, crude) as light yellow solid that was used without further purification.

$^1$H NMR (400 MHz, DMSO-$d_6$) δ 7.61 (m, 1H), 7.47-7.28 (m, 1H), 7.20-6.98 (m, 1H), 3.91-3.80 (m, 1H), 2.61 (m, 4H).

Step 3: 3-(2-bromo-5-fluorophenyl)pentane-1,5-diol

To a solution of 3-(2-bromo-5-fluorophenyl)pentanedioic acid (105 g, crude) in THE (1000 mL) was dropwise added $B_2H_6$ (172 mL, 17.2 mmol, 10 M in dimethyl sulfide) at 0° C. The solution was then warmed to RT and stirred for 2 hours. The reaction was cooled to 0° C. and quenched with MeOH (500 mL) and HCl (250 mL, 4M in EtOAc), and the solution was then concentrated. The residue was purified by FCC (5-100% EtOAc: DCM (3:1)/petroleum ether) to give the title intermediate (43.3 g, 156 mmol) as a white solid.

$^1$H NMR (400 MHz, $CD_3OD$) δ 7.58-7.54 (m, 1H), 7.12 (m, 1H), 6.89 (m, 1H), 3.55-3.38 (m, 5H), 2.00-1.79 (m, 4H).

Step 4: 3-(2-bromo-5-fluorophenyl)pentane-1,5-diyl bis(4-methylbenzenesulfonate)

3-(2-bromo-5-fluorophenyl)pentane-1,5-diol (5000 mg, 18.04 mmol) to a 250 mL rb flask and it was dissolved in MeCN (100 mL). Next, TEA (11.1 mL 79 mmol) and DMAP (220 mg, 1.804 mmol) were added and the reaction was cooled to 0° C. The reaction was incubated for 10 minutes at 0° C. and then tosyl anhydride (13000 mg, 39.8 mmol) was added and the reaction was slowly warmed to RT and the reaction was stirred overnight. The material was next concentrated onto celite for purification by FCC (0-60% EtOAc/heptanes) to yield the title intermediate as a light brown oil (9700 mg, 16.57 mmol).

LCMS: Rt: 1.29 min (LCMS Method 1); MS m/z 604.1 $[M+NH_4]^+$.

$^1$H NMR (400 MHz, $CDCl_3$) δ 7.75-7.67 (m, 4H), 7.42 (dd, J=8.8, 5.5 Hz, 1H), 7.31 (d, J=8.0 Hz, 4H), 6.78 (m, 1H), 6.73-6.62 (m, 1H), 3.88 (m, 2H), 3.80 (dt, J=10.1, 6.9 Hz, 2H), 3.34 (s, 1H), 2.44 (s, 6H), 2.05-1.93 (m, 2H), 1.89 (bs, 2H).

Intermediate 1G: 3-(2-(benzyloxy)-3-fluorophenyl)pentane-1,5-diyl bis(4-methylbenzenesulfonate)

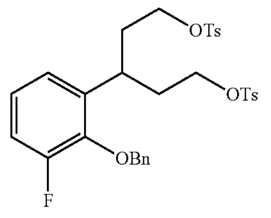 [SMILES: Cc1ccc(S(=O)(=O)OCCC(CCOS(=O)(=O)c2ccc(C)cc2)c2cccc(F)c2OCc2ccccc2)cc1]

Step 1: 4-(2-(benzyloxy)-3-fluorophenyl)tetrahydro-2H-pyran-2-one

A solution of potassium hydroxide (0.858 g, 15.29 mmol) in water (5.0 mL) was added dropwise to a solution of [RhCl(COD)]2 (0.075 g, 0.153 mmol), (2-(benzyloxy)-3-fluorophenyl)boronic acid (5.27 g, 21.41 mmol) and 5,6-dihydro-2H-pyran-2-one (1.317 mL, 15.29 mmol) in 1,4- dioxane (50 mL) at 0° C. over a period of 2 mins. The reaction solution was then warmed to 35° C. and stirred for 16 h. The reaction was diluted with ethyl acetate and 2M HCl. The layers were separated and the aqueous solution was back extracted with ethyl acetate. The combined organics were dried over $MgSO_4$ and the solvent was removed under reduced pressure. The residue was then purified by FCC (0-60% EtOAc/heptanes) to yield the title compound (3.71 g, 12.35 mmol).

LCMS: Rt: 2.36 min (LCMS Method 3); MS m/z 301.1 $[M+H]^+$.

Step 2: 3-(2-(benzyloxy)-3-fluorophenyl)pentane-1,5-diol

To a stirring solution of 4-(2-(benzyloxy)-3-fluorophenyl) tetrahydro-2H-pyran-2-one (3.71 g, 12.35 mmol) in THF (60 mL) and MeOH (12 mL) at 0° C., $LiBH_4$ (538 mg, 24.71 mmol) was added. The reaction was then stirred at RT for 16 hours. 100 mL of water was then added to the reaction to quench the excess $LiBH_4$ and the organic solvent was removed under reduced pressure. The product was extracted with DCM, washed with water and dried over $MgSO_4$. The solvent was removed under reduced pressure and the product was used without further purification (3.72 g, 11.61 mmol).

LCMS: Rt: 1.89 min (LCMS Method 3).

$^1H$ NMR (400 MHz, $CD_3OD$) δ 7.52-7.46 (m, 2H), 7.41-7.30 (m, 3H), 7.12-6.97 (m, 3H), 5.05 (s, 2H), 3.40-3.33 (m, 5H), 1.92-1.73 (m, 4H).

Step 3: 3-(2-(benzyloxy)-3-fluorophenyl)pentane-1,5-diyl bis(4-methylbenzenesulfonate)

To a solution of 3-(2-(benzyloxy)-3-fluorophenyl)pentane-1,5-diol (1.10 g, 3.61 mmol) and triethylamine (2.267 mL, 16.26 mmol) in MeCN (40 mL) was added pTsCl (1.585 g, 8.31 mmol) and DMAP (0.044 g, 0.361 mmol). The reaction was then stirred for 16 hours and then diluted with water, extracted 3 times with DCM, dried over $MgSO_4$ and concentrated. The residue was purified by FCC (0-50% EtOAc/heptanes) to yield the title compound (1.51 g, 2.46 mmol).

LCMS: Rt: 1.37 min (LCMS Method 1).

$^1H$ NMR (400 MHz, $CDCl_3$) δ 7.72-7.64 (m, 4H), 7.42-7.33 (m, 5H), 7.31-7.28 (m, 4H), 7.08-6.84 (m, 2H), 6.75-6.64 (m, 1H), 5.02 (s, 2H), 3.83 (m, 2H), 3.72 (m, 2H), 3.18 (p, J=7.5 Hz, 1H), 2.45 (s, 6H), 1.86 (m, 4H).

Intermediate 1H: 3-(2-(trifluoromethoxy)phenyl) pentane-1,5-diyl bis(4-methylbenzenesulfonate)

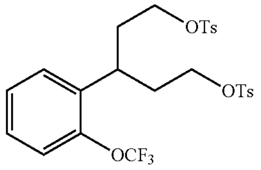 [SMILES: Cc1ccc(S(=O)(=O)OCCC(CCOS(=O)(=O)c2ccc(C)cc2)c2ccccc2OC(F)(F)F)cc1]

Step 1: 4-(2-(trifluoromethoxy)phenyl)tetrahydro-2H-pyran-2-one (2-(trifluoromethoxy)phenyl)boronic acid (2939 mg, 14.27 mmol), 5,6-dihydro-2H-pyran-2-one (1000 mg, 10.19 mmol) and chloro(1,5-cyclooctadiene)rhodium(I) dimer (503 mg, 1.019 mmol) were added to a 250 mL round bottom flask and dissolved in dioxane (40 mL). Separately in a 25 mL beaker, KOH (572 mg, 10.19 mmol) was dissolved in water (5 mL) and this solution was then added dropwise to the dioxane solution. The reaction was warmed to 35° C. and stirred for 24 hours. The reaction was diluted with EtOAc (100 mL) and washed with 2N HCl (2×25 mL) and water (1×10 mL) and brine (1×10 mL), dried over sodium sulfate, filtered and concentrated. The crude was then purified by FCC (0-75% EtOAc/heptanes) to afford the title intermediate (1880 mg, 7.22 mmol).

LCMS: Rt: 1.95 min (LCMS Method 3) MS m/z 261.0 $[M+H]^+$.

$^1H$ NMR (400 MHz, $CD_3OD$) δ 7.51-7.44 (m, 1H), 7.44-7.28 (m, 3H), 4.58-4.39 (m, 2H), 3.75-3.61 (m, 1H), 2.90-2.79 (m, 1H), 2.66 (dd, J=17.4, 10.4 Hz, 1H), 2.18-2.05 (m, 2H).

Step 2: 3-(2-(trifluoromethoxy)phenyl)pentane-1,5-diol 4-(2-(trifluoromethoxy)phenyl)tetrahydro-2H-pyran-2-one (1880 mg, 7.22 mmol) was dissolved in THF (60 mL) and MeOH (15 mL) and cooled to 0° C. The reaction was incubated for 10 minutes and then lithium borohydride (315 mg, 14.45 mmol) was added and the reaction was warmed to RT and stirred for 20 hours. The reaction was cooled to 0° C. and then quenched with acetone and concentrated and the residue was purified by FCC (0-10% MeOH/DCM) to yield the title compound as a colorless oil (1660 mg, 6.28 mmol).

LCMS: Rt: 1.95 min (LCMS Method 3) MS m/z 265.6 $[M+H]^+$.

$^1H$ NMR (400 MHz, $CD_3OD$) δ 7.50-7.37 (m, 1H), 7.37-7.21 (m, 3H), 3.48-3.37 (m, 4H), 3.30-3.25 (m, 1H), 2.03-1.77 (m, 4H).

Step 3: 3-(2-(trifluoromethoxy)phenyl)pentane-1,5-diyl bis(4-methylbenzenesulfonate)

3-(2-(trifluoromethoxy)phenyl)pentane-1,5-diol (1660 mg, 6.28 mmol) was dissolve in MeCN (30 mL) and DMAP and TEA (4.3 mL), 31.4 mmol) were added and the reaction was cooled to 0° C. and incubated for 10 min. Next, TsCl (2635 mg, 13.82 mmol) was added and the reaction was warmed to RT and stirred for 18 h. The reaction was then concentrated and dissolved in EtOAc and washed with water (3×20 mL) and brine (1×20 mL), dried over sodium sulfate, filtered and concentrated. The residue was then purified by FCC (0-40% EtOAc/heptanes) to yield the title compound as a yellow oil (1437 mg, 2.51 mmol).

LCMS: Rt: 1.95 min (LCMS Method 3) MS m/z 590.7 $[M+H_2O]^+$.

$^1H$ NMR (400 MHz, $CD_3OD$) δ 7.73-7.63 (m, 4H), 7.44-7.34 (m, 4H), 7.29-7.25 (m, 1H), 7.22-7.13 (m, 3H), 3.89-3.84 (m, 2H), 3.75-3.69 (m, 2H), 3.19-3.11 (m, 1H), 2.44 (s, 6H), 1.98-1.77 (m, 4H).

Intermediate 2A: tert-butyl (R)-6-amino-2-azaspiro[3.4]octane-2-carboxylate hydrochloride

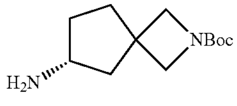

tert-butyl 6-oxo-2-azaspiro[3.4]octane-2-carboxylate (200 g, 0.887 mol), isopropylamine hydrochloride (845 g, 8.84 mol) and pyridoxal phosphate (10 g, 0.040 mmol) were added to a 10 L reactor and suspended in DMSO (800 mL) and 0.1M borate buffer (pH 9.0, 6200 mL). Aminotransferase ATA412 (Codexis) was dissolved in 0.1 M borate buffer (400 mL) and added to the DMSO solution. The flask containing the enzyme was washed with 0. μM borate buffer (400 mL) and this was added to the DMSO solution. This wash step was repeated with 0.1 M borate buffer (200 mL). The reaction was incubated at 40° C. with nitrogen bubbling through the solution until the ketone was consumed as judged by LCMS. The reaction was then cooled to 26° C. and citric acid was added until the solution pH reached 4.88. DCM (1.5 L) was added and the solution was filtered through microcrystalline cellulose. The phases were separated and the aqueous phase was added back to the reactor and NaCl (1200 g, 20.5 mol) was added and the pH was adjusted to 9.9 with 32% NaOH solution. The aqueous layer was extracted with DCM (3×2 L) and concentrated. The residue was dissolved in EtOAc (1.5 L) and washed with brine (2×100 mL). The organic layer was concentrated and the residue was dissolved in EtOAc (1.0 L) and filtered to remove NaCl and enzyme residue. The EtOAc layer was then concentrated and the residue was dissolved in EtOAc (0.87 L) and HCl in EtOAc (2M, 390 mL) was added over 1 hour. The solution was stirred for 2 hours and then filtered and washed with EtOAc to yield the title intermediate (133.9 g, 0.510 mol).

LCMS: Rt: 1.65 min (LCMS Method 4) MS m/z 227.7 $[M+H]^+$.

$^1H$ NMR (400 MHz, $CD_3OD$) δ 3.92-3.81 (m, 2H), 3.77 (q, J=8.3 Hz, 2H), 3.61 (p, J=7.6 Hz, 1H), 2.40 (dd, J=13.8, 8.1 Hz, 1H), 2.19-2.07 (m, 1H), 2.07-1.89 (m, 2H), 1.81 (dd, J=13.8, 7.4 Hz, 1H), 1.71-1.58 (m, 1H), 1.43 (s, 9H).

Intermediate 2B: 2-azaspiro[3.4]octan-6-one

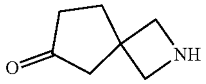

To a solution of tert-butyl 6-oxo-2-azaspiro[3.4]octane-2-carboxylate (15.69 g, 69.6 mmol) in DCM (60 mL) was added TFA (30 mL). The resulting solution was stirred at room temperature for 2 hours. It was concentrated to give a white solid which was taken on to the next step without purification. A 100% yield was assumed in the next step.

LCMS: Rt: 0.17 min (LCMS Method 1) MS m/z 126.2 $[M+H]^+$.

Intermediate 2C: 2-(1-fluorocyclopropanecarbonyl)-2-azaspiro[3.4]octan-6-one

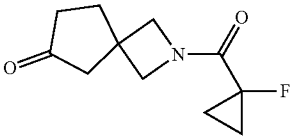 [SMILES: O=C1CCC2(C1)CN(C(=O)C1(F)CC1)C2]

To a solution of 2-azaspiro[3.4]octan-6-one (Intermediate 2B, 16.7 g, 35.7 mmol) in DCM (50 mL) was added DIPEA (46.6 mL, 267 mL). The reaction was stirred for 5 min and then the solvent was removed and DMF (20 mL) was added. Concurrently, 1-fluorocyclopropanecarboxylic acid (4.10 g 37.4 mmol) was dissolved in DMF (20 mL) and HATU (14.37 g, 37.8 mmol) was added. The reaction was stirred for 30 minutes and then DMF solution containing 2-azaspiro[3.4]octan-6-one was added and the reaction was stirred for 16 hr. Next, sat $NaHCO_3$ was added (300 mL) and the solution was extracted with EtOAc (3×500 mL). The combined organic layers were washed with brine and concentrated. The crude was then purified by FCC (0-70% EtOAc/heptanes) to yield the title compound (6.98 g, 29.7 mmol).

LCMS: Rt: 0.58 min (LCMS Method 2) MS m/z 212.2 $[M+H]^+$.

$^1H$ NMR (400 MHz, $CD_3OD$) δ 4.50-4.36 (m, 2H), 4.07-3.90 (m, 2H), 2.53 (s, 2H) 2.36-2.21 (m, 4H), 1.35-1.18 (m, 4H).

Intermediate 2D: 2-(oxetane-3-carbonyl)-2-azaspiro[3.4]octan-6-one

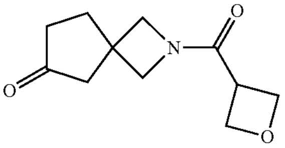 [SMILES: O=C1CCC2(C1)CN(C(=O)C1COC1)C2]

Oxetane-3-carboxylic acid (3.15 g, 30.9 mmol) and carbonyl diimidazole (5.68 g, 35.0 mmol) were suspended in dioxane (103 mL) and the reaction was stirred at 80° C. for 4 hours. DMF (10 mL) was then added and the reaction was stirred for an additional hour at 80° C. for 1 hour. The reaction was then cooled to room temperature. 2-azaspiro[3.4]octan-6-one (Intermediate 2B, 3.33 g, 20.60 mmol) was added by spatula. DMF (6 mL) was added to rinse the spatula and imidazole (0.701 g, 10.30 mmol) was added and the reaction was stirred overnight. The reaction was concentrated and purified by FCC (0→10% MeOH/DCM). The isolated compound contained DMF, so the residue was purified a second time by FCC (0→10% MeOH/DCM) to afford the title intermediate (1.583 g, 7.57 mmol) as an off-white solid.

LCMS: Rt: 0.37 min (LCMS Method 1), MS m/z 210.1 $[M+H]^+$.

$^1H$ NMR (400 MHz, $CDCl_3$) δ 4.98-4.90 (m, 2H), 4.90-4.81 (m, 1H), 4.77 (m, 2H), 3.97 (dd, J=17.4, 7.3 Hz, 3H), 3.83 (m, 1H), 2.49 (d, J=4.6 Hz, 2H), 2.38-2.29 (m, 2H), 2.29-2.19 (m, 2H).

Intermediate 2E: (R)-(6-amino-2-azaspiro[3.4]octan-2-yl)(oxetan-3-yl)methanone

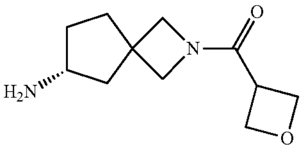 [SMILES: N[C@@H]1CCC2(C1)CN(C(=O)C1COC1)C2]

Step 1: tert-butyl (R)-6-(((benzyloxy)carbonyl)amino)-2-azaspiro[3.4]octane-2-carboxylate To a stirring suspension of tert-butyl (R)-6-amino-2-azaspiro[3.4]octane-2-carboxylate hydrochloride (Intermediate 2A, 1 g, 3.81 mmol) in DCM (5 mL) at −5° C., DIPEA (2.0 mL, 11.42 mmol) was added. The reaction was stirred for 5 min and then N-(benzyloxycarbonyloxy)succinimide (1.043 g, 4.19 mmol) was then added and the reaction was stirred at RT for 3 hr. The reaction was washed with 1M HCl, sat $NaHCO_3$, water and brine then dried over $Na_2SO_4$. The solvent was removed under reduced pressure. This gave the title intermediate, which was used without further purification (1.35 g, 3.37 mmol).

LCMS: Rt: 1.10 min (LCMS Method 1), MS m/z 261.5 $[M-Boc+H]^+$.

$^1H$ NMR (400 MHz, $CD_3OD$) δ 7.39-7.22 (m, 5H), 5.05 (s, 2H), 4.00-3.87 (m, 1H), 3.77 (m, 4H), 2.19 (dd, J=13.5, 7.5 Hz, 1H), 1.97 (m, 2H), 1.77 (m, 2H), 1.59-1.47 (m, 1H), 1.42 (s, 9H).

Step 2: benzyl (R)-(2-azaspiro[3.4]octan-6-yl)carbamate

To a stirring solution of tert-butyl (R)-6-(((benzyloxy)carbonyl)amino)-2-azaspiro[3.4]octane-2-carboxylate(1.35 g, 3.75 mmol) in DCM (15 mL), TFA (5.0 mL) was added. The reaction was stirred at RT for 1 hr. The reaction was concentrated and the crude product was dissolved in DCM and washed with 2M NaOH, until the aqueous layer was >pH12. The organic layer was then dried over magnesium sulfate, filtered and concentrated to yield the title intermediate that was used without purification (962 mg, 3.51 mmol).

LCMS: Rt: 0.60 min (LCMS Method 1), MS m/z 261.2 $[M+H]^+$.

$^1H$ NMR (400 MHz, $CD_3OD$) δ 7.44-7.21 (m, 5H), 5.05 (d, J=4.3 Hz, 2H), 3.89 (p, J=7.1 Hz, 1H), 3.67-3.45 (m, 4H), 2.23 (dd, J=13.3, 7.4 Hz, 1H), 2.05-1.63 (m, 4H), 1.57-1.39 (m, 1H).

Step 3: benzyl (R)-(2-(oxetane-3-carbonyl)-2-azaspiro[3.4]octan-6-yl)carbamate

To a stirring solution of oxetane-3-carboxylic acid (127 mg, 1.056 mmol) in DMF (2.0 mL), TBTU (462 mg, 1.440 mmol) was added. This was stirred for 15 min at RT and then this mixture was added to a stirring solution of benzyl (R)-(2-azaspiro[3.4]octan-6-yl)carbamate (250 mg, 0.960 mmol) and DIPEA (0.839 mL, 4.80 mmol) in DCM (10 mL). The reaction was then stirred at RT for 16 hr. The reaction was diluted with DCM and washed with water, brine, dried over $MgSO_4$, filtered and concentrated. The crude product was then purified by FCC (0-100% EtOAc/heptanes) to yield the title compound (225 mg, 0.621 mmol).

LCMS: Rt: 1.63 min (LCMS Method 4), MS m/z 345.3 $[M+H]^+$.

Step 4: (R)-(6-amino-2-azaspiro[3.4]octan-2-yl)(oxetan-3-yl)methanone

To a stirring solution of benzyl (R)-(2-(oxetane-3-carbonyl)-2-azaspiro[3.4]octan-6-yl)carbamate (225 mg, 0.653 mmol) in ethanol (10 mL), Pd/C (139 mg, 0.131 mmol) was added. The reaction was stirred under a balloon of hydrogen for 16 hr. The catalyst was filtered and the solvent was removed under reduced pressure to give the title intermediate which was used without further purification (128 mg, 0.609 mmol).

LCMS: Rt: 0.17 min (LCMS Method 1), MS m/z 211.4 $[M+H]^+$.

$^1H$ NMR (400 MHz, $CD_3OD$) δ 4.77 (dd, J=8.1, 2.1 Hz, 4H), 4.09-3.74 (m, 5H), 3.39-3.32 (m, 1H), 2.21 (m, 1H), 2.06-1.91 (m, 2H), 1.85 (m, 1H), 1.61 (m, 1H), 1.53-1.37 (m, 1H).

Intermediate 3A: tert-butyl (R)-6-(4-(2-(benzyloxy)phenyl)piperidin-1-yl)-2-azaspiro[3.4]octane-2-carboxylate

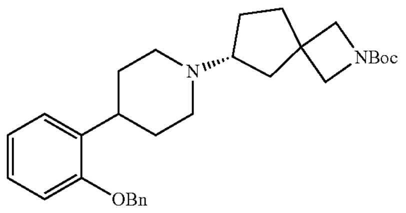 [SMILES: CC(C)(C)OC(=O)N1CC2(CC[C@@H](N3CCC(c4ccccc4OCc4ccccc4)CC3)C2)C1]

tert-butyl (R)-6-amino-2-azaspiro[3.4]octane-2-carboxylate (Intermediate 2A, 1.06 g, 4.04 mmol), 3-(2-(benzyloxy)phenyl)pentane-1,5-diyl bis(4-methylbenzenesulfonate) (Intermediate 1A, 2.40 g, 4.04 mmol), and potassium phosphate (2.74 g, 12.7 mmol) were suspended in acetonitrile (27 mL), and the reaction was stirred at 80° C. for 3 days. The reaction was cooled, concentrated, diluted with ethyl acetate (100 mL), filtered, and the filtrate was concentrated. The residue was purified by FCC (0-5% MeOH(10% $NH_4OH$)/DCM) to afford the title intermediate (1.7 g, 3.5 mmol) as a white foamy solid.

LCMS: Rt: 1.42 min (LCMS Method 2) MS m/z 477.1 $[M+H]^+$.

Intermediate 3B: tert-butyl (R)-6-(4-(2-bromophenyl)piperidin-1-yl)-2-azaspiro[3.4]octane-2-carboxylate

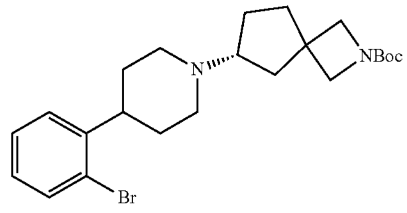 [SMILES: CC(C)(C)OC(=O)N1CC2(CC[C@@H](N3CCC(c4ccccc4Br)CC3)C2)C1]

3-(2-bromophenyl)pentane-1,5-diyl bis(4-methylbenzenesulfonate) (Intermediate 1D, 21.2 g, 35.9 mmol) was dissolved in MeCN (200 mL) and tert-butyl (R)-6-amino-2-azaspiro[3.4]octane-2-carboxylate (Intermediate 2A, 12.20 g, 39.4 mmol) and $K_3PO_4$ (24.36 g, 115 mmol) were added. The round bottom flask was fitted with a reflux condenser and the resulting suspension was stirred at 94° C. for 36 hours. The reaction mixture was concentrated under reduced pressure, and the residue was diluted with EtOAc and the organic phase was washed with water and brine. The organic layer was dried over sodium sulfate, filtered and concentrated under reduced pressure. The residue was then purified by FCC (0-6% MeOH/DCM) and further by a second round of FCC (0-20% EtOH (20% $NH_3$ in MeOH)/heptanes). The title compound was isolated as a beige oil (14.8 g, 35.9 mmol).

LCMS: Rt: 1.42 min (LCMS Method 2) MS m/z 451.4 $[M+H]^+$.

$^1H$ NMR (400 MHz, $CD_3OD$) δ 7.54 (d, J=8.0 Hz, 1H), 7.32 (d, J=4.4 Hz, 2H), 7.09 (dt, J=8.7, 4.5 Hz, 1H), 3.91-3.65 (m, 4H), 3.16 (m, 2H), 3.04 (m, 1H), 2.77-2.60 (m, 1H), 2.16 (m, 3H), 2.04-1.82 (m, 5H), 1.73 (m, 3H), 1.63-1.50 (m, 1H), 1.43 (s, 9H).

The following compounds in Table 1 were prepared using a similar procedure and the relevant starting materials:

TABLE 1

Intermediates 3C to 3F

| Intermediate | Structure | Retention time (min) and Method | Expected Mass | Observed Mass |
|---|---|---|---|---|
| 3C | 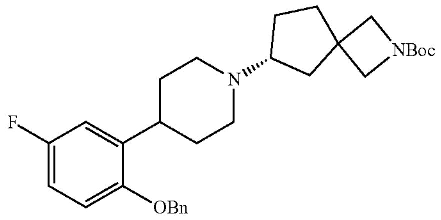 [SMILES: CC(C)(C)OC(=O)N1CC2(CC[C@@H](N3CCC(c4cc(F)ccc4OCc4ccccc4)CC3)C2)C1] | 1.42 LCMS Method 2 | 495.3 $[M + H]^+$ | 495.5 $[M + H]^+$ |
| 3D | 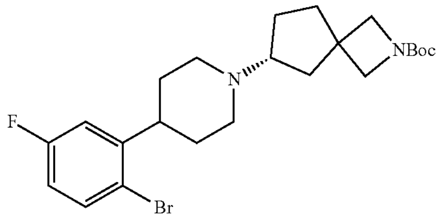 [SMILES: CC(C)(C)OC(=O)N1CC2(CC[C@@H](N3CCC(c4cc(F)ccc4Br)CC3)C2)C1] | 0.78 LCMS Method 2 | 467.2 $[M + H]^+$ | 469.1 $[M + H]^+$ |
| 3E | 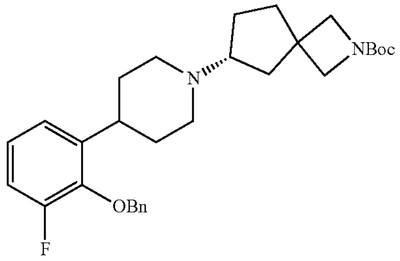 [SMILES: CC(C)(C)OC(=O)N1CC2(CC[C@@H](N3CCC(c4cccc(F)c4OCc4ccccc4)CC3)C2)C1] | 1.92 LCMS Method 3 | 495.3 $[M + H]^+$ | 495.6 $[M + H]^+$ |
| 3F | 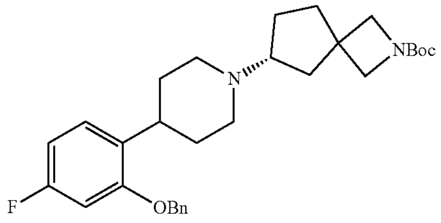 [SMILES: CC(C)(C)OC(=O)N1CC2(CC[C@@H](N3CCC(c4ccc(F)cc4OCc4ccccc4)CC3)C2)C1] | 3.59 LCMS Method 4 | 495.3 $[M + H]^+$ | 495.4 $[M + H]^+$ |

Intermediate 4A: (R)-6-(4-(2-(benzyloxy)phenyl)piperidin-1-yl)-2-azaspiro[3.4]octane

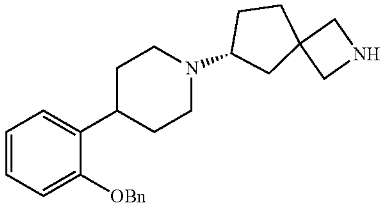 [SMILES: c1ccc(COc2ccccc2C2CCN([C@@H]3CCC4(CNC4)C3)CC2)cc1]

tert-butyl (R)-6-(4-(2-(benzyloxy)phenyl)piperidin-1l-yl)-2-azaspiro[3.4]octane-2-carboxylate (Intermediate 3A, 2.00 g, 4.20 mmol) was dissolved in DCM (30 mL), and TFA (10 mL) was added. The reaction was stirred at RT for 1 hour, concentrated under reduced pressure and the residue was dissolved in DCM and washed with a 1 M solution of NaOH until the combined aqueous extracts were basic (pH>8). The organic layer was washed with brine dried with MgSO4, filtered, and concentrated under reduce pressure to afford the title intermediate (1440 mg, 3.82 mmol).

LCMS: Rt: 0.64 min (LCMS Method 1) MS m/z 377.5 $[M+H]^+$.

$^1H$ NMR (400 MHz, $CD_3OD$) δ 7.47-7.27 (m, 5H), 7.25-7.07 (m, 2H), 7.03-6.84 (m, 2H), 5.10 (s, 2H), 3.74 (m, 3H), 3.20-2.95 (m, 4H), 2.64 (p, J=8.6 Hz, 1H), 2.34-1.65 (m, 12H), 1.53 (dt, J=12.0, 8.5 Hz, 1H).

The following compounds in Table 2 were prepared using a similar procedure and the relevant starting materials:

TABLE 2

Intermediates 4B to 4X

| Intermediate | Structure | Retention time (min) and Method | Expected Mass | Observed Mass |
|---|---|---|---|---|
| 4B | 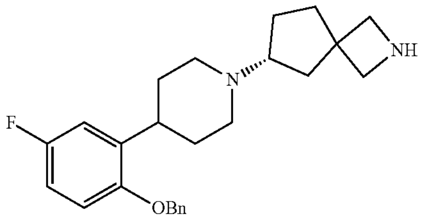 [SMILES: Fc1ccc(OCc2ccccc2)c(C2CCN([C@@H]3CCC4(CNC4)C3)CC2)c1] | 0.56 LCMS Method 1 | 395.2 $[M + H]^+$ | 395.4 $[M + H]^+$ |
| 4C | 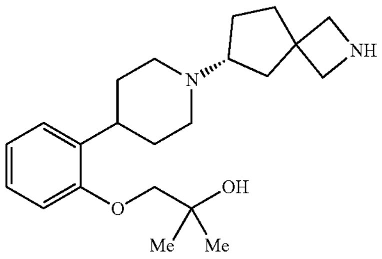 [SMILES: CC(C)(O)COc1ccccc1C1CCN([C@@H]2CCC3(CNC3)C2)CC1] | 0.46 LCMS Method 1 | 359.3 $[M + H]^+$ | 359.3 $[M + H]^+$ |
| 4D | 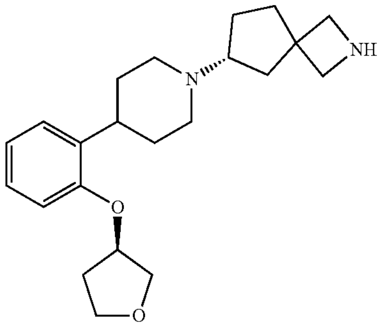 [SMILES: c1ccc(C2CCN([C@@H]3CCC4(CNC4)C3)CC2)c(O[C@@H]2CCOC2)c1] | 0.47 LCMS Method 1 | 357.3 $[M + H]^+$ | 357.3 $[M + H]^+$ |
| 4E | 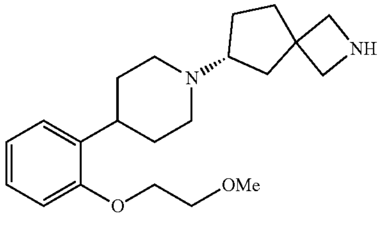 [SMILES: COCCOc1ccccc1C1CCN([C@@H]2CCC3(CNC3)C2)CC1] | 0.46 LCMS Method 1 | 345.3 $[M + H]^+$ | 345.1 $[M + H]^+$ |

TABLE 2-continued
Intermediates 4B to 4X
| Intermediate | Structure | Retention time (min) and Method | Expected Mass | Observed Mass |
|---|---|---|---|---|
| 4F | 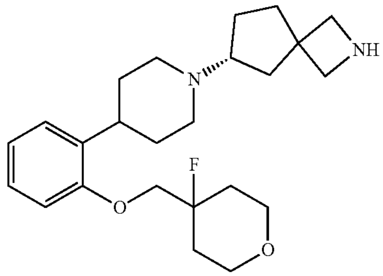 [SMILES: FC1(COc2ccccc2C2CCN([C@@H]3CCC4(CNC4)C3)CC2)CCOCC1] | 0.45 LCMS Method 1 | 403.3 $[M + H]^+$ | 403.3 $[M + H]^+$ |
| 4G | 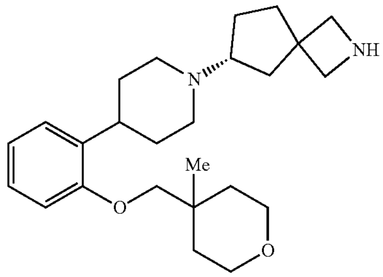 [SMILES: CC1(COc2ccccc2C2CCN([C@@H]3CCC4(CNC4)C3)CC2)CCOCC1] | 0.52 LCMS Method 1 | 399.3 $[M + H]^+$ | 399.5 $[M + H]^+$ |
| 4H | 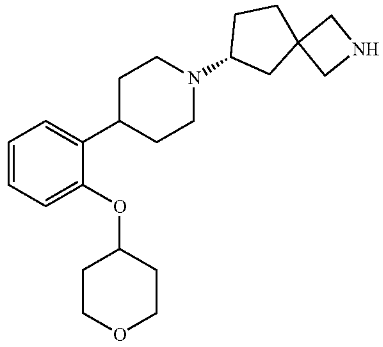 [SMILES: c1ccc(C2CCN([C@@H]3CCC4(CNC4)C3)CC2)c(OC2CCOCC2)c1] | 0.49 LCMS Method 1 | 371.3 $[M + H]^+$ | 371.7 $[M + H]^+$ |
| 4I | 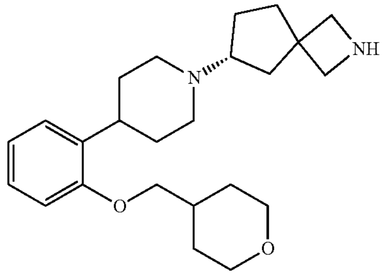 [SMILES: c1ccc(C2CCN([C@@H]3CCC4(CNC4)C3)CC2)c(OCC2CCOCC2)c1] | 0.54 LCMS Method 1 | 385.3 $[M + H]^+$ | 385.4 $[M + H]^+$ |
| 4J | 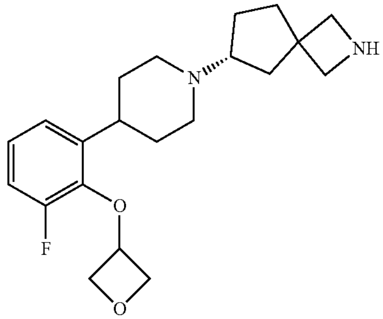 [SMILES: Fc1cccc(C2CCN([C@@H]3CCC4(CNC4)C3)CC2)c1OC1COC1] | 0.40 LCMS Method 1 | 361.2 $[M + H]^+$ | 361.6 $[M + H]^+$ |

TABLE 2-continued
| Intermediates 4B to 4X | | | | |
|---|---|---|---|---|
| Intermediate | Structure | Retention time (min) and Method | Expected Mass | Observed Mass |
| 4K | 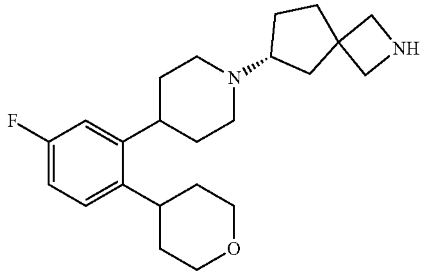 [SMILES: Fc1ccc(C2CCOCC2)c(C2CCN([C@@H]3CCC4(CNC4)C3)CC2)c1] | 0.52 LCMS Method 1 | 373.3 $[M + H]^+$ | 373.4 $[M + H]^+$ |
| 4L | 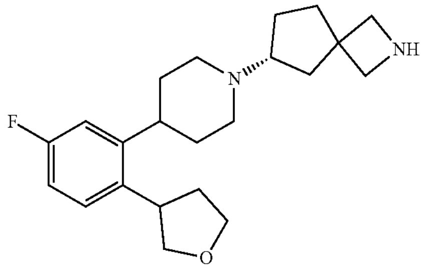 [SMILES: Fc1ccc(C2CCOC2)c(C2CCN([C@@H]3CCC4(CNC4)C3)CC2)c1] | 0.47 LCMS Method 1 | 359.2 $[M + H]^+$ | 359.4 $[M + H]^+$ |
| 4M | 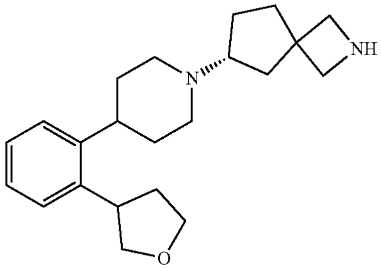 [SMILES: c1ccc(C2CCOC2)c(C2CCN([C@@H]3CCC4(CNC4)C3)CC2)c1] | 0.59 LCMS Method 1 | 341.3 $[M + H]^+$ | 341.2 $[M + H]^+$ |
| 4N | 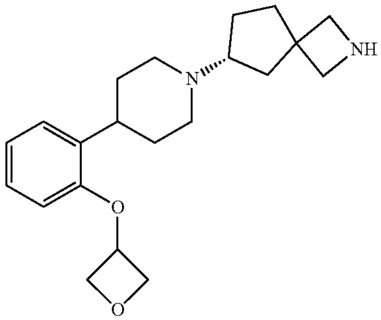 [SMILES: c1ccc(C2CCN([C@@H]3CCC4(CNC4)C3)CC2)c(OC2COC2)c1] | 0.44 LCMS Method 1 | 343.2 $[M + H]^+$ | 343.1 $[M + H]^+$ |
| 4O | 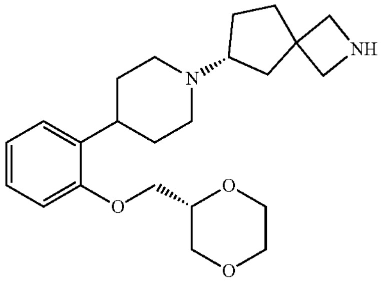 [SMILES: c1ccc(C2CCN([C@@H]3CCC4(CNC4)C3)CC2)c(OC[C@H]2COCCO2)c1] | 0.52 LCMS Method 1 | 387.3 $[M + H]^+$ | 387.3 $[M + H]^+$ |

TABLE 2-continued
| Intermediates 4B to 4X | | | | |
|---|---|---|---|---|
| Intermediate | Structure | Retention time (min) and Method | Expected Mass | Observed Mass |
| 4P | 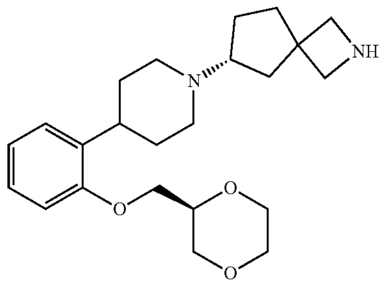 [SMILES: c1ccc(C2CCN([C@@H]3CCC4(CNC4)C3)CC2)c(OC[C@@H]2COCCO2)c1] | 0.47 LCMS Method 1 | 387.3 [M + H]+ | 387.3 [M + H]+ |
| 4Q | 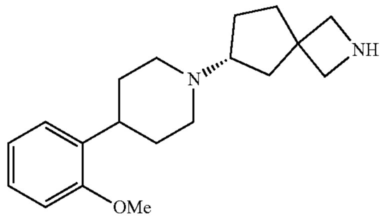 [SMILES: COc1ccccc1C1CCN([C@@H]2CCC3(CNC3)C2)CC1] | 0.46 LCMS Method 1 | 301.2 [M + H]+ | 301.2 [M + H]+ |
| 4R | 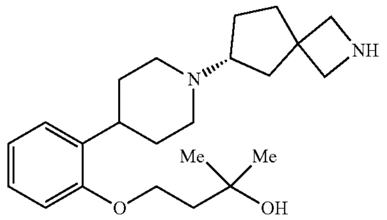 [SMILES: CC(C)(O)CCOc1ccccc1C1CCN([C@@H]2CCC3(CNC3)C2)CC1] | 0.51 LCMS Method 1 | 373.3 [M + H]+ | 373.1 [M + H]+ |
| 4S | 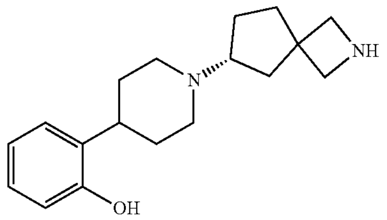 [SMILES: Oc1ccccc1C1CCN([C@@H]2CCC3(CNC3)C2)CC1] | 0.63 LCMS Method 1 | 287.4 [M + H]+ | 287.3 [M + H]+ |
| 4T | 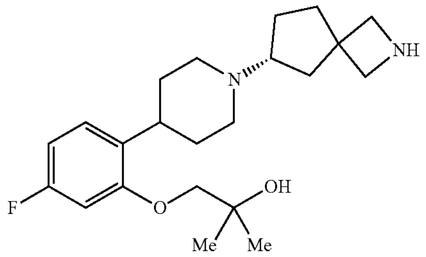 [SMILES: CC(C)(O)COc1cc(F)ccc1C1CCN([C@@H]2CCC3(CNC3)C2)CC1] | 0.53 LCMS Method 1 | 377.3 [M + H]+ | 377.3 [M + H]+ |
| 4U | 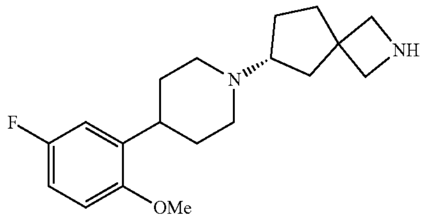 [SMILES: COc1ccc(F)cc1C1CCN([C@@H]2CCC3(CNC3)C2)CC1] | 0.43 LCMS Method 1 | 319.2 [M + H]+ | 319.4 [M + H]+ |

TABLE 2-continued

Intermediates 4B to 4X

| Intermediate | Structure | Retention time (min) and Method | Expected Mass | Observed Mass |
|---|---|---|---|---|
| 4V | 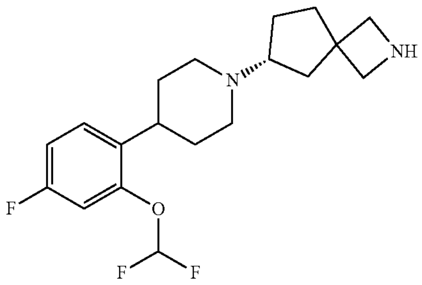 [SMILES: Fc1ccc(C2CCN([C@@H]3CCC4(CNC4)C3)CC2)c(OC(F)F)c1] | 0.52 LCMS Method 1 | 355.2 $[M+H]^+$ | 355.3 $[M+H]^+$ |
| 4W | 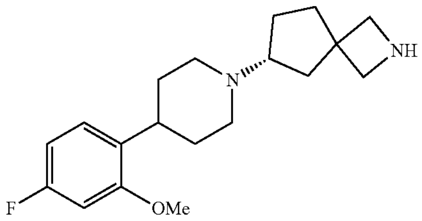 [SMILES: COc1cc(F)ccc1C1CCN([C@@H]2CCC3(CNC3)C2)CC1] | 0.44 LCMS Method 1 | 319.2 $[M+H]^+$ | 319.5 $[M+H]^+$ |
| 4X | 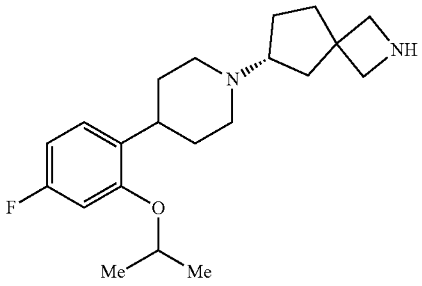 [SMILES: CC(C)Oc1cc(F)ccc1C1CCN([C@@H]2CCC3(CNC3)C2)CC1] | 0.58 LCMS Method 1 | 347.3 $[M+H]^+$ | 347.3 $[M+H]^+$ |

Intermediate 4Y: (R)-6-(4-(2-(tetrahydro-2H-pyran-4-yl)phenyl)piperidin-1-yl)-2-azaspiro[3.4]octane

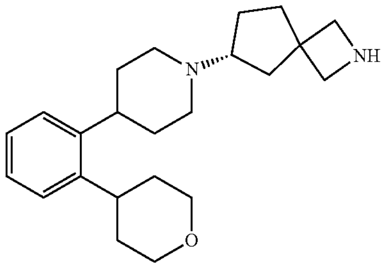 [SMILES: c1ccc(C2CCN([C@@H]3CCC4(CNC4)C3)CC2)c(C2CCOCC2)c1]

(R)-tert-butyl 6-(4-(2-(tetrahydro-2H-pyran-4-yl)phenyl)piperidin-1-yl)-2-azaspiro[3.4]octane-2-carboxylate (Intermediate 10A, 87 mg, 0.19 mmol) was dissolved in DCM (1 mL), and TFA (0.02 mL, 0.19 mmol) was added. The reaction was stirred at RT for 2 hours, concentrated and the solution was absorbed onto a 1 g SCX column. The column was washed with MeOH and then the product was eluted with 7N $NH_3$ in MeOH. The ammonia fraction was then concentrated to afford the title intermediate (62 mg, 0.18 mmol).

LCMS: Rt: 0.50 min (LCMS Method 1) MS m/z 355.6 $[M+H]^+$.

Intermediate 5A: (R)-2-(6-(4-(2-(benzyloxy)phenyl)piperidin-1-yl)-2-azaspiro[3.4]octan-2-yl)-1,3,4-oxadiazole

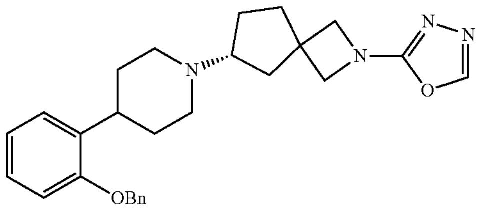 [SMILES: c1ccc(COc2ccccc2C2CCN([C@@H]3CCC4(C3)CN(c3nnco3)C4)CC2)cc1]

(R)-6-(4-(2-(benzyloxy)phenyl)piperidin-1-yl)-2-azaspiro[3.4]octane (Intermediate 4A, 0.79 g, 2.1 mmol), and ethyl 5-bromo-1,3,4-oxadiazole-2-carboxylate (556 mg, 2.52 mmol) were dissolved in THE (10 mL), and DIPEA (0.73 mL, 4.2 mmol) was added. The reaction was stirred at RT for 16 hours, concentrated, and diluted with EtOAc. The solution was washed with water, and concentrated. The residue was dissolved in a mixture of THE (10 mL), and water (5 mL), then LiOH (0.88 g, 21 mmol) was added. The reaction was stirred at RT for 1 hour and then a 6M solution of HCl (3.5 mL, 21 mmol) was added, and the reaction was stirred for 1 hour. Next, solid sodium carbonate was added to pH>9, then the solution was concentrated. The residue was diluted with EtOAc, washed with brine, and concentrated under reduced pressure. The residue was purified by FCC (0-5% MeOH(10% 7N $NH_3$)/ethyl acetate) to afford the title intermediate (480 mg, 1.07 mmol).

LCMS: Rt: 1.19 min (LCMS Method 4) MS m/z 445.4 $[M+H]^+$.

The following compound in Table 3 was prepared using a similar procedure and the relevant starting materials:

TABLE 3

Intermediate 5B

| Intermediate | Structure | Retention time (min) and Method | Expected Mass | Observed Mass |
|---|---|---|---|---|
| 5B | 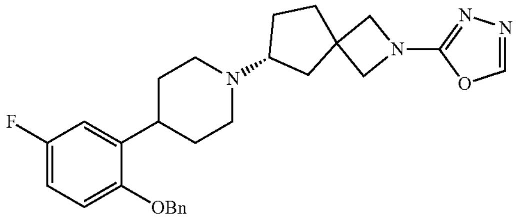 [SMILES: Fc1ccc(OCc2ccccc2)c(C2CCN([C@@H]3CCC4(C3)CN(c3nnco3)C4)CC2)c1] | 1.21 LCMS Method 2 | 463.3 $[M + H]^+$ | 463.4 $[M + H]^+$ |

Intermediate 5C: (R)-ethyl 5-(6-(4-(2-(benzyloxy) phenyl)piperidin-1-yl)-2-azaspiro[3.4]octan-2-yl)-1,3,4-oxadiazole-2-carboxylate

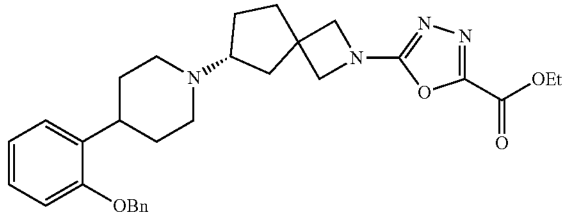 [SMILES: CCOC(=O)c1nnc(N2CC3(CC[C@@H](N4CCC(c5ccccc5OCc5ccccc5)CC4)C3)C2)o1]

(R)-6-(4-(2-(benzyloxy)phenyl)piperidin-1-yl)-2-azaspiro[3.4]octane (Intermediate 4A, 500 mg, 1.33 mmol), ethyl 5-bromo-1,3,4-oxadiazole-2-carboxylate (293 mg, 1.33 mmol), and potassium phosphate (282 mg, 1.33 mmol) were suspended in a mixture of 2% aqueous TPGS-750-M (2.4 mL), and THE (0.27 mL). The reaction was stirred at RT for 16 h, extracted with DCM, and the combined organic layers were concentrated. The residue was purified by FCC (0-7% MeOH/DCM) to afford the title intermediate (603 mg, 1.17 mmol).

LCMS: Rt: 0.81 min (LCMS Method 1) MS m/z 517.1 $[M+H]^+$.

Intermediate 5D: (R)-2-(1-(2-(1,3,4-thiadiazol-2-yl)-2-azaspiro[3.4]octan-6-yl)piperidin-4-yl)phenol

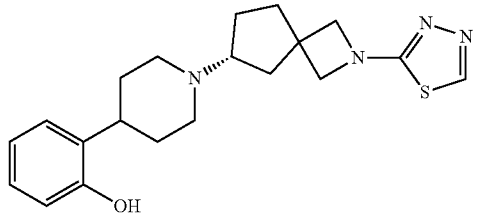 [SMILES: Oc1ccccc1C1CCN([C@@H]2CCC3(C2)CN(c2nncs2)C3)CC1]

(R)-2-(1-(2-azaspiro[3.4]octan-6-yl)piperidin-4-yl)phenol (Intermediate 4S, 713 mg, 0.722 mmol), 2-bromo-1,3,4-thiadiazole (143 mg, 0.866 mmol) and potassium phosphate (184 mg, 0.866 mmol) were suspended in a mixture of 2% aqueous TPGS-750-M (1.2 mL) and THE (0.26 mL). The reaction was stirred at RT for 16 hours, then at 50° C. for 16 hours. The reaction was then extracted with DCM (3×100 mL), and the combined organic layers were dried with $MgSO_4$, filtered and concentrated. The residue was purified by FCC (0-4% MeOH(10% $NH_4OH$)/DCM) to afford the title intermediate (55 mg, 0.15 mmol).

LCMS: Rt: 0.84 min (LCMS Method 2) MS m/z 371.3 $[M+H]^+$.

Intermediate 5E: (R)-6-(4-(2-(benzyloxy)phenyl) piperidin-1-yl)-2-(pyrimidin-5-yl)-2-azaspiro[3.4] octane

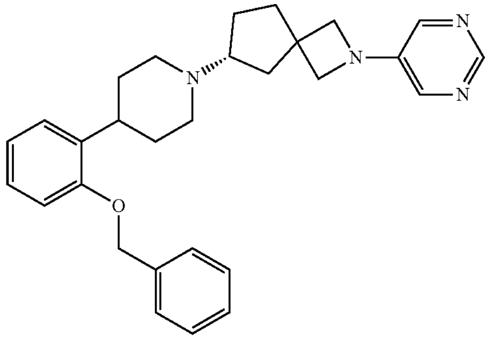 [SMILES: c1ccc(COc2ccccc2C2CCN([C@@H]3CCC4(C3)CN(c3cncnc3)C4)CC2)cc1]

(R)-6-(4-(2-(benzyloxy)phenyl)piperidin-1-yl)-2-azaspiro[3.4]octane (Intermediate 4A, 1.42 g, 3.77 mmol) and 5-bromopyrimidine (0.660 g, 4.15 mmol) in dioxane (30 mL) was placed under nitrogen. $Pd(dba)_2$ (0.217 g, 0.377 mmol), xantphos (0.262 g, 0.453 mmol) and 1M NaOtBu in THF (7.54 mL, 7.54 mmol) were added and the reaction was stirred at 80° C. for 16 hrs. The reaction was then cooled to room temperature, filtered, and rinsed through with MeCN and EtOAc. The filtrate was evaporated and the residue was purified by FCC (0-10% MeOH (1% $NH_4OH$)/EtOAc) to afford the title compound (788 mg).

LCMS: Rt: 0.83 min (LCMS Method 1) MS m/z 455.4 $[M+H]^+$.

$^1$H NMR (400 MHz, $CD_3OD$) δ 8.47 (s, 1H), 8.00 (s, 2H), 7.49-7.27 (m, 5H), 7.25-7.10 (m, 2H), 7.07-6.84 (m, 2H), 5.10 (s, 2H), 4.00-3.76 (m, 4H), 3.24-3.02 (m, 3H), 2.78 (s, 1H), 2.40-2.12 (m, 3H), 2.11-1.94 (m, 3H), 1.91-1.70 (m, 5H), 1.67-1.51 (m, 1H).

Intermediate 6A: (R)-2-(1-(2-(1,3,4-oxadiazol-2-yl)-2-azaspiro[3.4]octan-6-yl)piperidin-4-yl)phenol

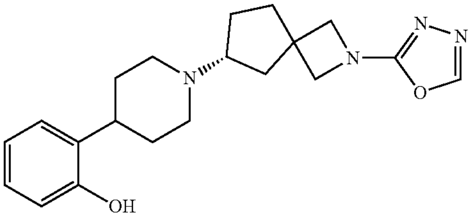 [SMILES: Oc1ccccc1C1CCN([C@@H]2CCC3(C2)CN(c2nnco2)C3)CC1]

(R)-2-(6-(4-(2-(benzyloxy)phenyl)piperidin-1-yl)-2-azaspiro[3.4]octan-2-yl)-1,3,4-oxadiazole (Intermediate 5A, 350 mg, 0.787 mmol) was dissolved in MeOH (5 mL), and 10% Pd/C (84 mg, 0.079 mmol) was added. The reaction was then stirred at RT under a balloon of hydrogen for 16 hours. The catalyst was filtered, and the filtrate was concentrated to afford the title intermediate (269 mg, 0.751 mmol) as a white solid.

LCMS: Rt: 0.84 min (LCMS Method 2) MS m/z 355.2 $[M+H]^+$.

The following compounds in Table 4 were prepared using a similar procedure and the relevant starting materials:

TABLE 4

Intermediates 6B to 6G

| Intermediate | Structure | Retention time (min) and Method | Expected Mass | Observed Mass |
|---|---|---|---|---|
| 6B | 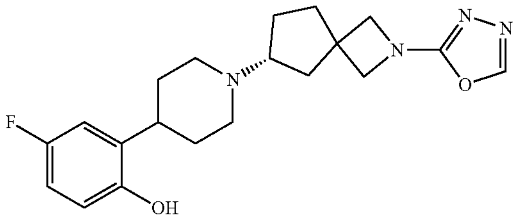 [SMILES: Oc1ccc(F)cc1C1CCN([C@@H]2CCC3(C2)CN(c2nnco2)C3)CC1] | 0.86 LCMS Method 2 | 373.2 $[M + H]^+$ | 373.4 $[M + H]^+$ |
| 6C | 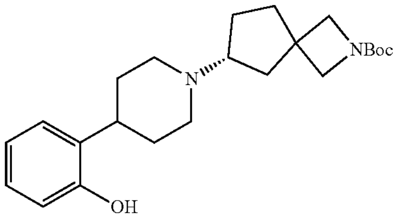 [SMILES: CC(C)(C)OC(=O)N1CC2(CC[C@@H](N3CCC(c4ccccc4O)CC3)C2)C1] | 1.08 LCMS Method 2 | 387.3 $[M + H]^+$ | 387.4 $[M + H]^+$ |
| 6D | 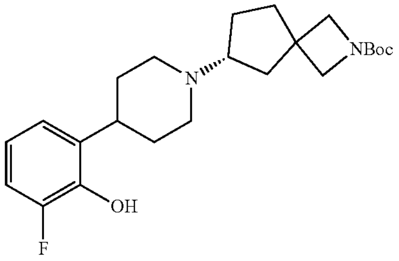 [SMILES: CC(C)(C)OC(=O)N1CC2(CC[C@@H](N3CCC(c4cccc(F)c4O)CC3)C2)C1] | 1.14 LCMS Method 2 | 405.3 $[M + H]^+$ | 405.4 $[M + H]^+$ |

TABLE 4-continued

Intermediates 6B to 6G

| Intermediate | Structure | Retention time (min) and Method | Expected Mass | Observed Mass |
| --- | --- | --- | --- | --- |
| 6E | 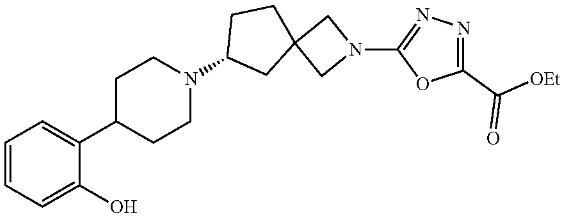 [SMILES: CCOC(=O)c1nnc(N2CC3(CC[C@@H](N4CCC(c5ccccc5O)CC4)C3)C2)o1] | 0.93 LCMS Method 2 | 427.2 $[M+H]^+$ | 427.3 $[M+H]^+$ |
| 6F | 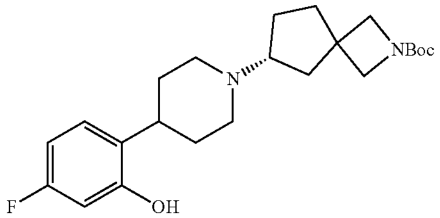 [SMILES: CC(C)(C)OC(=O)N1CC2(CC[C@@H](N3CCC(c4ccc(F)cc4O)CC3)C2)C1] | 2.57 LCMS Method 3 | 405.3 $[M+H]^+$ | 405.8 $[M+H]^+$ |
| 6G | 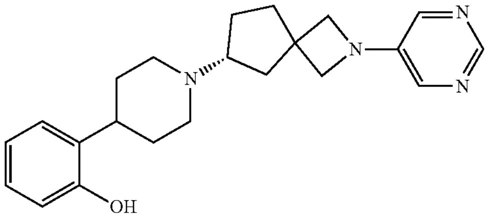 [SMILES: Oc1ccccc1C1CCN([C@@H]2CCC3(C2)CN(c2cncnc2)C3)CC1] | 2.57 LCMS Method 3 | 365.2 $[M+H]^+$ | 365.4 $[M+H]^+$ |

Intermediate 7A: 2-oxaspiro[3.3]heptan-6-yl 4-methylbenzenesulfonate

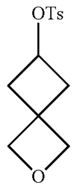 [SMILES: Cc1ccc(S(=O)(=O)OC2CC3(COC3)C2)cc1]

2-oxaspiro[3.3]heptan-6-ol (2.00 g, 17.5 mmol) was dissolved in DCM (50 mL), and DMAP (0.21 g, 1.7 mmol) was added followed by triethylamine (6.1 mL, 44 mmol). The solution was cooled to 0° C., and 4-methylbenzene-1-sulfonyl chloride (3.51 g, 18.4 mmol) was added, and the reaction was stirred for 16 hours at RT. The reaction mixture was washed with a 1N HCl (1×10 mL), dried over $MgSO_4$, filtered, and concentrated under reduced pressure. The residue was purified by FCC (0→80 ethyl acetate/heptane) to afford the title intermediate (4.17 g, 14.8 mmol).

LCMS: Rt: 0.86 min (LCMS Method 1) MS m/z 269.3 [M+H].

The following compounds in Table 5 were prepared using a similar procedure and the relevant starting materials:

TABLE 5

Intermediates 7B to 7M

| Intermediate | Structure | Retention time (min) and Method | Expected Mass | Observed Mass |
| --- | --- | --- | --- | --- |
| 7B | 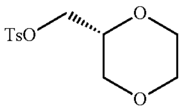 [SMILES: Cc1ccc(S(=O)(=O)OC[C@H]2COCCO2)cc1] | 0.82 LCMS Method 2 | 273.1 $[M+H]^+$ | 273.0 $[M+H]^+$ |
| 7C | 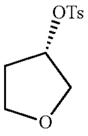 [SMILES: Cc1ccc(S(=O)(=O)O[C@H]2CCOC2)cc1] | 0.84 LCMS Method 1 | 243.1 $[M+H]^+$ | 243.1 $[M+H]^+$ |

TABLE 5-continued

| Intermediates 7B to 7M | | | | |
|---|---|---|---|---|
| Intermediate | Structure | Retention time (min) and Method | Expected Mass | Observed Mass |
| 7D | 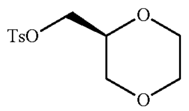 [SMILES: Cc1ccc(S(=O)(=O)OC[C@@H]2COCCO2)cc1] | 0.84 LCMS Method 1 | 273.1 $[M + H]^+$ | 273.1 $[M + H]^+$ |
| 7E | 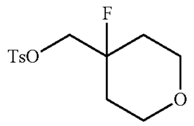 [SMILES: Cc1ccc(S(=O)(=O)OCC2(F)CCOCC2)cc1] | 0.91 LCMS Method 1 | 289.1 $[M + H]^+$ | Not observed |
| 7F | 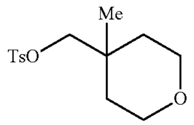 [SMILES: Cc1ccc(S(=O)(=O)OCC2(C)CCOCC2)cc1] | 0.98 LCMS Method 2 | 285.1 $[M + H]^+$ | Not observed |
| 7G | 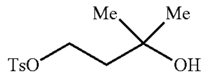 | 1.75 LCMS Method 4 | 276.1 $[M + H]^+$ | 276.3 $[M + H]^+$ |
| 7H | 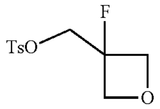 | 0.85 LCMS Method 1 | 261.1 $[M + H]^+$ | 261.1 $[M + H]^+$ |
| 7I | 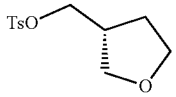 [SMILES: Cc1ccc(S(=O)(=O)OC[C@@H]2CCOC2)cc1] | 0.86 LCMS Method 1 | 257.1 $[M + H]^+$ | 257.2 $[M + H]^+$ |
| 7J | 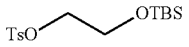 | 1.33 LCMS Method 2 | 331.1 $[M + H]^+$ | 331.2 $[M + H]^+$ |
| 7K | 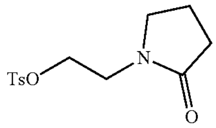 [SMILES: Cc1ccc(S(=O)(=O)OCCN2CCCC2=O)cc1] | 0.75 LCMS Method 2 | 284.1 $[M + H]^+$ | 284.2 $[M + H]^+$ |
| 7L | 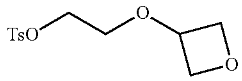 [SMILES: Cc1ccc(S(=O)(=O)OCCOC2COC2)cc1] | 0.79 LCMS Method 2 | 273.1 $[M + H]^+$ | 273.4 $[M + H]^+$ |
| 7M | 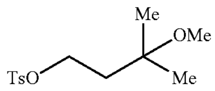 [SMILES: COC(C)(C)CCOS(=O)(=O)c1ccc(C)cc1] | 1.02 LCMS Method 2 | 273.1 $[M + H]^+$ | 273.2 $[M + H]^+$ |

Intermediate 8A: (R)-tert-butyl 6-(4-(2-(2-hydroxy-2-methylpropoxy)phenyl)piperidin-1-yl)-2-azaspiro[3.4]octane-2-carboxylate

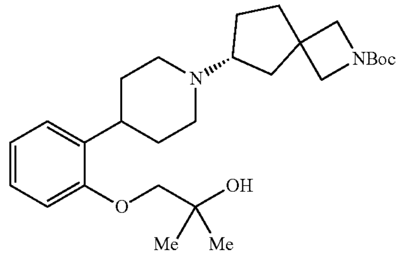 [SMILES: CC(C)(O)COc1ccccc1C1CCN([C@@H]2CCC3(C2)CN(C(=O)OC(C)(C)C)C3)CC1]

(R)-tert-butyl 6-(4-(2-hydroxyphenyl)piperidin-1-yl)-2-azaspiro[3.4]octane-2-carboxylate (Intermediate 6C, 310 mg, 0.802 mmol), 2,2-dimethyloxirane (289 mg, 4.01 mmol), and cesium carbonate (523 mg, 1.60 mmol) were suspended in DMF (8 mL), and the reaction was heated at 150° C. in a microwave reactor for 45 minutes, diluted with ethyl acetate (100 mL), washed with water (2×25 mL), and concentrated under reduced pressure. The residue was purified by FCC (0-10% MeOH/DCM) to afford the title intermediate (335 mg, 0.730 mmol).

LCMS: Rt: 0.73 min (LCMS Method 1) MS m/z 459.3 $[M+H]^+$.

The following compounds in Table 6 were prepared using a similar procedure and the relevant starting materials:

TABLE 6

| Intermediates 8B to 8C | | | | |
|---|---|---|---|---|
| Intermediate | Structure | Retention time (min) and Method | Expected Mass | Observed Mass |
| 8B | 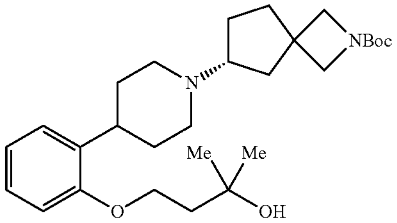 [SMILES: CC(C)(O)CCOc1ccccc1C1CCN([C@@H]2CCC3(C2)CN(C(=O)OC(C)(C)C)C3)CC1] | 1.21 LCMS Method 2 | 473.3 $[M + H]^+$ | 473.5 $[M + H]^+$ |
| 8C | 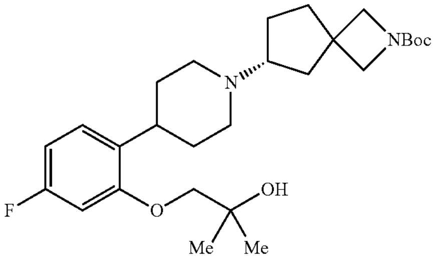 [SMILES: CC(C)(O)COc1cc(F)ccc1C1CCN([C@@H]2CCC3(C2)CN(C(=O)OC(C)(C)C)C3)CC1] | 0.82 LCMS Method 1 | 477.3 $[M + H]^+$ | 477.1 $[M + H]^+$ |

Intermediate 8D: tert-butyl (R)-6-(4-(4-fluoro-2-(oxetan-3-yloxy)phenyl)piperidin-1-yl)-2-azaspiro[3.4]octane-2-carboxylate

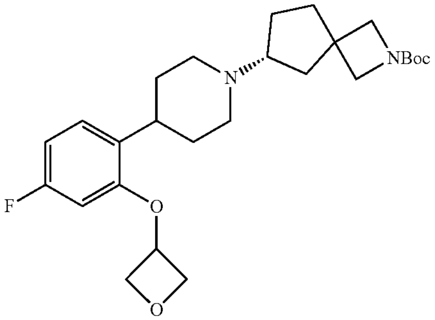 [SMILES: CC(C)(C)OC(=O)N1CC2(CC[C@@H](N3CCC(c4ccc(F)cc4OC4COC4)CC3)C2)C1]

To a DMF (30 mL) solution of (R)-tert-butyl 6-(4-(3-fluoro-2-hydroxyphenyl)piperidin-1-yl)-2-azaspiro[3.4]octane-2-carboxylate (Intermediate 6F, 811 mg, 2.005 mmol) and $Cs_2CO_3$ (1960 mg, 6.01 mmol) was added oxetan-3-yl 4-methylbenzenesulfonate (503 mg, 2.205 mmol). The resulting mixture was stirred at 80° C. for 16 hours. The crude was diluted with EtOAc and washed with water. The solvent was removed under reduced pressure and the residue was purified by FCC (0-10% MeOH/DCM) to yield the title compound (680 mg, 1.48 mmol).

LCMS: Rt: 2.79 min (LCMS Method 3) MS m/z 461.5 $[M+H]^+$.

The following compounds in Table 7 were prepared using a similar procedure and the relevant starting materials:

TABLE 7
| Intermediates 8E to 8N | | | | |
|---|---|---|---|---|
| Intermediate | Structure | Retentiom time (min) and Method | Expected Mass | Observed Mass |
| 8E | 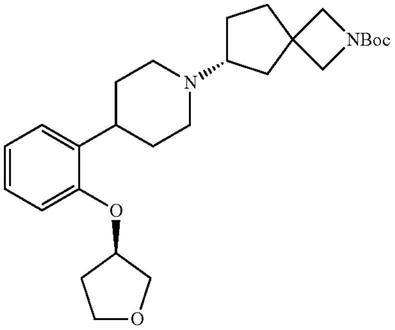 [SMILES: CC(C)(C)OC(=O)N1CC2(CC[C@@H](N3CCC(c4ccccc4O[C@@H]4CCOC4)CC3)C2)C1] | 1.23 LCMS Method 2 | 457.3 [M + H]$^+$ | 457.5 [M + H]$^+$ |
| 8F | 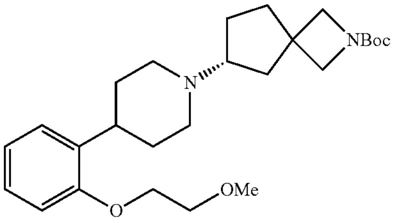 [SMILES: COCCOc1ccccc1C1CCN([C@@H]2CCC3(C2)CN(C(=O)OC(C)(C)C)C3)CC1] | 1.25 LCMS Method 2 | 445.3 [M + H]$^+$ | 445.2 [M + H]$^+$ |
| 8G | 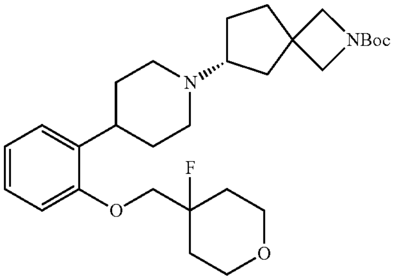 [SMILES: CC(C)(C)OC(=O)N1CC2(CC[C@@H](N3CCC(c4ccccc4OCC4(F)CCOCC4)CC3)C2)C1] | 1.26 LCMS Method 2 | 503.3 [M + H]$^+$ | 503.4 [M + H]$^+$ |
| 8H | 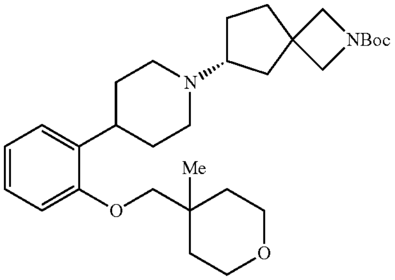 [SMILES: CC1(COc2ccccc2C2CCN([C@@H]3CCC4(C3)CN(C(=O)OC(C)(C)C)C4)CC2)CCOCC1] | 1.38 LCMS Method 2 | 499.4 [M + H]$^+$ | 499.4 [M + H]$^+$ |
| 8I | 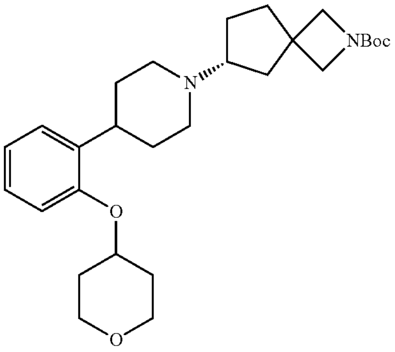 [SMILES: CC(C)(C)OC(=O)N1CC2(CC[C@@H](N3CCC(c4ccccc4OC4CCOCC4)CC3)C2)C1] | 1.24 LCMS Method 2 | 471.3 [M + H]$^+$ | 471.2 [M + H]$^+$ |

TABLE 7-continued
| Intermediates 8E to 8N | | | | |
|---|---|---|---|---|
| Intermediate | Structure | Retentiom time (min) and Method | Expected Mass | Observed Mass |
| 8J | 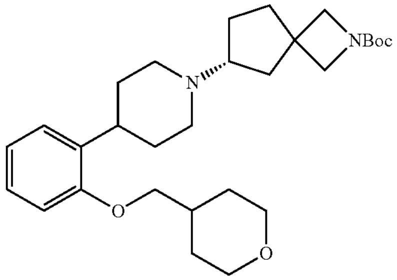 [SMILES: CC(C)(C)OC(=O)N1CC2(CC[C@@H](N3CCC(c4ccccc4OCC4CCOCC4)CC3)C2)C1] | 1.28 LCMS Method 2 | 485.3 [M + H]+ | 485.2 [M + H]+ |
| 8K | 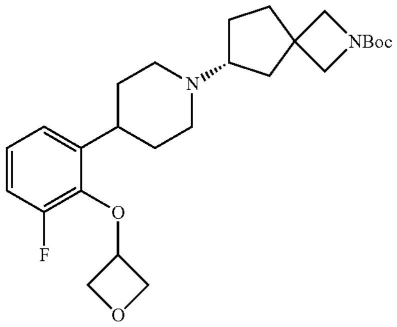 [SMILES: CC(C)(C)OC(=O)N1CC2(CC[C@@H](N3CCC(c4cccc(F)c4OC4COC4)CC3)C2)C1] | 2.79 LCMS Method 4 | 461.3 [M + H]+ | 461.5 [M + H]+ |
| 8L | 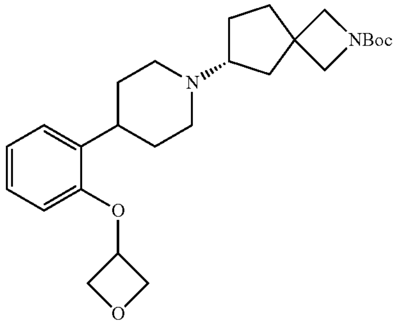 [SMILES: CC(C)(C)OC(=O)N1CC2(CC[C@@H](N3CCC(c4ccccc4OC4COC4)CC3)C2)C1] | 1.20 LCMS Method 2 | 443.2 [M + H]+ | 443.2 [M + H]+ |
| 8M | 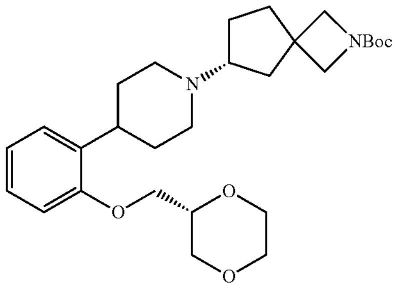 [SMILES: CC(C)(C)OC(=O)N1CC2(CC[C@@H](N3CCC(c4ccccc4OC[C@H]4COCCO4)CC3)C2)C1] | 1.21 LCMS Method 2 | 487.3 [M + H]+ | 487.2 [M + H]+ |

TABLE 7-continued

| Intermediates 8E to 8N | | | | |
|---|---|---|---|---|
| Intermediate | Structure | Retentiom time (min) and Method | Expected Mass | Observed Mass |
| 8N | 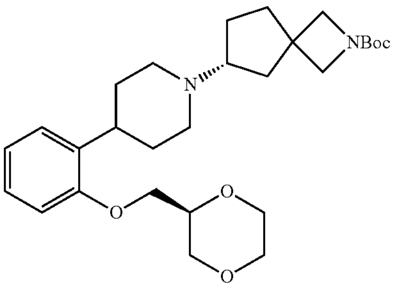 [SMILES: CC(C)(C)OC(=O)N1CC2(CC[C@@H](N3CCC(c4ccccc4OC[C@@H]4COCCO4)CC3)C2)C1] | 1.20 LCMS Method 2 | 487.3 [M + H]$^+$ | 487.2 [M + H]$^+$ |

Intermediate 8O: (R)-tert-butyl 6-(4-(2-methoxyphenyl)piperidin-1-yl)-2-azaspiro[3.4]octane-2-carboxylate

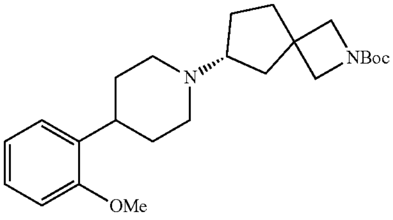 [SMILES: COc1ccccc1C1CCN([C@@H]2CCC3(C2)CN(C(=O)OC(C)(C)C)C3)CC1]

(R)-tert-butyl 6-(4-(2-hydroxyphenyl)piperidin-1-yl)-2-azaspiro[3.4]octane-2-carboxylate (Intermediate 6C, 1.087 g, 2.81 mmol) was added into a 45 mL falcon tube and dissolved in THE (25 mL) and methanol (1.0 mL, 24.72 mmol). $Ph_3P$ resin (3 mmol/g, 3.75 g, 11.25 mmol) was added, and the reaction mixture was cooled to 0° C. DEAD (4000 in toluene, 2.78 mL, 7.03 mmol) was added dropwise and the reaction was shaken for 24 hours. Additional MeOH (1.0 mL, 24.72 mmol) was added and the reaction was shaken for an additional 48 hours. Additional DEAD (40% in toluene, 2.78 mL) and $Ph_3P$ resin (3 mmol/g, 1.0 g, 3 mmol) was added and the reaction was stirred for an additional 24 hours. The reaction was then filtered and washed with MeCN and the filtrate was concentrated and purified by FCC (0-8% MeOH (1% $NH_4OH$)/DCM) to yield the title intermediate.

LCMS: Rt: 1.27 min (LCMS Method 2) MS m/z 401.3 [M+H]$^+$.

The following intermediates in Table 8 were prepared in a similar manner using the relevant starting materials:

TABLE 8

| Intermediates 8P to 8R | | | | |
|---|---|---|---|---|
| Intermediate | Structure | Retention time (min) and Method | Expected Mass | Observed Mass |
| 8P | 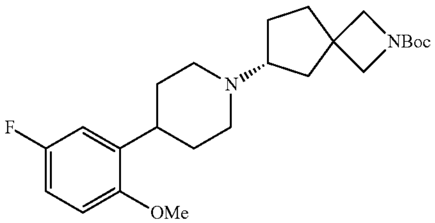 [SMILES: COc1ccc(F)cc1C1CCN([C@@H]2CCC3(C2)CN(C(=O)OC(C)(C)C)C3)CC1] | 1.32 LCMS Method 2 | 419.3 [M + H]$^+$ | 419.6 [M + H]$^+$ |
| 8Q | 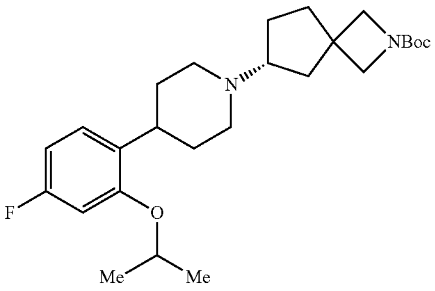 [SMILES: CC(C)Oc1cc(F)ccc1C1CCN([C@@H]2CCC3(C2)CN(C(=O)OC(C)(C)C)C3)CC1] | 1.76 LCMS Method 3 | 447.6 [M + H]$^+$ | 447.5 [M + H]$^+$ |

TABLE 8-continued

| Intermediates 8P to 8R | | | | |
|---|---|---|---|---|
| Intermediate | Structure | Retention time (min) and Method | Expected Mass | Observed Mass |
| 8R | 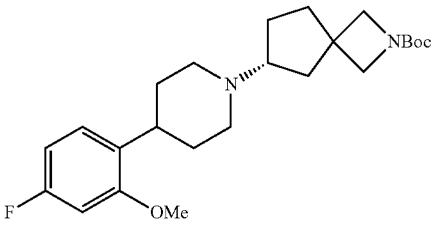 [SMILES: COc1cc(F)ccc1C1CCN([C@@H]2CCC3(C2)CN(C(=O)OC(C)(C)C)C3)CC1] | 3.17 LCMS Method 4 | 419.3 $[M + H]^+$ | 419.8 $[M + H]^+$ |

Intermediate 8S: (R)-tert-butyl 6-(4-(2-(difluoromethoxy)-4-fluorophenyl)piperidin-1-yl)-2-azaspiro[3.4]octane-2-carboxylate

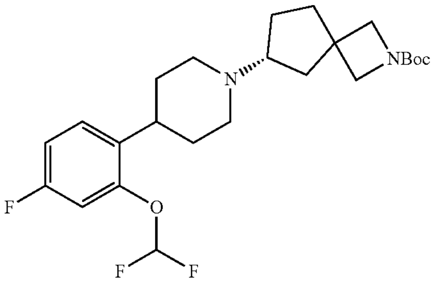 [SMILES: CC(C)(C)OC(=O)N1CC2(CC[C@@H](N3CCC(c4ccc(F)cc4OC(F)F)CC3)C2)C1]

(R)-tert-butyl 6-(4-(4-fluoro-2-hydroxyphenyl)piperidin-1-yl)-2-azaspiro[3.4]octane-2-carboxylate (Intermediate 6F, 425 mg, 1.051 mmol) was dissolved in a mixture of MeCN (5 mL) and 4M KOH (5.25 mL). The reaction mixture was frozen at −78° C. in a dry ice/acetone bath and diethyl (bromodifluoromethyl)phosphonate (0.373 mL, 2.101 mmol) was added dropwise and the solution was warmed to RT. The reaction mixture was diluted with water and extracted with EtOAc (2×). The combined organics were washed with brine, dried over magnesium sulfate, filtered, and concentrated. The isolated material (470 mg, 1.034 mmol) was used without further purification.

LCMS: Rt: 1.28 min (LCMS Method 2) MS m/z 455.4 $[M+H]^+$.

Intermediate 9A: (R)-tert-butyl 6-(4-(2-(3,6-dihydro-2H-pyran-4-yl)phenyl)piperidin-1-yl)-2-azaspiro[3.4]octane-2-carboxylate

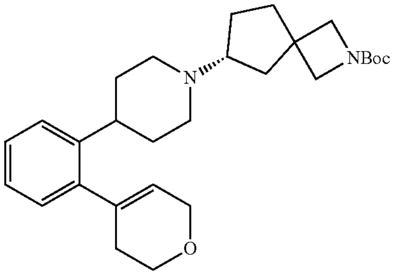 [SMILES: CC(C)(C)OC(=O)N1CC2(CC[C@@H](N3CCC(c4ccccc4C4=CCOCC4)CC3)C2)C1]

(R)-tert-butyl 6-(4-(2-bromophenyl)piperidin-1-yl)-2-azaspiro[3.4]octane-2-carboxylate (Intermediate 3B, 153 mg, 0.340 mmol), 2-(3,6-dihydro-2H-pyran-4-yl)-4,4,5,5-tetramethyl-1,3,2-dioxaborolane (86 mg, 0.41 mmol), dichloro[1,1'-bis(diphenylphosphino)ferrocene]palladium (II) DCM adduct (12 mg, 0.017 mmol) and potassium phosphate (217 mg, 1.02 mmol) were dissolved in a mixture of dioxane (3 mL) and water (0.4 mL). The reaction mixture was stirred at 100° C. for 2 hours, concentrated, and diluted with water (200 mL) and extracted with DCM (3×100 mL). The organic extracts were dried over sodium sulfate, filtered and concentrated. The residue was purified by FCC (0-30% EtOAc (20% 7N $NH_3$ in MeOH)/DCM) to afford the title intermediate (132 mg, 0.34 mmol).

LCMS: Rt: 1.28 min (LCMS Method 2) MS m/z 453.3 $[M+H]^+$.

The following compound in Table 9 were prepared using a similar procedure and the relevant starting materials:

TABLE 9

| Intermediates 9B to 9E | | | | |
|---|---|---|---|---|
| Intermediate | Structure | Retention time (min) and Method | Expected Mass | Observed Mass |
| 9B | 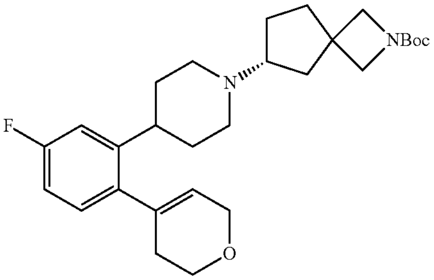 [SMILES: CC(C)(C)OC(=O)N1CC2(CC[C@@H](N3CCC(c4cc(F)ccc4C4=CCOCC4)CC3)C2)C1] | 1.26 LCMS Method 2 | 471.3 $[M + H]^+$ | 471.7 $[M + H]^+$ |

TABLE 9-continued

| Intermediates 9B to 9E | | | | |
|---|---|---|---|---|
| Intermediate | Structure | Retention time (min) and Method | Expected Mass | Observed Mass |
| 9C | 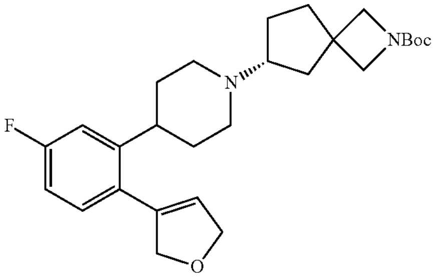 [SMILES: CC(C)(C)OC(=O)N1CC2(CC[C@@H](N3CCC(c4cc(F)ccc4C4=CCOC4)CC3)C2)C1] | 1.23 LCMS Method 2 | 457.3 $[M + H]^+$ | 457.7 $[M + H]^+$ |
| 9D | 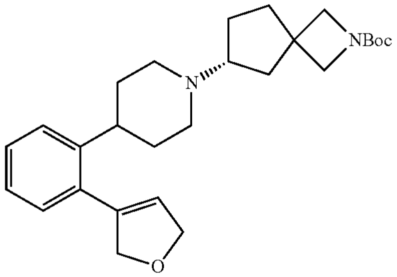 [SMILES: CC(C)(C)OC(=O)N1CC2(CC[C@@H](N3CCC(c4ccccc4C4=CCOC4)CC3)C2)C1] | 1.25 LCMS Method 2 | 439.3 $[M + H]^+$ | 439.5 $[M + H]^+$ |
| 9E | 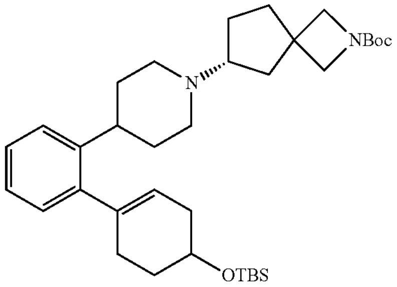 [SMILES: CC(C)(C)OC(=O)N1CC2(CC[C@@H](N3CCC(c4ccccc4C4=CCC(O[Si](C)(C)C(C)(C)C)CC4)CC3)C2)C1] | 1.78 LCMS Method 2 | 603.4 $[M + Na]^+$ | 603.9 $[M + Na]^+$ |

Intermediate 10A: (R)-tert-butyl 6-(4-(2-(tetrahydro-2H-pyran-4-yl)phenyl)piperidin-1-yl)-2-azaspiro[3.4]octane-2-carboxylate

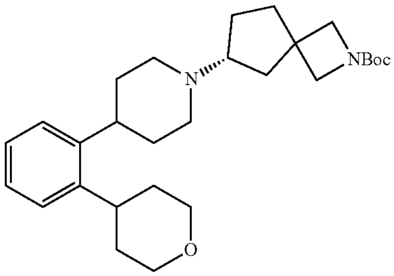 [SMILES: CC(C)(C)OC(=O)N1CC2(CC[C@@H](N3CCC(c4ccccc4C4CCOCC4)CC3)C2)C1]

(R)-tert-butyl 6-(4-(2-(3,6-dihydro-2H-pyran-4-yl)phenyl)piperidin-1-yl)-2-azaspiro[3.4]octane-2-carboxylate (Intermediate 9A, 132 mg, 0.248 mmol) was dissolved in MeOH (5 mL) and 1000 Pd/C (26 mg, 0.025 mmol) was added. The reaction was stirred under a balloon of hydrogen atmosphere for 48 hours and then the solution was filtered and concentrated. The residue was purified by FCC (0-6% MeOH/DCM) to afford the title intermediate (87 mg, 0.19 mmol) a yellow foamy solid. LCMS: Rt: 1.25 min (LCMS Method 2) MS m/z 455.4 $[M+H]^+$.

The following compounds in Table 10 were prepared using a similar procedure and the relevant starting materials:

TABLE 10

| Intermediates 10B to 10D | | | | |
|---|---|---|---|---|
| Intermediate | Structure | Retention time (min) and Method | Expected Mass | Observed Mass |
| 10B | 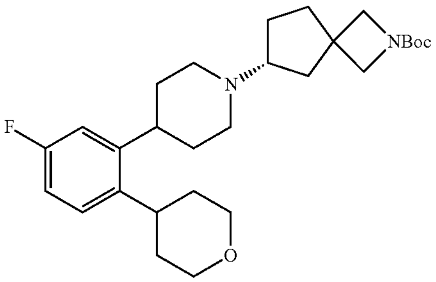 | 2.95 LCMS Method 4 | 473.3 $[M + H]^+$ | 473.8 $[M + H]^+$ |
| 10C | 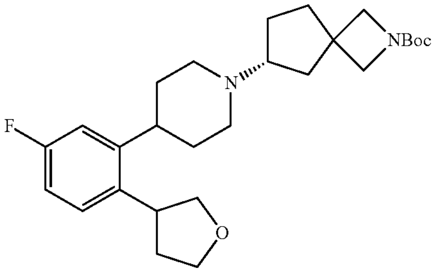 [SMILES: CC(C)(C)OC(=O)N1CC2(CC[C@@H](N3CCC(c4cc(F)ccc4C4CCOC4)CC3)C2)C1] | 2.86 LCMS Method 4 | 459.3 $[M + H]^+$ | 459.5 $[M + H]^+$ |
| 10D | 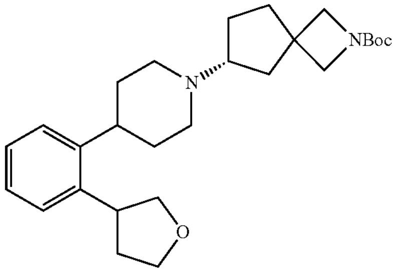 [SMILES: CC(C)(C)OC(=O)N1CC2(CC[C@@H](N3CCC(c4ccccc4C4CCOC4)CC3)C2)C1] | 1.21 LCMS Method 2 | 441.3 $[M + H]^+$ | 441.7 $[M + H]^+$ |

Intermediate 11A: 4-(2-chlorophenyl)tetrahydro-2H-pyran-4-ol

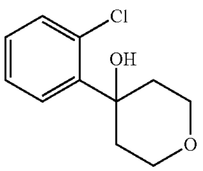 [SMILES: OC1(c2ccccc2Cl)CCOCC1]

To a solution of 1-bromo-2-chlorobenzene (3 g, 15.67 mmol) in THF (25 mL) at 25° C. was added iso-propyl magnesium chloride (7.8 mL, 15.67 mmol, 2.0 M in THF), and the reaction mixture was stirred at 25° C. for 2 hr. Then, a solution of tetrahydro-4H-pyran-4-one (1.57 g, 15.67 mmol) in THF (5 mL) was added dropwise. After the addition, the mixture was stirred at 25° C. for another 16 hr. The reaction mixture was then quenched with a saturated solution of $NH_4Cl$ (30 mL), extracted with EtOAc (3×20 mL) and the combined organic phases were dried with $Na_2SO_4$, filtered and concentrated. The crude product was purified by FCC (0-50% EtOAc/petroleum ether) to afford the title intermediate (900 mg, 4.23 mmol, 27.00% yield) as a yellow oil.

LCMS: Rt: 1.52 min (LCMS Method 5) MS m/z 195.1 $[M-H_2O+H]^+$.

$^1$H NMR (400 MHz, $CDCl_3$) δ 7.56-7.53 (m, 1H), 7.44-7.38 (m, 1H), 7.34-7.19 (m, 2H), 4.07-3.95 (m, 2H), 3.94-3.85 (m, 2H), 3.22-2.96 (m, 1H), 2.48-2.36 (m, 2H), 2.02-1.90 (m, 2H).

The following compound in Table 11 was prepared using a similar procedure using the relevant starting materials:

TABLE 11

| Intermediate 11B | | | | |
|---|---|---|---|---|
| Intermediate | Structure | Rt(min) Method | Expected Mass | Observed Mass |
| 11B | 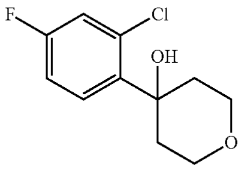 [SMILES: OC1(c2ccc(F)cc2Cl)CCOCC1] | 0.73 LCMS Method 5 | 213.0 $[M-OH]^+$ | 213.1 $[M-OH]^+$ |

Intermediate 12A: 4-(2-bromo-4-fluorophenyl)-3,6-dihydro-2H-pyran

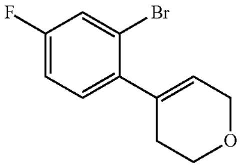 [SMILES: Fc1ccc(C2=CCOCC2)c(Br)c1]

To a solution of 2-bromo-4-fluoro-1-iodobenzene (2.0 g, 6.65 mmol) in a mixture of dioxane (20 mL) and $H_2O$ (2 mL) was added 2-(3,6-dihydro-2H-pyran-4-yl)-4,4,5,5-tetramethyl-1,3,2-dioxaborolane (1.40 g, 6.65 mmol), $K_2CO_3$ (2.76 g, 19.94 mmol) and Pd(dppf)$Cl_2$ (486 mg, 0.66 mmol). The reaction mixture was stirred at 60° C. for 4 hr under $N_2$ and then warmed to 80° C. for another 1 hr. The reaction mixture was quenched with saturated solution of NaCl (20 mL) and this solution was extracted with EtOAc (3×20 mL). The combined organic phases were dried over $Na_2SO_4$, filtered and concentrated. The crude product was purified by FCC (0-30% EtOAc/petroleum ether) to afford the title intermediate (1.2 g, 4.67 mmol, 70.22% yield) as a yellow oil.

$^1$H NMR (400 MHz, $CDCl_3$) δ 7.32-7.30 (m, 1H), 7.15-7.13 (m, 1H), 7.00-6.98 (m, 1H), 5.70-5.68 (m, 1H), 4.31-4.29 (m, 2H), 3.94-3.91 (m, 2H), 2.42-2.39 (m, 2H).

Intermediate 12B: tert-butyl 4-(2-(3,6-dihydro-2H-pyran-4-yl)phenyl)-3,6-dihydropyridine-1(2H)-carboxylate

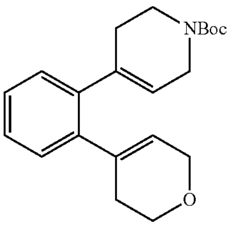 [SMILES: CC(C)(C)OC(=O)N1CC=C(c2ccccc2C2=CCOCC2)CC1]

To a solution of tert-butyl 4-(2-bromophenyl)-3,6-dihydropyridine-1(2H)-carboxylate3 (Intermediate 13J, 500 mg, 1.48 mmol) in dioxane (5 mL) and $H_2O$ (0.5 mL) was added 2-(3,6-dihydro-2H-pyran-4-yl)-4,4,5,5-tetramethyl-1,3,2-dioxaborolane (311 mg, 1.48 mmol), $K_2CO_3$ (614 mg, 4.44 mmol) and Pd(dppf)$Cl_2$ (110 mg, 0.15 mmol). The reaction mixture was stirred for 16 hr at 80° C. under $N_2$. The reaction mixture was then quenched with $H_2O$ (10 mL), extracted with EtOAc (3×5 mL), washed with brine (10 mL), dried with $Na_2SO_4$, filtered and concentrated. The crude product was purified by FCC (5-10% EtOAc/petroleum ether) to give the title compound (350 mg, 1.02 mmol) as a colorless oil.

LCMS: Rt: 1.12 min (LCMS Method 6) MS m/z 242.3 $[M-Boc+H]^+$.

Intermediate 13A: tert-butyl 4-(2-(benzyloxy)phenyl)-3,6-dihydropyridine-1(2H)-carboxylate

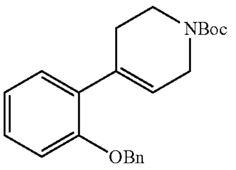

To a mixture of 1-(benzyloxy)-2-bromobenzene (6.53 mL, 34.3 mmol), tert-butyl 4-(4,4,5,5-tetramethyl-1,3,2-dioxaborolan-2-yl)-5,6-dihydropyridine-1(2H)-carboxylate (10.1 g, 32.7 mmol), $PdCl_2(dppf)\cdot CH_2Cl_2$ (1.334 g, 1.633 mmol) and potassium phosphate (20.80 g, 98 mmol) was added dioxane (115 mL) and water (15 mL). The reaction was then stirred at 100° C. for 16 hours. LCMS showed clean reaction. The reaction was washed with water, dried over magnesium sulfate, filtered and concentrated. The residue was then purified by FCC (0-20% EtOAc/heptanes) to yield the title compound (11.86 g, 32.1 mmol) as a beige oil.

LCMS: Rt: 1.37 min (LCMS Method 2) MS m/z 265.9 $[M-Boc+H]^+$.

Intermediate 13B: tert-butyl 4-(2-(trifluoromethoxy)phenyl)-3,6-dihydropyridine-1(2H)-carboxylate

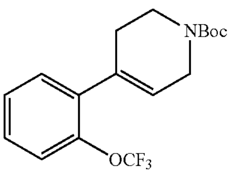 [SMILES: CC(C)(C)OC(=O)N1CC=C(c2ccccc2OC(F)(F)F)CC1]

1-bromo-2-(trifluoromethoxy)benzene (10 g, 41.5 mmol), tert-butyl 4-(4,4,5,5-tetramethyl-1,3,2-dioxaborolan-2-yl)-

5,6-dihydropyridine-1(2H)-carboxylate (14.11 g, 45.6 mmol), $PdCl_2(dppf)\cdot CH_2Cl_2$ adduct (1.694 g, 2.075 mmol), and $K_3PO_4$ (26.4 g, 124 mmol) were added to a 500 mL three neck flask. The reactants were dissolved in degassed dioxane (160 mL) and degassed water (40 mL) and stirred at 100° C. for 5 hours. The reaction was then cooled to RT and filtered through a pad of celite, washing with EtOAc (100 mL). The filtrate was diluted with 500 mL of EtOAc and washed with water (3×25 mL) and brine (1×10 mL), dried over $MgSO_4$, filtered and concentrated. The residue was then dissolved in 100 mL of EtOAc and filtered through a second pad of celite and concentrated and then purified by FCC (0→2500 EtOAc/heptanes) to yield the title intermediate as a yellow liquid (14.09 g, 41 mmol).

Rt: 3.13 min (LCMS Method 3). MS m/z 288.1 [M-Boc+formate]$^+$.

$^1$H NMR (400 MHz, $CDCl_3$) δ 7.35-7.21 (m, 4H), 5.83-5.76 (m, 1H), 4.08 (q, J=2.8 Hz, 2H), 3.63 (t, J=5.6 Hz, 2H), 2.47 (dq, J=5.4, 3.0 Hz, 2H), 1.52 (s, 9H).

The following compounds in Table 12 were prepared using a similar procedure and the relevant starting materials:

TABLE 12

Intermediates 13C to 13I

| Intermediate | Structure | Retention time (min) and Method | Expected Mass | Observed Mass |
|---|---|---|---|---|
| 13C | 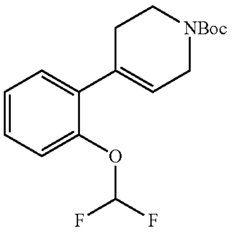 [SMILES: CC(C)(C)OC(=O)N1CC=C(c2ccccc2OC(F)F)CC1] | 1.20 LCMS Method 2 | 226.1 [M − Boc + H]$^+$ | 226.3 [M − Boc + H]$^+$ |
| 13D | 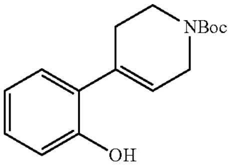 [SMILES: CC(C)(C)OC(=O)N1CC=C(c2ccccc2O)CC1] | 2.36 LCMS Method 3 | 176.1 [M − Boc + H]$^+$ | 176.1 [M − Boc + H]$^+$ |
| 13E | 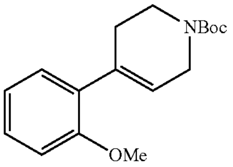 [SMILES: COc1ccccc1C1=CCN(C(=O)OC(C)(C)C)CC1] | 1.21 LCMS Method 2 | 190.1 [M − Boc + H]$^+$ | 190.3 [M − Boc + H]$^+$ |
| 13F | 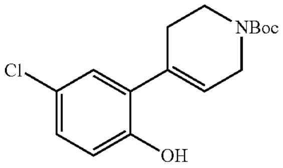 [SMILES: CC(C)(C)OC(=O)N1CC=C(c2cc(Cl)ccc2O)CC1] | 1.31 LCMS Method 1 | 224.1 [M − Boc + H]$^+$ | 223.9 [M − Boc + H]$^+$ |
| 13G | 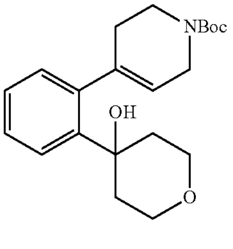 [SMILES: CC(C)(C)OC(=O)N1CC=C(c2ccccc2C2(O)CCOCC2)CC1] | 0.88 LCMS Method 5 | 360.2 [M + H]$^+$ | Not found |
| 13H | 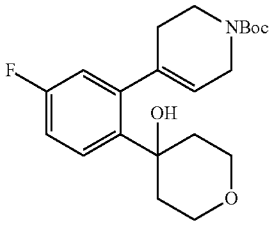 [SMILES: CC(C)(C)OC(=O)N1CC=C(c2cc(F)ccc2C2(O)CCOCC2)CC1] | 0.891 LCMS Method 5 | 378.2 [M + H]$^+$ | Not found |

TABLE 12-continued

| Intermediates 13C to 13I | | | | |
|---|---|---|---|---|
| Intermediate | Structure | Retention time (min) and Method | Expected Mass | Observed Mass |
| 13I | 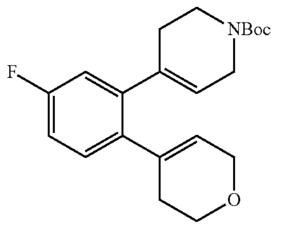 [SMILES: CC(C)(C)OC(=O)N1CC=C(c2cc(F)ccc2C2=CCOCC2)CC1] | 0.977 LCMS Method 5 | 260.1 [M − Boc + H]+ | 260.0 [M − Boc + H]+ |

Intermediate 13J: tert-butyl 4-(2-bromophenyl)-3,6-dihydropyridine-1(2H)-carboxylate

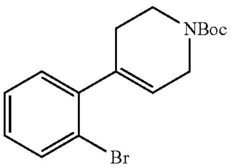 [SMILES: CC(C)(C)OC(=O)N1CC=C(c2ccccc2Br)CC1]

To a solution of 1-bromo-2-iodobenzene (1 g, 3.53 mmol) in dioxane (10 mL) and $H_2O$ (1 mL) was added tert-butyl 4-(4,4,5,5-tetramethyl-1,3,2-dioxaborolan-2-yl)-3,6-dihydropyridine-1(2H)-carboxylate (984 mg, 3.18 mmol), $K_2CO_3$ (1.46 g, 10.59 mmol) and Pd(dppf)$Cl_2$ (256 mg, 0.35 mmol). The reaction mixture was stirred for 2 hr at 60° C. under $N_2$ and the reaction mixture was then quenched with $H_2O$ (20 mL), extracted with EtOAc (3×10 mL), washed with NaCl (20 mL), dried with $Na_2SO_4$, filtered and concentrated. The crude product was purified by FCC (0-2.5% EtOAc/PE) to give and then purified a second time using the same conditions to yield the title compound (500 mg, 1.48 mmol).

$^1$H NMR (400 MHz, $CD_3OD$) δ 7.56 (d, J=8.0 Hz, 1H), 7.34-7.28 (m, 1H), 7.22-7.14 (m, 2H), 5.63 (br s, 1H), 4.03 (br s, 2H), 3.64 (t, J=5.0 Hz, 2H), 2.42 (d, J=1.5 Hz, 2H), 1.50 (s, 9H).

Intermediate 13K: tert-butyl 4-(2-(benzyloxy)-5-fluorophenyl)-3,6-dihydropyridine-1(2H)-carboxylate

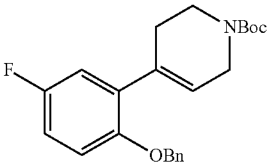 [SMILES: CC(C)(C)OC(=O)N1CC=C(c2cc(F)ccc2OCc2ccccc2)CC1]

To a solution of 1-(benzyloxy)-2-bromo-4-fluorobenzene (2.0 g, 7.11 mmol) in a mixture of dioxane (20 mL) and $H_2O$ (2 mL) was added tert-butyl 4-(4,4,5,5-tetramethyl-1,3,2-dioxaborolan-2-yl)-3,6-dihydropyridine-1(2H)-carboxylate (2.20 g, 7.11 mmol), $K_2CO_3$ (2.95 g, 21.34 mmol) and Pd(dppf)$Cl_2$ (520 mg, 0.71 mmol). The reaction mixture was stirred at 80° C. for 4 hr under $N_2$ and the reaction mixture was then quenched with a saturated solution of $NH_4Cl$ (20 mL). This solution was then extracted with EtOAc (3×20 mL) and the combined organic phases were dried over $Na_2SO_4$, filtered and concentrated. The crude product was purified FCC (0-30% EtOAc/petroleum ether) to give the title intermediate (1.87 g, 4.88 mmol) as a yellow oil.

$^1$H NMR (400 MHz, $CDCl_3$) δ 7.43-7.36 (m, 4H), 7.36-7.30 (m, 1H), 6.91-6.85 (m, 3H), 5.80 (br s, 1H), 5.03 (s, 2H), 4.04 (br s, 2H), 3.57-3.54 (m, 2H), 2.50 (br s, 2H), 1.49 (s, 9H).

Intermediate 14A: tert-butyl 4-(2-(trifluoromethoxy)phenyl)piperidine-1-carboxylate

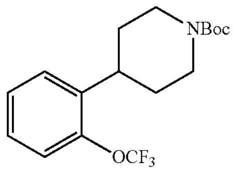 [SMILES: CC(C)(C)OC(=O)N1CCC(c2ccccc2OC(F)(F)F)CC1]

tert-butyl 4-(2-(trifluoromethoxy)phenyl)-5,6-dihydropyridine-1(2H)-carboxylate (Intermediate 13B, 14.09 g, 41.0 mmol) was added to a 250 mL rb flask followed by 10% Pd—C(4 grams). EtOH (82 mL) was added to the flask and the reaction was stirred under an atmosphere of hydrogen for 2 hours. Next, hydrogen was bubbled through the reaction for 4 hours. The reaction was filtered through a pad of celite twice and the filtrate was concentrated to yield the title intermediate as a clear, colorless oil (13.75 g, 39.8 mmol).

Rt: 3.18 min (LCMS Method 3). MS m/z 290.3 [M-Boc+formate]$^+$.

$^1$H NMR (400 MHz, $CDCl_3$) δ 7.36-7.19 (m, 4H), 4.36-4.20 (m, 2H), 3.09 (tt, J=12.1, 3.5 Hz, 1H), 2.85 (td, J=13.2, 2.5 Hz, 2H), 1.78 (d, J=13.1 Hz, 2H), 1.64 (td, J=12.5, 4.0 Hz, 2H), 1.51 (s, 9H).

The following compounds in Table 14 were prepared using a similar procedure and the relevant starting materials:

TABLE 14

| Intermediates 14B to 14I | | | | |
|---|---|---|---|---|
| Intermediate | Structure | Retention time (min) and Method | Expected Mass | Observed Mass |
| 14B | 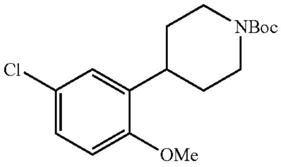 [SMILES: COc1ccc(Cl)cc1C1CCN(C(=O)OC(C)(C)C)CC1] | 3.09 LCMS Method 3 | 226.1 [M − Boc + H]$^+$ | 226.2 [M − Boc + H]$^+$ |
| 14C | 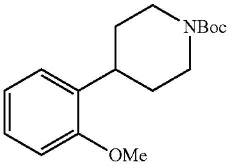 [SMILES: COc1ccccc1C1CCN(C(=O)OC(C)(C)C)CC1] | 1.24 LCMS Method 1 | 192.1 [M − Boc + H]$^+$ | 192.3 [M − Boc + H]$^+$ |
| 14D | 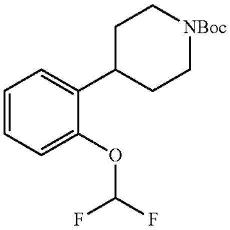 [SMILES: CC(C)(C)OC(=O)N1CCC(c2ccccc2OC(F)F)CC1] | 0.951 LCMS Method 6 | 272.1 [M − Boc + formate]$^+$ | 272.0 [M − Boc + formate]$^+$ |
| 14E | 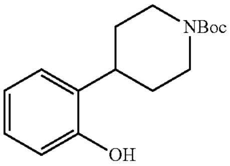 [SMILES: CC(C)(C)OC(=O)N1CCC(c2ccccc2O)CC1] | 1.04 LCMS Method 2 | 178.1 [M − Boc + H]$^+$ | 177.9 [M − Boc + H]$^+$ |
| 14F | 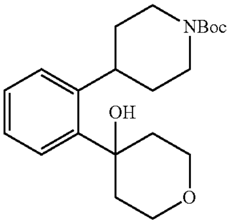 [SMILES: CC(C)(C)OC(=O)N1CCC(c2ccccc2C2(O)CCOCC2)CC1] | 0.868 LCMS Method 5 | 244.2 [M − Boc − OH]$^+$ | 244.1 [M − Boc − OH]$^+$ |
| 14G | 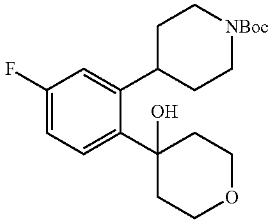 [SMILES: CC(C)(C)OC(=O)N1CCC(c2cc(F)ccc2C2(O)CCOCC2)CC1] | 1.036 LCMS Method 6 | 262.2 [M − Boc − OH]$^+$ | 262.2 [M − Boc − OH]$^+$ |
| 14H | 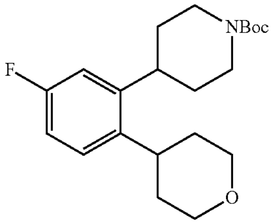 [SMILES: CC(C)(C)OC(=O)N1CCC(c2cc(F)ccc2C2CCOCC2)CC1] | 1.06 LCMS Method 6 | 264.2 [M − Boc + H]$^+$ | 264.4 [M − Boc + H]$^+$ |

TABLE 14-continued

| Intermediates 14B to 14I | | | | |
|---|---|---|---|---|
| Intermediate | Structure | Retention time (min) and Method | Expected Mass | Observed Mass |
| 14I | 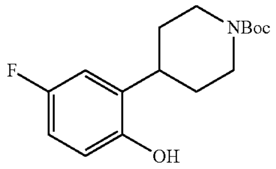 [SMILES: CC(C)(C)OC(=O)N1CCC(c2cc(F)ccc2O)CC1] | 1.05 LCMS Method 6 | 240.1 [M − Boc + formate]$^+$ | 240.3 [M − Boc + formate]$^+$ |

Intermediate 14J: tert-butyl 4-(2-(tetrahydro-2H-pyran-4-yl)phenyl)piperidine-1-carboxylate

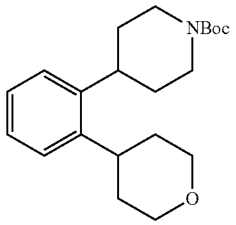 [SMILES: CC(C)(C)OC(=O)N1CCC(c2ccccc2C2CCOCC2)CC1]

To a solution of tert-butyl 4-(2-(3,6-dihydro-2H-pyran-4-yl)phenyl)-3,6-dihydropyridine-1(2H)-carboxylate (Intermediate 12B, 350 mg, 1.02 mmol) in MeOH (5 mL) was added $Pd(OH)_2/C$ (100 mg, 20%) and the reaction mixture was stirred for 3 hr at 25° C. under a balloon of $H_2$. The reaction mixture was filtered and concentrated to give the title compound (286 mg, 0.83 mmol) as a light yellow oil that was used without further purification.

Rt: 1.11 min (LCMS Method 6). MS m/z 246.4 [M−Boc+H]$^+$.

$^1$H NMR (400 MHz, $CD_3OD$) δ 7.28-7.25 (m, 1H), 7.23-7.19 (m, 1H), 7.19-7.14 (m, 2H), 4.22 (d, J=13.2 Hz, 2H), 4.05 (dd, J=4.1, 11.3 Hz, 2H), 3.62 (m, 2H), 3.21-3.02 (m, 2H), 2.92 (br s, 2H), 1.91-1.78 (m, 2H), 1.75-1.60 (m, 6H), 1.52-1.48 (m, 9H).

Intermediate 15A: tert-butyl 4-(5-fluoro-2-((tetrahydro-2H-pyran-4-yl)oxy)phenyl)piperidine-1-carboxylate

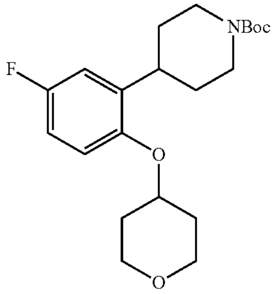 [SMILES: CC(C)(C)OC(=O)N1CCC(c2cc(F)ccc2OC2CCOCC2)CC1]

To a solution of tert-butyl 4-(5-fluoro-2-hydroxyphenyl)piperidine-1-carboxylate (Intermediate 14J, 850 mg, 2.88 mmol) in THF (10 mL) at 0° C. was added tetrahydro-2H-pyran-4-ol (669 mg, 5.76 mmol) and $PPh_3$ (1.51 g, 5.76 mmol) and then DIAD (1.16 g, 5.76 mmol) was added dropwise. The reaction was stirred at 25° C. for 16 hr under $N_2$. The reaction mixture was quenched with $H_2O$ (20 mL), extracted with EtOAc (3×10 mL), dried with $Na_2SO_4$, filtered and the filtrate was concentrated. The crude product was purified by FCC (0-80% EtOAc/PE) to yield the title compound (850 mg, 2.23 mmol) as yellow solid.

Rt: 1.126 min (LCMS Method 6) MS m/z 280.3 [M−Boc+H]$^+$.

The following compound in Table 15 was prepared using a similar procedure and the relevant starting materials:

TABLE 15

| Intermediate 15B | | | | |
|---|---|---|---|---|
| Intermediate | Structure | Retention time (min) and Method | Expected Mass | Observed Mass |
| 15B | 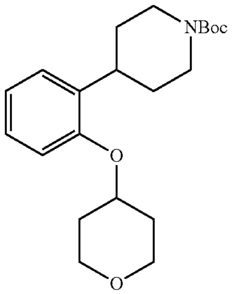 [SMILES: CC(C)(C)OC(=O)N1CCC(c2ccccc2OC2CCOCC2)CC1] | 1.133 LCMS Method 6 | 262.2 [M − Boc + H]$^+$ | 262.2 [M − Boc + H]$^+$ |

Intermediate 16A: 4-(2-(trifluoromethoxy)phenyl)piperidine

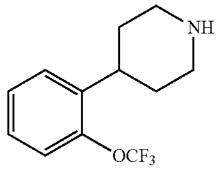

tert-butyl 4-(2-(trifluoromethoxy)phenyl)piperidine-1-carboxylate (Intermediate 14A, 13.75 g, 39.8 mmol) was added to a 500 mL RB flask and dissolved in DCM (80 mL). The reaction was cooled to 0° C. and incubated for 10 minutes and then TFA (80 mL, 39.8 mmol) was added and the reaction was slowly warmed to RT and stirred for 3 hours. The reaction was then cooled to 0° C. and quenched with 6N KOH (300 mL). DCM (200 mL) was added and the layers were separated and the aqueous phase was extracted with DCM (5×100 mL). The combined organic layers were washed brine (1×50 mL), dried over $MgSO_4$, filtered and concentrated to yield the title intermediate (9090 mg, 37.1 mmol) as a tan liquid that was used without further purification.

LCMS: Rt: 0.67 min (LCMS Method 3), MS m/z 246.1 $[M+H]^+$.

$^1H$ NMR (400 MHz, $CDCl_3$) δ 7.37 (d, J=7.5 Hz, 1H), 7.34-7.20 (m, 3H), 3.29-3.18 (m, 2H), 3.08 (tt, J=12.0, 3.7 Hz, 1H), 2.82 (m, 2H), 2.71 (s, 1H), 1.82 (s, 2H), 1.68 (m, 2H).

The following compounds in Table 16 were prepared using a similar procedure and the relevant starting materials:

TABLE 16

Intermediates 16B to 16M

| Intermediate | Structure | Retention time (min) and Method | Expected Mass | Observed Mass |
|---|---|---|---|---|
| 16B | 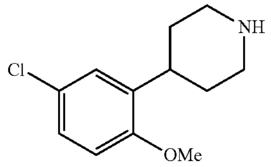 [SMILES: COc1ccc(Cl)cc1C1CCNCC1] | 1.10 LCMS Method 3 | 226.1 $[M + H]^+$ | 226.0 $[M + H]^+$ |
| 16C | 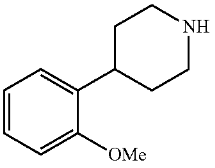 [SMILES: COc1ccccc1C1CCNCC1] | 0.50 LCMS Method 1 | 192.1 $[M + H]^+$ | 192.2 $[M + H]^+$ |
| 16D | 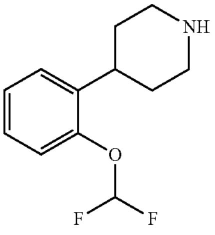 [SMILES: FC(F)Oc1ccccc1C1CCNCC1] | 0.92 LCMS Method 6 | 228.3 $[M + H]^+$ | 228.1 $[M + H]^+$ |
| 16E | 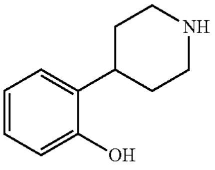 [SMILES: Oc1ccccc1C1CCNCC1] | 0.62 LCMS Method 2 | 178.1 $[M + H]^+$ | 178.3 $[M + H]^+$ |

TABLE 16-continued
| Intermediate | Structure | Retention time (min) and Method | Expected Mass | Observed Mass |
|---|---|---|---|---|
| Intermediates 16B to 16M | | | | |
| 16F | 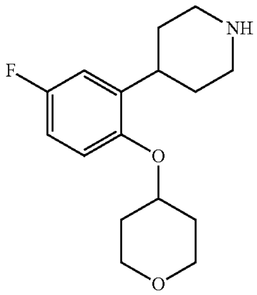 [SMILES: Fc1ccc(OC2CCOCC2)c(C2CCNCC2)c1] | 1.20 LCMS Method 6 | 280.2 $[M + H]^+$ | 280.2 $[M + H]^+$ |
| 16G | 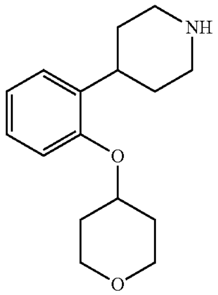 [SMILES: c1ccc(C2CCNCC2)c(OC2CCOCC2)c1] | 0.86 LCMS Method 6 | 262.2 $[M + H]^+$ | 262.2 $[M + H]^+$ |
| 16H | 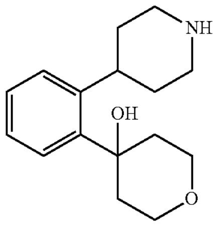 [SMILES: OC1(c2ccccc2C2CCNCC2)CCOCC1] | 0.86 LCMS Method 5 | 262.2 $[M + H]^+$ | 262.1 $[M + H]^+$ |
| 16I | 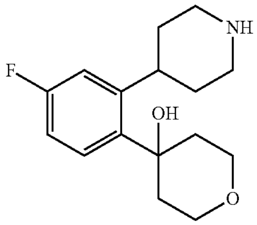 [SMILES: OC1(c2ccc(F)cc2C2CCNCC2)CCOCC1] | 0.69 LCMS Method 5 | 280.2 $[M + H]^+$ | 280.1 $[M + H]^+$ |
| 16J | 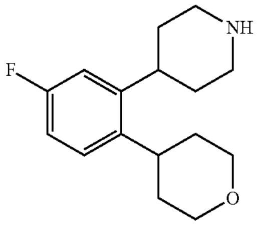 [SMILES: Fc1ccc(C2CCOCC2)c(C2CCNCC2)c1] | 0.884 LCMS Method 5 | 264.2 $[M + H]^+$ | 264.2 $[M + H]^+$ |
| 16K | 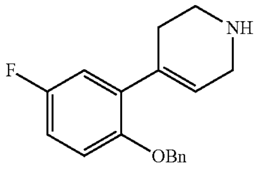 [SMILES: Fc1ccc(OCc2ccccc2)c(C2=CCNCC2)c1] | 0.968 LCMS Method 5 | 284.1 $[M + H]^+$ | 284.1 $[M + H]^+$ |

TABLE 16-continued

| Intermediates 16B to 16M | | | | |
|---|---|---|---|---|
| Intermediate | Structure | Retention time (min) and Method | Expected Mass | Observed Mass |
| 16L | 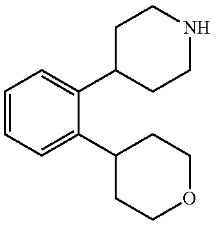 [SMILES: c1ccc(C2CCOCC2)c(C2CCNCC2)c1] | 0.884 LCMS Method 5 | 246.2 $[M + H]^+$ | 246.4 $[M + H]^+$ |
| 16M | 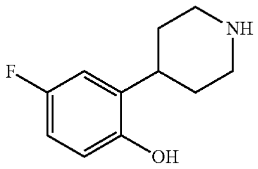 [SMILES: Oc1ccc(F)cc1C1CCNCC1] | 0.377 LCMS Method 5 | 196.1 $[M + H]^+$ | 196.2 $[M + H]^+$ |

Intermediate 16N: 4-(2-(tetrahydro-$2H_1$-pyran-4-yl)phenyl)piperidine hydrochloride

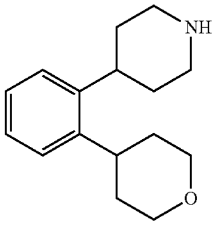 [SMILES: c1ccc(C2CCOCC2)c(C2CCNCC2)c1]

tert-butyl 4-(2-(tetrahydro-2H-pyran-4-yl)phenyl)piperidine-1l-carboxylate (Intermediate 14J, 0.3 g, 0.868 mmol) was added to HCl/dioxane (4M, 3 mL) at 25° C. The resulting solution was stirred at 25° C. for 1 hr. The reaction mixture was concentrated to afford the title intermediate (150 mg, 0.532 mmol) that was used without further purification.

LCMS: Rt: 0.67 min (LCMS Method 6), MS m/z 246.2 $[M+H]^+$.

Intermediate 17A: tert-butyl 6-(4-(2-(trifluoromethoxy)phenyl)piperidin-1-yl)-2-azaspiro[13.4]octane-2-carboxylate

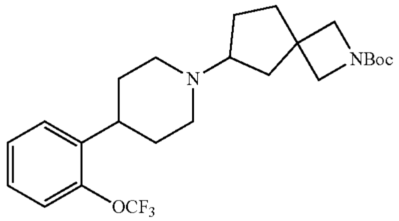 [SMILES: CC(C)(C)OC(=O)N1CC2(CCC(N3CCC(c4ccccc4OC(F)(F)F)CC3)C2)C1]

4-(2-(trifluoromethoxy)phenyl)piperidine (Intermediate 16A, 9090 mg, 37.1 mmol), tert-butyl 6-oxo-2-azaspiro[3.4]octane-2-carboxylate (8350 mg, 37.1 mmol) and 4 angstrom molecular sieves (10 grams) were added to a 500 mL rb flask followed by DCM (180 mL). The reaction was stirred for 90 minutes and then sodium triacetoxyborohydride (15.7 g, 74.1 mmol) was added in 3 portions over 5 minutes. The reaction was then stirred for 16 hours. The reaction was then warmed to 35° C. for 3 hours and then it was quenched with 1N KOH (200 mL) and transferred to a 500 mL separation funnel. The aqueous phase was extracted with DCM (5×100 mL) and the combined organic layers were washed with brine (1×50 mL), dried over $MgSO_4$ and purified by FCC (0-7% MeOH (1% $NH_4OH$)/DCM) to yield the title intermediate (9090 mg, 20.0 mmol) as a tan liquid.

LCMS: Rt: 3.30 mi (LCMS Method 4), MS m/z 455.3 $[M+H]^+$.

$^1$H NMR (400 MHz, $CDCl_3$) δ 7.38 (d, J=7.3 Hz, 1H), 7.31-7.20 (m, 3H), 3.92-3.83 (m, 2H), 3.83-3.71 (m, 3H), 3.13 (s, 2H), 3.04-2.89 (m, 1H), 2.63 (s, 1H), 2.24-2.01 (m, 3H), 1.90 (m, 7H), 1.62 (s, 1H), 1.47 (d, J 2.9 Hz, 9H).

The following compounds in Table 17 were prepared using a similar procedure and the relevant starting materials:

TABLE 17

Intermediates 17B to 17E

| Intermediate | Structure | Retention time (min) and Method | Expected Mass | Observed Mass |
|---|---|---|---|---|
| 17B | 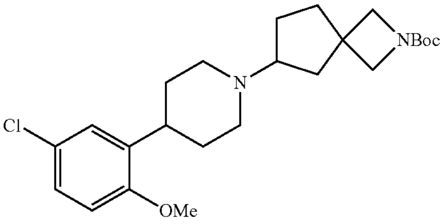 [SMILES: COc1ccc(Cl)cc1C1CCN(C2CCC3(C2)CN(C(=O)OC(C)(C)C)C3)CC1] | 1.62 LCMS Method 3 | 435.2 $[M + H]^+$ | 434.9 $[M + H]^+$ |
| 17C | 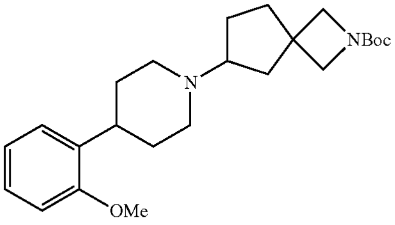 [SMILES: COc1ccccc1C1CCN(C2CCC3(C2)CN(C(=O)OC(C)(C)C)C3)CC1] | 0.82 LCMS Method 1 | 401.3 $[M + H]^+$ | 401.5 $[M + H]^+$ |
| 17D | 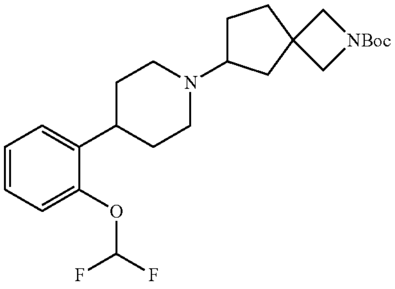 [SMILES: CC(C)(C)OC(=O)N1CC2(CCC(N3CCC(c4ccccc4OC(F)F)CC3)C2)C1] | 3.03 LCMS Method 3 | 437.3 $[M + H]^+$ | 437.4 $[M + H]^+$ |
| 17E | 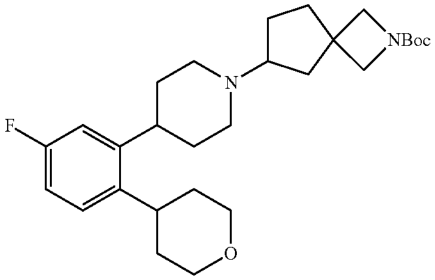 [SMILES: CC(C)(C)OC(=O)N1CC2(CCC(N3CCC(c4cc(F)ccc4C4CCOCC4)CC3)C2)C1] | 1.116 LCMS Method 5 | 473.3 $[M + H]^+$ | 473.5 $[M + H]^+$ |

Intermediate 17F: (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone and Intermediate 17G: (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone and Example 1711: rac-(1-fluorocyclopropyl)(6-(4-(2-hydroxyphenyl)piperidin-1-yl)-2-azaspiro[3.4]octan-2-yl)methanone

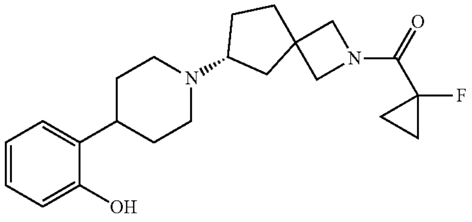

(R)-isomer

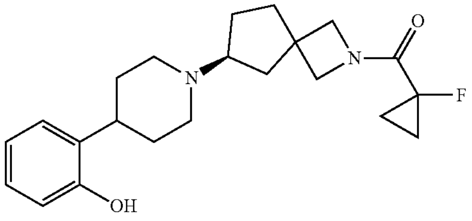

(S)-isomer

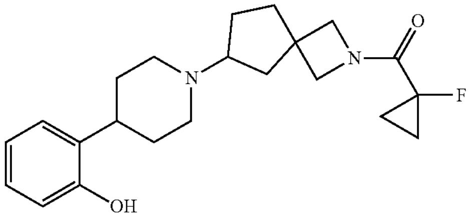

rac-isomer

To a MeOH (30 mL) solution of 2-(piperidin-4-yl)phenol (Intermediate 16E, 1722 mg, 4.25 mmol) and 2-(1-fluorocyclopropanecarbonyl)-2-azaspiro[3.4]octan-6-one (Intermediate 2C, 748 mg, 3.54 mmol), was added TEA (1.974 mL, 14.16 mmol) and zinc chloride (0.5M in THF, 10.62 mL, 5.31 mmol). The solution was stirred at 50° C. for 2 hr and then it was cooled to 0° C. and sodium cyanoborohydride (445 mg, 7.08 mmol) was added and then the reaction was warmed to RT and stirred for 2 hr. The solvent was removed under reduced pressure and the residue was dissolved in DCM, washed with water and dried over sodium sulfate and concentrated. The residue was then purified by FCC (0-5% MeOH/DCM) to yield Example 17H and then the enantiomers were separated by chiral SFC (CHIRALCEL© OD-H 20×250 mm, 30% EtOH (0.1% DEA)/$CO_2$, 100 bar, 60 mL/min). The faster running enantiomer was isolated as Intermediate 17F (426 mg, 1.09 mmol) and the slower running enantiomer was isolated as Intermediate 17G (463 mg, 1.18 mmol).

Intermediate 17F

SFC: Rt: 3.05 min (Chiralpak® IB 4.6×100 mm, 5 μM, 5-55% MeOH (10 mM $NH_4OH$)/CO2, 5 mL/min).

LCMS: Rt: 1.99 min (LCMS Method 4), MS m/z 373.3 $[M+H]^+$.

$^1H$ NMR (400 MHz, $CD_3OD$) δ 7.10 (d, J=7.5 Hz, 1H), 7.03-6.93 (m, 1H), 6.83-6.70 (m, 2H), 4.48-4.22 (m, 2H), 4.05-3.84 (m, 2H), 3.14 (d, J=11.5 Hz, 2H), 2.94 (m, 1H), 2.76-2.60 (m, 1H), 2.33-2.08 (m, 3H), 2.05-1.89 (m, 3H), 1.87-1.69 (m, 5H), 1.65-1.51 (m, 1H), 1.30-1.21 (m, 4H).

Intermediate 17G

SFC: Rt: 3.25 min (Chiralpak® IB 4.6×100 mm, 5 μM, 5-55% MeOH (10 mM $NH_4OH$)/CO2, 5 mL/min).

LCMS: Rt: 1.98 min (LCMS Method 4), MS m/z 373.0 $[M+H]^+$.

$^1H$ NMR (400 MHz, $CD_3OD$) δ 7.10 (dd, J=7.7, 1.4 Hz, 1H), 6.98 (td, J=7.7, 1.6 Hz, 1H), 6.82-6.69 (m, 2H), 4.47-4.24 (m, 2H), 4.04-3.81 (m, 2H), 3.21-3.10 (m, 2H), 2.94 (m, 1H), 2.69 (q, J=7.8 Hz, 1H), 2.25 (m, 1H), 2.20-2.08 (m, 2H), 1.96 (m, 3H), 1.86-1.70 (m, 5H), 1.59 (m, 1H), 1.31-1.21 (m, 4H).

Intermediate 17H

LCMS: Rt: 0.91 min (LCMS Method 2), MS m/z 372.9 $[M+H]^+$.

$^1H$ NMR (400 MHz, $CD_3OD$) δ 7.10 (dd, J=7.4, 1.7 Hz, 1H), 6.99 (td, J=7.6, 1.7 Hz, 1H), 6.89-6.66 (m, 2H), 4.48-4.23 (m, 2H), 4.10-3.80 (m, 2H), 3.22 (d, J=11.8 Hz, 2H), 2.97 (d, J=14.5 Hz, 2H), 2.82 (s, 1H), 2.28 (s, 3H), 2.10-1.71 (m, 8H), 1.62 (d, J=8.3 Hz, 1H), 1.36-1.16 (m, 3H).

The following compounds in Table 18 were prepared using a similar procedure and the relevant starting materials:

TABLE 18

Intermediates 17I to 17K

| Intermediate | Structure | Retention time (min) and Method | Expected Mass | Observed Mass |
|---|---|---|---|---|
| 17I | 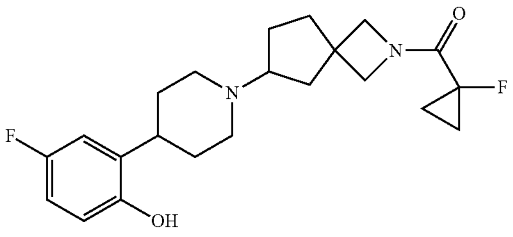 [SMILES: O=C(N1CC2(CCC(N3CCC(c4cc(F)ccc4O)CC3)C2)C1)C1(F)CC1] | 0.916 LCMS Method 6 | 391.2 $[M + H]^+$ | 391.4 $[M + H]^+$ |

TABLE 18-continued

| Intermediates 17I to 17K | | | | |
|---|---|---|---|---|
| Intermediate | Structure | Retention time (min) and Method | Expected Mass | Observed Mass |
| 17J | 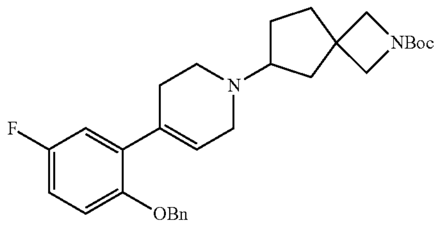 [SMILES: CC(C)(C)OC(=O)N1CC2(CCC(N3CC=C(c4cc(F)ccc4OCc4ccccc4)CC3)C2)C1] | 1.62 LCMS Method 6 | 493.3 $[M + H]^+$ | 493.5 $[M + H]^+$ |
| 17K | 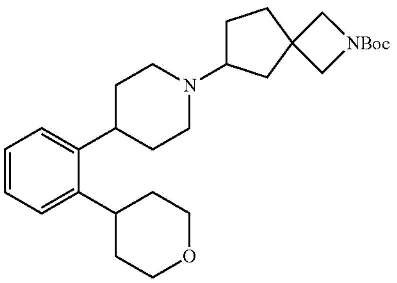 [SMILES: CC(C)(C)OC(=O)N1CC2(CCC(N3CCC(c4ccccc4C4CCOCC4)CC3)C2)C1] | 1.28 LCMS Method 2 | 455.3 $[M + H]^+$ | 455.5 $[M + H]^+$ |

Intermediate 18A: 6-(4-(2-(trifluoromethoxy)phenyl)piperidin-1-yl)-2-azaspiro[3.4]octane

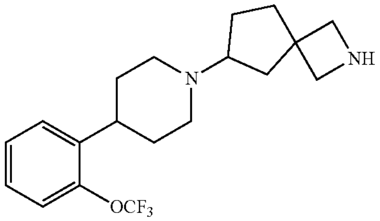 [SMILES: FC(F)(F)Oc1ccccc1C1CCN(C2CCC3(CNC3)C2)CC1]

tert-butyl 6-(4-(2-(trifluoromethoxy)phenyl)piperidin-1-yl)-2-azaspiro[3.4]octane-2-carboxylate (Intermediate 17A, 9090 mg, 20.00 mmol) was added to a 500 mL rb flask followed by DCM (100 mL). The reaction was stirred at 0° C. for 10 minutes and then TFA (50 mL) was slowly added. The reaction was warmed to RT and stirred for 1 hour and then the reaction was concentrated. The residue was taken up in DCM (200 mL) and quenched with 1N KOH (100 mL). The solution was transferred to a 500 mL separatory funnel and the layers were separated. The aqueous phase was extracted with 20% MeOH/DCM (5×100 mL) and the combined organic layers were washed with brine (1×50 mL), dried over $MgSO_4$, filtered and concentrated. The resulting brown oil (7690 mg, 21.7 mmol) was used in the next step without further purification.

LCMS: Rt: 0.65 min (LCMS Method 3) MS m/z 355.2 $[M+H]^+$.

$^1$H NMR (400 MHz, $CD_3OD$) δ 7.42-7.40 (m, 1H), 7.35-7.23 (m, 3H), 3.73-3.56 (m, 3H), 3.17-3.15 (m, 2H), 2.99-2.90 (m, 1H), 2.69-2.58 (m, 1H), 2.26 (dd, J=12.9, 7.3 Hz, 1H), 2.22-2.06 (m, 2H), 2.06-1.82 (m, 3H), 1.82-1.69 (m, 5H), 1.58-1.50 (m, 1H).

The following compounds in Table 19 were prepared using a similar procedure using the relevant starting materials:

TABLE 19

| Intermediates 18B to 18H | | | | |
|---|---|---|---|---|
| Intermediate | Structure | Rt(min) Method | Expected Mass | Observed Mass |
| 18B | 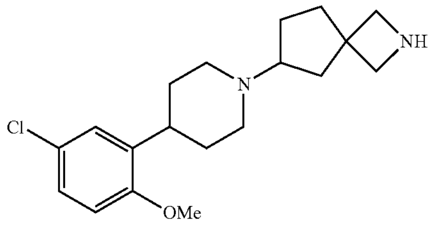 [SMILES: COc1ccc(Cl)cc1C1CCN(C2CCC3(CNC3)C2)CC1] | 0.57 LCMS Method 1 | 335.2 $[M + H]^+$ | 335.0 $[M + H]^+$ |

TABLE 19-continued
| Intermediates 18B to 18H | | | | |
|---|---|---|---|---|
| Intermediate | Structure | Rt(min) Method | Expected Mass | Observed Mass |
| 18C | 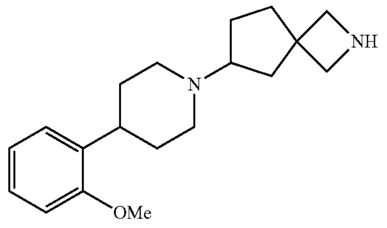 [SMILES: COc1ccccc1C1CCN(C2CCC3(CNC3)C2)CC1] | 0.43 LCMS Method 1 | 301.2 [M + H]+ | 301.4 [M + H]+ |
| 18D | 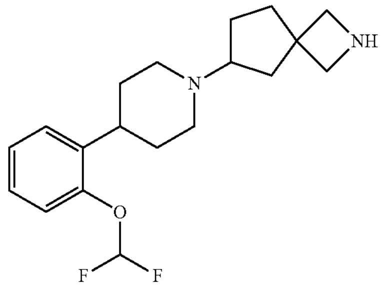 [SMILES: FC(F)Oc1ccccc1C1CCN(C2CCC3(CNC3)C2)CC1] | 0.85 LCMS Method 2 | 337.2 [M + H]+ | 337.3 [M + H]+ |
| 18E | 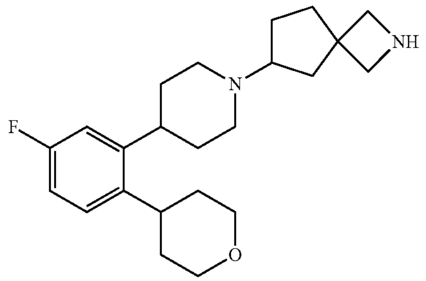 [SMILES: Fc1ccc(C2CCOCC2)c(C2CCN(C3CCC4(CNC4)C3)CC2)c1] | 0.765 LCMS Method 5 | 373.3 [M + H]+ | 373.2 [M + H]+ |
| 18F | 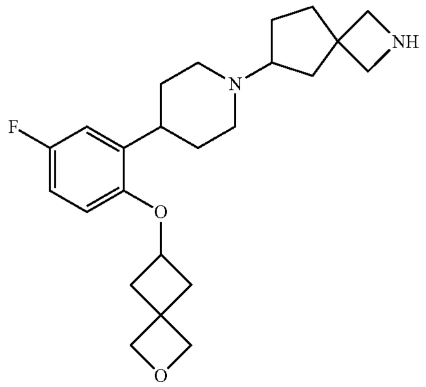 [SMILES: Fc1ccc(OC2CC3(COC3)C2)c(C2CCN(C3CCC4(CNC4)C3)CC2)c1] | 0.58 LCMS Method 5 | 401.3 [M + H]+ | 401.2 [M + H]+ |

TABLE 19-continued

Intermediates 18B to 18H

| Intermediate | Structure | Rt(min) Method | Expected Mass | Observed Mass |
|---|---|---|---|---|
| 18G | 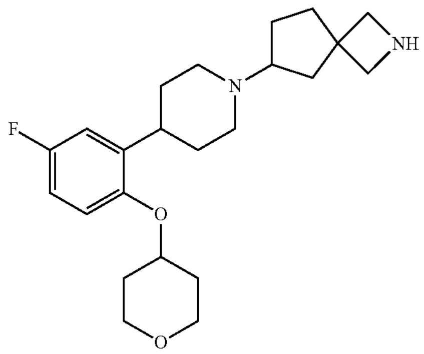 [SMILES: Fc1ccc(OC2CCOCC2)c(C2CCN(C3CCC4(CNC4)C3)CC2)c1] | 0.801 LCMS Method 5 | 389.3 $[M + H]^+$ | 389.3 $[M + H]^+$ |
| 18H | 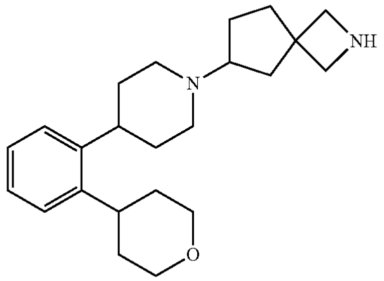 [SMILES: c1ccc(C2CCN(C3CCC4(CNC4)C3)CC2)c(C2CCOCC2)c1] | 0.51 LCMS Method 1 | 355.3 $[M + H]^+$ | 355.4 $[M + H]^+$ |

Intermediate 19A: (R)-(6-(4-(2-hydroxyphenyl)piperidin-1-yl)-2-azaspiro[3.4]octan-2-yl)(oxetan-3-yl) methanone

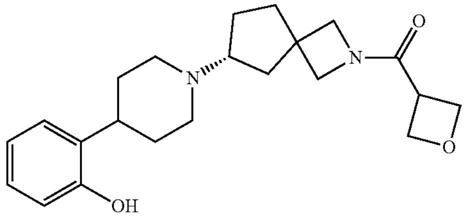 [SMILES: O=C(C1COC1)N1CC2(CC[C@@H](N3CCC(c4ccccc4O)CC3)C2)C1]

To a solution of DMF (5 mL) and DCM (5 mL) oxetane-3-carboxylic acid (0.633 g, 6.20 mmol) was added followed by TBTU (1.991 g, 6.20 mmol). The reaction was stirred for 10 min and then (R)-2-(1-(2-azaspiro[3.4]octan-6-yl)piperidin-4-yl)phenol (Intermediate 4S, 0.888 g, 3.1 mmol) and DIEA (2.166 mL, 12.40 mmol) were added as a solution in DMF (3 mL) and DCM (5 mL). The resulting mixture was then stirred at RT for 16 hours. The reaction mixture was concentrated under reduced pressure and the residue was dissolved in a mixture of THE (17 mL) and water (3 mL) and lithium hydroxide (742 mg, 31.0 mmol) was added. MeOH (1 mL) was added and the reaction was stirred at 60° C. for 3 hours. The reaction was concentrated and the residue was purified by FCC (0-8% MeOH (1% 7N $NH_3$ in MeOH)/DCM) to yield the title compound as a cream colored solid (790 mg, 2.11 mmol).

LCMS: Rt: 1.52 min (LCMS Method 3) MS m/z 371.4 $[M+H]^+$.

$^1$H NMR (400 MHz, $CD_3OD$) δ 7.12 (dd, J=7.6, 1.6 Hz, 1H), 7.07-6.95 (m, 1H), 6.78 (dd, J=17.5, 8.0 Hz, 2H), 4.80 (m, 4H), 4.08-3.80 (m, 5H), 3.17 (m, 2H), 2.97 (m, 1H), 2.72 (m, 1H), 2.31-2.11 (m, 3H), 1.99 (m, 2H), 1.93-1.72 (m, 6H), 1.70-1.53 (m, 1H).

Example 1A (R)-2-(6-(4-(2-((2-oxaspiro[3.3]heptan-6-yl)oxy)phenyl)piperidin-1-yl)-2-azaspiro[3.4]octan-2-yl)-1,3,4-oxadiazole

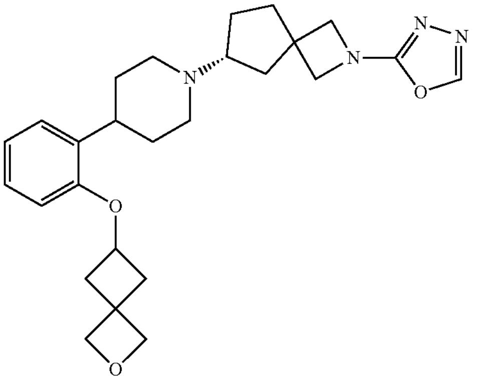 [SMILES: c1ccc(C2CCN([C@@H]3CCC4(C3)CN(c3nnco3)C4)CC2)c(OC2CC3(COC3)C2)c1]

(R)-2-(1-(2-(1,3,4-oxadiazol-2-yl)-2-azaspiro[3.4]octan-6-yl)piperidin-4-yl)phenol (Intermediate 6A, 36 mg, 0.10 mmol), 2-oxaspiro[3.3]heptan-6-yl 4-methylbenzenesulfonate (Intermediate 7A, 30 mg, 0.11 mmol), and cesium carbonate (66 mg, 0.20 mmol) were suspended in DMF (0.5 mL). The reaction was heated at 80° C. for 2 days, diluted with ethyl acetate (50 mL), washed with water (2×10 mL), and concentrated. The residue was purified by preparative HPLC (XBridge 30×50 mm 35-60% $MeCN/H_2O$ (5 mM $NH_4OH$)), and by FCC (0-5% MeOH(10% 7N $NH_3$)/DCM) to yield the title compound (25 mg, 0.055 mmol) as a white foamy solid. LCMS: Rt: 2.15 min (LCMS Method 4) MS m/z 451.5 $[M+H]^+$.

$^1H$ NMR (400 MHz, $CD_3OD$) δ 8.39 (s, 1H), 7.19 (d, J=7.5 Hz, 1H), 7.16-7.08 (m, 1H), 6.91 (t, J=7.5 Hz, 1H), 6.74 (d, J=8.1 Hz, 1H), 4.78 (s, 2H), 4.71 (s, 2H), 4.59 (m, 1H), 4.17-3.99 (m, 4H), 3.17 (m, 2H), 3.03-2.91 (m, 1H), 2.90-2.80 (m, 2H), 2.79-2.66 (m, 1H), 2.38-2.27 (m, 3H), 2.23-1.92 (m, 5H), 1.89-1.69 (m, 5H), 1.68-1.55 (m, 1H).

Example 1B: (R)-2-(6-(4-(2-((2-oxaspiro[3.3]heptan-6-yl)oxy)-5-fluorophenyl)piperidin-1-yl)-2-azaspiro[3.4]octan-2-yl)-1,3,4-oxadiazole

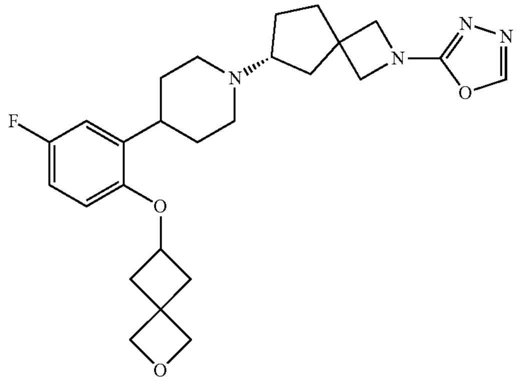 [SMILES: Fc1ccc(OC2CC3(COC3)C2)c(C2CCN([C@@H]3CCC4(C3)CN(c3nnco3)C4)CC2)c1]

(R)-2-(1-(2-(1,3,4-oxadiazol-2-yl)-2-azaspiro[3.4]octan-6-yl)piperidin-4-yl)-4-fluorophenol (Intermediate 6B, 22 mg, 0.059 mmol), 2-oxaspiro[3.3]heptan-6-yl 4-methylbenzenesulfonate (Intermediate 7A, 17 mg, 0.065 mmol), and cesium carbonate (38 mg, 0.12 mmol) were suspended in DMF (0.5 mL). The reaction was heated at 80° C. for 16 hr, diluted with ethyl acetate, washed with water, and concentrated. The residue was purified by preparative HPLC (XBridge 30×50 mm 35-60% $MeCN/H_2O$ (5 mM $NH_4OH$)), and by FCC (0-40% ethyl acetate (10% 7N $NH_3$)/heptane) to yield the title compound (7.3 mg, 0.015 mmol) as a white solid.

LCMS: Rt: 2.27 min (LCMS Method 4) MS m/z 469.4 $[M+H]^+$.

$^1H$ NMR (400 MHz, $CD_3OD$) δ 8.36 (s, 1H), 6.90 (dd, J=9.8, 3.0 Hz, 1H), 6.82 (td, J=8.4, 3.1 Hz, 1H), 6.70 (dd, J=8.9, 4.5 Hz, 1H), 4.72 (d, J=5.0 Hz, 2H), 4.67 (s, 2H), 4.53 (p, J=6.7 Hz, 1H), 4.17-3.95 (m, 4H), 3.16-3.13 (m, 2H), 2.93 (tt, J=12.0, 4.0 Hz, 1H), 2.86-2.76 (m, 2H), 2.70 (tt, J=9.3, 7.2 Hz, 1H), 2.33-2.25 (m, 3H), 2.19-1.90 (m, 5H), 1.86-1.75 (m, 3H), 1.75-1.54 (m, 3H).

Example 1C: 2-((R)-6-(4-(2-(((R)-1,4-dioxan-2-yl)methoxy)phenyl)piperidin-1-yl)-2-azaspiro[3.4]octan-2-yl)-1,3,4-oxadiazole

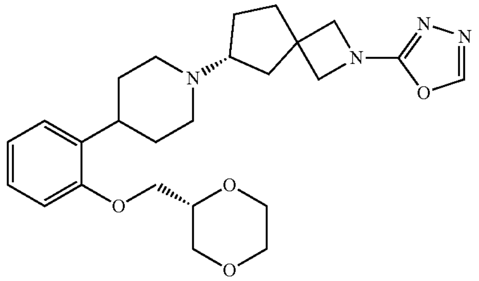

(R)-ethyl 5-(6-(4-(2-hydroxyphenyl)piperidin-1-yl)-2-azaspiro[3.4]octan-2-yl)-1,3,4-oxadiazole-2-carboxylate (Intermediate 6E, 180 mg, 0.422 mol), (R)-(1,4-dioxan-2-yl)methyl 4-methylbenzenesulfonate (Intermediate 7B, 138 mg, 0.506 mmol), and cesium carbonate (413 mg, 1.27 mmol) were suspended in DMF (1.8 mL), and the reaction was stirred at RT for 16 hours. Additional cesium carbonate (275 mg, 0.844 mmol) was added, and the reaction was stirred for an additional 16 hours at RT. Next, a solution of 4N HCl was added to adjust pH to 2, and the reaction was stirred at RT for 16 hours. The residue was concentrated, and purified by $C_{18}$ reverse phase FCC (0-80% $MeCN/H_2O$ (5 mM $NH_4OH$)) to afford the title compound (93 mg, 0.20 mmol).

LCMS: Rt: 2.10 min (LCMS Method 4) MS m/z 455.3 $[M+H]^+$.

$^1H$ NMR (DMSO-$d_6$) δ 8.69-8.55 (m, 1H), 7.15 (d, J=6.8 Hz, 2H), 7.00-6.83 (m, 2H), 4.06-3.82 (m, 8H), 3.81-3.73 (m, 1H), 3.72-3.58 (m, 2H), 3.55-3.42 (m, 2H), 3.30-3.26 (m, 1H), 3.16-2.94 (m, 2H), 2.92-2.73 (m, 1H), 2.63-2.56 (m, 1H), 2.26-2.09 (m, 1H), 2.07-1.42 (m, 10H).

Example 1D: (R)-2-(6-(4-(2-(oxetan-3-yloxy)phenyl)piperidin-1-yl)-2-azaspiro[3.4]octan-2-yl)-1,3,4-oxadiazole

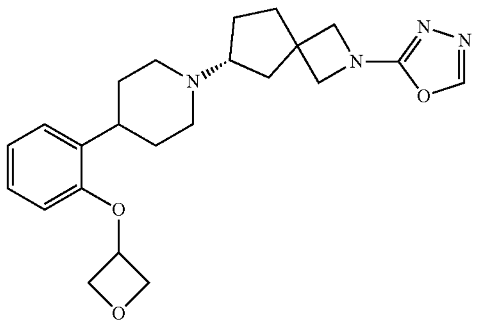

(R)-ethyl 5-(6-(4-(2-hydroxyphenyl)piperidin-1-yl)-2-azaspiro[3.4]octan-2-yl)-1,3,4-oxadiazole-2-carboxylate (Intermediate 6E, 75 mg, 0.18 mmol), oxetan-3-yl 4-methylbenzenesulfonate (80 mg, 0.35 mmol), and cesium carbonate (172 mg, 0.528 mmol) were suspended in DMF (0.70 mL), and the reaction was stirred at 80° C. for 16 hours. Next, a solution of 4N HCl was added to adjust pH to 2, and the reaction was stirred at RT for 5 hours. A 2M solution of LiOH was added to adjust pH to 8, and the solution was extracted with DCM. The combined organic layers were concentrated and the residue was purified by preparative HPLC (XBridge 30×50 mm 25-50% MeCN/$H_2O$ (5 mM $NH_4OH$)) to afford the title compound (28 mg, 0.065 mmol).

LCMS: Rt: 1.99 min (LCMS Method 4) MS m/z 411.2 $[M+H]^+$.

$^1H$ NMR (DMSO-$d_6$) δ 8.63 (s, 1H), 7.28-7.05 (m, 2H), 6.94 (br s, 1H), 6.53 (d, J=12.2 Hz, 1H), 5.28 (br s, 1H), 5.01-4.88 (m, 2H), 4.54 (br s, 2H), 4.13-3.85 (m, 4H), 3.70-3.47 (m, 1H), 3.29 (s, 1H), 3.15-2.84 (m, 2H), 2.23-1.38 (m, 12H).

Example 1E: 2-((R)-6-(4-(2-(((S)-1,4-dioxan-2-yl)methoxy)phenyl)piperidin-1-yl)-2-azaspiro[3.4]octan-2-yl)-1,3,4-oxadiazole

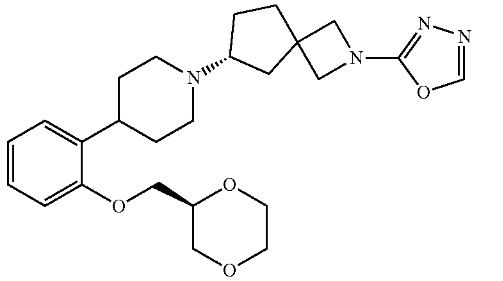

(R)-ethyl 5-(6-(4-(2-hydroxyphenyl)piperidin-1-yl)-2-azaspiro[3.4]octan-2-yl)-1,3,4-oxadiazole-2-carboxylate (Intermediate 6E, 150 mg, 0.352 mmol), (S)-(1,4-dioxan-2-yl)methyl 4-methylbenzenesulfonate (Intermediate 7D, 115 mg, 0.422 mmol), and cesium carbonate (344 mg, 1.06 mmol) were suspended in DMF (1.5 mL), and the reaction was stirred at RT for 16 h. Additional cesium carbonate (229 mg, 0.703 mmol) was added, and the reaction was stirred for another 16 hours at RT. A solution of 4N HCl was then added to adjust the pH to 2, and the reaction was stirred at RT for 16 hours. A 2M solution of LiOH was then added to adjust the pH to 8, and the solution was extracted with DCM. The combined organic layers were concentrated and the residue was purified by HPLC (XBridge 30×50 mm 25-50% MeCN/$H_2O$ (5 mM $NH_4OH$)), and further by FCC (0-10% MeOH/DCM) to afford the title compound (73 mg, 0.16 mmol).

LCMS: Rt: 2.09 min (LCMS Method 4) MS m/z 455.3 $[M+H]^+$.

$^1H$ NMR (DMSO-$d_6$) δ 8.62 (s, 1H), 7.18-7.09 (m, 2H), 6.95-6.86 (m, 2H), 4.04-3.82 (m, 8H), 3.81-3.74 (m, 1H), 3.72-3.59 (m, 2H), 3.54-3.44 (m, 2H), 3.07-2.96 (m, 2H), 2.87-2.75 (m, 1H), 2.64-2.54 (m, 1H), 2.19-2.09 (m, 1H), 2.04-1.77 (m, 5H), 1.77-1.65 (m, 3H), 1.65-1.40 (m, 3H).

Example 1F: (R)-ethyl 5-(6-(4-(2-hydroxyphenyl)piperidin-1-yl)-2-azaspiro[3.4]octan-2-yl)-1,3,4-oxadiazole-2-carboxylate

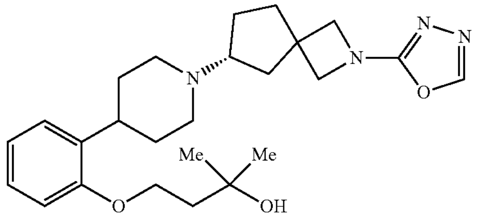 [SMILES: CC(C)(O)CCOc1ccccc1C1CCN([C@@H]2CCC3(C2)CN(c2nnco2)C3)CC1]

(R)-ethyl 5-(6-(4-(2-hydroxyphenyl)piperidin-1-yl)-2-azaspiro[3.4]octan-2-yl)-1,3,4-oxadiazole-2-carboxylate (Intermediate 6E, 103 mg, 0.241 mmol), 3-hydroxy-3-methylbutyl 4-methylbenzenesulfonate (Intermediate 7G, 69 mg, 0.27 mmol), and cesium carbonate (236 mg, 0.724 mmol) were suspended in DMF (1.0 mL), and the reaction was stirred at RT for 16 hours. Next, a solution of 4N HCl was added to adjust the pH to 2, and the reaction was stirred at RT for 16 hours. A 2M solution of LiOH was then added to adjust the pH to 8, and the solution was extracted with DCM. The combined organic layers were concentrated and the residue was purified by preparative HPLC (XBridge 30×50 mm 25-50% MeCN/$H_2O$ (5 mM $NH_4OH$)), and further by FCC (0-10% MeOH/DCM) to afford the title compound (36 mg, 0.080 mmol).

LCMS: Rt: 2.13 min (LCMS Method 4) MS m/z 441.2 $[M+H]^+$.

$^1H$ NMR (DMSO-$d_6$) δ 8.62 (s, 1H), 7.19-7.09 (m, 2H), 6.94 (d, J=8.3 Hz, 1H), 6.87 (t, J=7.3 Hz, 1H), 4.36 (s, 1H), 4.06 (t, J=6.8 Hz, 2H), 4.02-3.87 (m, 4H), 3.00 (br s, 2H), 2.86 (br s, 1H), 2.63-2.54 (m, 1H), 2.22-2.10 (m, 1H), 2.04-1.77 (m, 7H), 1.76-1.63 (m, 3H), 1.63-1.51 (m, 2H), 1.50-1.39 (m, 1H), 1.20-1.14 (m, 6H).

Example 1G: (R)-2-(6-(4-(2-(oxetan-3-ylmethoxy)phenyl)piperidin-1-yl)-2-azaspiro[3.4]octan-2-yl)-1,3,4-thiadiazole

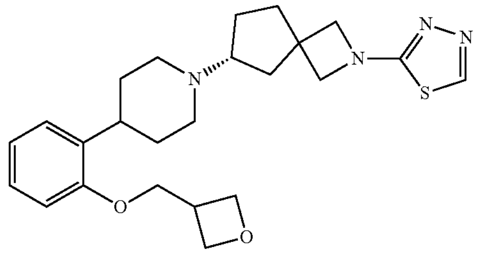 [SMILES: c1ccc(C2CCN([C@@H]3CCC4(C3)CN(c3nncs3)C4)CC2)c(OCC2COC2)c1]

(R)-2-(1-(2-(1,3,4-thiadiazol-2-yl)-2-azaspiro[3.4]octan-6-yl)piperidin-4-yl)phenol (Intermediate 5D, 7.6 mg, 0.021 mmol) was dissolved in DMF (0.3 mL) and 3-(iodomethyl)oxetane (8.1 mg, 0.041 mmol) was added followed by cesium carbonate (13 mg, 0.041 mmol). The reaction was stirred at RT for 16 hours and then filtered and purified by preparative HPLC (XBridge 30×50 mm 35-60% MeCN/$H_2O$ (5 mM $NH_4OH$)) to afford the title compound (3.3 mg, 0.0073 mmol).

LCMS: Rt: 2.11 min (LCMS Method 4) MS m/z 441.4 $[M+H]^+$.

$^1$H NMR (400 MHz, $CD_3OD$) δ 8.63 (s, 1H), 7.22-7.11 (m, 2H), 6.99-6.88 (m, 2H), 4.88 (dd, J=8.0, 6.1 Hz, 2H), 4.66 (t, J=6.0 Hz, 2H), 4.18 (d, J=5.8 Hz, 2H), 4.11-3.95 (m, 4H), 3.48 (m, 1H), 3.14 (s, 2H), 3.03 (m, 1H), 2.78-2.62 (m, 1H), 2.30 (dd, J=12.9, 7.3 Hz, 1H), 2.14 (q, J=11.0, 9.9 Hz, 2H), 2.08-1.91 (m, 3H), 1.89-1.65 (m, 5H), 1.65-1.54 (m, 1H).

Example 1H: (R)-2-(6-(4-(2-((3-fluorooxetan-3-yl)methoxy)phenyl)piperidin-1-yl)-2-azaspiro[3.4]octan-2-yl)-1,3,4-thiadiazole

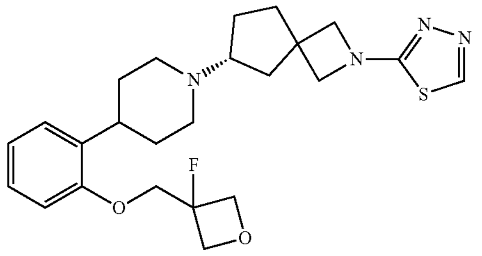 [SMILES: FC1(COc2ccccc2C2CCN([C@@H]3CCC4(C3)CN(c3nncs3)C4)CC2)COC1]

(R)-2-(1-(2-(1,3,4-thiadiazol-2-yl)-2-azaspiro[3.4]octan-6-yl)piperidin-4-yl)phenol (Intermediate 5D, 9.4 mg, 0.025 mmol) was dissolved in DMF (0.3 mL) and (3-fluorooxetan-3-yl)methyl 4-methylbenzenesulfonate (Intermediate 7H, 7.9 mg, 0.030 mmol) was added followed by cesium carbonate (17 mg, 0.053 mmol). The reaction was stirred at RT for 16 hours and then filtered and purified by preparative HPLC (XBridge 30×50 mm 15-40% $MeCN/H_2O$ (5 mM $NH_4OH$)) and further by FCC (0-5% MeOH(10% $NH_4OH$)/DCM) to afford the title compound (6.0 mg, 0.013 mmol).

LCMS: Rt: 2.15 min (LCMS Method 4) MS m/z 459.2 $[M+H]^+$.

$^1$H NMR (400 MHz, $CD_3OD$) δ 8.63 (s, 1H), 7.26-7.17 (m, 2H), 7.04-6.88 (m, 2H), 4.84-4.72 (m, 4H), 4.35 (d, J=18.9 Hz, 2H), 4.12-3.93 (m, 4H), 3.22-3.11 (m, 2H), 2.99 (m, 1H), 2.72 (m, 1H), 2.31 (dd, J=12.9, 7.3 Hz, 1H), 2.21-1.93 (m, 5H), 1.88-1.54 (m, 6H).

Example 1I: (R)-2-(6-(4-(2-((tetrahydro-2H-pyran-4-yl)methoxy)phenyl)piperidin-1-yl)-2-azaspiro[3.4]octan-2-yl)-1,3,4-thiadiazole

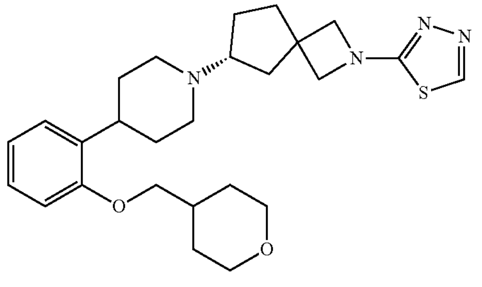 [SMILES: c1ccc(C2CCN([C@@H]3CCC4(C3)CN(c3nncs3)C4)CC2)c(OCC2CCOCC2)c1]

(R)-2-(1-(2-(1,3,4-thiadiazol-2-yl)-2-azaspiro[3.4]octan-6-yl)piperidin-4-yl)phenol (Intermediate 5D, 9.9 mg, 0.027 mmol) was dissolved in DMF (0.3 mL) and 4-(iodomethyl)tetrahydro-2H-pyran (7.3 mg, 0.032 mmol) was added followed by cesium carbonate (17 mg, 0.053 mmol). The reaction was stirred at RT for 48 hours and then incubated at 50° C. for 16 hr, filtered and purified by preparative HPLC (XBridge 30×50 mm 35-60% $MeCN/H_2O$ (5 mM $NH_4OH$)) to afford the title compound (8.1 mg, 0.017 mmol).

LCMS: Rt: 2.44 min (LCMS Method 4) MS m/z 469.2 $[M+H]^+$.

$^1$H NMR (400 MHz, $CD_3OD$) δ 8.63 (s, 1H), 7.21-7.07 (m, 2H), 6.89 (t, J=7.3 Hz, 2H), 4.14-3.93 (m, 6H), 3.85 (d, J=6.1 Hz, 2H), 3.49 (m, 2H), 3.22-3.12 (m, 2H), 3.00 (m, 1H), 2.78-2.62 (m, 1H), 2.31 (dd, J=12.9, 7.3 Hz, 1H), 2.20-1.91 (m, 6H), 1.89-1.45 (m, 10H).

Example 1J: (R)-2-(6-(4-(2-((4-fluorotetrahydro-2H-pyran-4-yl)methoxy)phenyl)piperidin-1-yl)-2-azaspiro[3.4]octan-2-yl)-1,3,4-thiadiazole

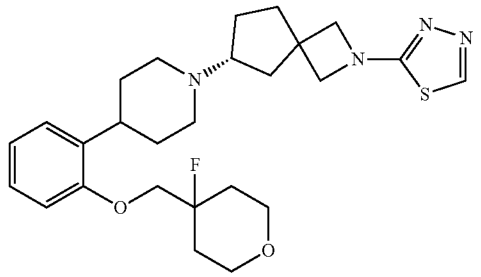

(R)-2-(1-(2-(1,3,4-thiadiazol-2-yl)-2-azaspiro[3.4]octan-6-yl)piperidin-4-yl)phenol (Intermediate 7D, 12 mg, 0.033 mmol) was dissolved in DMF (0.3 mL) and 4-(bromomethyl)-4-fluorotetrahydro-2H-pyran (7.8 mg, 0.040 mmol) was added followed by cesium carbonate (21 mg, 0.066 mmol). The reaction was stirred at RT for 16 hours. Next, additional 4-(bromomethyl)-4-fluorotetrahydro-2H-pyran (7.8 mg, 0.040 mmol) was added and the reaction was incubated at 50° C. for 24 hours, at 80° C. for 24 hours, at 100° C. for 96 hours, filtered and purified by preparative HPLC (XBridge 30×50 mm 35-60% $MeCN/H_2O$ (5 mM $NH_4OH$)) to afford the title compound (4.0 mg, 0.0081 mmol).

LCMS: Rt: 2.35 min (LCMS Method 4) MS m/z 487.2 $[M+H]^+$.

$^1$H NMR (400 MHz, $CD_3OD$) δ 8.63 (s, 1H), 7.17 (m, 2H), 6.93 (t, J=7.4 Hz, 2H), 4.12-3.95 (m, 6H), 3.86 (m, 2H), 3.77 (m, 2H), 3.24-3.10 (m, 2H), 3.02 (m, 1H), 2.71 (m, 1H), 2.31 (dd, J=12.9, 7.3 Hz, 1H), 2.19-1.55 (m, 15H).

Example 1K: (R)-6-(4-(2-(oxetan-3-yloxy)phenyl)piperidin-1-yl)-2-(pyrimidin-5-yl)-2-azaspiro[3.4]octane

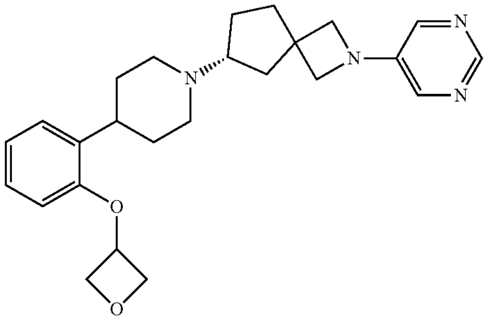 [SMILES: c1ccc(C2CCN([C@@H]3CCC4(C3)CN(c3cncnc3)C4)CC2)c(OC2COC2)c1]

(R)-2-(1-(2-(pyrimidin-5-yl)-2-azaspiro[3.4]octan-6-yl)piperidin-4-yl)phenol (Intermediate 6G, 79 mg, 0.217 mmol), oxetan-3-yl 4-methylbenzenesulfonate (43 mg, 0.188 mmol), and $Cs_2CO_3$ (246 mg, 0.754 mmol) were dissolved in MeCN (5 mL) and the reaction was stirred at 80° C. for 16 hr. Additional oxetan-3-yl 4-methylbenzenesulfonate (28 mg, 0.101) and MeCN (5 mL) were added and the reaction was stirred for an additional 16 hr at 95° C. The solvent was then removed under reduced pressure and the crude mixture was diluted with EtOAc and washed with water. The organic phase was separated, dried over $MgSO_4$ and the solvent was removed under reduced pressure. The residue was purified by FCC (0-10% MeOH (1% $NH_4OH$)/DCM) to afford the title compound (9.5 mg, 0.022 mmol).

LCMS: Rt: 0.64 (LCMS Method 1) MS m/z 421.4 $[M+H]^+$.

$^1H$ NMR (400 MHz, $CD_3OD$) δ 8.47 (s, 1H), 8.01 (s, 2H), 7.23 (dd, J=7.4, 1.7 Hz, 1H), 7.12 (td, J=7.8, 1.8 Hz, 1H), 6.94 (t, J=7.4 Hz, 1H), 6.49 (d, J=7.7 Hz, 1H), 5.28 (p, J=5.0 Hz, 1H), 5.03 (t, J=6.6 Hz, 2H), 4.70 (dd, J=7.3, 4.8 Hz, 2H), 3.98-3.82 (m, 4H), 3.24 (d, J=10.6 Hz, 2H), 3.07 (t, J=11.9 Hz, 1H), 2.82 (s, 1H), 2.38-2.19 (m, 3H), 2.12-1.95 (m, 3H), 1.95-1.75 (m, 5H), 1.71-1.60 (m, 1H).

Example 1L: (R)-2-(pyrimidin-5-yl)-6-(4-(2-((tetrahydro-2H-pyran-4-yl)oxy)phenyl)piperidin-1-yl)-2-azaspiro[3.4]octane

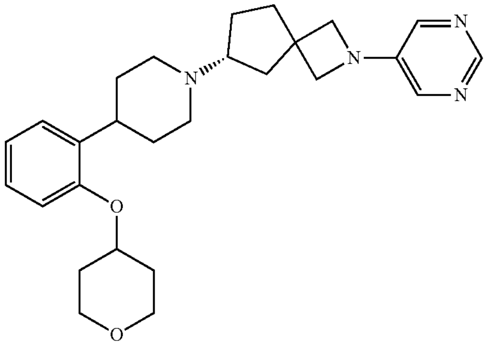 [SMILES: c1ccc(C2CCN([C@@H]3CCC4(C3)CN(c3cncnc3)C4)CC2)c(OC2CCOCC2)c1]

(R)-2-(1-(2-(pyrimidin-5-yl)-2-azaspiro[3.4]octan-6-yl)piperidin-4-yl)phenol (Intermediate 6G, 105 mg, 0.288 mmol), tetrahydro-2H-pyran-4-yl 4-methylbenzenesulfonate (73.8 mg, 0.288 mmol), and $Cs_2CO_3$ (375 mg, 1.152 mmol) were dissolved in MeCN (5 mL) and the solution was stirred at 80° C. for 16 hr. The solvent was then removed under reduced pressure and the crude mixture was diluted with EtOAc and washed with water. The organic phase was separated, dried over $MgSO_4$ and the solvent was removed under reduced pressure. The residue was purified by FCC (0-10% MeOH (1% $NH_4OH$)/DCM) and by preparative HPLC (XBridge 30×50 mm 35-60% $MeCN/H_2O$ (5 mM $NH_4OH$), 75 mL/min) to afford the title compound (10.4 mg, 0.023 mmol).

LCMS: Rt: 0.70 min (LCMS Method 1) MS m/z 449.5 $[M+H]^+$.

$^1H$ NMR (400 MHz, $CD_3OD$) δ 8.47 (s, 1H), 8.00 (s, 2H), 7.27-7.03 (m, 2H), 7.02-6.82 (m, 2H), 4.59 (m, 1H), 4.01-3.79 (m, 6H), 3.62 (m, 2H), 3.20 (t, J=10.1 Hz, 2H), 3.05 (m, 1H), 2.76 (p, J=8.1 Hz, 1H), 2.31 (dd, J=12.8, 7.3 Hz, 1H), 2.18 (q, J=11.7 Hz, 2H), 2.02 (m, 5H), 1.90-1.55 (m, 8H).

Example 1M: (R)-2-(pyrimidin-5-yl)-6-(4-(2-((tetrahydro-2H-pyran-4-yl)methoxy)phenyl)piperidin-1-yl)-2-azaspiro[3.4]octane

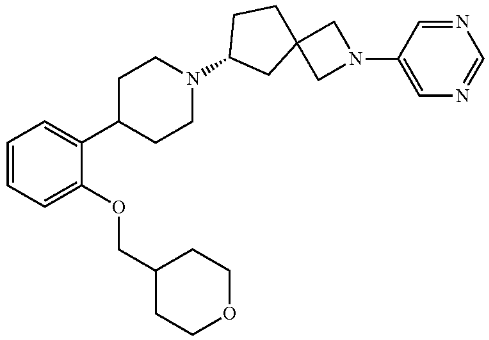 [SMILES: c1ccc(C2CCN([C@@H]3CCC4(C3)CN(c3cncnc3)C4)CC2)c(OCC2CCOCC2)c1]

(R)-2-(1-(2-(pyrimidin-5-yl)-2-azaspiro[3.4]octan-6-yl)piperidin-4-yl)phenol (Intermediate 6G, 80 mg, 0.219 mmol), (tetrahydro-2H-pyran-4-yl)methyl 4-methylbenzenesulfonate (68.2 mg, 0.252 mmol), and $Cs_2CO_3$ (286 mg, 0.878 mmol) were dissolved in MeCN (5 mL) and the reaction was stirred at 91° C. for 16 hr. The solvent was then removed under reduced pressure and the crude mixture was diluted with EtOAc and washed with water. The organic phase was separated, dried over $MgSO_4$ and the solvent was removed under reduced pressure. The residue was purified by FCC (0-10% MeOH (1% $NH_4OH$)/DCM) to afford the title compound (6.8 mg, 0.015 mmol).

LCMS: Rt: 0.74 min (LCMS Method 1) MS m/z 463.6 $[M+H]^+$.

$^1H$ NMR (400 MHz, $CD_3OD$) δ 8.48 (s, 1H), 8.00 (s, 2H), 7.21-7.10 (m, 2H), 6.90 (t, J=7.7 Hz, 2H), 4.04-3.81 (m, 7H), 3.49 (m, 2H), 3.34 (s, 2H), 3.25 (s, 1H), 3.10-2.99 (m, 1H), 2.86 (t, J=8.4 Hz, 1H), 2.38-2.23 (m, 3H), 2.16-1.92 (m, 4H), 1.92-1.44 (m, 10H).

Example 1N: (R)-6-(4-(2-(oxetan-3-ylmethoxy)phenyl)piperidin-1-yl)-2-(pyrimidin-5-yl)-2-azaspiro[3.4]octane

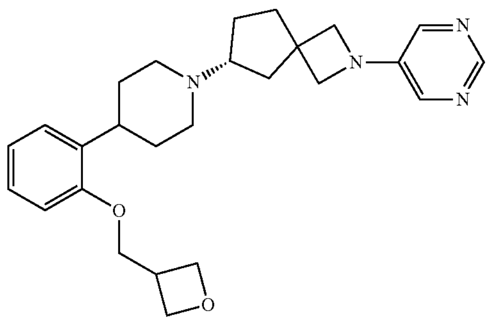 [SMILES: c1ccc(C2CCN([C@@H]3CCC4(C3)CN(c3cncnc3)C4)CC2)c(OCC2COC2)c1]

(R)-2-(1-(2-(pyrimidin-5-yl)-2-azaspiro[3.4]octan-6-yl)piperidin-4-yl)phenol (Intermediate 6G, 80 mg, 0.219 mmol), 3-(iodomethyl)oxetane (50 mg, 0.252 mmol) and $Cs_2CO_3$ (286 mg, 0.878 mmol) were dissolved in MeCN (5 mL) and the solution was stirred at 90° C. for 16 hr. The solvent was then removed under reduced pressure and the crude mixture was diluted with EtOAc and washed with water. The organic phase was separated, dried over $MgSO_4$ and the solvent was removed under reduced pressure. The residue was next purified by FCC (0-10% MeOH (1% $NH_4OH$)/DCM) and further by preparative HPLC (XBridge 30×50 mm 35-60% MeCN/$H_2O$ (5 mM $NH_4OH$), 75 mL/min) to afford the title compound (4.5 mg, 0.103 mmol).

LCMS: Rt: 1.14 min (LCMS Method 3) MS m/z 435.5 $[M+H]^+$.

$^1H$ NMR (400 MHz, $CD_3OD$) δ 8.47 (s, 1H), 8.00 (s, 2H), 7.27-7.07 (m, 2H), 7.00-6.82 (m, 2H), 4.89 (dd, J=8.0, 6.1 Hz, 2H), 4.66 (t, J=6.1 Hz, 2H), 4.18 (d, J=5.6 Hz, 2H), 3.96-3.81 (m, 4H), 3.49 (m, 1H), 3.18 (s, 2H), 3.04 (m, 1H), 2.75 (s, 1H), 2.30 (dd, J=12.9, 7.2 Hz, 1H), 2.19 (s, 2H), 2.10-1.92 (m, 3H), 1.90-1.56 (m, 6H).

Example 1O: (R)-6-(4-(2-((2-oxaspiro[3.3]heptan-6-yl)oxy)phenyl)piperidin-1-yl)-2-(pyrimidin-5-yl)-2-azaspiro[3.4]octane

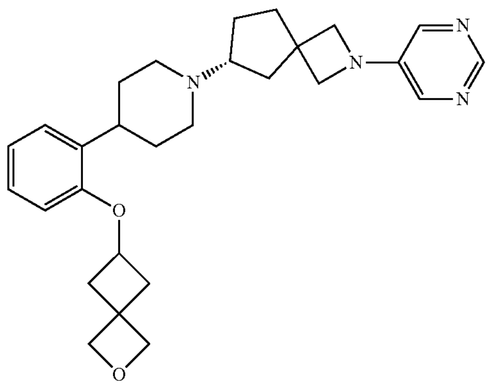 [SMILES: c1ccc(C2CCN([C@@H]3CCC4(C3)CN(c3cncnc3)C4)CC2)c(OC2CC3(COC3)C2)c1]

(R)-2-(1-(2-(pyrimidin-5-yl)-2-azaspiro[3.4]octan-6-yl)piperidin-4-yl)phenol (Intermediate 6G, 80 mg, 0.219 mmol), 2-oxaspiro[3.3]heptan-6-yl 4-methylbenzenesulfonate (Intermediate 7A, 67.7 mg, 0.252 mmol), and $Cs_2CO_3$ (286 mg, 0.878 mmol) was dissolved in MeCN (5 mL) and the solution was stirred at 95° C. for 16 hr. The solvent was then removed under reduced pressure and the crude mixture was diluted with EtOAc and washed with water. The organic phase was separated, dried over $MgSO_4$ and the solvent was removed under reduced pressure. The residue was purified by FCC (0-10% MeOH (1% $NH_4OH$)/DCM) to afford the title compound (10.6 mg, 0.203 mmol).

LCMS: Rt: 0.67 min (LCMS Method 1) MS m/z 461.4 $[M+H]^+$.

$^1H$ NMR (400 MHz, $CD_3OD$) δ 8.47 (s, 1H), 8.00 (s, 2H), 7.22-7.04 (m, 2H), 6.88 (t, J=7.4 Hz, 1H), 6.72 (d, J=8.2 Hz, 1H), 4.76 (s, 2H), 4.68 (s, 2H), 4.57 (p, J=6.6 Hz, 1H), 3.97-3.81 (m, 4H), 3.18 (s, 2H), 3.02-2.88 (m, 1H), 2.86-2.72 (m, 3H), 2.36-2.26 (m, 3H), 2.18 (s, 2H), 2.11-1.92 (m, 3H), 1.87-1.57 (m, 6H).

Example 1P: (R)-2-(pyrimidin-5-yl)-6-(4-(2-(((R)-tetrahydrofuran-3-yl)oxy)phenyl)piperidin-1-yl)-2-azaspiro[3.4]octane

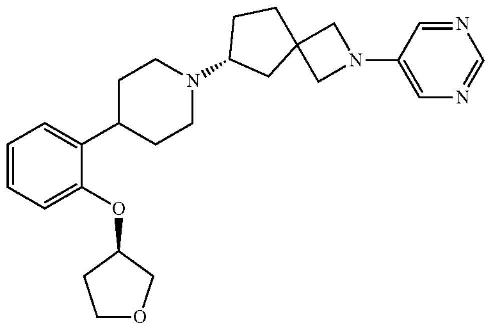 [SMILES: c1ccc(C2CCN([C@@H]3CCC4(C3)CN(c3cncnc3)C4)CC2)c(O[C@@H]2CCOC2)c1]

(R)-2-(1-(2-(pyrimidin-5-yl)-2-azaspiro[3.4]octan-6-yl)piperidin-4-yl)phenol (Intermediate 6G, 80 mg, 0.219 mmol), (S)-tetrahydrofuran-3-yl 4-methylbenzenesulfonate (Intermediate 7C, 61.2 mg, 0.252 mmol), and $Cs_2CO_3$ (286 mg, 0.878 mmol) were dissolved in MeCN (5 mL) to give a yellow solution. The solution was stirred at 95° C. for 16 hrs and the solvent was then removed under reduced pressure. The crude mixture was diluted with EtOAc and washed with water. The organic phase was separated, dried over $MgSO_4$ and the solvent was removed under reduced pressure. The residue was purified by FCC (0-10% MeOH (1% 7N $NH_3$ in MeOH)/DCM) and preparative HPLC (XBridge 30×50 mm 35-60% MeCN/$H_2O$ (5 mM $NH_4OH$)) to afford the title compound (16 mg, 0.036 mmol).

LCMS: Rt: 0.64 min (LCMS Method 1) MS m/z 435.5. $[M+H]^+$.

$^1H$ NMR (400 MHz, $CD_3OD$) δ 8.47 (s, 1H), 8.00 (s, 2H), 7.23-7.12 (m, 2H), 6.95-6.87 (m, 2H), 5.09-5.02 (m, 1H), 4.01-3.81 (m, 8H), 3.22 (s, 3H), 3.00 (s, 1H), 2.81 (s, 1H), 2.39-2.20 (m, 3H), 2.16-1.92 (m, 4H), 1.89-1.56 (m, 6H).

Example 2A: (R)-1-(2-(1-(2-(1,3,4-oxadiazol-2-yl)-2-azaspiro[3.4]octan-6-yl)piperidin-4-yl)phenoxy)-2-methylpropan-2-ol

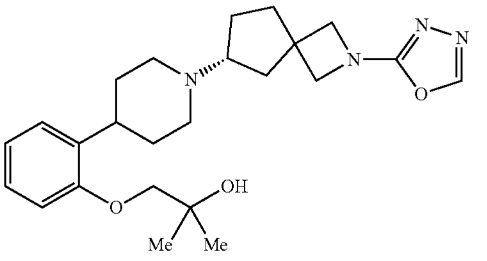 [SMILES: CC(C)(O)COc1ccccc1C1CCN([C@@H]2CCC3(C2)CN(c2nnco2)C3)CC1]

(R)-1-(2-(1-(2-azaspiro[3.4]octan-6-yl)piperidin-4-yl)phenoxy)-2-methylpropan-2-ol (Intermediate 4C, 65 mg, 0.21 mmol), ethyl 5-bromo-1,3,4-oxadiazole-2-carboxylate (46 mg, 0.21 mmol), and potassium phosphate (44 mg, 0.21 mmol) were suspended in a mixture of 2% aqueous TPGS-750-M (0.38 mL), and THE (0.042 mL). The reaction was stirred at RT for 16 hr, and then the mixture was extracted with DCM, and the combined organic layers were concentrated. The residue was purified by FCC (0-7% MeOH/DCM). The obtained intermediate (66 mg, 0.13 mmol) was dissolved in MeOH (1.3 mL), and a 2M solution of LiOH (0.59 mL, 1.2 mmol) was added. The reaction was stirred at RT for 4 hours, and a 4N HCl solution was added to adjust pH<3. The reaction was stirred at RT for 16 hr, concentrated, and purified by preparative HPLC (XBridge 30×50 mm 25-50% MeCN/$H_2O$ (5 mM $NH_4OH$)) to afford the title compound (31 mg, 0.070 mmol).

LCMS: Rt: 2.06 min (LCMS Method 4) MS m/z 427.2 $[M+H]^+$.

$^1H$ NMR (DMSO-$d_6$) δ 8.62 (s, 1H), 7.19-7.08 (m, 2H), 6.93-6.83 (m, 2H), 4.63 (s, 1H), 4.03-3.86 (m, 4H), 3.67 (s, 2H), 3.08-2.97 (m, 2H), 2.95-2.82 (m, 1H), 2.64-2.54 (m, 1H), 2.13 (dd, J=12.7, 6.8 Hz, 1H), 2.04-1.78 (m, 5H), 1.77-1.65 (m, 3H), 1.64-1.37 (m, 3H), 1.23 (s, 6H).

Example 2B: 2-((R)-6-(4-(2-(((R)-tetrahydrofuran-3-yl)oxy)phenyl)piperidin-1-yl)-2-azaspiro[3.4]octan-2-yl)-1,3,4-oxadiazole

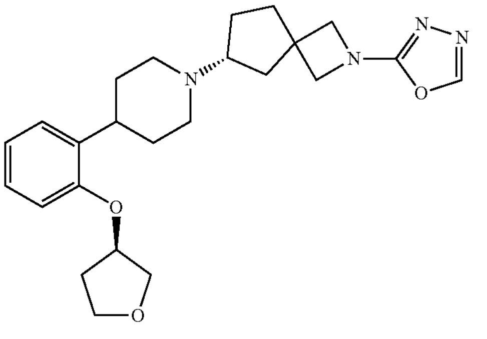 [SMILES: c1ccc(C2CCN([C@@H]3CCC4(C3)CN(c3nnco3)C4)CC2)c(O[C@@H]2CCOC2)c1]

(R)-6-(4-(2-(((R)-tetrahydrofuran-3-yl)oxy)phenyl)piperidin-1-yl)-2-azaspiro[3.4]octane (Intermediate 4D, 144 mg, 0.404 mmol), ethyl 5-bromo-1,3,4-oxadiazole-2-carboxylate (89 mg, 0.40 mmol), and potassium phosphate (257 mg, 1.21 mmol) were suspended in a mixture of 2% aqueous TPGS-750-M (0.73 mL), and THF (0.081 mL). The reaction was treated similarly to Example 2A and the product was purified by FCC (0-7% MeOH/DCM), and by preparative HPLC (XBridge 30×50 mm 35-60% MeCN/$H_2O$ (5 mM $NH_4OH$)) to afford the title compound (38 mg, 0.086 mmol).

LCMS: Rt: 2.15 min (LCMS Method 4) MS m/z 425.3 $[M+H]^+$.

$^1H$ NMR (DMSO-$d_6$) δ 8.62 (s, 1H), 7.20-7.10 (m, 2H), 6.95-6.85 (m, 2H), 5.07-5.00 (m, 1H), 4.02-3.85 (m, 5H), 3.84-3.71 (m, 3H), 3.08-2.95 (m, 2H), 2.87-2.74 (m, 1H), 2.65-2.54 (m, 1H), 2.25-2.09 (m, 2H), 2.04-1.87 (m, 4H), 1.87-1.77 (m, 2H), 1.76-1.64 (m, 3H), 1.63-1.51 (m, 2H), 1.51-1.40 (m, 1H).

Example 2C: (R)-ethyl 5-(6-(4-(2-(2-methoxyethoxy)phenyl)piperidin-1-yl)-2-azaspiro[3.4]octan-2-yl)-1,3,4-oxadiazole-2-carboxylate

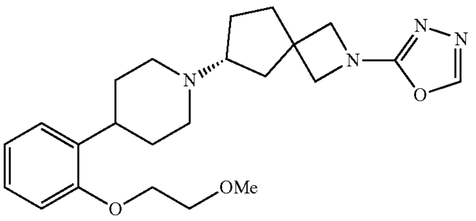 [SMILES: COCCOc1ccccc1C1CCN([C@@H]2CCC3(C2)CN(c2nnco2)C3)CC1]

(R)-6-(4-(2-(2-methoxyethoxy)phenyl)piperidin-1-yl)-2-azaspiro[3.4]octane (Intermediate 4E, 86 mg, 0.25 mmol), ethyl 5-bromo-1,3,4-oxadiazole-2-carboxylate (55 mg, 0.25 mmol), and potassium phosphate (53 mg, 0.25 mmol) were suspended in a mixture of 2% aqueous TPGS-750-M (0.50 mL), and THE (0.05 mL). The reaction was treated similarly to Example 2A and the product was purified by preparative HPLC (XBridge 30×50 mm 25-50% MeCN/$H_2O$ (5 mM $NH_4OH$)), and by FCC (0-10% MeOH/DCM) to afford the title compound (18 mg, 0.043 mmol). LCMS: Rt: 2.16 min (LCMS Method 4) MS m/z 413.3 $[M+H]^+$.

$^1H$ NMR (DMSO-$d_6$) δ 8.62 (s, 1H), 7.18-7.10 (m, 2H), 6.96-6.86 (m, 2H), 4.11-4.06 (m, 2H), 4.01-3.87 (m, 4H), 3.69-3.65 (m, 2H), 3.33 (s, 3H), 3.07-2.95 (m, 2H), 2.93-2.80 (m, 1H), 2.64-2.53 (m, 1H), 2.18-2.08 (m, 1H), 2.03-1.79 (m, 5H), 1.76-1.66 (m, 3H), 1.65-1.51 (m, 2H), 1.50-1.41 (m, 1H).

Example 2D: (R)-2-(6-(4-(2-((4-fluorotetrahydro-2H-pyran-4-yl)methoxy)phenyl)piperidin-1-yl)-2-azaspiro[3.4]octan-2-yl)-1,3,4-oxadiazole

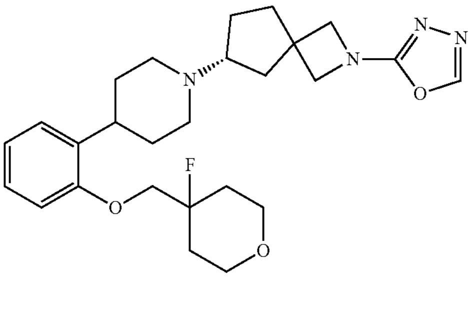 [SMILES: FC1(COc2ccccc2C2CCN([C@@H]3CCC4(C3)CN(c3nnco3)C4)CC2)CCOCC1]

(R)-6-(4-(2-((4-fluorotetrahydro-2H-pyran-4-yl)methoxy)phenyl)piperidin-1-yl)-2-azaspiro[3.4]octane (Intermediate 4F, 58 mg, 0.14 mmol), ethyl 5-bromo-1,3,4-oxadiazole-2-carboxylate (35 mg, 0.16 mmol), and potassium phosphate (34 mg, 0.16 mmol) were suspended in a mixture of 2% aqueous TPGS-750-M (0.26 mL), and THE (0.029 mL). The reaction was treated similarly to Example 2A and the product was purified by preparative HPLC (XBridge 30×50 mm 35-60% $MeCN/H_2O$ (5 mM $NH_4OH$)) to afford the title compound (18 mg, 0.039 mmol).

LCMS: Rt: 1.18 min (LCMS Method 3) MS m/z 471.0 $[M+H]^+$.

$^1H$ NMR (400 MHz, $CD_3OD$) δ 8.36 (s, 1H), 7.23-7.08 (m, 2H), 6.93 (t, J=7.5 Hz, 2H), 4.14-3.97 (m, 6H), 3.86 (m, 2H), 3.77 (m, 2H), 3.21-3.11 (m, 2H), 3.01 (m, 1H), 2.75-2.63 (m, 1H), 2.29 (dd, J=12.9, 7.3 Hz, 1H), 2.19-1.52 (m, 15H).

Example 2E: (R)-2-(6-(4-(2-((4-methyltetrahydro-2H-pyran-4-yl)methoxy)phenyl)piperidin-1-yl)-2-azaspiro[3.4]octan-2-yl)-1,3,4-oxadiazole

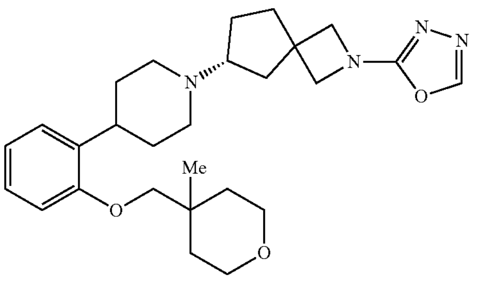 [SMILES: CC1(COc2ccccc2C2CCN([C@@H]3CCC4(C3)CN(c3nnco3)C4)CC2)CCOCC1]

(R)-6-(4-(2-((4-methyltetrahydro-2H-pyran-4-yl) methoxy)phenyl)piperidin-1-yl)-2-azaspiro[3.4]octane (Intermediate 4G, 56 mg, 0.14 mmol), ethyl 5-bromo-1,3,4-oxadiazole-2-carboxylate (34 mg, 0.16 mmol), and potassium phosphate (33 mg, 0.16 mmol) were suspended in a mixture of 2% aqueous TPGS-750-M (0.26 mL), and THE (0.03 mL). The reaction was treated similarly to Example 2A and the product was purified by preparative HPLC (XBridge 30×50 mm 35-60% $MeCN/H_2O$ (5 mM $NH_4OH$)) to afford the title compound (16 mg, 0.033 mmol).

LCMS: Rt: 2.49 min (LCMS Method 3) MS m/z 467.4 $[M+H]^+$.

$^1H$ NMR (400 MHz, $CD_3OD$) δ 8.36 (s, 1H), 7.23-7.11 (m, 2H), 6.95-6.84 (m, 2H), 4.13-3.97 (m, 4H), 3.83-3.64 (m, 6H), 3.17 (d, J=8.8 Hz, 2H), 3.02 (m, 1H), 2.73-2.63 (m, 1H), 2.29 (dd, J=12.9, 7.3 Hz, 1H), 2.18-1.93 (m, 5H), 1.89-1.64 (m, 7H), 1.58 (m, 1H), 1.45 (m, 3.4 Hz, 2H), 1.20 (s, 3H).

Example 2F: (R)-2-(6-(4-(2-((tetrahydro-2H-pyran-4-yl)oxy)phenyl)piperidin-1-yl)-2-azaspiro[3.4]octan-2-yl)-1,3,4-oxadiazole

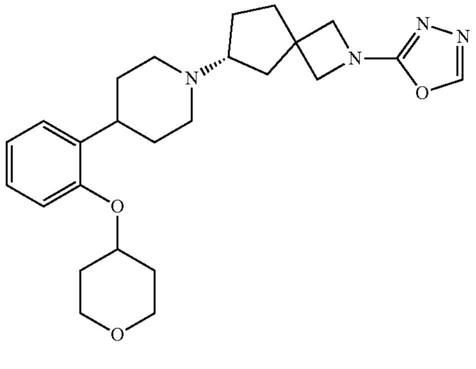 [SMILES: c1ccc(C2CCN([C@@H]3CCC4(C3)CN(c3nnco3)C4)CC2)c(OC2CCOCC2)c1]

(R)-6-(4-(2-((tetrahydro-2H-pyran-4-yl)oxy)phenyl)piperidin-1-yl)-2-azaspiro[3.4]octane (Intermediate 4H, 108 mg, 0.291 mmol), ethyl 5-bromo-1,3,4-oxadiazole-2-carboxylate (64 mg, 0.29 mmol), and potassium phosphate (186 mg, 0.874 mmol) were suspended in a mixture of 2% aqueous TPGS-750-M (0.53 mL), and THE (0.06 mL). The reaction was treated similarly to Example 2A and the product was purified by FCC (0-10% MeOH/DCM), and by preparative HPLC (XBridge 30×50 mm 35-60% $MeCN/H_2O$ (5 mM $NH_4OH$)) to afford the title compound (57 mg, 0.13 mmol).

LCMS: Rt: 2.23 min (LCMS Method 4) MS m/z 439.2 $[M+H]^+$.

$^1H$ NMR (DMSO-$d_6$) δ 8.62 (s, 1H), 7.22-7.07 (m, 2H), 6.99 (d, J=7.8 Hz, 1H), 6.92-6.82 (m, 1H), 4.66-4.51 (m, 1H), 4.03-3.86 (m, 4H), 3.85-3.75 (m, 2H), 3.57-3.45 (m, 2H), 3.08-2.96 (m, 2H), 2.93-2.81 (m, 1H), 2.64-2.53 (m, 1H), 2.13 (dd, J=12.7, 6.8 Hz, 1H), 2.05-1.90 (m, 5H), 1.89-1.77 (m, 2H), 1.76-1.66 (m, 3H), 1.66-1.55 (m, 4H), 1.51-1.40 (m, 1H).

Example 2G: (R)-2-(6-(4-(2-((tetrahydro-2H-pyran-4-yl)methoxy)phenyl)piperidin-1-yl)-2-azaspiro[3.4]octan-2-yl)-1,3,4-oxadiazole

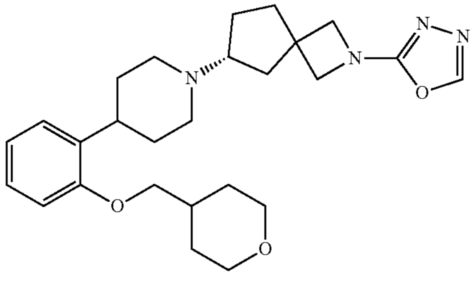

(R)-ethyl 5-(6-(4-(2-((tetrahydro-2H-pyran-4-yl) methoxy)phenyl)piperidin-1-yl)-2-azaspiro[3.4]octan-2-yl)-1,3,4-oxadiazole-2-carboxylate (Intermediate 41, 119 mg, 0.309 mmol), ethyl 5-bromo-1,3,4-oxadiazole-2-carboxylate (68 mg, 0.31 mmol), and potassium phosphate (66 mg, 0.31 mmol) were suspended in a mixture of 2% aqueous TPGS-750-M (0.56 mL), and THE (0.06 mL). The reaction was treated similarly to Example 2A and the product was purified by preparative HPLC (XBridge 30×50 mm 35-60% MeCN/$H_2O$ (5 mM $NH_4OH$)) to afford the title compound (50 mg, 0.11 mmol).

LCMS: Rt: 2.38 min (LCMS Method 4) MS m/z 453.2 $[M+H]^+$.

$^1H$ NMR (DMSO-$d_6$) δ 8.62 (s, 1H), 7.20-7.08 (m, 2H), 6.96-6.82 (m, 2H), 4.02-3.78 (m, 8H), 3.40-3.34 (m, 2H), 3.07-2.95 (m, 2H), 2.89-2.78 (m, 1H), 2.62-2.54 (m, 1H), 2.18-2.09 (m, 1H), 2.07-1.77 (m, 6H), 1.75-1.64 (m, 5H), 1.63-1.49 (m, 2H), 1.49-1.31 (m, 3H).

Example 2H: (R)-2-(6-(4-(2-(tetrahydro-2H-pyran-4-yl)phenyl)piperidin-1-yl)-2-azaspiro[3.4]octan-2-yl)-1,3,4-oxadiazole

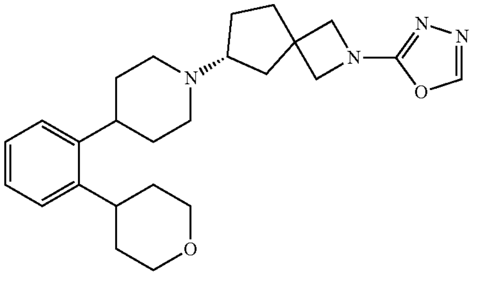 [SMILES: c1ccc(C2CCN([C@@H]3CCC4(C3)CN(c3nnco3)C4)CC2)c(C2CCOCC2)c1]

(R)-6-(4-(2-(tetrahydro-2H-pyran-4-yl)phenyl)piperidin-1-yl)-2-azaspiro[3.4]octane (Intermediate 4Y, 27 mg, 0.076 mmol), ethyl 5-bromo-1,3,4-oxadiazole-2-carboxylate (18 mg, 0.084 mmol), and potassium phosphate (18 mg, 0.084 mmol) were suspended in a mixture 2% aqueous TPGS-750-M (0.14 mL) and THE (0.02 mL). The reaction was stirred at RT for 16 hours and then MeOH (1 mL) was added followed by water (0.5 mL) and LiOH (25 mg, 0.61 mmol). The reaction was stirred at RT for 2 hours, and then a 6M solution of HCl was added until the was pH<2. The reaction was stirred at RT for 1 hour and then concentrated and basified with a saturated solution of sodium carbonate. The solution was extracted with EtOAc, and the combined organic layers were concentrated. The residue was purified by preparative HPLC (XBridge 30×50 mm 10-30% MeCN/$H_2O$ (0.1% formic acid)) to afford the title compound (6.8 mg, 0.014 mmol) as a white solid.

LCMS: Rt: 2.15 min (LCMS Method 4) MS m/z 423.4 $[M+H]^+$.

$^1H$ NMR (DMSO-$d_6$) δ 8.64 (s, 1H), 7.27-7.20 (m, 2H), 7.18-7.11 (m, 2H), 4.03-3.88 (m, 6H), 3.53-3.43 (m, 2H), 3.11-2.96 (m, 3H), 2.87-2.73 (m, 1H), 2.70-2.57 (m, 1H), 2.21-2.10 (m, 1H), 2.10-1.98 (m, 2H), 1.98-1.87 (m, 1H), 1.87-1.78 (m, 2H), 1.77-1.58 (m, 7H), 1.58-1.50 (m, 2H), 1.50-1.42 (m, 1H).

Example 2I: (R)-2-(6-(4-(5-fluoro-2-(tetrahydro-2H-pyran-4-yl)phenyl)piperidin-1-yl)-2-azaspiro[3.4]octan-2-yl)-1,3,4-oxadiazole

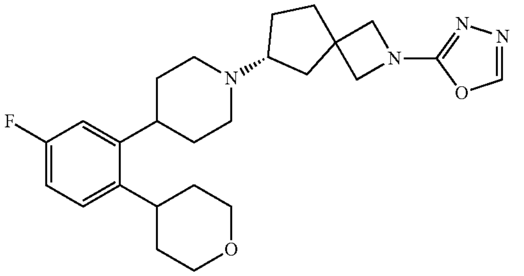 [SMILES: Fc1ccc(C2CCOCC2)c(C2CCN([C@@H]3CCC4(C3)CN(c3nnco3)C4)CC2)c1]

(R)-6-(4-(5-fluoro-2-(tetrahydro-2H-pyran-4-yl)phenyl)piperidin-1-yl)-2-azaspiro[3.4]octane (Intermediate 4K, 47 mg, 0.10 mmol), ethyl 5-bromo-1,3,4-oxadiazole-2-carboxylate (27 mg, 0.12 mmol) and potassium phosphate (24 mg, 0.11 mmol) were suspended in a mixture 2% aqueous TPGS-750-M (1.8 mL) and THE (0.20 mL). The reaction was stirred at RT for 16 hours and then MeOH (0.5 mL) was added followed by water (0.5 mL) and LiOH (34 mg, 0.81 mmol). The reaction was stirred at RT for 2 hours and then a 6M solution of HCl was added until the pH<2. The reaction was stirred at RT for 1 hour, concentrated and basified with a saturated solution of sodium carbonate. The solution was then extracted with EtOAc, and the combined organic layers were concentrated. The residue was purified by preparative HPLC (XBridge 30×50 mm 35-60% MeCN/$H_2O$ (5 mM $NH_4OH$)) and by FCC (0-5% MeOH(1% $NH_3$ in MeOH)/DCM) to afford the title compound (5.8 mg, 0.013 mmol) as a beige solid.

LCMS: Rt: 2.17 min (LCMS Method 4) MS m/z 441.3 $[M+H]^+$.

$^1H$ NMR (400 MHz, $CD_3OD$) δ 8.36 (s, 1H), 7.27 (dd, J=8.7, 6.0 Hz, 1H), 6.97 (dd, J=10.9, 2.8 Hz, 1H), 6.90 (td, J=8.4, 2.7 Hz, 1H), 4.17-3.98 (m, 6H), 3.59 (m, 2H), 3.25-3.16 (m, 2H), 3.07 (m, 1H), 2.94 (m, 1H), 2.87-2.73 (m, 1H), 2.39-2.18 (m, 3H), 2.11-1.93 (m, 3H), 1.91-1.73 (m, 7H), 1.68-1.56 (m, 3H).

Example 2J: 2-((6R)-6-(4-(5-fluoro-2-(tetrahydrofuran-3-yl)phenyl)piperidin-1-yl)-2-azaspiro[3.4]octan-2-yl)-1,3,4-oxadiazole

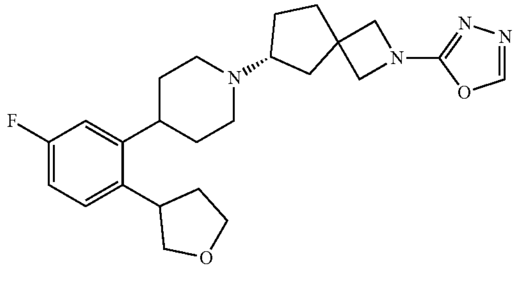 [SMILES: Fc1ccc(C2CCOC2)c(C2CCN([C@@H]3CCC4(C3)CN(c3nnco3)C4)CC2)c1]

(6R)-6-(4-(5-fluoro-2-(tetrahydrofuran-3-yl)phenyl)piperidin-1-yl)-2-azaspiro[3.4]octane (Intermediate 4L, 52 mg, 0.12 mmol), ethyl 5-bromo-1,3,4-oxadiazole-2-carboxylate (31 mg, 0.14 mmol) and potassium phosphate (30 mg, 0.14 mmol) were suspended in a mixture 2% aqueous TPGS- 750-M (0.21 mL) and THF (0.023 mL). The reaction was stirred at RT for 16 hours and then MeOH (0.5 mL) was added followed by water (0.5 mL) and LiOH (39 mg, 0.93 mmol). The reaction was stirred at RT for 2 hours and then a 6M solution of HCl was added until the pH<2. The reaction was stirred at RT for 1 hour, concentrated and it was then basified with a saturated solution of sodium carbonate. The reaction was extracted with EtOAc, and the combined organic layers were concentrated. The residue was purified by preparative HPLC (XBridge 30×50 mm 25-50% MeCN/$H_2O$ (5 mM $NH_4OH$)) and further by FCC (0-5% MeOH (1% $NH_3$ in MeOH)/DCM) to afford the title compound (6.1 mg, 0.014 mmol) as a mixture of diastereomers.

LCMS: Rt: 2.11 min (LCMS Method 4) MS m/z 427.4 $[M+H]^+$.

$^1$H NMR (400 MHz, $CD_3OD$) δ 8.36 (s, 1H), 7.32 (dd, J=8.7, 5.9 Hz, 1H), 6.98 (dd, J=10.8, 2.8 Hz, 1H), 6.91 (m, 1H), 4.16-3.98 (m, 6H), 3.90 (q, J=7.6 Hz, 1H), 3.75-3.65 (m, 2H), 3.25-3.16 (m, 2H), 2.97 (m, 1H), 2.78 (m, 1H), 2.41-2.20 (m, 4H), 2.11-1.89 (m, 4H), 1.88-1.74 (m, 5H), 1.68-1.56 (m, 1H).

Example 2K: 2-((6R)-6-(4-(2-(tetrahydrofuran-3-yl)phenyl)piperidin-1-yl)-2-azaspiro[3.4]octan-2-yl)-1,3,4-oxadiazole

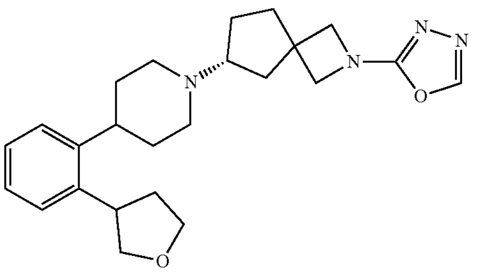 [SMILES: c1ccc(C2CCOC2)c(C2CCN([C@@H]3CCC4(C3)CN(c3nnco3)C4)CC2)c1]

(6R)-6-(4-(2-(tetrahydrofuran-3-yl)phenyl)piperidin-1-yl)-2-azaspiro[3.4]octane (Intermediate 4M, 50 mg, 0.12 mmol), ethyl 5-bromo-1,3,4-oxadiazole-2-carboxylate (31 mg, 0.14 mmol) and potassium phosphate (30 mg, 0.14 mmol) were suspended in a mixture 2% aqueous TPGS-750-M (0.21 mL) and THF (0.023 mL). The reaction was stirred at RT for 16 hours and then MeOH (0.5 mL) was added followed by water (0.5 mL) and LiOH (39 mg, 0.93 mmol). The reaction was stirred at RT for 2 hours and then a 6M solution of HCl (0.29 mL) was added until the pH<2. The reaction was stirred at RT for 1 hour, concentrated and basified with a saturated solution of sodium carbonate. The solution was then extracted with EtOAc, and the combined organic layers were concentrated. The residue was purified by preparative HPLC (XBridge 30×50 mm 25-50% MeCN/$H_2O$ (5 mM $NH_4OH$)) and further by FCC (0-5% MeOH (1% $NH_3$ in MeOH)/DCM) to afford the title compound (6.4 mg, 0.015 mmol) as a mixture of diastereomers.

LCMS: Rt: 2.00 min (LCMS Method 4) MS m/z 409.4 $[M+H]^+$.

$^1$H NMR (400 MHz, $CD_3OD$) δ 8.36 (s, 1H), 7.33-7.28 (m, 1H), 7.28-7.23 (m, 1H), 7.21-7.14 (m, 2H), 4.15-3.98 (m, 6H), 3.91 (q, J=7.6 Hz, 1H), 3.79-3.67 (m, 2H), 3.24-3.14 (m, 2H), 2.95 (m, 1H), 2.76 (m, 1H), 2.41-2.17 (m, 4H), 2.12-1.93 (m, 4H), 1.90-1.72 (m, 5H), 1.67-1.54 (m, 1H).

Example 2L: (R)-2-(6-(4-(2-((tetrahydro-2H-pyran-4-yl)methyl)phenyl)piperidin-1-yl)-2-azaspiro[3.4]octan-2-yl)-1,3,4-oxadiazole

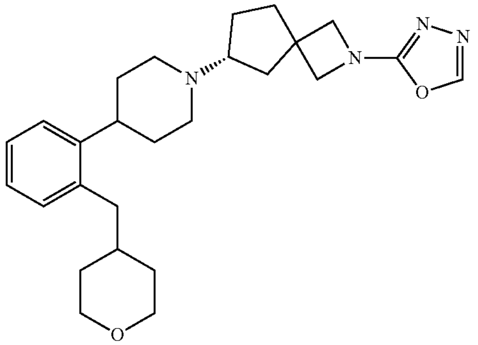 [SMILES: c1ccc(C2CCN([C@@H]3CCC4(C3)CN(c3nnco3)C4)CC2)c(CC2CCOCC2)c1]

Step 1: tert-butyl (R)-6-(4-(2-(((trifluoromethyl)sulfonyl)oxy)phenyl)piperidin-1-yl)-2-azaspiro[3.4]octane-2-carboxylate tert-butyl (R)-6-(4-(2-hydroxyphenyl)piperidin-1-yl)-2-azaspiro[3.4]octane-2-carboxylate (Intermediate 6C, 300 mg, 0.776 mmol) was dissolved in DCM (7 mL) and pyridine (0.13 mL, 1.5 mmol) was added. The reaction was cooled to 0° C. and a solution of $Tf_2O$ in DCM (1M, 0.85 mL, 0.85 mmol) was added. The reaction was stirred at RT for 1 hour then cooled at 0° C., and pyridine (0.038 mL, 0.47 mmol) was added followed by additional $Tf_2O$ in DCM (1M, 0.23 mL, 0.23 mmol). The reaction was stirred at RT 1 hour, neutralized with a saturated solution of sodium bicarbonate, extracted 3 times with DCM, and the combined organic layers were dried with magnesium sulfate, filtered and concentrated. The residue was purified by FCC (0-10% MeOH/DCM) to afford the title compound (333 mg, 0.642 mmol).

LCMS: Rt: 1.36 min (LCMS Method 2) MS m/z 519.2 $[M+H]^+$.

Step 2: 4-(bromomethylene)tetrahydro-2H-pyran

To a suspension of (bromomethyl)triphenylphosphonium bromide (1.13 g, 2.60 mmol) in THF (10 mL) at −78° C. was added potassium tert-butoxide (291 mg, 2.60 mmol). The reaction was stirred at 0° C. for 1 hour, and then a solution of tetrahydro-4H-pyran-4-one (200 mg, 2.00 mmol) in THF (10 mL) was added. The reaction was then stirred at 0° C. for 16 hr. Additional (bromomethyl)triphenylphosphonium bromide (261 mg, 0.599 mmol), and potassium tert-butoxide (67 mg, 0.60 mmol) were added. The reaction was stirred at RT for 4 hours, and the reaction was concentrated under reduced pressure. Water was added and the aqueous layer was extracted with diethyl ether (3×). The combined organic layers were dried with $MgSO_4$, filtered, and concentrated under reduced pressure. The residue was purified by FCC (0-10% EtOAc/heptanes) to afford the title intermediate (162 mg, 0.641 mmol).

$^1$H NMR (400 MHz, $CD_2Cl_2$) δ 5.89 (t, J=1.2 Hz, 1H), 3.61-3.53 (m, 4H), 2.37-2.28 (m, 2H), 2.24-2.15 (m, 2H).

Step 3: tert-butyl (R)-6-(4-(2-((tetrahydro-4H-pyran-4-ylidene)methyl)phenyl)piperidin-1-yl)-2-azaspiro[3.4]octane-2-carboxylate To an oven-dried glass vessel was added XPhosPd G2 (15.17 mg, 0.019 mmol), XPhos (18.76 mg, 0.039 mmol), tetrahydroxydiboron (51.9 mg, 0.578 mmol) and potassium acetate (34.7 mg, 0.578 mmol). The vessel was sealed and then evacuated and back-filled with $N_2$ gas (the process was repeated four times). EtOH (3 mL) was added via syringe and tert-butyl (R)-6-(4-(2-(((trifluoromethyl)sulfonyl)oxy) phenyl)piperidin-1-yl)-2-azaspiro[3.4]octane-2-carboxylate (100 mg, 0.193 mmol) in EtOH (2 mL) was added via syringe. The reaction mixture was then stirred at 80° C. for 2 hr. Next, $K_2CO_3$ (93 mg, 0.675 mmol) dissolved in degassed water (3.0 mL) was added into the above reaction solution, followed by the addition of 4-(bromomethylene) tetrahydro-2H-pyran (51.2 mg, 0.289 mmol) in THE (1.5 mL). The reaction mixture was stirred at 80° C. for 16 hours. The reaction was diluted with EtOAc and water and the layers were separated and the organic layer was dried over sodium sulfate, filtered and concentrated. The residue was then purified by FCC (0-60% EtOAc (1% 7N $NH_3$ in MeOH)/heptanes) to yield the title compound (90 mg, 0.193 mmol).

LCMS: Rt: 0.85 min (LCMS Method 1) MS m/z 467.5 $[M+H]^+$.

Step 4: tert-butyl (R)-6-(4-(2-((tetrahydro-2H-pyran-4-yl)methyl)phenyl)piperidin-1-yl)-2-azaspiro [3.4]octane-2-carboxylate tert-butyl (R)-6-(4-(2-((tetrahydro-4H-pyran-4-ylidene) methyl)phenyl)piperidin-1-yl)-2-azaspiro[3.4]octane-2-carboxylate (90 mg, 0.19 mmol) was dissolved in ethanol (10 mL) and 20% wet $Pd(OH)_2$ (27 mg, 0.029 mmol) was added. The reaction was stirred under a hydrogen balloon at RT for 16 hr, and then filtered and concentrated. The residue was purified by FCC (0-80% EtOAc/heptanes) to afford the title intermediate (70 mg, 0.11 mmol).

LCMS: Rt: 1.33 min (LCMS Method 2) MS m/z 469.6 $[M+H]^+$.

Step 5: (R)-6-(4-(2-((tetrahydro-2H-pyran-4-yl) methyl)phenyl)piperidin-1-yl)-2-azaspiro[3.4]octane To a solution of tert-butyl (R)-6-(4-(2-((tetrahydro-2H-pyran-4-yl)methyl)phenyl)piperidin-1-yl)-2-azaspiro[3.4] octane-2-carboxylate (70 mg, 0.149 mmol) in DCM (2 mL) was added TFA (1 mL, 0.149 mmol). The reaction solution was stirred at RT for 2 hr. The solvent was then removed and the product was used without further purification (70 mg, 0.15 mmol).

LCMS: Rt: 0.58 min (LCMS Method 2) MS m/z 369 $[M+H]^+$.

Step 6: (R)-2-(6-(4-(2-((tetrahydro-2H-pyran-4-yl) methyl)phenyl)piperidin-1-yl)-2-azaspiro[3.4]octan-2-yl)-1,3,4-oxadiazole (R)-6-(4-(2-((tetrahydro-2H-pyran-4-yl)methyl)phenyl) piperidin-1-yl)-2-azaspiro[3.4]octane (70 mg, 0.15 mmol), ethyl 5-bromo-1,3,4-oxadiazole-2-carboxylate (38 mg, 0.17 mmol) were dissolved in THF (4.0 mL) and DIPEA (0.076 mL, 0.44 mmol) was added. The reaction was stirred at RT for 2 hours, then a 2M solution of LiOH (2.0 mL, 4.0 mmol) was added followed by MeOH (1 mL). The reaction was stirred at RT for 2 hours, then a 4M solution of HCl (~3 mL) was added until pH<2. The reaction was stirred at RT for 3 hours, then basified with a 7N solution of $NH_3$ in MeOH, concentrated, extracted with DCM (3×), and the combined organic layers were concentrated. The residue was purified by preparative HPLC (XBridge Peptide BEH C18 19×150 mm 40-55% MeCN/$H_2O$ (10 mM $NH_4OH$)), and by preparative HPLC (XSelect CSH C18 5 μm 19×150 mm 20-35% MeCN/$H_2O$ (0.1% TFA)). The residue was dissolved in MeOH and the solution was passed through an Agilent PL-HCO3 MP resin ion-exchange column, eluting with MeOH. The obtained freebase was purified by FCC (0-6% MeOH/DCM) to afford the title compound (9.0 mg, 0.020 mmol).

LCMS: Rt: 2.31 min (LCMS Method 4) MS m/z 437.7 $[M+H]^+$.

$^1H$ NMR (400 MHz, $CD_3OD$) δ 8.37 (s, 1H), 7.30-7.24 (m, 1H), 7.19-7.13 (m, 1H), 7.12-7.05 (m, 2H), 4.17-3.96 (m, 4H), 3.91 (m, 2H), 3.38-3.32 (m, 2H), 3.21 (d, J=11.5 Hz, 2H), 2.89-2.71 (m, 2H), 2.62 (d, J=7.3 Hz, 2H), 2.33 (dd, J=13.1, 7.4 Hz, 1H), 2.22 (s, 2H), 2.11-1.92 (m, 3H), 1.90-1.47 (m, 9H), 1.35 (m, 2H).

Example 2M: (R)-2-(6-(4-(2-(oxazol-2-yl)phenyl) piperidin-1-yl)-2-azaspiro[3.4]octan-2-yl)-1,3,4-oxadiazole

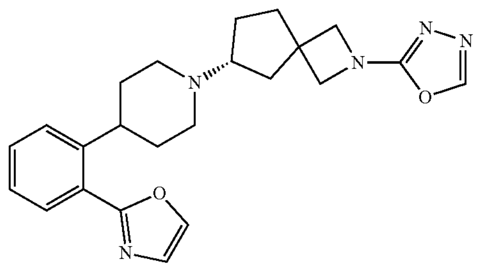 [SMILES: c1ccc(C2CCN([C@@H]3CCC4(C3)CN(c3nnco3)C4)CC2)c(-c2ncco2)c1]

Step 1: tert-butyl (R)-6-(4-(2-(oxazol-2-yl)phenyl) piperidin-1-yl)-2-azaspiro[3.4]octane-2-carboxylate To an oven-dried glass microwave vial, XPhos Pd G2 (21 mg, 0.027 mmol), XPhos (26 mg, 0.054 mmol), tetrahydroxydiboron (73 mg, 0.81 mmol), and potassium acetate (49 mg, 0.81 mmol) were added. The vessel was sealed, then evacuated and back-filled with nitrogen gas (the process was repeated four times). EtOH (3 mL) was added via syringe, followed by a solution of a tert-butyl (R)-6-(4-(2-(((trifluoromethyl)sulfonyl)oxy)phenyl)piperidin-1-yl)-2-azaspiro [3.4]octane-2-carboxylate (Example 2L, Step 1, 140 mg, 0.270 mmol) in EtOH (3 mL). The reaction mixture was stirred at 80° C. for 2 hours and then potassium carbonate (112 mg, 0.81 mmol) in water (3 mL, degassed) was added, followed by a solution of 2-bromo-1,3-oxazole (63 mg, 0.41 mmol) in THE (3 mL, degassed). The reaction mixture was stirred at 80° C. for 16 hr, then filtered and concentrated under reduced pressure. The residue was purified by FCC (0-100% EtOAc (1% 7N $NH_3$ in MeOH)/heptanes) to afford the title intermediate (47 mg, 0.11 mmol).

LCMS: Rt: 1.23 min (LCMS Method 2), MS m/z 438.8 $[M+H]^+$.

Step 2: (R)-2-(2-(1-(2-azaspiro[3.4]octan-6-yl)piperidin-4-yl)phenyl)oxazole tert-butyl (R)-6-(4-(2-(oxazol-2-yl)phenyl)piperidin-1-yl)-2-azaspiro[3.4]octane-2-carboxylate (22 mg, 0.050 mmol) was dissolved in DCM (1 mL) and TFA (0.2 mL) was added. The reaction was stirred at RT for 2 hours, concentrated, diluted with DCM, basified with a saturated solution of sodium bicarbonate and extracted with DCM (3×). The combined organic layers were dried with magnesium sulfate, filtered and concentrated to afford the title intermediate (17 mg, 0.050 mmol).

LCMS: Rt: 0.54 min (LCMS Method 1) MS m/z 338.6 $[M+H]^+$.

Step 3: (R)-2-(6-(4-(2-(oxazol-2-yl)phenyl)piperidin-1-yl)-2-azaspiro[3.4]octan-2-yl)-1,3,4-oxadiazole (R)-2-(2-(1-(2-azaspiro[3.4]octan-6-yl)piperidin-4-yl)phenyl)oxazole (17 mg, 0.050 mmol), ethyl 5-bromo-1,3,4-oxadiazole-2-carboxylate (14 mg, 0.065 mmol) and potassium phosphate (14 mg, 0.065 mmol) were suspended in a mixture 2% aqueous TPGS-750-M (0.30 mL) and THE (0.030 mL). The reaction was stirred at RT for 16 hr, then a 2M solution of LiOH (2.2 mL, 4.4 mmol) was added The reaction was stirred at RT for 2 hours, then a 4M solution of HCl was added until pH<2. The reaction was stirred at RT for 3 hours, basified with a saturated solution of sodium bicarbonate, extracted 3 times with ethyl acetate, and the combined organic layers were concentrated. The residue was purified by preparative HPLC (XBridge Peptide BEH C18 19×150 mm 40-55% $MeCN/H_2O$ (10 mM $NH_4OH$)) to afford the title compound (4.0 mg, 0.0095 mmol).

LCMS: Rt: 2.05 min (LCMS Method 4) MS m/z 406.4 $[M+H]^+$.

$^1H$ NMR (400 MHz, $CD_3OD$) δ 8.36 (s, 1H), 8.01 (s, 1H), 7.81-7.68 (m, 1H), 7.57-7.44 (m, 2H), 7.37-7.23 (m, 2H), 4.20-3.81 (m, 4H), 3.46 (m, 1H), 3.21-3.05 (m, 2H), 2.70 (m, 1H), 2.29 (dd, J=13.2, 7.4 Hz, 1H), 2.17-1.92 (m, 5H), 1.82 (m, 5H), 1.66-1.47 (m, 1H).

Example 2N: (1S,4s)-4-(2-(1-((R)-2-(1,3,4-oxadiazol-2-yl)-2-azaspiro[3.4]octan-6-yl)piperidin-4-yl)phenyl)cyclohexan-1-ol or (1R,4r)-4-(2-(1-((R)-2-(1,3,4-oxadiazol-2-yl)-2-azaspiro[3.4]octan-6-yl)piperidin-4-yl)phenyl)cyclohexan-1-ol and Example 2O: (1s,4r)-4-(2-(1-((R)-2-(1,3,4-oxadiazol-2-yl)-2-azaspiro[3.4]octan-6-yl)piperidin-4-yl)phenyl)cyclohexan-1-ol or (1r,4r)-4-(2-(1-((R)-2-(1,3,4-oxadiazol-2-yl)-2-azaspiro[3.4]octan-6-yl)piperidin-4-yl)phenyl)cyclohexan-1-ol

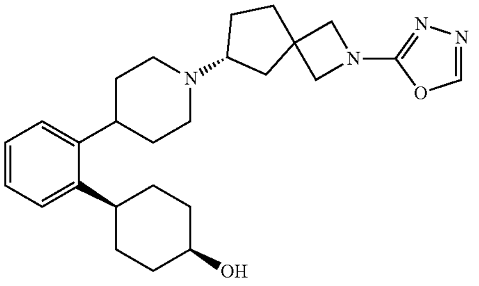

1S,4s
cyclohexane

-continued

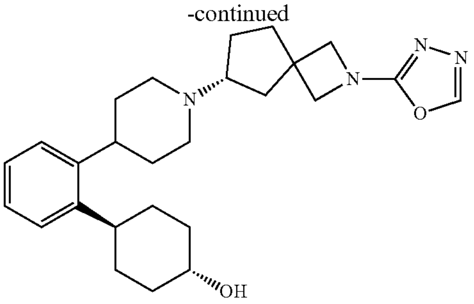

1R,4r
cyclohexane

Step 1: tert-butyl (6R)-6-(4-(4'-hydroxy-2',3',4',5'-tetrahydro-[1,1'-biphenyl]-2-yl)piperidin-1-yl)-2-azaspiro[3.4]octane-2-carboxylate To a THF (3 mL) solution of tert-butyl (6R)-6-(4-(4'-((tert-butyldimethylsilyl)oxy)-2',3',4',5'-tetrahydro-[1,1'-biphenyl]-2-yl)piperidin-1-yl)-2-azaspiro[3.4]octane-2-carboxylate (Intermediate 9E, 259 mg, 0.446 mmol) was added TBAF in THE (1M, 0.580 mL, 0.580 mmol). The reaction mixture was stirred for 16 hours. Next, additional TBAF in THF (1M, 0.580 mL, 0.580 mmol) was added and the reaction was stirred for 24 hours. Next, additional TBAF in THE (1M, 0.580 mL, 0.580 mmol) was added to the reaction and it was stirred at 50° C. for 3 hr. The reaction was then concentrated and purified by FCC (0-8% 7N $NH_3$MeOH in 32% EtOAc/heptanes) to yield the title compound (173 mg, 0.367 mmol).

LCMS: Rt: 1.23 min (LCMS Method 2) MS m/z 467.4 $[M+H]^+$.

Step 2: tert-butyl (R)-6-(4-(2-(4-hydroxycyclohexyl)phenyl)piperidin-1-yl)-2-azaspiro[3.4]octane-2-carboxylate To a MeOH (3.7 mL) solution of tert-butyl (6R)-6-(4-(4'-hydroxy-2',3',4',5'-tetrahydro-[1,1'-biphenyl]-2-yl)piperidin-1-yl)-2-azaspiro[3.4]octane-2-carboxylate (173 mg, 0.371 mmol), was added Pd—C(3.95 mg, 0.037 mmol). The reaction mixture was stirred under a $H_2$ balloon for 72 hours. The crude was filtered and concentrated under reduced pressure. The residue was purified by FCC (0-8% 7N $NH_3$ in MeOH/32% EtOAc/heptanes) to yield the title compound as a yellow solid (145 mg, 0.248 mmol).

LCMS: Rt: 1.21 min (LCMS Method 2) MS m/z 469.5 $[M+H]^+$.

Step 3: (R)-4-(2-(1-(2-azaspiro[3.4]octan-6-yl)piperidin-4-yl)phenyl)cyclohexan-1-ol tert-butyl (R)-6-(4-(2-(4-hydroxycyclohexyl)phenyl)piperidin-1-yl)-2-azaspiro[3.4]octane-2-carboxylate (145 mg, 0.248 mmol) was dissolved in DCM (0.75 mL) and TFA (0.48 mL, 6.19 mmol) and the reaction was stirred for 3 hours. The reaction was then concentrated and dissolved in DCM and washed with 1N NaOH to yield the title compound that was used without further purification (90 mg, 0.122 mmol).

LCMS: Rt: 0.79 min (LCMS Method 2) MS m/z 369.4 $[M+H]^+$.

Step 4: (1S,4s)-4-(2-(1-((R)-2-(1,3,4-oxadiazol-2-yl)-2-azaspiro[3.4]octan-6-yl)piperidin-4-yl)phenyl)cyclohexan-1-ol and (1R,4r)-4-(2-(1-((R)-2-(1,3,4-oxadiazol-2-yl)-2-azaspiro[3.4]octan-6-yl)piperidin-4-yl)phenyl)cyclohexan-1-ol To a THF (1 mL) solution of (R)-4-(2-(1-(2-azaspiro[3.4]octan-6-yl)piperidin-4-yl)phenyl)cyclohexan-1-ol (90 mg, 0.122 mmol) and ethyl 5-bromo-1,3,4-oxadiazole-2-carboxylate (40.5 mg, 0.147 mmol) was added DIPEA (0.047 mL, 0.269 mmol) at 0° C. The reaction was stirred for 2 hr and then it was concentrated and diluted with EtOAc and washed with water and brine. The organic layer was dried over magnesium sulfate, filtered and concentrated. The residue was dissolved in THE (1 mL) and LiOH (30.7 mg, 0.733 mmol) dissolved in water (1 mL) was added. The reaction was stirred for 72 hours. The reaction was then cooled to −5° C. and 4N HCl (0.203 mL, 1.221 mmol) was added and the reaction was warmed to RT and stirred for 2 hours. Aq sodium carbonate was added until the pH was greater than 9 and the reaction was concentrated and diluted with EtOAc. The organic layer was washed with brine, dried over magnesium sulfate, filtered and concentrated. The crude was then purified by FCC (0-5% 7N $NH_3$ in MeOH/32% EtOAc/heptanes) and further by preparative HPLC (XBridge $C_{18}$ OBD 30×50 mm, MeCN/$H_2O$+5 mM $NH_4OH$, 75 mL/min). The two diastereomers were then separated by preparative HPLC (XBridge C18 OBD 30×50 mm, MeCN/$H_2O$ (0.1% formic acid), 75 mL/min). The faster running diastereomer was isolated as Example 2N (1.8 mg, 3.54 μmol) as the formate salt and the slower running diastereomer was isolated as Example 2O (2.2 mg, 4.33 μmol) as the formate salt.

Example 2N Formate Salt

LCMS: Rt: 1.00 min (LCMS Method 3) MS m/z 437.3 $[M+H]^+$.

$^1H$ NMR (400 MHz, $CD_3OD$) δ 8.50 (s, 1H), 8.39 (s, 1H), 7.33 (dd, J=7.0, 2.1 Hz, 1H), 7.25-7.12 (m, 3H), 4.23-4.00 (m, 5H), 3.69-3.59 (m, 2H), 3.54 (t, J=8.6 Hz, 1H), 3.26-3.14 (m, 1H), 3.06 (m, 2H), 2.87 (m 1H), 2.55 (dd, J=13.3, 7.9 Hz, 1H), 2.29-1.80 (m, 13H), 1.72 (m, 2H), 1.55-1.43 (m, 2H).

Example 2O Formate Salt

LCMS: Rt: 1.13 min (LCMS Method 3) MS m/z 437.3 $[M+H]^+$.

$^1H$ NMR (400 MHz, $CD_3OD$) δ 8.47 (d, J=4.7 Hz, 1H), 8.39 (s, 1H), 7.31-7.25 (m, 1H), 7.24-7.20 (m, 1H), 7.17 (td, J=5.2, 4.5, 3.2 Hz, 2H), 4.21-4.01 (m, 4H), 3.64 (m, 3H), 3.57-3.45 (m, 1H), 3.24-3.11 (m, 1H), 3.04 (d, J=14.5 Hz, 2H), 2.82 (m, 1H), 2.55 (dd, J=13.3, 7.8 Hz, 1H), 2.19 (m, 2H), 2.12-1.91 (m, 8H), 1.90-1.72 (m, 3H), 1.63 (m, 2H), 1.52-1.38 (m, 2H).

Example 3A: (R)-2-(6-(4-(2-(oxetan-3-yloxy)phenyl)piperidin-1-yl)-2-azaspiro[3.4]octan-2-yl)-1,3,4-thiadiazole

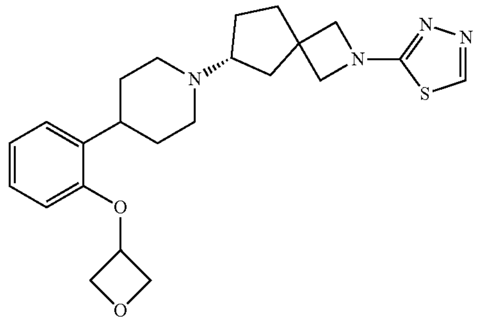 [SMILES: c1ccc(C2CCN([C@@H]3CCC4(C3)CN(c3nncs3)C4)CC2)c(OC2COC2)c1]

(R)-6-(4-(2-(oxetan-3-yloxy)phenyl)piperidin-1-yl)-2-azaspiro[3.4]octane (Intermediate 4N, 70 mg, 0.20 mmol), 2-bromo-1,3,4-thiadiazole (34 mg, 0.20 mmol) and potassium phosphate (43 mg, 0.20 mmol) were suspended in a mixture of 2% aqueous TPGS-750-M (0.37 mL) and THE (0.04 mL). The reaction was stirred at RT for 16 hours and then the solution was extracted with DCM, and the combined organic layers were concentrated. The residue was purified by FCC (0-7% MeOH/DCM) and further by preparative HPLC (XBridge 30×50 mm 25-50% MeCN/$H_2O$ (5 mM $NH_4OH$)) to afford the title compound (21 mg, 0.048 mmol).

LCMS: Rt: 2.09 min (LCMS Method 4) MS m/z 427.3 $[M+H]^+$.

$^1H$ NMR (DMSO-$d_6$) δ 8.78 (s, 1H), 7.21 (dd, J=7.8, 1.5 Hz, 1H), 7.16-7.04 (m, 1H), 6.98-6.87 (m, 1H), 6.53 (d, J=7.8 Hz, 1H), 5.75 (s, 1H), 5.27 (q, J=5.5 Hz, 1H), 4.93 (t, J=6.8 Hz, 2H), 4.53 (dd, J=7.6, 5.1 Hz, 2H), 4.03-3.84 (m, 4H), 3.29 (br s, 1H), 3.04 (br s, 2H), 2.91 (t, J=11.7 Hz, 1H), 2.21-2.12 (m, 1H), 2.12-1.81 (m, 4H), 1.80-1.69 (m, 3H), 1.69-1.43 (m, 3H).

Example 3B: 2-((R)-6-(4-(2-(((R)-1,4-dioxan-2-yl)methoxy)phenyl)piperidin-1-yl)-2-azaspiro[3.4]octan-2-yl)-1,3,4-thiadiazole

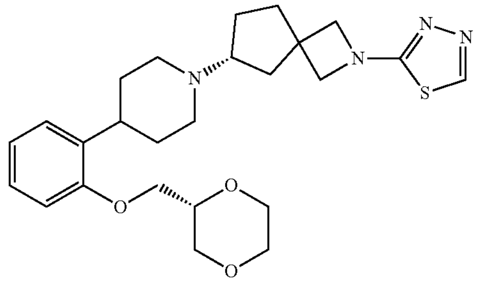 [SMILES: c1ccc(C2CCN([C@@H]3CCC4(C3)CN(c3nncs3)C4)CC2)c(OC[C@H]2COCCO2)c1]

(R)-6-(4-(2-(((R)-1,4-dioxan-2-yl)methoxy)phenyl)piperidin-1-yl)-2-azaspiro[3.4]octane (Intermediate 40, 142 mg, 0.367 mmol)), 2-bromo-1,3,4-thiadiazole (61 mg, 0.37 mmol) and potassium phosphate (78 mg, 0.37 mmol) were suspended in a mixture of 2% aqueous TPGS-750-M (0.66 mL) and THF (0.07 mL). The reaction was stirred at RT for 16 hours and then it was extracted with DCM, and the combined organic layers were concentrated. The residue was purified by FCC (0-7% MeOH/DCM) and further by preparative HPLC (XBridge 30×50 mm 25-50% MeCN/$H_2O$ (5 mM $NH_4OH$)) to afford the title compound (52 mg, 0.11 mmol).

LCMS: Rt: 2.18 min (LCMS Method 4) MS m/z 471.2 $[M+H]^+$.

$^1$H NMR (DMSO-$d_6$) δ 8.77 (s, 1H), 7.19-7.11 (m, 2H), 6.95-6.85 (m, 2H), 4.04-3.82 (m, 8H), 3.80-3.75 (m, 1H), 3.72-3.59 (m, 2H), 3.54-3.44 (m, 2H), 3.10-3.00 (m, 2H), 2.88-2.78 (m, 1H), 2.71-2.57 (m, 1H), 2.16 (dd, J=12.7, 6.8 Hz, 1H), 2.09-1.80 (m, 5H), 1.79-1.66 (m, 3H), 1.66-1.43 (m, 3H).

Example 3C: 2-((R)-6-(4-(2-(((S)-1,4-dioxan-2-yl)methoxy)phenyl)piperidin-1-yl)-2-azaspiro[3.4]octan-2-yl)-1,3,4-thiadiazole

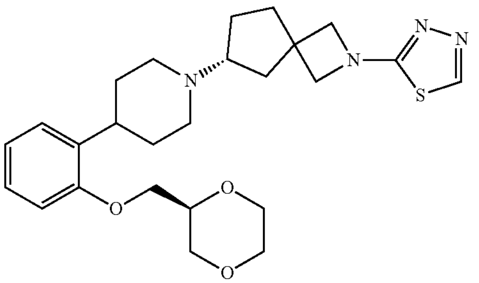 [SMILES: c1ccc(C2CCN([C@@H]3CCC4(C3)CN(c3nncs3)C4)CC2)c(OC[C@@H]2COCCO2)c1]

(R)-6-(4-(2-(((S)-1,4-dioxan-2-yl)methoxy)phenyl)piperidin-1-yl)-2-azaspiro[3.4]octane (Intermediate 4P, 164 mg, 0.424 mmol), 2-bromo-1,3,4-thiadiazole (70 mg, 0.42 mmol) and potassium phosphate (90 mg, 0.42 mmol) were suspended in a mixture of 2% aqueous TPGS-750-M (0.76 mL) and THF (0.09 mL). The reaction was stirred at RT for 16 hours and it was then extracted with DCM, and the combined organic layers were concentrated. The residue was purified by FCC (0-7% MeOH/DCM) and further by preparative HPLC (XBridge 30×50 mm 35-60% MeCN/$H_2O$ (5 mM $NH_4OH$)) to afford the title compound (74 mg, 0.15 mmol).

LCMS: Rt: 2.18 min (LCMS Method 4) MS m/z 471.7 $[M+H]^+$.

$^1$H NMR (DMSO-$d_6$) δ 8.78 (s, 1H), 7.19-7.10 (m, 2H), 6.95-6.87 (m, 2H), 4.03-3.82 (m, 8H), 3.81-3.74 (m, 1H), 3.71-3.60 (m, 2H), 3.55-3.44 (m, 2H), 3.04 (br s, 2H), 2.90-2.78 (m, 1H), 2.66-2.57 (m, 1H), 2.16 (dd, J=12.2, 7.3 Hz, 1H), 2.08-1.80 (m, 5H), 1.80-1.67 (m, 3H), 1.66-1.43 (m, 3H).

Example 3D: (R)-2-(6-(4-(2-methoxyphenyl)piperidin-1-yl)-2-azaspiro[3.4]octan-2-yl)-1,3,4-thiadiazole

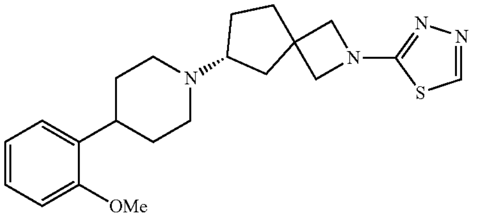 [SMILES: COc1ccccc1C1CCN([C@@H]2CCC3(C2)CN(c2nncs2)C3)CC1]

(R)-6-(4-(2-methoxyphenyl)piperidin-1-yl)-2-azaspiro[3.4]octane (Intermediate 4Q, 127 mg, 0.423 mmol), 2-bromo-1,3,4-thiadiazole (70 mg, 0.42 mmol) and potassium phosphate (90 mg, 0.42 mmol) were suspended in a mixture of 2% aqueous TPGS-750-M (0.76 mL) and THE (0.09 mL). The reaction was stirred at RT for 16 hours and then extracted with DCM and the combined organic layers were concentrated. The residue was purified by FCC (0-10% MeOH/DCM) and further by preparative HPLC (XBridge 30×50 mm 35-60% MeCN/$H_2O$ (5 mM $NH_4OH$)) to afford the title compound (60 mg, 0.15 mmol).

LCMS: Rt: 1.33 min (LCMS Method 3) MS m/z 385.4 $[M+H]^+$.

$^1$H NMR (400 MHz, DMSO-$d_6$) δ 8.78 (s, 1H), 7.22-7.12 (m, 2H), 7.00-6.85-7.00 (m, 2H), 4.02-3.85 (m, 4H), 3.77 (s, 3H), 3.29 (s, 1H), 3.00 (br s, 2H), 2.91-2.81 (m, 1H), 2.23-2.10 (m, 1H), 2.05-1.79 (m, 5H), 1.78-1.42 (m, 6H).

Example 3E: (R)-2-(6-(4-(3-fluoro-2-(oxetan-3-yloxy)phenyl)piperidin-1-yl)-2-azaspiro[3.4]octan-2-yl)-1,3,4-thiadiazole

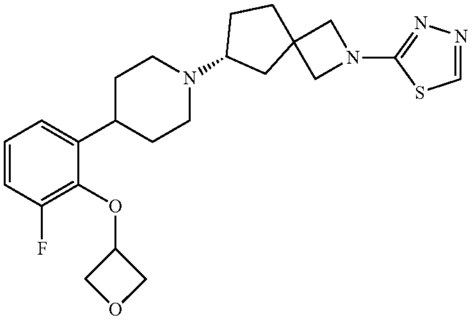 [SMILES: Fc1cccc(C2CCN([C@@H]3CCC4(C3)CN(c3nncs3)C4)CC2)c1OC1COC1]

(R)-6-(4-(3-fluoro-2-(oxetan-3-yloxy)phenyl)piperidin-1-yl)-2-azaspiro[3.4]octane (Intermediate 4J, 50 mg, 0.14 mmol), 2-bromo-1,3,4-thiadiazole (70 mg, 0.42 mmol) and potassium phosphate (90 mg, 0.42 mmol) were suspended in a mixture of 2% aqueous TPGS-750-M (0.76 mL) and THE (0.085 mL). The reaction was stirred at RT for 16 hours and then extracted with ethyl acetate, and the combined organic layers were washed with water, dried with $MgSO_4$, filtered and concentrated. The residue was purified by preparative HPLC (XBridge 30×50 mm 25-50% MeCN/$H_2O$ (5 mM $NH_4OH$)) to afford the title compound (16 mg, 0.034 mmol).

LCMS: Rt: 2.10 min (LCMS Method 4) MS m/z 445.2 $[M+H]^+$.

$^1$H NMR (400 MHz, $CD_3OD$) δ 8.64 (s, 1H), 7.08-6.89 (m, 3H), 5.11 (m, 1H), 4.92 (dd, J=7.5, 6.2 Hz, 2H), 4.84-4.78 (m, 2H), 4.18-3.90 (m, 4H), 3.16 (m, 2H), 3.01 (m, 1H), 2.73 (m, 1H), 2.31 (dd, J=12.9, 7.2 Hz, 1H), 2.22-1.91 (m, 5H), 1.89-1.68 (m, 5H), 1.66-1.52 (m, 1H).

Example 3F: (R)-2-(6-(4-(2-(2-methoxyethoxy)phenyl)piperidin-1-yl)-2-azaspiro[3.4]octan-2-yl)-1,3,4-thiadiazole

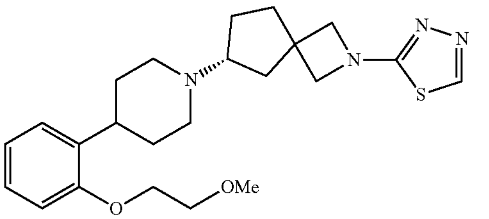 [SMILES: COCCOc1ccccc1C1CCN([C@@H]2CCC3(C2)CN(c2nncs2)C3)CC1]

(R)-6-(4-(2-(2-methoxyethoxy)phenyl)piperidin-1-yl)-2-azaspiro[3.4]octane (Intermediate 4E, 89 mg, 0.26 mmol), 2-bromo-1,3,4-thiadiazole (43 mg, 0.26 mmol) and potassium phosphate (55 mg, 0.26 mmol) were suspended in a mixture of 2% aqueous TPGS-750-M (0.46 mL) and THE (0.05 mL). The reaction was stirred at RT for 16 hours and then extracted with EtOAc and the combined organic layers were washed with water, dried with $MgSO_4$, filtered and concentrated. The residue was purified by preparative HPLC (XBridge 30×50 mm 35-60% $MeCN/H_2O$ (5 mM $NH_4OH$)) to afford the title compound (46 mg, 0.11 mmol).

LCMS: Rt: 2.25 min (LCMS Method 4) MS m/z 429.2 $[M+H]^+$.

$^1H$ NMR (DMSO-$d_6$) δ 8.78 (s, 1H), 7.19-7.11 (m, 2H), 6.96-6.87 (m, 2H), 4.11-4.06 (m, 2H), 3.99-3.87 (m, 4H), 3.67 (dd, J=5.4, 3.9 Hz, 2H), 3.33 (s, 3H), 3.10-2.96 (m, 2H), 2.93-2.82 (m, 1H), 2.65-2.54 (m, 1H), 2.21-2.11 (m, 1H), 2.03-1.80 (m, 5H), 1.79-1.67 (m, 3H), 1.65-1.45 (m, 3H).

Example 3G: (R)-1-(2-(1-(2-(1,3,4-thiadiazol-2-yl)-2-azaspiro[3.4]octan-6-yl)piperidin-4-yl)phenoxy)-2-methylpropan-2-ol

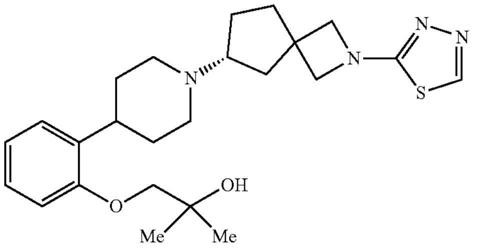 [SMILES: CC(C)(O)COc1ccccc1C1CCN([C@@H]2CCC3(C2)CN(c2nncs2)C3)CC1]

(R)-1-(2-(1-(2-azaspiro[3.4]octan-6-yl)piperidin-4-yl)phenoxy)-2-methylpropan-2-ol (Intermediate 4C, 75 mg, 0.21 mmol), 2-bromo-1,3,4-thiadiazole (35 mg, 0.21 mmol) and potassium phosphate (44 mg, 0.21 mmol) were suspended in a mixture of 2% aqueous TPGS-750-M (0.38 mL) and THE (0.04 mL). The reaction was stirred at RT for 16 hours and then extracted with EtOAc and the combined organic layers were washed with water, dried with $MgSO_4$, filtered and concentrated. The residue was purified by preparative HPLC (XBridge 30×50 mm 25-50% $MeCN/H_2O$ (5 mM $NH_4OH$)) to afford the title compound (25 mg, 0.055 mmol).

LCMS: Rt: 2.13 min (LCMS Method 4) MS m/z 443.3 $[M+H]^+$.

$^1H$ NMR (DMSO-$d_6$) δ 8.77 (s, 1H), 7.19-7.09 (m, 2H), 6.92-6.83 (m, 2H), 4.63 (s, 1H), 4.01-3.83 (m, 4H), 3.68 (s, 2H), 3.09-2.98 (m, 2H), 2.94-2.84 (m, 1H), 2.66-2.54 (m, 1H), 2.14 (dd, J=13.0, 7.1 Hz, 1H), 2.04-1.79 (m, 5H), 1.78-1.67 (m, 3H), 1.65-1.40 (m, 3H), 1.23 (s, 6H).

Example 3H: (R)-4-(2-(1-(2-(1,3,4-thiadiazol-2-yl)-2-azaspiro[3.4]octan-6-yl)piperidin-4-yl)phenoxy)-2-methylbutan-2-ol

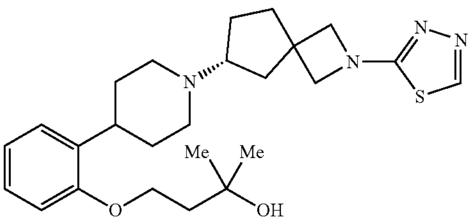 [SMILES: CC(C)(O)CCOc1ccccc1C1CCN([C@@H]2CCC3(C2)CN(c2nncs2)C3)CC1]

(R)-4-(2-(1-(2-azaspiro[3.4]octan-6-yl)piperidin-4-yl)phenoxy)-2-methylbutan-2-ol (Intermediate 4R, 550 mg, 1.48 mmol), 2-bromo-1,3,4-thiadiazole (244 mg, 1.48 mmol) and potassium phosphate (313 mg, 1.48 mmol) were suspended in a mixture of 2% aqueous TPGS-750-M (2.7 mL) and THF (0.3 mL). The reaction was stirred at RT for 16 hours and then extracted with DCM and the combined organic layers were washed with water, dried with $MgSO_4$, filtered and concentrated. The residue was purified by FCC (0-7% MeOH/DCM) and further by preparative HPLC (XBridge 30×50 mm 35-60% $MeCN/H_2O$ (5 mM $NH_4OH$)) to afford the title compound (155 mg, 0.333 mmol).

LCMS: Rt: 2.23 min (LCMS Method 4) MS m/z 457.3 $[M+H]^+$.

$^1H$ NMR (400 MHz, DMSO-$d_6$) δ 8.77 (s, 1H), 7.20-7.08 (m, 2H), 6.94 (d, J=7.8 Hz, 1H), 6.87 (t, J=7.3 Hz, 1H), 4.36 (s, 1H), 4.06 (t, J=6.8 Hz, 2H), 4.02-3.84 (m, 4H), 3.00 (d, J=10.8 Hz, 2H), 2.88-2.82 (m, 1H), 2.59 (s, 1H), 2.14 (dd, J=12.8, 7.0 Hz, 1H), 2.02-1.77 (m, 7H), 1.77-1.40 (m, 6H), 1.18 (s, 6H).

Example 3I: (R)-5-(6-(4-(2-methoxyphenyl)piperidin-1-yl)-2-azaspiro[3.4]octan-2-yl)isothiazole

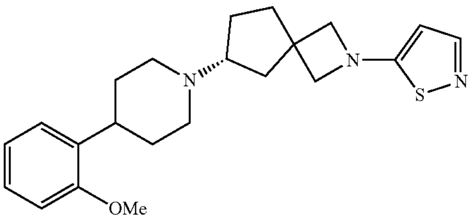 [SMILES: COc1ccccc1C1CCN([C@@H]2CCC3(C2)CN(c2ccns2)C3)CC1]

(R)-6-(4-(2-methoxyphenyl)piperidin-1-yl)-2-azaspiro[3.4]octane (Example 4Q, 90 mg, 0.30 mmol) and 5-bromoisothiazole (59 mg, 0.36 mmol) were dissolved in toluene (3 mL) and purged with nitrogen. Sodium tert-butoxide (86 mg, 0.90 mmol), $Pd_2(dba)_3$ (27 mg, 0.030 mmol) and racemic-BINAP (37 mg, 0.060 mmol) were added and the reaction was heated in the microwave at 120° C. for 1 hour and then filtered, and concentrated under reduced pressure. The residue was purified by FCC (0-10% MeOH(10% $NH_4OH$)/DCM) to afford the title compound (43 mg, 0.11 mmol).

LCMS: Rt: 2.80 min (LCMS Method 4) MS m/z 384.4 $[M+H]^+$.

$^1H$ NMR (400 MHz, $CD_3OD$) δ 7.97 (d, J=2.4 Hz, 1H), 7.23-7.11 (m, 2H), 6.97-6.84 (m, 2H), 6.12 (d, J=2.0 Hz, 1H), 3.97-3.82 (m, 4H), 3.81 (s, 3H), 3.22-3.10 (m, 2H), 2.98 (m, 1H), 2.78-2.65 (m, 1H), 2.29 (dd, J=12.9, 7.2 Hz, 1H), 2.22-2.10 (m, 2H), 2.10-1.92 (m, 3H), 1.86-1.73 (m, 5H), 1.67-1.53 (m, 1H).

Example 3J: (R)-5-(6-(4-(2-(2-methoxyethoxy)phenyl)piperidin-1-yl)-2-azaspiro[3.4]octan-2-yl)-1,2,4-thiadiazole

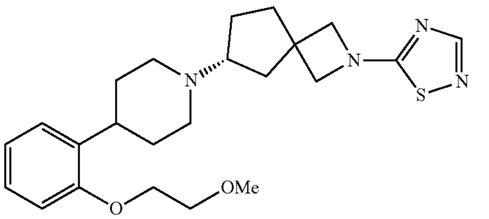

(R)-6-(4-(2-(2-methoxyethoxy)phenyl)piperidin-1-yl)-2-azaspiro[3.4]octane (Intermediate 4E, 78 mg, 0.23 mmol) was dissolved in IPA (2 mL) and DIPEA (145 mg, 1.13 mmol) was added followed by 5-bromo-1,2,4-thiadiazole (56 mg, 0.34 mmol). The reaction was stirred at RT for 1 hour and then purified by preparative HPLC (XBridge 30×50 mm 35-60% $MeCN/H_2O$ (5 mM $NH_4OH$)) to afford the title compound (70 mg, 0.16 mmol).

LCMS: Rt: 2.39 min (LCMS Method 4) MS m/z 429.5 $[M+H]^+$.

$^1H$ NMR (400 MHz, $CD_3OD$) δ 7.94 (s, 1H), 7.27-7.09 (m, 2H), 6.93 (t, J=7.6 Hz, 2H), 4.18-4.12 (m, 3H), 4.06 (m, 3H), 3.82-3.76 (m, 2H), 3.46 (s, 3H), 3.21 (s, 2H), 3.09 (m, 1H), 2.87-2.73 (m, 1H), 2.35 (m, 1H), 2.23 (m, 2H), 2.15-1.96 (m, 3H), 1.95-1.85 (m, 3H), 1.83-1.59 (m, 3H).

Example 3K: (R)-1-(2-(1-(2-(1,2,4-thiadiazol-5-yl)-2-azaspiro[3.4]octan-6-yl)piperidin-4-yl)phenoxy)-2-methylpropan-2-ol

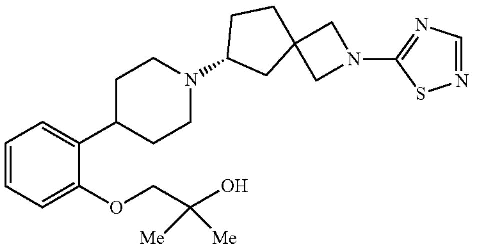 [SMILES: CC(C)(O)COc1ccccc1C1CCN([C@@H]2CCC3(C2)CN(c2ncns2)C3)CC1]

(R)-1-(2-(1-(2-azaspiro[3.4]octan-6-yl)piperidin-4-yl)phenoxy)-2-methylpropan-2-ol (Intermediate 4C, 75 mg, 0.21 mmol) was dissolved in THE (2 mL) and 5-bromo-1,2,4-thiadiazole (52 mg, 0.31 mmol) was added as a solution in THE (0.5 mL). The reaction was stirred at RT for 4 hours, then concentrated and purified by FCC (0-10% MeOH (10% $NH_4OH$)/DCM) to afford the title compound (38 mg, 0.084 mmol).

LCMS: Rt: 2.26 min (LCMS Method 4) MS m/z 443.4 $[M+H]^+$.

$^1H$ NMR (400 MHz, $CD_3OD$) δ 7.92 (s, 1H), 7.25-7.07 (m, 2H), 6.90 (t, J=7.4 Hz, 2H), 5.49 (s, 1H), 4.19-3.95 (m, 4H), 3.77 (s, 2H), 3.26-3.04 (m, 3H), 2.76 (s, 1H), 2.33 (dd, J=13.0, 7.3 Hz, 1H), 2.20 (s, 2H), 2.14-1.95 (m, 3H), 1.95-1.82 (m, 3H), 1.75 (m, 2H), 1.68-1.53 (m, 1H), 1.35 (s, 6H).

Example 3L: (R)-4-(2-(1-(2-(1,2,4-thiadiazol-5-yl)-2-azaspiro[3.4]octan-6-yl)piperidin-4-yl)phenoxy)-2-methylbutan-2-ol

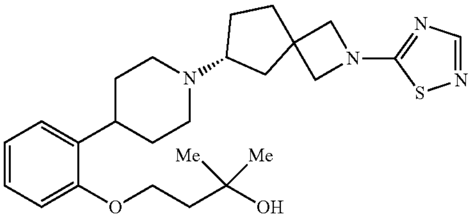 [SMILES: CC(C)(O)CCOc1ccccc1C1CCN([C@@H]2CCC3(C2)CN(c2ncns2)C3)CC1]

(R)-4-(2-(1-(2-azaspiro[3.4]octan-6-yl)piperidin-4-yl)phenoxy)-2-methylbutan-2-ol (Intermediate 4R, 80 mg, 0.21 mmol) was dissolved in IPA (3 mL) and 5-bromo-1,2,4-thiadiazole (53 mg, 0.32 mmol) was added as a solution in IPA (0.5 mL). The reaction was stirred at RT for 16 h, and then concentrated and purified by FCC (0-10% MeOH(10% $NH_4OH$)/DCM) to afford the title compound (45 mg, 0.094 mmol).

LCMS: Rt: 2.37 min (LCMS Method 4) MS m/z 457.5 $[M+H]^+$.

$^1H$ NMR (400 MHz, $CD_3OD$) δ 7.92 (s, 1H), 7.15 (m, 2H), 6.96-6.84 (m, 2H), 5.49 (s, 1H), 4.17-4.09 (m, 3H), 4.03 (m, 3H), 3.15 (d, J=11.9 Hz, 2H), 3.01 (m, 1H), 2.73 (d, J=9.0 Hz, 1H), 2.32 (dd, J=12.9, 7.3 Hz, 1H), 2.22-2.09 (m, 2H), 2.09-1.96 (m, 5H), 1.90-1.55 (m, 6H), 1.29 (s, 6H).

Example 3M: (R)-5-(6-(4-(2-methoxyphenyl)piperidin-1-yl)-2-azaspiro[3.4]octan-2-yl)-3-methyl-1,2,4-thiadiazole

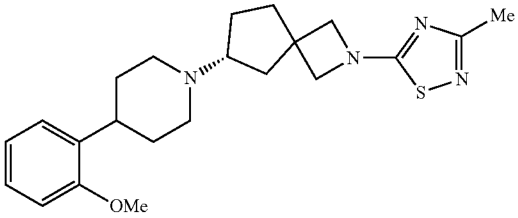 [SMILES: COc1ccccc1C1CCN([C@@H]2CCC3(C2)CN(c2nc(C)ns2)C3)CC1]

Step 1: (R)-3-bromo-5-(6-(4-(2-methoxyphenyl)piperidin-1-yl)-2-azaspiro[3.4]octan-2-yl)-1,2,4-thiadiazole (R)-6-(4-(2-methoxyphenyl)piperidin-1-yl)-2-azaspiro[3.4]octane (Intermediate 4Q, 71 mg, 0.236 mmol) was added to a vial followed by a solution of 3-bromo-5-chloro-1,2,4-thiadiazole (71 mg, 0.354 mmol) in dioxane (2.4 mL). A white solid formed and the reaction was sonicated to break up clumps of solid on the bottom of the vial and this was placed under nitrogen and stirred for 16 hours. The reaction was left in solution for 7 days and then it was concentrated and purified by FCC (0-15% MeOH (10% $NH_4OH$)/DCM) to yield the product as a colorless oil.

LCMS: Rt: 2.89 mins (LCMS Method 4) MS m/z 463.3 $[M+H]^+$.

Step 2: (R)-5-(6-(4-(2-methoxyphenyl)piperidin-1-yl)-2-azaspiro[3.4]octan-2-yl)-3-methyl-1,2,4-thiadiazole (R)-3-bromo-5-(6-(4-(2-methoxyphenyl)piperidin-1-yl)-2-azaspiro[3.4]octan-2-yl)-1,2,4-thiadiazole (35 mg, 0.076 mmol) was dissolved in THE (0.5 mL) and under nitrogen was added XPhos Pd G2 (15 mg, 0.019 mmol) and dimethylzinc (2.0 M in toluene, 0.076 mL, 0.151 mmol) was added dropwise via syringe. The reaction was stirred for 16 hours at RT and then it was quenched with water (1 mL) and extracted with EtOAc (2×25 mL) and 3:1 DCM:iPrOH (2×25 mL). The combined organic layers were dried over magnesium sulfate, filtered and concentrated. The residue was purified by preparative HPLC (XBridge 30×50 mm, 35-60% $MeCN/H_2O$ (5 mM $NH_4OH$) to yield the title compound as an off white solid.

LCMS: Rt: 2.53 mins (LCMS Method 4) MS m/z 399.4 $[M+H]^+$.

$^1H$ NMR (400 MHz, $CD_3OD$) δ 7.22-7.11 (m, 2H), 6.96-6.86 (m, 2H), 4.15-3.94 (m, 4H), 3.81 (s, 3H), 3.28-3.17 (m, 2H), 3.11-2.85 (m, 2H), 2.45-2.25 (m, 6H), 2.16-1.73 (m, 8H), 1.73-1.57 (m, 1H).

Example 3N: (R)-1-(5-fluoro-2-(1-(2-(4-methyloxazol-2-yl)-2-azaspiro[3.4]octan-6-yl)piperidin-4-yl)phenoxy)-2-methylpropan-2-ol

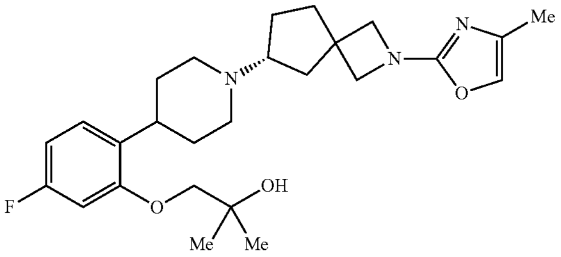 [SMILES: Cc1coc(N2CC3(CC[C@@H](N4CCC(c5ccc(F)cc5OCC(C)(C)O)CC4)C3)C2)n1]

Into a vial was added (R)-1-(2-(1-(2-azaspiro[3.4]octan-6-yl)piperidin-4-yl)-5-fluorophenoxy)-2-methylpropan-2-ol (Intermediate 4T, 100 mg, 0.266 mmol) followed by a solution of 2-bromo-4-methyloxazole (51.6 mg, 0.319 mmol) in dioxane (3 mL) and this was placed under nitrogen. $Pd_2(dba)_3$ (15.27 mg, 0.027 mmol), xantphos (18.44 mg, 0.032 mmol) and NaOtBu (51.0 mg, 0.531 mmol) were added and the reaction was stirred at 75° C. for 2.5 hr. The reaction was cooled to room temperature, filtered, and rinsed through with MeCN and EtOAc. The filtrate was concentrated and the residue was purified by FCC (0-10% MeOH (1% $NH_4OH$)/DCM) to yield the title compound (24 mg, 0.047 mmol) as a light yellow glassy solid.

LCMS: Rt: 2.54 min (LCMS Method 3) MS m/z 458.3 $[M+H]^+$.

$^1H$ NMR (400 MHz, $CD_3OD$) δ 7.29-6.99 (m, 2H), 6.81-6.48 (m, 2H), 4.09-3.83 (m, 4H), 3.76 (s, 2H), 3.22-3.09 (m, 2H), 3.02 (m, 1H), 2.81-2.60 (m, 1H), 2.33-2.08 (m, 3H), 2.07-1.65 (m, 11H), 1.65-1.52 (m, 1H), 1.34 (s, 6H).

Example 3O: (R)-2-methyl-1-(2-(1-(2-(4-methyloxazol-2-yl)-2-azaspiro[3.4]octan-6-yl)piperidin-4-yl)phenoxy)propan-2-ol

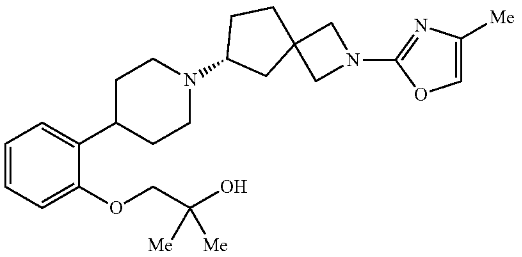 [SMILES: Cc1coc(N2CC3(CC[C@@H](N4CCC(c5ccccc5OCC(C)(C)O)CC4)C3)C2)n1]

Into a vial was added (R)-1-(2-(1-(2-azaspiro[3.4]octan-6-yl)piperidin-4-yl)phenoxy)-2-methylpropan-2-ol (Intermediate 4C, 90 mg, 0.251 mmol) followed by a solution of 2-bromo-4-methyloxazole (48.8 mg, 0.301 mmol) in dioxane (3 mL) and this was placed under nitrogen. $Pd_2(dba)_3$ (14.43 mg, 0.025 mmol), xantphos (17.43 mg, 0.030 mmol) and NaOtBu (48.3 mg, 0.502 mmol) were added and this was stirred at 75° C. for 16 hours. The reaction was then cooled to room temperature, filtered, and rinsed through with MeCN and EtOAc. The filtrate was concentrated and the residue was purified by FCC (0-10% MeOH(1% $NH_4OH$)/DCM) to yield the title compound (15 mg, 0.031 mmol).

LCMS: Rt: 2.40 min (LCMS Method 3) MS m/z 440.5 $[M+H]^+$.

$^1H$ NMR (400 MHz, $CD_3OD$) δ 7.28-7.01 (m, 3H), 6.90 (t, J=7.3 Hz, 2H), 4.08-3.83 (m, 4H), 3.77 (s, 2H), 3.23-3.09 (m, 3H), 2.74 (s, 1H), 2.42-2.08 (m, 3H), 2.07-1.69 (m, 11H), 1.66-1.47 (m, 1H), 1.35 (s, 6H).

Example 4A: (R)-3-(6-(4-(2-methoxyphenyl)piperidin-1-yl)-2-azaspiro[3.4]octan-2-yl)-1,2,4-oxadiazole

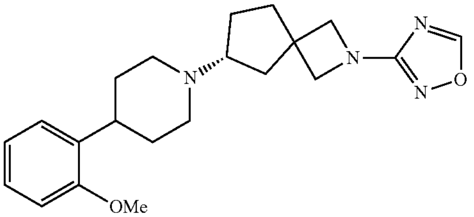 [SMILES: COc1ccccc1C1CCN([C@@H]2CCC3(C2)CN(c2ncon2)C3)CC1]

Step 1: 3-bromo-5-(trichloromethyl)-1,2,4-oxadiazole

Sodium bicarbonate (2.65 g, 31.6 mmol) and 2,2,2-trichloroacetonitrile (1.98 mL, 19.7 mmol) were suspended in toluene (3.3 mL), and incubated at 80° C. under nitrogen. Next, a solution of dibromoformaldoxime (2.0 g, 9.9 mmol) in toluene (3.3 mL) was added dropwise over 25 minutes, and the reaction was incubated at 80° C. for 16 h, then cooled and diluted with water (25 mL), and extracted with EtOAc (2×50 mL). The combined organic layers were dried with $MgSO_4$, filtered and concentrated. The residue was then purified by FCC (0-40% EtOAc/heptanes) to afford the title intermediate (1.38 g, 5.18 mmol) as a pale yellow oil. $^{13}C$ NMR (101 MHz, MeOD) δ 176.66, 151.34, 83.60.

Step 2: (R)-3-(6-(4-(2-methoxyphenyl)piperidin-1-yl)-2-azaspiro[3.4]octan-2-yl)-5-(trichloromethyl)-1,2,4-oxadiazole (R)-6-(4-(2-methoxyphenyl)piperidin-1-yl)-2-azaspiro[3.4]octane (Intermediate 4Q, 0.16 g, 0.53 mmol), 3-bromo-5-(trichloromethyl)-1,2,4-oxadiazole (0.15 g, 0.16 mmol) and potassium phosphate (0.17 g, 0.80 mmol) were suspended in a mixture of 2% (wt) aqueous TPGS-750-M (2.4 mL) and THE (0.27 mL). The reaction was stirred for 20 minutes and then diluted with water (25 mL) and brine (25 mL) and extracted with EtOAc (3×50 mL). The combined organic layers were washed with brine (1×10 mL), dried with $MgSO_4$, filtered and concentrated. The residue was purified by FCC (0-10% MeOH(10% $NH_4OH$)/DCM) to afford the title intermediate (68 mg, 0.14 mmol).

LCMS: Rt: 0.91 min (LCMS Method 1) MS m/z 485.2 $[M+H]^+$.

Step 3: (R)-3-(6-(4-(2-methoxyphenyl)piperidin-1-yl)-2-azaspiro[3.4]octan-2-yl)-1,2,4-oxadiazole (R)-3-(6-(4-(2-methoxyphenyl)piperidin-1-yl)-2-azaspiro[3.4]octan-2-yl)-5-(trichloromethyl)-1,2,4-oxadiazole (68 mg, 0.14 mmol) was dissolved in a mixture of THE (0.7 mL) and MeOH (0.7 mL) under nitrogen, and sodium borohydride (0.016 g, 0.420 mmol) was added. The reaction was stirred for 16 hr at RT, then diluted with water (10 mL) and brine (10 mL) and extracted with EtOAc (3×25 mL). The combined organic layers were washed with water (1×10 mL), dried with $MgSO_4$, filtered and concentrated. The residue was purified by FCC (0-10% MeOH (10% $NH_4OH$)/DCM) and further by preparative HPLC (XBridge 30×50 mm 10-30% $MeCN/H_2O$ (0.1% formic acid)). The residue was concentrated, diluted with a 1N solution of NaOH until pH ~13, and then extracted with ethyl acetate (3×25 mL). The combined organic extracts were washed with a 0.1 N solution of NaOH (3×10 mL), dried with $MgSO_4$, filtered and concentrated. The residue was purified twice by preparative HPLC (XBridge Peptide BEH C18 5 μm 19×150 mm 50-65% $MeCN/H_2O$ (10 mM $NH_4OH$)) to afford the title compound (8.0 mg, 0.020 mmol).

LCMS: Rt: 2.46 min (LCMS Method 4) MS m/z 369.4 $[M+H]^+$.

$^1H$ NMR (400 MHz, $CD_3OD$) δ 8.77 (s, 1H), 7.22-7.10 (m, 2H), 6.97-6.81 (m, 2H), 4.03-3.85 (m, 4H), 3.81 (s, 3H), 3.22-3.08 (m, 2H), 3.05-2.90 (m, 1H), 2.79-2.63 (m, 1H), 2.28 (dd, J=12.8, 7.3 Hz, 1H), 2.22-2.10 (m, 2H), 2.10-1.87 (m, 3H), 1.86-1.68 (m, 5H), 1.67-1.49 (m, 1H).

Example 5A: (R)-6-(4-(2-methoxyphenyl)piperidin-1-yl)-2-(pyrimidin-5-yl)-2-azaspiro[3.4]octane formate salt

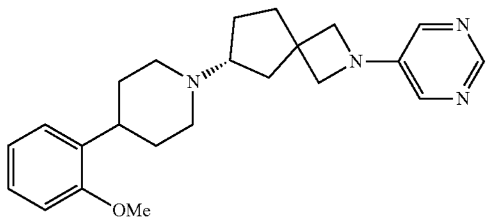 [SMILES: COc1ccccc1C1CCN([C@@H]2CCC3(C2)CN(c2cncnc2)C3)CC1]

Into a vial was added (R)-6-(4-(2-methoxyphenyl)piperidin-1-yl)-2-azaspiro[3.4]octane (Intermediate 4Q, 22.00 mg, 0.073 mmol) followed by a solution of 5-bromopyrimidine (17.46 mg, 0.110 mmol) in toluene (1.0 mL) and this was placed under nitrogen. $Pd_2(dba)_3$ (6.71 mg, 7.32 μmol), rac-BINAP (4.56 mg, 7.32 μmol) and NaOtBu (10.56 mg, 0.110 mmol) were added and this was stirred at 110° C. for 4 hours. The reaction mixture was then cooled to RT, filtered and the filtrate was concentrated. The residue was then purified by FCC (0-10% MeOH (1% $NH_4OH$)/DCM) and further by preparative HPLC (XBridge 30×50 mm 10-30% $MeCN/H_2O$ (0.1% formic acid)) to yield the title compound (15 mg, 0.038 mmol) as a formate salt.

LCMS: Rt: 0.59 min (LCMS Method 1) MS m/z 380.5 $[M+H]^+$.

$^1H$ NMR (400 MHz, $CDCl_3$) δ 8.62 (s, 1H), 8.49 (s, 1H), 7.92 (s, 2H), 7.19 (m, 2H), 6.92 (td, J=7.5, 1.1 Hz, 1H), 6.86-6.81 (m, 1H), 3.97 (d, J=7.3 Hz, 1H), 3.88 (d, J=7.3 Hz, 1H), 3.80 (s, 3H), 3.79 (s, 2H), 3.55 (t, J=11.9 Hz, 2H), 3.20-3.02 (m, 2H), 2.66-2.48 (m, 2H), 2.41 (dd, J=13.4, 9.0 Hz, 1H), 2.32 (dd, J=13.3, 8.1 Hz, 1H), 2.25-2.10 (m, 4H), 2.07 (m, 1H), 1.99-1.85 (m, 3H).

Example 5B: (R)-2-methyl-1-(2-(1-(2-(pyrimidin-5-yl)-2-azaspiro[3.4]octan-6-yl)piperidin-4-yl)phenoxy)propan-2-ol formate salt

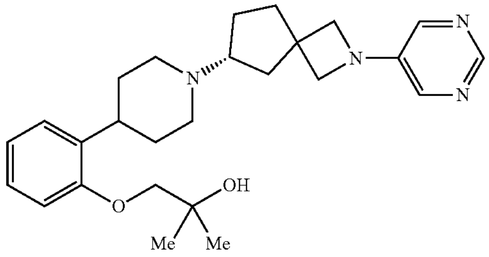 [SMILES: CC(C)(O)COc1ccccc1C1CCN([C@@H]2CCC3(C2)CN(c2cncnc2)C3)CC1]

Into a vial was added (R)-1-(2-(1-(2-azaspiro[3.4]octan-6-yl)piperidin-4-yl)phenoxy)-2-methylpropan-2-ol (Intermediate 4C, 60 mg, 0.167 mmol) and 5-bromopyrimidine (39.9 mg, 0.251 mmol) followed by a solution of cesium carbonate (136 mg, 0.418 mmol) in dioxane (2.0 mL) and this was placed under nitrogen. xantphos (19.37 mg, 0.033 mmol), $Pd_2(dba)_3$ (9.62 mg, 0.017 mmol) and cesium carbonate (136 mg, 0.418 mmol) were added and this was stirred at 110° C. for 4 hours. The reaction mixture was then cooled to RT and filtered and the filtrate was concentrated. The residue was then purified by FCC (0-10% MeOH (1% $NH_4OH$)/DCM) and further by preparative HPLC (XBridge 30×50 mm 10-30% $MeCN/H_2O$ (0.1% formic acid)) to yield the title compound (41 mg, 0.09 mmol) as a formate salt.

LCMS: Rt: 0.66 min (LCMS Method 1) MS m/z 437.2 $[M+H]^+$.

$^1H$ NMR (400 MHz, $CDCl_3$) δ 8.63 (s, 1H), 8.53 (s, 1H), 7.93 (s, 2H), 7.19 (ddd, J=9.8, 7.6, 2.1 Hz, 2H), 6.93 (t, J=7.5 Hz, 1H), 6.86 (d, J=8.2 Hz, 1H), 3.97 (d, J=7.3 Hz, 1H), 3.89 (d, J=7.3 Hz, 1H), 3.80 (s, 4H), 3.53 (t, J=11.3 Hz, 2H), 3.16 (p, J=8.5 Hz, 1H), 2.98-2.92 (m, 1H), 2.60-2.45 (m, 2H), 2.45-2.26 (m, J=9.6, 8.1 Hz, 4H), 2.20-2.05 (m, 3H), 1.96-1.91 (m, 3H), 1.36 (s, 6H).

Example 5C: (R)-2-methyl-1-(2-(1-(2-(4-methylpyrimidin-5-yl)-2-azaspiro[3.4]octan-6-yl)piperidin-4-yl)phenoxy)propan-2-ol formate salt

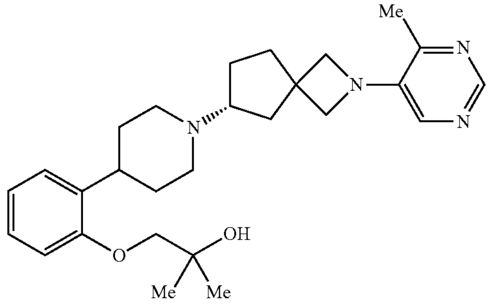 [SMILES: Cc1ncncc1N1CC2(CC[C@@H](N3CCC(c4ccccc4OCC(C)(C)O)CC3)C2)C1]

Into a vial was added (R)-1-(2-(1-(2-azaspiro[3.4]octan-6-yl)piperidin-4-yl)phenoxy)-2-methylpropan-2-ol (Intermediate 4C, 60 mg, 0.167 mmol) and 5-bromo-4-methylpyrimidine (43.4 mg, 0.251 mmol) followed by a solution of cesium carbonate (136 mg, 0.418 mmol) in dioxane (2.0 mL) and this was placed under nitrogen. xantphos (19.37 mg, 0.033 mmol), $Pd_2(dba)_3$ (9.62 mg, 0.017 mmol) and cesium carbonate (136 mg, 0.418 mmol) were added and this was stirred at 110° C. for 4 hours. The reaction was cooled to RT and filtered and the filtrate was concentrated. The residue was then purified by HPLC (XBridge C18 OBD 30×50 mm 15-40% MeCN/$H_2O$ (0.1% formic Acid) 75 mL/min) to yield the title compound (46 mg, 0.099 mmol) as a brown oil and a formate salt.

LCMS: Rt: 0.64 min (LCMS Method 1) MS m/z 451.7 $[M+H]^+$.

$^1H$ NMR (400 MHz, $CDCl_3$) δ 8.57 (s, 1H), 8.36 (s, 1H) 7.78 (s, 1H), 7.22-7.15 (m, 2H), 6.92 (t, J=7.5 Hz, 1H), 6.85 (d, J=8.1 Hz, 1H), 4.03 (d, J=7.3 Hz, 1H), 3.92 (d, J=7.2 Hz, 1H), 3.79 (s, 4H), 3.64 (q, J=9.3, 8.8 Hz, 2H), 3.26 (t, J=8.5 Hz, 1H), 2.98 (t, J=11.9 Hz, 1H), 2.55 (m, 5H), 2.37 (s, 3H), 2.36-2.04 (m, 4H), 2.01-1.85 (m, 3H), 1.35 (s, 6H).

Example 5D: (R)-6-(4-(2-methoxyphenyl)piperidin-1-yl)-2-(6-methylpyridin-3-yl)-2-azaspiro[3.4]octane formate salt

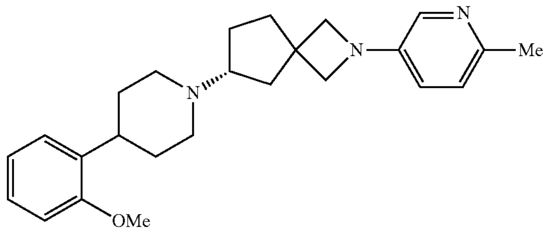 [SMILES: COc1ccccc1C1CCN([C@@H]2CCC3(C2)CN(c2ccc(C)nc2)C3)CC1]

Into a vial was added (R)-6-(4-(2-methoxyphenyl)piperidin-1-yl)-2-azaspiro[3.4]octane (Intermediate 4Q, 45 mg, 0.150 mmol) followed by a solution of 5-bromo-2-methylpyridine (38.6 mg, 0.225 mmol) in toluene (1.5 mL) and this was placed under nitrogen. $Pd_2(dba)_3$ (13.72 mg, 0.015 mmol), rac-BINAP (9.33 mg, 0.015 mmol) and NaOtBu (21.59 mg, 0.225 mmol) were added and this was stirred at 110° C. for 4 hours. The reaction was cooled to RT, filtered and the filtrate was concentrated. The residue was then purified by FCC (0-10% MeOH (1% $NH_4OH$)/DCM) and further by preparative HPLC (XBridge C18 OBD 30×50 mm 5-20% MeCN/$H_2O$ (0.1% formic Acid) 75 mL/min) to yield the title compound (17 mg, 0.041 mmol).

LCMS: Rt: 0.42 min (LCMS Method 1) MS m/z 392.4 $[M+H]^+$.

$^1H$ NMR (400 MHz, $CDCl_3$) δ 8.46 (s, 1H), 7.76 (d, J=2.9 Hz, 1H), 7.21 (t, J=7.5 Hz, 2H), 7.01 (d, J=8.3 Hz, 1H), 6.94 (t, J=7.4 Hz, 1H), 6.85 (d, J=8.2 Hz, 1H), 6.74 (dd, J=8.3, 2.9 Hz, 1H), 3.91 (d, J=7.3 Hz, 1H), 3.82 (d, J=3.7 Hz, 4H), 3.70 (d, J=27.2 Hz, 4H), 3.47 (s, 1H), 3.30-3.23 (m, 1H), 3.13 (tt, J=12.2, 3.6 Hz, 1H), 2.70 (t, J=12.5 Hz, 2H), 2.46 (s, 4H), 2.40-2.03 (m, 6H), 2.03-1.85 (m, 3H).

Example 5E: (R)-6-(4-(2-methoxyphenyl)piperidin-1-yl)-2-(2-methylpyrimidin-5-yl)-2-azaspiro[3.4]octane

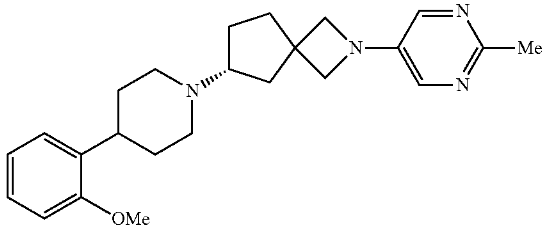 [SMILES: COc1ccccc1C1CCN([C@@H]2CCC3(C2)CN(c2cnc(C)nc2)C3)CC1]

Into a vial was added (R)-6-(4-(2-methoxyphenyl)piperidin-1-yl)-2-azaspiro[3.4]octane (Intermediate 4Q, 25 mg, 0.083 mmol) followed by a solution of 5-bromo-2-methylpyrimidine (21.59 mg, 0.125 mmol) in toluene (1.0 mL) and this was placed under nitrogen. $Pd_2(dba)_3$ (7.62 mg, 8.32 µmol), rac-BINAP (5.18 mg, 8.32 µmol) and NaOtBu (12.00 mg, 0.125 mmol) were added and this was stirred at 110° C. for 4 hours. The reaction was then cooled to RT and filtered and the filtrate was concentrated. The residue was then purified by FCC (0-10% MeOH (1% $NH_4OH$)/DCM) to yield the title compound (20 mg, 0.048 mmol).

LCMS: Rt: 0.66 min (LCMS Method 1) MS m/z 393.4 $[M+H]^+$.

$^1H$ NMR (400 MHz, $CDCl_3$) δ 7.85 (s, 2H), 7.22-7.15 (m, 2H), 6.95-6.80 (m, 2H), 3.93 (d, J=7.1 Hz, 1H), 3.82 (d, J=16.8 Hz, 4H), 3.75 (s, 2H), 3.57 (t, J=12.3 Hz, 2H), 3.21-3.01 (m, 2H), 2.59 (s, 5H), 2.44-2.01 (m, 7H), 1.92 (dd, J=13.6, 9.9 Hz, 3H).

Example 5F: (R)-2-(5-fluoropyridin-3-yl)-6-(4-(2-methoxyphenyl)piperidin-1-yl)-2-azaspiro[3.4]octane

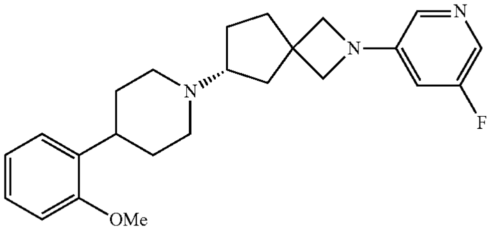 [SMILES: COc1ccccc1C1CCN([C@@H]2CCC3(C2)CN(c2cncc(F)c2)C3)CC1]

Into a vial was added (R)-6-(4-(2-methoxyphenyl)piperidin-1-yl)-2-azaspiro[3.4]octane (Intermediate 4Q, 150 mg, 0.499 mmol) followed by a solution of 3-bromo-5-fluoropyridine (132 mg, 0.749 mmol) in dioxane (2.0 mL) and this was placed under nitrogen. $Pd_2(dba)_3$ (29 mg, 0.05 mmol), xantphos (58 mg, 0.10 mmol) and cesium carbonate (407 mg, 1.248 mmol) were added and this was stirred at 110° C. for 2 hours. The reaction was then cooled to RT and the reaction was filtered and the filtrate was concentrated. The residue was then purified by FCC (0-10% MeOH (1% $NH_4OH$)/DCM) and further by preparative HPLC (XBridge C18 OBD 30×50 mm 5 μm column MeCN/$H_2O$w/5 mM $NH_4OH$ 75 mL/min) to yield the title compound (54 mg, 0.135 mmol).

LCMS: Rt: 1.22 min (LCMS Method 2) MS m/z 396.6 $[M+H]^+$.

$^1H$ NMR (400 MHz, $CDCl_3$) δ 7.81 (d, J=2.4 Hz, 1H), 7.62 (t, J=1.8 Hz, 1H), 7.22-7.12 (m, 2H), 6.91 (t, J=7.4 Hz, 1H), 6.83 (d, J=8.3 Hz, 1H), 6.37 (m, 1H), 3.85 (d, J=7.2 Hz, 1H), 3.81 (d, J=2.5 Hz, 4H), 3.74 (s, 2H), 3.17 (t, J=12.8 Hz, 2H), 2.97 (m, 1H), 2.69 (m, 1H), 2.24 (dd, J=12.9, 7.2 Hz, 1H), 2.18-1.87 (m, 6H), 1.84 (m, 4H), 1.75-1.65 (m, 1H).

Example 5G: (R)-6-(4-(2-methoxyphenyl)piperidin-1-yl)-2-(6-methylpyrazin-2-yl)-2-azaspiro[3.4]octane

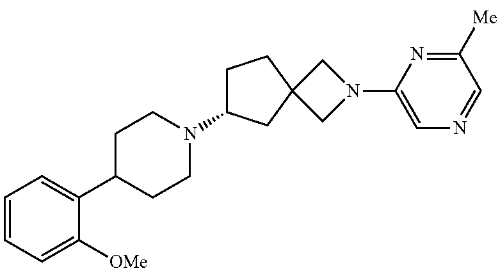 [SMILES: COc1ccccc1C1CCN([C@@H]2CCC3(C2)CN(c2cncc(C)n2)C3)CC1]

(R)-6-(4-(2-methoxyphenyl)piperidin-1-yl)-2-azaspiro[3.4]octane (Intermediate 4Q, 75 mg, 0.250 mmol) was dissolved in IPA (2 mL) and cooled to 0° C. under nitrogen. Triethylamine (0.08 mL, 0.549 mmol) was added, followed by a solution of 2-chloro-6-methylpyrazine (35.3 mg, 0.275 mmol) in IPA (0.5 mL) and the reaction was stirred at 0° C. for 10 minutes. The reaction was then warmed to 50° C. and stirred for 18 hours. The reaction was then cooled to room temperature and concentrated. The residue was purified via FCC (0-10% MeOH (1% $NH_4OH$)/DCM) to afford the title compound (10 mg, 0.025 mmol).

LCMS: RT: 2.63 min (LCMS Method 4) MS m/z 393.4 $[M+H]^+$.

$^1H$ NMR (400 MHz, $CD_3OD$) δ 7.66 (s, 1H), 7.57 (s, 1H), 7.16 (td, J=7.5, 1.5 Hz, 2H), 6.97-6.83 (m, 2H), 4.08-3.88 (m, 5H), 3.81 (s, 3H), 3.26 (s, 1H), 3.21 (s, 1H), 3.01 (s, 1H), 2.35 (s, 3H), 2.33-2.13 (m, 3H), 2.11-1.90 (m, 3H), 1.80 (m, 5H), 1.64 (s, 1H).

Example 5H: (R)-6-(4-(2-methoxyphenyl)piperidin-1-yl)-2-(pyrazin-2-yl)-2-azaspiro[3.4]octane

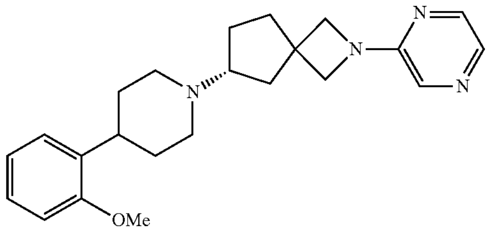 [SMILES: COc1ccccc1C1CCN([C@@H]2CCC3(C2)CN(c2cnccn2)C3)CC1]

(R)-6-(4-(2-methoxyphenyl)piperidin-1-yl)-2-azaspiro[3.4]octane (Intermediate 4Q, 70 mg, 0.233 mmol) was dissolved in DMF (2 mL) and cooled to 0° C. under nitrogen. Triethylamine (0.08 mL, 0.513 mmol) was added, followed by a solution of 2-chloropyrazine (0.023 mL, 0.256 mmol) in DMF (0.5 mL) and the reaction was stirred at 0° C. for 10 minutes. The reaction was then warmed to 50° C. and stirred for 18 hours. The reaction was then cooled to room temperature and diluted with saturated aqueous sodium bicarbonate. The solution was extracted with DCM, and the combined organic layers were washed with brine, dried over magnesium sulfate, filtered, and concentrated. The residue was purified via FCC (0-10% MeOH (1% $NH_4OH$)/DCM) and further by preparative HPLC (XBridge 30×50 mm 35-60% MeCN/$H_2O$ (5 mM $NH_4OH$)) to afford the title compound (8.5 mg, 0.022 mmol).

LCMS: RT: 2.42 min (LCMS Method 4) MS m/z 379.4 $[M+H]^+$.

$^1H$ NMR (400 MHz, $CD_3OD$) δ 8.02 (dd, J=2.9, 1.5 Hz, 1H), 7.83 (d, J=1.5 Hz, 1H), 7.80 (d, J=2.9 Hz, 1H), 7.19 (t, J=7.7 Hz, 2H), 6.98-6.87 (m, 2H), 4.11-3.93 (m, 4H), 3.84 (s, 3H), 3.19 (m, 2H), 3.02 (s, 1H), 2.80 (s, 1H), 2.33 (dd, J=13.1, 7.5 Hz, 1H), 2.22 (s, 2H), 2.14-1.94 (m, 3H), 1.93-1.73 (m, 5H), 1.68 (d, J=11.3 Hz, 1H).

Example 5I: (R)-6-(4-(2-methoxyphenyl)piperidin-1-yl)-2-(3-(trifluoromethyl)pyrazin-2-yl)-2-azaspiro[3.4]octane

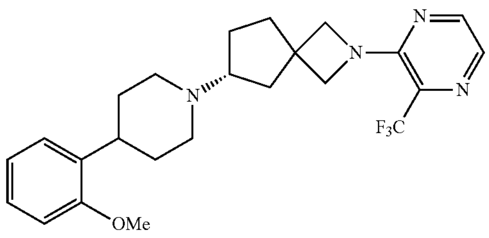 [SMILES: COc1ccccc1C1CCN([C@@H]2CCC3(C2)CN(c2nccnc2C(F)(F)F)C3)CC1]

To a vial containing (R)-6-(4-(2-methoxyphenyl)piperidin-1-yl)-2-azaspiro[3.4]octane (Intermediate 4Q, 65 mg, 0.216 mmol) under an atmosphere of nitrogen was added a solution of 2-bromo-3-(trifluoromethyl)pyrazine (58.9 mg, 0.260 mmol) in dioxane (2.1 mL). $Pd(dba)_2$ (12.44 mg, 0.022 mmol), xantphos (15.02 mg, 0.026 mmol) and NaOtBu (41.6 mg, 0.433 mmol) were added and the reaction mixture was stirred at 75° C. for 18 hours. The reaction was then cooled to room temperature and filtered, rinsing with MeCN and EtOAc. The filtrate was purified via FCC (0-10% MeOH (1% $NH_4OH$))/DCM) to afford the title compound (38 mg, 0.082 mmol).

LCMS: RT: 3.20 min (LCMS Method 4) MS m/z 447.8 $[M+H]^+$.

$^1$H NMR (400 MHz, $CD_3OD$) δ 8.28 (d, J=2.5 Hz, 1H), 7.86 (d, J=2.4 Hz, 1H), 7.19-7.12 (m, 2H), 6.96-6.83 (m, 2H), 4.20-4.00 (m, 4H), 3.81 (s, 3H), 3.23-3.11 (m, 2H), 2.99 (m, 1H), 2.74 (m, 1H), 2.27 (dd, J=12.8, 7.3 Hz, 1H), 2.15 (m, 2H), 2.09-1.99 (m, 2H), 1.99-1.88 (m, 1H), 1.79 (m, 5H), 1.70-1.56 (m, 1H).

Example 5J: (R)-6-(4-(2-methoxyphenyl)piperidin-1-yl)-2-(3-methylpyrazin-2-yl)-2-azaspiro[3.4]octane

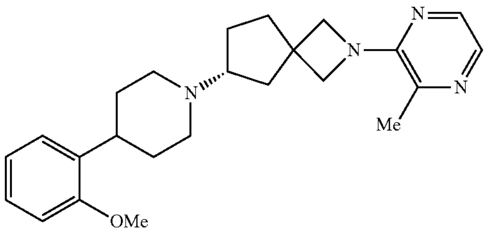 [SMILES: COc1ccccc1C1CCN([C@@H]2CCC3(C2)CN(c2nccnc2C)C3)CC1]

(R)-6-(4-(2-methoxyphenyl)piperidin-1-yl)-2-azaspiro[3.4]octane (Intermediate 4Q, 65 mg, 0.216 mmol) was dissolved in THF (2 mL) and cooled to 0° C. under an atmosphere of nitrogen. Triethylamine (0.07 mL, 0.476 mmol) was added, followed by a solution of 2-chloro-3-methylpyrazine (30.6 mg, 0.238 mmol) in THF (0.5 mL). The reaction was stirred at 0° C. for 10 minutes and then warmed to 50° C. and stirred for 18 hours. The reaction mixture was then cooled to room temperature and diluted with saturated aqueous sodium bicarbonate. The solution was extracted with DCM, and the combined organic layers were washed with brine, dried over magnesium sulfate, filtered, and concentrated. The residue was purified via preparative HPLC (XBridge 30×50 mm 45-70% MeCN/$H_2O$ (5 mM $NH_4OH$)) to afford the title compound (3.5 mg, 0.0085 mmol).

LCMS: RT: 2.61 min (LCMS Method 4) MS m/z 393.6 $[M+H]^+$.

$^1$H NMR (400 MHz, $CD_3OD$) δ 7.93 (d, J=2.9 Hz, 1H), 7.72 (d, J=2.9 Hz, 1H), 7.25-7.09 (m, 2H), 7.00-6.85 (m, 2H), 4.26-3.96 (m, 4H), 3.83 (d, J=1.7 Hz, 3H), 3.18 (d, J=14.2 Hz, 2H), 3.10-2.93 (m, 1H), 2.76 (s, 1H), 2.45 (s, 3H), 2.30 (dd, J=12.7, 7.2 Hz, 1H), 2.19 (d, J=8.1 Hz, 3H), 2.10-1.93 (m, 2H), 1.87-1.76 (m, 5H), 1.71-1.54 (m, 1H).

Example 5K: (R)-6-(4-(2-methoxyphenyl)piperidin-1-yl)-2-(pyridin-3-yl)-2-azaspiro[3.4]octane

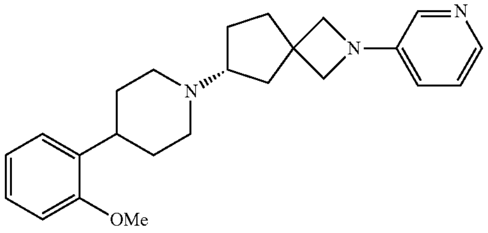 [SMILES: COc1ccccc1C1CCN([C@@H]2CCC3(C2)CN(c2cccnc2)C3)CC1]

(R)-6-(4-(2-methoxyphenyl)piperidin-1-yl)-2-azaspiro[3.4]octane (Intermediate 4Q, 45 mg, 0.150 mmol) and 3-bromopyridine (22 μL, 0.225 mmol) were dissolved in toluene (1.5 mL) under an atmosphere of nitrogen. $Pd_2(dba)_3$ (13.72 mg, 0.015 mmol), rac-BINAP (9.33 mg, 0.015 mmol), and NaOtBu (21.59 mg, 0.225 mmol) were added and the reaction mixture was stirred at 110° C. for 3 hours. The reaction was then cooled to room temperature and filtered to remove solids, rinsing with EtOAc. The filtrate was concentrated and the residue was purified via FCC (0-10% MeOH (1% $NH_4OH$)/DCM) to afford the title compound (30 mg, 0.074 mmol).

LCMS: RT: 2.65 min (LCMS Method 4) MS m/z 378.5 $[M+H]^+$.

$^1$H NMR (400 MHz, $CD_3OD$) δ 7.86 (dd, J=4.8, 1.4 Hz, 1H), 7.75 (d, J=2.9 Hz, 1H), 7.24-7.12 (m, 3H), 6.93-6.86 (m, 3H), 3.88-3.74 (m, 7H), 3.24-3.12 (m, 2H), 2.99 (m, 1H), 2.74 (p, J=8.4 Hz, 1H), 2.28 (dd, J=12.8, 7.3 Hz, 1H), 2.17 (m, 2H), 2.11-1.90 (m, 3H), 1.85-1.73 (m, 5H), 1.68-1.56 (m, 1H).

Example 5L: (R)-2-(6-methylpyridin-3-yl)-6-(4-(2-(((R)-tetrahydrofuran-3-yl)oxy)phenyl)piperidin-1-yl)-2-azaspiro[3.4]octane

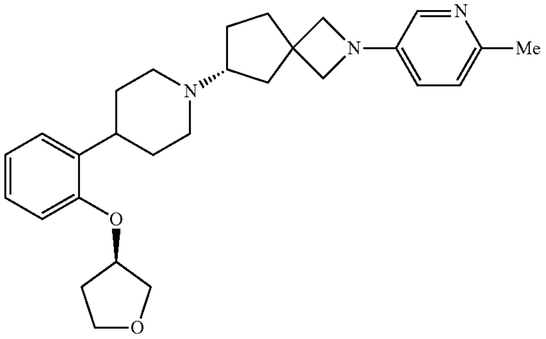 [SMILES: Cc1ccc(N2CC3(CC[C@@H](N4CCC(c5ccccc5O[C@@H]5CCOC5)CC4)C3)C2)cn1]

(R)-6-(4-(2-(((R)-tetrahydrofuran-3-yl)oxy)phenyl)piperidin-1-yl)-2-azaspiro[3.4]octane (Intermediate 4D, 120 mg, 0.337 mmol) and 5-bromo-2-methylpyridine (87 mg, 0.505 mmol) were dissolved in dioxane (3.4 mL) under an atmosphere of nitrogen. $Cs_2CO_3$ (274 mg, 0.841 mmol), xantphos (39.0 mg, 0.067 mmol), and $Pd(dba)_2$ (19.35 mg, 0.034 mmol) were added and the reaction mixture was stirred at 80° C. for 72 hours. The reaction mixture was cooled to room temperature and filtered to remove solids, rinsing with EtOAc. The filtrate was concentrated and the residue was then purified via FCC (0-10% MeOH(1% $NH_4OH$))/DCM) to afford the title compound (34 mg, 0.072 mmol).

LCMS: RT: 2.64 min (LCMS Method 4) MS m/z 448.5 $[M+H]^+$.

$^1$H NMR (400 MHz, $CD_3OD$) δ 7.63 (d, J=2.9 Hz, 1H), 7.24-7.04 (m, 3H), 6.97-6.82 (m, 3H), 5.05 (m, 1H), 4.01-3.86 (m, 4H), 3.84-3.77 (m, 2H), 3.77-3.68 (m, 2H), 3.17 (q, J=10.2 Hz, 2H), 2.98 (m, 1H), 2.73 (q, J=8.4 Hz, 1H), 2.39 (s, 3H), 2.31-2.09 (m, 5H), 2.09-1.88 (m, 3H), 1.78 (m, 5H), 1.61 (m, 1H).

Example 5M: (R)-6-(4-(2-methoxyphenyl)piperidin-1-yl)-2-(4-methyl-1,3,5-triazin-2-yl)-2-azaspiro[3.4]octane

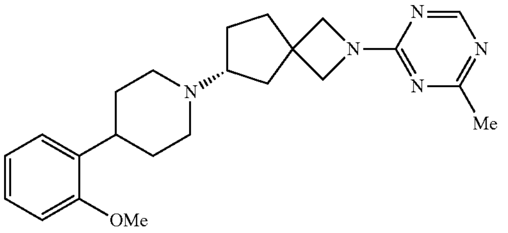 [SMILES: COc1ccccc1C1CCN([C@@H]2CCC3(C2)CN(c2ncnc(C)n2)C3)CC1]

Step 1: (R)-2-(4-chloro-6-methyl-1,3,5-triazin-2-yl)-6-(4-(2-methoxyphenyl)piperidin-1-yl)-2-azaspiro[3.4]octane To a solution of (R)-6-(4-(2-methoxyphenyl)piperidin-1-yl)-2-azaspiro[3.4]octane (Intermediate 4Q, 100 mg, 0.333 mmol) in THF (3 mL) under nitrogen at −78° C. was added triethylamine (0.10 mL, 0.732 mmol) followed by a solution of 2,4-dichloro-6-methyl-1,3,5-triazine (60.0 mg, 0.366 mmol) in THE (0.5 mL). The reaction mixture was stirred at −78° C. for 10 min, then warmed to room temperature over 10 min. The mixture was diluted with saturated aqueous sodium bicarbonate and extracted with DCM. The combined organic extracts were washed with brine, dried over magnesium sulfate, filtered, and concentrated to afford the title compound (142 mg, 0.333 mmol) as a pale yellow solid that was taken into the next step without further purification.

LCMS: RT: 1.16 min (LCMS Method 2) MS m/z 428.2 $[M+H]^+$.

Step 2: (R)-6-(4-(2-methoxyphenyl)piperidin-1-yl)-2-(4-methyl-1,3,5-triazin-2-yl)-2-azaspiro[3.4]octane (R)-2-(4-chloro-6-methyl-1,3,5-triazin-2-yl)-6-(4-(2-methoxyphenyl)piperidin-1-yl)-2-azaspiro[3.4]octane (140 mg, 0.327 mmol) was dissolved in MeOH (15 mL) and subjected to the H-Cube™ with a 10% Pd/C catalyst cartridge for 1 hour at 35° C. and 13 psi $H_2$. The resulting solution was concentrated and purified via FCC (0-10% MeOH (1% $NH_4OH$))/DCM) to afford the title compound (22 mg, 0.055 mmol).

LCMS: RT: 2.28 min (LCMS Method 4) MS m/z 394.8 $[M+H]^+$.

$^1H$ NMR (400 MHz, $CD_3OD$) δ 8.37 (s, 1H), 7.17 (t, J=7.6 Hz, 2H), 6.91 (td, J=7.8, 6.5 Hz, 2H), 4.14 (d, J=9.6 Hz, 1H), 4.11-3.96 (m, 3H), 3.83 (s, 3H), 3.17 (d, J=10.2 Hz, 2H), 3.00 (m, 1H), 2.76 (d, J=9.4 Hz, 1H), 2.38 (s, 3H), 2.29 (dd, J=13.0, 7.3 Hz, 1H), 2.20 (d, J=17.2 Hz, 2H), 2.11-1.91 (m, 3H), 1.91-1.71 (m, 5H), 1.71-1.58 (m, 1H).

Example 5N: (R)-2-(6-chloropyridazin-3-yl)-6-(4-(2-methoxyphenyl)piperidin-1-yl)-2-azaspiro[3.4]octane

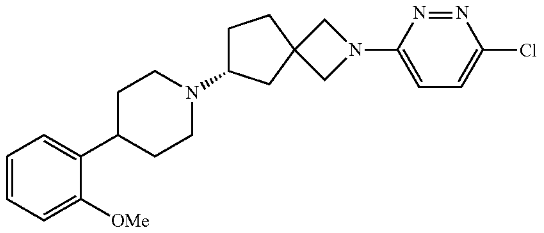 [SMILES: COc1ccccc1C1CCN([C@@H]2CCC3(C2)CN(c2ccc(Cl)nn2)C3)CC1]

To a solution of (R)-6-(4-(2-methoxyphenyl)piperidin-1-yl)-2-azaspiro[3.4]octane (Intermediate 4Q, 75 mg, 0.250 mmol) in isopropanol (2 mL) under nitrogen at 0° C. was added triethylamine (0.08 mL, 0.549 mmol) followed by a solution of 3,6-dichloropyridazine (40.9 mg, 0.275 mmol) in isopropanol (0.5 mL). The reaction mixture was stirred at 0° C. for 10 minutes then heated to 50° C. and stirred for 18 hr. The reaction mixture was then diluted with saturated sodium bicarbonate and extracted with DCM. The combined organic extracts were washed with brine, dried over magnesium sulfate, filtered and concentrated. The crude product was purified via preparative HPLC (XBridge 30×50 mm 35-60% $MeCN/H_2O$ (5 mM $NH_4OH$), 75 mL/min) to afford the title compound (60 mg, 0.145 mmol).

LCMS: RT: 2.53 min (LCMS Method 4) MS m/z 413.3 $[M+H]^+$.

$^1H$ NMR (400 MHz, $CD_3OD$) δ 7.40 (d, J=9.3 Hz, 1H), 7.16 (t, J=7.5 Hz, 2H), 6.95-6.83 (m, 3H), 4.10-3.91 (m, 4H), 3.81 (s, 3H), 3.19 (s, 2H), 3.00 (s, 1H), 2.78 (s, 1H), 2.31 (dd, J=13.1, 7.2 Hz, 1H), 2.20 (s, 2H), 2.12-1.91 (m, 3H), 1.83 (d, J=13.4 Hz, 5H), 1.64 (s, 1H).

Example 5O: (R)-6-(4-(2-methoxyphenyl)piperidin-1-yl)-2-(pyridazin-3-yl)-2-azaspiro[3.4]octane

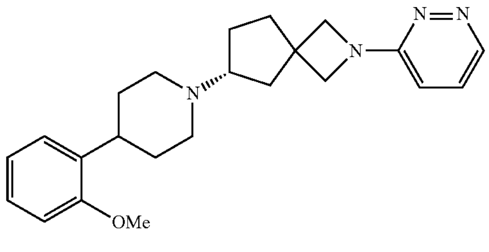

(R)-2-(6-chloropyridazin-3-yl)-6-(4-(2-methoxyphenyl)piperidin-1-yl)-2-azaspiro[3.4]octane (Example 5N, 60 mg, 0.145 mmol) was dissolved in MeOH (15 mL) and subjected to the H-Cube™ with a 10% Pd/C catalyst cartridge for 25 min at 25° C. and 10 psi $H_2$. The resulting solution was concentrated and purified via preparative HPLC (XBridge 30×50 mm 35-60% $MeCN/H_2O$ (5 mM $NH_4OH$)) to afford the title compound (6.9 mg, 0.018 mmol).

LCMS: RT: 2.27 min (LCMS Method 4) MS m/z 379.5 $[M+H]^+$.

$^1H$ NMR (400 MHz, $CD_3OD$) δ 8.45 (dd, J=4.4, 1.4 Hz, 1H), 7.38 (dd, J=9.0, 4.5 Hz, 1H), 7.16 (t, J=7.5 Hz, 2H), 6.97-6.86 (m, 2H), 6.83 (dd, J=9.1, 1.6 Hz, 1H), 4.11-3.91

(m, 4H), 3.81 (s, 3H), 3.21 (s, 2H), 3.01 (m, 1H), 2.83 (s, 1H), 2.38-2.14 (m, 3H), 2.13-1.92 (m, 3H), 1.83 (m, 5H), 1.71-1.57 (m, 1H).

Example 5P: (R)-6-(4-(5-chloro-2-methoxyphenyl)piperidin-1-yl)-2-(pyridazin-4-yl)-2-azaspiro[3.4]octane

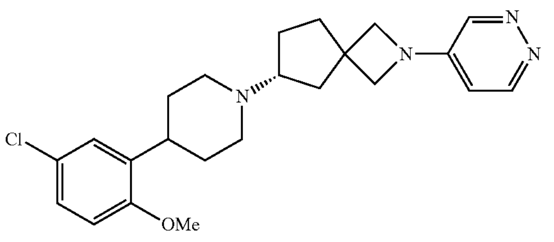 [SMILES: COc1ccc(Cl)cc1C1CCN([C@@H]2CCC3(C2)CN(c2ccnnc2)C3)CC1]

Step 1: (R)-tert-butyl 6-(4-(5-chloro-2-methoxyphenyl)piperidin-1-yl)-2-azaspiro[3.4]octane-2-carboxylate To a solution of (R)-tert-butyl 6-(4-(2-methoxyphenyl)piperidin-1-yl)-2-azaspiro[3.4]octane-2-carboxylate (Intermediate 80, 0.17 g, 0.43 mmol) in DMF (4.3 mL) under nitrogen at 0° C. was added CBMG (0.11 g, 0.51 mmol) and then HCl (4.0M in dioxane, 0.13 mL, 0.51 mmol) dropwise. After 20 minutes additional HCl (4.0 M in dioxane, 0.13 mL, 0.51 mmol) was added and the reaction was allowed to warm to room temperature over 2.5 hours. The reaction was diluted with water and EtOAc and basified with 0.1 N NaOH (pH ~13). The water layer was extracted with EtOAc (2×). All organic layers were combined, diluted with heptanes, washed with water (3×), and then with 0.1 N NaOH (3×), dried with $MgSO_4$, filtered and concentrated. The crude material was purified by FCC (0-10% MeOH (10% $NH_4OH$): DCM) to afford the title compound (70 mg, 0.16 mmol) as a white solid.

LCMS: Rt: 0.83 min (LCMS Method 1) MS m/z 435.6 $[M+H]^+$.

Step 2: (R)-6-(4-(5-chloro-2-methoxyphenyl)piperidin-1-yl)-2-azaspiro[3.4]octane In a round bottom flask, to a solution of (R)-tert-butyl 6-(4-(5-chloro-2-methoxyphenyl)piperidin-1-yl)-2-azaspiro[3.4]octane-2-carboxylate (0.040 g, 0.092 mmol) in DCM (0.7 mL) under nitrogen was added TFA (0.21 mL, 2.8 mmol). After 25 minutes the reaction was concentrated, taken up in MeOH (2.5 mL), and Isoelute Si-Propylsulfonic acid (SCX-2) resin (0.64 mmol/g, 0.43 g, 0.28 mmol) was added and this was stirred for 1 hour. The resin was filtered and rinsed twice with MeOH to remove TFA. The resin was then washed with 7N Ammonia in Methanol (3×) to elute the product and these washes were concentrated to afford the title compound (32 mg, 0.096 mmol) as a colorless oil.

LCMS: Rt: 0.52 min (LCMS Method 1) MS m/z 335.5 $[M+H]^+$.

Step 3: (R)-6-(4-(5-chloro-2-methoxyphenyl)piperidin-1-yl)-2-(3,6-dichloropyridazin-4-yl)-2-azaspiro[3.4]octane In a round bottom flask, to a solution of (R)-6-(4-(5-chloro-2-methoxyphenyl)piperidin-1-yl)-2-azaspiro[3.4]octane (0.032 g, 0.096 mmol) in DMF (1.0 mL) was added $K_2CO_3$ (0.040 g, 0.29 mmol) and 4-bromo-3,6-dichloropyridazine (0.024 g, 0.10 mmol). After 1 hour the reaction was diluted with water, brine and EtOAc, and extracted with EtOAc (3×). The combined organic layers were diluted with heptanes, washed with brine (2×), dried with $MgSO_4$, filtered and concentrated. The residue was purified by FCC (0-15% MeOH (10% $NH_4OH$): DCM) to afford the title compound (32 mg, 0.066 mmol) as an off-white solid.

LCMS: Rt: 0.78 min (LCMS Method 1) MS m/z 483.1 $[M+H]^+$.

Step 4: (R)-6-(4-(5-chloro-2-methoxyphenyl)piperidin-1-yl)-2-(pyridazin-4-yl)-2-azaspiro[3.4]octane In a 40 mL vial, SiliaCat Pd(0) (SiliCycle, 0.24 mmol/g, 0.028 g, 6.6 μmol) was placed under nitrogen atmosphere. To this was added a solution of (R)-6-(4-(5-chloro-2-methoxyphenyl)piperidin-1-yl)-2-(3,6-dichloropyridazin-4-yl)-2-azaspiro[3.4]octane (0.032 g, 0.066 mmol) in MeOH (0.66 mL). This was placed under a hydrogen balloon and the reaction was stirred at room temperature for 3 days. The reaction was filtered through celite, rinsing with 1:1 DCM:MeOH, and the filtrate was concentrated. This was purified by preparative HPLC (XBridge $C_{18}$ OBD 30×50 mm 5 μm column MeCN/$H_2O$w/5 mM $NH_4OH$ 75 mL/min) to afford the title compound (6 mg, 0.014 mmol) as a white solid.

LCMS: Rt: 0.78 min (LCMS Method 3) MS m/z 413.4 $[M+H]^+$.

$^1H$ NMR (400 MHz, $CD_3OD$) δ 8.51 (d, J=6.2 Hz, 1H), 8.37 (d, J=3.0 Hz, 1H), 7.19-7.09 (m, 2H), 6.96-6.86 (m, 1H), 6.53 (dd, J=6.3, 3.0 Hz, 1H), 4.08-3.88 (m, 4H), 3.81 (s, 3H), 3.23-3.09 (m, 2H), 3.02-2.90 (m, 1H), 2.82-2.68 (m, 1H), 2.30 (dd, J=12.9, 7.3 Hz, 1H), 2.23-2.10 (m, 2H), 2.10-1.91 (m, 3H), 1.90-1.55 (m, 6H).

Example 5Q: (R)-6-(4-(2-((tetrahydro-2H-pyran-4-yl)methoxy)phenyl)piperidin-1-yl)-2-(1,3,5-triazin-2-yl)-2-azaspiro[3.4]octane

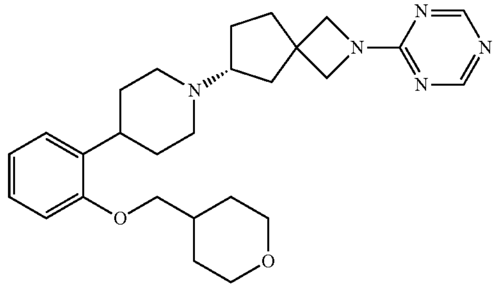 [SMILES: c1ccc(C2CCN([C@@H]3CCC4(C3)CN(c3ncncn3)C4)CC2)c(OCC2CCOCC2)c1]

Step 1: (R)-2-(4-chloro-1,3,5-triazin-2-yl)-6-(4-(2-((tetrahydro-2H-pyran-4-yl)methoxy)phenyl)piperidin-1-yl)-2-azaspiro[3.4]octane In a round bottom flask, to a solution of (R)-6-(4-(2-((tetrahydro-2H-pyran-4-yl)methoxy)phenyl)piperidin-1-yl)-2-azaspiro[3.4]octane (Intermediate 41, 0.10 g, 0.26 mmol) in THF (2.6 mL) under nitrogen at −78° C. was added triethylamine (0.079 mL, 0.57 mmol) followed by a solution of 2,4-dichloro-1,3,5-triazine (0.042 g, 0.28 mmol) in THF (1.2 mL) dropwise. After 10 minutes the reaction was warmed to room temperature, diluted with saturated aqueous sodium bicarbonate, extracted with DCM (3×), washed with brine, dried with $MgSO_4$, filtered and concentrated to afford the title compound (101 mg, 0.203 mmol) as a light yellow solid which was taken forward without further purification.

LCMS: Rt: 0.77 min (LCMS Method 1) MS m/z 498.4 $[M+H]^+$.

Step 2: (R)-6-(4-(2-((tetrahydro-2H-pyran-4-yl)methoxy)phenyl)piperidin-1-yl)-2-(1,3,5-triazin-2-yl)-2-azaspiro[3.4]octane In a round bottom flask, SiliaCat Pd(0) (SiliCycle, 0.20 mmol/g, 0.25 g, 0.051 mmol) was placed under nitrogen atmosphere. To this was added a solution of (R)-2-(4-chloro-1,3,5-triazin-2-yl)-6-(4-(2-((tetrahydro-2H-pyran-4-yl)methoxy)phenyl)piperidin-1-yl)-2-azaspiro[3.4]octane (0.10 g, 0.20 mmol) in MeOH (6.8 mL). This was placed under a hydrogen balloon and the reaction was stirred at room temperature overnight. The reaction was filtered through celite, rinsing with 1:1 DCM:MeOH, and the filtrate was concentrated. The crude material was purified by reverse phase $C_{18}$ FCC (20-70% MeCN:water, with 0.1% $NH_4OH$) to afford the title compound (46 mg, 0.095 mmol) as a white solid.

LCMS: Rt: 1.26 min (LCMS Method 3) MS m/z 464.5 $[M+H]^+$.

$^1H$ NMR (400 MHz, $CD_3OD$) δ 8.47 (s, 2H), 7.24-7.09 (m, 2H), 6.99-6.86 (m, 2H), 4.21-3.96 (m, 6H), 3.87 (d, J=6.0 Hz, 2H), 3.52 (m, 2H), 3.27-3.13 (m, 2H), 3.11-2.96 (m, 1H), 2.82-2.65 (m, 1H), 2.37-2.24 (m, 1H), 2.24-1.46 (m, 16H).

Example 5R: (R)-2-(3,6-dichloropyridazin-4-yl)-6-(4-(2-methoxyphenyl)piperidin-1-yl)-2-azaspiro[3.4]octane

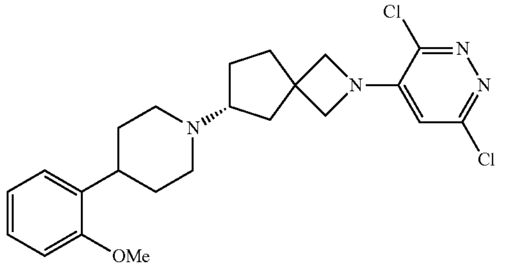 [SMILES: COc1ccccc1C1CCN([C@@H]2CCC3(C2)CN(c2cc(Cl)nnc2Cl)C3)CC1]

To a solution of (R)-6-(4-(2-methoxyphenyl)piperidin-1-yl)-2-azaspiro[3.4]octane (Intermediate 4Q, 140 mg, 0.466 mmol) and $K_2CO_3$ (193 mg, 1.398 mmol) in DMF (5 mL) was added 4-bromo-3,6-dichloropyridazine (117 mg, 0.513 mmol). The reaction was stirred at room temperature for 18 hours. The reaction mixture was then diluted with water and extracted EtOAc (3×25 mL). The combined organic layers were washed with brine (3×10 mL), dried over magnesium sulfate, filtered, and concentrated. The resulting residue was purified via FCC (0-10% MeOH (1% $NH_4OH$)/DCM to afford the title compound (100 mg, 0.212 mmol).

LCMS: RT: 2.90 min (LCMS Method 4) MS m/z: 447.3 $[M+H]^+$.

$^1H$ NMR (400 MHz, $CD_3OD$) δ 7.15 (t, J=7.6 Hz, 2H), 6.94-6.85 (m, 2H), 6.57 (s, 1H), 4.22 (m, 4H), 3.81 (s, 3H), 3.21-3.11 (m, 2H), 3.04-2.93 (m, 1H), 2.78-2.68 (m, 1H), 2.28 (dd, J=12.9, 7.3 Hz, 1H), 2.15 (m, 2H), 2.10-1.90 (m, 3H), 1.85-1.73 (m, 5H), 1.67-1.56 (m, 1H).

Example 5S: (R)-6-(4-(2-methoxyphenyl)piperidin-1-yl)-2-(pyridazin-4-yl)-2-azaspiro[3.4]octane

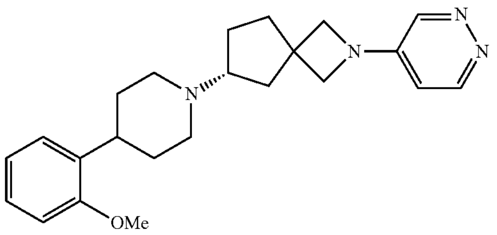 [SMILES: COc1ccccc1C1CCN([C@@H]2CCC3(C2)CN(c2ccnnc2)C3)CC1]

(R)-2-(3,6-dichloropyridazin-4-yl)-6-(4-(2-methoxyphenyl)piperidin-1-yl)-2-azaspiro[3.4]octane (Example 5R, 90 mg, 0.201 mmol) was dissolved in MeOH (15 mL) and subjected to the H-Cube™ with a 10% Pd/C catalyst cartridge for 45 min at 25° C. and 10 psi $H_2$. The resulting solution was concentrated and purified via FCC (0-10% MeOH (1% $NH_4OH$)/DCM) to afford the title compound (36.3 mg, 0.095 mmol).

LCMS: RT: 2.33 min (LCMS Method 4) MS m/z: 379.3 $[M+H]^+$.

$^1H$ NMR (400 MHz, $CD_3OD$) δ 8.50 (d, J=5.9 Hz, 1H), 8.36 (d, J=3.0 Hz, 1H), 7.16 (t, J=7.7 Hz, 2H), 6.95-6.83 (m, 2H), 6.53 (dd, J=6.3, 3.0 Hz, 1H), 4.08-3.89 (m, 4H), 3.81 (s, 3H), 3.23-3.11 (m, 2H), 2.99 (m, 1H), 2.75 (m, 1H), 2.30 (dd, J=12.9, 7.3 Hz, 1H), 2.16 (m, 2H), 2.10-1.91 (m, 3H), 1.90-1.72 (m, 5H), 1.69-1.56 (m, 1H).

Example 5T: (R)-2-methyl-1-(2-(1-(2-(3-methylpyrazin-2-yl)-2-azaspiro[3.4]octan-6-yl)piperidin-4-yl)phenoxy)propan-2-ol

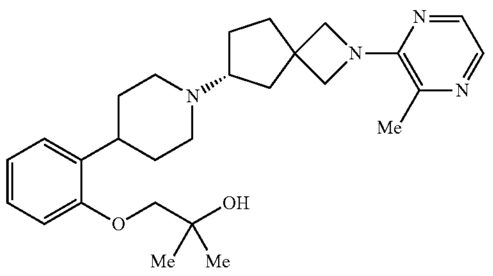 [SMILES: Cc1nccnc1N1CC2(CC[C@@H](N3CCC(c4ccccc4OCC(C)(C)O)CC3)C2)C1]

In a microwave vial, to a solution of (R)-1-(2-(1-(2-azaspiro[3.4]octan-6-yl)piperidin-4-yl)phenoxy)-2-methylpropan-2-ol (Intermediate 4C, 110 mg, 0.307 mmol) in isopropanol (3 mL) at 0° C. was added triethylamine (0.094 mL, 0.675 mmol) followed by a solution of 2-chloro-3-methylpyrazine (43.4 mg, 0.338 mmol) in isopropanol (0.5 mL). The reaction mixture was stirred at 0° C. for 10 min and then stirred at 140° C. in the microwave for 2 hours. The reaction solvent was evaporated and the residue purified via FCC (0-10% MeOH (1% $NH_4OH$)/DCM) to afford the title compound (21.3 mg, 0.046 mmol).

LCMS: RT: 2.37 min (LCMS Method 4) MS m/z: 451.5 $[M+H]^+$.

$^1H$ NMR (400 MHz, $CD_3OD$) δ 7.90 (d, J=2.8 Hz, 1H), 7.70 (d, J=2.9 Hz, 1H), 7.22-7.10 (m, 2H), 6.90 (t, J=7.5 Hz,

2H), 5.49 (s, 1H), 4.20-3.93 (m, 4H), 3.77 (s, 2H), 3.21 (s, 4H), 3.15-3.01 (m, 1H), 2.77 (s, 1H), 2.43 (s, 3H), 2.36-2.13 (m, 3H), 2.05 (m, 1H), 1.98-1.69 (m, 5H), 1.63 (t, J=8.8 Hz, 1H), 1.35 (s, 6H).

Example 5U: (R)-1-(2-(1-(2-(1,3,5-triazin-2-yl)-2-azaspiro[3.4]octan-6-yl)piperidin-4-yl)phenoxy)-2-methylpropan-2-ol

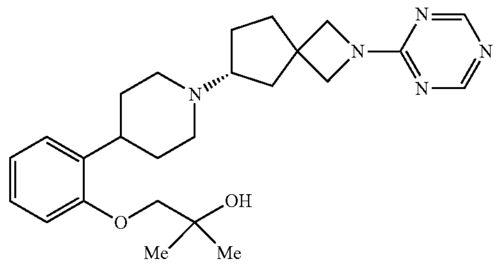 [SMILES: CC(C)(O)COc1ccccc1C1CCN([C@@H]2CCC3(C2)CN(c2ncncn2)C3)CC1]

Step 1: (R)-1-(2-(1-(2-(4-chloro-1,3,5-triazin-2-yl)-2-azaspiro[3.4]octan-6-yl)piperidin-4-yl)phenoxy)-2-methylpropan-2-ol To a solution of (R)-1-(2-(1-(2-azaspiro[3.4]octan-6-yl)piperidin-4-yl)phenoxy)-2-methylpropan-2-ol (Intermediate 4C, 75 mg, 0.209 mmol) in THE (2 mL) under nitrogen at −78° C. was added triethylamine (0.06 mL, 0.460 mmol) followed by a solution of 2,4-dichloro-1,3,5-triazine (34.5 mg, 0.230 mmol) in THE (0.5 mL). The reaction mixture was stirred at −78° C. for 15 min before warming to room temperature over 10 min. The reaction mixture was diluted with saturated aqueous sodium bicarbonate and extracted with DCM (3×25 mL). The combined organic extracts were washed with brine (1×25 mL), dried over magnesium sulfate, filtered, and concentrated to afford the title compound (99 mg, 0.209 mmol) that was used without further purification.

LCMS: RT: 1.05 min (LCMS Method 2) MS m/z: 472.4 $[M+H]^+$.

Step 2: (R)-1-(2-(1-(2-(1,3,5-triazin-2-yl)-2-azaspiro[3.4]octan-6-yl)piperidin-4-yl)phenoxy)-2-methylpropan-2-ol (R)-1-(2-(1-(2-(4-chloro-1,3,5-triazin-2-yl)-2-azaspiro[3.4]octan-6-yl)piperidin-4-yl)phenoxy)-2-methylpropan-2-ol (100 mg, 0.212 mmol) was dissolved in MeOH (10 mL) and subjected to the H-Cube™ with a 10% Pd/C catalyst cartridge for 60 min at 35° C. and 13 psi $H_2$. The resulting solution was concentrated and purified via FCC (0-10% MeOH (1% $NH_4OH$)/DCM) to afford the title compound (33.7 mg, 0.073 mmol).

LCMS: RT: 2.05 min (LCMS Method 4) MS m/z: 438.4 $[M+H]^+$.

$^1H$ NMR (400 MHz, $CD_3OD$) δ 8.45 (s, 2H), 7.25-7.09 (m, 2H), 6.90 (t, J=7.4 Hz, 2H), 4.20-3.97 (m, 4H), 3.77 (s, 2H), 3.26-3.07 (m, 3H), 2.75 (d, J=9.0 Hz, 1H), 2.28 (dd, J=13.0, 7.3 Hz, 1H), 2.25-2.13 (m, 2H), 2.09-1.93 (m, 3H), 1.93-1.82 (m, 3H), 1.75 (m, 2H), 1.68-1.57 (m, 1H), 1.35 (s, 6H).

Example 5V: (R)-6-(4-(5-fluoro-2-methoxyphenyl)piperidin-1-yl)-2-(pyridazin-4-yl)-2-azaspiro[3.4]octane

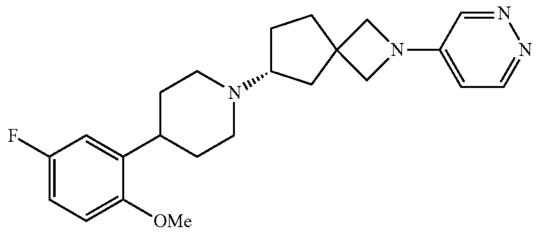 [SMILES: COc1ccc(F)cc1C1CCN([C@@H]2CCC3(C2)CN(c2ccnnc2)C3)CC1]

Step 1: (R)-2-(3,6-dichloropyridazin-4-yl)-6-(4-(5-fluoro-2-methoxyphenyl)piperidin-1-yl)-2-azaspiro[3.4]octane To a stirring solution of (R)-6-(4-(5-fluoro-2-methoxyphenyl)piperidin-1-yl)-2-azaspiro[3.4]octane (Intermediate 4U, 26 mg, 0.082 mmol) in DMF (3 mL), 4-bromo-3,6-dichloropyridazine (20.5 mg, 0.090 mmol) was added, followed by potassium carbonate (33.9 mg, 0.245 mmol). The reaction mixture was stirred at room temperature for 16 hr. The reaction was then diluted with water and extracted with EtOAc. The combined organic layers were washed with brine, dried over magnesium sulfate, filtered, and concentrated to afford the title compound that was used without further purification (38 mg, 0.082 mmol).

LCMS: Rt: 1.23 min (LCMS Method 2) MS m/z 465.2 $[M+H]^+$.

Step 2: (R)-6-(4-(5-fluoro-2-methoxyphenyl)piperidin-1-yl)-2-(pyridazin-4-yl)-2-azaspiro[3.4]octane A solution of (R)-2-(3,6-dichloropyridazin-4-yl)-6-(4-(5-fluoro-2-methoxyphenyl)piperidin-1-yl)-2-azaspiro[3.4]octane (156 mg, 0.335 mmol) in MeOH (5 mL) was passed through the H-Cube™ at 22° C. and 10 bar pressure of hydrogen using a 10% Pd/C cartridge for 2 hrs. The solvent was removed under reduced pressure and the residue was purified by FCC (0-10% MeOH (1% $NH_4OH$)/DCM) to afford the title compound (18 mg, 0.045 mmol).

LCMS: Rt: 0.52 min (LCMS Method 1) MS m/z 397.3 $[M+H]^+$.

$^1H$ NMR (400 MHz, $CD_3OD$) δ 8.51 (d, J=6.1 Hz, 1H), 8.36 (d, J=2.9 Hz, 1H), 6.97-6.82 (m, 3H), 6.53 (dd, J=6.2, 3.1 Hz, 1H), 4.12-3.87 (m, 4H), 3.80 (s, 3H), 3.23-3.11 (m, 2H), 2.98 (m, 1H), 2.83-2.66 (m, 1H), 2.36-2.23 (m, 1H), 2.22-1.42 (m, 11H).

Example 5W: (R)-6-(4-(3-fluoro-2-(oxetan-3-yloxy)phenyl)piperidin-1-yl)-2-(pyrimidin-5-yl)-2-azaspiro[3.4]octane

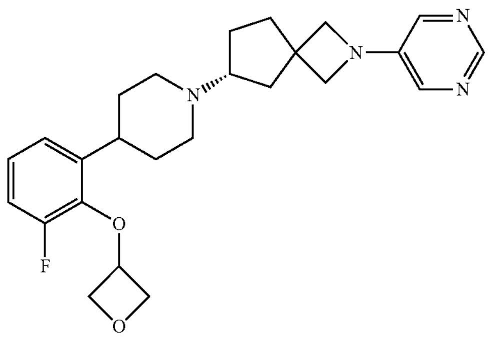 [SMILES: Fc1cccc(C2CCN([C@@H]3CCC4(C3)CN(c3cncnc3)C4)CC2)c1OC1COC1]

Into a vial was added (R)-6-(4-(3-fluoro-2-(oxetan-3-yloxy)phenyl)piperidin-1-yl)-2-azaspiro[3.4]octane (Intermediate 4J, 100 mg, 0.277 mmol) followed by a solution of 5-bromopyrimidine (48.5 mg, 0.305 mmol) in dioxane (3 mL) and this was placed under nitrogen. $Pd(dba)_2$ (15.95 mg, 0.028 mmol), xantphos (19.26 mg, 0.033 mmol) and NaOtBu (53.3 mg, 0.555 mmol) were added and this was stirred at 80° C. for 2 hr. The reaction was then cooled to room temperature, filtered, and rinsed through with MeCN and EtOAc. The filtrate was concentrated and the residue was purified by preparative HPLC (XBridge 30×50 mm 35-60% MeCN/$H_2O$ (5 mM $NH_4OH$), 75 mL/min) to afford the title compound (41 mg, 0.098 mmol).

LCMS: Rt: 2.19 min (LCMS Method 4) MS m/z 439.6 $[M+H]^+$.

$^1H$ NMR (400 MHz, $CD_3OD$) δ 8.47 (s, 1H), 8.00 (s, 2H), 7.17-6.86 (m, 3H), 5.12 (m, 1H), 4.92 (dd, J=7.5, 6.1 Hz, 2H), 4.84-4.78 (m, 2H), 4.01-3.75 (m, 4H), 3.17 (m, 2H), 3.09-2.91 (m, 1H), 2.84-2.62 (m, 1H), 2.30 (dd, J=12.8, 7.2 Hz, 1H), 2.22-1.90 (m, 5H), 1.88-1.52 (m, 6H).

Example 5X: (R)-6-(4-(2-(2-methoxyethoxy)phenyl)piperidin-1-yl)-2-(pyridazin-3-yl)-2-azaspiro[3.4]octane

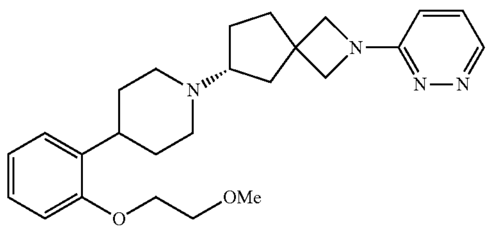 [SMILES: COCCOc1ccccc1C1CCN([C@@H]2CCC3(C2)CN(c2cccnn2)C3)CC1]

Step 1: (R)-2-(6-chloropyridazin-3-yl)-6-(4-(2-(2-methoxyethoxy)phenyl)piperidin-1-yl)-2-azaspiro[3.4]octane To an IPA (2 mL) solution of (R)-6-(4-(2-(2-methoxyethoxy)phenyl)piperidin-1-yl)-2-azaspiro[3.4]octane (Intermediate 4E, 85 mg, 0.247 mmol) was added DIEA (0.215 mL, 1.234 mmol) and 3,6-dichloropyridazine (76 mg, 0.493 mmol) and this was stirred at 45° C. for 48 hours. The reaction was then concentrated under reduced pressure and was purified by FCC (0-5% MeOH/DCM) to afford the title compound. (65 mg, 0.141 mmol).

LCMS: Rt: 1.11 min (LCMS Method 2) MS m/z 457.4 $[M+H]^+$.

Step 2: (R)-6-(4-(2-(2-methoxyethoxy)phenyl)piperidin-1-yl)-2-(pyridazin-3-yl)-2-azaspiro[3.4]octane To a MeOH (2 mL) solution of (R)-2-(6-chloropyridazin-3-yl)-6-(4-(2-(2-methoxyethoxy)phenyl)piperidin-1-yl)-2-azaspiro[3.4]octane (85 mg, 0.186 mmol) was added Pd—C (20 mg, 0.019 mmol). The resulting mixture was stirred under a hydrogen balloon for 4 hrs and the reaction was then filtered through a celite plug, concentrated and purified by preparative HPLC (XBridge C18 30×50 mm 35-60% MeCN/$H_2O$ (5 mM $NH_4OH$), 75 mL/min). It was further purified by FCC (0-5% MeOH (1% $NH_4OH$)/DCM) to afford the title compound (23.4 mg, 0.055 mmol) as a white solid.

LCMS: Rt: 0.72 min (LCMS Method 1) MS m/z 423.6 $[M+H]^+$.

$^1H$ NMR (400 MHz, $CD_3OD$) δ 8.44 (dd, J=4.5, 1.2 Hz, 1H), 7.37 (dd, J=9.1, 4.5 Hz, 1H), 7.23-7.10 (m, 2H), 6.95-6.88 (m, 2H), 6.81 (dd, J=9.0, 1.2 Hz, 1H), 4.13-4.09 (m, 2H), 4.07-3.98 (m, 2H), 3.98-3.90 (m, 2H), 3.78-3.73 (m, 2H), 3.43 (s, 3H), 3.20-3.11 (m, 2H), 3.04 (m, 1H), 2.79-2.68 (m, 1H), 2.28 (dd, J=12.8, 7.2 Hz, 1H), 2.14 (m, 2H), 2.10-1.91 (m, 3H), 1.88-1.56 (m, 6H).

Example 5Y: (R)-6-(4-(2-(2-methoxyethoxy)phenyl)piperidin-1-yl)-2-(5-methylpyrazin-2-yl)-2-azaspiro[3.4]octane

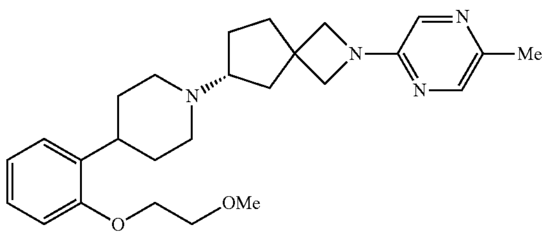 [SMILES: COCCOc1ccccc1C1CCN([C@@H]2CCC3(C2)CN(c2cnc(C)cn2)C3)CC1]

To a toluene (1 mL) solution of (R)-6-(4-(2-(2-methoxyethoxy)phenyl)piperidin-1-yl)-2-azaspiro[3.4]octane (Intermediate 4E, 33 mg, 0.096 mmol) was added $Pd_2(dba)_3$ (17.54 mg, 0.019 mmol), rac-BINAP (11.93 mg, 0.019 mmol), 2-bromo-5-methylpyrazine (24.86 mg, 0.144 mmol) and sodium tert-butoxide (13.81 mg, 0.144 mmol). The reaction mixture was stirred under $N_2$ at 110° C. for 2 hours and the reaction was then filtered through a celite plug, concentrated and purified by preparative HPLC (XBridge C18 30×50 mm 45-70% MeCN/$H_2O$ (5 mM $NH_4OH$), 75 mL/min) to afford the title compound (10.6 mg, 0.023 mmol) as a pale yellow oil.

LCMS: Rt: 2.51 min (LCMS Method 2) MS m/z 437.6 $[M+H]^+$.

$^1H$ NMR (400 MHz, $CD_3OD$) δ 7.93 (s, 1H), 7.74 (d, J=1.4 Hz, 1H), 7.24-7.11 (m, 2H), 6.99-6.89 (m, 2H), 4.20-4.10 (m, 2H), 4.05-3.96 (m, 2H), 3.93 (q, J=7.8 Hz, 2H), 3.82-3.76 (m, 2H), 3.46 (s, 3H), 3.30-3.20 (m, 2H), 3.18-3.05 (m, 1H), 2.89 (s, 1H), 2.50-2.21 (m, 6H), 2.08 (m, 2H), 2.00 (m, 1H), 1.95-1.59 (m, 6H).

Example 5Z: (R)-6-(4-(2-(2-methoxyethoxy)phenyl)piperidin-1-yl)-2-(pyridazin-4-yl)-2-azaspiro[3.4]octane

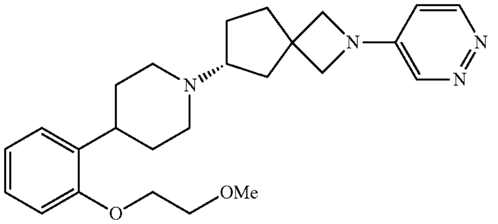 [SMILES: COCCOc1ccccc1C1CCN([C@@H]2CCC3(C2)CN(c2ccnnc2)C3)CC1]

To an IPA (2 mL) solution of (R)-6-(4-(2-(2-methoxyethoxy)phenyl)piperidin-1-yl)-2-azaspiro[3.4]octane (Intermediate 4E, 78 mg, 0.226 mmol) was added DIEA (146 mg, 1.132 mmol) and 4-bromo-3,6-dichloropyridazine (56.8 mg, 0.249 mmol). The resulting mixture was stirred at 50° C. for 1.5 hours. The reaction was then concentrated under reduced pressure and purified by FCC (0-10% MeOH/DCM) to afford a white solid as (R)-2-(3,6-dichloropyridazin-4-yl)-6-(4-(2-(2-methoxyethoxy)phenyl)piperidin-1-yl)-2-azaspiro[3.4]octane. This material was dissolved in MeOH (2 mL) and 10% Pd—C(24 mg, 0.023 mmol) was added. The resulting mixture was stirred under a hydrogen balloon for 16 hours. The reaction was then filtered through a celite plug concentrated, and purified by preparative HPLC (XBridge C18 30×50 mm 35-60% MeCN/$H_2O$ (5 mM $NH_4OH$), 75 mL/min) to afford the title compound (10.6 mg, 0.023 mmol) as a colorless oil.

LCMS: Rt: 2.21 min (LCMS Method 2) MS m/z 423.4 $[M+H]^+$.

$^1H$ NMR (400 MHz, $CD_3OD$) δ 8.53 (d, J=6.3 Hz, 1H), 8.38 (d, J=2.8 Hz, 1H), 7.24-7.11 (m, 2H), 6.93 (t, J=7.3 Hz, 2H), 6.55 (dd, J=6.2, 3.0 Hz, 1H), 4.14 (dd, J=5.3, 3.9 Hz, 2H), 4.08-3.90 (m, 4H), 3.81-3.75 (m, 2H), 3.45 (s, 3H), 3.18 (t, J=9.9 Hz, 2H), 3.07 (m, 1H), 2.76 (m, 1H), 2.31 (dd, J=12.8, 7.3 Hz, 1H), 2.25-2.12 (m, 2H), 2.03 (m, 3H), 1.92-1.57 (m, 6H).

Example 5AA: (R)-2-(5-fluoropyridin-3-yl)-6-(4-(2-(tetrahydro-2H-pyran-4-yl)phenyl)piperidin-1-yl)-2-azaspiro[3.4]octane

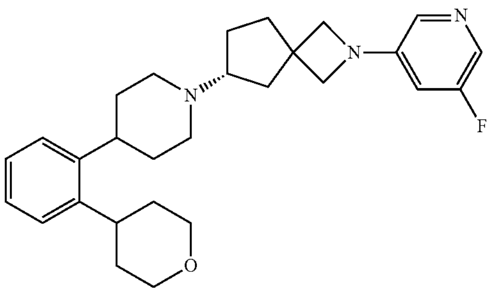 [SMILES: Fc1cncc(N2CC3(CC[C@@H](N4CCC(c5ccccc5C5CCOCC5)CC4)C3)C2)c1]

A dioxane (3 mL) suspension of (R)-6-(4-(2-(tetrahydro-2H-pyran-4-yl)phenyl)piperidin-1-yl)-2-azaspiro[3.4]octane (Intermediate 4Y, 95 mg, 0.268 mmol), 3-bromo-5-fluoropyridine (66.0 mg, 0.375 mmol), cesium carbonate (218 mg, 0.670 mmol) and BrettPhos Pd G3 (24.29 mg, 0.027 mmol) was stirred at 90° C. under $N_2$ for 16 hours. The reaction mixture was concentrated under reduced pressure, redissolved in MeOH, filtered through a celite plug and purified by preparative HPLC (XBridge C18 30×50 mm 45-70% MeCN/$H_2O$ (5 mM $NH_4OH$), 75 mL/min) to afford the title compound (53.8 mg, 0.118 mmol) as a cream colored solid.

LCMS: Rt: 2.75 min (LCMS Method 2) MS m/z 450.4 $[M+H]^+$.

$^1H$ NMR (400 MHz, $CD_3OD$) δ 7.72 (d, J=2.4 Hz, 1H), 7.59 (t, J=2.0 Hz, 1H), 7.29-7.22 (m, 2H), 7.19-7.13 (m, 2H), 6.67 (dt, J=11.0, 2.4 Hz, 1H), 4.05 (dd, J=11.3, 4.2 Hz, 2H), 3.87 (q, J=7.3 Hz, 2H), 3.83-3.76 (m, 2H), 3.60 (m, 2H), 3.24-3.07 (m, 3H), 2.92 (m, 1H), 2.75 (m, 1H), 2.29 (dd, J=12.9, 7.2 Hz, 1H), 2.20 (m, 2H), 2.01 (m, 3H), 1.91-1.71 (m, 7H), 1.63 (m, 3H).

Example 5BB: (R)-2-(pyrimidin-5-yl)-6-(4-(2-(tetrahydro-2H-pyran-4-yl)phenyl)piperidin-1-yl)-2-azaspiro[3.4]octane

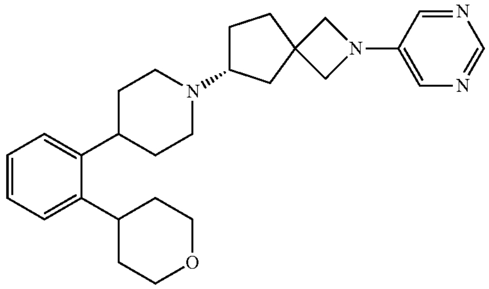 [SMILES: c1ccc(C2CCN([C@@H]3CCC4(C3)CN(c3cncnc3)C4)CC2)c(C2CCOCC2)c1]

A dioxane (3 mL) suspension of (R)-6-(4-(2-(tetrahydro-2H-pyran-4-yl)phenyl)piperidin-1-yl)-2-azaspiro[3.4]octane (Intermediate 4Y, 97 mg, 0.274 mmol), 5-bromopyrimidine (60.9 mg, 0.383 mmol), cesium carbonate (232 mg, 0.684 mmol) and BrettPhos Pd G3 (24.8 mg, 0.027 mmol) was stirred at 90° C. under $N_2$ for 16 hours. The reaction mixture was concentrated under reduced pressure, redissolved in MeOH, filtered through a celite plug and then purified by preparative HPLC (XBridge C18 30×50 mm 35-60% MeCN/$H_2O$ (5 mM $NH_4OH$), 75 mL/min) to afford the title compound (49 mg, 0.112 mmol) as a cream colored solid.

LCMS: Rt: 2.29 min (LCMS Method 2) MS m/z 433.9 $[M+H]^+$.

$^1H$ NMR (400 MHz, $CD_3OD$) δ 8.47 (s, 1H), 8.01 (s, 2H), 7.26 (m, 2H), 7.21-7.12 (m, 2H), 4.05 (dd, J=11.0, 4.3 Hz, 2H), 3.93 (q, J=7.3 Hz, 2H), 3.89-3.83 (m, 2H), 3.60 (td, J=12.0, 1.9 Hz, 2H), 3.23-3.06 (m, 3H), 2.92 (m, 1H), 2.82-2.70 (m, 1H), 2.31 (dd, J=12.8, 7.3 Hz, 1H), 2.20 (m, 2H), 2.13-1.93 (m, 3H), 1.92-1.70 (m, 7H), 1.63 (m, 3H).

Example 5CC: (R)-2-(6-fluoropyridin-3-yl)-6-(4-(2-(tetrahydro-2H-pyran-4-yl)phenyl)piperidin-1-yl)-2-azaspiro[3.4]octane

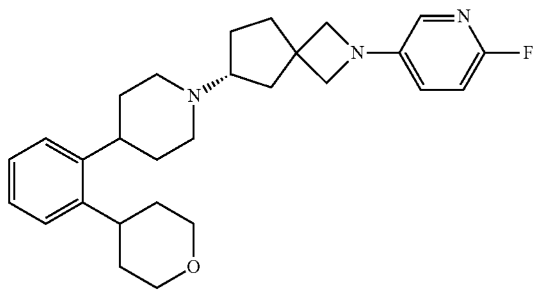 [SMILES: Fc1ccc(N2CC3(CC[C@@H](N4CCC(c5ccccc5C5CCOCC5)CC4)C3)C2)cn1]

A dioxane (3 mL) suspension of (R)-6-(4-(2-(tetrahydro-2H-pyran-4-yl)phenyl)piperidin-1-yl)-2-azaspiro[3.4]octane (Intermediate 4Y, 99 mg, 0.279 mmol), 5-bromo-2-fluoropyridine (68.8 mg, 0.391 mmol), cesium carbonate (227 mg, 0.698 mmol) and BrettPhos Pd G3 (25.3 mg, 0.028 mmol) was stirred at 90° C. under $N_2$ for 16 hours. The reaction mixture was concentrated under reduced pressure, redissolved in MeOH, filtered through a celite plug and purified by preparative HPLC (XBridge C18 30×50 mm 45-70% MeCN/$H_2O$ (5 mM $NH_4OH$), 75 mL/min) to afford the title compound (18.7 mg, 0.041 mmol) as a white solid.

LCMS: Rt: 2.77 min (LCMS Method 2) MS m/z 450.8 $[M+H]^+$.

$^1H$ NMR (400 MHz, $CD_3OD$) δ 7.32 (dd, J=2.9, 1.8 Hz, 1H), 7.25 (m, 2H), 7.19-7.13 (m, 2H), 7.06 (m, 1H), 6.88 (dd, J=8.8, 2.6 Hz, 1H), 4.11-3.99 (m, 2H), 3.84-3.77 (m, 2H), 3.77-3.71 (m, 2H), 3.60 (m, 2H), 3.15 (m, 3H), 2.91 (m, 1H), 2.74 (m, 1H), 2.28 (dd, J=12.8, 7.3 H/z, 1H), 2.19 (m, 2H), 2.09-1.91 (m, 3H), 1.90-1.70 (m, 7H), 1.67-1.55 (m, 3H).

Example 5DD: (R)-6-(4-(2-methoxyphenyl)piperidin-1-yl)-2-(5-methylpyrazin-2-yl)-2-azaspiro[3.4]octane

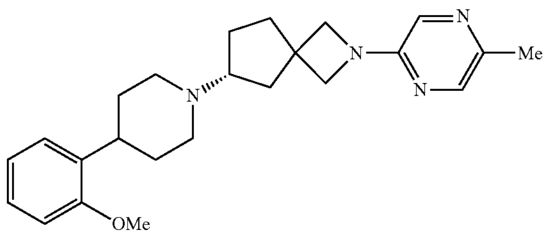

(R)-6-(4-(2-methoxyphenyl)piperidin-1-yl)-2-azaspiro[3.4]octane (Intermediate 4Q, 75 mg, 0.250 mmol) was dissolved in IPA (2 mL) and cooled to 0° C. TEA (0.08 mL, 0.549 mmol) was added followed by 2-chloro-5-methylpyrazine (35 mg, 0.275 mmol) dissolved in IPA (0.5 mL). The reaction was stirred for 10 min at 0° C. and then warmed to 50° C. and stirred for 16 hr. The reaction was then stirred at 150° C. for 2 hr and the solvent was concentrated. The residue was purified by FCC (0-10% MeOH (1% $NH_4OH$)/DCM) to yield the title compound (18 mg, 0.045 mmol).

LCMS: Rt: 2.55 min (LCMS Method 4) MS m/z 393.0 $[M+H]^+$.

$^1H$ NMR (400 MHz, $CD_3OD$) δ 7.91 (d, J=1.4 Hz, 1H), 7.71 (d, J=1.8 Hz, 1H), 7.19-7.11 (m, 2H), 6.95-6.84 (m, 2H), 4.04-3.85 (m, 4H), 3.81 (s, 3H), 3.18 (s, 2H), 2.98 (m, 1H), 2.75 (s, 1H), 2.36 (s, 3H), 2.28 (dd, J=12.9, 7.4 Hz, 1H), 2.16 (d, J=12.8 Hz, 2H), 2.11-1.90 (m, 3H), 1.87-1.70 (m, 5H), 1.70-1.56 (m, 1H).

Example 6A: (R)-(6-(4-(5-fluoro-2-methoxyphenyl)piperidin-1-yl)-2-azaspiro[3.4]octan-2-yl)(oxetan-3-yl)methanone

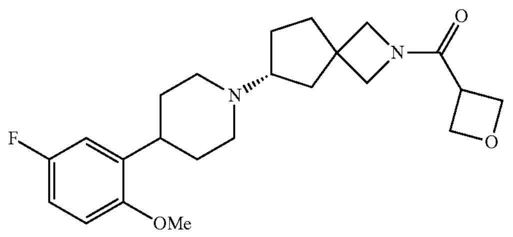 [SMILES: COc1ccc(F)cc1C1CCN([C@@H]2CCC3(C2)CN(C(=O)C2COC2)C3)CC1]

To a stirring solution of oxetane-3-carboxylic acid (105 mg, 0.871 mmol) in DMF (5.0 mL), TBTU (280 mg, 0.871 mmol) was added. This was stirred for 15 min at room temperature. The mixture was then added to a stirring solution of (R)-6-(4-(5-fluoro-2-methoxyphenyl)piperidin-1-yl)-2-azaspiro[3.4]octane (Example 4U, 185 mg, 0.581 mmol) and DIPEA (0.51 mL, 2.90 mmol) in DCM (10 mL). The reaction mixture was stirred at room temperature for 16 hr. The DCM was removed under reduced pressure and the remaining reaction mixture poured into EtOAc. This was washed with sat $NaHCO_3$, water and brine then dried over $Na_2SO_4$. The solvent was removed under reduced pressure. The crude product was purified by preparative HPLC (XBridge 30×50 mm 25-50% MeCN/$H_2O$ (5 mM $NH_4OH$), 75 mL/min) to afford the title compound (18 mg, 0.042 mmol).

LCMS: Rt: 2.10 (LCMS Method 4) MS m/z 403.3 $[M+H]^+$.

$^1H$ NMR (400 MHz, $CD_3OD$) δ 7.00-6.72 (m, 3H), 4.77 (dd, J=8.2, 2.0 Hz, 4H), 4.09-3.73 (m, 8H), 3.21-3.04 (m, 2H), 2.96 (m, 1H), 2.68 (m, 1H), 2.30-1.47 (m, 12H).

Example 6B: (R)-(6-(4-(2-(difluoromethoxy)-4-fluorophenyl)piperidin-1-yl)-2-azaspiro[3.4]octan-2-yl)(oxetan-3-yl)methanone

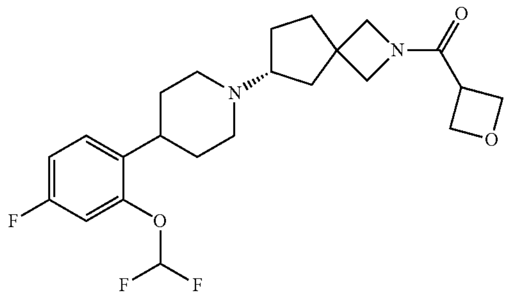 [SMILES: O=C(C1COC1)N1CC2(CC[C@@H](N3CCC(c4ccc(F)cc4OC(F)F)CC3)C2)C1]

To a stirring solution of oxetane-3-carboxylic acid (42 mg, 0.346 mmol) in DMF (2 mL) and DCM (2.5 mL), TBTU (111 mg, 0.346 mmol) was added. This was stirred for 15 min at RT. The mixture was then added to a stirring solution of (R)-6-(4-(2-(difluoromethoxy)-4-fluorophenyl) piperidin-1-yl)-2-azaspiro[3.4]octane TFA salt (Intermediate 4V, 108 mg, 0.231 mmol) and DIPEA (0.201 mL, 1.153 mmol) in DCM (10 mL). The reaction mixture was stirred at room temperature for 16 hr. The DCM was removed and the remaining reaction mixture poured into EtOAc. This was washed with sat $NaHCO_3$, water and brine then dried over $Na_2SO_4$. The solvent was removed under reduced pressure and the crude product was purified by preparative HPLC (XBridge 30×50 mm 35-60% MeCN/$H_2O$ (5 mM $NH_4OH$), 75 mL/min) to afford the title compound (15 mg, 0.031 mmol).

LCMS: Rt: 1.03 min (LCMS Method 3) MS m/z 439.3, $[M+H]^+$.

$^1$H NMR (400 MHz, $CD_3OD$) δ 7.34 (dd, J=8.6, 6.4 Hz, 1H), 7.14-6.62 (m, 3H), 4.77 (dd, J=8.0, 2.0 Hz, 4H), 4.09-3.71 (m, 5H), 3.14 (m, 2H), 2.94 (m, 1H), 2.78-2.60 (m, 1H), 2.27-2.06 (m, 3H), 2.02-1.85 (m, 3H), 1.82-1.67 (m, 5H), 1.64-1.46 (m, 1H).

Example 6C: (R)-(6-(4-(4-fluoro-2-methoxyphenyl) piperidin-1-yl)-2-azaspiro[3.4]octan-2-yl)(oxetan-3-yl)methanone

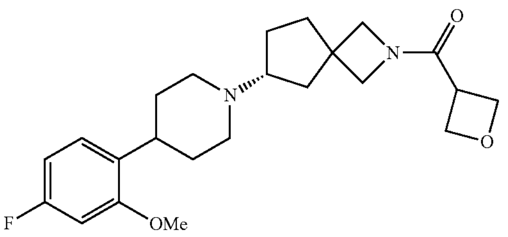 [SMILES: COc1cc(F)ccc1C1CCN([C@@H]2CCC3(C2)CN(C(=O)C2COC2)C3)CC1]

To a stirring solution of oxetane-3-carboxylic acid (115 mg, 0.961 mmol) in DMF (2 mL) and DCM (2.5 mL), TBTU (308 mg, 0.961 mmol) was added. This was stirred for 15 mins at RT and it was then added to a stirring solution of (R)-6-(4-(4-fluoro-2-methoxyphenyl)piperidin-1-yl)-2-azaspiro[3.4]octane TFA salt (Intermediate 4W, 277 mg, 0.641 mmol) and DIPEA (0.559 mL, 3.20 mmol) in DCM (10 mL). The reaction mixture was stirred at room temperature for 16 hr. The DCM was removed and the residue was poured into EtOAc. This was washed with sat. $NaHCO_3$, water and brine then dried over $Na_2SO_4$. The solvent was removed under reduced pressure and the crude product was purified by preparative HPLC (XBridge 30×50 mm 35-60% MeCN/$H_2O$ (5 mM $NH_4OH$), 75 mL/min) to afford the title compound (23 mg, 0.054 mmol).

LCMS: Rt: 2.12 min (LCMS Method 4) MS m/z 403.6 $[M+H]^+$.

$^1$H NMR (400 MHz, $CDCl_3$) δ 7.03 (dd, J=8.5, 6.7 Hz, 1H), 6.60-6.43 (m, 2H), 4.82 (ddd, J=6.8, 5.6, 3.0 Hz, 2H), 4.72-4.58 (m, 2H), 3.93-3.64 (m, 8H), 3.00 (s, 2H), 2.80 (m, 1H), 2.52 (s, 1H), 2.15-1.47 (m, 12H).

Example 6D: (R)-(6-(4-(4-fluoro-2-isopropoxyphenyl)piperidin-1-yl)-2-azaspiro[3.4]octan-2-yl)(oxetan-3-yl)methanone

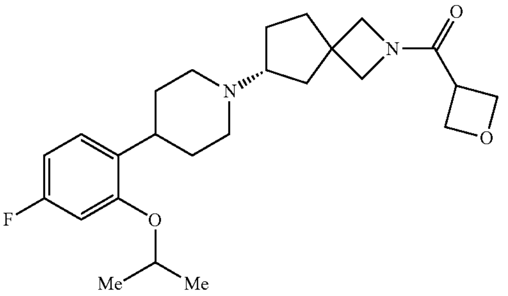 [SMILES: CC(C)Oc1cc(F)ccc1C1CCN([C@@H]2CCC3(C2)CN(C(=O)C2COC2)C3)CC1]

To a stirring solution of oxetane-3-carboxylic acid (122 mg, 1.013 mmol) in DMF (2.5 mL) and DCM (2.5 mL), TBTU (325 mg, 1.013 mmol) was added. This was stirred for 15 min at room temperature and then the mixture was then added to a stirring solution of (R)-6-(4-(4-fluoro-2-isopropoxyphenyl)piperidin-1-yl)-2-azaspiro[3.4]octane TFA salt (Intermediate 4X, 311 mg, 0.675 mmol) and DIPEA (0.590 mL, 3.38 mmol) in DCM (10 mL). The reaction mixture was stirred at room temperature for 16 hr. The DCM was removed and the residue was poured into EtOAc. This was washed with sat $NaHCO_3$, water and brine then dried over $Na_2SO_4$. The solvent was removed under reduced pressure and the crude product was purified by preparative HPLC (XBridge 30×50 mm 35-60% MeCN/$H_2O$ (5 mM $NH_4OH$), 75 mL/min) to afford the title compound (10 mg, 0.022 mmol).

LCMS: Rt: 2.46 min (LCMS Method 4) MS m/z 431.5 $[M+H]^+$.

$^1$H NMR (400 MHz, $CD_3OD$) δ 7.13 (dd, J=8.6, 6.8 Hz, 1H), 6.69 (dd, J=11.3, 2.5 Hz, 1H), 6.58 (td, J=8.4, 2.5 Hz, 1H), 4.77 (dd, J=8.2, 2.0 Hz, 4H), 4.57 (m, 1H), 4.06-3.78 (m, 5H), 3.13 (m, 2H), 2.90 (m, 1H), 2.68 (m, 1H), 2.25-2.05 (m, 3H), 2.02-1.84 (m, 3H), 1.84-1.62 (m, 5H), 1.57 (m, 1H), 1.32 (d, J=5.9 Hz, 6H).

Example 6E: (R)-(1-fluorocyclopropyl)(6-(4-(2-(tetrahydro-2H-pyran-4-yl)phenyl)piperidin-1-yl)-2-azaspiro[3.4]octan-2-yl)methanone

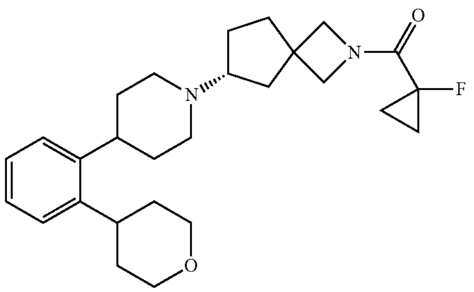 [SMILES: O=C(N1CC2(CC[C@@H](N3CCC(c4ccccc4C4CCOCC4)CC3)C2)C1)C1(F)CC1]

To a DCM (21 mL) solution of 1-fluorocyclopropanecarboxylic acid (0.754 g, 6.88 mmol) was added TBTU (3.01 g, 9.38 mmol) and this was stirred at RT for 10 min. Next, (R)-6-(4-(2-(tetrahydro-2H-pyran-4-yl)phenyl)piperidin-1-yl)-2-azaspiro[3.4]octane (Intermediate 4Y, 2.41 g, 6.25 mmol) and DIEA (4.37 ml, 25.02 mmol) in DCM (21 mL) was added to the reaction. The resulting mixture was stirred at RT for 16 h. Separately, a second reaction using the same conditions was also conducted with 1-fluorocyclopropanecarboxylic acid (161 mg, 1.474 mmol), TBTU (645 mg, 2.010 mmol), DIEA (0.933 mL, 5.36 mmol) and (R)-6-(4-(2-(tetrahydro-2H-pyran-4-yl)phenyl)piperidin-1-yl)-2-azaspiro[3.4]octane (500 mg, 1.34 mmol). The two reactions were then combined and concentrated and purified by successive FCC runs (04% 7N $NH_3$/MeOH/DCM); (7% MeOH/DCM); (6% 7N $NH_3$ in MeOH/40% EtOAc/heptanes); (3% 7N $NH_3$ in MeOH/EtOAc) to yield the title compound as a cream colored solid (2.04 g, 4.58 mmol).

LCMS: Rt: 2.46 min (LCMS Method 4) MS m/z 441.8 $[M+H]^+$.

$^1$H NMR (400 MHz, $CD_3OD$) δ 7.27-7.24 (m, 2H), 7.17-7.13 (m, 2H), 4.48-4.24 (m, 2H), 4.12-3.82 (m, 4H), 3.60 (td, J=11.9, 2.0 Hz, 2H), 3.27-3.03 (m, 3H), 2.92 (tt, J=11.9, 3.9 Hz, 1H), 2.75 (s, 1H), 2.37-2.12 (m, 3H), 2.10-1.68 (m, 10H), 1.68-1.55 (m, 3H), 1.35-1.18 (m, 4H).

Example 7A: (R)-(6-(4-(2-cyclopropoxyphenyl)piperidin-1-yl)-2-azaspiro[3.4]octan-2-yl)(oxetan-3-yl)methanone

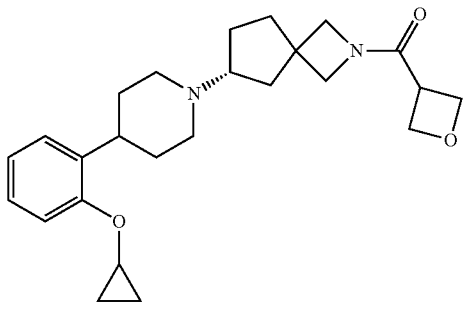 [SMILES: O=C(C1COC1)N1CC2(CC[C@@H](N3CCC(c4ccccc4OC4CC4)CC3)C2)C1]

(R)-(6-(4-(2-hydroxyphenyl)piperidin-1-yl)-2-azaspiro[3.4]octan-2-yl)(oxetan-3-yl)methanone (Intermediate 19A, 22 mg, 0.059 mmol) was dissolved in DMF (0.7 mL) and bromocyclopropane (20 µL, 0.25 mmol) was added, followed by $Cs_2CO_3$ (29.0 mg, 0.089 mmol). The reaction mixture was heated at 175° C. in the microwave for 2 hours. The reaction mixture was concentrated and purified via preparative HPLC (XBridge 30×50 mm 35-60% MeCN/$H_2O$ (5 mM $NH_4OH$) 75 mL/min) to afford the title compound (4.2 mg, 0.010 mmol) as an off-white solid.

LCMS: Rt: 2.33 min (LCMS Method 4) MS m/z 411.4 $[M+H]^+$.

$^1$H NMR (400 MHz, $CDCl_3$) δ 7.20 (d, J=7.34 Hz, 3H), 6.98-6.91 (m, 1H), 5.00-4.85 (m, 2H), 4.80-4.65 (m, 2H), 4.04-3.64 (m, 6H), 3.16-2.99 (m, 2H), 2.95-2.81 (m, 1H), 2.68-2.50 (m, 1H), 2.24-1.60 (m, 12H), 0.89-0.62 (m, 4H).

Example 7B: (R)-(6-(4-(2-(2-fluoro-2-methylpropoxy)phenyl)piperidin-1-yl)-2-azaspiro[3.4]octan-2-yl)(oxetan-3-yl)methanone

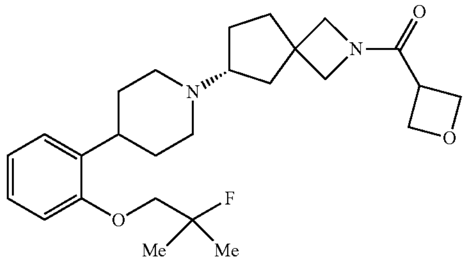 [SMILES: CC(C)(F)COc1ccccc1C1CCN([C@@H]2CCC3(C2)CN(C(=O)C2COC2)C3)CC1]

(R)-(6-(4-(2-hydroxyphenyl)piperidin-1-yl)-2-azaspiro[3.4]octan-2-yl)(oxetan-3-yl)methanone (Intermediate 19A, 20 mg, 0.054 mmol), 1-bromo-2-fluoro-2-methylpropane (19 mg, 0.123 mmol) and $Cs_2CO_3$ (45 mg, 0.138 mmol) were dissolved in DMF (0.5 mL). The reaction mixture was stirred at 70° C. for 18 hours. The crude reaction mixture was purified via preparative HPLC (XBridge 30×50 mm 35-60% MeCN/$H_2O$ (5 mM $NH_4OH$) 75 mL/min) to afford the title compound (1.2 mg, 0.0026 mmol) as a white solid.

LCMS: RT: 2.32 min (LCMS Method 3) MS m/z 445.5 $[M+H]^+$.

$^1$H NMR (400 MHz, $CDCl_3$) δ 7.19 (d, J=14.18 Hz, 2H), 6.96 (s, 1H), 6.82 (d, J=8.31 Hz, 1H), 4.97-4.88 (m, 2H), 4.78-4.69 (m, 2H), 3.94 (d, J=17.12 Hz, 7H), 3.20-2.93 (m, 3H), 2.68-2.54 (m, 1H), 2.26-1.64 (m, 12H), 1.55 (s, 3H), 1.50 (s, 3H).

Example 7C: (R)-oxetan-3-yl(6-(4-(2-(thiazol-2-yloxy)phenyl)piperidin-1-yl)-2-azaspiro[3.4]octan-2-yl)methanone

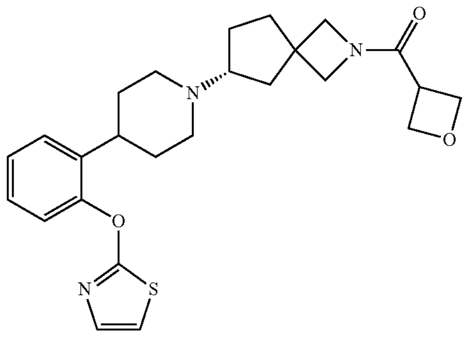 [SMILES: O=C(C1COC1)N1CC2(CC[C@@H](N3CCC(c4ccccc4Oc4nccs4)CC3)C2)C1]

(R)-(6-(4-(2-hydroxyphenyl)piperidin-1-yl)-2-azaspiro[3.4]octan-2-yl)(oxetan-3-yl)methanone (Intermediate 19A, 31 mg, 0.084 mmol), 2-bromothiazole (44 mg, 0.268 mmol) and $Cs_2CO_3$ (32 mg, 0.098 mmol) were dissolved in DMF (0.75 mL). The reaction mixture was stirred at 100° C. for 18 hours at which time additional 2-bromothiazole (44 mg, 0.268 mmol) was added. The reaction mixture was heated at 110° C. for an additional 2 hours, then concentrated and purified via preparative HPLC (XBridge 30×50 mm 35-60% MeCN/$H_2O$ (5 mM $NH_4OH$) 75 mL/min) to afford the title compound (7.5 mg, 0.016 mmol) as an off-white solid.

LCMS: RT: 1.99 min (LCMS Method 3) MS m/z 454.5 $[M+H]^+$.

$^1$H NMR (400 MHz, $CDCl_3$) δ 7.43-7.35 (m, 1H), 7.27-7.19 (m, 4H), 6.83-6.76 (m, 1H), 4.99-4.85-(m, 2H), 4.78-4.68 (m, 2H), 4.01-3.72 (m, 5H), 3.15-2.98 (m, 2H), 2.95-2.81 (m, 1H), 2.65-2.49 (m, 1H), 2.22-2.06 (m, 1H), 1.80 (d, J=6.85 Hz, 9H), 2.06-1.64 (m, 2H).

Example 7D: (R)-3-(2-(1-(2-(oxetane-3-carbonyl)-2-azaspiro[3.4]octan-6-yl)piperidin-4-yl)phenoxy) propanenitrile

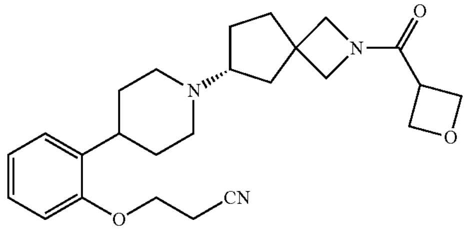 [SMILES: N#CCCOc1ccccc1C1CCN([C@@H]2CCC3(C2)CN(C(=O)C2COC2)C3)CC1]

(R)-(6-(4-(2-hydroxyphenyl)piperidin-1-yl)-2-azaspiro[3.4]octan-2-yl)(oxetan-3-yl)methanone (Intermediate 19A, 18 mg, 0.049 mmol), triethylamine (6.77 μL, 0.049 mmol), and acrylonitrile (1 mL, 0.049 mmol) were added to a vial and the reaction was stirred at 80° C. for 18 hours. $Cs_2CO_3$ (3 mg, 9.21 μmol), THE (0.5 mL) and additional acrylonitrile (1 mL, 0.049 mmol) were then added, and the reaction was heated at 80° C. for an additional 24 hours. The reaction mixture was concentrated, diluted with MeOH and purified via preparative HPLC (XBridge 30×50 mm 25-50% MeCN/$H_2O$ (5 mM $NH_4OH$)) to afford the title compound (13.2 mg, 0.030 mmol) as a cream colored solid.

LCMS: RT: 1.80 min (LCMS Method 3) MS m/z 424.3 $[M+H]^+$.

$^1$H NMR (400 MHz, $CDCl_3$) δ 7.38-7.31 (m, 1H), 7.27-7.16 (m, 1H), 7.10-6.98 (m, 1H), 6.90-6.79 (m, 1H), 4.93 (d, J=5.87 Hz, 2H), 4.76 (s, 2H), 4.24 (t, J=5.87 Hz, 2H), 4.04-3.64 (m, 6H), 3.38-2.52 (m, 8H), 1.88 (m, 9H).

Example 7E: oxetan-3-yl((R)-6-(4-(2-(((R)-tetrahydrofuran-3-yl)methoxy)phenyl)piperidin-1-yl)-2-azaspiro[3.4]octan-2-yl)methanone

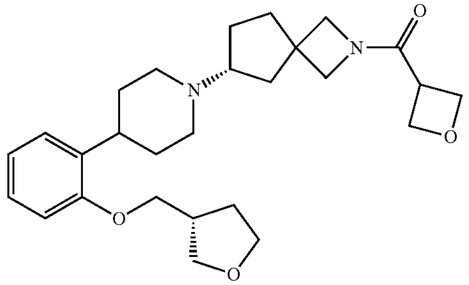 [SMILES: O=C(C1COC1)N1CC2(CC[C@@H](N3CCC(c4ccccc4OC[C@@H]4CCOC4)CC3)C2)C1]

(R)-(6-(4-(2-hydroxyphenyl)piperidin-1-yl)-2-azaspiro[3.4]octan-2-yl)(oxetan-3-yl)methanone (Intermediate 19A, 16 mg, 0.043 mmol), (R)-(tetrahydrofuran-3-yl)methyl 4-methylbenzenesulfonate (Intermediate 71, 20 mg, 0.078 mmol) and $Cs_2CO_3$ (35.2 mg, 0.108 mmol) were dissolved in DMF (0.8 mL). The reaction was stirred at 80° C. for 18 hours, then diluted with methanol and purified via preparative HPLC (XBridge 30×50 mm 25-50% MeCN/$H_2O$ (5 mM $NH_4OH$) 75 mL/min) to afford the title compound (11.1 mg, 0.023 mmol).

LCMS: RT: 2.06 min (LCMS Method 3) MS m/z 455.5 $[M+H]^+$.

$^1$H NMR (400 MHz, $CDCl_3$) δ 7.19 (d, J=12.23 Hz, 2H), 6.94 (s, 1H), 6.84 (d, J=8.31 Hz, 1H), 5.01-4.86 (m, 2H), 4.81-4.64 (m, 2H), 4.06-3.76 (m, 11H), 3.75-3.66 (m, 1H), 3.19-3.05 (m, 2H), 3.02-2.87 (m, 1H), 2.85-2.71 (m, 1H), 2.67-2.52 (m, 1H), 2.26-1.68 (m, 13H).

Example 7F: (R)-(6-(4-(2-isobutoxyphenyl)piperidin-1-yl)-2-azaspiro[3.4]octan-2-yl)(oxetan-3-yl) methanone

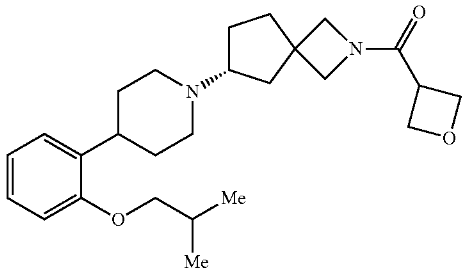 [SMILES: CC(C)COc1ccccc1C1CCN([C@@H]2CCC3(C2)CN(C(=O)C2COC2)C3)CC1]

(R)-(6-(4-(2-hydroxyphenyl)piperidin-1-yl)-2-azaspiro[3.4]octan-2-yl)(oxetan-3-yl)methanone (Intermediate 19A, 15 mg, 0.040 mmol) was dissolved in DMF (0.7 mL). $Cs_2CO_3$ (30 mg, 0.092 mmol) and 1-iodo-2-methylpropane (11 mg, 0.061 mmol) were added and the reaction was stirred at room temperature. After 3 days additional 1-iodo-2-methylpropane (11 mg, 0.061 mmol) was added and the reaction was heated at 50° C. for 2 hours. The reaction was then cooled to room temperature, diluted with MeOH and purified directly by preparative HPLC (XBridge 30×50 mm 45-70% MeCN/$H_2O$ (5 mM $NH_4OH$) 75 mL/min) to provide the title compound as a colorless oil (2.2 mg, 5.0 μmol).

LCMS: Rt: 1.15 min (LCMS Method 2), MS m/z 427.4 $[M+H]^+$.

$^1$H NMR (400 MHz, $CDCl_3$) δ 7.27-7.24 (m, 1H), 7.24-7.16 (m, 1H), 6.99-6.92 (m, 1H), 6.87-6.81 (m, 1H), 4.96-4.83 (m, 2H), 4.81-4.69 (m, 2H), 4.27-4.23 (m, 1H), 3.98-3.68 (m, 7H), 3.33-3.15 (m, 2H), 2.85-2.69 (m, 2H), 2.58-2.39 (m, 2H), 2.37-1.99 (m, 5H), 1.96-1.76 (m, 1H), 1.53 (m, 4H), 1.04 (d, J=6.36 Hz, 6H).

Example 7G: (R)-(6-(4-(2-(cyclopentyloxy)phenyl) piperidin-1-yl)-2-azaspiro[3.4]octan-2-yl)(oxetan-3-yl)methanone

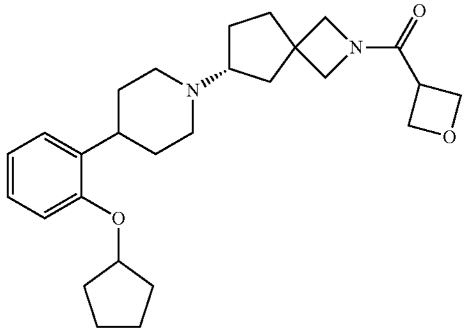 [SMILES: O=C(C1COC1)N1CC2(CC[C@@H](N3CCC(c4ccccc4OC4CCCC4)CC3)C2)C1]

(R)-(6-(4-(2-hydroxyphenyl)piperidin-1-yl)-2-azaspiro[3.4]octan-2-yl)(oxetan-3-yl)methanone (Intermediate 19A, 21 mg, 0.057 mmol) was dissolved in MeCN (0.8 mL). $Cs_2CO_3$ (50 mg, 0.15 mmol) and bromocyclopentane (0.020 mL, 0.19 mmol) were added and the reaction was heated at 60° C. for 5 hours then stirred at room temperature for 16 hours. The reaction was purified directly by preparative HPLC (XBridge 30×50 mm 35-60% MeCN/$H_2O$ (5 mM $NH_4OH$) 75 mL/min) to provide the title compound as a white foam (11.8 mg, 0.026 mmol).

LCMS: Rt: 0.82 min (LCMS Method 1), MS m/z 439.4 $[M+H]^+$.

$^1H$ NMR (400 MHz, $CDCl_3$) δ 7.22 (m, 2H), 6.98-6.84 (m, 2H), 4.92 (dd, J=14.0, 7.6 Hz, 2H), 4.77 (td, J=14.6, 14.0, 8.3 Hz, 3H), 4.01-3.68 (m, 5H), 3.19 (d, J=50.2 Hz, 2H), 2.76 (s, 2H), 2.50 (s, 2H), 2.22 (d, J=57.4 Hz, 2H), 2.08-1.61 (m, 13H). 3 peaks are obscured by the water signal.

Example 7H: (R)-(6-(4-(2-cyclobutoxyphenyl)piperidin-1-yl)-2-azaspiro[3.4]octan-2-yl)(oxetan-3-yl)methanone

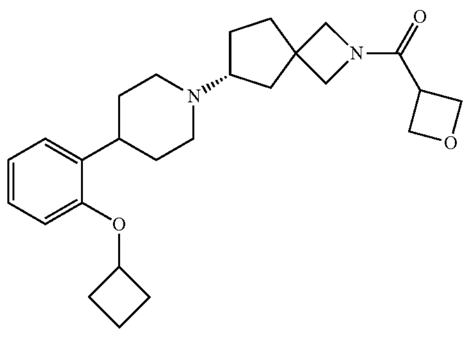 [SMILES: O=C(C1COC1)N1CC2(CC[C@@H](N3CCC(c4ccccc4OC4CCC4)CC3)C2)C1]

(R)-(6-(4-(2-hydroxyphenyl)piperidin-1-yl)-2-azaspiro[3.4]octan-2-yl)(oxetan-3-yl)methanone (Intermediate 19A, 18 mg, 0.049 mmol) was dissolved in DMF (0.7 mL). $Cs_2CO_3$ (55 mg, 0.17 mmol) and bromocyclobutane (9.8 mg, 0.073 mmol) were added and the reaction was stirred at 65° C. for 16 hr. The reaction was then cooled to room temperature, diluted with MeOH and purified directly by preparative HPLC (XBridge 30×50 mm 45-70% MeCN/$H_2O$ (5 mM $NH_4OH$) 75 mL/min) to provide the title compound as a white solid (9.9 mg, 0.023 mmol).

LCMS: Rt: 1.12 min (LCMS Method 2), MS m/z 425.3 $[M+H]^+$.

$^1H$ NMR (400 MHz, $CDCl_3$) δ 7.22 (d, J=7.5 Hz, 1H), 7.15 (s, 1H), 6.93 (t, J=7.4 Hz, 1H), 6.71 (d, J=8.2 Hz, 1H), 4.97-4.88 (m, 2H), 4.76 (ddd, J=9.0, 5.9, 4.1 Hz, 2H), 4.66 (p, J=7.2 Hz, 1H), 3.98-3.81 (m, 5H), 3.18-2.95 (m, 3H), 2.63 (s, 1H), 2.54-2.39 (m, 3H), 2.23-1.65 (m, 15H).

Example 7I: (R)-(6-(4-(2-(cyclopropylmethoxy)phenyl)piperidin-1-yl)-2-azaspiro[3.4]octan-2-yl)(oxetan-3-yl)methanone

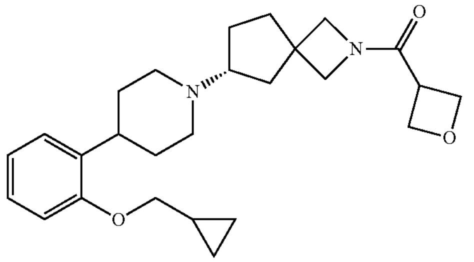 [SMILES: O=C(C1COC1)N1CC2(CC[C@@H](N3CCC(c4ccccc4OCC4CC4)CC3)C2)C1]

(R)-(6-(4-(2-hydroxyphenyl)piperidin-1-yl)-2-azaspiro[3.4]octan-2-yl)(oxetan-3-yl)methanone (Intermediate 19A, 7 mg, 0.046 mmol) was dissolved in DMF (0.75 mL). $Cs_2CO_3$ (45 mg, 0.14 mmol) and (iodomethyl)cyclopropane (12.5 mg, 0.069 mmol) were added and the reaction was stirred at 60° C. for 16 hr. The reaction was then cooled to room temperature, diluted with MeOH and purified directly by preparative HPLC (XBridge 30×50 mm 35-60% MeCN/$H_2O$ (5 mM $NH_4OH$) 75 mL/min) to provide the title compound as a sticky solid (8.6 mg, 0.020 mmol).

LCMS: Rt: 1.09 min (LCMS Method 2), MS m/z 425.4 $[M+H]^+$.

$^1H$ NMR (400 MHz, $CDCl_3$) δ 7.25-7.09 (m, 2H), 6.96-6.89 (m, 1H), 6.83 (d, J=7.34 Hz, 1H), 4.97-4.85 (m, 2H), 4.80-4.67 (m, 2H), 3.85 (d, J=6.36 Hz, 7H), 3.19-2.93 (m, 3H), 2.70-2.53 (m, 1H), 2.29-1.56 (m, 12H), 1.34-1.15 (m, 1H), 0.67-0.52 (m, 2H), 0.42-0.28 (m, 2H).

Example 7J: (R)-(6-(4-(2-ethoxyphenyl)piperidin-1-yl)-2-azaspiro[3.4]octan-2-yl)(oxetan-3-yl)methanone

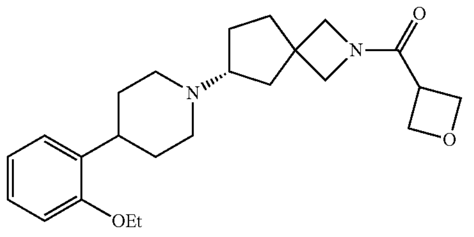 [SMILES: CCOc1ccccc1C1CCN([C@@H]2CCC3(C2)CN(C(=O)C2COC2)C3)CC1]

(R)-(6-(4-(2-hydroxyphenyl)piperidin-1-yl)-2-azaspiro[3.4]octan-2-yl)(oxetan-3-yl)methanone (Intermediate 19A, 17 mg, 0.045 mmol) was dissolved in DMF (0.75 mL). $Cs_2CO_3$ (44 mg, 0.13 mmol) and ethyl iodide (5.5 μl, 0.068 mmol) were added and the reaction was stirred at room temperature for 16 hr. The reaction was diluted with MeOH and purified directly by preparative HPLC (XBridge 30×50 mm 35-60% MeCN/$H_2O$ (5 mM $NH_4OH$) 75 mL/min) to provide the title compound as a white solid (11.6 mg, 0.029 mmol).

LCMS: Rt: 0.66 min (LCMS Method 1), MS m/z 399.5 $[M+H]^+$.

$^1H$ NMR (400 MHz, $CDCl_3$) δ 7.25-7.10 (m, 2H), 6.92 (t, J=7.58 Hz, 1H), 6.85 (d, J=8.31 Hz, 1H), 4.97-4.86 (m, 2H), 4.74 (d, J=1.47 Hz, 2H), 4.05 (q, J=6.85 Hz, 2H), 3.99-3.74

(m, 5H), 3.19-2.92 (m, 3H), 2.70-2.52 (m, 1H), 1.83 (d, J=4.89 Hz, 12H), 1.42 (t, J=6.85 Hz, 3H).

Example 7K: (R)-(6-(4-(2-isopropoxyphenyl)piperidin-1-yl)-2-azaspiro[3.4]octan-2-yl)(oxetan-3-yl) methanone

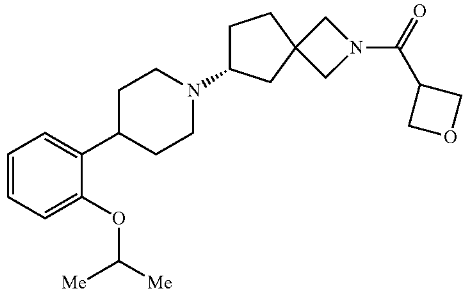 [SMILES: CC(C)Oc1ccccc1C1CCN([C@@H]2CCC3(C2)CN(C(=O)C2COC2)C3)CC1]

(R)-(6-(4-(2-hydroxyphenyl)piperidin-1-yl)-2-azaspiro [3.4]octan-2-yl)(oxetan-3-yl)methanone (Intermediate 19A, 10 mg, 0.027 mmol) was dissolved in DMF (0.8 mL). $Cs_2CO_3$ (45 mg, 0.14 mmol) and 2-iodopropane (9.2 mg, 0.054 mmol) were added and the reaction was stirred at room temperature for 16 hr. The reaction was diluted with MeOH and purified directly by preparative HPLC (XBridge 30×50 mm 35-60% $MeCN/H_2O$ (5 mM $NH_4OH$) 75 mL/min) to provide the title compound as a white foam (5.7 mg, 0.013 mmol).

LCMS: Rt: 1.05 min (LCMS Method 2), MS m/z 413.4 $[M+H]^+$.

$^1H$ NMR (400 MHz, $CDCl_3$) δ 7.23-7.18 (m, 1H), 7.18-7.10 (m, 1H), 6.94-6.81 (m, 2H), 4.96-4.87 (m, 2H), 4.78-4.70 (m, 2H), 4.60-4.47 (m, 1H), 4.02-3.74 (m, 5H), 3.17-2.90 (m, 3H), 2.71-2.52 (m, 1H), 2.26-1.60 (m, 12H), 1.34 (d, J=5.87 Hz, 6H).

Example 7L: (R)-(6-(4-(2-(2-hydroxy-2-methylpropoxy)phenyl)piperidin-1-yl)-2-azaspiro[3.4]octan-2-yl)(oxetan-3-yl)methanone

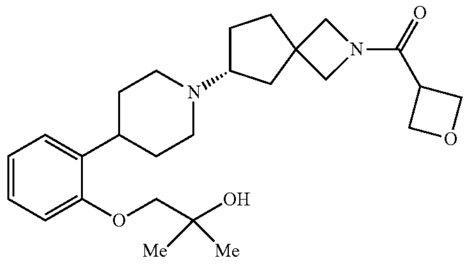 [SMILES: CC(C)(O)COc1ccccc1C1CCN([C@@H]2CCC3(C2)CN(C(=O)C2COC2)C3)CC1]

(R)-(6-(4-(2-hydroxyphenyl)piperidin-1-yl)-2-azaspiro [3.4]octan-2-yl)(oxetan-3-yl)methanone (Intermediate 19A, 15 mg, 0.040 mmol) was dissolved in DMF (0.4 mL). $Cs_2CO_3$ (30 mg, 0.092 mmol) and 2,2-dimethyloxirane (300 μL, 3.33 mmol) were added and the reaction was heated at 100° C. for 16 hr. The reaction was then cooled to room temperature, concentrated, diluted with MeOH and purified directly by preparative HPLC (XBridge 30×50 mm 25-50% $MeCN/H_2O$ (5 mM $NH_4OH$) 75 mL/min) to provide the title compound as a white solid (6.7 mg, 0.015 mmol).

LCMS: Rt: 0.93 min (LCMS Method 2), MS m/z 443.4 $[M+H]^+$.

$^1H$ NMR (400 MHz, $CDCl_3$) δ 7.13-7.25 (m, 2H), 6.92-7.00 (m, 1H), 6.80-6.88 (m, 1H), 4.88-4.96 (m, 2H), 4.67-4.79 (m, 2H), 3.97-3.88 (m, 2H), 3.85-3.75 (m, 6H), 3.04-3.23 (m, 2H), 2.90-3.01 (m, 1H), 2.51-2.67 (m, 1H), 1.68-2.21 (m, 11H), 1.38 (s, 6H).

Example 7M: (R)-(1-fluorocyclopropyl)(6-(4-(2-(pyrimidin-2-ylmethoxy)phenyl)piperidin-1-yl)-2-azaspiro[3.4]octan-2-yl)methanone or (S)-(1-fluorocyclopropyl)(6-(4-(2-(pyrimidin-2-ylmethoxy) phenyl)piperidin-1-yl)-2-azaspiro[3.4]octan-2-yl) methanone

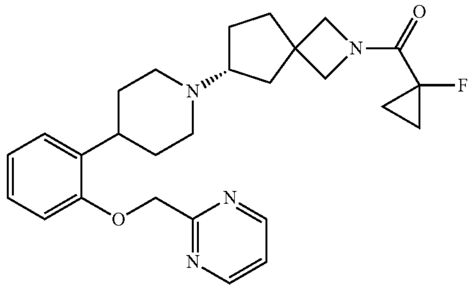

(R)-isomer

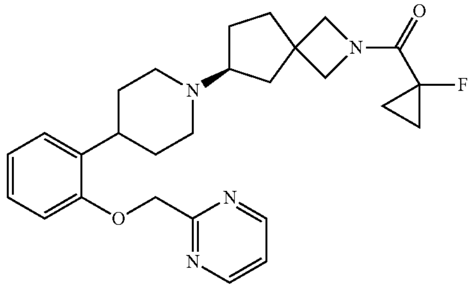

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 15.8 mg, 0.042 mmol), 2-(chloromethyl)pyrimidine (10.91 mg, 0.085 mmol) and $Cs_2CO_3$ (41.5 mg, 0.127 mmol) were dissolved in DMF (Volume: 0.75 mL) and the reaction was stirred at 60° C. for 16 hours. The reaction was then diluted with MeOH and purified by preparative HPLC (XBridge C18 OBD 30×50 mm 5 μm column $MeCN/H_2O$ w/5 mM $NH_4OH$ 75 mL/min) to yield the title compound (12 mg, 0.025 mmol) as a white solid.

LCMS: Rt: 0.95 min (LCMS Method 2), MS m/z 465.4 $[M+H]^+$.

$^1H$ NMR (400 MHz, $CDCl_3$) δ 8.78 (d, J=4.89 Hz, 2H), 7.27-7.22 (m, 2H), 7.16-7.06 (m, 1H), 6.95 (s, 1H), 6.88 (d, J=7.83 Hz, 1H), 5.33 (s, 2H), 4.42-4.19 (m, 2H), 4.06-3.84 (m, 2H), 3.25-3.02 (m, 3H), 2.69-2.52 (m, 1H), 2.28-2.16 (m, 1H), 2.15-2.03 (m, 2H), 1.92 (m, 5H), 1.83-1.69 (m, 3H), 1.68-1.56 (m, 1H), 1.41-1.32 (m, 2H), 1.25-1.14 (m, 2H).

Example 7N: (R)-(1-fluorocyclopropyl)(6-(4-(2-(2-hydroxyethoxy)phenyl)piperidin-1-yl)-2-azaspiro[3.4]octan-2-yl)methanone or (S)-(1-fluorocyclopropyl)(6-(4-(2-(2-hydroxyethoxy)phenyl)piperidin-1-yl)-2-azaspiro[3.4]octan-2-yl)methanone

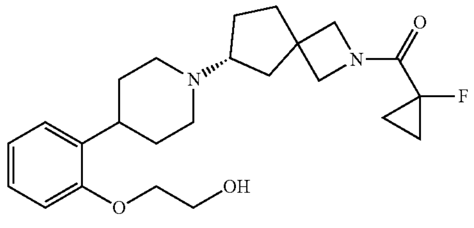

(R)-isomer

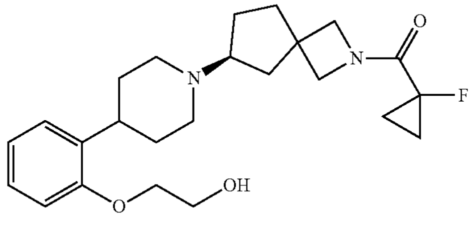

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 30 mg, 0.081 mmol), 2-((tert-butyldimethylsilyl)oxy)ethyl 4-methylbenzenesulfonate (Intermediate 7J, 31.9 mg, 0.097 mmol) and $Cs_2CO_3$ (65.6 mg, 0.201 mmol) were dissolved in DMF (1.0 mL). The reaction mixture was stirred at room temperature for 18 hours and then concentrated. The residue was dissolved in THE (1.5 mL) and tetrabutylammonium fluoride (1M in THF, 0.25 mL, 0.250 mmol) was added. The reaction mixture was stirred at room temperature for 90 minutes, then quenched with water and methanol, and concentrated. The crude residue was purified via preparative HPLC (XBridge 30×50 mm 35-60% $MeCN/H_2O$ (5 mM $NH_4OH$) 75 mL/min) to afford the title compound (8.5 mg, 0.019 mmol) as a white solid.

LCMS: Rt: 2.11 min (LCMS Method 3) MS m/z 417.3 $[M+H]^+$.

$^1$H NMR (400 MHz, $CDCl_3$) δ 7.20 (d, J=16.14 Hz, 2H), 6.96 (s, 1H), 6.88 (d, J=8.31 Hz, 1H), 4.41-4.22 (m, 2H), 4.11 (d, J=4.89 Hz, 2H), 4.00 (m, 4H), 3.19-3.04 (m, 2H), 3.04-2.90 (m, 1H), 2.73-2.53 (m, 1H), 2.28-2.14 (m, 1H), 2.13-1.88 (m, 5H), 1.82 (m, 4H), 1.73-1.54 (m, 3H), 1.43-1.31 (m, 2H), 1.27-1.14 (m, 2H).

Example 7O: (R)-(6-(4-(2-(cyclopropylmethoxy)phenyl)piperidin-1-yl)-2-azaspiro[3.4]octan-2-yl)(1-fluorocyclopropyl)methanone or (R)-(6-(4-(2-(cyclopropylmethoxy)phenyl)piperidin-1-yl)-2-azaspiro[3.4]octan-2-yl)(1-fluorocyclopropyl)methanone

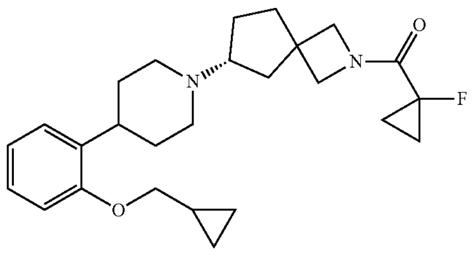

(R)-isomer

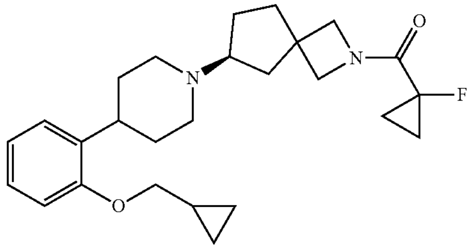

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 15 mg, 0.040 mmol), (iodomethyl)cyclopropane (11 mg, 0.060 mmol), and $Cs_2CO_3$ (39.4 mg, 0.121 mmol) were dissolved in DMF (0.75 mL). The reaction was stirred at room temperature for 18 hours, then diluted with methanol and purified via preparative HPLC (XBridge 30×50 mm 35-60% $MeCN/H_2O$ (5 mM $NH_4OH$) 75 mL/min) to afford the title compound (12.4 mg, 0.029 mmol) as a colorless oil.

LCMS: Rt: 2.93 min (LCMS Method 4) MS m/z 427.4 $[M+H]^+$.

$^1$H NMR (400 MHz, $CDCl_3$) δ 7.26-7.10 (m, 2H), 6.93 (s, 1H), 6.86-6.80 (m, 1H), 4.46-4.28 (m, 1H), 4.27-4.22 (m, 1H), 4.08-3.92 (m, 1H), 3.90 (s, 1H), 3.85 (d, J=6.36 Hz, 2H), 3.23-2.93 (m, 3H), 2.75-2.54 (m, 1H), 2.33-2.16 (m, 1H), 2.16-1.60 (m, 10H), 1.43-1.11 (m, 6H), 0.67-0.53 (m, 2H), 0.42-0.26 (m, 2H).

Example 7P: (R)-1-(2-(2-(1-(2-(1-fluorocyclopropane-1-carbonyl)-2-azaspiro[3.4]octan-6-yl)piperidin-4-yl)phenoxy)ethyl)pyrrolidin-2-one formate salt or (S)-1-(2-(2-(1-(2-(1-fluorocyclopropane-1-carbonyl)-2-azaspiro[3.4]octan-6-yl)piperidin-4-yl)phenoxy)ethyl)pyrrolidin-2-one formate salt

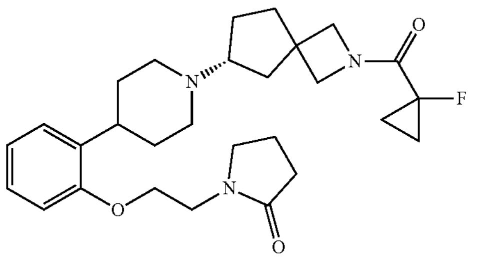

(R)-isomer

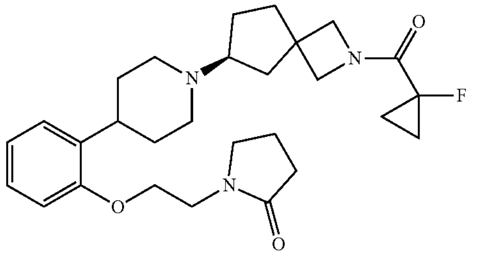

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 15 mg, 0.040 mmol), 2-(2-oxopyrrolidin-1-yl)ethyl 4-methylbenzenesulfonate (Intermediate 7K, 22.8 mg, 0.081 mmol) and $Cs_2CO_3$ (39.4 mg, 0.121 mmol) were dissolved in DMF (1.0 mL), and the reaction mixture was stirred at room temperature for 18 hours. Additional 2-(2-oxopyrrolidin-1-yl)ethyl 4-methylbenzenesulfonate (Intermediate 7K, 22.8 mg, 0.081 mmol) was added, and the reaction mixture was heated to 75° C. for 5 hours. The reaction mixture was diluted with methanol and purified via preparative HPLC (XBridge 30×50 mm 15-40% $MeCN/H_2O$ (0.1% formic acid) 75 mL/min) to afford the title compound (3.6 mg, 0.0067 mmol) as a formate salt.

LCMS: RT: 2.13 min (LCMS Method 3) MS m/z 484.4 $[M+H]^+$.

$^1H$ NMR (400 MHz, $CDCl_3$) δ 8.54 (s, 1H), 7.25-7.15 (m, 2H), 7.02-6.90 (m, 1H), 6.81 (d, J=8.31 Hz, 1H), 4.47-4.21 (m, 2H), 4.10 (s, 2H), 4.07-3.85 (m, 2H), 3.78-3.69 (m, 2H), 3.59-3.49 (m, 2H), 3.44-3.24 (m, 2H), 3.13-2.78 (m, 3H), 2.40 (s, 5H), 2.15-1.80 (m, 11H), 1.43-1.31 (m, 2H), 1.27-1.14 (m, 2H).

Example 7Q: (R)-(1-fluorocyclopropyl)(6-(4-(2-((tetrahydro-2H-pyran-4-yl)methoxy)phenyl)piperidin-1-yl)-2-azaspiro[3.4]octan-2-yl)methanone or (S)-(1-fluorocyclopropyl)(6-(4-(2-((tetrahydro-2H-pyran-4-yl)methoxy)phenyl)piperidin-1-yl)-2-azaspiro[3.4]octan-2-yl)methanone

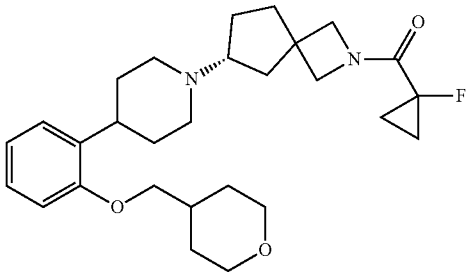

(R)-isomer

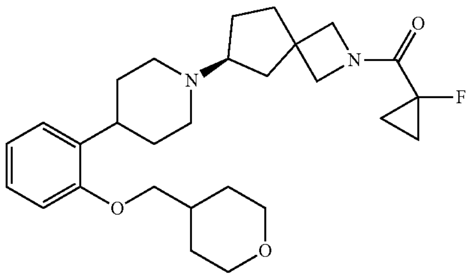

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 15 mg, 0.040 mmol), 4-(iodomethyl)tetrahydro-2H-pyran (18.2 mg, 0.081 mmol) and $Cs_2CO_3$ (39.4 mg, 0.121 mmol) were dissolved in DMF (0.75 mL) and stirred at room temperature for 18 hours. The reaction mixture was then diluted with methanol and purified via preparative HPLC (XBridge 30×50 mm 45-70% $MeCN/H_2O$ (5 mM $NH_4OH$) 75 mL/min) to afford the title compound (5.6 mg, 0.012 mmol) as a sticky solid.

LCMS: RT: 2.72 min (LCMS Method 3) MS m/z 471.5 $[M+H]^+$.

$^1H$ NMR (400 MHz, $CDCl_3$) δ 7.25-7.13 (m, 2H), 6.97-6.90 (m, 1H), 6.84 (d, J=8.31 Hz, 1H), 4.42-4.21 (m, 2H), 4.11-3.87 (m, 4H), 3.83 (d, J=6.36 Hz, 2H), 3.55-3.42 (m, 2H), 3.19-3.08 (m, 2H), 3.03-2.91 (m, 1H), 2.73-2.55 (m, 1H), 2.28-2.17 (m, 1H), 1.74 (m, 13H), 1.53-1.46 (m, 2H), 1.42-1.32 (m, 2H), 1.30-1.14 (m, 3H).

Example 7R: (R)-(1-fluorocyclopropyl)(6-(4-(2-((5-methyl-1,3,4-thiadiazol-2-yl)methoxy)phenyl)piperidin-1-yl)-2-azaspiro[3.4]octan-2-yl)methanone or (S)-(1-fluorocyclopropyl)(6-(4-(2-((5-methyl-1,3,4-thiadiazol-2-yl)methoxy)phenyl)piperidin-1-yl)-2-azaspiro[3.4]octan-2-yl)methanone

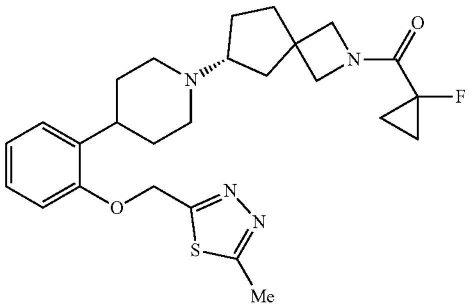

(R)-isomer

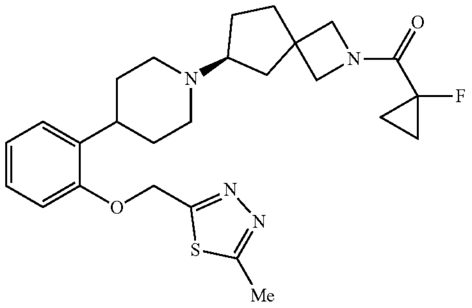

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17G, 12 mg, 0.032 mmol) was dissolved in DMF (0.75 mL). $Cs_2CO_3$ (31.5 mg, 0.097 mmol) and 2-(chloromethyl)-5-methyl-1,3,4-thiadiazole (7.2 mg, 0.048 mmol) were added and the reaction was stirred at room temperature for 16 hours. The reaction was diluted with MeOH and purified directly by preparative HPLC (XBridge 30×50 mm 35-60% MeCN/$H_2O$ (5 mM $NH_4OH$) 75 mL/min) to provide the title compound as a white solid (10.8 mg, 0.022 mmol).

LCMS: Rt: 0.99 min (LCMS Method 2), MS m/z 485.3 $[M+H]^+$.

$^1H$ NMR (400 MHz, $CDCl_3$) δ 7.27-7.24 (m, 1H), 7.23-7.16 (m, 1H), 7.06-6.98 (m, 1H), 6.97-6.90 (m, 1H), 5.47 (s, 2H), 4.45-4.21 (m, 2H), 4.06-3.93 (m, 1H), 3.90 (s, 1H), 3.21-3.09 (m, 2H), 3.05-2.93 (m, 1H), 2.82 (s, 3H), 2.70-2.57 (m, 1H), 2.29-2.17 (m, 1H), 2.14-1.71 (m, 8H), 1.56 (s, 3H), 1.36 (m, 2H), 1.27-1.15 (m, 2H).

Example 7S: (R)-(6-(4-(2-ethoxyphenyl)piperidin-1-yl)-2-azaspiro[3.4]octan-2-yl)(1-fluorocyclopropyl)methanone or (S)-(6-(4-(2-ethoxyphenyl)piperidin-1-yl)-2-azaspiro[3.4]octan-2-yl)(1-fluorocyclopropyl)methanone

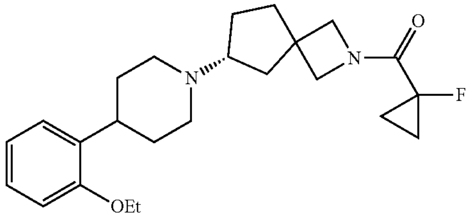

(R)-isomer

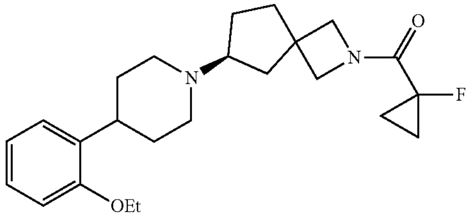

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17G, 15 mg, 0.040 mmol) was dissolved in DMF (0.75 mL). $Cs_2CO_3$ (39 mg, 0.12 mmol) and iodoethane (9.4 mg, 0.060 mmol) were added and the reaction was stirred at room temperature for 16 hr. The reaction was diluted with MeOH and purified directly by preparative HPLC (XBridge 30×50 mm 45-70% MeCN/$H_2O$ (5 mM $NH_4OH$) 75 mL/min) to provide the title compound as a colorless oil (10.5 mg, 0.026 mmol).

LCMS: Rt: 0.78 min (LCMS Method 2), MS m/z 401.4 $[M+H]^+$.

$^1H$ NMR (400 MHz, $CDCl_3$) δ 7.22 (d, J=7.82 Hz, 1H), 7.19-7.13 (m, 1H), 6.92 (s, 1H), 6.85 (d, J=7.34 Hz, 1H), 4.42-4.28 (m, 1H), 4.27-4.22 (m, 1H), 4.06-3.86 (m, 4H), 3.19-3.06 (m, 2H), 3.05-2.94 (m, 1H), 2.71-2.55 (m, 1H), 2.28-2.16 (m, 1H), 2.14-1.61 (m, 11H), 1.43 (t, J=7.09 Hz, 3H), 1.39-1.31 (m, 2H), 1.20 (m, 2H).

Example 7T: (R)-(6-(4-(2-(cyclopropylmethoxy)phenyl)piperidin-1-yl)-2-azaspiro[3.4]octan-2-yl)(1-fluorocyclopropyl)methanone or (R)-(6-(4-(2-(cyclopropylmethoxy)phenyl)piperidin-1-yl)-2-azaspiro[3.4]octan-2-yl)(1-fluorocyclopropyl)methanone

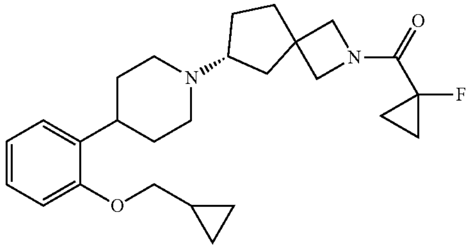

(R)-isomer

-continued

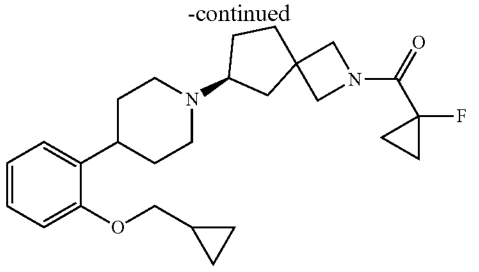

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17G, 15 mg, 0.040 mmol) was dissolved in DMF (0.75 mL). $Cs_2CO_3$ (39 mg, 0.12 mmol) and (iodomethyl)cyclopropane (11 mg, 0.060 mmol) were added and the reaction was stirred at room temperature for 16 hr. The reaction was diluted with MeOH and purified directly by preparative HPLC (XBridge 30×50 mm 55-80% MeCN/$H_2O$ (5 mM $NH_4OH$) 75 mL/min) to provide the title compound as a colorless oil (14.1 mg, 0.032 mmol).

LCMS: Rt: 1.28 min (LCMS Method 2), MS m/z 427.4 $[M+H]^+$.

$^1H$ NMR (400 MHz, $CDCl_3$) δ 7.26-7.10 (m, 2H), 6.93 (s, 1H), 6.86-6.80 (m, 1H), 4.46-4.28 (m, 1H), 4.27-4.22 (m, 1H), 4.08-3.92 (m, 1H), 3.90 (s, 1H), 3.85 (d, J=6.36 Hz, 2H), 3.23-2.93 (m, 3H), 2.75-2.54 (m, 1H), 2.33-2.16 (m, 1H), 2.16-1.60 (m, 10H), 1.43-1.11 (m, 6H), 0.67-0.53 (m, 2H), 0.42-0.26 (m, 2H).

Example 7U: (R)-(6-(4-(2-((3,5-dimethylisoxazol-4-yl)methoxy)phenyl)piperidin-1-yl)-2-azaspiro[3.4]octan-2-yl)(1-fluorocyclopropyl)methanone or (S)-(6-(4-(2-((3,5-dimethylisoxazol-4-yl)methoxy)phenyl)piperidin-1-yl)-2-azaspiro[3.4]octan-2-yl)(1-fluorocyclopropyl)methanone

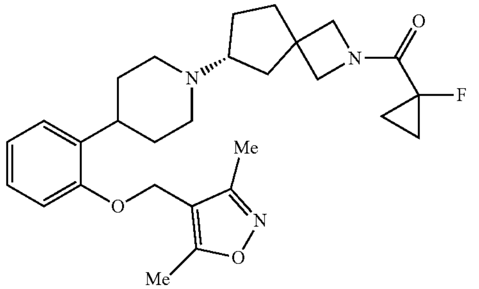

(R)-isomer

-continued

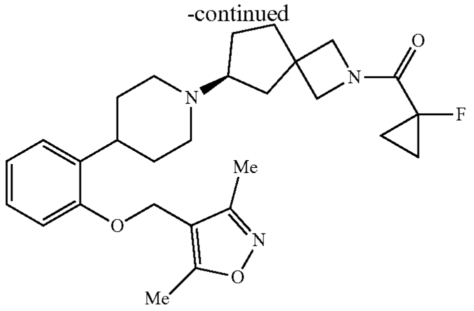

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17G, 18 mg, 0.048 mmol) was dissolved in DMF (0.7 mL). $Cs_2CO_3$ (31 mg, 0.097 mmol) and 4-(chloromethyl)-3,5-dimethylisoxazole (10.5 mg, 0.072 mmol) were added and the reaction was stirred at room temperature for 16 hr. The reaction was diluted with MeOH and purified directly by preparative HPLC (XBridge 30×50 mm 35-60% MeCN/$H_2O$ (5 mM $NH_4OH$) 75 mL/min) to provide the title compound as a white solid (16.9 mg, 0.034 mmol).

LCMS: Rt: 1.09 min (LCMS Method 2), MS m/z 482.4 $[M+H]^+$.

$^1H$ NMR (400 MHz, $CDCl_3$) δ 7.26-7.16 (m, 2H), 7.01-6.94 (m, 2H), 4.79 (s, 2H), 4.38-4.27 (m, 1H), 4.24 (s, 1H), 3.96 (d, J=13.6 Hz, 1H), 3.88 (s, 1H), 3.07 (s, 2H), 2.89 (s, 1H), 2.58 (s, 1H), 2.38 (s, 3H), 2.29 (s, 3H), 2.18 (s, 1H), 1.93 (d, J=27.8 Hz, 4H), 1.73 (s, 4H), 1.35 (d, J=7.4 Hz, 2H), 1.27-1.12 (m, 2H). 3 protons are obscured by the HDO peak.

Example 7V: (R)-(1-fluorocyclopropyl)(6-(4-(2-((2-methyloxazol-5-yl)methoxy)phenyl)piperidin-1-yl)-2-azaspiro[3.4]octan-2-yl)methanone or (S)-(1-fluorocyclopropyl)(6-(4-(2-((2-methyloxazol-5-yl)methoxy)phenyl)piperidin-1-yl)-2-azaspiro[3.4]octan-2-yl)methanone

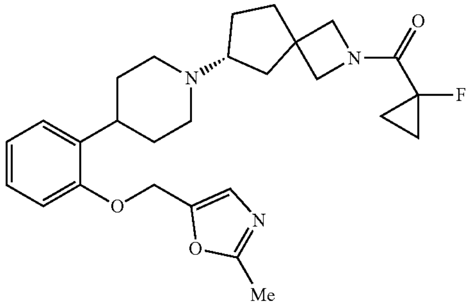

(R)-isomer

-continued

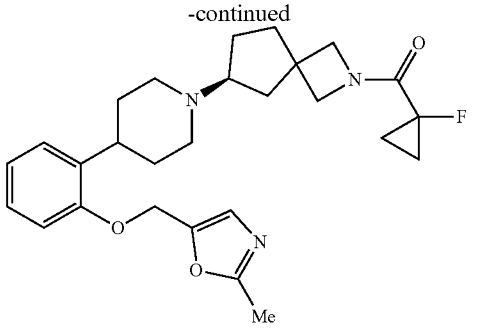

(S)-isomer (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17G, 15 mg, 0.040 mmol) was dissolved in DMF (0.75 mL). $Cs_2CO_3$ (39 mg, 0.12 mmol) and 5-(chloromethyl)-2-methyloxazole (7.9 mg, 0.060 mmol) were added and the reaction was stirred at room temperature for 16 hours. The reaction was diluted with MeOH and purified directly by preparative HPLC (XBridge 30×50 mm 35-60% MeCN/$H_2O$ (5 mM $NH_4OH$) 75 mL/min) to provide the title compound as a sticky solid (14.8 mg, 0.032 mmol).

LCMS: Rt: 0.75 min (LCMS Method 1), MS m/z 468.4 $[M+H]^+$.

$^1$H NMR (400 MHz, $CDCl_3$) δ 7.28-7.15 (m, 2H), 7.06-6.92 (m, 3H), 5.04 (s, 2H), 4.44-4.22 (m, 2H), 4.08-3.86 (m, 2H), 3.52 (d, J=4.8 Hz, 1H), 3.19-2.88 (m, 3H), 2.73-2.54 (m, 1H), 2.50 (s, 3H), 2.31-2.15 (m, 1H), 2.14-1.61 (m, 10H), 1.44-1.32 (m, 2H), 1.28-1.14 (m, 2H).

Example 7W: (R)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone or (S)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone

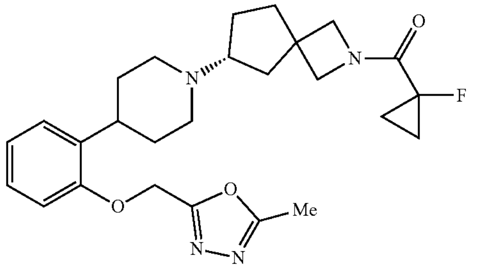

(R)-isomer

-continued

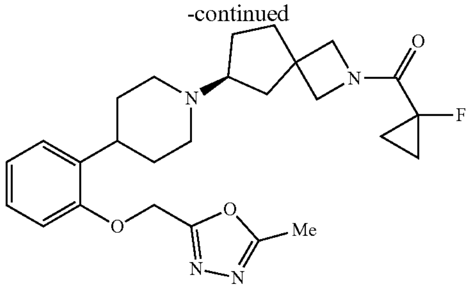

(S)-isomer

To a DMF (1 mL) solution of (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 30 mg, 0.081 mmol) and cesium carbonate (79 mg, 0.242 mmol), was added 2-(chloromethyl)-5-methyl-1,3,4-oxadiazole (12.81 mg, 0.097 mmol). The resulting mixture was stirred at room temperature for 16 hr. The crude mixture was diluted with DCM (20 mL) and washed with water (2×20 mL). The organics were dried over $MgSO_4$ and concentrated. The residue was then purified by preparative HPLC (XBridge 30×50 mm 25-50% MeCN/$H_2O$ (5 mM $NH_4OH$)) to afford the title compound as a clear oil (27.5 mg, 0.058 mmol).

LCMS: Rt: 1.11 min (LCMS Method 3) MS m/z 469.5 $[M+H]^+$.

$^1$H NMR (400 MHz, $CD_3OD$) δ 7.23 (dd, J=7.7, 1.4 Hz, 1H), 7.18 (td, J=7.8, 1.7 Hz, 1H), 7.07 (dd, J=8.2, 0.8 Hz, 1H), 6.99 (td, J=7.4, 0.8 Hz, 1H), 5.31 (s, 2H), 4.45-4.23 (m, 2H), 4.03-3.83 (m, 2H), 3.19-3.09 (m, 2H), 3.00 (m, 1H), 2.76-2.61 (m, 1H), 2.55 (s, 3H), 2.24 (m, 1H), 2.12 (m, 2H), 2.05-1.86 (m, 3H), 1.86-1.67 (m, 5H), 1.58 (m, 1H), 1.30-1.17 (m, 4H).

Example 7X: (R)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone or (S)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone

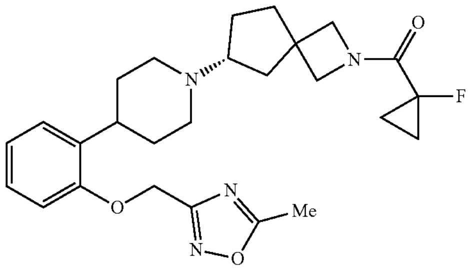

(R)-isomer

-continued

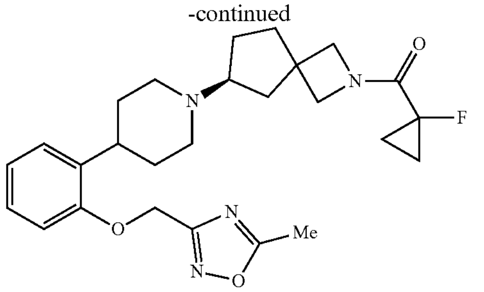

(S)-isomer

-continued

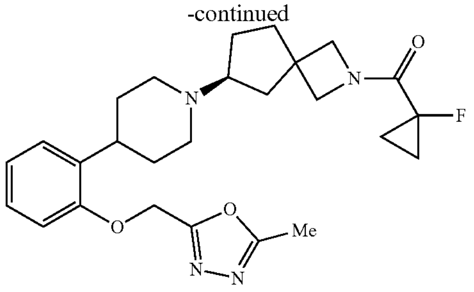

(S)-isomer

To a DMF (1 mL) solution of (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 30 mg, 0.081 mmol) and cesium carbonate (79 mg, 0.242 mmol), was added 3-(chloromethyl)-5-methyl-1,2,4-oxadiazole (12.81 mg, 0.097 mmol). The resulting mixture was stirred at room temperature for 16 hr. The crude mixture was diluted with DCM (20 mL) and washed with water (2×20 mL). The organics were dried over $MgSO_4$ and concentrated. The residue was purified by preparative HPLC (XBridge 30×50 mm 25-50% $MeCN/H_2O$ (5 mM $NH_4OH$)) to afford the title compound as a clear oil (28.2 mg, 0.060 mmol).

LCMS: Rt: 0.71 min (LCMS Method 4) MS m/z 469.2 $[M+H]^+$.

$^1H$ NMR (400 MHz, $CD_3OD$) δ 7.23 (dd, J=7.6, 1.4 Hz, 1H), 7.20-7.15 (m, 1H), 7.11-7.05 (m, 1H), 6.99 (td, J=7.4, 0.8 Hz, 1H), 5.31 (s, 2H), 4.48-4.23 (m, 2H), 4.04-3.82 (m, 2H), 3.19-3.09 (m, 2H), 3.00 (m, 1H), 2.76-2.62 (m, 1H), 2.55 (s, 3H), 2.24 (m, 1H), 2.12 (m, 2H), 2.05-1.86 (m, 3H), 1.78 (m, 5H), 1.58 (m, 1H), 1.32-1.19 (m, 4H).

To a DMF (1 mL) solution of (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17G, 30 mg, 0.081 mmol) and cesium carbonate (79 mg, 0.242 mmol), was added 2-(chloromethyl)-5-methyl-1,3,4-oxadiazole (12.81 mg, 0.097 mmol). The resulting mixture was stirred at room temperature for 16 hr. The crude mixture was diluted with DCM (20 mL) and washed with water (2×20 mL). The organics were dried over $MgSO_4$ and concentrated. The residue was purified by preparative HPLC (XBridge 30×50 mm 25-50% $MeCN/H_2O$ (5 mM $NH_4OH$)) to afford the title compound as a clear oil (29.4 mg, 0.062 mmol).

LCMS: Rt: 2.40 min (LCMS Method 4) MS m/z 469.4 $[M+H]^+$.

$^1H$ NMR (400 MHz, $CD_3OD$) δ 7.21 (dd, J=7.5, 1.4 Hz, 1H), 7.18-7.12 (m, 1H), 7.05 (d, J=7.3 Hz, 1H), 6.96 (td, J=7.4, 0.8 Hz, 1H), 5.18 (s, 2H), 4.45-4.24 (m, 2H), 4.03-3.83 (m, 2H), 3.18-3.10 (m, 2H), 3.04 (m, 1H), 2.75-2.64 (m, 1H), 2.61 (s, 3H), 2.24 (m, 1H), 2.12 (m, 2H), 2.04-1.89 (m, 3H), 1.87-1.66 (m, 5H), 1.58 (m, 1H), 1.31-1.20 (m, 4H).

Example 7Y: (R)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone or (S)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone

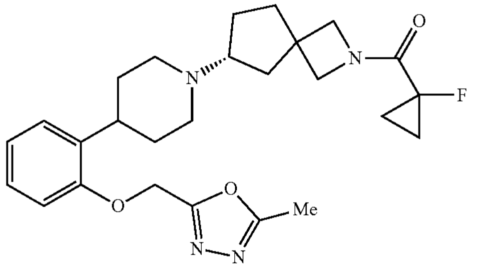

(R)-isomer

Example 7Z: (R)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone or (S)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone

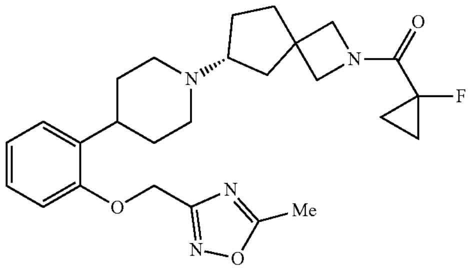

(R)-isomer

-continued

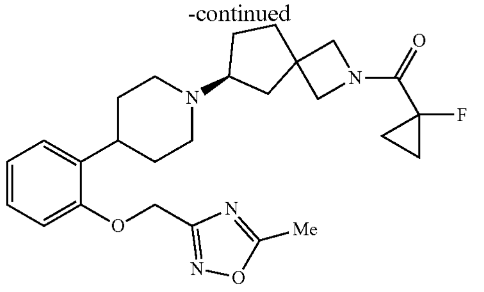

(S)-isomer

To a DMF (1 mL) solution of (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17G, 30 mg, 0.081 mmol) and cesium carbonate (79 mg, 0.242 mmol), was added 3-(chloromethyl)-5-methyl-1,2,4-oxadiazole (12.81 mg, 0.097 mmol). The resulting mixture was stirred at room temperature for 16 hr. The crude mixture was diluted with DCM (20 mL) and washed with water (2×20 mL). The organics were dried over $MgSO_4$ and concentrated. The residue was purified by preparative HPLC (XBridge 30×50 mm 25-50% $MeCN/H_2O$ (5 mM $NH_4OH$)) to afford the title compound as a clear oil (27.5 mg, 0.058 mmol).

LCMS: Rt: 2.39 min (LCMS Method 4) MS m/z 468.9 $[M+H]^+$.

$^1H$ NMR (400 MHz, $CD_3OD$) δ 7.21 (dd, J=7.5, 1.4 Hz, 1H), 7.16 (td, J=7.7, 1.7 Hz, 1H), 7.05 (dd, J=8.2, 0.7 Hz, 1H), 6.96 (td, J=7.4, 0.8 Hz, 1H), 5.18 (s, 2H), 4.44-4.23 (m, 2H), 4.04-3.83 (m, 2H), 3.18-3.10 (m, 2H), 3.04 (m, 1H), 2.68 (q, J=8.3 Hz, 1H), 2.61 (s, 3H), 2.24 (m, 1H), 2.12 (m, 2H), 2.06-1.88 (m, 3H), 1.87-1.66 (m, 5H), 1.57 (m, 1H), 1.32-1.18 (m, 4H).

Example 7AA: (R)-(1-fluorocyclopropyl)(6-(4-(2-(3,3,3-trifluoropropoxy)phenyl)piperidin-1-yl)-2-azaspiro[3.4]octan-2-yl)methanone or (S)-(1-fluorocyclopropyl)(6-(4-(2-(3,3,3-trifluoropropoxy)phenyl)piperidin-1-yl)-2-azaspiro[3.4]octan-2-yl)methanone

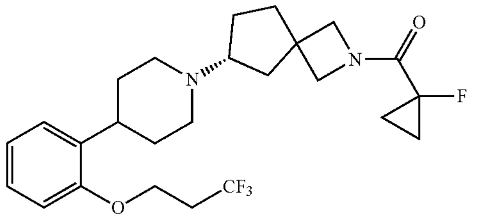

(R)-isomer

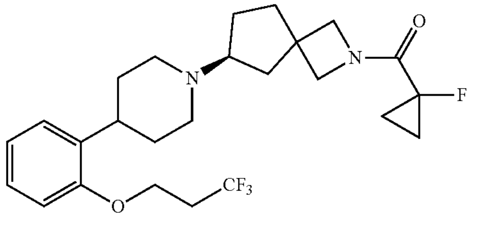

(S)-isomer

To a THF (1 mL) solution of (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 20 mg, 0.054 mmol) was added 3,3,3-trifluoropropan-1-ol (12.25 mg, 0.107 mmol), triphenylphosphine (28.2 mg, 0.107 mmol) and di-tert-butyl azodicarboxylate (24.73 mg, 0.107 mmol). The resulting mixture was stirred at RT for 72 hr. Further 3,3,3-trifluoropropan-1-ol (12.25 mg, 0.107 mmol) and di-tert-butyl azodicarboxylate (24.73 mg, 0.107 mmol) were added at 24 and 48 hr after initializing the reaction. The reaction mixture was passed through a SCX resin cartridge, the cartridge was washed multiple times with DCM and MeOH before eluting with 7N $NH_3$ in MeOH. The MeOH solution was concentrated and the residue was purified by preparative HPLC (XBridge 30×50 mm 45-70% $MeCN/H_2O$ (5 mM $NH_4OH$)) to afford the title compound as a clear oil (3 mg, 0.006 mmol).

LCMS: Rt: 2.77 min (LCMS Method 4) MS m/z 469.3 $[M+H]^+$.

$^1H$ NMR (400 MHz, $CD_3OD$) δ 7.27-7.12 (m, 2H), 6.95 (t, J=7.5 Hz, 2H), 4.48-4.28 (m, 2H), 4.24 (t, J=5.9 Hz, 2H), 4.07-3.86 (m, 2H), 3.17 (dd, J=10.4, 4.9 Hz, 2H), 3.04 (m, 1H), 2.73 (m, 3H), 2.28 (m, 1H), 2.15 (q, J=9.6 Hz, 2H), 1.99 (m, 3H), 1.88-1.48 (m, 6H), 1.36-1.19 (m, 4H).

Example 7BB: (R)-(1-fluorocyclopropyl)(6-(4-(2-(3-hydroxy-3-methylbutoxy)phenyl)piperidin-1-yl)-2-azaspiro[3.4]octan-2-yl)methanone or (S)-(1-fluorocyclopropyl)(6-(4-(2-(3-hydroxy-3-methylbutoxy)phenyl)piperidin-1-yl)-2-azaspiro[3.4]octan-2-yl)methanone

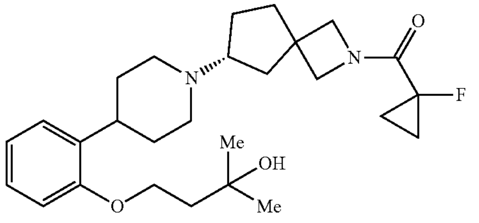

(R)-isomer

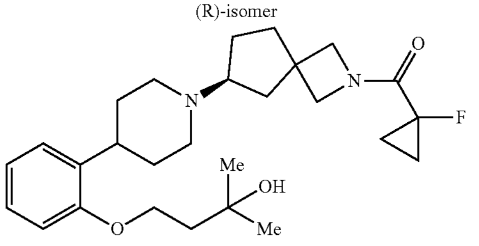

(S)-isomer

To a DMF (0.5 mL) solution of (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 20 mg, 0.054 mmol) and cesium carbonate (52.5 mg, 0.161 mmol), was added 3-hydroxy-3-methylbutyl 4-methylbenzenesulfonate (16.65 mg, 0.064 mmol). The resulting mixture was stirred at room temperature for 16 hr. The crude mixture was diluted with DCM (20 mL) and washed with water (2×20 mL). The organics were dried over $MgSO_4$ and concentrated. The residue was purified by preparative HPLC (XBridge 30×50 mm 35-60% $MeCN/H_2O$ (5 mM $NH_4OH$)) to afford the title compound as a clear oil (19.6 mg, 0.042 mmol).

LCMS: Rt: 2.39 min (LCMS Method 4) MS m/z 459.5 $[M+H]^+$.

$^1H$ NMR (400 MHz, $CD_3OD$) δ 7.26-7.10 (m, 2H), 6.98-6.85 (m, 2H), 4.50-4.23 (m, 2H), 4.14 (t, J=6.7 Hz, 2H), 4.07-3.84 (m, 2H), 3.17 (d, J=11.0 Hz, 2H), 3.03 (m, 1H), 2.78-2.64 (m, 1H), 2.32-2.22 (m, 1H), 2.13 (q, J=10.2 Hz, 2H), 2.07-1.89 (m, 5H), 1.89-1.68 (m, 5H), 1.60 (m, 1H), 1.35-1.22 (m, 10H).

Example 7CC: (R)-(6-(4-(2-(3-hydroxy-3-methylbutoxy)phenyl)piperidin-1-yl)-2-azaspiro[3.4]octan-2-yl)(oxetan-3-yl)methanone

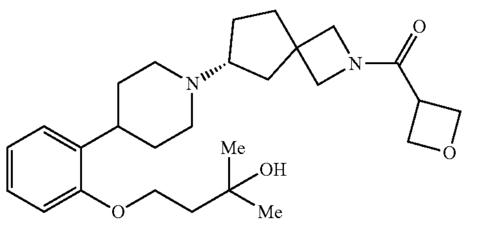 [SMILES: CC(C)(O)CCOc1ccccc1C1CCN([C@@H]2CCC3(C2)CN(C(=O)C2COC2)C3)CC1]

To a DMF (1 mL) solution of ((R)-(6-(4-(2-hydroxyphenyl)piperidin-1-yl)-2-azaspiro[3.4]octan-2-yl)(oxetan-3-yl) methanone) (Intermediate 19A, 20 mg, 0.054 mmol) and cesium carbonate (35.2 mg, 0.108 mmol), was added 3-hydroxy-3-methylbutyl 4-methylbenzenesulfonate (18.13 mg, 0.070 mmol). The resulting mixture was stirred at room temperature for 16 hr. The crude mixture was diluted with DCM (20 mL) and washed with water (2×20 mL). The organics were dried over $MgSO_4$ and concentrated. The residue was purified by preparative HPLC (XBridge 30×50 mm 25-50% $MeCN/H_2O$ (5 mM $NH_4OH$)) to afford the title compound as a clear oil (10.4 mg, 0.023 mmol).

LCMS: Rt: 1.92 min (LCMS Method 4) MS m/z 457.7 $[M+H]^+$.

$^1H$ NMR (400 MHz, $CD_3OD$) δ 7.21-7.13 (m, 2H), 6.97-6.87 (m, 2H), 4.84-4.76 (m, 4H), 4.14 (t, J=6.7 Hz, 2H), 4.08-3.80 (m, 5H), 3.16 (dt, J=9.5, 5.8 Hz, 2H), 3.09-2.96 (m, 1H), 2.70 (m, 1H), 2.22 (dd, J=12.8, 7.3 Hz, 1H), 2.18-2.07 (m, 2H), 2.06-1.68 (m, 10H), 1.67-1.52 (m, 1H), 1.32 (s, 6H).

Example 7DD: (R)-oxetan-3-yl(6-(4-(2-(2-(trifluoromethoxy)ethoxy)phenyl)piperidin-1-yl)-2-azaspiro[3.4]octan-2-yl)methanone

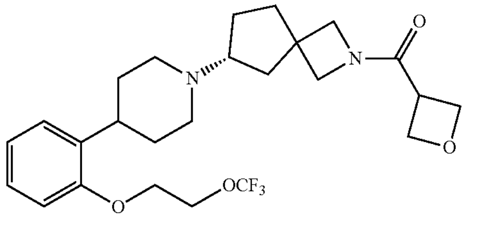 [SMILES: O=C(C1COC1)N1CC2(CC[C@@H](N3CCC(c4ccccc4OCCOC(F)(F)F)CC3)C2)C1]

To a DMF (1 mL) solution of ((R)-(6-(4-(2-hydroxyphenyl)piperidin-1-yl)-2-azaspiro[3.4]octan-2-yl)(oxetan-3-yl) methanone) (Intermediate 19A, 20 mg, 0.054 mmol) and cesium carbonate (35.2 mg, 0.108 mmol), was added 1-bromo-2-(trifluoromethoxy)ethane (20.83 mg, 0.108 mmol). The resulting mixture was stirred at room temperature for 16 hr. The crude mixture was diluted with DCM (20 mL) and washed with water (2×20 mL). The organics were dried over $MgSO_4$ and concentrated. The residue was purified by preparative HPLC (XBridge 30×50 mm 35-60% $MeCN/H_2O$ (5 mM $NH_4OH$)) to afford the title compound as a clear oil (16.4 mg, 0.033 mmol).

LCMS: Rt: 1.34 min (LCMS Method 3) MS m/z 483.3 $[M+H]^+$.

$^1H$ NMR (400 MHz, $CD_3OD$) δ 7.26-7.13 (m, 2H), 6.96 (td, J=8.2, 1.9 Hz, 2H), 4.84-4.75 (m, 4H), 4.42-4.36 (m, 2H), 4.27-4.22 (m, 2H), 4.08-3.80 (m, 5H), 3.23-3.13 (m, 2H), 3.06 (m, 1H), 2.73 (m, 1H), 2.20 (m, 3H), 2.07-1.84 (m, 5H), 1.83-1.69 (m, 3H), 1.67-1.53 (m, 1H).

Example 7EE: (R)-oxetan-3-yl(6-(4-(2-(2-(oxetan-3-yloxy)ethoxy)phenyl)piperidin-1-yl)-2-azaspiro[3.4]octan-2-yl)methanone

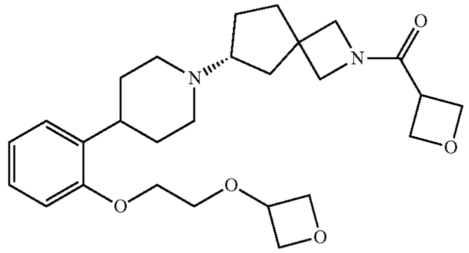 [SMILES: O=C(C1COC1)N1CC2(CC[C@@H](N3CCC(c4ccccc4OCCOC4COC4)CC3)C2)C1]

To a DMF (1 mL) solution of ((R)-(6-(4-(2-hydroxyphenyl)piperidin-1-yl)-2-azaspiro[3.4]octan-2-yl)(oxetan-3-yl) methanone) (Intermediate 19A, 19 mg, 0.051 mmol) and cesium carbonate (33.4 mg, 0.103 mmol), was added 2-(oxetan-3-yloxy)ethyl 4-methylbenzenesulfonate (Intermediate 7L, 15.36 mg, 0.056 mmol). The resulting mixture was stirred at room temperature for 16 hr. The crude mixture was diluted with DCM (20 mL) and washed with water (2×20 mL). The organics were dried over $MgSO_4$ and concentrated. The residue was purified by preparative HPLC (XBridge 30×50 mm 15-40% $MeCN/H_2O$ (5 mM $NH_4OH$)) to afford the title compound as a clear oil (17.6 mg, 0.037 mmol).

LCMS: Rt: 0.97 min (LCMS Method 3) MS m/z 471.3 $[M+H]^+$.

$^1H$ NMR (400 MHz, $CD_3OD$) δ 7.25-7.11 (m, 2H), 6.99-6.89 (m, 2H), 4.86-4.76 (m, 6H), 4.71 (p, J=5.4 Hz, 1H), 4.61 (dd, J=6.7, 5.2 Hz, 2H), 4.13 (dd, J=5.4, 3.6 Hz, 2H), 4.07-3.75 (m, 7H), 3.17 (t, J=9.0 Hz, 2H), 3.07 (m, 1H), 2.71 (m, 1H), 2.29-2.12 (m, 3H), 2.08-1.85 (m, 5H), 1.84-1.70 (m, 3H), 1.67-1.51 (m, 1H).

Example 7FF: (R)-(1-fluorocyclopropyl)(6-(4-(2-(3-methoxy-3-methylbutoxy)phenyl)piperidin-1-yl)-2-azaspiro[3.4]octan-2-yl)methanone or (S)-(1-fluorocyclopropyl)(6-(4-(2-(3-methoxy-3-methylbutoxy)phenyl)piperidin-1-yl)-2-azaspiro[3.4]octan-2-yl)methanone

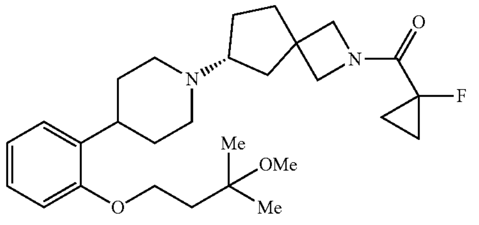

(R)-isomer

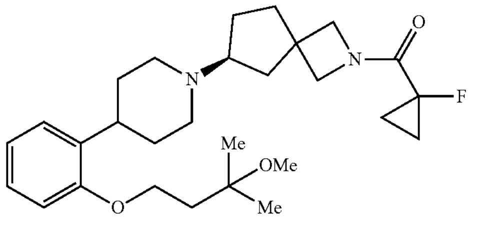

(S)-isomer

To a DMF (0.5 mL) solution of (R)-(1-fluorocyclopropyl)(6-(4-(2-hydroxyphenyl)piperidin-1-yl)-2-azaspiro[3.4]octan-2-yl)methanone or (S)-(1-fluorocyclopropyl)(6-(4-(2-hydroxyphenyl)piperidin-1-yl)-2-azaspiro[3.4]octan-2-yl)methanone (Intermediate 17F, 8 mg, 0.021 mmol) and cesium carbonate (20.99 mg, 0.064 mmol), was added 3-methoxy-3-methylbutyl 4-methylbenzenesulfonate (Intermediate 7M, 7.02 mg, 0.026 mmol). The resulting mixture was stirred at room temperature for 16 hr. The crude mixture was diluted with DCM (20 mL) and washed with water (2×20 mL). The organics were dried over $MgSO_4$ and concentrated. The residue was purified by preparative HPLC (XBridge 30×50 mm 45-70% $MeCN/H_2O$ (5 mM $NH_4OH$)) to afford the title compound as a clear oil (6.8 mg, 0.014 mmol).

LCMS: Rt: 1.50 min (LCMS Method 3) MS m/z 473.4 $[M+H]^+$.

1H NMR (400 MHz, $CD_3OD$) δ 7.26-7.11 (m, 2H), 6.99-6.83 (m, 2H), 4.50-4.25 (m, 2H), 4.09 (t, J=6.8 Hz, 2H), 4.05-3.86 (m, 2H), 3.26 (s, 3H), 3.22-3.13 (m, 2H), 3.04 (m, 1H), 2.78-2.65 (m, 1H), 2.27 (m, 1H), 2.14 (q, J=9.4 Hz, 2H), 2.08-1.88 (m, 5H), 1.88-1.68 (m, 5H), 1.68-1.54 (m, 1H), 1.33-1.22 (m, 10H).

Example 7GG: (R)-oxetan-3-yl(6-(4-(2-(3,3,3-trifluoropropoxy)phenyl)piperidin-1-yl)-2-azaspiro[3.4]octan-2-yl)methanone

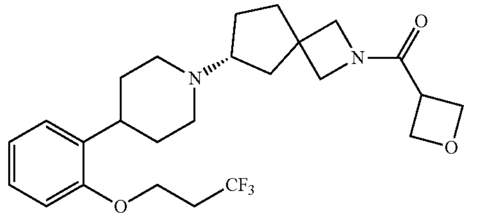 [SMILES: O=C(C1COC1)N1CC2(CC[C@@H](N3CCC(c4ccccc4OCCC(F)(F)F)CC3)C2)C1]

To a EtOH (0.5 mL) solution of ((R)-(6-(4-(2-hydroxyphenyl)piperidin-1-yl)-2-azaspiro[3.4]octan-2-yl)(oxetan-3-yl)methanone) (Intermediate 19A, 24 mg, 0.065 mmol) and potassium carbonate (26.9 mg, 0.194 mmol) was added 3,3,3-trifluoropropyl 4-methylbenzenesulfonate (16.66 mg, 0.062 mmol). The resulting mixture was stirred at 90° C. for 72 hr. The crude mixture was diluted with DCM (20 mL) and washed with water (2×20 mL). The organics were dried over $MgSO_4$ and concentrated. The residue was purified by preparative HPLC (XBridge 30×50 mm 35-60% MeCN/$H_2O$ (5 mM $NH_4OH$)) to afford the title compound as a white solid (7.2 mg, 0.015 mmol).

LCMS: Rt: 2.30 min (LCMS Method 4) MS m/z 467.4 $[M+H]^+$.

$^1$H NMR (400 MHz, $CD_3OD$) δ 7.26-7.13 (m, 2H), 6.96 (t, J=7.3 Hz, 2H), 4.83-4.76 (m, 4H), 4.24 (t, J=5.8 Hz, 2H), 4.08-3.81 (m, 5H), 3.21 (s, 2H), 3.06 (m, 1H), 2.73 (m, 3H), 2.25 (dd, J=12.6, 7.4 Hz, 3H), 2.09-1.56 (m, 9H).

Example 7HH: (R)-(6-(4-(2-(2-methoxy-2-methylpropoxy)phenyl)piperidin-1-yl)-2-azaspiro[3.4]octan-2-yl)(oxetan-3-yl)methanone

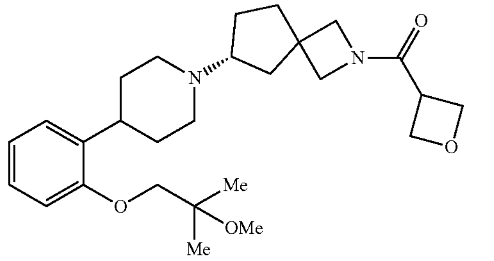 [SMILES: COC(C)(C)COc1ccccc1C1CCN([C@@H]2CCC3(C2)CN(C(=O)C2COC2)C3)CC1]

To a DMF (1 mL) solution of ((R)-(6-(4-(2-hydroxyphenyl)piperidin-1-yl)-2-azaspiro[3.4]octan-2-yl)(oxetan-3-yl)methanone) (20 mg, 0.054 mmol) and cesium carbonate (35.2 mg, 0.108 mmol), was added 1-bromo-2-methoxy-2-methylpropane (18.04 mg, 0.108 mmol). The resulting mixture was stirred at 90° C. for 72 hr. The crude mixture was diluted with DCM (20 mL) and washed with water (2×20 mL). The organics were dried over $MgSO_4$ and concentrated. The residue was purified by preparative HPLC (XBridge 30×50 mm 35-60% MeCN/$H_2O$ (5 mM $NH_4OH$)) to afford the title compound as a clear oil (2.8 mg, 0.006 mmol).

LCMS: Rt: 2.24 min (LCMS Method 3) MS m/z 457.4 $[M+H]^+$.

$^1$H NMR (400 MHz, $CD_3OD$) δ 7.23-7.10 (m, 2H), 6.98-6.87 (m, 2H), 4.84-4.74 (m, 4H), 4.08-3.79 (m, 7H), 3.32 (s, 3H), 3.23-3.02 (m, 3H), 2.71 (q, J=8.3 Hz, 1H), 2.20 (m, 3H), 2.06-1.54 (m, 9H), 1.35 (s, 6H).

Example 7H: (R)-oxetan-3-yl(6-(4-(2-((1-(trifluoromethyl)cyclopropyl)methoxy)phenyl)piperidin-1-yl)-2-azaspiro[3.4]octan-2-yl)methanone

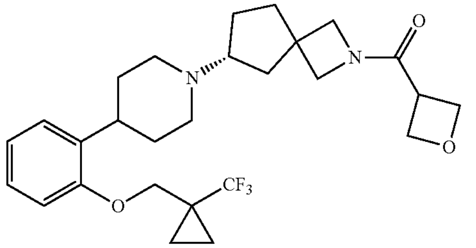 [SMILES: O=C(C1COC1)N1CC2(CC[C@@H](N3CCC(c4ccccc4OCC4(C(F)(F)F)CC4)CC3)C2)C1]

To a EtOH (1 mL) solution of ((R)-(6-(4-(2-hydroxyphenyl)piperidin-1-yl)-2-azaspiro[3.4]octan-2-yl)(oxetan-3-yl) methanone) (Intermediate 19A, 19 mg, 0.051 mmol) and potassium carbonate (14.18 mg, 0.103 mmol) was added (1-(trifluoromethyl)cyclopropyl)methyl benzenesulfonate (13.43 mg, 0.062 mmol). The resulting mixture was stirred at 90° C. for 72 hr. The crude mixture was diluted with DCM (20 mL) and washed with water (2×20 mL). The organics were dried over $MgSO_4$ and concentrated. The residue was purified by preparative HPLC (XBridge 30×50 mm 35-60% $MeCN/H_2O$ (5 mM $NH_4OH$)) to afford the title compound as a white solid (15.5 mg, 0.031 mmol).

LCMS: Rt: 2.50 min (LCMS Method 4) MS m/z 493.2 $[M+H]^+$.

$^1$H NMR (400 MHz, $CD_3OD$) δ 7.24-7.12 (m, 2H), 6.98-6.85 (m, 2H), 4.84-4.74 (m, 4H), 4.10 (s, 2H), 4.07-3.79 (m, 5H), 3.22-3.13 (m, 2H), 3.07 (t, J=12.1 Hz, 1H), 2.77-2.62 (m, 1H), 2.17 (m, 3H), 1.95 (m, 5H), 1.82-1.52 (m, 4H), 1.19-1.12 (m, 2H), 1.03-0.96 (m, 2H).

Example 7JJ: (R)-(6-(4-(2-(2,2-difluoroethoxy)phenyl)piperidin-1-yl)-2-azaspiro[3.4]octan-2-yl) (oxetan-3-yl)methanone

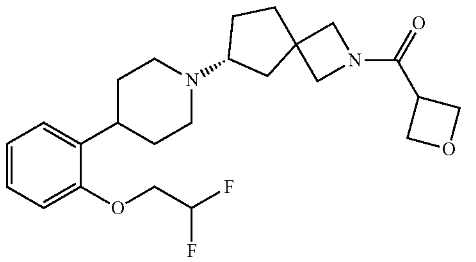 [SMILES: O=C(C1COC1)N1CC2(CC[C@@H](N3CCC(c4ccccc4OCC(F)F)CC3)C2)C1]

To an EtOH (1 mL) solution of ((R)-(6-(4-(2-hydroxyphenyl)piperidin-1-yl)-2-azaspiro[3.4]octan-2-yl)(oxetan-3-yl)methanone) (Intermediate 19A, 20 mg, 0.054 mmol) and potassium carbonate (14.92 mg, 0.108 mmol) was added 2,2-difluoroethyl 4-methylbenzenesulfonate (15.3 mg, 0.065 mmol). The resulting mixture was stirred at 80° C. for 72 hr. The crude mixture was diluted with DCM (20 mL) and washed with water (2×20 mL). The organics were dried over $MgSO_4$ and concentrated. The residue was purified by preparative HPLC (XBridge 30×50 mm 40-55% MeCN/$H_2O$ (5 mM $NH_4OH$)) to afford the title compound as a clear oil (11.7 mg, 0.027 mmol).

LCMS: Rt: 2.15 min (LCMS Method 4) MS m/z 435.4 $[M+H]^+$.

$^1$H NMR (400 MHz, $CD_3OD$) δ 7.27-7.14 (m, 2H), 7.05-6.91 (m, 2H), 6.22 (tt, J=55.0, 3.7 Hz, 1H), 4.84-4.76 (m, 4H), 4.25 (m, 2H), 4.08-3.80 (m, 5H), 3.21-3.10 (m, 2H), 3.03 (m, 1H), 2.71 (m, 1H), 2.27-2.09 (m, 3H), 2.06-1.69 (m, 8H), 1.67-1.52 (m, 1H).

Example 7KK: (R)-oxetan-3-yl(6-(4-(2-(2-(oxetan-3-yl)ethoxy)phenyl)piperidin-1-yl)-2-azaspiro[3.4] octan-2-yl)methanone

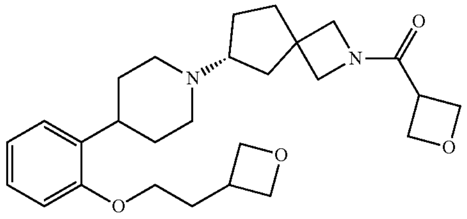 [SMILES: O=C(C1COC1)N1CC2(CC[C@@H](N3CCC(c4ccccc4OCCC4COC4)CC3)C2)C1]

To an EtOH (1 mL) solution of ((R)-(6-(4-(2-hydroxyphenyl)piperidin-1-yl)-2-azaspiro[3.4]octan-2-yl)(oxetan-3-yl)methanone) (Intermediate 19A, 20 mg, 0.054 mmol) and potassium carbonate (14.92 mg, 0.108 mmol) was added 2-(oxetan-3-yl)ethyl 4-methylbenzenesulfonate (16.6 mg, 0.065 mmol). The resulting mixture was stirred at 80° C. for 48 hr. The crude mixture was diluted with DCM (20 mL) and washed with water (2×20 mL). The organics were dried over $MgSO_4$ and concentrated. The residue was purified by preparative HPLC (XBridge 30×50 mm 25-40% MeCN/$H_2O$ (5 mM $NH_4OH$)) to afford the title compound as a clear oil (11.7 mg, 0.027 mmol).

LCMS: Rt: 2.13 min (LCMS Method 4) MS m/z 455.5 $[M+H]^+$.

$^1$H NMR (400 MHz, $CD_3OD$) δ 7.24-7.10 (m, 2H), 6.92 (t, J=7.8 Hz, 2H), 4.84-4.76 (m, 4H), 4.07-3.78 (m, 10H), 3.72 (dd, J=8.6, 5.8 Hz, 1H), 3.24-3.11 (m, 2H), 3.00 (t, J=12.0 Hz, 1H), 2.76 (m, 2H), 2.18 (m, 4H), 2.07-1.68 (m, 9H), 1.67-1.51 (m, 1H).

Example 8A: (S)-(6-(4-(5-chloro-2-methoxyphenyl)piperidin-1-yl)-2-azaspiro[3.4]octan-2-yl)(1-fluorocyclopropyl)methanone or (R)-(6-(4-(5-chloro-2-methoxyphenyl)piperidin-1-yl)-2-azaspiro[3.4]octan-2-yl)(1-fluorocyclopropyl)methanone and Example 8B: (S)-(6-(4-(5-chloro-2-methoxyphenyl)piperidin-1-yl)-2-azaspiro[3.4]octan-2-yl)(1-fluorocyclopropyl)methanone or (R)-(6-(4-(5-chloro-2-methoxyphenyl)piperidin-1-yl)-2-azaspiro[3.4]octan-2-yl)(1-fluorocyclopropyl)methanone

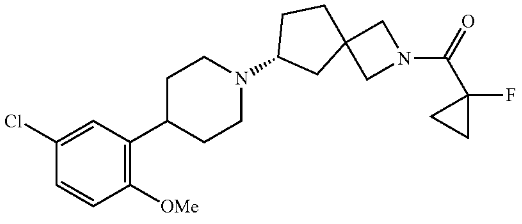

(R)-isomer

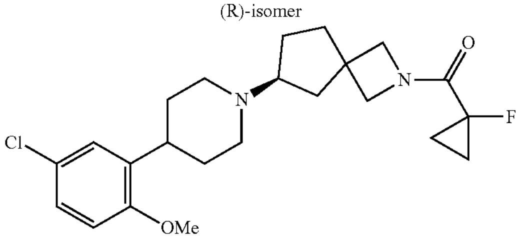

(S)-isomer 1-fluorocyclopropanecarboxylic acid (114 mg, 1.098 mmol) was dissolved in DMF (2 mL) and HATU (417 mg, 1.098 mmol) was added and the reaction was stirred at RT for 20 min. 6-(4-(5-chloro-2-methoxyphenyl)piperidin-1-yl)-2-azaspiro[3.4]octane (Intermediate 18B, 407 mg, 0.998 mmol), was dissolved in DCM (10 mL) and cooled to 0° C. and DIPEA (387 mg, 2.99 mmol) was added and the solution was concentrated. The residue was then dissolved in DMF (4 mL) and added to the initial DMF solution. The reaction was stirred for 2 hr and it was then quenched with water (50 mL). The aq layer was extracted with EtOAc (2×50 mL) and the combined organic layers were dried over $MgSO_4$, filtered and concentrated. The crude was purified by FCC (0-10% MeOH (1% $NH_4OH$)/DCM and the two enantiomers were then separated by chiral chromatography (IC 2×25 cm column, 60 mL/min, 30% MeOH/$CO_2$) to give the faster eluting enantiomer Example 8A (52 mg, 0.117 mmol) and the slower running enantiomer Example 8B (52 mg, 0.117 mmol).

Example 8A

SFC: Rt: 3.52 min (ID 4.6×100 mm, 5-55% MeOH (10 mM $NH_4OH$)/$CO_2$, 5 mL/min)

LCMS: Rt: 1.36 min (LCMS Method 3) MS m/z 421.0 $[M+H]^+$.

$^1$H NMR (400 MHz, $CD_3OD$) δ 7.22-7.09 (m, 2H), 6.99-6.85 (m, 1H), 4.49-4.26 (m, 2H), 4.05-3.86 (m, 2H), 3.83 (s, 3H), 3.23-3.11 (m, 2H), 2.98 (m, 1H), 2.72 (d, J=9.2 Hz, 1H), 2.27 (m, 1H), 2.16 (q, J=10.5 Hz, 2H), 2.08-1.50 (m, 9H), 1.35-1.20 (m, 4H).

Example 8B

SFC: Rt: 3.81 min (ID 4.6×100 mm, 5-55% MeOH (10 mM $NH_4OH$)/$CO_2$, 5 mL/min)

LCMS: Rt: 1.36 min (LCMS Method 3) MS m/z 421.0 $[M+H]^+$.

$^1$H NMR (400 MHz, $CD_3OD$) δ 7.22-7.09 (m, 2H), 6.99-6.85 (m, 1H), 4.49-4.26 (m, 2H), 4.05-3.86 (m, 2H), 3.83 (s, 3H), 3.23-3.11 (m, 2H), 2.98 (tt, J=12.1, 3.8 Hz, 1H), 2.72 (d, J=9.2 Hz, 1H), 2.27 (dt, J=12.8, 6.4 Hz, 1H), 2.16 (q, J=10.5 Hz, 2H), 2.08-1.50 (m, 9H), 1.35-1.20 (m, 4H).

Example 8C: (S)-(6-(4-(2-methoxyphenyl)piperidin-1-yl)-2-azaspiro[3.4]octan-2-yl)(oxetan-3-yl)methanone or (R)-(6-(4-(2-methoxyphenyl)piperidin-1-yl)-2-azaspiro[3.4]octan-2-yl)(oxetan-3-yl)methanone and Example 8D: (S)-(6-(4-(2-methoxyphenyl)piperidin-1-yl)-2-azaspiro[3.4]octan-2-yl)(oxetan-3-yl)methanone or (R)-(6-(4-(2-methoxyphenyl)piperidin-1-yl)-2-azaspiro[3.4]octan-2-yl)(oxetan-3-yl)methanone

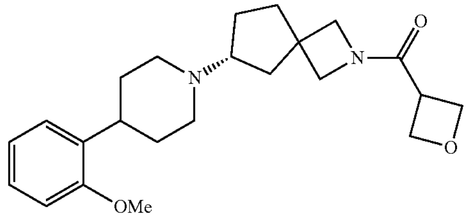

(R)-isomer

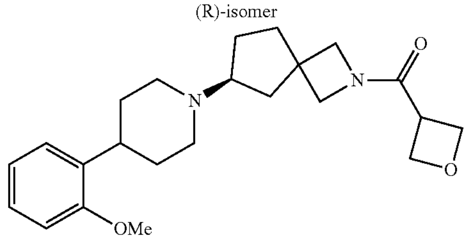

(S)-isomer 6-(4-(2-methoxyphenyl)piperidin-1-yl)-2-azaspiro[3.4]octane (Intermediate 18C, 490 mg, 1.63 mmol), oxetane-3-carboxylic acid (183 mg, 1.79 mmol), DIPEA (632 mg, 4.89 mmol) and TBTU (786 mg, 2.45 mmol) were reacted in a similar manner to Example 8A. The enantiomers were then separated by chiral SFC (OJ-H, 2×25 cm, 10% MeOH (0.1% DEA)/$CO_2$, 75 mL/min). Example 8C, the faster eluting enantiomer was isolated as a white solid (89 mg, 1.63 mmol) and Example 8D, the slower eluting enantiomer was also isolated as a white solid (89 mg, 1.63 mmol).

Example 8C

SFC: Rt: 3.40 min (Chiralpak® IB 4.6×100 mm, 5 uM, 5-55% 1:1 MeOH/IPA (10 mM $NH_4OH$)/$CO_2$ 5 mL/min)

LCMS: Rt: 0.91 min (LCMS Method 3), MS m/z 385.2 $[M+H]^+$.

$^1$H NMR (400 MHz, $CD_3OD$) δ 7.14-7.21 (m, 2H) 6.87-6.96 (m, 2H) 4.76-4.83 (m, 4H) 3.83-4.07 (m, 5H) 3.83 (s, 3H) 3.12-3.21 (m, 2H) 2.95-3.05 (m, 1H) 2.67-2.78 (m, 1H) 2.10-2.28 (m, 3H) 1.87-2.06 (m, 3H) 1.73-1.87 (m, 5H) 1.53-1.67 (m, 1H).

Example 8D

SFC: Rt: 3.55 min (Chiralpak® IB 4.6×100 mm, 5 uM, 5-55% 1:1 MeOH/IPA (10 mM $NH_4OH$)/$CO_2$ 5 mL/min)

LCMS: Rt: 0.92 min (LCMS Method 3), MS m/z 385.4 $[M+H]^+$.

$^1H$ NMR (400 MHz, $CD_3OD$) δ 7.14-7.21 (m, 2H) 6.87-6.96 (m, 2H) 4.77-4.83 (m, 4H) 3.83-4.07 (m, 5H) 3.83 (s, 3H) 3.11-3.21 (m, 2H) 2.94-3.05 (m, 1H) 2.67-2.77 (m, 1H) 2.10-2.26 (m, 3H) 1.86-2.07 (m, 3H) 1.71-1.86 (m, 5H) 1.54-1.67 (m, 1H).

Example 8E: (S)-(6-(4-(2-(difluoromethoxy)phenyl)piperidin-1-yl)-2-azaspiro[3.4]octan-2-yl)(oxetan-3-yl)methanone or (R)-(6-(4-(2-(difluoromethoxy)phenyl)piperidin-1-yl)-2-azaspiro[3.4]octan-2-yl)(oxetan-3-yl)methanone citrate salt and Example 8F: (S)-(6-(4-(2-(difluoromethoxy)phenyl)piperidin-1-yl)-2-azaspiro[3.4]octan-2-yl)(oxetan-3-yl)methanone or (R)-(6-(4-(2-(difluoromethoxy)phenyl)piperidin-1-yl)-2-azaspiro[3.4]octan-2-yl)(oxetan-3-yl)methanone citrate salt

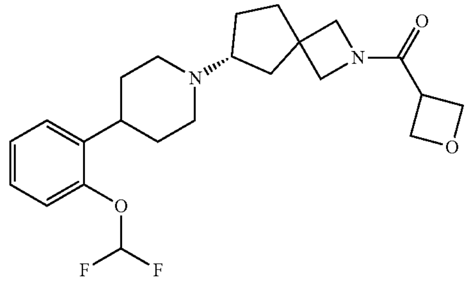

(R)-isomer

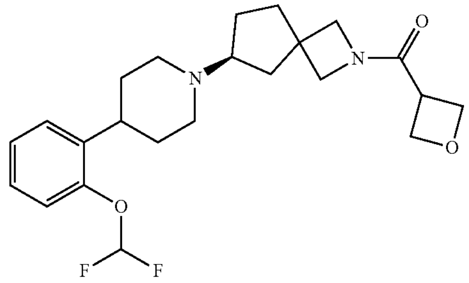

(S)-isomer 6-(4-(2-(trifluoromethoxy)phenyl)piperidin-1-yl)-2-azaspiro[3.4]octane (Intermediate 17D, 763 mg, 2.27 mmol), oxetane-3-carboxylic acid (255 mg, 2.50 mmol), DIPEA (879 mg, 6.80 mmol) and TBTU (1092 mg, 3.40 mmol) were reacted in a similar manner to Example 8A. The enantiomers were separated by SFC (Chiralpak® IG 21×250 mm, 5 uM, 40% MeOH/$CO_2$, 80 g/min) to generate the faster eluting Example 8E (82 mg, 0.195 mmol) and the slower eluting Example 8F (81 mg, 0.193 mmol). Each compound was individually dissolved in MeOH (1 mL) and 0.5M citric acid (0.385 mL, 0.193 mL) was added. The samples were then freeze dried to generate the two examples as citrate salts Example 8E SFC: Rt: 3.89 min (Chiralpak® IG 4.6×100 mm, 5 uM, 5-55% MeOH (10 mM $NH_4OH$)/$CO_2$, 5 mL/min)

LCMS: Rt: 1.05 min (LCMS Method 1), MS m/z 421.4 $[M+H]^+$.

$^1H$ NMR (400 MHz, $CD_3OD$) δ 7.38 (m, 1H), 7.33-7.20 (m, 2H), 7.19-7.13 (m, 1H), 6.87 (m, 1H), 4.82-4.73 (m, 4H), 4.19-3.78 (m, 5H), 3.63 (d, 3H), 3.17-2.96 (m, 2H), 2.92-2.68 (m, 4H), 2.44 (m, 1H), 2.28-1.83 (m, 9H). One proton is obscured by the solvent peak.

Example 8F

SFC: Rt: 4.92 min (Chiralpak® IG 4.6×100 mm, 5 uM, 5-55% MeOH (10 mM $NH_4OH$)/$CO_2$, 5 mL/min)

LCMS: Rt: 2.10 min (LCMS Method 2), MS m/z 421.3 $[M+H]^+$.

$^1H$ NMR (400 MHz, $CD_3OD$) δ 7.46-7.32 (m, 1H), 7.33-7.19 (m, 2H), 7.15 (d, 1H), 6.87 (m, 1H), 4.78 (d, 4H), 4.26-3.75 (m, 5H), 3.63 (d, 3H), 3.07 (s, 2H), 2.91-2.68 (m, 4H), 2.53-2.33 (m, 1H), 2.31-1.78 (m, 9H). One proton is obscured by the solvent peak.

Example 8G: (S)-oxetan-3-yl(6-(4-(2-(trifluoromethoxy)phenyl)piperidin-1-yl)-2-azaspiro[3.4]octan-2-yl)methanone

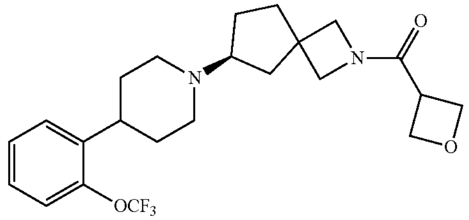 [SMILES: O=C(C1COC1)N1CC2(CC[C@H](N3CCC(c4ccccc4OC(F)(F)F)CC3)C2)C1]

Oxetane-3-carboxylic acid (1.451 g, 14.21 mmol) was dissolved in DMF (40 mL) and TBTU (4.56 g, 14.21 mmol) was added and the reaction was stirred at 50° C. for 20 minutes. Next, 6-(4-(2-(trifluoromethoxy)phenyl)piperidin-1-yl)-2-azaspiro[3.4]octane (Intermediate 18A, 3.65 g, 9.47 mmol) and DIPEA (6.62 mL, 37.9 mmol) dissolved in DCM (30 mL) were added to the reaction. The resulting mixture was stirred at RT for 16 hours. The solvent was then concentrated and the crude was purified by FCC (0-5% MeOH (1% 7N $NH_3$ in MeOH)/DCM) to yield racemic material (2.0 g, 4.56 mmol). This procedure was then repeated on a second batch of 6-(4-(2-(trifluoromethoxy)phenyl)piperidin-1-yl)-2-azaspiro[3.4]octane (Intermediate 18A, 3.65 g, 9.47 mmol) to yield a second batch of purified racemic product (2.0 g, 4.56 mmol). The combined four grams of racemic product were then purified by chiral SFC (Chiralpak® IG 21×250 mm, 5 μM, 40% MeOH/$CO_2$, 80 g/min) to yield the two enantiomers Peak 1 (1.079 g, 2.44 mmol) and Peak 2 (1.129 g, 2.55 mmol). Comparison of the retention time of the faster running enantiomer (Rt=2.22 min Chiralpak® IG-3 3×100 mm, 3 μM, 5-55% MeOH (0.1% $NH_4OH$)/$CO_2$, 2.5 mL/min) and Example 12A (Rt=2.22 min Chiralpak® IG-3 3×100 mm, 3 μM, 5-55% MeOH (0.1% $NH_4OH$)/$CO_2$, 2.5 mL/min) showed them to be equivalent. Therefore, the slower running enantiomer Example 8G (Rt=2.65 min Chiralpak® IG-3 3×100 mm, 3 μM, 5-55% MeOH (0.1% $NH_4OH$)/$CO_2$, 2.5 mL/min) is the (S) enantiomer.

Example 8G

SFC: Rt: 2.65 min (Chiralpak® IG-3 3×100 mm, 3 μM, 5-55% MeOH (0.1% $NH_4OH$)/$CO_2$, 2.5 mL/min).

LCMS: Rt: 2.37 min (LCMS Method 4), MS m/z 439.6 $[M+H]^+$.

$^1H$ NMR (400 MHz, $CD_3OD$) δ 7.43 (d, J=7.6 Hz, 1H), 7.39-7.23 (m, 3H), 4.84-4.75 (m, 4H), 4.10-3.80 (m, 5H), 3.24-3.13 (m, 2H), 2.98 (m, 1H), 2.73 (q, J=7.5 Hz, 1H), 2.28-2.10 (m, 3H), 2.07-1.86 (m, 3H), 1.79 (ddd, J=15.6, 9.3, 4.3 Hz, 5H), 1.68-1.53 (m, 1H).

Example 9A: (R)-(1-fluorocyclopropyl)(6-(4-(2-(trifluoromethoxy)phenyl)piperidin-1-yl)-2-azaspiro[3.4]octan-2-yl)methanone or (S)-(1-fluorocyclopropyl)(6-(4-(2-(trifluoromethoxy)phenyl)piperidin-1-yl)-2-azaspiro[3.4]octan-2-yl)methanone and Example 9B: (R)-(1-fluorocyclopropyl)(6-(4-(2-(trifluoromethoxy)phenyl)piperidin-1-yl)-2-azaspiro[3.4]octan-2-yl)methanone or (S)-(1-fluorocyclopropyl)(6-(4-(2-(trifluoromethoxy)phenyl)piperidin-1-yl)-2-azaspiro[3.4]octan-2-yl)methanone

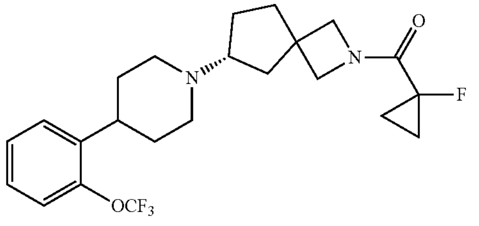

(R)-isomer

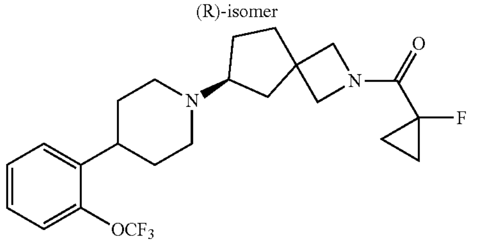

(S)-isomer 2-(1-fluorocyclopropanecarbonyl)-2-azaspiro[3.4]octan-6-one (Intermediate 2C, 280 mg, 1.326 mmol) and 4-(2-(trifluoromethoxy)phenyl)piperidine (Intermediate 16A, 364 mg, 1.484 mmol) were dissolved in DCM (7 mL) and AcOH (0.15 mL, 2.65 mmol) was added. The reaction mixture was stirred at room temperature for 1 hour and then $NaBH(OAc)_3$ (421 mg, 1.988 mmol) was added and the reaction mixture was stirred at room temperature for 18 hours. The reaction mixture was neutralized with saturated aqueous sodium bicarbonate, extracted with DCM, dried over magnesium sulfate, filtered, and concentrated. The crude residue was purified via FCC (0-100% EtOAc/heptanes; 0-25% MeOH/EtOAc; then 100% MeOH) and the enantiomers were separated by chiral SFC (Chiralpak® IC 21×250 mm, 25% MeOH w/10 mM $NH_4OH/CO_2$ 80 g/min). The faster eluting enantiomer afforded Example 9A (80 mg, 0.181 mmol) as an oil and the slower eluting enantiomer afforded Example 9B (80 mg, 0.181 mmol), also as an oil.

Example 9A

SFC RT: 2.55 min (ChiralPak® IC 4.6×100 mm, 5-55% MeOH w/10 mM $NH_4OH/CO_2$ 5 mL/min).

LCMS: RT: 2.88 min (LCMS Method 3) MS m/z 441.3 $[M+H]^+$.

$^1H$ NMR (400 MHz, $CDCl_3$) δ 7.36 (d, J=6.85 Hz, 1H), 7.23 (m, 3H), 4.44-4.21 (m, 2H), 3.90 (s, 2H), 3.19-3.05 (m, 2H), 3.02-2.88 (m, 1H), 2.72-2.56 (m, 1H), 2.27-2.15 (m, 1H), 2.15-1.95 (m, 3H), 1.94-1.87 (m, 1H), 1.80 (s, 5H), 1.37 (m, 2H), 1.29-1.08 (m, 4H).

Example 9B

SFC RT: 2.78 min (ChiralPak® IC 4.6×100 mm, 5-55% MeOH w/l0 mM $NH_4OH/CO_2$ 5 mL/min).

LCMS: RT: 2.87 min (LCMS Method 3) MS m/z 441.0 $[M+H]^+$.

$^1H$ NMR (400 MHz, $CDCl_3$) δ 7.36 (d, J=7.4 Hz, 1H), 7.29-7.18 (m, 3H), 4.41-4.20 (m, 2H), 4.05-3.91 (m, 1H), 3.89 (s, 1H), 3.11 (s, 2H), 2.93 (s, 1H), 2.63 (s, 1H), 2.20 (s, 1H), 2.14-1.85 (m, 5H), 1.79 (s, 5H), 1.35 (m, 2H), 1.30-1.11 (m, 3H).

Example 9C: (R)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone or (S)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone and Example 9D: (R)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone or (S)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone

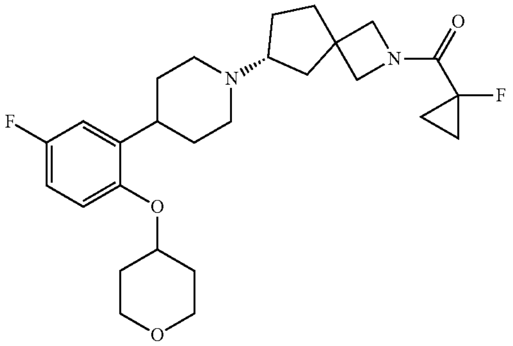

(R)-enantiomer

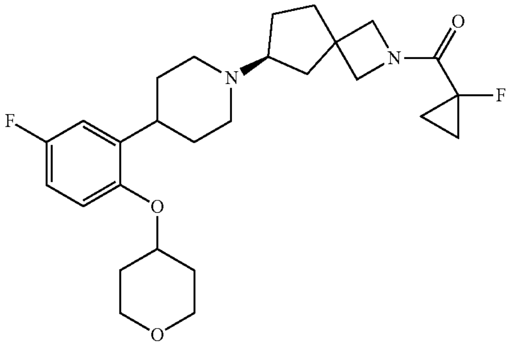

(S)-enantiomer

To a solution of 4-(5-fluoro-2-((tetrahydro-2H-pyran-4-yl)oxy)phenyl)piperidine hydrochloride (Intermediate 16F, 200 mg, 0.716 mmol) in DCE (2 mL) was added DIPEA (246 mg, 1.90 mmol) and 2-(1-fluorocyclopropane-1-carbonyl)-2-azaspiro[3.4]octan-6-one (Intermediate 2C, 200 mg, 0.947 mmol) followed by 4A molecular sieves (200 mg) and $NaBH(OAc)_3$ (671 mg, 3.17 mmol) at RT and stirred for 16 hr. The reaction mixture was diluted with DCM (5 mL) and filtered through a Celite pad, and the filtrate was washed with saturated solution of $NaHCO_3$ (10 mL). The aqueous phase was extracted with DCM (2×5 mL), the combined organic layers were dried by $Na_2SO_4$, filtered and concentrated. The crude was purified by preparative HPLC (XBridge C18 25×150 mm, 10 μM, 5-95% $MeCN/H_2O$, 25 mL/min). The enantiomers were then separated by chiral SFC Chiralpak® IC 30×250 mm, 30% EtOH w/0.1% $NH_4OH/CO_2$ 34 mL/min) to yield peak 1 as Example 9C (51 mg, 0.11 mmol) and peak 2 as Example 9D (52 mg, 0.11 mmol).

Example 9C

SFC RT: 1.53 min (ChiralPak® AD-3 4.6×50 mm, 5-40% EtOH w/0.05% $DEA/CO_2$ 3 mL/min).

LCMS: RT: 1.08 min (LCMS Method 6) MS m/z 475.4 $[M+H]^+$.

$^1H$ NMR (400 MHz, $CD_3OD$) δ 6.97-6.91 (m, 2H), 6.88-6.86 (m, 1H), 4.54-4.51 (m, 1H), 4.36-4.30 (m, 2H), 3.99-3.88 (m, 4H), 3.62-3.57 (m, 2H), 3.20-3.17 (m, 2H), 3.07-3.01 (m, 1H), 2.77-2.73 (m, 1H), 2.28-2.16 (m, 3H), 2.04-2.00 (m, 5H), 1.83-1.60 (m, 8H), 1.28-1.23 (m, 4H).

Example 9D

SFC RT: 1.67 min (ChiralPak® AD-3 4.6×50 mm, 5-40% EtOH w/0.05% $DEA/CO_2$ 3 mL/min).

LCMS: RT: 1.08 min (LCMS Method 6) MS m/z 475.4 $[M+H]^+$.

$^1H$ NMR (400 MHz, $CD_3OD$) δ 6.97-6.91 (m, 2H), 6.87-6.85 (m, 1H), 4.44-4.41 (m, 1H), 4.26-4.20 (m, 2H), 3.89-3.78 (m, 4H), 3.52-3.47 (m, 2H), 3.09-3.06 (m, 2H), 2.96-2.90 (m, 1H), 2.67-2.57 (m, 1H), 2.17-2.16 (m, 3H), 2.07-1.46 (m, 13H), 1.18-1.34 (m, 4H).

Example 9E: (R)-(1-fluorocyclopropyl)(6-(4-(2-((tetrahydro-2H-pyran-4-yl)oxy)phenyl)piperidin-1-yl)-2-azaspiro[3.4]octan-2-yl)methanone or (S)-(1-fluorocyclopropyl)(6-(4-(2-((tetrahydro-2H-pyran-4-yl)oxy)phenyl)piperidin-1-yl)-2-azaspiro[3.4]octan-2-yl)methanone and Example 9F: (R)-(1-fluorocyclopropyl)(6-(4-(2-((tetrahydro-2H-pyran-4-yl)oxy)phenyl)piperidin-1-yl)-2-azaspiro[3.4]octan-2-yl)methanone or (S)-(1-fluorocyclopropyl)(6-(4-(2-((tetrahydro-2H-pyran-4-yl)oxy)phenyl)piperidin-1-yl)-2-azaspiro[3.4]octan-2-yl)methanone

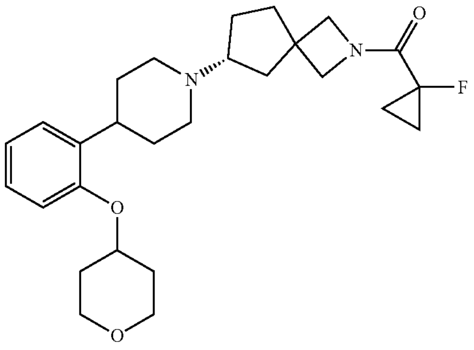

(R)-enantiomer

-continued

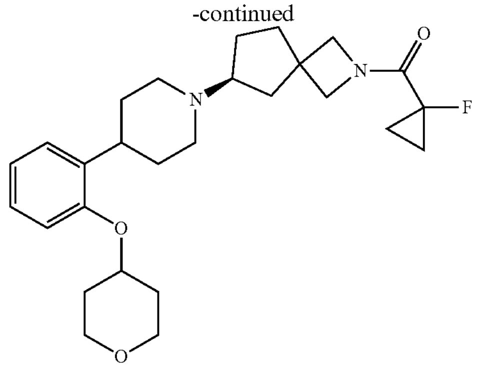

(S)-enantiomer

To a solution of 4-(2-((tetrahydro-2H-pyran-4-yl)oxy)phenyl)piperidine hydrochloride (Intermediate 16G, 150 mg, 0.503 mmol) in DCE (1.5 mL) was added DIPEA (195 mg, 1.512 mmol) and 2-(1-fluorocyclopropane-1-carbonyl)-2-azaspiro[3.4]octan-6-one (Intermediate 2C, 127 mg, 0.604 mmol) followed by 4A molecular sieves (150 mg) and $NaBH(OAc)_3$ (534 mg, 2.52 mmol) at 25° C. The reaction mixture was stirred for 16 hrs at 25° C. and it was then diluted with DCM (5 mL) and filtered through a Celite pad, and the filtrate was washed with saturated solution of $NaHCO_3$ (5 mL). The aqueous phase was extracted with DCM (2×5 mL), and the combined organic phases were dried with $Na_2SO_4$, filtered and concentrated. The residue was then purified by Prep-HPLC (XBridge C18 25×150 mm, 10 μM, 5-95% $MeCN/H_2O$, 25 mL/min) and the enantiomers were separated by chiral SFC (Chiralpak® AD 30×250 mm, 30% EtOH w/0.1% $NH_4OH/CO_2$ 35 mL/min) to yield the initial peak as Example 9E (33 mg, 0.076 mmol) and the trailing peak as Example 9F (35 mg, 0.076 mmol).

Example 9E

SFC RT: 1.52 min (ChiralPak® AD-3 4.6×50 mm, 5-40% EtOH w/0.05% $DEA/CO_2$ 3 mL/min).

LCMS: RT: 1.05 min (LCMS Method 6) MS m/z 457.4 $[M+H]^+$.

$^1H$ NMR (400 MHz, $CD_3OD$) δ 7.14-6.99 (m, 2H), 6.92-6.73 (m, 2H), 4.51-4.49 (m, 2H), 4.39-4.12 (m, 2H), 3.99-3.72 (m, 4H), 3.54-3.52 (m, 2H), 3.09-3.06 (m, 2H), 2.97-2.90 (m, 1H), 2.72-2.53 (m, 1H), 2.19-2.15 (m, 1H), 2.11-2.00 (m, 2H), 1.98-1.87 (m, 4H), 1.78-1.60 (m, 7H), 1.55-1.44 (m, 1H), 1.19-1.12 (m, 4H), Example 9F SFC RT: 1.70 min (ChiralPak® AD-3 4.6×50 mm, 5-40% EtOH w/0.05% $DEA/CO_2$ 3 mL/min).

LCMS: RT: 1.05 min (LCMS Method 6) MS m/z 457.4 $[M+H]^+$.

$^1H$ NMR (400 MHz, $CD_3OD$) δ 7.25-7.11 (m, 2H), 7.02-6.88 (m, 2H), 4.63-4.60 (m, 2H), 4.47-4.29 (m, 2H), 4.06-3.86 (m, 4H), 3.66-3.64 (m, 2H), 3.21-3.18 (m, 2H), 3.10-3.02 (m, 1H), 2.80-2.67 (m, 1H), 2.34-2.24 (m, 1H), 2.24-2.12 (m, 2H), 2.10-1.99 (m, 4H), 1.90-1.71 (m, 7H), 1.68-1.55 (m, 1H), 1.32-1.25 (m, 4H).

Example 9G: (R)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone or (S)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone and Example 9H: (R)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone or (S)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone

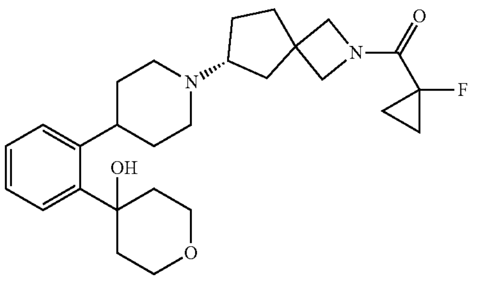

(R)-isomer

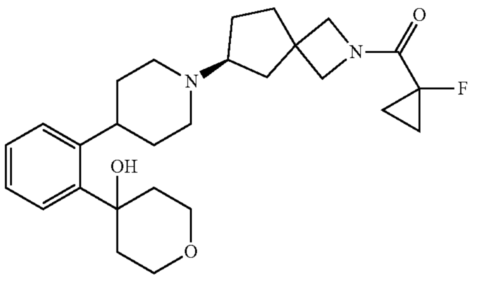

(S)-isomer

To a solution of 4-(2-(piperidin-4-yl)phenyl)tetrahydro-2H-pyran-4-ol hydrochloride (Intermediate 16H, 600 mg, 2.01 mmol) in DCE (6 mL) was 2-(1-fluorocyclopropane-1-carbonyl)-2-azaspiro[3.4]octan-6-one (Intermediate 2C, 234 mg, 1.11 mmol) followed by 4A molecular sieves (600 mg) and $NaBH(OAc)_3$ (1.17 g, 5.53 mmol) at 25° C. The reaction mixture was stirred for 16 hr at 25° C. The reaction mixture was diluted with DCM (10 mL), filtered and the filter cake was washed with DCM (2×5 mL). The combined organic phases were washed with $NaHCO_3$ (10 mL), dried over $Na_2SO_4$, filtered and concentrated. The crude product was purified by FCC (0-50% MeOH/DCM) and enantiomers were then separated by chiral SFC (Chiralpak® AS-H 30×250 mm, 25% MeOH w/0.1% $NH_4OH/CO_2$ 50 g/min) to give Example 9G (37.54 mg, 0.08 mmol), the faster running enantiomer, as off-white solid and Example 9H (52.4 mg, 0.11 mmol) the slower running enantiomer as a white solid.

Example 9G

SFC: Rt: 1.455 min (Chiralpak® IC-3 4.6×50 mm, 40% MeOH (0.05% DEA)/$CO_2$ 3 mL/min).

LCMS: Rt: 0.945 min (LCMS Method 6) MS m/z 457.4 $[M+H]^+$.

$^1H$ NMR (400 MHz, $CD_3OD$) δ 7.42-7.35 (m, 2H), 7.25-7.20 (m, 1H), 7.17-7.12 (m, 1H), 4.46-4.27 (m, 2H), 4.06-3.74 (m, 7H), 3.20-3.17 (m, 2H), 2.86-2.71 (m, 1H), 2.31-2.13 (m, 5H), 2.06-1.97 (m, 3H), 1.96-1.76 (m, 7H), 1.66-1.61 (m, 1H), 1.29-1.23 (m, 4H).

Example 9H

SFC: Rt: 2.001 min (Chiralpak® IC-3 4.6×50 mm, 40% MeOH (0.05% DEA)/$CO_2$ 3 mL/min).

LCMS: Rt: 0.939 min (LCMS Method 6) MS m/z 457.3 $[M+H]^+$.

$^1H$ NMR (400 MHz, $CD_3OD$) δ 7.42-7.36 (m, 2H), 7.26-7.21 (m, 1H), 7.17-7.12 (m, 1H), 4.45-4.28 (m, 2H), 4.06-3.75 (m, 7H), 3.25-3.22 (m, 2H), 2.88-2.84 (m, 1H), 2.33-2.15 (m, 5H), 2.07-1.86 (m, 10H), 1.71-1.62 (m, 1H), 1.29-1.22 (m, 4H).

Example 9I: (R)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone or (S)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone and Example 9J: (R)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone or (S)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone

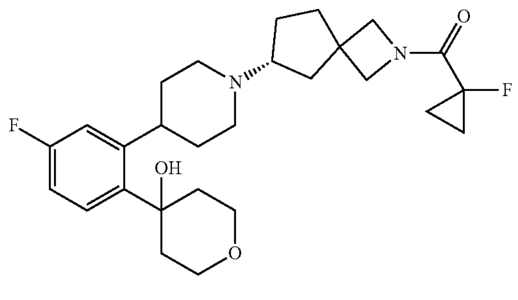

(R)-isomer

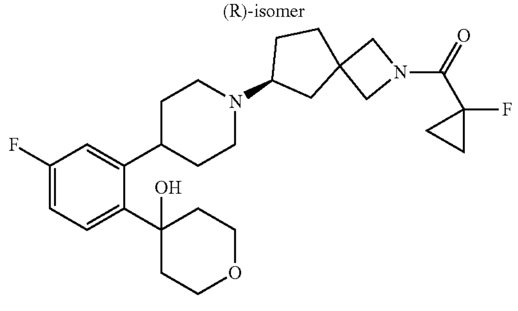

(S)-isomer

To a solution of 4-(4-fluoro-2-(piperidin-4-yl)phenyl)tetrahydro-2H-pyran-4-ol hydrochloride (Intermediate 161, 300 mg, 0.949 mmol) in DCE (3 mL) was added 2-(1-fluorocyclopropane-1-carbonyl)-2-azaspiro[3.4]octan-6-one (Intermediate 2C, 340 mg, 1.61 mmol) followed by 4A molecular sieves (300 mg) and $NaBH(OAc)_3$ (1133 mg, 5.35 mmol) at 25° C. The reaction mixture was stirred for 16 hr at 25° C. and it was then diluted with DCM (10 mL), filtered through a Celite pad, and the filtrate was washed with saturated solution of $NaHCO_3$ (10 mL). The aqueous phase was extracted with DCM (2×10 mL) and the combined organic phases were dried with $Na_2SO_4$, filtered and concentrated. The crude was purified by preparative HPLC (XBridge 25×150 mm 5-95% $MeCN/H_2O$ (10 mM $NH_4HCO_3$) 25 mL/min), and enantiomers were separated by chiral SFC (Chiralpak® AD-H 30×250 mm, 30% EtOH w/0.1% $NH_4OH/CO_2$ 60 g/min). The faster running enantiomer was isolated as Example 9I (23 mg, 0.49 mmol) as a brown gum and the slower running enantiomer was isolated as Example 9J (27 mg, 0.56 mmol) as a brown gum.

Example 9I

SFC: Rt: 1.406 min (Chiralpak® AD-3 4.6×50 mm, 5-40% EtOH (0.05% DEA)/$CO_2$ 3 mL/min).

LCMS: Rt: 0.949 min (LCMS Method 6) MS m/z 475.4 $[M+H]^+$.

$^1$H NMR (400 MHz, $CD_3OD$) δ 7.45-7.41 (m, 1H), 7.12-7.08 (m, 1H), 6.95-6.82 (m, 1H), 4.51-4.27 (m, 2H), 4.08-3.89 (m, 4H), 3.88-3.75 (m, 3H), 3.26-3.14 (m, 2H), 2.95-2.67 (m, 1H), 2.34-2.12 (m, 5H), 2.08-1.79 (m, 10H), 1.70-1.58 (m, 1H), 1.32-1.24 (m, 4H).

Example 9J

SFC: Rt: 1.490 min (Chiralpak® AD-3 4.6×50 mm, 5-40% EtOH (0.05% DEA)/$CO_2$ 3 mL/min).

LCMS: Rt: 0.950 min (LCMS Method 6) MS m/z 475.4 $[M+H]^+$.

$^1$H NMR (400 MHz, $CD_3OD$) δ 7.45-7.43 (m, 1H), 7.12-7.08 (m, 1H), 6.94-6.81 (m, 1H), 4.50-4.24 (m, 2H), 4.11-3.71 (m, 7H), 3.28-3.12 (m, 2H), 2.92-2.71 (m, 1H), 2.36-2.10 (m, 5H), 2.09-1.78 (m, 10H), 1.71-1.55 (m, 1H), 1.32-1.24 (m, 4H).

Example 9K: (R)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone or (S)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone and Example 9L: (R)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone or (S)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone

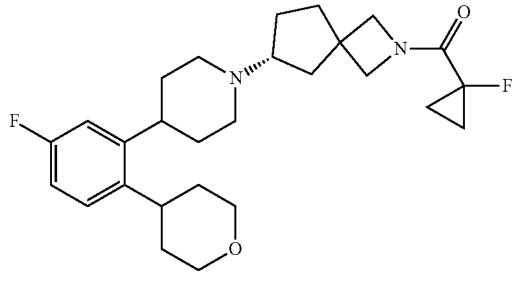

(R)-isomer

-continued

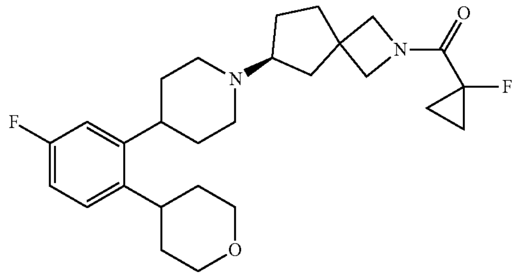

(S)-isomer

To a solution of 4-(5-fluoro-2-(tetrahydro-2H-pyran-4-yl)phenyl)piperidine trifluoroacetate (Intermediate 16J, 250 mg, 0.693 mmol) in DCE (3.0 mL) was added DIPEA (459 mg, 3.55 mmol) and 2-(1-fluorocyclopropane-1-carbonyl)-2-azaspiro[3.4]octan-6-one (Intermediate 2C, 150 mg, 0.71 mmol) followed by 4A molecular sieves (150 mg) and $NaBH(OAc)_3$ (753 mg, 3.55 mmol) at 25° C. The reaction mixture was stirred for 16 hr at 25° C. The reaction mixture was diluted with DCM (5 mL) and filtered, the filter cake was washed with DCM (2×10 mL). The combined organic phases were washed with $NaHCO_3$ (10 mL), dried with $Na_2SO_4$, filtered and concentrated. The crude product was purified by preparative HPLC (XBridge 25×150 mm 5-95% $MeCN/H_2O$ (0.05% mM $NH_4HCO_3$) 25 mL/min) and further by preparative HPLC (XBridge 25×150 mm 5-95% $MeCN/H_2O$ (10 mM $NH_4OH$) 25 mL/min), and enantiomers were separated by chiral SFC (Chiralpak® AD-H 30×250 mm, 30% EtOH w/0.1% $NH_4OH/CO_2$ 60 g/min) to give the faster running enantiomer as Example 9K (44.46 mg, 0.097 mmol) as a white solid and the slower running enantiomer as Example 9L (59.97 mg, 0.130 mmol) as a white solid.

Example 9K

SFC: Rt: 1.310 min (Chiralpak® AD-3 4.6×50 mm, 5-40% EtOH (0.05% DEA)/$CO_2$ 3 mL/min).

LCMS: Rt: 1.006 min (LCMS Method 6) MS m/z 459.5 $[M+H]^+$.

$^1$H NMR (400 MHz, $CD_3OD$) δ 7.28-7.25 (m, 1H), 6.99-6.96 (m, 2H), 4.32-4.31 (m, 2H), 4.05-4.02 (m, 4H), 3.99-3.90 (m, 2H), 3.88-3.56 (m, 2H), 3.19-3.16 (m, 1H), 2.99-2.88 (m, 1H), 2.81-2.68 (m, 1H), 2.32-2.15 (m, 3H), 1.84-1.80 (m, 3H), 1.80-1.79 (m, 7H), 1.64-1.60 (m, 3H), 1.28-1.23 (m, 4H).

Example 9L

SFC: Rt: 1.418 min (Chiralpak® AD-3 4.6×50 mm, 5-40% EtOH (0.05% DEA)/$CO_2$ 3 mL/min).

LCMS: Rt: 1.003 min (LCMS Method 6) MS m/z 459.5 $[M+H]^+$.

$^1$H NMR (400 MHz, $CD_3OD$) δ 7.29-7.25 (m, 1H), 6.99-6.96 (m, 2H), 4.45-4.32 (m, 2H), 4.06-4.00 (m, 4H), 3.64-3.56 (m, 2H), 3.28-3.19 (m, 2H), 3.16-3.03 (m, 1H), 3.01-2.92 (m, 1H), 2.83 (d, J=7.2 Hz, 1H), 2.31-2.28 (m, 3H), 2.08-1.91 (m, 3H), 1.89-1.76 (m, 7H), 1.69-1.58 (m, 3H), 1.28-1.23 (m, 4H).

Example 9M: (S)-(1-fluorocyclopropyl)(6-(4-(2-(tetrahydro-2H-pyran-4-yl)phenyl)piperidin-1-yl)-2-azaspiro[3.4]octan-2-yl)methanone

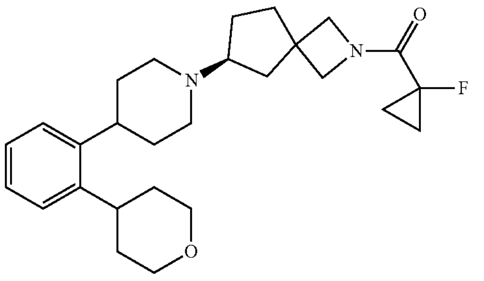 [SMILES: O=C(N1CC2(CC[C@H](N3CCC(c4ccccc4C4CCOCC4)CC3)C2)C1)C1(F)CC1]

To a solution of 4-(2-(tetrahydro-2H-pyran-4-yl)phenyl) piperidine hydrochloride (Intermediate 16N, 150 mg, 0.539 mmol) in DCE (1.5 mL) was added DIPEA (205 mg, 1.59 mmol) and 2-(1-fluorocyclopropane-1-carbonyl)-2-azaspiro [3.4]octan-6-one (Intermediate 2C, 112 mg, 0.53 mmol) followed by 4A molecular sieves (150 mg) and NaBH $(OAc)_3$ (562 mg, 2.65 mmol) at 25° C. The reaction mixture was stirred for 16 hr at 25° C. The reaction mixture was then diluted with DCM (5 mL) and filtered through a Celite pad, and the filtrate was washed with saturated solution of $NaHCO_3$ (10 mL), the aqueous phase was extracted with DCM (2×5 mL) and the combined organic phases were dried over $Na_2SO_4$, filtered and concentrated. The crude was purified by preparative HPLC (XBridge 25×150 mm 5-95% $MeCN/H_2O$ (0.05% mM $NH_4HCO_3$)), and enantiomers were separated by chiral SFC (Chiralpak® AD-3 4.6×50 mm, 5-40% EtOH w/0.05% $DEA/CO_2$ 3 mL/min). Comparison of the retention time of the slower running enantiomer (Rt: 3.55 min Chiralpak® IC-3 3×100 mm, 3 μM 5-55% MeOH (0.1% $NH_4OH)/CO_2$ 3 mL/min) and Example 6E (Rt: 3.55 min Chiralpak® IC-3 3×100 mm, 3 M 5-55% MeOH (0.1% $NH_4OH)/CO_2$ 3 mL/min) showed them to be equivalent. Based on this, the faster running enantiomer is the (50 mg, 0.11 mmol) is the title compound.

Example 9M

SFC: Rt: 3.27 min (Chiralpak® IC-3 3×100 mm, 3 M 5-55% MeOH (0.1% $NH_4OH)/CO_2$ 3 mL/min)

LCMS: Rt: 0.989 min (LCMS Method 6) MS m/z 441.5 $[M+H]^+$.

$^1H$ NMR (400 MHz, $CD_3OD$) δ 7.30-7.22 (m, 2H), 7.20-7.12 (m, 2H), 4.47-4.27 (m, 2H), 4.11-3.87 (m, 4H), 3.63-3.57 (m, 2H), 3.23-3.06 (m, 3H), 2.98-2.87 (m, 1H), 2.82-2.69 (m, 1H), 2.31-2.15 (m, 3H), 2.05-1.73 (m, 10H), 1.70-1.55 (m, 3H), 1.31-1.21 (m, 4H)

Example 10A: (R)-6-(4-(5-fluoro-2-((tetrahydro-2H-pyran-4-yl)oxy)phenyl)piperidin-1-yl)-2-(5-fluoro-pyridin-3-yl)-2-azaspiro[3.4]octane or (S)-6-(4-(5-fluoro-2-((tetrahydro-2H-pyran-4-yl)oxy)phenyl) piperidin-1-yl)-2-(5-fluoropyridin-3-yl)-2-azaspiro [3.4]octane and Example 10B: (R)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane or (S)-6-(4-(5-fluoro-2-((tetrahydro-2H-pyran-4-yl) oxy)phenyl)piperidin-1-yl)-2-(5-fluoropyridin-3-yl)-2-azaspiro[3.4]octane

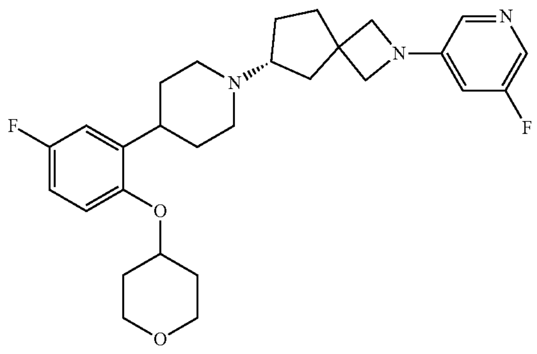

(R)-isomer

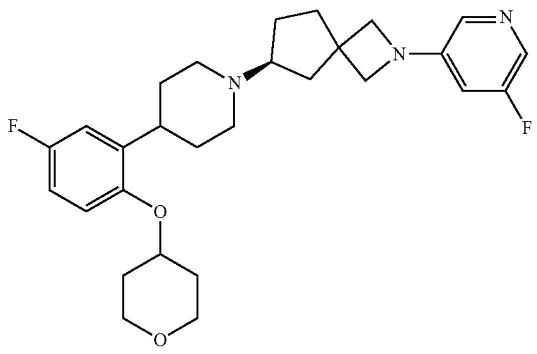

(S)-isomer

To a solution of 6-(4-(5-fluoro-2-((tetrahydro-2H-pyran-4-yl)oxy)phenyl)piperidin-1-yl)-2-azaspiro[3.4]octane (Intermediate 18G, 400 mg, 1.07 mmol) in toluene (4 mL) was added 3-bromo-5-fluoropyridine (420 mg, 2.39 mmol), $Cs_2CO_3$ (1.56 g, 4.78 mmol) and RuPhos Pd G2 (124 mg, 0.16 mmol) at 25° C. and then $N_2$ was blown into the vial for 1 minute. The reaction was stirred at 120° C. for 2 hr. The reaction mixture was quenched with $H_2O$ (10 mL) and extracted with EtOAc (3×5 mL), washed with saturation solution of NaCl (10 mL), dried over $Na_2SO_4$, filtered and concentrated. The crude product was purified by FCC (0-50% MeOH/DCM) and further purified by preparative HPLC (XBridge 25×150 mm 5-95% $MeCN/H_2O$ (0.05% mM $NH_4HCO_3$)). The enantiomers were then separated by chiral SFC (Chiralpak® AD 30×250 mm, 50% EtOH w/0.1% $NH_4OH/CO_2$ 70 g/min) to give the faster running enantiomer as Example 10A (58.95 mg, 0.12 mmol) as a yellow solid and the slower running enantiomer as Example 10B (61.56 mg, 0.13 mmol) as a yellow solid.

Example 10A

SFC: Rt: 2.111 min (Chiralpak® AD-3 4.6×50 mm, 5-40% EtOH (0.05% DEA)/$CO_2$ 3 mL/min).

LCMS: Rt: 1.132 min (LCMS Method 6) MS m/z 484.4 $[M+H]^+$.

$^1H$ NMR (400 MHz, $CD_3OD$) δ 7.72 (d, J=2.4 Hz, 1H), 7.58-7.57 (m, 1H), 6.96-6.94 (m, 2H), 6.93-6.91 (m, 1H), 6.85-6.63 (m, 1H), 4.53-4.49 (m, 1H), 3.94-3.90 (m, 4H), 3.81-3.75 (m, 2H), 3.59-3.18 (m, 2H), 3.18 (t, J=9.8 Hz, 2H), 3.03 (br s, 1H), 2.75 (t, J=8.0 Hz, 1H), 2.28-2.16 (m, 1H), 2.23-2.12 (m, 2H), 2.08-1.92 (m, 5H), 1.91-1.79 (m, 3H), 1.74-1.67 (m, 5H)

Example 10B

SFC: Rt: 2.146 min (Chiralpak® AD-3 4.6×50 mm, 5-40% EtOH (0.05% DEA)/$CO_2$ 3 mL/min).

LCMS: Rt: 1.155 min (LCMS Method 6) MS m/z 484.4 $[M+H]^+$.

$^1H$ NMR (400 MHz, $CD_3OD$) δ 7.73 (d, J=2.4 Hz, 1H), 7.64-7.55 (m, 1H), 7.00-6.91 (m, 2H), 6.89-6.82 (m, 1H), 6.67-6.64 (m, 1H), 4.53-4.52 (m, 1H), 3.93-3.91 (m, 4H), 3.87-3.78 (m, 2H), 3.62-3.19 (m, 2H), 3.16-3.13 (m, 2H), 3.12-2.97 (m, 1H), 2.83-2.69 (m, 1H), 2.29-2.04 (m, 1H), 2.17 (d, J=9.8 Hz, 2H), 2.09-1.94 (m, 5H), 1.89-1.78 (m, 3H), 1.75-1.69 (m, 5H).

Example 10C: (R)-6-(4-(5-fluoro-2-(tetrahydro-2H-pyran-4-yl)phenyl)piperidin-1-yl)-2-(pyrimidin-5-yl)-2-azaspiro[3.4]octane or (S)-6-(4-(5-fluoro-2-(tetrahydro-2H-pyran-4-yl)phenyl)piperidin-1-yl)-2-(pyrimidin-5-yl)-2-azaspiro[3.4]octane and Example 10D: (R)-6-(4-(5-fluoro-2-(tetrahydro-2H-pyran-4-yl)phenyl)piperidin-1-yl)-2-(pyrimidin-5-yl)-2-azaspiro[3.4]octane or (S)-6-(4-(5-fluoro-2-(tetrahydro-2H-pyran-4-yl)phenyl)piperidin-1-yl)-2-(pyrimidin-5-yl)-2-azaspiro[3.4]octane

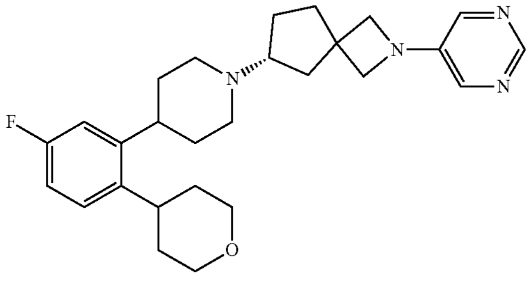

(R)-isomer

-continued

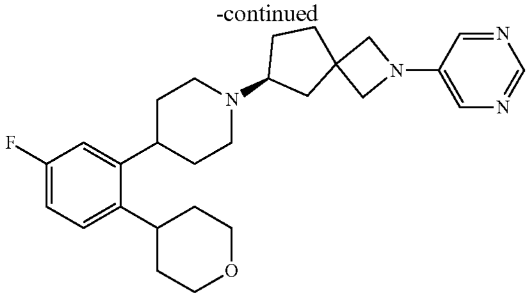

(S)-isomer

To the solution of 6-(4-(5-fluoro-2-(tetrahydro-2H-pyran-4-yl)phenyl)piperidin-1-yl)-2-azaspiro[3.4]octane (Intermediate 18E, 400 mg, 1.075 mmol) in toluene (4 mL) was added $Cs_2CO_3$ (1.9 g, 4.28 mmol), 5-bromopyrimidine (853 mg, 5.37 mmol) and RuPhos Pd G2 (78 mg, 0.11 mmol). The reaction mixture was stirred for 2 hr at 110° C. under $N_2$. The reaction mixture was then diluted with $H_2O$ (5 mL), and extracted with EtOAc (3×5 mL). The combined organic phases were dried over $Na_2SO_4$, filtered and concentrated. The residue was purified by FCC (0-30% MeOH/DCM) and the material was further purified by preparative HPLC (XBridge 25×150 mm 5-95% $MeCN/H_2O$ (0.05% mM $NH_4HCO_3$). The enantiomers were then separated by chiral SFC (Chiralpak® AS 30×250 mm, 30% IPA w/0.1% $NH_4OH/CO_2$ 60 g/min) to give the faster running enantiomer as Example 10C (89.77 mg, 0.078 mmol) as a white solid and the slower running enantiomer as Example 10D (94.67 mg, 0.210 mmol) as a white solid.

Example 10C

SFC: Rt: 2.013 min (Chiralpak® AD-3 4.6×50 mm, 5-40% EtOH (0.05% DEA)/$CO_2$ 3 mL/min).

LCMS: Rt: 0.989 min (LCMS Method 6) MS m/z 451.4 $[M+H]^+$.

$^1H$ NMR (400 MHz, $CD_3OD$) δ 8.48 (s, 1H), 8.01 (s, 2H), 7.29-7.25 (m, 1H), 7.00-6.96 (m, 1H), 6.90-6.89 (m, 1H), 4.06-4.02 (m, 2H), 3.94-3.92 (m, 2H), 3.87-3.85 (m, 2H), 3.62-3.59 (m, 2H), 3.23-3.15 (m, 2H), 3.12-3.04 (m, 1H), 2.99-2.89 (m, 1H), 2.84-2.72 (m, 1H), 2.34-2.18 (m, 3H), 2.09-1.95 (m, 3H), 1.87-1.75 (m, 7H), 1.64-1.61 (m, 3H).

Example 10D

SFC: Rt: 1.902 min (Chiralpak® AD-3 4.6×50 mm, 5-40% EtOH (0.05% DEA)/$CO_2$ 3 mL/min).

LCMS: Rt: 0.993 min (LCMS Method 6) MS m/z 451.4 $[M+H]^+$.

$^1H$ NMR (400 MHz, $CD_3OD$) δ 8.48 (s, 1H), 8.01 (s, 2H), 7.29-7.25 (m, 1H), 7.00-6.96 (m, 1H), 6.90-6.89 (m, 1H), 4.05-4.02 (m, 2H), 3.96-3.90 (m, 2H), 3.89-3.83 (m, 2H), 3.63-3.56 (m, 2H), 3.22-3.17 (m, 2H), 3.12-3.04 (m, 1H), 3.00-2.88 (m, 1H), 2.83-2.75 (m, 1H), 2.34-2.19 (m, 3H), 2.10-1.96 (m, 3H), 1.87-1.76 (m, 7H), 1.64-1.61 (m, 3H).

Example 10E: (R)-6-(4-(2-((2-oxaspiro[3.3]heptan-6-yl)oxy)-5-fluorophenyl)piperidin-1-yl)-2-(pyrimidin-5-yl)-2-azaspiro[3.4]octane or (S)-6-(4-(2-((2-oxaspiro[3.3]heptan-6-yl)oxy)-5-fluorophenyl)piperidin-1-yl)-2-(pyrimidin-5-yl)-2-azaspiro[3.4]octane and Example 10F: (R)-6-(4-(2-((2-oxaspiro[3.3]heptan-6-yl)oxy)-5-fluorophenyl)piperidin-1-yl)-2-(pyrimidin-5-yl)-2-azaspiro[3.4]octane or (S)-6-(4-(2-((2-oxaspiro[3.3]heptan-6-yl)oxy)-5-fluorophenyl)piperidin-1-yl)-2-(pyrimidin-5-yl)-2-azaspiro[3.4]octane

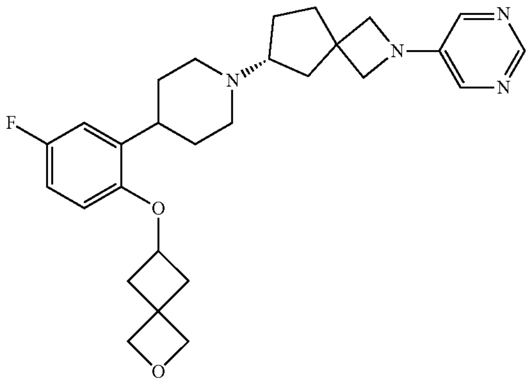

(R)-isomer

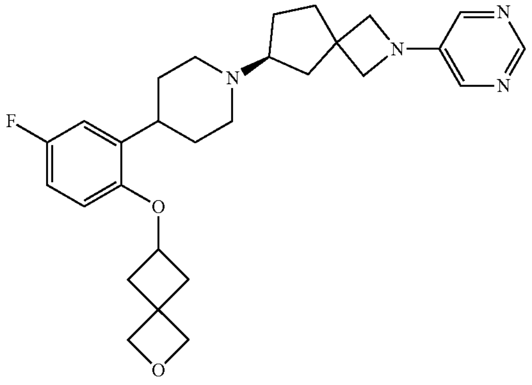

(S)-isomer

To a solution of 6-(4-(2-((2-oxaspiro[3.3]heptan-6-yl)oxy)-5-fluorophenyl)piperidin-1-yl)-2-azaspiro[3.4]octane (Intermediate 18F, 100 mg, 0.209 mmol) in toluene (1 mL) was added 5-bromopyrimidine (198 mg, 1.25 mmol), $Cs_2CO_3$ (407 mg, 1.25 mmol) and RuPhos Pd G2 (23 mg, 0.03 mmol). The reaction mixture was stirred for 2 hr at 110° C. under $N_2$ and the reaction mixture was diluted with $H_2O$ (3 mL), and then extracted with EtOAc (3×5 mL). The combined organic phases were dried over $Na_2SO_4$, filtered and concentrated and the crude was purified by FCC (0-20% MeOH/DCM). The material was further purified by preparative HPLC (XBridge 25×150 mm 5-95% MeCN/$H_2O$ (0.05% mM $NH_4HCO_3$)) and the enantiomers were separated by chiral SFC (Chiralpak® AS 30×250 mm, 35% IPA w/0.1% $NH_4OH/CO_2$ 60 g/min) to give the faster running enantiomer as Example 10E (3.45 mg, 0.007 mmol) as a brown gum and the slower running enantiomer as Example 10F (6.94 mg, 0.014 mmol) as a brown gum.

Example 10E

SFC: Rt: 1.674 min (Chiralpak® AS-3 4.6×50 mm, 5-40% IPA (0.05% DEA)/$CO_2$ 3 mL/min).

LCMS: Rt: 1.014 min (LCMS Method 6) MS m/z 479.4 $[M+H]^+$.

$^1H$ NMR (400 MHz, $CD_3OD$) δ 8.50 (s, 1H), 8.03 (s, 2H), 6.95-6.92 (m, 1H), 6.89-6.81 (m, 1H), 6.75-6.72 (m, 1H), 4.78 (s, 2H), 4.70 (s, 2H), 4.59-4.52 (m, 1H), 3.98-3.92 (m, 2H), 3.91-3.85 (m, 2H), 3.24-3.16 (m, 2H), 3.00-2.93 (m, 1H), 2.86-2.75 (m, 3H), 2.35-2.30 (m, 3H), 2.25-2.14 (m, 2H), 2.10-1.97 (m, 3H), 1.88-1.81 (m, 3H), 1.77-1.62 (m, 3H)

Example 10F

SFC: Rt: 1.842 min (Chiralpak® AS-3 4.6×50 mm, 5-40% IPA (0.05% DEA)/$CO_2$ 3 mL/min).

LCMS: Rt: 1.028 min (LCMS Method 6) MS m/z 479.4 $[M+H]^+$.

$^1H$ NMR (400 MHz, $CD_3OD$) δ 8.50 (s, 1H), 8.03 (s, 2H), 6.95-6.92 (m, 1H), 6.88-6.82 (m, 1H), 6.75-6.71 (m, 1H), 4.78 (s, 2H), 4.70 (s, 2H), 4.57-4.54 (m, 1H), 3.98-3.92 (m, 2H), 3.90-3.85 (m, 2H), 3.23-3.15 (m, 2H), 2.99-2.93 (m, 1H), 2.86-2.80 (m, 2H), 2.78-2.71 (m, 1H), 2.35-2.29 (m, 3H), 2.20-2.13 (m, 2H), 2.09-1.97 (m, 3H), 1.87-1.81 (m, 3H), 1.76-1.61 (m, 3H).

Example 10G: (R)-6-(4-(5-fluoro-2-((tetrahydro-2H-pyran-4-yl)oxy)phenyl)piperidin-1-yl)-2-(pyrimidin-5-yl)-2-azaspiro[3.4]octane or (S)-6-(4-(5-fluoro-2-((tetrahydro-2H-pyran-4-yl)oxy)phenyl)piperidin-1-yl)-2-(pyrimidin-5-yl)-2-azaspiro[3.4]octane and Example 10H: (R)-6-(4-(5-fluoro-2-((tetrahydro-2H-pyran-4-yl)oxy)phenyl)piperidin-1-yl)-2-(pyrimidin-5-yl)-2-azaspiro[3.4]octane or (S)-6-(4-(5-fluoro-2-((tetrahydro-2H-pyran-4-yl)oxy)phenyl)piperidin-1-yl)-2-(pyrimidin-5-yl)-2-azaspiro[3.4]octane

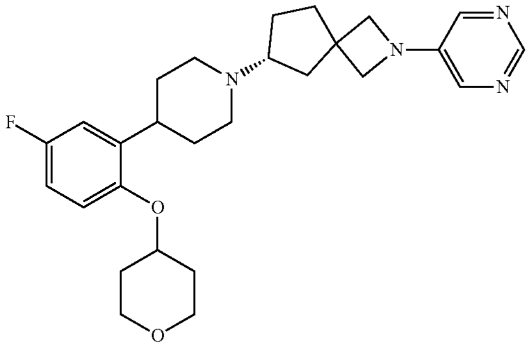

(R)-isomer

-continued

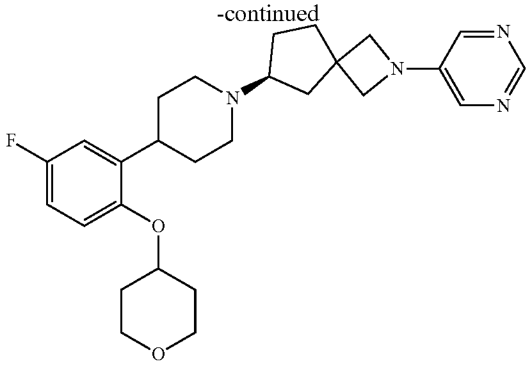

(S)-isomer

To a solution of 6-(4-(5-fluoro-2-((tetrahydro-2H-pyran-4-yl)oxy)phenyl)piperidin-1-yl)-2-azaspiro[3.4]octane (Intermediate 18G, 150 mg, 0.386 mmol) in toluene (1.5 mL) was added $Cs_2CO_3$ (629 mg, 1.93 mmol), 5-bromopyrimidine (184 mg, 1.16 mmol) and RuPhos Pd G2 (30 mg, 0.039 mmol). The reaction mixture was stirred for 2 hr at 120° C. under $N_2$ and then the reaction mixture was diluted with $H_2O$ (3 mL), and extracted with EtOAc (3×5 mL). The combined organic phases were dried over $Na_2SO_4$, filtered, concentrated and purified by prep TLC (DCM: MeOH: 10:1 w/0.1% $NH_4OH$). The material was further purified by preparative HPLC (XBridge 25×150 mm 5-95% MeCN/$H_2O$ (0.05% $NH_4HCO_3$)), and enantiomers were separated by chiral SFC (Chiralpak® AS 30×250 mm, 30% IPA w/0.1% $NH_4OH/CO_2$ 60 g/min) to give the faster running enantiomer as Example 10G (19.8 mg, 0.042 mmol) as a yellow solid and the slower running enantiomer as Example 10H (22.15 mg, 0.047 mmol) as a yellow gum.

Example 10G

SFC: Rt: 1.639 min (Chiralpak® AS-3 4.6×50 mm, 5-40% IPA (0.05% DEA)/$CO_2$ 3 mL/min).

LCMS: Rt: 1.057 min (LCMS Method 6) MS m/z 467.4 $[M+H]^+$.

$^1H$ NMR (400 MHz, $CD_3OD$) δ 8.48 (s, 1H), 8.01 (s, 2H), 6.98-6.93 (m, 2H), 6.92-6.86 (m, 1H), 4.55-4.49 (m, 1H), 3.96-3.91 (m, 4H), 3.86-3.85 (m, 2H), 3.63-3.57 (m, 2H), 3.26-3.24 (m, 2H), 3.09-3.03 (m, 1H), 2.86-2.79 (m, 1H), 2.36-2.29 (m, 3H), 2.29-2.00 (m, 5H), 1.88-1.87 (m, 3H), 1.75-1.60 (m, 5H)

Example 10H

SFC: Rt: 1.752 min (Chiralpak® AS-3 4.6×50 mm, 5-40% IPA (0.05% DEA)/$CO_2$ 3 mL/min).

LCMS: Rt: 0.867 min (LCMS Method 6) MS m/z 467.4 $[M+H]^+$.

$^1H$ NMR (400 MHz, $CD_3OD$) δ 8.48 (s, 1H), 8.01 (s, 2H), 6.98-6.92 (m, 2H), 6.87-6.86 (m, 1H), 4.55-4.51 (m, 1H), 3.96-3.94 (m, 4H), 3.92-3.90 (m, 2H), 3.63-3.57 (m, 2H), 3.21-3.19 (m, 2H), 3.10-3.00 (m, 1H), 2.80-2.76 (m, 1H), 2.34-2.31 (m, 1H), 2.29-2.17 (m, 2H), 2.05-1.84 (m, 8H), 1.75-1.62 (m, 5H).

Example 10I: S)-2-(6-(4-(2-methoxyphenyl)piperidin-1-yl)-2-azaspiro[3.4]octan-2-yl)oxazole or (R)-2-(6-(4-(2-methoxyphenyl)piperidin-1-yl)-2-azaspiro[3.4]octan-2-yl)oxazole and Example 10J (S)-2-(6-(4-(2-methoxyphenyl)piperidin-1-yl)-2-azaspiro[3.4]octan-2-yl)oxazole or (R)-2-(6-(4-(2-methoxyphenyl)piperidin-1-yl)-2-azaspiro[3.4]octan-2-yl)oxazole

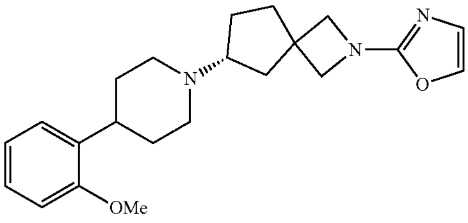

(R)-isomer

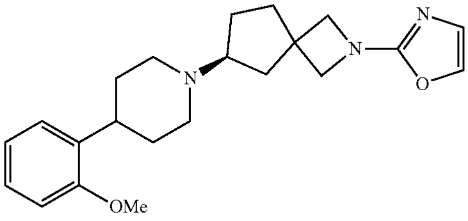

(S)-isomer 6-(4-(2-methoxyphenyl)piperidin-1-yl)-2-azaspiro[3.4]octane (Intermediate 18C, 111 mg, 0.369 mmol), 2-bromooxazole (0.066 g, 0.443 mmol), $Pd(dba)_2$ (21 mg, 0.037 mmol), xantphos (26 mg, 0.044 mmol), and NaOtBu (71 mg, 0.739 mmol) were dissolved in dioxane (4 mL). The reaction was stirred for 16 hours at 75° C. and it was then filtered and the filtrate was concentrated and purified by FCC (0-25% MeOH(10% $NH_4OH$)/EtOAc) to give the racemic title compound. The enantiomers were then separated by chiral SFC (Chiralcel OD-H 21×250 mm column, 80 g/min flow rate, 35% IPA (10 mM $NH_4OH)/CO_2$). The faster running enantiomer was isolated as Example 101 (51 mg, 0.137 mmol) and the slower running enantiomer was isolated as Example 10J (42 mg, 0.111 mmol).

Example 10I

SFC: Rt: 3.57 min (Chiralcel© OD-H 4.6×100 mm, 5-55% IPA (10 mM $NH_4OH)/CO_2$, 5 mL/min).

LCMS: Rt: 0.93 min (LCMS Method 3), MS m/z 368.6 $[M+H]^+$.

$^1H$ NMR (400 MHz, $CD_3OD$) δ 7.37 (d, J=1.4 Hz, 1H), 7.15 (t, J=7.6 Hz, 2H), 6.95-6.84 (m, 2H), 6.80 (d, J=1.3 Hz, 1H), 4.08-3.88 (m, 4H), 3.81 (s, 3H), 3.21-3.10 (m, 2H), 3.05-2.91 (m, 1H), 2.70 (d, J=8.3 Hz, 1H), 2.27 (dd, J=12.9, 7.3 Hz, 1H), 2.22-2.08 (m, 2H), 2.08-1.86 (m, 3H), 1.86-1.68 (m, 5H), 1.59 (d, J=3.5 Hz, 1H).

Example 10J

SFC: Rt: 4.18 min (Chiralcel© OD-H 4.6×100 mm, 5-55% IPA (10 mM $NH_4OH)/CO_2$, 5 mL/min).

LCMS: Rt: 0.89 min (LCMS Method 3), MS m/z 368.3 $[M+H]^+$.

$^1$H NMR (400 MHz, $CD_3OD$) δ 7.37 (d, J=1.4 Hz, 1H), 7.20-7.10 (m, 2H), 6.95-6.85 (m, 2H), 6.80 (d, J=1.4 Hz, 1H), 4.07-3.88 (m, 4H), 3.81 (s, 3H), 3.20-3.10 (m, 2H), 3.04-2.90 (m, 1H), 2.77-2.63 (m, 1H), 2.27 (dd, J=12.9, 7.3 Hz, 1H), 2.21-2.08 (m, 2H), 2.08-1.88 (m, 3H), 1.85-1.67 (m, 5H), 1.67-1.48 (m, 1H).

Example 10K: (R)-2-(6-(4-(2-(trifluoromethoxy)phenyl)piperidin-1-yl)-2-azaspiro[3.4]octan-2-yl)oxazole or (S)-2-(6-(4-(2-(trifluoromethoxy)phenyl)piperidin-1-yl)-2-azaspiro[3.4]octan-2-yl)oxazole and Example 10L: (R)-2-(6-(4-(2-(trifluoromethoxy)phenyl)piperidin-1-yl)-2-azaspiro[3.4]octan-2-yl)oxazole or (S)-2-(6-(4-(2-(trifluoromethoxy)phenyl)piperidin-1-yl)-2-azaspiro[3.4]octan-2-yl)oxazole

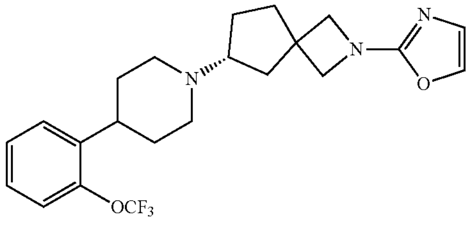

(R)-isomer

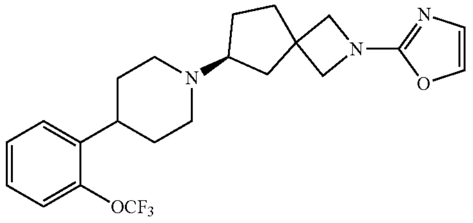

(S)-isomer 6-(4-(2-(trifluoromethoxy)phenyl)piperidin-1-yl)-2-azaspiro[3.4]octane (Intermediate 18A, 166 mg, 0.468 mmol) was added to a vial followed by a solution of 2-bromooxazole (83 mg, 0.562 mmol) in dioxane (4.7 mL) and this was placed under nitrogen. $Pd(dba)_2$ (26.9 mg, 0.047 mmol), xantphos (32.5 mg, 0.056 mmol) and NaOtBu (90 mg, 0.937 mmol) were added and this was heated to 75° C. for 16 hr. The reaction was cooled to room temperature, filtered, and rinsed through with MeCN and EtOAc. The filtrate was evaporated and the residue was then purified by FCC (0-10% MeOH (1% $NH_4OH$)/DCM). The purified racemic material was then separated by chiral SFC (Chiralpak® IG 21×250 mm column, 80 g/min flow rate, 18% MeOH (10 mM $NH_4OH$)/$CO_2$). The faster running enantiomer was isolated as Example 10K (19 mg, 0.043 mmol) and the slower running enantiomer was isolated as Example 10L (19 mg, 0.043 mmol).

Example 10K

SFC: Rt: 2.55 min (Chiralpak® ID 4.6×100 mm, 5-55% MeOH (10 mM $NH_4OH$)/$CO_2$, 5 mL/min).

LCMS: Rt: 2.88 min (LCMS Method 4), MS m/z 422.3 $[M+H]^+$.

$^1$H NMR (400 MHz, $CD_3OD$) δ 7.42 (dd, J=7.5, 1.8 Hz, 1H), 7.37 (d, J=1.3 Hz, 1H), 7.37-7.22 (m, 3H), 6.80 (d, J=1.4 Hz, 1H), 4.06-3.88 (m, 4H), 3.18 (d, J=11.5 Hz, 2H), 3.04-2.91 (m, 1H), 2.81-2.66 (m, 1H), 2.28 (dd, J=13.0, 7.3 Hz, 1H), 2.16 (s, 2H), 2.09-1.89 (m, 3H), 1.79 (m, 5H), 1.67-1.51 (m, 1H).

Example 10L

SFC: Rt: 2.69 min (Chiralpak® ID 4.6×100 mm, 5-55% MeOH (10 mM $NH_4OH$)/$CO_2$, 5 mL/min).

LCMS: Rt: 2.84 min (LCMS Method 4), MS m/z 422.3 $[M+H]^+$.

$^1$H NMR (400 MHz, $CD_3OD$) δ 7.42 (dd, J=7.7, 1.8 Hz, 1H), 7.38 (d, J=1.0 Hz, 1H), 7.36-7.22 (m, 3H), 6.80 (s, 1H), 4.08-3.89 (m, 4H), 3.18 (d, J=11.3 Hz, 2H), 2.97 (p, J=8.5 Hz, 1H), 2.81-2.67 (m, 1H), 2.28 (dd, J=12.8, 7.3 Hz, 1H), 2.16 (s, 2H), 2.08-1.89 (m, 3H), 1.80 (m, 5H), 1.59 (m, 1H).

Example 10M: (R)-2-(6-(4-(2-(trifluoromethoxy)phenyl)piperidin-1-yl)-2-azaspiro[3.4]octan-2-yl)-1,3,4-thiadiazole or (S)-2-(6-(4-(2-(trifluoromethoxy)phenyl)piperidin-1-yl)-2-azaspiro[3.4]octan-2-yl)-1,3,4-thiadiazole and Example 10N: (R)-2-(6-(4-(2-(trifluoromethoxy)phenyl)piperidin-1-yl)-2-azaspiro[3.4]octan-2-yl)-1,3,4-thiadiazole or (S)-2-(6-(4-(2-(trifluoromethoxy)phenyl)piperidin-1-yl)-2-azaspiro[3.4]octan-2-yl)-1,3,4-thiadiazole

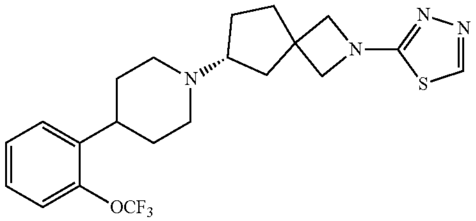

(R)-isomer

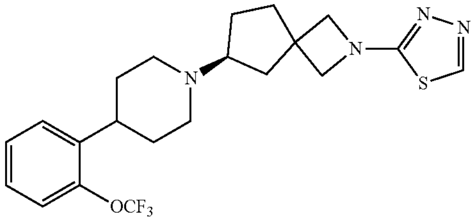

(S)-isomer

To the solution of 6-(4-(2-(trifluoromethoxy)phenyl)piperidin-1-yl)-2-azaspiro[3.4]octane (Intermediate 18A, 300 mg, 0.846 mmol) in 2% aqueous TPGS-750-M (1.5 mL) and THF (0.15 mL) was added 2-bromo-1,3,4-thiadiazole (140 mg, 0.846 mmol), followed by $K_3PO_4$ (180 mg, 0.846 mmol). The mixture was stirred under $N_2$ for 16 hr and then the reaction was extracted with DCM. The DCM was concentrated and the crude was purified by FCC (0-7% MeOH/DCM). The racemic material was then separated by chiral SFC (Chiralpak® IG 21×250 mm column, 80 mL/min flow rate, 30% MeOH (10 mM $NH_4OH$)/$CO_2$) to give the faster running enantiomer as Example 10M (72 mg, 0.161 mmol) and the slower running enantiomer as Example 10N (78 mg, 0.174 mmol).

Example 10M

SFC: Rt: 3.15 min (Chiralpak® IG 4.6×100 mm, 5-55% MeOH (10 mM $NH_4OH$)/$CO_2$, 5 mL/min).

LCMS: Rt: 1.27 min (LCMS Method 3), MS m/z 439.1 $[M+H]^+$.

$^1H$ NMR (400 MHz, DMSO-$d_6$) δ 8.78 (s, 1H), 7.51-7.45 (m, 1H), 7.40-7.27 (m, 3H), 4.02-3.84 (m, 4H), 3.10-2.97 (m, 2H), 2.87-2.72 (m, 1H), 2.70-2.57 (m, 1H), 2.20-2.10 (m, 1H), 2.05-1.92 (m, 3H), 1.92-1.78 (m, 2H), 1.78-1.60 (m, 5H), 1.57-1.42 (m, 1H).

Example 10N

SFC: Rt: 3.46 min (Chiralpak® IG 4.6×100 mm, 5-55% MeOH (10 mM $NH_4OH$)/$CO_2$, 5 mL/min).

LCMS: Rt: 1.28 min (LCMS Method 3), MS m/z 439.3 $[M+H]^+$.

$^1H$ NMR (400 MHz, DMSO-$d_6$) δ 8.78 (s, 1H), 7.53-7.44 (m, 1H), 7.41-7.26 (m, 3H), 4.04-3.84 (m, 4H), 3.11-2.96 (m, 2H), 2.88-2.74 (m, 1H), 2.70-2.59 (m, 1H), 2.15 (dd, J=12.7, 6.8 Hz, 1H), 2.05-1.78 (m, 5H), 1.77-1.60 (m, 5H), 1.58-1.41 (m, 1H).

Example 10O: (R)-2-(6-(4-(2-(difluoromethoxy)phenyl)piperidin-1-yl)-2-azaspiro[3.4]octan-2-yl)-1,3,4-thiadiazole or (S)-2-(6-(4-(2-(difluoromethoxy)phenyl)piperidin-1-yl)-2-azaspiro[3.4]octan-2-yl)-1,3,4-thiadiazole and Example 10P: (R)-2-(6-(4-(2-(difluoromethoxy)phenyl)piperidin-1-yl)-2-azaspiro[3.4]octan-2-yl)-1,3,4-thiadiazole or (S)-2-(6-(4-(2-(difluoromethoxy)phenyl)piperidin-1-yl)-2-azaspiro[3.4]octan-2-yl)-1,3,4-thiadiazole

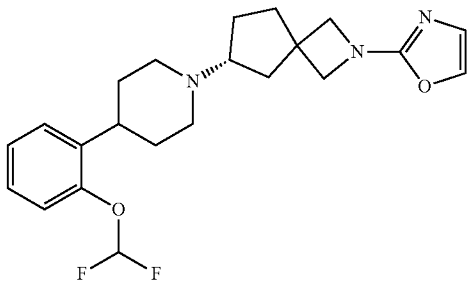

(R)-isomer

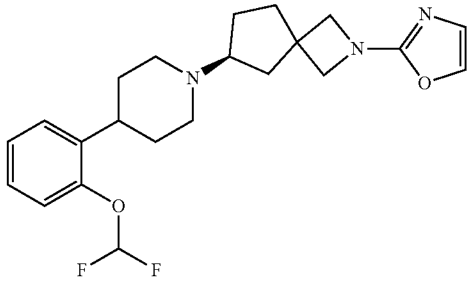

(S)-isomer 6-(4-(2-(difluoromethoxy)phenyl)piperidin-1-yl)-2-azaspiro[3.4]octane (Example 18D, 120 mg, 0.357 mmol) was added to a vial followed by a solution of 2-bromooxazole (63.3 mg, 0.428 mmol) in dioxane (3.5 mL) and this was placed under nitrogen. $Pd(dba)_2$ (20.51 mg, 0.036 mmol), xantphos (24.77 mg, 0.043 mmol) and NaOtBu (68.6 mg, 0.713 mmol) were added and this was heated to 75° C. The reaction was stirred for 16 hr and then it was filtered, rinsed with EtOAc and concentrated. The residue was then purified by FCC (0-10% MeOH (10% $NH_4OH$)/DCM to yield the racemic product. The enantiomers were then separated by chiral SFC (Chiralpak® AD-H 21×250 mm column, 80 g/min flow rate, 20% MeOH (1% isopropylamine)/$CO_2$) to give the faster running enantiomer as Example 10O (13 mg, 0.03 mmol) and the slower running enantiomer as Example 10P (16 mg, 0.038 mmol).

Example 10O

SFC: Rt: 3.11 min (Chiralpak® IG 4.6×100 mm, 5-55% MeOH (10 mM $NH_4OH$)/$CO_2$, 5 mL/min).

LCMS: Rt: 2.55 min (LCMS Method 3), MS m/z 404.3 $[M+H]^+$.

$^1H$ NMR (400 MHz, $CD_3OD$) δ 7.46-7.35 (m, 2H), 7.35-7.23 (m, 2H), 7.16 (t, J=7.8 Hz, 1H), 6.85 (d, J=9.2 Hz, 1H), 4.13-3.92 (m, 4H), 3.24 (s, 2H), 3.07 (d, J=10.6 Hz, 1H), 2.79 (d, J=9.8 Hz, 1H), 2.34 (dd, J=13.0, 7.5 Hz, 1H), 2.27 (d, J=22.3 Hz, 2H), 2.17-1.92 (m, 3H), 1.92-1.77 (m, 6H), 1.73-1.58 (m, 1H).

Example 10P

SFC: Rt: 3.40 min (Chiralpak® IG 4.6×100 mm, 5-55% MeOH (10 mM $NH_4OH$)/$CO_2$, 5 mL/min).

LCMS: Rt: 2.52 min (LCMS Method 3), MS m/z 404.3 $[M+H]^+$.

$^1H$ NMR (400 MHz, $CD_3OD$) δ 7.28 (d, J=1.4 Hz, 1H), 7.24 (dd, J=7.2, 2.2 Hz, 1H), 7.13 (m, 2H), 7.06-6.99 (m, 1H), 6.71 (d, J=2.2 Hz, 1H), 4.00-3.75 (m, 4H), 3.14 (s, 2H), 2.94 (dt, J=11.3, 6.7 Hz, 1H), 2.72 (s, 1H), 2.21 (dd, J=12.9, 7.5 Hz, 3H), 1.98-1.82 (m, 3H), 1.72 (m, 6H), 1.56-1.46 (m, 1H).

Example 10Q: (R)-5-(6-(4-(2-methoxyphenyl)piperidin-1-yl)-2-azaspiro[3.4]octan-2-yl)-1,2,4-thiadiazole or (S)-5-(6-(4-(2-methoxyphenyl)piperidin-1-yl)-2-azaspiro[3.4]octan-2-yl)-1,2,4-thiadiazole and Example 10R: (R)-5-(6-(4-(2-methoxyphenyl)piperidin-1-yl)-2-azaspiro[3.4]octan-2-yl)-1,2,4-thiadiazole or (S)-5-(6-(4-(2-methoxyphenyl)piperidin-1-yl)-2-azaspiro[3.4]octan-2-yl)-1,2,4-thiadiazole

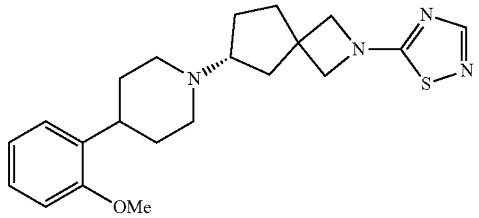

(R)-isomer

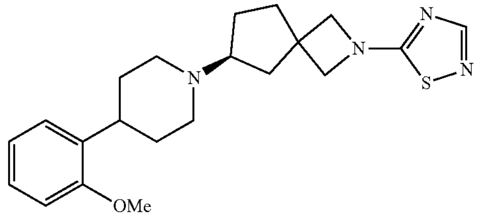

(S)-isomer

Into a vial was added 6-(4-(2-methoxyphenyl)piperidin-1-yl)-2-azaspiro[3.4]octane (Intermediate 18C, 0.055 g, 0.183 mmol) followed by a solution of 5-bromo-1,2,4-thiadiazole (0.036 g, 0.220 mmol) in dioxane (1.8 mL) and this was placed under nitrogen. A white precipitate formed and ten minutes later, additional 5-bromo-1,2,4-thiadiazole (0.018 g, 0.11 mmol) in dioxane (0.5 mL) was added and the reaction was sonicated. The reaction was stirred for 72 hours and then it was diluted with saturated aqueous sodium bicarbonate and EtOAc, extracted with EtOAc (2×), dried with $MgSO_4$, filtered and concentrated. The residue was purified by FCC (0-15% MeOH (10% $NH_4OH$/EtOAc) to give the purified racemate. The enantiomers were then separated by chiral SFC (Chiralpak® AD-H 21×250 mm column, 80 g/min flow rate, 30% MeOH (1% isopropylamine)/$CO_2$) to give the faster running enantiomer as Example 10Q (9 mg, 0.023 mmol) and the slower running enantiomer as Example 10R (9 mg, 0.023 mmol).

Example 10Q

SFC: Rt: 3.14 min (Chiralpak® IG 4.6×100 mm, 5-55% MeOH (10 mM $NH_4OH$)/$CO_2$, 5 mL/min).

LCMS: Rt: 1.15 min (LCMS Method 3), MS m/z 385.2 $[M+H]^+$.

$^1H$ NMR (400 MHz, $CD_3OD$) δ 7.92 (s, 1H), 7.20-7.11 (m, 2H), 6.95-6.85 (m, 2H), 4.17-3.96 (m, 4H), 3.81 (s, 3H), 3.22-3.10 (m, 2H), 3.05-2.91 (m, 1H), 2.84-2.65 (m, 1H), 2.32 (dd, J=12.9, 7.3 Hz, 1H), 2.26-1.92 (m, 5H), 1.92-1.69 (m, 5H), 1.69-1.52 (m, 1H).

Example 10R

SFC: Rt: 3.60 min (Chiralpak® IG 4.6×100 mm, 5-55% MeOH (10 mM $NH_4OH$)/$CO_2$, 5 mL/min).

LCMS: Rt: 1.13 min (LCMS Method 3), MS m/z 385.3 $[M+H]^+$.

$^1H$ NMR (400 MHz, $CD_3OD$) δ 7.92 (s, 1H), 7.21-7.08 (m, 2H), 6.98-6.82 (m, 2H), 4.17-3.95 (m, 4H), 3.81 (s, 3H), 3.23-3.08 (m, 2H), 3.07-2.92 (m, 1H), 2.86-2.64 (m, 1H), 2.32 (dd, J=13.0, 7.4 Hz, 1H), 2.25-1.92 (m, 5H), 1.92-1.70 (m, 5H), 1.70-1.50 (m, 1H).

Example 10T: (S)-2-(6-(4-(2-(tetrahydro-2H-pyran-4-yl)phenyl)piperidin-1-yl)-2-azaspiro[3.4]octan-2-yl)-1,3,4-oxadiazole

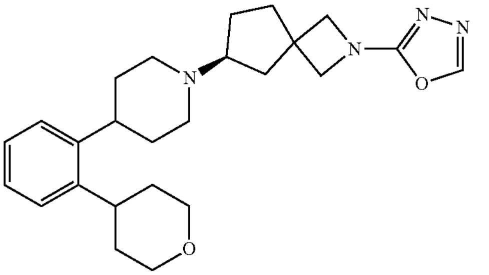 [SMILES: c1ccc(C2CCN([C@H]3CCC4(C3)CN(c3nnco3)C4)CC2)c(C2CCOCC2)c1]

To a THF (7 mL) solution of 6-(4-(2-(tetrahydro-2H-pyran-4-yl)phenyl)piperidin-1-yl)-2-azaspiro[3.4]octane (Intermediate 18H, 490 mg, 1.313 mmol) and ethyl 5-bromo-1,3,4-oxadiazole-2-carboxylate (348 mg, 1.576 mmol) were cooled to 0° C. and DIEA (0.55 mL, 3.15 mmol) was added. The reaction was stirred for 2 h at RT and then the reaction mixture was concentrated under vacuum and diluted with DCM. The crude organic was washed with water and brine then dried over sodium sulfate, filtered and concentrated. The residue was dissolved in THE (4 mL) and LiOH (331 mg, 7.88 mmol) in water (3 mL) was added. The reaction was stirred for 16 h and then it was cooled to 0° C. and 6N HCl (2.2 mL, 13.13 mmol) was added and the reaction was stirred for 2 h. Next, solid sodium carbonate was added until the was pH >12 and then the reaction was concentrated. The residue was dissolved in EtOAc and the organic layer was washed with brine, dried over sodium sulfate and concentrated. The crude was then purified by FCC (0-10% 7N $NH_3$ in MeOH/40% EtOAc/heptanes) to yield the racemate (284 mg, 0.672 mmol). 262 mg of this material was then subjected to chiral SFC to separate the enantiomers (Chiralpak® IG-3 21×250 mm column, 80 g/min flow rate, 30% MeOH (1% isopropylamine)/$CO_2$ Comparison of the SFC retention time of Example 2H (Rt: 1.92 min; Chiralpak® OJ-3 3 μM, 3×100 mm, 5-55% IPA (0.1% $NH_4OH$)/$CO_2$, 2.5 mL/min) shows that the trailing peak from this separation (Rt: 1.92 min; Chiralpak® OJ-3 3 μM, 3×100 mm, 5-55% IPA (0.1% $NH_4OH$)/$CO_2$, 2.5 mL/min) is equivalent to Example 2H. Therefore, the faster running enantiomer from this separation is title compound (91 mg, 0.213 mmol).

SFC: Rt: 1.73 min (Rt: 1.92 min; Chiralpak® OJ-3 3 μM, 3×100 mm, 5-55% IPA (0.1% $NH_4OH$)/$CO_2$, 2.5 mL/min)

LCMS: Rt: 2.14 min (LCMS Method 3), MS m/z 423.4 $[M+H]^+$.

$^1H$ NMR (400 MHz, $CD_3OD$) δ 8.36 (s, 1H), 7.27-7.24 (m, 2H), 7.21-7.12 (m, 2H), 4.13 (d, J=7.8 Hz, 1H), 4.09-3.97 (m, 5H), 3.60 (td, J=11.8, 2.0 Hz, 2H), 3.23-3.06 (m, 3H), 2.92 (tt, J=11.8, 4.0 Hz, 1H), 2.83-2.69 (m, 1H), 2.31 (dd, J=13.1, 7.3 Hz, 1H), 2.24-2.17 (m, 2H), 2.12-1.91 (m, 3H), 1.91-1.70 (m, 7H), 1.70-1.55 (m, 3H).

Example 11A: (R)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone or (S)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone and Example 11B: (R)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone or (S)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone

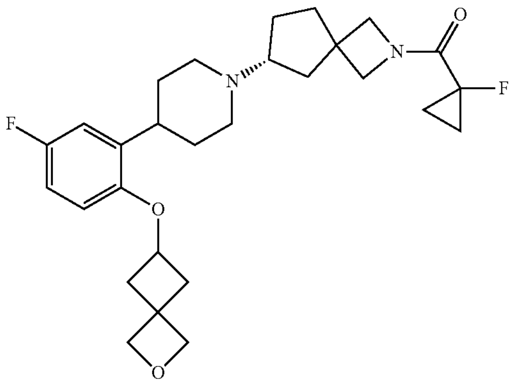

(R)-isomer

-continued

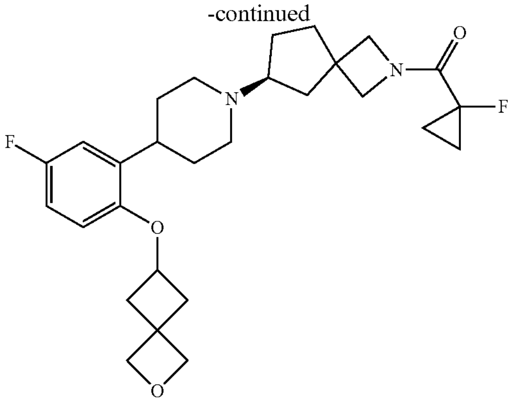

(S)-isomer

To a solution of (6-(4-(5-fluoro-2-hydroxyphenyl)piperidin-1-yl)-2-azaspiro[3.4]octan-2-yl)(1-fluorocyclopropyl)methanone (Intermediate 171, 500 mg, 1.02 mmol) in DMF (5 mL) was added 2-oxaspiro[3.3]heptan-6-yl 4-methylbenzenesulfonate (Intermediate 7A, 410 mg, 1.53 mmol) and $Cs_2CO_3$ (995 mg, 3.05 mmol) at 25° C. The reaction was stirred at 25° C. for 16 hr. The reaction mixture was filtered and filter cake was washed with MeOH (1 mL). The filtrate was purified by preparative HPLC (XBridge 25×150 mm 5-95% $MeCN/H_2O$ (0.05% $NH_4OH$)) and the enantiomers were then purified by chiral SFC (Chiralpak® IC 30×250 mm column, 60 g/min flow rate, 70% MeOH (0.1% $NH_4OH$)/$CO_2$) to yield the faster running enantiomer as Example 11A (74 mg, 0.15 mmol) and the slower running enantiomer as Example 11B (69 mg, 0.14 mmol).

Example 11A

SFC: Rt: 2.148 min (Chiralpak® IC-3 4.6×50 mm, 40% EtOH (0.05% DEA)/$CO_2$ 3 mL/min).

LCMS: Rt: 0.995 min (LCMS Method 6) MS m/z 487.5 $[M+H]^+$.

$^1H$ NMR (400 MHz, $CD_3OD$) δ 6.91-6.90 (m, 1H), 6.89-6.82 (m, 1H), 6.72-6.69 (m, 1H), 4.75 (s, 2H), 4.67 (s, 2H), 4.53 (t, J=6.4 Hz, 1H), 4.51-4.32 (m, 2H), 4.31-3.29 (m, 2H), 4.01-3.99 (m, 2H), 3.00-2.89 (m, 1H), 2.86-2.69 (m, 3H), 2.32-2.29 (m, 5H), 2.28-2.16 (m, 3H), 2.01-1.93 (m, 6H), 1.28-1.23 (m, 4H).

Example 11B

SFC: Rt: 2.875 min (Chiralpak® IC-3 4.6×50 mm, 40% EtOH (0.05% DEA)/$CO_2$ 3 mL/min)

LCMS: Rt: 0.997 min (LCMS Method 6) MS m/z 487.5 $[M+H]^+$.

$^1H$ NMR (400 MHz, $CD_3OD$) δ 6.92-6.90 (m, 1H), 6.89-6.83 (m, 1H), 6.73-6.69 (m, 1H), 4.76 (s, 2H), 4.68 (s, 2H), 4.53 (t, J=6.6 Hz, 1H), 4.46-4.26 (m, 2H), 4.04-3.85 (m, 2H), 3.18 (d, J=11.0 Hz, 2H), 3.02-2.90 (m, 1H), 2.86-2.71 (m, 3H), 2.35-2.13 (m, 5H), 2.08-1.88 (m, 3H), 1.83-1.80 (m, 6H), 1.28-1.23 (m, 4H).

Example 11C: (R)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone or (S)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone and Example 11D: (R)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone or (S)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone

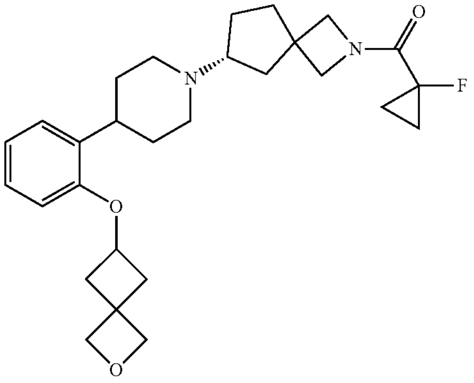

(R)-isomer

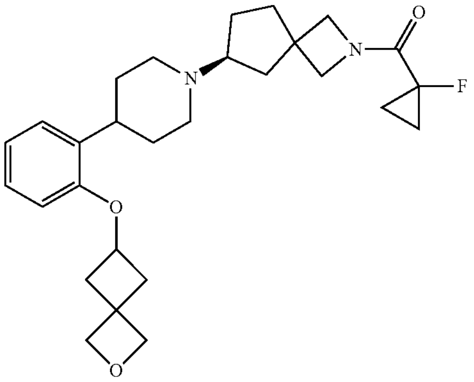

(S)-isomer

To a solution of (1-fluorocyclopropyl)(6-(4-(2-hydroxyphenyl)piperidin-1-yl)-2-azaspiro[3.4]octan-2-yl)methanone (Intermediate 17H, 200 mg, 0.54 mmol) in DMF (2 mL) was added 2-oxaspiro[3.3]heptan-6-yl 4-methylbenzenesulfonate (Intermediate 7A, 216 mg, 0.81 mmol) and $Cs_2CO_3$ (525 mg, 1.61 mmol) at 25° C. The reaction was stirred at 100° C. for 16 hr. The reaction mixture was filtered and filter cake was washed with DMF (0.5 mL). The crude product was purified by preparative HPLC (XBridge 25×150 mm 5-95% $MeCN/H_2O$ (0.05% mM $NH_4HCO_3$) and the enantiomers were separated by chiral SFC (Chiralpak® AD 30×250 mm column, 70 g/min flow rate, 40% MeOH (0.1% $NH_4OH$)/$CO_2$) to give the faster running enantiomer as Example 11C (36.44 mg, 0.078 mmol) as a yellow gum. The slower running enantiomer was further purified by prep-TLC (DCM:MeOH, 10:1) to give Example 11D (20.03 mg, 0.043 mmol) as a brown gum.

Example 11C

SFC: Rt: 1.740 min (Chiralpak® AD-3 4.6×50 mm, 5-40% EtOH (0.05% DEA)/$CO_2$ 3 mL/min).

LCMS: Rt: 1.083 min (LCMS Method 6) MS m/z 469.4 $[M+H]^+$.

$^1$H NMR (400 MHz, $CD_3OD$) δ 7.17-7.11 (m, 2H), 7.09-7.08 (m, 1H), 6.90-6.71 (m, 1H), 4.76 (s, 2H), 4.68 (s, 2H), 4.57 (t, J=6.6 Hz, 1H), 4.46-4.26 (m, 2H), 4.07-3.84 (m, 2H), 3.21-3.13 (m, 2H), 3.01-2.91 (m, 1H), 2.88-2.68 (m, 3H), 2.35-2.12 (m, 5H), 2.06-1.88 (m, 3H), 1.82-1.79 (m, 5H), 1.79-1.76 (m, 1H), 1.28-1.23 (m, 4H).

Example 11D

SFC: Rt: 1.982 min (Chiralpak® AD-3 4.6×50 mm, 5-40% EtOH (0.05% DEA)/$CO_2$ 3 mL/min).

LCMS: Rt: 1.075 min (LCMS Method 6) MS m/z 469.4 $[M+H]^+$.

$^1$H NMR (400 MHz, $CD_3OD$) δ 7.19-7.07 (m, 2H), 6.92-6.85 (m, 1H), 6.72 (d, J=7.7 Hz, 1H), 4.76 (s, 2H), 4.68 (s, 2H), 4.57 (q, J=6.6 Hz, 1H), 4.45-4.26 (m, 2H), 4.02-3.84 (m, 2H), 3.16 (d, J=10.4 Hz, 2H), 3.01-2.90 (m, 1H), 2.87-2.78 (m, 2H), 2.72 (d, J=4.0 Hz, 1H), 2.36-2.09 (m, 5H), 2.05-1.89 (m, 3H), 1.85-1.68 (m, 5H), 1.66-1.53 (m, 1H), 1.32-1.18 (m, 4H).

Example 12A: (R)-oxetan-3-yl(6-(4-(2-(trifluoromethoxy)phenyl)piperidin-1-yl)-2-azaspiro[3.4]octan-2-yl)methanone

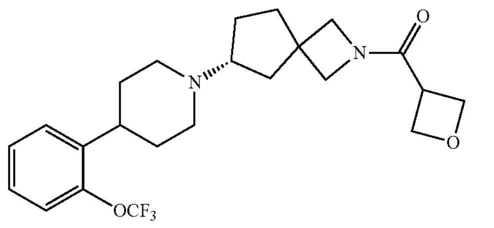 [SMILES: O=C(C1COC1)N1CC2(CC[C@@H](N3CCC(c4ccccc4OC(F)(F)F)CC3)C2)C1]

3-(2-(trifluoromethoxy)phenyl)pentane-1,5-diyl bis(4-methylbenzenesulfonate) (Intermediate 1H, 300 mg, 0.524 mmol) and (R)-(6-amino-2-azaspiro[3.4]octan-2-yl)(oxetan-3-yl)methanone (Intermediate 2E, 121 mg, 0.576 mmol) were suspended in MeCN (5 mL) at RT and potassium phosphate tribasic (389 mg, 1.834 mmol) was added to the solution. The reaction was warmed to 90° C. and stirred for 48 h. The solvent was removed under reduced pressure and the solid residue was suspended in EtOAc. The organic layer was separated and washed with water and brine, dried over sodium sulfate and concentrated. The residue was then purified by FCC (0-8% MeOH (1% $NH_4OH$)/DCM to yield the title compound (135 mg, 0.305 mmol).

LCMS: Rt: 2.42 min (LCMS Method 4) MS m/z 439.1 $[M+H]^+$.

$^1$H NMR (400 MHz, $CD_3OD$) δ 7.41 (d, J=6.8 Hz, 1H), 7.36-7.22 (m, 3H), 4.77 (dd, J=8.1, 1.7 Hz, 4H), 4.08-3.76 (m, 5H), 3.23-3.10 (m, 2H), 3.03-2.89 (m, 1H), 2.73 (s, 1H), 2.21 (dd, J=12.8, 7.3 Hz, 3H), 1.94 (dtd, J=24.0, 13.9, 7.8 Hz, 3H), 1.79 (dt, J=9.3, 4.6 Hz, 5H), 1.68-1.50 (m, 1H).

8.2. Biological Activity and Selectivity of Novel Chemical Matter on M1, M2, M3, M4, and M5 Stable Cell Lines The above examples were characterized by measuring the intracellular mobilization of Ca++ ions caused by signaling events mediated by the receptor. The Intra-cellular Calcium flux levels were captured by the highly sensitive Ca++ indicator, Calcium Assay Kit (BD Biosciences, Catalog Number 640178). The fluorescent activity from all receptors were monitored by the fluorescent imager, FDSS 7000EX (Hamamatsu) over a span of 3 minutes. The change in Calcium flux was readily captured upon activation with the muscarinic orthosteric agonist, carbachol.

CHRM4 Cell Line Maintenance

CHO-$K_1$ cells stably expressing the human cloned CHRM4 receptor (M4_CHO cells) were grown and maintained in a monolayer culture with F12/HAM (Life Technologies) supplemented with 10% Fetal Bovine Serum, 1× Pen-Strep, and 0.4 mg/mL Geneticin in a humidified atmosphere (5% $CO_2$) at 37° C. The cultures were grown to 80-90% confluency in T150 flasks (Corning) and washed with 1×DPBS then lifted with 0.05% Trypsin (Life Technologies). The cells were harvested in growth media then spun (1K rpm, 3 minutes) and cryopreserved using Recovery Cell Culture Freezing Media (Gibco Technologies). Cells were stored in liquid nitrogen and thawed a day before the assay.

CHRM1 Cell Line Maintenance

Cloned human M1 receptor (CHRM1) was stably expressed in HEK293 cells and were grown and maintained in a monolayer culture with DMEM/High Glucose (Life Technologies) supplemented with 10% Fetal Bovine Serum, 1× Pen-Strep, and 0.5 mg/mL Geneticin in a humidified atmosphere (5% $CO_2$) at 37° C. The cultures were grown to 90% confluency in T150 flasks (Corning) and washed with 1×DPBS and lifted with 0.05% Trypsin (Life Technologies). The cells were then spun (1K rpm, 3 minutes) and frozen using Recovery Cell Culture Freezing Media (Gibco Technologies). Cells were stored in liquid nitrogen and thawed a day before the assay.

CHRM2 Cell Line Maintenance

CHO-K1 cells stably expressing the human cloned CHRM2 receptor (M2_CHO cells) were grown and maintained in a monolayer culture with F12/HAM (Life Technologies) supplemented with 10% Fetal Bovine Serum, 1× Pen-Strep, and 0.4 mg/mL Geneticin in a humidified atmosphere (5% $CO_2$) at 37° C. The cultures were grown to 80-9 0% confluency in T150 flasks (Corning) and washed with 1×DPBS and lifted with 0.05% Trypsin (Life Technologies). The cells were then spun (1K rpm, 3 minutes) and frozen using Recovery Cell Culture Freezing Media (Gibco Technologies). Cells were stored in liquid nitrogen and thawed a day before the assay.

CHRM3 and CHRM5 Cell Line Maintenance

CHO-$K_1$ cells stably expressing the human cloned CHRM3 receptor (M3_CHO cells) were grown and maintained in a monolayer culture with F12/HAM (Life Technologies) supplemented with 10% Fetal Bovine Serum, 1× Pen-Strep, and 0.4 mg/mL Geneticin in a humidified atmosphere (5% $CO_2$) at 37° C. The cultures were grown to 80-9 0% confluency in T150 flasks (Corning) and washed with 1×DPBS and lifted with 0.05% Trypsin (Life Technologies). The cells were then spun (1K rpm, 3 minutes) and frozen using Recovery Cell Culture Freezing Media (Gibco Technologies). Cells were stored in liquid nitrogen and thawed a day before the assay. A similar procedure was used for cells stably expressing the human cloned CHRM5 receptor (M5_CHO).

CHRM4 $Ca^{++}$ Flux Assay

Prior to the day of the assay, stable M4_CHO cells were thawed and plated on 384 well black walled clear bottom TC treated plates (Greiner Cat #781091) at 12K cells/well using F12/HAM Media supplemented with 10% FBS (Life Technologies) and kept overnight in a humidified atmosphere (5% $CO_2$) at 37° C. The next day, cells were loaded with 20 L $Ca^{++}$ dye (BD Biosciences) using Loading Buffer (HBSS +Ca/+Mg, 20 mM HEPES, 2.5 mM Probenecid) and placed back in cell incubator for a minimum of 1 hour. After incubation, the dye was replaced with 45 µL Assay Buffer (HBSS −Ca/−Mg, 20 mM HEPES, 2.5 mM Probenecid) supplemented with 20 µM ATP (Sigma Aldrich) and kept at room temperature in the dark for 60 minutes before running on a cell imager. The FDSS 7000EX (Hamamatsu) was used to capture $Ca^{++}$ traces for a span of 3 minutes from cells treated with 11 point dose of compound in triplicate in order to generate dose response curves in agonist mode. All compounds were serially diluted in DMSO then prepared in Assay Buffer for $Ca^{++}$ flux studies. The dose response curves were generated from the average of triplicate wells obtained from each data point and used a non-linear regression of four parameter dose response algorithm. The Percent Activity (PA) was measured to $EC_{100}$ of Carbachol.

CHRM1 $Ca^{++}$ Flux Assay

Prior to the day of the assay, stable HEK293 M1 cells were thawed and plated on 384 well black walled clear bottom TC treated plates (Greiner Cat #781091) at 25K cells/well with DMEM/High Glucose supplemented with 10% FBS (Hyclone) Pen-Strep (Life Technologies) and kept overnight in a humidified atmosphere (5% $CO_2$) at 37° C. The following day, cells were loaded with 20 uL $Ca^{++}$ dye (BD Biosciences) using Loading Buffer (HBSS +Ca/+Mg, 20 mM HEPES) and placed back in cell incubator for a minimum of 1 hour. The dye was replaced with 45 µL Assay Buffer (HBSS −Ca/−Mg, 20 mM HEPES) and kept at room temperature prior to running on cell imager. Compounds were prepared in Assay Buffer and 5 uL was added to the cells. The FDSS 7000EX (Hamamatsu) was used to acquire Ca++ traces for 3 minutes from cells treated with 11 point dose in triplicate in order to generate dose response curves in agonist mode. All compounds were serially diluted in DMSO then prepared in Assay Buffer for $Ca^{++}$ flux studies. The dose response curves were generated from the average of triplicate wells obtained from each data point and used a non-linear regression of four parameter dose response algorithm. The Percent Activity (PA) was measured to $EC_{100}$ of Carbachol.

CHRM2 $Ca^{++}$ Flux Assay

Prior to the day of the assay, stable M2 CHO cells were thawed and plated on Greiner 384 well TC treated plate at a density of 12K cells/well and kept overnight in a humidified atmosphere (5% $CO_2$) at 37° C. The following day, the cells were loaded with $Ca^{++}$ dye (BD Biosciences) using Loading Buffer (HBSS +Ca/+Mg, 20 mM HEPES, 2.5 mM Probenecid) and placed back in cell incubator for a minimum of 1 hour and maximum of 2 hours. After incubation, the dye was replaced with Assay Buffer (HBSS −Ca/−Mg, 20 mM HEPES, 2.5 mM Probenecid) supplemented with 20 µM ATP (Sigma Aldrich) and kept at room temperature for 60 minutes prior before running on cell imager. The FDSS 7000EX (Hamamatsu) was used to acquire $Ca^{++}$ traces from cells in response to compound treatment and the data was used to generate dose response curves in agonist mode. All compounds were serially diluted in DMSO then prepared in Assay Buffer for $Ca^{++}$ flux studies. The dose response curves were generated from the average of triplicate wells obtained from each data point and used a non-linear regression of four parameter dose response algorithm. The Percent Activity (PA) was measured to $EC_{100}$ of Carbachol.

CHRM3 and CHRM5 $Ca^{++}$ Flux Assay

Prior to the day of the assay, stable M3_CHO or M5_CHO cells were thawed and plated on Greiner 384 well black TC treated plates at 12K cells/well in F12/DMEM supplemented with 10% FBS (Hyclone) and kept overnight in a humidified atmosphere (5% $CO_2$) at 37° C. The next day, cells were loaded with $Ca^{++}$ dye (BD Biosciences) using Loading Buffer (HBSS +Ca/+Mg, 20 mM HEPES, 2.5 mM Probenecid) and placed back in cell incubator for a minimum of 1 hour. After incubation, the dye was replaced with Assay Buffer (HBSS −Ca/−Mg, 20 mM HEPES, 2.5 mM Probenecid) and kept at room temperature in the dark before running on cell imager. The FDSS 7000EX (Hamamatsu) was used to acquire $Ca^{++}$ traces from cells treated with 11 point dose response of compounds in triplicate in order to generate dose response curves in agonist mode. All compounds were serially diluted in DMSO then prepared in Assay Buffer for $Ca^{++}$ flux studies. The dose response curves were generated from the average of triplicate wells obtained from each data point and used a non-linear regression of four parameter dose response algorithm. The Percent Activity (PA) was measured to $EC_{100}$ of Carbachol.

If an Example was tested more than once in an assay, then the values below represent the geometric mean of the results from each independent experiment.

TABLE 20

$Ca^{++}$ Flux Assay Results

| Example | M1 FDSS EC50 (µM) | M1 FDSS PA % | M2 FDSS EC50 (µm) | M2 FDSS PA % | M3 FDSS EC50 (µM) | M3 FDSS PA % | M4 FDSS EC50 (µM) | M4 FDSS PA % | M5 FDSS EC50 (µM) | M5 FDSS PA % |
|---|---|---|---|---|---|---|---|---|---|---|
| Example 1A | 0.237 | 63 | <25 | 0 | <25 | 0 | 0.001 | 81 | <25 | 0 |
| Example 1B | 0.322 | 48 | <25 | 0 | <25 | 0 | 0.001 | 69 | <25 | 0 |
| Example 1C | 0.056 | 85 | 0.017 | 15 | <25 | 0 | <0.0004 | 75 | <25 | 0 |
| Example 1D | 0.019 | 89 | 0.035 | 40 | <25 | 0 | 0.001 | 79 | 4.387 | 0 |
| Example 1E | 0.057 | 85 | 0.021 | 14 | <25 | 0 | 0.001 | 72 | <25 | 0 |
| Example 1F | 0.031 | 79 | <25 | 0 | <25 | 0 | 0.004 | 48 | <25 | 0 |
| Example 1G | 0.072 | 80 | 0.075 | 38 | <25 | 0 | 0.001 | 82 | <25 | 0 |

TABLE 20-continued

Ca++ Flux Assay Results

| Example | M1 FDSS EC50 (μM) | M1 FDSS PA % | M2 FDSS EC50 (μm) | M2 FDSS PA % | M3 FDSS EC50 (μM) | M3 FDSS PA % | M4 FDSS EC50 (μM) | M4 FDSS PA % | M5 FDSS EC50 (μM) | M5 FDSS PA % |
|---|---|---|---|---|---|---|---|---|---|---|
| Example 1H | 0.048 | 88 | 0.030 | 41 | <25 | 0 | 0.001 | 71 | 2.015 | 10 |
| Example 1I | 0.616 | 55 | 0.092 | 28 | <25 | 0 | 0.004 | 61 | <25 | 0 |
| Example 1J | 0.182 | 78 | 0.051 | 72 | <25 | 0 | 0.006 | 50 | <25 | 0 |
| Example 1K | 0.024 | 85 | 0.029 | 19 | <25 | 0 | 0.001 | 74 | <25 | 0 |
| Example 1L | 0.166 | 42 | 0.214 | 28 | <25 | 0 | 0.002 | 67 | <25 | 0 |
| Example 1M | 1.548 | 11 | 0.402 | 30 | <25 | 0 | 0.003 | 53 | <25 | 0 |
| Example 1N | 0.069 | 70 | 0.007 | 10 | <25 | 0 | <0.0004 | 62 | <25 | 0 |
| Example 1O | <25 | 0 | <25 | 0 | <25 | 0 | 0.003 | 59 | <25 | 0 |
| Example 1P | 0.098 | 43 | 0.007 | 7 | <25 | 0 | 0.001 | 61 | <25 | 0 |
| Example 2A | 0.147 | 74 | 0.117 | 12 | <25 | 0 | 0.010 | 69 | <25 | 0 |
| Example 2B | 0.036 | 107 | 0.039 | 32 | <25 | 0 | <0.0004 | 95 | <25 | 0 |
| Example 2C | 0.059 | 79 | <25 | 0 | <25 | 0 | 0.001 | 72 | <25 | 0 |
| Example 2D | 0.141 | 82 | 0.050 | 8 | <25 | 0 | 0.001 | 72 | <25 | 0 |
| Example 2E | 0.381 | 78 | 0.090 | 10 | <25 | 0 | 0.002 | 86 | <25 | 0 |
| Example 2F | 0.277 | 112 | 0.064 | 22 | <25 | 0 | 0.007 | 88 | <25 | 0 |
| Example 2G | 0.429 | 51 | 0.136 | 19 | <25 | 0 | 0.007 | 70 | <25 | 0 |
| Example 2H | 0.178 | 61 | 0.458 | 32 | <25 | 0 | 0.003 | 83 | <25 | 0 |
| Example 2I | 0.106 | 89 | 0.125 | 41 | <25 | 0 | 0.001 | 96 | <25 | 0 |
| Example 2J | 0.046 | 97 | 0.036 | 37 | <25 | 0 | 0.002 | 92 | <25 | 0 |
| Example 2K | 0.133 | 97 | 0.159 | 29 | <25 | 0 | 0.003 | 93 | <25 | 0 |
| Example 2L | 0.540 | 69 | <25 | 0 | <25 | 0 | 0.011 | 77 | <25 | 0 |
| Example 2M | 0.093 | 99 | 0.343 | 18 | <25 | 0 | 0.006 | 82 | <25 | 0 |
| Example 2N formate sale | 0.302 | 69 | <25 | 0 | <25 | 0 | 0.001 | 81 | <25 | 0 |
| Example 2O formate salt | 0.081 | 77 | 0.090 | 28 | <25 | 0 | <0.0004 | 89 | <25 | 0 |
| Example 3A | 0.008 | 92 | 0.076 | 21 | <25 | 0 | <0.0004 | 88 | <25 | 0 |
| Example 3B | 0.051 | 83 | 0.018 | 16 | <25 | 0 | 0.001 | 70 | <25 | 0 |
| Example 3C | 0.041 | 88 | 0.024 | 18 | <25 | 0 | 0.002 | 66 | <25 | 0 |
| Example 3D | 0.042 | 78 | <25 | 17 | <25 | 0 | 0.002 | 71 | <25 | 0 |
| Example 3E | 0.054 | 87 | 0.191 | 31 | <25 | 0 | 0.003 | 87 | <25 | 0 |
| Example 3F | 0.040 | 68 | <25 | 0 | <25 | 0 | 0.006 | 60 | <25 | 0 |
| Example 3G | 0.135 | 66 | 0.304 | 20 | <25 | 0 | 0.007 | 57 | <25 | 0 |
| Example 3H | 0.020 | 84 | <25 | 0 | <25 | 0 | 0.008 | 48 | <25 | 0 |
| Example 3I | 0.054 | 70 | <25 | 40 | <25 | 0 | 0.001 | 70 | <25 | 0 |
| Example 3J | 0.085 | 58 | <25 | 0 | <25 | 0 | 0.004 | 57 | <25 | 0 |

TABLE 20-continued

| Ca++ Flux Assay Results | | | | | | | | | | |
|---|---|---|---|---|---|---|---|---|---|---|
| Example | M1 FDSS EC50 (μM) | M1 FDSS PA % | M2 FDSS EC50 (μm) | M2 FDSS PA % | M3 FDSS EC50 (μM) | M3 FDSS PA % | M4 FDSS EC50 (μM) | M4 FDSS PA % | M5 FDSS EC50 (μM) | M5 FDSS PA % |
| Example 3K | 0.186 | 57 | <25 | 0 | <25 | 0 | 0.005 | 68 | <25 | 0 |
| Example 3L | 0.062 | 67 | <25 | 0 | <25 | 0 | 0.019 | 34 | <25 | 0 |
| Example 3M | <25 | 0 | <25 | 0 | <25 | 0 | 0.018 | 30 | <25 | 0 |
| Example 3N | <25 | 0 | <25 | 0 | <25 | 0 | <25 | 0 | <25 | 0 |
| Example 3O | <25 | 0 | <25 | 0 | <25 | 0 | <25 | 1 | <25 | 0 |
| Example 4A | 0.015 | 83 | 0.019 | 21 | <25 | 0 | <0.0004 | 77 | 0.700 | 6 |
| Example 5A formate salt | 0.105 | 64 | <25 | 0 | <25 | 0 | 0.002 | 64 | <25 | 0 |
| Example 5B formate salt | 0.191 | 35 | <25 | 0 | <25 | 0 | 0.004 | 53 | <25 | 0 |
| Example 5C formate salt | 0.420 | 69 | <25 | 0 | <25 | 0 | <25 | 6 | <25 | 0 |
| Example 5D | <25 | 0 | <25 | 0 | <25 | 0 | 0.156 | 36 | <25 | 0 |
| Example 5E | <25 | 0 | <25 | 0 | <25 | 0 | <25 | 2 | <25 | 0 |
| Example 5F | 3.762 | 7 | <25 | 26 | <25 | 0 | 0.006 | 59 | 14.316 | 17 |
| Example 5G | <25 | 0 | <25 | 0 | <25 | 0 | <25 | 1 | <25 | 0 |
| Example 5H | 0.048 | 50 | <25 | 0 | <25 | 0 | 0.001 | 61 | <25 | 0 |
| Example 5I | 0.272 | 55 | 13.189 | 49 | <25 | 0 | 0.084 | 16 | <25 | 0 |
| Example 5J | 0.100 | 60 | <25 | 0 | <25 | 0 | 0.009 | 60 | <25 | 0 |
| Example 5K | 0.284 | 54 | <25 | 18 | <25 | 0 | 0.009 | 64 | <25 | 0 |
| Example 5L | <25 | 0 | 7.879 | 36 | 11.72 | 0 | 0.029 | 61 | 14.417 | 17 |
| Example 5M | <25 | 0 | <25 | 0 | <25 | 0 | 0.051 | 43 | <25 | 0 |
| Example 5N | <25 | 0 | <25 | 35 | 11.27 | 9 | 0.026 | 50 | 22.941 | 8 |
| Example 5O | 1.335 | 27 | <25 | 0 | <25 | 0 | 0.055 | 39 | <25 | 0 |
| Example 5P | 0.196 | 60 | <25 | 16 | <25 | 0 | 0.043 | 55 | 13.425 | 8 |
| Example 5Q | <25 | 0 | <25 | 0 | <25 | 0 | 0.021 | 54 | <25 | 0 |
| Example 5R | 2.033 | 41 | <25 | 0 | <25 | 0 | 0.131 | 51 | <25 | 1 |
| Example 5S | 1.044 | 45 | <25 | 0 | <25 | 0 | 0.129 | 55 | <25 | 0 |
| Example 5T | 0.537 | 34 | <25 | 0 | <25 | 0 | 0.063 | 25 | <25 | 0 |
| Example 5U | 0.672 | 2 | <25 | 0 | <25 | 0 | 0.028 | 49 | <25 | 0 |
| Example 5V | 0.215 | 60 | <25 | 0 | <25 | 0 | 0.020 | 59 | <25 | 0 |
| Example 5W | 0.052 | 60 | 0.057 | 16 | <25 | 0 | 0.001 | 90 | <25 | 0 |
| Example 5X | <25 | 0 | <25 | 0 | <25 | 0 | 0.054 | 24 | <25 | 0 |
| Example 5Y | <25 | 0 | <26 | 0 | <25 | 0 | <25 | 0 | <25 | 0 |
| Example 5Z | 0.413 | 21 | <25 | 0 | <25 | 0 | 0.042 | 44 | <25 | 0 |
| Example 5AA | 0.102 | 61 | 1.769 | 28 | <25 | 0 | 0.010 | 83 | <25 | 0 |

TABLE 20-continued

Ca++ Flux Assay Results

| Example | M1 FDSS EC50 (μM) | M1 FDSS PA % | M2 FDSS EC50 (μm) | M2 FDSS PA % | M3 FDSS EC50 (μM) | M3 FDSS PA % | M4 FDSS EC50 (μM) | M4 FDSS PA % | M5 FDSS EC50 (μM) | M5 FDSS PA % |
|---|---|---|---|---|---|---|---|---|---|---|
| Example 5BB | 0.201 | 72 | 0.739 | 13 | <25 | 0 | 0.017 | 80 | <25 | 0 |
| Example 5CC | 0.335 | 36 | 0.466 | 35 | <25 | 0 | 0.022 | 84 | <25 | 0 |
| Example 5DD | 1.264 | 0 | >25 | 0 | >25 | 0 | 0.082 | 26 | >25 | 0 |
| Example 6A | 0.003 | 73 | 0.032 | 10 | <25 | 0 | 0.001 | 52 | <25 | 0 |
| Example 6B | 0.012 | 90 | <25 | 0 | <25 | 0 | 0.005 | 50 | <25 | 0 |
| Example 6C | 0.030 | 83 | <25 | 0 | <25 | 0 | 0.008 | 50 | <25 | 0 |
| Example 6D | 0.018 | 18 | <25 | 0 | <25 | 0 | 0.011 | 53 | <25 | 0 |
| Example 6E | 0.12 | 67 | <25 | 0 | <25 | 0 | 0.003 | 65 | <25 | 0 |
| Example 7A | 0.009 | 75 | 0.142 | 55 | 9.78 | 9 | 0.004 | 71 | <25 | 0 |
| Example 7B | 0.015 | 78 | 0.651 | 77 | <25 | 0 | 0.004 | 44 | <25 | 0 |
| Example 7C | 0.011 | 87 | <25 | 0 | <25 | 0 | 0.004 | 39 | <25 | 0 |
| Example 7D | 0.003 | 114 | 0.092 | 31 | <25 | 0 | 0.002 | 57 | 2.196 | 16 |
| Example 7E | 0.046 | 101 | 0.141 | 23 | <25 | 0 | 0.003 | 59 | 1.563 | 13 |
| Example 7F | 0.042 | 75 | <25 | 0 | <25 | 0 | 0.014 | 60 | <25 | 0 |
| Example 7G | 0.037 | 65 | <25 | 0 | <25 | 0 | 0.009 | 61 | <25 | 0 |
| Example 7H | 0.009 | 71 | <25 | 0 | <25 | 0 | 0.004 | 70 | <25 | 0 |
| Example 7I | 0.015 | 86 | 0.123 | 16 | <25 | 0 | 0.007 | 55 | <25 | 0 |
| Example 7J | 0.024 | 81 | 0.207 | 33 | <25 | 0 | 0.006 | 65 | <25 | 0 |
| Example 7K | 0.024 | 72 | 0.590 | 23 | <25 | 0 | 0.009 | 76 | <25 | 0 |
| Example 7L | 0.324 | 85 | <25 | 0 | <25 | 0 | 0.020 | 58 | <25 | 0 |
| Example 7M | 0.010 | 84 | <25 | 0 | <25 | 0 | 0.001 | 50 | <25 | 0 |
| Example 7N | 0.022 | 45 | <25 | 0 | <25 | 0 | 0.001 | 68 | <25 | 0 |
| Example 7O | 0.037 | 57 | <25 | 0 | <25 | 0 | 0.009 | 42 | <25 | 0 |
| Example 7P | 0.029 | 46 | <25 | 0 | <25 | 0 | 0.001 | 49 | <25 | 0 |
| Example 7Q | 0.135 | 37 | <25 | 0 | <25 | 0 | 0.003 | 48 | <25 | 0 |
| Example 7R | <25 | 0 | 6.595 | 15 | <25 | 0 | 0.062 | 36 | <25 | 0 |
| Example 7S | <25 | 0 | <25 | 0 | <25 | 0 | 2.647 | 26 | <25 | 0 |
| Example 7T | 4.346 | 32 | 18.60 | 19 | <25 | 0 | 12.12 | 5 | <25 | 0 |
| Example 7U | <25 | 0 | <25 | 0 | <25 | 0 | <25 | 1 | <25 | 0 |
| Example 7V | 2.304 | 18 | <25 | 0 | <25 | 0 | 0.353 | 23 | <25 | 0 |
| Example 7W | 0.002 | 80 | <25 | 0 | <25 | 0 | <0.0004 | 67 | 0.077 | 8 |
| Example 7X | 0.003 | 86 | <25 | 0 | <25 | 0 | <0.0004 | 66 | 0.071 | 9 |
| Example 7Y | 0.246 | 67 | <25 | 0 | <25 | 0 | 0.022 | 49 | <25 | 0 |
| Example 7Z | 0.211 | 77 | <25 | 0 | <25 | 0 | 0.009 | 50 | <25 | 0 |
| Example 7AA | 0.139 | 57 | <25 | 0 | <25 | 0 | 0.011 | 54 | <25 | 0 |
| Example 7BB | 0.013 | 55 | <25 | 0 | <25 | 0 | 0.002 | 38 | <25 | 0 |

TABLE 20-continued

Ca++ Flux Assay Results

| Example | M1 FDSS EC50 (μM) | M1 FDSS PA % | M2 FDSS EC50 (μm) | M2 FDSS PA % | M3 FDSS EC50 (μM) | M3 FDSS PA % | M4 FDSS EC50 (μM) | M4 FDSS PA % | M5 FDSS EC50 (μM) | M5 FDSS PA % |
|---|---|---|---|---|---|---|---|---|---|---|
| Example 7CC | 0.006 | 94 | <25 | 0 | <25 | 0 | 0.005 | 46 | 2.009 | 9 |
| Example 7DD | 0.116 | 86 | <25 | 0 | <25 | 0 | 0.027 | 42 | 1.120 | 18 |
| Example 7EE | 0.073 | 98 | 0.464 | 17 | <25 | 0 | 0.006 | 61 | <25 | 0 |
| Example 7FF | 0.182 | 7 | <25 | 0 | <25 | 0 | 0.005 | 38 | <25 | 0 |
| Example 7GG | 0.039 | 91 | 0.724 | 9 | <25 | 0 | 0.007 | 48 | 0.974 | 14 |
| Example 7HH | 0.159 | 82 | 0.154 | 16 | <25 | 0 | 0.019 | 50 | <25 | 0 |
| Example 7II | 0.103 | 89 | 6.885 | 12 | <25 | 0 | 0.009 | 50 | 1.640 | 13 |
| Example 7JJ | 0.012 | 87 | 0.098 | 22 | <25 | 0 | 0.002 | 49 | 0.935 | 9 |
| Example 7KK | 0.011 | 80 | 0.091 | 21 | <25 | 0 | 0.002 | 47 | <25 | 0 |
| Example 8A | 0.438 | 16 | <25 | 0 | <25 | 0 | 0.036 | 43 | <25 | 0 |
| Example 8B | 0.030 | 63 | <25 | 0 | <25 | 0 | 0.001 | 64 | <25 | 0 |
| Example 8C | 0.030 | 90 | 0.203 | 22 | <25 | 0 | 0.006 | 65 | <25 | 0 |
| Example 8D | 2.024 | 30 | <25 | 0 | <25 | 0 | 0.347 | 43 | <25 | 0 |
| Example 8E citrate salt | 0.014 | 92 | 0.096 | 26 | <25 | 0 | 0.002 | 61 | 2.155 | 1 |
| Example 8F citrate salt | <25 | 0 | <25 | 0 | <25 | 0 | 1.106 | 10 | <25 | 0 |
| Example 8G | <25 | 0 | <25 | 0 | <25 | 0 | 0.274 | 24 | <25 | 0 |
| Example 9A | 2.651 | 43 | 11.792 | 31 | <25 | 0 | 0.342 | 36 | <25 | 0 |
| Example 9B | 0.047 | 55 | <25 | 0 | <25 | 0 | 0.005 | 66 | <25 | 0 |
| Example 9C | 0.048 | 27 | <25 | 0 | <25 | 0 | 0.001 | 54 | <25 | 0 |
| Example 9D | 1.773 | 23 | <26 | 0 | <25 | 0 | 0.075 | 43 | <25 | 0 |
| Example 9E | 0.120 | 34 | <25 | 0 | <25 | 0 | 0.001 | 55 | <25 | 0 |
| Example 9F | <25 | 0 | <25 | 0 | <25 | 0 | 0.156 | 47 | <25 | 0 |
| Example 9G | 0.301 | 16 | <25 | 0 | <25 | 0 | 0.076 | 14 | <25 | 0 |
| Example 9H | <25 | 0 | <25 | 0 | <25 | 0 | <25 | 0 | <25 | 0 |
| Example 9I | 0.092 | 23 | <25 | 0 | <25 | 0 | 0.015 | 17 | <25 | 0 |
| Example 9J | 2.691 | 3 | <25 | 0 | <25 | 0 | 0.241 | 1 | <25 | 0 |
| Example 9K | 0.036 | 58 | <25 | 0 | <25 | −1 | 0.001 | 56 | <25 | 0 |
| Example 9L | 0.569 | 31 | <25 | 0 | <25 | 0 | 0.026 | 49 | <25 | 0 |
| Example 9M | 6.440 | 0 | <25 | 0 | <25 | 0 | 0.100 | 35 | <25 | 0 |
| Example 10A | 1.331 | 34 | <25 | 42 | <25 | 0 | 0.005 | 60 | <25 | 0 |
| Example 10B | <25 | o | 14.416 | 31 | <25 | 0 | 0.045 | 41 | <25 | 0 |
| Example 10C | 0.080 | 76 | 0.035 | 30 | <25 | 0 | <0.0004 | 62 | <25 | 0 |
| Example 10D | 1.409 | 55 | 0.506 | 11 | <25 | 0 | 0.025 | 50 | <25 | 0 |
| Example 10E | 3.987 | 4 | 3.987 | 11 | <25 | 0 | 0.027 | 59 | <25 | 0 |

TABLE 20-continued

Ca++ Flux Assay Results

| Example | M1 FDSS EC50 (μM) | M1 FDSS PA % | M2 FDSS EC50 (μm) | M2 FDSS PA % | M3 FDSS EC50 (μM) | M3 FDSS PA % | M4 FDSS EC50 (μM) | M4 FDSS PA % | M5 FDSS EC50 (μM) | M5 FDSS PA % |
|---|---|---|---|---|---|---|---|---|---|---|
| Example 10F | <25 | 0 | <25 | 0 | <25 | 0 | 0.0047 | 71 | <25 | 0 |
| Example 10G | 0.063 | 64 | <25 | 0 | <25 | 0 | 0.005 | 56 | <25 | 0 |
| Example 10H | 1.390 | 36 | <25 | 0 | <25 | 0 | 0.019 | 51 | <25 | 0 |
| Example 10I | <25 | 0 | <25 | 0 | <25 | 0 | 1.068 | 17 | <25 | 0 |
| Example 10J | 0.020 | 66 | <25 | 42 | <25 | 0 | 0.001 | 67 | 14.057 | 0 |
| Example 10K | 0.094 | 65 | <25 | 0 | <25 | 0 | 0.007 | 65 | <25 | 0 |
| Example 10L | 0.736 | 50 | 13.181 | 44 | 12.41 | 2 | 0.098 | 57 | <25 | 2 |
| Example 10M | 0.049 | 77 | >25 | 0 | >25 | 0 | 0.011 | 67 | >25 | 0 |
| Example 10N | <25 | 0 | <25 | 28 | <25 | 0 | <25 | 1 | <25 | 0 |
| Example 10O | 0.044 | 83 | <25 | 17 | <25 | 0 | 0.001 | 67 | <25 | 0 |
| Example 10P | 0.700 | 20 | <25 | 0 | <25 | 0 | 0.093 | 48 | <25 | 0 |
| Example 10Q | 0.170 | 66 | <25 | 18 | <25 | 0 | 0.008 | 71 | <25 | 0 |
| Example 10R | <25 | 0 | <25 | 0 | <25 | 0 | 0.122 | 36 | <25 | 0 |
| Example 10T | 3.92 | 21 | <25 | 0 | <25 | 0 | 0.170 | 67 | <25 | 0 |
| Example 11A | <25 | 9 | <25 | 0 | <25 | 0 | 0.038 | 45 | <25 | 0 |
| Example 11B | 0.030 | 9 | <25 | 0 | <25 | 0 | 0.002 | 51 | <25 | 0 |
| Example 11C | <25 | 1 | <25 | 0 | <25 | −1 | 0.002 | 47 | <25 | 0 |
| Example 11D | <25 | 1 | <25 | 0 | <25 | 0 | 0.097 | 38 | <25 | 0 |
| Example 12A | 0.008 | 79 | 110 | 18 | <25 | 0 | 0.002 | 73 | <25 | 0 |

Testing Novel Compounds in a Mouse Amphetamine Induced Hyperlocomotion Assay

The aim of these studies is to determine the effect of test compounds on the hyperactivity in mice induced by the stimulant d-amphetamine. Clinically efficacious muscarinic antipsychotics such as xanomeline are active in this assay and it is therefore considered appropriate as a test for novel M4 agonists. Studies described in this report were performed in a manner approved by the Novartis Institutes for BioMedical Research, Inc. Animal Care and Use Committee. Treatment groups were randomized and counterbalanced by chamber and run. Locomotor activity was assessed in an open-field (40 cm×40 cm) setup. Each chamber is enclosed behind light-blocking curtains and illuminated by an LED light. Mice were acclimated to the room for a minimum of 60 minutes and then administered test article (Vehicle, dose 1, dose 2, dose 3, PO) just prior to being placed in the chamber for the habituation (minutes 1-30) phase. After the habituation phase mice were administered either d-amphetamine (2.0 mg/kg) or Saline (IP), as well as Xanomeline as a positive control (1.0 mg/kg, SC) if they did not previously receive a PO injection of test article. The injection volume for all injections was 10 mL/kg. Measurements were captured via infrared beam breaks by Accuscan hardware and Superflex 5.6 software. Locomotor activity was monitored for an additional 2-hour test phase (minutes 31-150) after amphetamine injections. Animals were returned to their home cage and housing location after the conclusion of the test.

Data Analysis

All statistical analyses were performed within Graphpad Prism 7.04. AUC's were calculated by summing the distance traveled during each the 10-minute bins and compared via t-test or one-way ANOVA. A t-test comparing the AUC30-150 of the d-Amphetamine-vehicle injected group to the vehicle-vehicle injected group determined whether d-amphetamine produced an effective stimulation of activity. An ordinary one-way ANOVA was performed to compare each test compound-treated group to the d-Amphetamine-vehicle group using a Dunnett's multiple comparison test. Because d-Amphetamine is primarily active during the first hour of the test phase, these analyses are performed on the first half (minutes 31-90). A p-value of $<0.05$ was considered statistically significant. Data for Examples 2H, 6E, 8C, and 9B are shown in FIG. 1 and the data for Example 12A is shown in FIG. 2.

Figure 2:
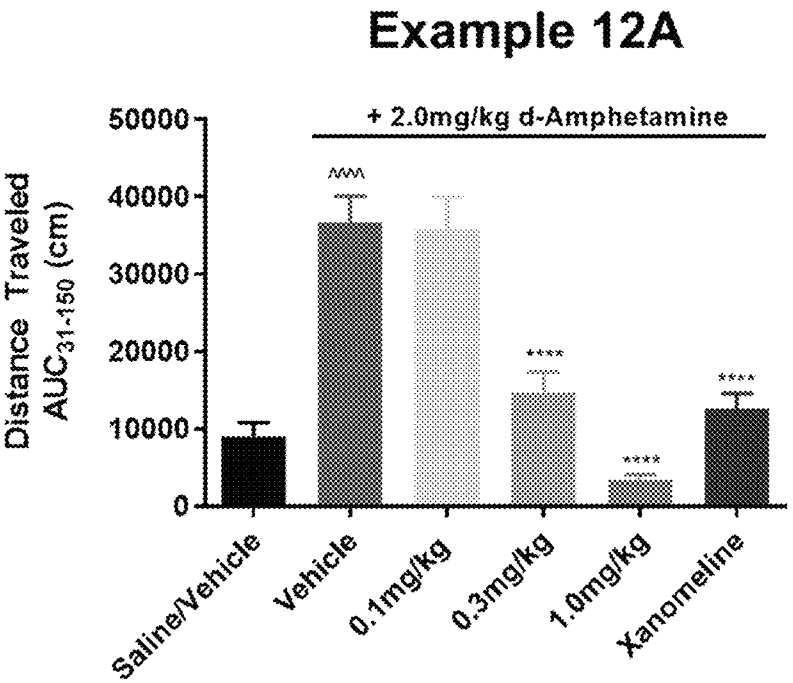
FIG. 2 illustrates the effect of Example 12A on the hyperactivity in mice induced by the stimulant d-amphetamine using a mouse amphetamine induced hyperlocomotion assay.

Altogether, the experimental data presented herein indicate that the disclosed compounds are potent and highly selective M4 receptor agonists (see Table 20) and are effective in vivo as indicated by their efficacy in reducing hyperactivity induced by the stimulant d-amphetamine in mice in a dose-dependent manner (see FIG. 1-2).

What is claimed is:

1. A method for the treatment of psychosis comprising administration of a therapeutically effective amount of a compound according to Formula (I) or a pharmaceutically acceptable salt thereof to a patient in need thereof, wherein the compound according to Formula (I) is (I)

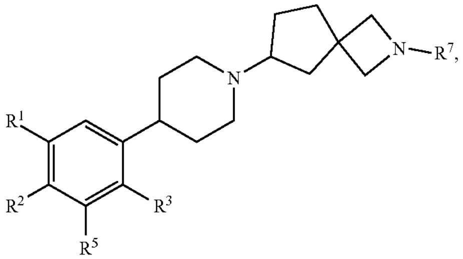

wherein $R^1$ is halogen or hydrogen;

$R^2$ is halogen or hydrogen;

$R^3$ is

- $C_{1-6}$ alkyl, said alkyl is optionally substituted with one or two substituents independently selected from the group consisting of 4 to 6-membered heterocycloalkyl and —OH,
- 5 to 6-membered heteroaryl,
- 3 to 6-membered cycloalkyl, said cycloalkyl is optionally substituted with one —OH,
- 5 to 6-membered heterocycloalkyl, said heterocycloalkyl is optionally substituted with one —OH, or
- —$OR^4$;

$R^4$ is

- —$CF_3$,
- —$CF_2H$,
- $C_{1-6}$ alkyl, said alkyl is optionally substituted with one or two $R^6$,
- 3 to 6-membered cycloalkyl,
- 4 to 7-membered heterocycloalkyl, said heterocycloalkyl is optionally substituted with one $R^6$,
- 5 to 6-membered heteroaryl, or
- $R^4$ is one of the following groups:

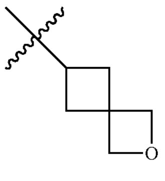 or 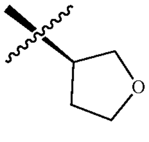 ;

$R^5$ is halogen or hydrogen;

each $R^6$ is

- independently halogen,
- —OH,
- —$CF_3$,
- —$CF_2H$,
- cyano,
- —$OCF_3$,
- —$OCH_3$,
- —O-heterocycloalkyl,
- $C_1$-$C_4$ alkyl,
- 4 to 7-membered heterocycloalkyl, said heterocycloalkyl is optionally substituted with one or two substituents independently selected from the group consisting of halogen, —OH, and $C_{1-3}$ alkyl,
- 5 to 6-membered heteroaryl, said heteroaryl is optionally substituted with one or two $C_{1-3}$ alkyl,
- 3 to 6-membered cycloalkyl, said cycloalkyl is optionally substituted with one —$CF^3$, or each of $R^6$ is independently one of the following groups:

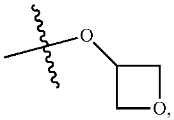, 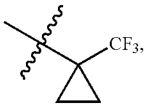, 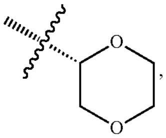,

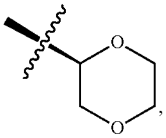, 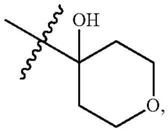, 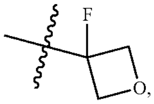,

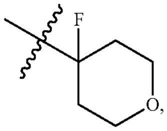, 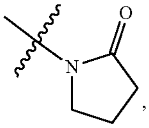, or 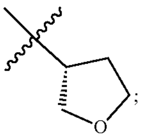;

$R^7$ is

- a 5 to 6-membered heteroaryl, said heteroaryl is optionally substituted with one substituent selected from the group consisting of $C_1$-$C_6$ alkyl, —$CF_3$, and halogen, or $C(O)R^8$; and $R^8$ is

- 3 to 6-membered cycloalkyl, said cycloalkyl is optionally substituted with one halogen, or
- 4 to 6-membered heterocycloalkyl.

2. The method according to claim 1, wherein the compound according to Formula (I) is of Formula (Ia)

(Ia)

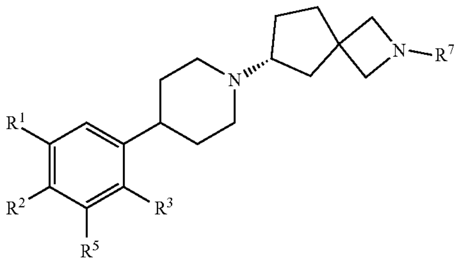

or a pharmaceutically acceptable salt or stereoisomer thereof.

3. The method according to claim 1, wherein the compound according to Formula (I) is of Formula (Ib)

(Ib)

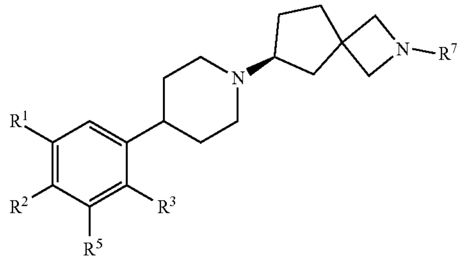

or a pharmaceutically acceptable salt or stereoisomer thereof.

4. The method according to claim 1, wherein $R^1$ is selected from the group consisting of H, chloro, and fluoro.

5. The method according to claim 1, wherein $R^2$ is H or fluoro.

6. The method according to claim 1, wherein $R^5$ is H or fluoro.

7. The method according to claim 1, wherein $R^1$, $R^2$, and $R^5$ are H.

8. The method according to claim 1, wherein $R^3$ is selected from the group consisting of:

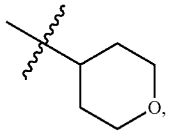 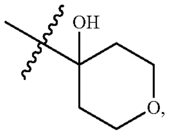

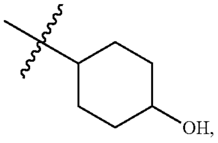 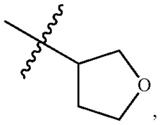

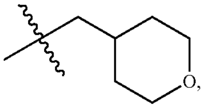 and 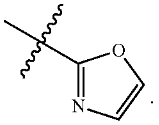

9. The method according to claim 1, wherein $R^3$ is $—OR^4$.

10. The method according to claim 1, wherein $R^4$ is selected from the group consisting of $—CH_3$, $—CF_3$, $—CF_2H$, $—CH_2CH_3$, $—CH(CH_3)_2$, $—CH_2CF_2H$, $—CH_2CH_2F$, $—(CH_2)_2CF_3$, $—CH_2C(CH_3)_2F$, $—(CH_2)_2OCF_3$, $—(CH_2)_2OH$, $—(CH_2)_2OCH_3$, $—CH_2C(CH_3)_2OH$, $—(CH_2)_2C(CH_3)_2OH$, $—(CH_2)_2C(CH_3)_2OCH_3$, $—CH_2C(CH_3)_2OCH_3$, $—(CH_2)_2CN$, and $—CH_2CH(CH_3)_2$.

11. The method according to claim 1, wherein $R^4$ is selected from the group consisting of:

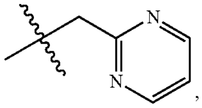 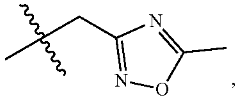

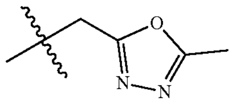 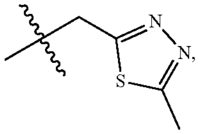

-continued

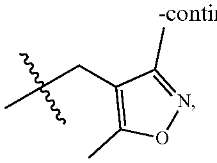 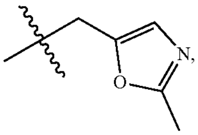

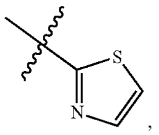 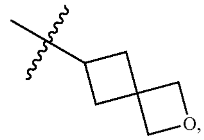 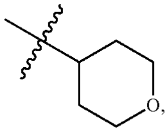

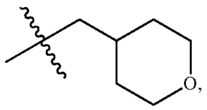 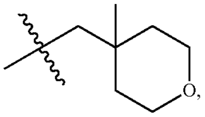

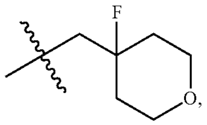 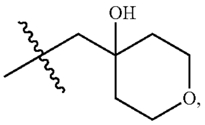

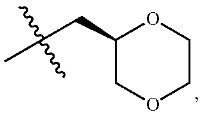 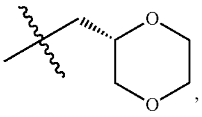

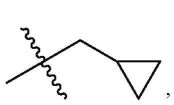 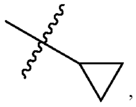 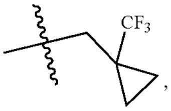

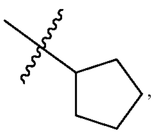 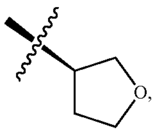 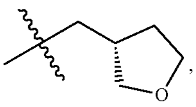

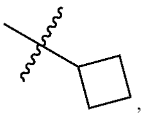 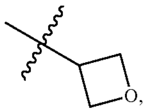 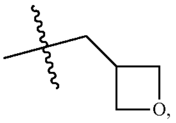

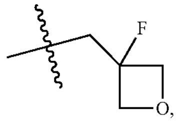 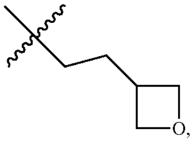

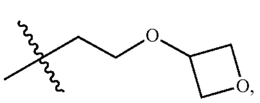 and 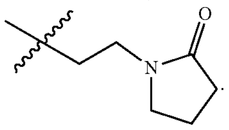

12. The method according to claim 1, wherein $R^7$ is 5 to 6-membered heteroaryl or $—C(O)R^8$.

13. The method according to claim 1, wherein $R^7$ is

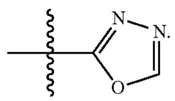 [SMILES: *c1nnco1]

14. The method according to claim 1, wherein $R^7$ is $—C(O)R^8$.

15. The method according to claim 14, wherein $R^8$ is 4 to 6-membered heterocycloalkyl or 3 to 6-membered cycloalkyl.

16. The method according to claim 14, wherein $R^8$ is 4 to 6-membered heterocycloalkyl.

17. The method according to claim 14, wherein $R^8$ is

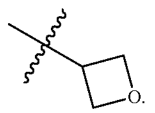 [SMILES: *C1COC1]

18. The method according to claim 14, wherein $R^8$ is 3 to 6-membered cycloalkyl, said 3 to 6-membered cycloalkyl is substituted with one halogen.

19. A method for the treatment of psychosis comprising administration of a therapeutically effective amount of a compound or a pharmaceutically acceptable salt thereof to a patient in need thereof, wherein the compound is selected from the group consisting of:

(R)-2-(6-(4-(2-((2-oxaspiro[3.3]heptan-6-yl)oxy)phenyl) piperidin-1-yl)-2-azaspiro[3.4]octan-2-yl)-1,3,4-oxadiazole;

(R)-2-(6-(4-(2-((2-oxaspiro[3.3]heptan-6-yl)oxy)-5-fluorophenyl)piperidin-1-yl)-2-azaspiro[3.4]octan-2-yl)-1,3,4-oxadiazole;

2-((R)-6-(4-(2-(((R)-1,4-dioxan-2-yl)methoxy)phenyl)piperidin-1-yl)-2-azaspiro[3.4]octan-2-yl)-1,3,4-oxadiazole;

(R)-2-(6-(4-(2-(oxetan-3-yloxy)phenyl)piperidin-1-yl)-2-azaspiro[3.4]octan-2-yl)-1,3,4-oxadiazole;

2-((R)-6-(4-(2-(((S)-1,4-dioxan-2-yl)methoxy)phenyl)piperidin-1-yl)-2-azaspiro[3.4]octan-2-yl)-1,3,4-oxadiazole;

(R)-ethyl 5-(6-(4-(2-hydroxyphenyl)piperidin-1-yl)-2-azaspiro[3.4]octan-2-yl)-1,3,4-oxadiazole-2-carboxylate;

(R)-2-(6-(4-(2-(oxetan-3-ylmethoxy)phenyl)piperidin-1-yl)-2-azaspiro[3.4]octan-2-yl)-1,3,4-thiadiazole;

(R)-2-(6-(4-(2-((3-fluorooxetan-3-yl)methoxy)phenyl)piperidin-1-yl)-2-azaspiro[3.4]octan-2-yl)-1,3,4-thiadiazole;

(R)-2-(6-(4-(2-((tetrahydro-2H-pyran-4-yl)methoxy)phenyl)piperidin-1-yl)-2-azaspiro[3.4]octan-2-yl)-1,3,4-thiadiazole;

(R)-2-(6-(4-(2-((4-fluorotetrahydro-2H-pyran-4-yl) methoxy)phenyl)piperidin-1-yl)-2-azaspiro[3.4]octan-2-yl)-1,3,4-thiadiazole;

(R)-6-(4-(2-(oxetan-3-yloxy)phenyl)piperidin-1-yl)-2-(pyrimidin-5-yl)-2-azaspiro[3.4]octane;

(R)-2-(pyrimidin-5-yl)-6-(4-(2-((tetrahydro-2H-pyran-4-yl)oxy)phenyl)piperidin-1-yl)-2-azaspiro[3.4]octane;

(R)-2-(pyrimidin-5-yl)-6-(4-(2-((tetrahydro-2H-pyran-4-yl)methoxy)phenyl)piperidin-1-yl)-2-azaspiro[3.4]octane;

(R)-6-(4-(2-(oxetan-3-ylmethoxy)phenyl)piperidin-1-yl)-2-(pyrimidin-5-yl)-2-azaspiro[3.4]octane;

(R)-6-(4-(2-((2-oxaspiro[3.3]heptan-6-yl)oxy)phenyl)piperidin-1-yl)-2-(pyrimidin-5-yl)-2-azaspiro[3.4]octane;

(R)-2-(pyrimidin-5-yl)-6-(4-(2-(((R)-tetrahydrofuran-3-yl)oxy)phenyl)piperidin-1-yl)-2-azaspiro[3.4]octane;

(R)-1-(2-(1-(2-(1,3,4-oxadiazol-2-yl)-2-azaspiro[3.4]octan-6-yl)piperidin-4-yl)phenoxy)-2-methylpropan-2-ol;

2-((R)-6-(4-(2-(((R)-tetrahydrofuran-3-yl)oxy)phenyl)piperidin-1-yl)-2-azaspiro[3.4]octan-2-yl)-1,3,4-oxadiazole;

(R)-ethyl 5-(6-(4-(2-(2-methoxyethoxy)phenyl)piperidin-1-yl)-2-azaspiro[3.4]octan-2-yl)-1,3,4-oxadiazole-2-carboxylate;

(R)-2-(6-(4-(2-((4-fluorotetrahydro-2H-pyran-4-yl) methoxy)phenyl)piperidin-1-yl)-2-azaspiro[3.4]octan-2-yl)-1,3,4-oxadiazole;

(R)-2-(6-(4-(2-((4-methyltetrahydro-2H-pyran-4-yl) methoxy)phenyl)piperidin-1-yl)-2-azaspiro[3.4]octan-2-yl)-1,3,4-oxadiazole;

(R)-2-(6-(4-(2-((tetrahydro-2H-pyran-4-yl)oxy)phenyl) piperidin-1-yl)-2-azaspiro[3.4]octan-2-yl)-1,3,4-oxadiazole;

(R)-2-(6-(4-(2-((tetrahydro-2H-pyran-4-yl)methoxy)phenyl)piperidin-1-yl)-2-azaspiro[3.4]octan-2-yl)-1,3,4-oxadiazole;

(R)-2-(6-(4-(2-(tetrahydro-2H-pyran-4-yl)phenyl)piperidin-1-yl)-2-azaspiro[3.4]octan-2-yl)-1,3,4-oxadiazole;

(R)-2-(6-(4-(5-fluoro-2-(tetrahydro-2H-pyran-4-yl)phenyl)piperidin-1-yl)-2-azaspiro[3.4]octan-2-yl)-1,3,4-oxadiazole;

2-((6R)-6-(4-(5-fluoro-2-(tetrahydrofuran-3-yl)phenyl) piperidin-1-yl)-2-azaspiro[3.4]octan-2-yl)-1,3,4-oxadiazole;

2-((6R)-6-(4-(2-(tetrahydrofuran-3-yl)phenyl)piperidin-1-yl)-2-azaspiro[3.4]octan-2-yl)-1,3,4-oxadiazole;

(R)-2-(6-(4-(2-((tetrahydro-2H-pyran-4-yl)methyl)phenyl)piperidin-1-yl)-2-azaspiro[3.4]octan-2-yl)-1,3,4-oxadiazole;

(R)-2-(6-(4-(2-(oxazol-2-yl)phenyl)piperidin-1-yl)-2-azaspiro[3.4]octan-2-yl)-1,3,4-oxadiazole;

(1S,4s)-4-(2-(1-((R)-2-(1,3,4-oxadiazol-2-yl)-2-azaspiro [3.4]octan-6-yl)piperidin-4-yl)phenyl)cyclohexan-1-ol;

(1R,4r)-4-(2-(1-((R)-2-(1,3,4-oxadiazol-2-yl)-2-azaspiro [3.4]octan-6-yl)piperidin-4-yl)phenyl)cyclohexan-1-ol;

(1s,4r)-4-(2-(1-((R)-2-(1,3,4-oxadiazol-2-yl)-2-azaspiro [3.4]octan-6-yl)piperidin-4-yl)phenyl)cyclohexan-1-ol;

(1r,4r)-4-(2-(1-((R)-2-(1,3,4-oxadiazol-2-yl)-2-azaspiro [3.4]octan-6-yl)piperidin-4-yl)phenyl)cyclohexan-1-ol;

(R)-2-(6-(4-(2-(oxetan-3-yloxy)phenyl)piperidin-1-yl)-2-azaspiro[3.4]octan-2-yl)-1,3,4-thiadiazole;

2-((R)-6-(4-(2-(((R)-1,4-dioxan-2-yl)methoxy)phenyl)piperidin-1-yl)-2-azaspiro[3.4]octan-2-yl)-1,3,4-thiadiazole;

2-((R)-6-(4-(2-(((S)-1,4-dioxan-2-yl)methoxy)phenyl)piperidin-1-yl)-2-azaspiro[3.4]octan-2-yl)-1,3,4-thiadiazole;

(R)-2-(6-(4-(2-methoxyphenyl)piperidin-1-yl)-2-azaspiro [3.4]octan-2-yl)-1,3,4-thiadiazole;

(R)-2-(6-(4-(3-fluoro-2-(oxetan-3-yloxy)phenyl)piperidin-1-yl)-2-azaspiro[3.4]octan-2-yl)-1,3,4-thiadiazole;

(R)-2-(6-(4-(2-(2-methoxyethoxy)phenyl)piperidin-1-yl)-2-azaspiro[3.4]octan-2-yl)-1,3,4-thiadiazole;

(R)-1-(2-(1-(2-(1,3,4-thiadiazol-2-yl)-2-azaspiro[3.4]octan-6-yl)piperidin-4-yl)phenoxy)-2-methylpropan-2-ol;

(R)-4-(2-(1-(2-(1,3,4-thiadiazol-2-yl)-2-azaspiro[3.4]octan-6-yl)piperidin-4-yl)phenoxy)-2-methylbutan-2-ol;

(R)-5-(6-(4-(2-methoxyphenyl)piperidin-1-yl)-2-azaspiro [3.4]octan-2-yl)isothiazole;

(R)-5-(6-(4-(2-(2-methoxyethoxy)phenyl)piperidin-1-yl)-2-azaspiro[3.4]octan-2-yl)-1,2,4-thiadiazole;

(R)-1-(2-(1-(2-(1,2,4-thiadiazol-5-yl)-2-azaspiro[3.4]octan-6-yl)piperidin-4-yl)phenoxy)-2-methylpropan-2-ol;
(R)-4-(2-(1-(2-(1,2,4-thiadiazol-5-yl)-2-azaspiro[3.4]octan-6-yl)piperidin-4-yl)phenoxy)-2-methylbutan-2-ol;
(R)-5-(6-(4-(2-methoxyphenyl)piperidin-1-yl)-2-azaspiro[3.4]octan-2-yl)-3-methyl-1,2,4-thiadiazole;
(R)-1-(5-fluoro-2-(1-(2-(4-methyloxazol-2-yl)-2-azaspiro[3.4]octan-6-yl)piperidin-4-yl)phenoxy)-2-methylpropan-2-ol;
(R)-2-methyl-1-(2-(1-(2-(4-methyloxazol-2-yl)-2-azaspiro[3.4]octan-6-yl)piperidin-4-yl)phenoxy)propan-2-ol;
(R)-3-(6-(4-(2-methoxyphenyl)piperidin-1-yl)-2-azaspiro[3.4]octan-2-yl)-1,2,4-oxadiazole;
(R)-6-(4-(2-methoxyphenyl)piperidin-1-yl)-2-(pyrimidin-5-yl)-2-azaspiro[3.4]octane formate salt;
(R)-2-methyl-1-(2-(1-(2-(pyrimidin-5-yl)-2-azaspiro[3.4]octan-6-yl)piperidin-4-yl)phenoxy)propan-2-ol formate salt;
(R)-2-methyl-1-(2-(1-(2-(4-methylpyrimidin-5-yl)-2-azaspiro[3.4]octan-6-yl)piperidin-4-yl)phenoxy)propan-2-ol formate salt;
(R)-6-(4-(2-methoxyphenyl)piperidin-1-yl)-2-(6-methylpyridin-3-yl)-2-azaspiro[3.4]octane formate salt;
(R)-6-(4-(2-methoxyphenyl)piperidin-1-yl)-2-(2-methylpyrimidin-5-yl)-2-azaspiro[3.4]octane;
(R)-2-(5-fluoropyridin-3-yl)-6-(4-(2-methoxyphenyl)piperidin-1-yl)-2-azaspiro[3.4]octane;
(R)-6-(4-(2-methoxyphenyl)piperidin-1-yl)-2-(6-methylpyrazin-2-yl)-2-azaspiro[3.4]octane;
(R)-6-(4-(2-methoxyphenyl)piperidin-1-yl)-2-(pyrazin-2-yl)-2-azaspiro[3.4]octane;
(R)-6-(4-(2-methoxyphenyl)piperidin-1-yl)-2-(3-(trifluoromethyl)pyrazin-2-yl)-2-azaspiro[3.4]octane;
(R)-6-(4-(2-methoxyphenyl)piperidin-1-yl)-2-(3-methylpyrazin-2-yl)-2-azaspiro[3.4]octane;
(R)-6-(4-(2-methoxyphenyl)piperidin-1-yl)-2-(pyridin-3-yl)-2-azaspiro[3.4]octane;
(R)-2-(6-methylpyridin-3-yl)-6-(4-(2-(((R)-tetrahydrofuran-3-yl)oxy)phenyl)piperidin-1-yl)-2-azaspiro[3.4]octane;
(R)-6-(4-(2-methoxyphenyl)piperidin-1-yl)-2-(4-methyl-1,3,5-triazin-2-yl)-2-azaspiro[3.4]octane;
(R)-2-(6-chloropyridazin-3-yl)-6-(4-(2-methoxyphenyl)piperidin-1-yl)-2-azaspiro[3.4]octane;
(R)-6-(4-(2-methoxyphenyl)piperidin-1-yl)-2-(pyridazin-3-yl)-2-azaspiro[3.4]octane;
(R)-6-(4-(5-chloro-2-methoxyphenyl)piperidin-1-yl)-2-(pyridazin-4-yl)-2-azaspiro[3.4]octane;
(R)-6-(4-(2-((tetrahydro-2H-pyran-4-yl)methoxy)phenyl)piperidin-1-yl)-2-(1,3,5-triazin-2-yl)-2-azaspiro[3.4]octane;
(R)-2-(3,6-dichloropyridazin-4-yl)-6-(4-(2-methoxyphenyl)piperidin-1-yl)-2-azaspiro[3.4]octane;
(R)-6-(4-(2-methoxyphenyl)piperidin-1-yl)-2-(pyridazin-4-yl)-2-azaspiro[3.4]octane;
(R)-2-methyl-1-(2-(1-(2-(3-methylpyrazin-2-yl)-2-azaspiro[3.4]octan-6-yl)piperidin-4-yl)phenoxy)propan-2-ol;
(R)-1-(2-(1-(2-(1,3,5-triazin-2-yl)-2-azaspiro[3.4]octan-6-yl)piperidin-4-yl)phenoxy)-2-methylpropan-2-ol;
(R)-6-(4-(5-fluoro-2-methoxyphenyl)piperidin-1-yl)-2-(pyridazin-4-yl)-2-azaspiro[3.4]octane;
(R)-6-(4-(3-fluoro-2-(oxetan-3-yloxy)phenyl)piperidin-1-yl)-2-(pyrimidin-5-yl)-2-azaspiro[3.4]octane;
(R)-6-(4-(2-(2-methoxyethoxy)phenyl)piperidin-1-yl)-2-(pyridazin-3-yl)-2-azaspiro[3.4]octane;
(R)-6-(4-(2-(2-methoxyethoxy)phenyl)piperidin-1-yl)-2-(5-methylpyrazin-2-yl)-2-azaspiro[3.4]octane;
(R)-6-(4-(2-(2-methoxyethoxy)phenyl)piperidin-1-yl)-2-(pyridazin-4-yl)-2-azaspiro[3.4]octane;
(R)-2-(5-fluoropyridin-3-yl)-6-(4-(2-(tetrahydro-2H-pyran-4-yl)phenyl)piperidin-1-yl)-2-azaspiro[3.4]octane;
(R)-2-(pyrimidin-5-yl)-6-(4-(2-(tetrahydro-2H-pyran-4-yl)phenyl)piperidin-1-yl)-2-azaspiro[3.4]octane;
(R)-2-(6-fluoropyridin-3-yl)-6-(4-(2-(tetrahydro-2H-pyran-4-yl)phenyl)piperidin-1-yl)-2-azaspiro[3.4]octane;
(R)-6-(4-(2-methoxyphenyl)piperidin-1-yl)-2-(5-methylpyrazin-2-yl)-2-azaspiro[3.4]octane;
(R)-(6-(4-(5-fluoro-2-methoxyphenyl)piperidin-1-yl)-2-azaspiro[3.4]octan-2-yl)(oxetan-3-yl)methanone;
(R)-(6-(4-(2-(difluoromethoxy)-4-fluorophenyl)piperidin-1-yl)-2-azaspiro[3.4]octan-2-yl)(oxetan-3-yl)methanone;
(R)-(6-(4-(4-fluoro-2-methoxyphenyl)piperidin-1-yl)-2-azaspiro[3.4]octan-2-yl)(oxetan-3-yl)methanone;
(R)-(6-(4-(4-fluoro-2-isopropoxyphenyl)piperidin-1-yl)-2-azaspiro[3.4]octan-2-yl)(oxetan-3-yl)methanone;
(R)-(6-(4-(2-cyclopropoxyphenyl)piperidin-1-yl)-2-azaspiro[3.4]octan-2-yl)(oxetan-3-yl)methanone;
(R)-(6-(4-(2-(2-fluoro-2-methylpropoxy)phenyl)piperidin-1-yl)-2-azaspiro[3.4]octan-2-yl)(oxetan-3-yl)methanone;
(R)-oxetan-3-yl(6-(4-(2-(thiazol-2-yloxy)phenyl)piperidin-1-yl)-2-azaspiro[3.4]octan-2-yl)methanone;
(R)-3-(2-(1-(2-(oxetane-3-carbonyl)-2-azaspiro[3.4]octan-6-yl)piperidin-4-yl)phenoxy)propanenitrile;
oxetan-3-yl((R)-6-(4-(2-(((R)-tetrahydrofuran-3-yl)methoxy)phenyl)piperidin-1-yl)-2-azaspiro[3.4]octan-2-yl)methanone;
(R)-(6-(4-(2-isobutoxyphenyl)piperidin-1-yl)-2-azaspiro[3.4]octan-2-yl)(oxetan-3-yl)methanone;
(R)-(6-(4-(2-(cyclopentyloxy)phenyl)piperidin-1-yl)-2-azaspiro[3.4]octan-2-yl)(oxetan-3-yl)methanone;
(R)-(6-(4-(2-cyclobutoxyphenyl)piperidin-1-yl)-2-azaspiro[3.4]octan-2-yl)(oxetan-3-yl)methanone;
(R)-(6-(4-(2-(cyclopropylmethoxy)phenyl)piperidin-1-yl)-2-azaspiro[3.4]octan-2-yl)(oxetan-3-yl)methanone;
(R)-(6-(4-(2-ethoxyphenyl)piperidin-1-yl)-2-azaspiro[3.4]octan-2-yl)(oxetan-3-yl)methanone;
(R)-(6-(4-(2-isopropoxyphenyl)piperidin-1-yl)-2-azaspiro[3.4]octan-2-yl)(oxetan-3-yl)methanone;
(R)-(6-(4-(2-(2-hydroxy-2-methylpropoxy)phenyl)piperidin-1-yl)-2-azaspiro[3.4]octan-2-yl)(oxetan-3-yl)methanone;
(R)-(1-fluorocyclopropyl)(6-(4-(2-(pyrimidin-2-ylmethoxy)phenyl)piperidin-1-yl)-2-azaspiro[3.4]octan-2-yl)methanone;
(S)-(1-fluorocyclopropyl)(6-(4-(2-(pyrimidin-2-ylmethoxy)phenyl)piperidin-1-yl)-2-azaspiro[3.4]octan-2-yl)methanone;
(R)-(1-fluorocyclopropyl)(6-(4-(2-(2-hydroxyethoxy)phenyl)piperidin-1-yl)-2-azaspiro[3.4]octan-2-yl)methanone;
(S)-(1-fluorocyclopropyl)(6-(4-(2-(2-hydroxyethoxy)phenyl)piperidin-1-yl)-2-azaspiro[3.4]octan-2-yl)methanone;
(R)-(6-(4-(2-(cyclopropylmethoxy)phenyl)piperidin-1-yl)-2-azaspiro[3.4]octan-2-yl)(1-fluorocyclopropyl)methanone;

(R)-(6-(4-(2-(cyclopropylmethoxy)phenyl)piperidin-1-yl)-2-azaspiro[3.4]octan-2-yl)(1-fluorocyclopropyl)methanone;

(R)-1-(2-(2-(1-(2-(1-fluorocyclopropane-1-carbonyl)-2-azaspiro[3.4]octan-6-yl)piperidin-4-yl)phenoxy)ethyl)pyrrolidin-2-one formate salt;

(S)-1-(2-(2-(1-(2-(1-fluorocyclopropane-1-carbonyl)-2-azaspiro[3.4]octan-6-yl)piperidin-4-yl)phenoxy)ethyl)pyrrolidin-2-one formate salt;

(R)-(1-fluorocyclopropyl)(6-(4-(2-((tetrahydro-2H-pyran-4-yl)methoxy)phenyl)piperidin-1-yl)-2-azaspiro[3.4]octan-2-yl)methanone;

(S)-(1-fluorocyclopropyl)(6-(4-(2-((tetrahydro-2H-pyran-4-yl)methoxy)phenyl)piperidin-1-yl)-2-azaspiro[3.4]octan-2-yl)methanone;

(R)-(1-fluorocyclopropyl)(6-(4-(2-((5-methyl-1,3,4-thiadiazol-2-yl)methoxy)phenyl)piperidin-1-yl)-2-azaspiro[3.4]octan-2-yl)methanone;

(S)-(1-fluorocyclopropyl)(6-(4-(2-((5-methyl-1,3,4-thiadiazol-2-yl)methoxy)phenyl)piperidin-1-yl)-2-azaspiro[3.4]octan-2-yl)methanone;

(R)-(6-(4-(2-ethoxyphenyl)piperidin-1-yl)-2-azaspiro[3.4]octan-2-yl)(1-fluorocyclopropyl)methanone;

(S)-(6-(4-(2-ethoxyphenyl)piperidin-1-yl)-2-azaspiro[3.4]octan-2-yl)(1-fluorocyclopropyl)methanone;

(R)-(6-(4-(2-(cyclopropylmethoxy)phenyl)piperidin-1-yl)-2-azaspiro[3.4]octan-2-yl)(1-fluorocyclopropyl)methanone;

(R)-(6-(4-(2-(cyclopropylmethoxy)phenyl)piperidin-1-yl)-2-azaspiro[3.4]octan-2-yl)(1-fluorocyclopropyl)methanone;

(R)-(6-(4-(2-((3,5-dimethylisoxazol-4-yl)methoxy)phenyl)piperidin-1-yl)-2-azaspiro[3.4]octan-2-yl)(1-fluorocyclopropyl)methanone;

(S)-(6-(4-(2-((3,5-dimethylisoxazol-4-yl)methoxy)phenyl)piperidin-1-yl)-2-azaspiro[3.4]octan-2-yl)(1-fluorocyclopropyl)methanone;

(R)-(1-fluorocyclopropyl)(6-(4-(2-((2-methyloxazol-5-yl)methoxy)phenyl)piperidin-1-yl)-2-azaspiro[3.4]octan-2-yl)methanone;

(S)-(1-fluorocyclopropyl)(6-(4-(2-((2-methyloxazol-5-yl)methoxy)phenyl)piperidin-1-yl)-2-azaspiro[3.4]octan-2-yl)methanone;

(R)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;

(S)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;

(R)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;

(S)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;

(R)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;

(S)-(1-fluorocyclopropyl)(6-(4-(2-((5-methyl-1,3,4-oxadiazol-2-yl)methoxy)phenyl)piperidin-1-yl)-2-azaspiro[3.4]octan-2-yl)methanone;

(R)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;

(S)-(1-fluorocyclopropyl)(6-(4-(2-((5-methyl-1,2,4-oxadiazol-3-yl)methoxy)phenyl)piperidin-1-yl)-2-azaspiro[3.4]octan-2-yl)methanone;

(R)-(1-fluorocyclopropyl)(6-(4-(2-(3,3,3-trifluoropropoxy)phenyl)piperidin-1-yl)-2-azaspiro[3.4]octan-2-yl)methanone;

(S)-(1-fluorocyclopropyl)(6-(4-(2-(3,3,3-trifluoropropoxy)phenyl)piperidin-1-yl)-2-azaspiro[3.4]octan-2-yl)methanone;

(R)-(1-fluorocyclopropyl)(6-(4-(2-(3-hydroxy-3-methylbutoxy)phenyl)piperidin-1-yl)-2-azaspiro[3.4]octan-2-yl)methanone;

(S)-(1-fluorocyclopropyl)(6-(4-(2-(3-hydroxy-3-methylbutoxy)phenyl)piperidin-1-yl)-2-azaspiro[3.4]octan-2-yl)methanone;

(R)-(6-(4-(2-(3-hydroxy-3-methylbutoxy)phenyl)piperidin-1-yl)-2-azaspiro[3.4]octan-2-yl)(oxetan-3-yl)methanone;

(R)-oxetan-3-yl(6-(4-(2-(2-(trifluoromethoxy)ethoxy)phenyl)piperidin-1-yl)-2-azaspiro[3.4]octan-2-yl)methanone;

(R)-oxetan-3-yl(6-(4-(2-(2-(oxetan-3-yloxy)ethoxy)phenyl)piperidin-1-yl)-2-azaspiro[3.4]octan-2-yl)methanone;

(R)-(1-fluorocyclopropyl)(6-(4-(2-(3-methoxy-3-methylbutoxy)phenyl)piperidin-1-yl)-2-azaspiro[3.4]octan-2-yl)methanone;

(S)-(1-fluorocyclopropyl)(6-(4-(2-(3-methoxy-3-methylbutoxy)phenyl)piperidin-1-yl)-2-azaspiro[3.4]octan-2-yl)methanone;

(R)-oxetan-3-yl(6-(4-(2-(3,3,3-trifluoropropoxy)phenyl)piperidin-1-yl)-2-azaspiro[3.4]octan-2-yl)methanone;

(R)-(6-(4-(2-(2-methoxy-2-methylpropoxy)phenyl)piperidin-1-yl)-2-azaspiro[3.4]octan-2-yl)(oxetan-3-yl)methanone;

(R)-oxetan-3-yl(6-(4-(2-((1-(trifluoromethyl)cyclopropyl)methoxy)phenyl)piperidin-1-yl)-2-azaspiro[3.4]octan-2-yl)methanone;

(R)-(6-(4-(2-(2,2-difluoroethoxy)phenyl)piperidin-1-yl)-2-azaspiro[3.4]octan-2-yl)(oxetan-3-yl)methanone;

(R)-oxetan-3-yl(6-(4-(2-(2-(oxetan-3-yl)ethoxy)phenyl)piperidin-1-yl)-2-azaspiro[3.4]octan-2-yl)methanone;

(S)-(6-(4-(5-chloro-2-methoxyphenyl)piperidin-1-yl)-2-azaspiro[3.4]octan-2-yl)(1-fluorocyclopropyl)methanone;

(R)-(6-(4-(5-chloro-2-methoxyphenyl)piperidin-1-yl)-2-azaspiro[3.4]octan-2-yl)(1-fluorocyclopropyl)methanone;

(S)-(6-(4-(5-chloro-2-methoxyphenyl)piperidin-1-yl)-2-azaspiro[3.4]octan-2-yl)(1-fluorocyclopropyl)methanone;

(R)-(6-(4-(5-chloro-2-methoxyphenyl)piperidin-1-yl)-2-azaspiro[3.4]octan-2-yl)(1-fluorocyclopropyl)methanone;

(S)-(6-(4-(2-methoxyphenyl)piperidin-1-yl)-2-azaspiro[3.4]octan-2-yl)(oxetan-3-yl)methanone;

(R)-(6-(4-(2-methoxyphenyl)piperidin-1-yl)-2-azaspiro[3.4]octan-2-yl)(oxetan-3-yl)methanone;

(S)-(6-(4-(2-methoxyphenyl)piperidin-1-yl)-2-azaspiro[3.4]octan-2-yl)(oxetan-3-yl)methanone;

(R)-(6-(4-(2-methoxyphenyl)piperidin-1-yl)-2-azaspiro[3.4]octan-2-yl)(oxetan-3-yl)methanone;

(S)-(6-(4-(2-(difluoromethoxy)phenyl)piperidin-1-yl)-2-azaspiro[3.4]octan-2-yl)(oxetan-3-yl)methanone;

(R)-(6-(4-(2-(difluoromethoxy)phenyl)piperidin-1-yl)-2-azaspiro[3.4]octan-2-yl)(oxetan-3-yl)methanone citrate salt;

(S)-(6-(4-(2-(difluoromethoxy)phenyl)piperidin-1-yl)-2-azaspiro[3.4]octan-2-yl)(oxetan-3-yl)methanone;

(R)-(6-(4-(2-(difluoromethoxy)phenyl)piperidin-1-yl)-2-azaspiro[3.4]octan-2-yl)(oxetan-3-yl)methanone citrate salt;

(S)-oxetan-3-yl(6-(4-(2-(trifluoromethoxy)phenyl)piperidin-1-yl)-2-azaspiro[3.4]octan-2-yl)methanone;

(R)-oxetan-3-yl(6-(4-(2-(trifluoromethoxy)phenyl)piperidin-1-yl)-2-azaspiro[3.4]octan-2-yl)methanone;

(R)-(1-fluorocyclopropyl)(6-(4-(2-(trifluoromethoxy)phenyl)piperidin-1-yl)-2-azaspiro[3.4]octan-2-yl)methanone;

(S)-(1-fluorocyclopropyl)(6-(4-(2-(trifluoromethoxy)phenyl)piperidin-1-yl)-2-azaspiro[3.4]octan-2-yl)methanone;

(R)-(1-fluorocyclopropyl)(6-(4-(2-(trifluoromethoxy)phenyl)piperidin-1-yl)-2-azaspiro[3.4]octan-2-yl)methanone;

(S)-(1-fluorocyclopropyl)(6-(4-(2-(trifluoromethoxy)phenyl)piperidin-1-yl)-2-azaspiro[3.4]octan-2-yl)methanone;

(R)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;

(S)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;

(R)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;

(S)-(6-(4-(5-fluoro-2-((tetrahydro-2H-pyran-4-yl)oxy)phenyl)piperidin-1-yl)-2-azaspiro[3.4]octan-2-yl)(1-fluorocyclopropyl)methanone;

(R)-(1-fluorocyclopropyl)(6-(4-(2-((tetrahydro-2H-pyran-4-yl)oxy)phenyl)piperidin-1-yl)-2-azaspiro[3.4]octan-2-yl)methanone;

(S)-(1-fluorocyclopropyl)(6-(4-(2-((tetrahydro-2H-pyran-4-yl)oxy)phenyl)piperidin-1-yl)-2-azaspiro[3.4]octan-2-yl)methanone;

(R)-(1-fluorocyclopropyl)(6-(4-(2-((tetrahydro-2H-pyran-4-yl)oxy)phenyl)piperidin-1-yl)-2-azaspiro[3.4]octan-2-yl)methanone;

(S)-(1-fluorocyclopropyl)(6-(4-(2-((tetrahydro-2H-pyran-4-yl)oxy)phenyl)piperidin-1-yl)-2-azaspiro[3.4]octan-2-yl)methanone;

(R)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;

(S)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;

(R)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;

(S)-(1-fluorocyclopropyl)(6-(4-(2-(4-hydroxytetrahydro-2H-pyran-4-yl)phenyl)piperidin-1-yl)-2-azaspiro[3.4]octan-2-yl)methanone;

(R)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(4-hydroxytetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(R)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(S)-(6-(4-(5-fluoro-2-(tetrahydro-2H-pyran-4-yl)phenyl)piperidin-1-yl)-2-azaspiro[3.4]octan-2-yl)(1-fluorocyclopropyl)methanone;

(R)-(1-fluorocyclopropyl)(6-(4-(2-(tetrahydro-2H-pyran-4-yl)phenyl)piperidin-1-yl)-2-azaspiro[3.4]octan-2-yl)methanone;

(S)-(1-fluorocyclopropyl)(6-(4-(2-(tetrahydro-2H-pyran-4-yl)phenyl)piperidin-1-yl)-2-azaspiro[3.4]octan-2-yl)methanone;

(R)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(S)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(R)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(S)-6-(4-(5-fluoro-2-((tetrahydro-2H-pyran-4-yl)oxy)phenyl)piperidin-1-yl)-2-(5-fluoropyridin-3-yl)-2-azaspiro[3.4]octane;

(R)-6-(4-(5-fluoro-2-(tetrahydro-2H-pyran-4-yl)phenyl)piperidin-1-yl)-2-(pyrimidin-5-yl)-2-azaspiro[3.4]octane;

(S)-6-(4-(5-fluoro-2-(tetrahydro-2H-pyran-4-yl)phenyl)piperidin-1-yl)-2-(pyrimidin-5-yl)-2-azaspiro[3.4]octane;

(R)-6-(4-(5-fluoro-2-(tetrahydro-2H-pyran-4-yl)phenyl)piperidin-1-yl)-2-(pyrimidin-5-yl)-2-azaspiro[3.4]octane;

(S)-6-(4-(5-fluoro-2-(tetrahydro-2H-pyran-4-yl)phenyl)piperidin-1-yl)-2-(pyrimidin-5-yl)-2-azaspiro[3.4]octane;

(R)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(S)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(R)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(S)-6-(4-(2-((2-oxaspiro[3.3]heptan-6-yl)oxy)-5-fluorophenyl)piperidin-1-yl)-2-(pyrimidin-5-yl)-2-azaspiro[3.4]octane;

(R)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(R)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-6-(4-(5-fluoro-2-((tetrahydro-2H-pyran-4-yl)oxy)phenyl)piperidin-1-yl)-2-(pyrimidin-5-yl)-2-azaspiro[3.4]octane;

(S)-2-(6-(4-(2-methoxyphenyl)piperidin-1-yl)-2-azaspiro[3.4]octan-2-yl)oxazole;

(R)-2-(6-(4-(2-methoxyphenyl)piperidin-1-yl)-2-azaspiro[3.4]octan-2-yl)oxazole;

(S)-2-(6-(4-(2-methoxyphenyl)piperidin-1-yl)-2-azaspiro[3.4]octan-2-yl)oxazole;

(R)-2-(6-(4-(2-methoxyphenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)oxazole;

(S)-2-(6-(4-(2-(trifluoromethoxy)phenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)oxazole;

(S)-2-(6-(4-(2-(trifluoromethoxy)phenyl)piperidin-1-yl)-2-azaspiro[3.4]octan-2-yl)oxazole;

(R)-2-(6-(4-(2-(trifluoromethoxy)phenyl)piperidin-1-yl)-2-azaspiro[3.4]octan-2-yl)-1,3,4-thiadiazole;

(S)-2-(6-(4-(2-(trifluoromethoxy)phenyl)piperidin-1-yl)-2-azaspiro[3.4]octan-2-yl)-1,3,4-thiadiazole;

(R)-2-(6-(4-(2-(trifluoromethoxy)phenyl)piperidin-1-yl)-2-azaspiro[3.4]octan-2-yl)-1,3,4-thiadiazole;

(S)-2-(6-(4-(2-(trifluoromethoxy)phenyl)piperidin-1-yl)-2-azaspiro[3.4]octan-2-yl)-1,3,4-thiadiazole;

(R)-2-(6-(4-(2-(difluoromethoxy)phenyl)piperidin-1-yl)-2-azaspiro[3.4]octan-2-yl)-1,3,4-thiadiazole;

(S)-2-(6-(4-(2-(difluoromethoxy)phenyl)piperidin-1-yl)-2-azaspiro[3.4]octan-2-yl)-1,3,4-thiadiazole;

(R)-2-(6-(4-(2-(difluoromethoxy)phenyl)piperidin-1-yl)-2-azaspiro[3.4]octan-2-yl)-1,3,4-thiadiazole;

(S)-2-(6-(4-(2-(difluoromethoxy)phenyl)piperidin-1-yl)-2-azaspiro[3.4]octan-2-yl)-1,3,4-thiadiazole;

(R)-5-(6-(4-(2-methoxyphenyl)piperidin-1-yl)-2-azaspiro[3.4]octan-2-yl)-1,2,4-thiadiazole;

(S)-5-(6-(4-(2-methoxyphenyl)piperidin-1-yl)-2-azaspiro[3.4]octan-2-yl)-1,2,4-thiadiazole;

(R)-5-(6-(4-(2-methoxyphenyl)piperidin-1-yl)-2-azaspiro[3.4]octan-2-yl)-1,2,4-thiadiazole;

(S)-5-(6-(4-(2-methoxyphenyl)piperidin-1-yl)-2-azaspiro[3.4]octan-2-yl)-1,2,4-thiadiazole;

(R)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)-5-fluorophenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone;

(S)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone;

(R)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone; and (S)-(6-(4-(2-((2-oxaspiro[3.3]heptan-6-yl)oxy)phenyl)piperidin-1-yl)-2-azaspiro[3.4]octan-2-yl)(1-fluorocyclopropyl)methanone, and pharmaceutically acceptable salts thereof.

20. The method according to claim 19, wherein the compound is selected from the group consisting of:

(R)-2-(6-(4-(2-(tetrahydro-2H-pyran-4-yl)phenyl)piperidin-1-yl)-2-azaspiro[3.4]octan-2-yl)-1,3,4-oxadiazole;

(S)-2-(6-(4-(2-(tetrahydro-2H-pyran-4-yl)phenyl)piperidin-1-yl)-2-azaspiro[3.4]octan-2-yl)-1,3,4-oxadiazole;

(R)-(1-fluorocyclopropyl)(6-(4-(2-(tetrahydro-2H-pyran-4-yl)phenyl)piperidin-1-yl)-2-azaspiro[3.4]octan-2-yl)methanone;

(S)-(1-fluorocyclopropyl)(6-(4-(2-(tetrahydro-2H-pyran-4-yl)phenyl)piperidin-1-yl)-2-azaspiro[3.4]octan-2-yl)methanone;

(R)-2-(pyrimidin-5-yl)-6-(4-(2-(tetrahydro-2H-pyran-4-yl)phenyl)piperidin-1-yl)-2-azaspiro[3.4]octane;

(S)-oxetan-3-yl(6-(4-(2-(trifluoromethoxy)phenyl)piperidin-1-yl)-2-azaspiro[3.4]octan-2-yl)methanone; and (R)-oxetan-3-yl(6-(4-(2-(trifluoromethoxy)phenyl)piperidin-1-yl)-2-azaspiro[3.4]octan-2-yl)methanone, or a pharmaceutically acceptable salt thereof.

21. The method according to claim 19, wherein the compound is selected from the group consisting of:

(R)-2-(6-(4-(2-(tetrahydro-2H-pyran-4-yl)phenyl)piperidin-1-yl)-2-azaspiro[3.4]octan-2-yl)-1,3,4-oxadiazole, having the following structure:

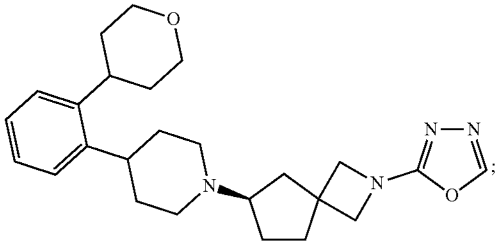 [SMILES: c1ccc(C2CCN([C@@H]3CCC4(C3)CN(c3nnco3)C4)CC2)c(C2CCOCC2)c1]

;

(R)-(1-fluorocyclopropyl)(6-(4-(2-(tetrahydro-2H-pyran-4-yl)phenyl)piperidin-1-yl)-2-azaspiro[3.4]octan-2-yl)methanone, having the following structure:

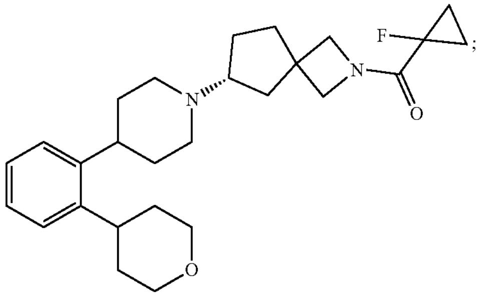 [SMILES: O=C(N1CC2(CC[C@@H](N3CCC(c4ccccc4C4CCOCC4)CC3)C2)C1)C1(F)CC1]

;

(R)-2-(pyrimidin-5-yl)-6-(4-(2-(tetrahydro-2H-pyran-4-yl)phenyl)piperidin-1-yl)-2-azaspiro[3.4]octane, having the following structure:

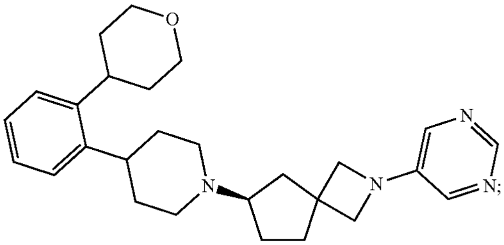 [SMILES: c1ccc(C2CCN([C@@H]3CCC4(C3)CN(c3cncnc3)C4)CC2)c(C2CCOCC2)c1]

;

and (R)-oxetan-3-yl(6-(4-(2-(trifluoromethoxy)phenyl)piperidin-1-yl)-2-azaspiro[3.4]octan-2-yl)methanone, having the following structure:

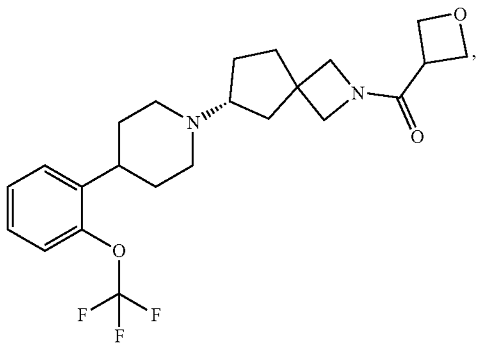 [SMILES: O=C(C1COC1)N1CC2(CC[C@@H](N3CCC(c4ccccc4OC(F)(F)F)CC3)C2)C1]

or a pharmaceutically acceptable salt thereof.

22. The method according to claim 1, wherein the psychosis is associated with Alzheimer's disease or frontotemporal dementia.

23. The method according to claim 19, wherein the psychosis is associated with Alzheimer's disease or frontotemporal dementia.

24. The method of claim 21, wherein the compound is (R)-2-(6-(4-(2-(tetrahydro-2H-pyran-4-yl)phenyl)piperidin-1-yl)-2-azaspiro[3.4]octan-2-yl)-1,3,4-oxadiazole, having the following structure:

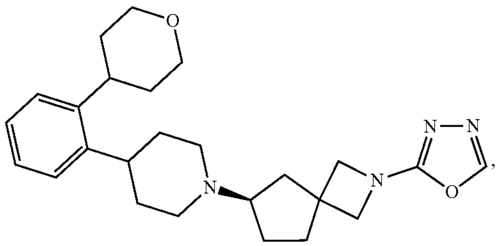 [SMILES: c1ccc(C2CCN([C@@H]3CCC4(C3)CN(c3nnco3)C4)CC2)c(C2CCOCC2)c1]

or a pharmaceutically acceptable salt thereof.

25. The method of claim 21, wherein the compound is (R)-(1-fluorocyclopropyl)(6-(4-(2-(tetrahydro-2H-pyran-4-yl)phenyl)piperidin-1-yl)-2-azaspiro[3.4]octan-2-yl)methanone, having the following structure:

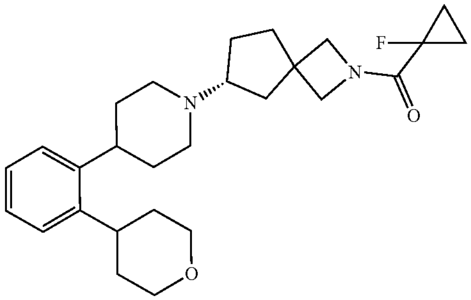 [SMILES: O=C(N1CC2(CC[C@@H](N3CCC(c4ccccc4C4CCOCC4)CC3)C2)C1)C1(F)CC1]

or a pharmaceutically acceptable salt thereof.

* * * * *